(12) United States Patent
Smith

(10) Patent No.: US 12,408,974 B2
(45) Date of Patent: Sep. 9, 2025

(54) SYSTEMS AND METHODS FOR MODULATING NERVES OR OTHER TISSUE

(71) Applicant: Medtronic Ireland Manufacturing Unlimited Company, Dublin (IE)

(72) Inventor: Scott Raymond Smith, Chaska, MN (US)

(73) Assignee: Medtronic Ireland Manufacturing Unlimited Company, Dublin (IE)

( * ) Notice: Subject to any disclaimer, the term of this patent is extended or adjusted under 35 U.S.C. 154(b) by 437 days.

(21) Appl. No.: 16/874,467

(22) Filed: May 14, 2020

(65) Prior Publication Data
US 2020/0337765 A1 Oct. 29, 2020

Related U.S. Application Data

(63) Continuation of application No. 15/532,650, filed as application No. PCT/US2015/063807 on Dec. 3, 2015, now abandoned.
(Continued)

(51) Int. Cl.
*A61B 18/14* (2006.01)
*A61B 8/08* (2006.01)
(Continued)

(52) U.S. Cl.
CPC ........ *A61B 18/1492* (2013.01); *A61B 17/122* (2013.01); *A61B 17/320068* (2013.01); *A61B 18/02* (2013.01); *A61B 18/06* (2013.01); *A61B 18/16* (2013.01); *A61M 25/0147* (2013.01); *A61B 8/12* (2013.01); *A61B 8/485* (2013.01); *A61B 2017/00402* (2013.01); *A61B 2017/00867* (2013.01); *A61B 2017/320069* (2017.08);
(Continued)

(58) Field of Classification Search
None
See application file for complete search history.

(56) References Cited

U.S. PATENT DOCUMENTS

| 4,033,331 A | 7/1977 | Guss et al. |
| 5,561,165 A | 10/1996 | Lautt et al. |

(Continued)

FOREIGN PATENT DOCUMENTS

| CN | 1817382 | 8/2006 |
| CN | 201642315 U | 11/2010 |

(Continued)

OTHER PUBLICATIONS

Adkins-Marshall, B. et al, "Role of hepatic nerves in response of liver to intraportal glucose deliverin dogs," American Journal of Physiology—Endocrinology and Metabolism, vol. 262, pp. E679-E686 (1992).

(Continued)

*Primary Examiner* — Ronald Hupczey, Jr.
(74) *Attorney, Agent, or Firm* — Shumaker & Sieffert, P.A.

(57) ABSTRACT

According to various embodiments, systems, devices and methods for modulating targeted nerve fibers (e.g., hepatic neuromodulation) or other tissue are provided. The systems may be configured to access tortuous anatomy of or adjacent hepatic vasculature. The systems may be configured to target nerves surrounding (e.g., within adventitia of or within perivascular space of) an artery or other blood vessel, such as the common hepatic artery.

21 Claims, 167 Drawing Sheets

Related U.S. Application Data

(60) Provisional application No. 62/130,469, filed on Mar. 9, 2015, provisional application No. 62/087,179, filed on Dec. 3, 2014.

(51) Int. Cl.

| | | |
|---|---|---|
| *A61B 8/12* | (2006.01) | |
| *A61B 17/00* | (2006.01) | |
| *A61B 17/122* | (2006.01) | |
| *A61B 17/32* | (2006.01) | |
| *A61B 18/00* | (2006.01) | |
| *A61B 18/02* | (2006.01) | |
| *A61B 18/04* | (2006.01) | |
| *A61B 18/06* | (2006.01) | |
| *A61B 18/16* | (2006.01) | |
| *A61B 18/18* | (2006.01) | |
| *A61B 18/22* | (2006.01) | |
| *A61B 18/24* | (2006.01) | |
| *A61M 25/01* | (2006.01) | |
| *A61M 25/09* | (2006.01) | |
| *A61N 7/00* | (2006.01) | |
| *A61B 8/00* | (2006.01) | |

(52) U.S. Cl.
CPC ............ *A61B 2018/00023* (2013.01); *A61B 2018/00047* (2013.01); *A61B 2018/00214* (2013.01); *A61B 2018/0022* (2013.01); *A61B 2018/00267* (2013.01); *A61B 2018/00279* (2013.01); *A61B 2018/00285* (2013.01); *A61B 2018/00404* (2013.01); *A61B 2018/00434* (2013.01); *A61B 2018/00529* (2013.01); *A61B 2018/00577* (2013.01); *A61B 2018/00821* (2013.01); *A61B 2018/00875* (2013.01); *A61B 2018/0212* (2013.01); *A61B 2018/048* (2013.01); *A61B 2018/068* (2013.01); *A61B 2018/1425* (2013.01); *A61B 2018/1435* (2013.01); *A61B 2018/1467* (2013.01); *A61B 2018/1475* (2013.01); *A61B 18/1815* (2013.01); *A61B 2018/1861* (2013.01); *A61B 18/22* (2013.01); *A61B 18/24* (2013.01); *A61B 2218/007* (2013.01); *A61M 25/09* (2013.01); *A61N 2007/0021* (2013.01); *A61N 2007/0043* (2013.01)

(56) References Cited

U.S. PATENT DOCUMENTS

| | | | |
|---|---|---|---|
| 5,680,860 A | 10/1997 | Imran | |
| 5,683,366 A | 11/1997 | Eggers et al. | |
| 5,707,400 A | 1/1998 | Baker | |
| 5,893,885 A | 4/1999 | Webster | |
| 6,012,457 A * | 1/2000 | Lesh .............. | A61M 25/1002 |
| | | | 601/2 |
| 6,113,593 A | 9/2000 | Tu et al. | |
| 6,142,994 A | 11/2000 | Swanson et al. | |
| 6,161,049 A | 12/2000 | Rudie et al. | |
| 6,178,354 B1 | 1/2001 | Gibson | |
| 6,183,468 B1 | 2/2001 | Swanson et al. | |
| 6,235,022 B1 | 5/2001 | Hallock et al. | |
| 6,283,959 B1 | 9/2001 | Lalonde et al. | |
| 6,290,697 B1 | 9/2001 | Tu et al. | |
| 6,292,695 B1 | 9/2001 | Webster, Jr. et al. | |
| 6,381,499 B1 | 4/2002 | Taylor et al. | |
| 6,425,877 B1 | 7/2002 | Edwards | |
| 6,428,537 B1 | 8/2002 | Swanson et al. | |
| 6,451,011 B2 | 9/2002 | Tu et al. | |
| 6,491,710 B2 | 12/2002 | Satake | |
| 6,494,880 B1 | 12/2002 | Swanson et al. | |
| 6,496,737 B2 | 12/2002 | Rudie et al. | |
| 6,511,478 B1 | 1/2003 | Burnside et al. | |
| 6,514,249 B1 | 2/2003 | Maguire et al. | |
| 6,542,781 B1 | 4/2003 | Koblish et al. | |
| 6,551,274 B2 | 4/2003 | Heiner | |
| 6,564,096 B2 | 5/2003 | Mest | |
| 6,575,932 B1 | 6/2003 | O'Brien et al. | |
| 6,582,423 B1 | 6/2003 | Thapliyal et al. | |
| 6,585,638 B1 | 7/2003 | Yamamoto | |
| 6,589,238 B2 | 7/2003 | Edwards et al. | |
| 6,623,504 B2 * | 9/2003 | Vrba .................. | A61M 25/008 |
| | | | 606/192 |
| 6,623,736 B2 | 9/2003 | Tobinick | |
| 6,638,278 B2 | 10/2003 | Falwell et al. | |
| 6,648,879 B2 | 11/2003 | Lafontaine | |
| 6,666,858 B2 | 12/2003 | Joye et al. | |
| 6,666,862 B2 | 12/2003 | Jain et al. | |
| 6,676,675 B2 | 1/2004 | Mallapragada et al. | |
| 6,690,971 B2 | 2/2004 | Schauerte et al. | |
| 6,699,242 B2 | 3/2004 | Heggeness | |
| 6,728,563 B2 | 4/2004 | Rashidi | |
| 6,730,078 B2 | 5/2004 | Simpson et al. | |
| 6,745,080 B2 | 6/2004 | Koblish | |
| 6,796,979 B2 | 9/2004 | Lentz | |
| 6,832,114 B1 | 12/2004 | Whitehurst | |
| 6,837,885 B2 * | 1/2005 | Koblish ............. | A61B 18/1492 |
| | | | 606/41 |
| 6,845,267 B2 | 1/2005 | Harrison | |
| 6,878,273 B2 | 4/2005 | Kawaguchi | |
| 6,885,888 B2 | 4/2005 | Rezai | |
| 6,887,236 B2 | 5/2005 | Gilboa | |
| 6,893,433 B2 | 5/2005 | Lentz | |
| 6,926,669 B1 | 8/2005 | Stewart et al. | |
| 6,936,047 B2 | 8/2005 | Nasab et al. | |
| 6,937,896 B1 | 8/2005 | Kroll | |
| 6,952,615 B2 | 10/2005 | Satake | |
| 6,955,675 B2 | 10/2005 | Jain | |
| 6,972,015 B2 | 12/2005 | Joye et al. | |
| 6,972,016 B2 | 12/2005 | Hill, III et al. | |
| 6,978,174 B2 | 12/2005 | Gelfand et al. | |
| 7,004,961 B2 | 2/2006 | Wong et al. | |
| 7,013,170 B2 | 3/2006 | Bowe | |
| 7,037,269 B2 | 5/2006 | Nix et al. | |
| 7,048,716 B1 | 5/2006 | Kucharczyk et al. | |
| 7,054,689 B1 | 5/2006 | Whitehurst et al. | |
| 7,058,447 B2 | 6/2006 | Hill et al. | |
| 7,089,063 B2 | 8/2006 | Lesh et al. | |
| 7,101,368 B2 | 9/2006 | Lafontaine | |
| 7,112,198 B2 | 9/2006 | Satake | |
| 7,144,407 B1 | 12/2006 | Lasersohn | |
| 7,149,574 B2 | 12/2006 | Yun et al. | |
| 7,150,745 B2 | 12/2006 | Stern et al. | |
| 7,155,278 B2 | 12/2006 | King et al. | |
| 7,155,284 B1 | 12/2006 | Whitehurst et al. | |
| 7,160,292 B2 * | 1/2007 | Moorman .......... | A61B 18/1815 |
| | | | 606/41 |
| 7,162,303 B2 | 1/2007 | Levin et al. | |
| 7,184,828 B2 | 2/2007 | Hill et al. | |
| 7,195,625 B2 | 3/2007 | Lentz | |
| 7,195,629 B2 | 3/2007 | Behl et al. | |
| 7,220,257 B1 | 5/2007 | Lafontaine | |
| 7,277,757 B2 | 10/2007 | Casavant et al. | |
| 7,288,089 B2 | 10/2007 | Yon et al. | |
| 7,309,310 B2 | 12/2007 | Milbocker | |
| 7,322,973 B2 | 1/2008 | Nahon | |
| 7,340,306 B2 | 3/2008 | Barrett et al. | |
| 7,363,076 B2 | 4/2008 | Yun et al. | |
| 7,371,231 B2 | 5/2008 | Rioux et al. | |
| 7,373,204 B2 | 5/2008 | Gelfand et al. | |
| 7,387,628 B1 | 6/2008 | Behl et al. | |
| 7,416,549 B2 | 8/2008 | Young et al. | |
| 7,419,487 B2 | 9/2008 | Johnson et al. | |
| 7,477,944 B1 | 1/2009 | Whitehurst et al. | |
| 7,477,945 B2 | 1/2009 | Rezai et al. | |
| 7,494,661 B2 | 2/2009 | Sanders | |
| 7,510,536 B2 | 3/2009 | Foley et al. | |
| 7,517,349 B2 | 4/2009 | Truckai et al. | |
| 7,524,318 B2 | 4/2009 | Young et al. | |
| 7,529,582 B1 | 5/2009 | DiLorenzo | |
| 7,556,628 B2 | 7/2009 | Utley et al. | |

(56) References Cited

U.S. PATENT DOCUMENTS

| | | |
|---|---|---|
| 7,591,816 B2 | 9/2009 | Wang et al. |
| 7,599,736 B2 | 10/2009 | DiLorenzo |
| 7,599,737 B2 | 10/2009 | Yomtov et al. |
| 7,617,005 B2 | 11/2009 | Demarais et al. |
| 7,620,451 B2 | 11/2009 | Demarais et al. |
| 7,620,454 B2 | 11/2009 | Dinsmoor et al. |
| 7,630,760 B2 | 12/2009 | Libbus |
| 7,647,115 B2 | 1/2010 | Levin et al. |
| 7,653,438 B2 | 1/2010 | Deem et al. |
| 7,653,440 B1 | 1/2010 | Bornzin et al. |
| 7,655,006 B2 | 2/2010 | Sauvageau et al. |
| 7,660,631 B2 | 2/2010 | Whitehurst et al. |
| 7,670,337 B2 | 3/2010 | Young |
| 7,689,276 B2 | 3/2010 | Dobak |
| 7,689,277 B2 | 3/2010 | Dobak, III |
| 7,702,386 B2 | 4/2010 | Dobak et al. |
| 7,706,875 B2 | 4/2010 | Buras et al. |
| 7,717,948 B2 | 5/2010 | Demarais et al. |
| 7,727,228 B2 | 6/2010 | Abboud et al. |
| 7,738,952 B2 | 6/2010 | Yun et al. |
| 7,756,583 B2 | 7/2010 | Demarais et al. |
| 7,758,623 B2 | 7/2010 | Dzeng et al. |
| 7,765,007 B2 | 7/2010 | Martino et al. |
| 7,769,442 B2 | 8/2010 | Shafer |
| 7,769,469 B2 | 8/2010 | Carr et al. |
| 7,769,470 B1 | 8/2010 | Rezai et al. |
| 7,778,704 B2 | 8/2010 | Rezai |
| 7,797,050 B2 | 9/2010 | Libbus et al. |
| 7,819,826 B2 | 10/2010 | Diederich |
| 7,819,870 B2 | 10/2010 | Thao et al. |
| 7,831,308 B2 | 11/2010 | Rezai et al. |
| 7,850,685 B2 | 12/2010 | Kunis et al. |
| 7,853,333 B2 | 12/2010 | Demarais |
| 7,856,273 B2 | 12/2010 | Maschino et al. |
| 7,862,563 B1 | 1/2011 | Cosman et al. |
| 7,865,237 B2 | 1/2011 | Machado et al. |
| 7,873,417 B2 | 1/2011 | Demarais et al. |
| 7,877,146 B2 | 1/2011 | Rezai |
| 7,881,784 B2 | 2/2011 | Pasricha et al. |
| 7,904,175 B2 | 3/2011 | Scott et al. |
| 7,917,230 B2 | 3/2011 | Bly |
| 7,925,351 B2 | 4/2011 | Khawaled et al. |
| 7,931,647 B2 * | 4/2011 | Wizeman ............... A61B 18/14 607/42 |
| 7,937,143 B2 | 5/2011 | Demarais et al. |
| 7,937,144 B2 | 5/2011 | Dobak |
| 7,937,145 B2 | 5/2011 | Dobak |
| 7,938,828 B2 | 5/2011 | Koblish |
| 7,963,287 B2 | 6/2011 | Lanphere et al. |
| 7,991,474 B2 | 8/2011 | Aldrich et al. |
| 8,000,764 B2 | 8/2011 | Rashidi |
| 8,010,199 B2 | 8/2011 | Sunagawa et al. |
| 8,021,361 B2 | 9/2011 | Paul et al. |
| 8,021,384 B2 | 9/2011 | Weiss et al. |
| 8,042,251 B2 | 10/2011 | Asmus et al. |
| 8,043,289 B2 | 10/2011 | Behl et al. |
| 8,043,351 B2 | 10/2011 | Yon et al. |
| RE42,961 E | 11/2011 | Rahme |
| 8,052,672 B2 | 11/2011 | Laufer et al. |
| 8,060,209 B2 | 11/2011 | Jaax et al. |
| 8,066,702 B2 | 11/2011 | Rittman, III |
| 8,075,498 B2 | 12/2011 | Leo et al. |
| 8,095,218 B2 | 1/2012 | Gross et al. |
| 8,116,883 B2 | 2/2012 | Williams et al. |
| 8,123,741 B2 | 2/2012 | Marrouche et al. |
| 8,123,742 B2 | 2/2012 | Berger |
| 8,123,789 B2 | 2/2012 | Khanna |
| 8,128,617 B2 | 3/2012 | Bencini et al. |
| 8,131,362 B2 | 3/2012 | Moffitt et al. |
| 8,131,371 B2 | 3/2012 | Demarais et al. |
| 8,131,372 B2 | 3/2012 | Levin et al. |
| 8,137,342 B2 | 3/2012 | Crossman |
| 8,140,170 B2 | 3/2012 | Rezai et al. |
| 8,145,299 B2 | 3/2012 | Dobak, III |
| 8,145,316 B2 | 3/2012 | Deem et al. |
| 8,145,317 B2 | 3/2012 | Demarais et al. |
| 8,150,518 B2 | 4/2012 | Levin et al. |
| 8,150,519 B2 | 4/2012 | Demarais et al. |
| 8,150,520 B2 | 4/2012 | Demarais et al. |
| 8,155,744 B2 | 4/2012 | Rezai |
| 8,160,690 B2 | 4/2012 | Wilfley et al. |
| 8,162,935 B2 | 4/2012 | Paul et al. |
| 8,172,693 B1 | 5/2012 | Guerzini et al. |
| 8,175,711 B2 | 5/2012 | Demarais et al. |
| 8,182,433 B2 | 5/2012 | Leo et al. |
| 8,197,409 B2 | 6/2012 | Foley et al. |
| 8,207,138 B2 | 6/2012 | Thakker et al. |
| 8,211,017 B2 | 7/2012 | Foley et al. |
| 8,211,102 B2 | 7/2012 | Paul et al. |
| 8,216,228 B2 | 7/2012 | Mateos et al. |
| 8,216,231 B2 | 7/2012 | Behl et al. |
| 8,219,189 B2 | 7/2012 | Knoblich |
| 8,224,416 B2 | 7/2012 | De La Rama et al. |
| 8,226,602 B2 | 7/2012 | Quijana et al. |
| 8,226,648 B2 | 7/2012 | Paul et al. |
| 8,229,564 B2 | 7/2012 | Rezai |
| 8,257,413 B2 | 9/2012 | Danek et al. |
| 8,265,745 B2 | 9/2012 | Hauck et al. |
| 8,267,926 B2 | 9/2012 | Paul et al. |
| 8,277,398 B2 | 10/2012 | Weng et al. |
| 8,285,374 B2 | 10/2012 | Hamdan |
| 8,295,902 B2 | 10/2012 | Salahieh et al. |
| 8,295,912 B2 | 10/2012 | Gertner |
| 8,295,926 B2 | 10/2012 | Dobak |
| 8,313,482 B2 | 11/2012 | McIntyre et al. |
| 8,317,783 B2 | 11/2012 | Cao et al. |
| 8,321,030 B2 | 11/2012 | Maniak et al. |
| 8,323,274 B2 | 12/2012 | Jakus |
| 8,326,428 B2 | 12/2012 | Wenzel et al. |
| 8,337,492 B2 | 12/2012 | Kunis et al. |
| 8,340,772 B2 | 12/2012 | Vase et al. |
| 8,343,031 B2 | 1/2013 | Gertner |
| 8,347,891 B2 | 1/2013 | Demarais et al. |
| 8,348,884 B2 | 1/2013 | Hildebrand et al. |
| 8,352,029 B2 | 1/2013 | Ternes et al. |
| 8,364,237 B2 | 1/2013 | Stone et al. |
| 8,364,285 B2 | 1/2013 | Rezai |
| 8,369,943 B2 | 2/2013 | Shuros et al. |
| 8,372,009 B2 | 2/2013 | Emery et al. |
| 8,374,674 B2 | 2/2013 | Gertner |
| 8,386,053 B2 | 2/2013 | Kornet |
| 8,391,970 B2 | 3/2013 | Tracey et al. |
| 8,396,548 B2 | 3/2013 | Perry et al. |
| 8,401,641 B2 | 3/2013 | Peters et al. |
| 8,401,667 B2 | 3/2013 | Gustus et al. |
| 8,403,925 B2 | 3/2013 | Miller et al. |
| 8,406,866 B2 | 3/2013 | Deno et al. |
| 8,409,195 B2 | 4/2013 | Young |
| 8,410,140 B2 | 4/2013 | Brummett |
| 8,412,350 B2 | 4/2013 | Bly |
| 8,414,508 B2 | 4/2013 | Thapliyal et al. |
| 8,417,331 B2 | 4/2013 | Pasricha et al. |
| 8,417,354 B2 | 4/2013 | Zhang et al. |
| 8,435,232 B2 | 5/2013 | Aeby et al. |
| 8,439,909 B2 | 5/2013 | Wang et al. |
| 8,444,640 B2 | 5/2013 | Demarais et al. |
| 8,447,394 B2 | 5/2013 | Libbus et al. |
| 8,449,535 B2 | 5/2013 | Deno et al. |
| 8,454,594 B2 | 6/2013 | Demarais et al. |
| 8,463,376 B2 | 6/2013 | Curtis |
| 8,465,486 B2 | 6/2013 | Danek et al. |
| 8,469,904 B2 | 6/2013 | Gertner |
| 8,475,449 B2 | 7/2013 | Werneth et al. |
| 8,483,830 B2 | 7/2013 | Tweden et al. |
| 8,489,184 B2 | 7/2013 | Wilfley et al. |
| 8,492,442 B2 | 7/2013 | Beppu et al. |
| 8,504,132 B2 | 8/2013 | Friedman et al. |
| 8,504,147 B2 | 8/2013 | Deem et al. |
| 8,504,161 B1 | 8/2013 | Kornet et al. |
| 8,512,262 B2 | 8/2013 | Gertner |
| 8,512,335 B2 | 8/2013 | Cheng et al. |
| 8,517,962 B2 | 8/2013 | Gertner et al. |
| 8,521,291 B1 | 8/2013 | Cholette et al. |
| 8,536,667 B2 | 9/2013 | De Graff et al. |

(56) References Cited

U.S. PATENT DOCUMENTS

| | | |
|---|---|---|
| 8,560,072 B2 | 10/2013 | Caparso et al. |
| 8,568,399 B2 | 10/2013 | Azamian et al. |
| 8,577,447 B2 | 11/2013 | Tegg et al. |
| 8,579,891 B2 | 11/2013 | Coe et al. |
| 8,583,229 B2 | 11/2013 | Rezai et al. |
| 8,585,696 B2 | 11/2013 | Young |
| 8,588,886 B2 | 11/2013 | De la Rama et al. |
| 8,609,082 B2 | 12/2013 | Ben-David et al. |
| 8,612,022 B1 | 12/2013 | Morero et al. |
| 8,617,156 B2 | 12/2013 | Werneth et al. |
| 8,634,930 B2 | 1/2014 | Dalal et al. |
| 8,641,704 B2 | 2/2014 | Werneth et al. |
| 8,641,705 B2 | 2/2014 | Leo et al. |
| 8,641,711 B2 | 2/2014 | Kelly et al. |
| 8,652,129 B2 | 2/2014 | Wu et al. |
| 8,672,930 B2 | 3/2014 | Wittenberger |
| 8,672,936 B2 | 3/2014 | Thao et al. |
| 8,676,309 B2 | 3/2014 | Deem et al. |
| 8,676,322 B2 | 3/2014 | Whitehurst et al. |
| 8,679,109 B2 | 3/2014 | Paul |
| 8,700,161 B2 | 4/2014 | Harel et al. |
| 8,702,619 B2 | 4/2014 | Wang |
| 8,712,550 B2 | 4/2014 | Grunewald |
| 8,715,209 B2 | 5/2014 | Gertner |
| 8,718,764 B2 | 5/2014 | Stahmann |
| 8,721,637 B2 | 5/2014 | Zarins et al. |
| 8,728,068 B2 | 5/2014 | Nye et al. |
| 8,728,069 B2 | 5/2014 | Azamian et al. |
| 8,728,070 B2 | 5/2014 | Azamian et al. |
| 8,728,075 B2 | 5/2014 | Wu et al. |
| 8,728,077 B2 | 5/2014 | Kunis et al. |
| 8,731,677 B2 | 5/2014 | Pastore et al. |
| 8,738,127 B1 | 5/2014 | Lebovitz et al. |
| 8,740,896 B2 | 6/2014 | Zarins et al. |
| 8,755,907 B2 | 6/2014 | Kieval et al. |
| 8,758,334 B2 | 6/2014 | Coe et al. |
| 8,764,742 B2 | 7/2014 | Pappone et al. |
| 8,771,267 B2 | 7/2014 | Kunis et al. |
| 8,774,942 B2 | 7/2014 | Lund et al. |
| 8,777,943 B2 | 7/2014 | Mayse et al. |
| 8,790,281 B2 | 7/2014 | Diederich et al. |
| 8,792,986 B2 | 7/2014 | Cigaina |
| 8,805,466 B2 | 8/2014 | Salahieh et al. |
| 8,808,345 B2 | 8/2014 | Clark et al. |
| 8,818,501 B2 | 8/2014 | Machado et al. |
| 8,818,514 B2 | 8/2014 | Zarins et al. |
| 8,819,928 B2 | 9/2014 | Nix et al. |
| 8,834,464 B2 | 9/2014 | Stewart et al. |
| 8,838,231 B2 | 9/2014 | Dobak |
| 8,838,239 B2 | 9/2014 | Libbus et al. |
| 8,845,629 B2 | 9/2014 | Demarais et al. |
| 8,845,707 B2 | 9/2014 | Lafontaine |
| 8,855,778 B2 | 10/2014 | Rezai |
| 8,868,188 B2 | 10/2014 | Hershey |
| 8,870,773 B2 | 10/2014 | Narouze |
| 8,874,216 B2 | 10/2014 | Kim et al. |
| 8,876,815 B2 | 11/2014 | Coe et al. |
| 8,880,185 B2 | 11/2014 | Hastings et al. |
| 8,888,699 B2 | 11/2014 | Buschman et al. |
| 8,888,773 B2 | 11/2014 | Chang et al. |
| 8,894,589 B2 | 11/2014 | Leo et al. |
| 8,894,639 B2 | 11/2014 | Azamian et al. |
| 8,894,642 B2 | 11/2014 | Gibson et al. |
| 8,897,882 B2 | 11/2014 | Nakatomi et al. |
| 8,903,501 B2 | 12/2014 | Perryman |
| 8,909,316 B2 | 12/2014 | Ng |
| 8,911,485 B2 | 12/2014 | Brian, III et al. |
| 8,920,414 B2 | 12/2014 | Stone et al. |
| 8,929,990 B2 | 1/2015 | Moffitt et al. |
| 8,934,968 B2 | 1/2015 | Whitehurst et al. |
| 8,934,978 B2 | 1/2015 | Deem et al. |
| 8,939,970 B2 | 1/2015 | Stone et al. |
| 8,940,010 B2 | 1/2015 | Lee et al. |
| 8,945,110 B2 | 2/2015 | Fish et al. |
| 8,951,251 B2 | 2/2015 | Willard |
| 8,951,296 B2 | 2/2015 | Melder et al. |
| 8,956,352 B2 | 2/2015 | Mauch et al. |
| 8,961,436 B2 | 2/2015 | Leo et al. |
| 8,974,451 B2 | 3/2015 | Smith |
| 8,975,233 B2 | 3/2015 | Stein et al. |
| 8,979,839 B2 | 3/2015 | De la Rama et al. |
| 8,979,841 B2 | 3/2015 | Kunis et al. |
| 8,983,601 B2 | 3/2015 | Fukamachi et al. |
| 8,983,609 B2 | 3/2015 | Rezai et al. |
| 8,986,294 B2 | 3/2015 | Demarais et al. |
| 8,989,862 B2 | 3/2015 | Rezai et al. |
| 8,996,091 B2 | 3/2015 | De la Rama et al. |
| 9,002,446 B2 | 4/2015 | Wenzel et al. |
| 9,005,190 B2 | 4/2015 | Azamian et al. |
| 9,005,191 B2 | 4/2015 | Azamian et al. |
| 9,011,422 B2 | 4/2015 | Azamian et al. |
| 9,014,821 B2 | 4/2015 | Wang |
| 9,023,010 B2 | 5/2015 | Chiu et al. |
| 9,023,023 B2 | 5/2015 | McKay et al. |
| 9,023,037 B2 | 5/2015 | Zarins et al. |
| 9,028,391 B2 | 5/2015 | Gnanashanmugam et al. |
| 9,028,470 B2 | 5/2015 | Marrouche et al. |
| 9,028,472 B2 | 5/2015 | Mathur et al. |
| 9,033,966 B2 | 5/2015 | McKay |
| 9,033,969 B2 | 5/2015 | Azamian et al. |
| 9,037,244 B2 | 5/2015 | Sharma |
| 9,037,259 B2 | 5/2015 | Mathur |
| 9,039,700 B2 | 5/2015 | Kirschenman |
| 9,044,245 B2 | 6/2015 | Condie et al. |
| 9,050,106 B2 | 6/2015 | Hill et al. |
| 9,055,950 B2 | 6/2015 | Beani et al. |
| 9,060,755 B2 | 6/2015 | Buckley et al. |
| 9,060,756 B2 | 6/2015 | Bencini et al. |
| 9,060,761 B2 | 6/2015 | Hastings et al. |
| 9,060,784 B2 | 6/2015 | Coe et al. |
| 9,061,153 B1 | 6/2015 | Lebovitz |
| 9,066,713 B2 | 6/2015 | Turovskiy |
| 9,066,725 B2 | 6/2015 | Christian |
| 9,066,726 B2 | 6/2015 | Srivastava |
| 9,067,070 B2 | 6/2015 | Connor |
| 9,072,902 B2 | 7/2015 | Mathur et al. |
| 9,084,609 B2 | 7/2015 | Smith |
| 9,084,610 B2 | 7/2015 | Goshgarian et al. |
| 9,084,611 B2 | 7/2015 | Amirana et al. |
| 9,089,341 B2 | 7/2015 | Chomas et al. |
| 9,089,350 B2 | 7/2015 | Willard |
| 9,089,541 B2 | 7/2015 | Azamian et al. |
| 9,089,542 B2 | 7/2015 | Azamian et al. |
| 9,095,719 B2 | 8/2015 | Farazi |
| 9,101,365 B2 | 8/2015 | Highsmith |
| 9,114,123 B2 | 8/2015 | Azamian et al. |
| 9,114,124 B2 | 8/2015 | Azamian et al. |
| 9,119,600 B2 | 9/2015 | Richardson et al. |
| 9,125,666 B2 | 9/2015 | Steinke et al. |
| 9,126,048 B2 | 9/2015 | Ransbury et al. |
| 9,131,975 B2 | 9/2015 | McKay |
| 9,131,982 B2 | 9/2015 | VanScoy et al. |
| 9,138,292 B2 | 9/2015 | Chang et al. |
| 9,138,575 B2 | 9/2015 | Osypka |
| 9,144,678 B2 | 9/2015 | Marsh et al. |
| 9,149,328 B2 | 10/2015 | Dimmer et al. |
| 9,149,329 B2 | 10/2015 | Azamian et al. |
| 9,155,589 B2 | 10/2015 | Jenson |
| 9,162,046 B2 | 10/2015 | Hill et al. |
| 9,162,073 B2 | 10/2015 | Rezai et al. |
| 9,168,093 B2 | 10/2015 | Mihalik et al. |
| 9,168,094 B2 | 10/2015 | Lee et al. |
| 9,173,586 B2 | 11/2015 | Deno et al. |
| 9,173,696 B2 | 11/2015 | Schauer et al. |
| 9,174,050 B2 | 11/2015 | Mathur et al. |
| 9,179,974 B2 | 11/2015 | Ku et al. |
| 9,186,060 B2 | 11/2015 | De Graff et al. |
| 9,186,209 B2 | 11/2015 | Weber et al. |
| 9,186,210 B2 | 11/2015 | Jenson |
| 9,186,211 B2 | 11/2015 | Mathur et al. |
| 9,192,435 B2 | 11/2015 | Jenson |
| 9,192,790 B2 | 11/2015 | Hastings et al. |
| 9,204,929 B2 | 12/2015 | Solis |
| 9,216,289 B2 | 12/2015 | Libbus et al. |

(56) References Cited

U.S. PATENT DOCUMENTS

| | | |
|---|---|---|
| 9,220,433 B2 | 12/2015 | Ditter et al. |
| 9,220,558 B2 | 12/2015 | Willard |
| 9,220,561 B2 | 12/2015 | Crow et al. |
| 9,220,899 B2 | 12/2015 | Cattaneo et al. |
| 9,237,920 B2 | 1/2016 | Leo et al. |
| 9,241,754 B2 | 1/2016 | McKay |
| 9,254,163 B2 | 2/2016 | Paul et al. |
| 9,259,568 B2 | 2/2016 | Zhao et al. |
| 9,265,563 B2 | 2/2016 | Racz et al. |
| 9,265,575 B2 | 2/2016 | Coe et al. |
| 9,271,782 B2 | 3/2016 | Paul et al. |
| 9,272,132 B2 | 3/2016 | Laufer et al. |
| 9,277,955 B2 | 3/2016 | Herscher et al. |
| 9,283,026 B2 | 3/2016 | Paul et al. |
| 9,283,035 B2 | 3/2016 | Lanphere |
| 9,283,374 B2 | 3/2016 | Hollett et al. |
| 9,289,255 B2 | 3/2016 | Deem et al. |
| 9,314,208 B1 | 4/2016 | Altmann et al. |
| 9,314,300 B2 | 4/2016 | Nabutovsky et al. |
| 9,314,644 B2 | 4/2016 | Wu et al. |
| 9,320,565 B2 | 4/2016 | Schneider et al. |
| 9,326,816 B2 | 5/2016 | Srivastava |
| 9,327,123 B2 | 5/2016 | Yamasaki et al. |
| 9,333,031 B2 | 5/2016 | Salahieh et al. |
| 9,333,033 B2 | 5/2016 | Gliner |
| 9,333,113 B2 | 5/2016 | Abunassar et al. |
| 9,339,325 B2 | 5/2016 | Miller et al. |
| 9,339,331 B2 | 5/2016 | Tegg et al. |
| 9,345,538 B2 | 5/2016 | Deem et al. |
| 9,345,540 B2 | 5/2016 | Maillin et al. |
| 9,345,880 B1 | 5/2016 | DiLorenzo |
| 9,358,020 B2 | 6/2016 | Smith |
| 9,358,076 B2 | 6/2016 | Moll et al. |
| 9,358,401 B2 | 6/2016 | Gertner et al. |
| 9,364,284 B2 | 6/2016 | Groff et al. |
| 9,364,668 B2 | 6/2016 | Marsh et al. |
| 9,364,671 B2 | 6/2016 | Pless et al. |
| 9,375,154 B2 | 6/2016 | Wang |
| 9,381,063 B2 | 7/2016 | Gang et al. |
| 9,386,927 B2 | 7/2016 | Kaiser |
| 9,386,990 B2 | 7/2016 | Muir et al. |
| 9,393,068 B1 | 7/2016 | Leo et al. |
| 9,402,684 B2 | 8/2016 | Mathur et al. |
| 9,403,007 B2 | 8/2016 | Mokelke et al. |
| 9,408,661 B2 | 8/2016 | Haverkost |
| 9,408,663 B2 | 8/2016 | Hall et al. |
| 9,414,885 B2 | 8/2016 | Willard |
| 9,427,579 B2 | 8/2016 | Fain et al. |
| 9,433,428 B2 | 9/2016 | Hakala et al. |
| 9,439,598 B2 | 9/2016 | Shimada et al. |
| 9,446,240 B2 | 9/2016 | Masson et al. |
| 9,452,017 B2 | 9/2016 | Chang et al. |
| 9,463,062 B2 | 10/2016 | Smith et al. |
| 9,463,065 B2 | 10/2016 | Sugimoto et al. |
| 9,463,066 B2 | 10/2016 | Deem et al. |
| 9,504,518 B2 | 11/2016 | Condie et al. |
| 9,510,777 B2 | 12/2016 | Hezi-Yamit et al. |
| 9,510,901 B2 | 12/2016 | Steinke et al. |
| 9,511,228 B2 | 12/2016 | Amurthur et al. |
| 9,522,036 B2 | 12/2016 | Panescu et al. |
| 9,526,572 B2 | 12/2016 | Kunis |
| 9,526,893 B2 | 12/2016 | Averina et al. |
| 9,545,216 B2 | 1/2017 | D'Angelo et al. |
| 9,554,848 B2 | 1/2017 | Stewart et al. |
| 9,554,850 B2 | 1/2017 | Lee et al. |
| 9,555,020 B2 | 1/2017 | Pasricha et al. |
| 9,561,370 B2 | 2/2017 | Rezai et al. |
| 9,566,114 B2 | 2/2017 | Mathur |
| 9,572,982 B2 | 2/2017 | Burnes et al. |
| 9,579,149 B2 | 2/2017 | Kelly et al. |
| 9,579,507 B2 | 2/2017 | Cakmak |
| 9,585,587 B2 | 3/2017 | Roy et al. |
| 9,586,046 B2 | 3/2017 | Knudson et al. |
| 9,592,386 B2 | 3/2017 | Mathur et al. |
| 9,597,148 B2 | 3/2017 | Olson |
| 9,616,226 B2 | 4/2017 | Lockwood et al. |
| 9,616,228 B2 | 4/2017 | Shuros et al. |
| 9,616,231 B2 | 4/2017 | Tweden et al. |
| 9,629,675 B2 | 4/2017 | Kleshinski et al. |
| 9,649,156 B2 | 5/2017 | Jenson et al. |
| 9,655,677 B2 | 5/2017 | Salahieh et al. |
| 9,656,080 B2 | 5/2017 | Chiu et al. |
| 9,662,171 B2 | 5/2017 | Dimmer et al. |
| 9,662,490 B2 | 5/2017 | Tracey et al. |
| 9,668,811 B2 | 6/2017 | Sogard et al. |
| 9,687,166 B2 | 6/2017 | Subramaniam et al. |
| 9,693,821 B2 | 7/2017 | Hanson et al. |
| 9,700,372 B2 | 7/2017 | Schaer |
| 9,707,000 B2 | 7/2017 | Hoke et al. |
| 9,707,391 B2 | 7/2017 | Ahmed |
| 9,713,730 B2 | 7/2017 | Mathur et al. |
| 9,717,557 B2 | 8/2017 | Salahieh et al. |
| 9,717,559 B2 | 8/2017 | Ditter et al. |
| 9,723,998 B2 | 8/2017 | Wang |
| 9,743,984 B1 | 8/2017 | Curley et al. |
| 9,750,560 B2 | 9/2017 | Ballakur et al. |
| 9,750,568 B2 | 9/2017 | Sobotka |
| 9,757,193 B2 | 9/2017 | Zarins et al. |
| 9,789,275 B2 | 10/2017 | Iyer et al. |
| 9,795,442 B2 | 10/2017 | Salahieh et al. |
| 9,795,780 B2 | 10/2017 | Serna et al. |
| 9,801,557 B2 | 10/2017 | Ghaffari et al. |
| 9,808,303 B2 | 11/2017 | Ryba et al. |
| 9,808,616 B2 | 11/2017 | Cederna et al. |
| 9,820,799 B2 | 11/2017 | Serna et al. |
| 9,821,003 B2 | 11/2017 | Yun |
| 9,827,041 B2 | 11/2017 | Zarins et al. |
| 9,833,283 B2 | 12/2017 | Hanson et al. |
| 9,833,623 B2 | 12/2017 | Gnanashanmugam et al. |
| 9,844,405 B2 | 12/2017 | Weber et al. |
| 9,844,668 B2 | 12/2017 | Ahmed |
| 9,848,795 B2 | 12/2017 | Zarins et al. |
| 9,848,948 B2 | 12/2017 | Mareckim et al. |
| 9,855,096 B2 | 1/2018 | Chang et al. |
| 9,855,317 B2 | 1/2018 | Bright |
| 9,861,504 B2 | 1/2018 | Abunassar et al. |
| 9,861,547 B2 | 1/2018 | Crunick et al. |
| 9,872,717 B2 | 1/2018 | Bencini et al. |
| 9,872,985 B2 | 1/2018 | Butera et al. |
| 9,883,909 B2 | 2/2018 | Brennan |
| 9,895,543 B2 | 2/2018 | Lian et al. |
| 9,918,822 B2 | 3/2018 | Abunassar et al. |
| 9,919,144 B2 | 3/2018 | Meyer |
| 9,925,001 B2 | 3/2018 | Willard et al. |
| 9,943,354 B2 | 4/2018 | Yamit et al. |
| 9,943,365 B2 | 4/2018 | Haverkost et al. |
| 9,943,666 B2 | 4/2018 | Warnking |
| 9,950,099 B2 | 4/2018 | Romero-Ortega et al. |
| 9,950,164 B2 | 4/2018 | Lipani |
| 9,955,892 B2 | 5/2018 | Arora et al. |
| 9,956,033 B2 | 5/2018 | Squire et al. |
| 9,956,034 B2 | 5/2018 | Toth et al. |
| 9,974,477 B2 | 5/2018 | Cholette et al. |
| 9,999,461 B2 | 6/2018 | Azamian et al. |
| 9,999,532 B2 | 6/2018 | Mische |
| 10,004,557 B2 | 6/2018 | Gross |
| 10,010,364 B2 | 7/2018 | Harrington |
| 10,022,182 B2 | 7/2018 | Willard et al. |
| 10,022,516 B2 | 7/2018 | Papay |
| 10,052,495 B2 | 8/2018 | Ben-Haim |
| 10,058,372 B1 | 8/2018 | Shadduck |
| 10,064,674 B2 | 9/2018 | Azamian et al. |
| 10,065,037 B2 | 9/2018 | Nelson et al. |
| 10,070,911 B2 | 9/2018 | Azamian et al. |
| 10,076,384 B2 | 9/2018 | Kasprzyk et al. |
| 10,085,799 B2 | 10/2018 | Smith |
| 10,092,352 B2 | 10/2018 | Rudie |
| 10,092,756 B2 | 10/2018 | Bonnet et al. |
| 10,118,004 B2 | 11/2018 | Fischell et al. |
| 10,123,896 B2 | 11/2018 | Farrugia et al. |
| 10,124,173 B2 | 11/2018 | Bonnet et al. |
| 10,179,029 B2 | 1/2019 | Rudie et al. |
| 10,194,979 B1 | 2/2019 | Brar et al. |
| 10,194,980 B1 | 2/2019 | Brar et al. |

(56) References Cited

U.S. PATENT DOCUMENTS

| | | |
|---|---|---|
| 10,195,467 B2 | 2/2019 | Tran et al. |
| 10,201,705 B2 | 2/2019 | Bharmi et al. |
| 10,201,706 B2 | 2/2019 | Schwab et al. |
| 10,207,110 B1 | 2/2019 | Gelfand et al. |
| 10,231,778 B2 | 3/2019 | Highsmith et al. |
| 10,232,180 B2 | 3/2019 | Kramer et al. |
| 10,238,875 B2 | 3/2019 | Masiach |
| 10,265,122 B2 | 4/2019 | Wang et al. |
| 10,271,898 B2 | 4/2019 | Cao et al. |
| 10,272,269 B2 | 4/2019 | Garrison et al. |
| 10,285,751 B2 | 5/2019 | Highsmith et al. |
| 10,286,191 B2 | 5/2019 | Wang et al. |
| 10,292,610 B2 | 5/2019 | Srivastava |
| 10,307,324 B2 | 6/2019 | Osorio |
| 10,321,946 B2 | 6/2019 | Horn et al. |
| 10,328,258 B2 | 6/2019 | Gittard et al. |
| 10,335,280 B2 | 7/2019 | Keogh et al. |
| 10,342,592 B2 | 7/2019 | Tunev et al. |
| 10,350,005 B2 | 7/2019 | Mathur et al. |
| 10,363,362 B2 | 7/2019 | Osorio |
| 10,368,944 B2 | 8/2019 | Schaer |
| 10,376,310 B2 | 8/2019 | Fain et al. |
| 10,376,516 B2 | 8/2019 | Gelfand et al. |
| 10,376,694 B2 | 8/2019 | Sharma |
| 10,383,685 B2 | 8/2019 | Gross et al. |
| 10,390,881 B2 | 8/2019 | Rudie |
| 10,426,956 B2 | 10/2019 | Williamson et al. |
| 10,449,002 B2 | 10/2019 | Wybo |
| 10,456,573 B1 | 10/2019 | Feinstein |
| 10,463,423 B2 | 11/2019 | Sutton et al. |
| 10,463,858 B2 | 11/2019 | Perryman et al. |
| 10,470,837 B2 | 11/2019 | Lin et al. |
| 10,471,257 B2 | 11/2019 | Ahmad et al. |
| 10,478,249 B2 | 11/2019 | Gross et al. |
| 10,478,633 B2 | 11/2019 | Schwarz et al. |
| 10,492,713 B2 | 12/2019 | Haber et al. |
| 10,512,498 B2 | 12/2019 | Saadat |
| 10,512,504 B2 | 12/2019 | Chang et al. |
| 10,517,672 B2 | 12/2019 | Long |
| 10,518,112 B2 | 12/2019 | Gilad |
| 10,524,859 B2 | 1/2020 | Vrba et al. |
| 10,531,913 B2 | 1/2020 | Haverkost |
| 10,537,375 B2 | 1/2020 | Wang |
| 10,537,387 B2 | 1/2020 | Ben Oren et al. |
| 10,543,034 B2 | 1/2020 | Azamian et al. |
| 10,543,037 B2 | 1/2020 | Shah |
| 10,543,039 B2 | 1/2020 | Lindquist et al. |
| 10,561,461 B2 | 2/2020 | Panescu et al. |
| 10,561,846 B2 | 2/2020 | Tracey et al. |
| 10,575,893 B2 | 3/2020 | Mayse |
| 10,583,286 B2 | 3/2020 | Swanson et al. |
| 10,583,295 B2 | 3/2020 | Gupte et al. |
| 10,617,460 B2 | 4/2020 | Azamian et al. |
| 10,646,710 B2 | 5/2020 | Feinstein |
| 10,646,713 B2 | 5/2020 | Hettrick et al. |
| 10,660,703 B2 | 5/2020 | Rizq et al. |
| 10,674,963 B2 | 6/2020 | Toth |
| 10,675,085 B2 | 6/2020 | Clark et al. |
| 10,695,124 B2 | 6/2020 | Groff et al. |
| 10,702,533 B2 | 7/2020 | Yun et al. |
| 10,709,490 B2 | 7/2020 | Turovskiy |
| 10,716,749 B2 | 7/2020 | Yun et al. |
| 10,722,714 B2 | 7/2020 | Thornton et al. |
| 10,722,716 B2 | 7/2020 | Waldhauser et al. |
| 10,729,365 B2 | 8/2020 | Beasley et al. |
| 10,743,933 B2 | 8/2020 | Smith et al. |
| 10,751,536 B1 | 8/2020 | Heit et al. |
| 10,751,539 B2 | 8/2020 | Zitzewitz et al. |
| 10,758,713 B2 | 9/2020 | Wang et al. |
| 10,765,482 B2 | 9/2020 | Hastings |
| 10,772,759 B2 | 9/2020 | Khanna |
| 10,786,295 B2 | 9/2020 | Buelna |
| 10,792,098 B2 | 10/2020 | Ku et al. |
| 10,799,289 B2 | 10/2020 | Alas et al. |
| 10,828,090 B2 | 11/2020 | Haverkost et al. |
| 10,828,460 B2 | 11/2020 | Chang |
| 10,828,491 B2 | 11/2020 | Schepis et al. |
| 10,835,305 B2 | 11/2020 | Sutermeister et al. |
| 10,842,494 B2 | 11/2020 | Agarwal et al. |
| 10,842,556 B1 | 11/2020 | Tandri et al. |
| 10,849,685 B2 | 12/2020 | Denison et al. |
| 10,849,879 B2 | 12/2020 | Seward |
| 10,850,100 B2 | 12/2020 | Cakmak et al. |
| 10,856,926 B2 | 12/2020 | Azamian et al. |
| 10,857,352 B2 | 12/2020 | Ransbury et al. |
| 10,869,997 B2 | 12/2020 | Mayse |
| 10,874,454 B2 | 12/2020 | Chen |
| 10,888,377 B2 | 1/2021 | Ben-Oren et al. |
| 10,905,495 B2 | 2/2021 | Toth et al. |
| 10,933,259 B2 | 3/2021 | Sverdlik et al. |
| 10,952,790 B2 | 3/2021 | Haverkost et al. |
| 10,959,669 B2 | 3/2021 | Neidert et al. |
| 10,960,209 B2 | 3/2021 | Sridhar et al. |
| 10,974,041 B2 | 4/2021 | Chew et al. |
| 10,987,163 B2 | 4/2021 | Pike |
| 11,007,001 B1 | 5/2021 | Carignan et al. |
| 11,007,329 B2 | 5/2021 | Fischell et al. |
| 11,013,459 B2 | 5/2021 | Toth et al. |
| 11,013,549 B2 | 5/2021 | Barman et al. |
| 11,013,938 B2 | 5/2021 | Konofagou et al. |
| 11,040,197 B2 | 6/2021 | Ludwig et al. |
| 11,052,253 B2 | 7/2021 | Cakmak |
| 11,058,482 B2 | 7/2021 | Bae et al. |
| 11,058,484 B2 | 7/2021 | Asirvatham et al. |
| 11,065,046 B2 | 7/2021 | Edidin |
| 11,083,877 B2 | 8/2021 | Seward |
| 11,103,692 B2 | 8/2021 | Cakmak |
| 11,116,561 B2 | 9/2021 | Melder |
| 11,129,673 B2 | 9/2021 | Barry et al. |
| 11,129,674 B2 | 9/2021 | Naga et al. |
| 11,134,998 B2 | 10/2021 | Cross et al. |
| 11,154,351 B2 | 10/2021 | Rothman et al. |
| 11,154,547 B2 | 10/2021 | Bright et al. |
| 11,154,712 B2 | 10/2021 | Sullivan et al. |
| 11,160,975 B2 | 11/2021 | Mercanzini et al. |
| 11,179,195 B2 | 11/2021 | Sobotka |
| 11,179,196 B2 | 11/2021 | Cao et al. |
| 11,185,361 B2 | 11/2021 | Toth et al. |
| 11,185,662 B2 | 11/2021 | Warnking |
| 11,185,699 B2 | 11/2021 | Masson et al. |
| 11,202,671 B2 | 12/2021 | Hanson et al. |
| 11,207,070 B2 | 12/2021 | Berman et al. |
| 11,213,340 B2 | 1/2022 | Su et al. |
| 11,213,345 B2 | 1/2022 | Willard |
| 11,213,674 B2 | 1/2022 | Barman et al. |
| 11,235,154 B2 | 2/2022 | Phillips et al. |
| 11,246,654 B2 | 2/2022 | Weber et al. |
| 11,247,057 B1 | 2/2022 | Gliner |
| 11,304,633 B2 | 4/2022 | Koya et al. |
| 11,305,115 B2 | 4/2022 | Caldwell et al. |
| 11,318,310 B1 | 5/2022 | Bradley |
| 11,318,331 B2 | 5/2022 | Shabtay et al. |
| 11,324,408 B2 | 5/2022 | Wang |
| 11,324,673 B2 | 5/2022 | Velis et al. |
| 11,337,748 B2 | 5/2022 | Wang et al. |
| 11,338,120 B2 | 5/2022 | Yun et al. |
| 11,344,364 B2 | 5/2022 | Herth et al. |
| 11,344,731 B2 | 5/2022 | Toth et al. |
| 11,350,992 B2 | 6/2022 | Pilcher et al. |
| 11,357,447 B2 | 6/2022 | Sverdlik et al. |
| 11,382,515 B2 | 7/2022 | Buelna et al. |
| 11,382,689 B2 | 7/2022 | Wang |
| 11,389,534 B2 | 7/2022 | Yun et al. |
| 11,413,090 B2 | 8/2022 | Iranitalab et al. |
| 11,419,681 B2 | 8/2022 | Coates et al. |
| 11,433,235 B2 | 9/2022 | Narayan et al. |
| 11,433,237 B2 | 9/2022 | Lovett |
| 11,439,809 B2 | 9/2022 | Whipple et al. |
| 11,439,819 B2 | 9/2022 | Imran |
| 11,446,359 B2 | 9/2022 | Bright |
| 11,446,498 B2 | 9/2022 | Schepis et al. |
| 11,446,502 B2 | 9/2022 | Donega et al. |
| 11,457,819 B2 | 10/2022 | Trudel |
| 11,464,971 B2 | 10/2022 | Schepis et al. |

(56) References Cited

U.S. PATENT DOCUMENTS

| | | |
|---|---|---|
| 11,464,976 B2 | 10/2022 | Hunsberger et al. |
| 11,471,208 B2 | 10/2022 | Waldstreicher et al. |
| 11,471,210 B2 | 10/2022 | Pellegrino et al. |
| 11,478,297 B2 | 10/2022 | Viswanadha et al. |
| 11,478,582 B2 | 10/2022 | Toth et al. |
| 11,490,844 B2 | 11/2022 | Imran et al. |
| 11,497,775 B2 | 11/2022 | Lefer et al. |
| 11,497,915 B2 | 11/2022 | Tehrani |
| 11,504,185 B2 | 11/2022 | Iranitalab et al. |
| 11,510,731 B2 | 11/2022 | Puryear et al. |
| 11,515,029 B2 | 11/2022 | Sullivan et al. |
| 11,517,499 B2 | 12/2022 | Spector |
| 11,517,754 B2 | 12/2022 | Sridhar et al. |
| 11,524,159 B2 | 12/2022 | Caban et al. |
| 11,534,611 B2 | 12/2022 | Baldoni et al. |
| 11,534,631 B2 | 12/2022 | Gilad |
| 11,547,480 B2 | 1/2023 | Weiss |
| 11,559,687 B2 | 1/2023 | Goedeke et al. |
| 11,564,616 B2 | 1/2023 | Toth et al. |
| 11,564,743 B1 | 1/2023 | Ben Oren et al. |
| 11,565,113 B2 | 1/2023 | Curtis |
| 11,589,919 B2 | 2/2023 | Long |
| 11,596,468 B2 | 3/2023 | Pellegrino et al. |
| 11,596,469 B2 | 3/2023 | Nair |
| 11,607,176 B2 | 3/2023 | Brockway et al. |
| 11,607,275 B2 | 3/2023 | Brar et al. |
| 11,622,805 B2 | 4/2023 | Salazar et al. |
| 11,623,093 B2 | 4/2023 | Cuchiara et al. |
| 11,633,601 B2 | 4/2023 | Vervoordeldonk et al. |
| 11,638,745 B2 | 5/2023 | Jackson et al. |
| 11,660,474 B2 | 5/2023 | Puleo et al. |
| 11,672,456 B2 | 6/2023 | Dubhashi |
| 11,672,595 B1 | 6/2023 | Melton et al. |
| 11,672,597 B2 | 6/2023 | Tajima et al. |
| 11,673,006 B2 | 6/2023 | Sobotka et al. |
| 11,691,015 B2 | 7/2023 | Minassian et al. |
| 11,701,172 B2 | 7/2023 | Asirvatham et al. |
| 11,712,283 B2 | 8/2023 | Mayse et al. |
| 11,712,296 B2 | 8/2023 | Panescu et al. |
| 11,723,719 B2 | 8/2023 | Sachs et al. |
| 11,724,102 B2 | 8/2023 | Donega et al. |
| 11,724,108 B2 | 8/2023 | Chew et al. |
| 11,730,506 B2 | 8/2023 | Sverdlik et al. |
| 11,738,196 B2 | 8/2023 | Vervoordeldonk et al. |
| 11,744,640 B2 | 9/2023 | Amaoua et al. |
| 11,759,608 B2 | 9/2023 | Fischell et al. |
| 11,771,497 B2 | 10/2023 | Townley et al. |
| 11,779,392 B2 | 10/2023 | Hezi-Yamit et al. |
| 11,794,001 B2 | 10/2023 | Imran |
| 11,801,092 B2 | 10/2023 | Levin et al. |
| 11,806,070 B2 | 11/2023 | Wright et al. |
| 11,806,072 B2 | 11/2023 | Hakimimehr |
| 11,806,073 B2 | 11/2023 | Bapna et al. |
| 11,826,569 B2 | 11/2023 | Mishra et al. |
| 11,832,965 B2 | 12/2023 | Wang |
| 11,839,766 B2 | 12/2023 | Scheltienne et al. |
| 11,844,558 B2 | 12/2023 | Lazarus et al. |
| 11,844,565 B2 | 12/2023 | Asirvatham et al. |
| 11,844,569 B1 | 12/2023 | Panescu et al. |
| 11,857,249 B2 | 1/2024 | Ku et al. |
| 11,857,778 B2 | 1/2024 | Hamner et al. |
| 11,857,783 B2 | 1/2024 | Lo et al. |
| 11,864,826 B2 | 1/2024 | Levin et al. |
| 11,864,904 B2 | 1/2024 | Dubhashi et al. |
| 11,865,343 B2 | 1/2024 | Gallagher et al. |
| 11,883,087 B2 | 1/2024 | Tunev et al. |
| 11,883,091 B2 | 1/2024 | Townley |
| 11,883,103 B2 | 1/2024 | Toth et al. |
| 11,890,393 B2 | 2/2024 | Bright et al. |
| 11,896,818 B2 | 2/2024 | Townley |
| 11,911,634 B2 | 2/2024 | Puleo et al. |
| 11,918,362 B2 | 3/2024 | Fagin et al. |
| 11,918,595 B2 | 3/2024 | Bright et al. |
| 11,923,063 B2 | 3/2024 | Georgiou et al. |
| 11,937,868 B2 | 3/2024 | Mayse et al. |
| 2001/0029393 A1 | 10/2001 | Tierney et al. |
| 2001/0037081 A1 | 11/2001 | Heiner |
| 2002/0016565 A1 | 2/2002 | Zadno-Azizi et al. |
| 2002/0026228 A1 | 2/2002 | Schauerte |
| 2002/0087208 A1 | 7/2002 | Koblish et al. |
| 2002/0122815 A1 | 9/2002 | Peroutka |
| 2002/0147480 A1 | 10/2002 | Mamayek |
| 2002/0183735 A1 | 12/2002 | Edwards et al. |
| 2003/0060813 A1 | 3/2003 | Loeb et al. |
| 2003/0065371 A1 | 4/2003 | Satake |
| 2003/0088240 A1 | 5/2003 | Saadat |
| 2003/0120271 A1 | 6/2003 | Burnside et al. |
| 2003/0144708 A1 | 7/2003 | Starkebaum |
| 2003/0149368 A1 | 8/2003 | Hennemann et al. |
| 2003/0152637 A1 | 8/2003 | Chasin et al. |
| 2003/0195501 A1 | 10/2003 | Sherman et al. |
| 2004/0019364 A1 | 1/2004 | Kieval et al. |
| 2004/0082859 A1 | 4/2004 | Schaer |
| 2004/0082947 A1 | 4/2004 | Oral et al. |
| 2004/0087936 A1 | 5/2004 | Stern et al. |
| 2004/0254572 A1 | 12/2004 | McIntyre et al. |
| 2004/0260328 A1 | 12/2004 | Zvuloni et al. |
| 2004/0267191 A1 | 12/2004 | Gifford, III et al. |
| 2004/0267250 A1 | 12/2004 | Yon et al. |
| 2005/0004563 A1 | 1/2005 | Racz et al. |
| 2005/0015084 A1 | 1/2005 | Hill, III et al. |
| 2005/0027328 A1 | 2/2005 | Greenstein |
| 2005/0033136 A1 | 2/2005 | Govari et al. |
| 2005/0033137 A1 | 2/2005 | Lautt |
| 2005/0049293 A1 | 3/2005 | Lautt |
| 2005/0075701 A1 | 4/2005 | Shafer |
| 2005/0113295 A1 | 5/2005 | Dolle |
| 2005/0215990 A1 | 9/2005 | Govari |
| 2005/0288661 A1 | 12/2005 | Sauvageau et al. |
| 2005/0288730 A1 | 12/2005 | Deem et al. |
| 2006/0009815 A1 | 1/2006 | Boveja et al. |
| 2006/0025821 A1 | 2/2006 | Gelfand et al. |
| 2006/0034847 A1 | 2/2006 | Yun et al. |
| 2006/0047326 A1 | 3/2006 | Wheeler |
| 2006/0089637 A1 | 4/2006 | Wernet et al. |
| 2006/0089678 A1 | 4/2006 | Shalev |
| 2006/0111704 A1 | 5/2006 | Brenneman et al. |
| 2006/0111754 A1 | 5/2006 | Rezai |
| 2006/0121085 A1 | 6/2006 | Warren et al. |
| 2006/0122508 A1 | 6/2006 | Slayton et al. |
| 2006/0161217 A1 | 7/2006 | Jaax et al. |
| 2006/0167498 A1 | 7/2006 | Di Lorenzo |
| 2006/0212076 A1 | 9/2006 | Demaris et al. |
| 2006/0217698 A1 | 9/2006 | Starkebaum et al. |
| 2006/0235286 A1 | 10/2006 | Stone et al. |
| 2006/0258978 A1 | 11/2006 | Vanney |
| 2006/0265014 A1 | 11/2006 | Demaris et al. |
| 2006/0271111 A1 | 11/2006 | Demaris et al. |
| 2007/0016274 A1 | 1/2007 | Boveja et al. |
| 2007/0021786 A1 | 1/2007 | Parnis et al. |
| 2007/0027484 A1 | 2/2007 | Guzman et al. |
| 2007/0027497 A1 | 2/2007 | Parnis |
| 2007/0060971 A1 | 3/2007 | Glasberg et al. |
| 2007/0083239 A1 | 4/2007 | Demaris et al. |
| 2007/0100380 A1 | 5/2007 | Fukui |
| 2007/0106293 A1 | 5/2007 | Oral et al. |
| 2007/0106337 A1 | 5/2007 | Errico et al. |
| 2007/0129720 A1 | 6/2007 | Demaris et al. |
| 2007/0129760 A1 | 6/2007 | Demaris et al. |
| 2007/0142879 A1 | 6/2007 | Greenberg |
| 2007/0156179 A1 | 7/2007 | S.E. |
| 2007/0197970 A1 | 8/2007 | Shen-Gunther |
| 2007/0208388 A1 | 9/2007 | Jahns et al. |
| 2007/0225781 A1 | 9/2007 | Saadat et al. |
| 2007/0265563 A1 | 11/2007 | Heuser |
| 2007/0265687 A1 | 11/2007 | Deem et al. |
| 2007/0287994 A1 | 12/2007 | Patel |
| 2007/0299476 A1 | 12/2007 | Park et al. |
| 2008/0004596 A1 | 1/2008 | Yun et al. |
| 2008/0009917 A1 | 1/2008 | Rossing et al. |
| 2008/0009925 A1 | 1/2008 | Abboud et al. |
| 2008/0015642 A1 | 1/2008 | Johnson et al. |
| 2008/0027346 A1 | 1/2008 | Litt et al. |
| 2008/0027358 A1 | 1/2008 | Gregersen et al. |

(56) References Cited

U.S. PATENT DOCUMENTS

| | | |
|---|---|---|
| 2008/0044392 A1 | 2/2008 | Kues et al. |
| 2008/0064957 A1 | 3/2008 | Spence |
| 2008/0077165 A1 | 3/2008 | Murphy |
| 2008/0086180 A1 | 4/2008 | Ben-Ezra et al. |
| 2008/0140074 A1 | 6/2008 | Horne et al. |
| 2008/0147137 A1 | 6/2008 | Cohen et al. |
| 2008/0161803 A1 | 7/2008 | Oral et al. |
| 2008/0161865 A1 | 7/2008 | Hagen |
| 2008/0183237 A1 | 7/2008 | Errico et al. |
| 2008/0188912 A1 | 8/2008 | Stone et al. |
| 2008/0195171 A1 | 8/2008 | Sharma |
| 2008/0208305 A1 | 8/2008 | Rezai et al. |
| 2008/0213331 A1 | 9/2008 | Gelfand et al. |
| 2008/0243071 A1 | 10/2008 | Quijano et al. |
| 2008/0255642 A1 | 10/2008 | Zarins et al. |
| 2008/0275424 A1 | 11/2008 | Doshi et al. |
| 2008/0294096 A1 | 11/2008 | Uber, III et al. |
| 2008/0300587 A1 | 12/2008 | Anderson |
| 2008/0312642 A1 | 12/2008 | Kania et al. |
| 2008/0312643 A1 | 12/2008 | Kania et al. |
| 2008/0312714 A1 | 12/2008 | Pasricha et al. |
| 2009/0036948 A1 | 2/2009 | Levin et al. |
| 2009/0060873 A1 | 3/2009 | Sporn et al. |
| 2009/0062873 A1 | 3/2009 | Wu et al. |
| 2009/0062874 A1 | 3/2009 | Tracey et al. |
| 2009/0076409 A1 | 3/2009 | Wu et al. |
| 2009/0093801 A1 | 4/2009 | Crossman |
| 2009/0118777 A1 | 5/2009 | Iki et al. |
| 2009/0118780 A1 | 5/2009 | DiLorenzo |
| 2009/0131993 A1 | 5/2009 | Rousso et al. |
| 2009/0182303 A1 | 7/2009 | Walak et al. |
| 2009/0240306 A1 | 9/2009 | Kapoor |
| 2009/0247933 A1 | 10/2009 | Maor et al. |
| 2009/0253974 A1 | 10/2009 | Rahme |
| 2009/0254142 A1 | 10/2009 | Edwards et al. |
| 2009/0254143 A1 | 10/2009 | Tweden et al. |
| 2009/0275827 A1 | 11/2009 | Aiken et al. |
| 2009/0275996 A1 | 11/2009 | Burnes et al. |
| 2009/0275997 A1 | 11/2009 | Faltys et al. |
| 2009/0312690 A1 | 12/2009 | Kim |
| 2009/0324701 A1 | 12/2009 | Williams |
| 2010/0010567 A1 | 1/2010 | Deem et al. |
| 2010/0030210 A1 | 2/2010 | Paulus |
| 2010/0057161 A1 | 3/2010 | Machado et al. |
| 2010/0076425 A1 | 3/2010 | Carroux |
| 2010/0076519 A1 | 3/2010 | Kornet et al. |
| 2010/0106207 A1 | 4/2010 | Dobak, III |
| 2010/0114195 A1 | 5/2010 | Burnes et al. |
| 2010/0114244 A1 | 5/2010 | Manda et al. |
| 2010/0137860 A1 | 6/2010 | Demaris et al. |
| 2010/0137952 A1 | 6/2010 | Demaris et al. |
| 2010/0152731 A1 | 6/2010 | De La Rama et al. |
| 2010/0168731 A1 | 7/2010 | Wu et al. |
| 2010/0168739 A1 | 7/2010 | Wu et al. |
| 2010/0174282 A1 | 7/2010 | Demaris et al. |
| 2010/0191112 A1 | 7/2010 | Demaris et al. |
| 2010/0222851 A1 | 9/2010 | Deem et al. |
| 2010/0228310 A1 | 9/2010 | Shuros et al. |
| 2010/0249773 A1 | 9/2010 | Clark et al. |
| 2010/0249859 A1 | 9/2010 | DiLorenzo |
| 2010/0255123 A1 | 10/2010 | Lohajoti et al. |
| 2010/0256629 A1 | 10/2010 | Wylie et al. |
| 2010/0268288 A1 | 10/2010 | Hunter et al. |
| 2010/0268307 A1 | 10/2010 | Demaris et al. |
| 2010/0286684 A1 | 11/2010 | Hata et al. |
| 2010/0303617 A1 | 12/2010 | Chen |
| 2011/0029037 A1 | 2/2011 | Rezai |
| 2011/0060324 A1 | 3/2011 | Wu et al. |
| 2011/0092781 A1 | 4/2011 | Gertner |
| 2011/0092880 A1 | 4/2011 | Gertner |
| 2011/0098762 A1 | 4/2011 | Rezai |
| 2011/0112400 A1 | 5/2011 | Emery et al. |
| 2011/0118600 A1 | 5/2011 | Gertner |
| 2011/0118726 A1 | 5/2011 | De La Rama et al. |
| 2011/0118747 A1 | 5/2011 | Pasricha et al. |
| 2011/0118812 A1 | 5/2011 | Pasricha et al. |
| 2011/0137298 A1 | 6/2011 | Nguyen et al. |
| 2011/0144637 A1 | 6/2011 | Pageard et al. |
| 2011/0152855 A1 | 6/2011 | Mayse et al. |
| 2011/0152857 A1 | 6/2011 | Ingle |
| 2011/0152974 A1 | 6/2011 | Rezai et al. |
| 2011/0160514 A1 | 6/2011 | Long et al. |
| 2011/0166499 A1 | 7/2011 | Demaris et al. |
| 2011/0168739 A1 | 7/2011 | Brouwer |
| 2011/0172527 A1 | 7/2011 | Gertner |
| 2011/0178570 A1 | 7/2011 | Demaris |
| 2011/0200171 A1 | 8/2011 | Beetel et al. |
| 2011/0202098 A1 | 8/2011 | Demaris et al. |
| 2011/0207758 A1 | 8/2011 | Sobotka et al. |
| 2011/0208096 A1 | 8/2011 | Demaris et al. |
| 2011/0208173 A1 | 8/2011 | Sobotka et al. |
| 2011/0208175 A1 | 8/2011 | Sobotka et al. |
| 2011/0230939 A1 | 9/2011 | Weinstock |
| 2011/0257523 A1 | 10/2011 | Hastings et al. |
| 2011/0257561 A1 | 10/2011 | Gertner et al. |
| 2011/0257562 A1 | 10/2011 | Schaer |
| 2011/0257564 A1 | 10/2011 | Demaris et al. |
| 2011/0257641 A1 | 10/2011 | Hastings et al. |
| 2011/0257647 A1 | 10/2011 | Hastings et al. |
| 2011/0263921 A1 | 10/2011 | Vrba et al. |
| 2011/0264011 A1 | 10/2011 | Wu et al. |
| 2011/0264075 A1 | 10/2011 | Leung et al. |
| 2011/0264086 A1 | 10/2011 | Ingle |
| 2011/0264116 A1 | 10/2011 | Kocur et al. |
| 2011/0270046 A1 | 11/2011 | Paul et al. |
| 2011/0270238 A1 | 11/2011 | Rizq et al. |
| 2011/0275891 A1 | 11/2011 | Shemi |
| 2011/0276047 A1 | 11/2011 | Sklar et al. |
| 2011/0301664 A1 | 12/2011 | Rezai |
| 2011/0306851 A1 | 12/2011 | Wang |
| 2011/0307034 A1 | 12/2011 | Hastings et al. |
| 2011/0313417 A1 | 12/2011 | De La Rama et al. |
| 2012/0016256 A1 | 1/2012 | Mabary et al. |
| 2012/0022409 A1 | 1/2012 | Gertner et al. |
| 2012/0029496 A1 | 2/2012 | Smith |
| 2012/0029505 A1 | 2/2012 | Jenson |
| 2012/0029511 A1 | 2/2012 | Smith et al. |
| 2012/0029512 A1 | 2/2012 | Willard et al. |
| 2012/0035601 A1 | 2/2012 | Wittenberger |
| 2012/0059286 A1 | 3/2012 | Hastings et al. |
| 2012/0065493 A1 | 3/2012 | Gertner |
| 2012/0065494 A1 | 3/2012 | Gertner et al. |
| 2012/0065506 A1 | 3/2012 | Smith |
| 2012/0065554 A1 | 3/2012 | Pikus |
| 2012/0089047 A1 | 4/2012 | Ryba et al. |
| 2012/0101413 A1 | 4/2012 | Beetel et al. |
| 2012/0101538 A1 | 4/2012 | Ballakur et al. |
| 2012/0116382 A1 | 5/2012 | Ku et al. |
| 2012/0116383 A1 | 5/2012 | Mauch et al. |
| 2012/0116486 A1 | 5/2012 | Naga et al. |
| 2012/0123261 A1 | 5/2012 | Jenson et al. |
| 2012/0123276 A1 | 5/2012 | Govari et al. |
| 2012/0130269 A1 | 5/2012 | Rea |
| 2012/0130289 A1 | 5/2012 | Demarais et al. |
| 2012/0130345 A1 | 5/2012 | Levin et al. |
| 2012/0130359 A1 | 5/2012 | Turovskiy |
| 2012/0130360 A1 | 5/2012 | Buckley et al. |
| 2012/0130368 A1 | 5/2012 | Jenson |
| 2012/0130458 A1 | 5/2012 | Ryba et al. |
| 2012/0136344 A1 | 5/2012 | Buckley et al. |
| 2012/0136346 A1 | 5/2012 | Condie et al. |
| 2012/0136348 A1 | 5/2012 | Condie et al. |
| 2012/0136350 A1 | 5/2012 | Goshgarian et al. |
| 2012/0136417 A1 | 5/2012 | Buckley et al. |
| 2012/0136418 A1 | 5/2012 | Buckley et al. |
| 2012/0143177 A1 | 6/2012 | Avitall |
| 2012/0143179 A1* | 6/2012 | Avitall ............... A61B 18/1492 606/41 |
| 2012/0143181 A1 | 6/2012 | Demarais et al. |
| 2012/0143293 A1 | 6/2012 | Mauch et al. |
| 2012/0143294 A1 | 6/2012 | Clark et al. |
| 2012/0150267 A1 | 6/2012 | Buckley et al. |
| 2012/0157986 A1 | 6/2012 | Stone et al. |
| 2012/0157987 A1 | 6/2012 | Steinke et al. |

(56) References Cited

U.S. PATENT DOCUMENTS

| | | |
|---|---|---|
| 2012/0157988 A1 | 6/2012 | Stone et al. |
| 2012/0157992 A1 | 6/2012 | Smith et al. |
| 2012/0158101 A1 | 6/2012 | Stone et al. |
| 2012/0158104 A1 | 6/2012 | Huynh et al. |
| 2012/0172680 A1 | 7/2012 | Gelfand et al. |
| 2012/0172723 A1 | 7/2012 | Gertner |
| 2012/0191083 A1 | 7/2012 | Moll et al. |
| 2012/0197246 A1 | 8/2012 | Mauch |
| 2012/0221082 A1 | 8/2012 | Khanna |
| 2012/0232436 A1 | 9/2012 | Warnking |
| 2012/0253239 A1 | 10/2012 | Gertner et al. |
| 2012/0265198 A1 | 10/2012 | Crow et al. |
| 2012/0271302 A1 | 10/2012 | Behl et al. |
| 2012/0283756 A1 | 11/2012 | Moonly et al. |
| 2012/0303098 A1 | 11/2012 | Perryman |
| 2012/0310239 A1 | 12/2012 | Stewart et al. |
| 2012/0316451 A1 | 12/2012 | Province et al. |
| 2013/0006232 A1 | 1/2013 | Pellegrino et al. |
| 2013/0012866 A1 | 1/2013 | Deem et al. |
| 2013/0012867 A1 | 1/2013 | Demarais et al. |
| 2013/0023802 A1 | 1/2013 | McIntosh et al. |
| 2013/0035681 A1 | 2/2013 | Subramaniam et al. |
| 2013/0035682 A1 | 2/2013 | Weil |
| 2013/0041424 A1 | 2/2013 | Neisz |
| 2013/0053732 A1 | 2/2013 | Heuser |
| 2013/0053792 A1 | 2/2013 | Fischell et al. |
| 2013/0053821 A1 | 2/2013 | Fischell |
| 2013/0066308 A1 | 3/2013 | Landman |
| 2013/0066316 A1 | 3/2013 | Steinke et al. |
| 2013/0090563 A1 | 4/2013 | Weber |
| 2013/0090578 A1 | 4/2013 | Smith et al. |
| 2013/0090637 A1 | 4/2013 | Sliwa |
| 2013/0090647 A1 | 4/2013 | Smith |
| 2013/0090649 A1 | 4/2013 | Smith et al. |
| 2013/0090650 A1 | 4/2013 | Jenson et al. |
| 2013/0090651 A1 | 4/2013 | Smith |
| 2013/0090652 A1 | 4/2013 | Jenson |
| 2013/0096471 A1 | 4/2013 | Slayton et al. |
| 2013/0096550 A1 | 4/2013 | Hill |
| 2013/0096553 A1 | 4/2013 | Hill et al. |
| 2013/0096554 A1 | 4/2013 | Groff et al. |
| 2013/0110106 A1 | 5/2013 | Richardson |
| 2013/0116505 A1 | 5/2013 | Seidel |
| 2013/0116683 A1 | 5/2013 | Shadduck et al. |
| 2013/0116685 A1 | 5/2013 | Deem et al. |
| 2013/0116737 A1 | 5/2013 | Edwards et al. |
| 2013/0123770 A1 | 5/2013 | Smith |
| 2013/0144283 A1 | 6/2013 | Barman |
| 2013/0165921 A1 | 6/2013 | Sutermeister et al. |
| 2013/0165923 A1 | 6/2013 | Mathur et al. |
| 2013/0165924 A1 | 6/2013 | Mathur et al. |
| 2013/0172875 A1 | 7/2013 | Govari et al. |
| 2013/0172877 A1 | 7/2013 | Subramaniam et al. |
| 2013/0172880 A1 | 7/2013 | Willard |
| 2013/0184703 A1 | 7/2013 | Shireman et al. |
| 2013/0184789 A1 | 7/2013 | Stett et al. |
| 2013/0197499 A1 | 8/2013 | Lalonde et al. |
| 2013/0197555 A1 | 8/2013 | Schaer |
| 2013/0197614 A1 | 8/2013 | Gustus et al. |
| 2013/0211292 A1 | 8/2013 | Sverdlik et al. |
| 2013/0211396 A1 | 8/2013 | Sverdlik et al. |
| 2013/0218029 A1 | 8/2013 | Cholette et al. |
| 2013/0231658 A1 | 9/2013 | Wang et al. |
| 2013/0231659 A1 | 9/2013 | Hill et al. |
| 2013/0237948 A1 | 9/2013 | Donders et al. |
| 2013/0245622 A1 | 9/2013 | Wang et al. |
| 2013/0253628 A1 | 9/2013 | Smith et al. |
| 2013/0274658 A1 | 10/2013 | Steinke et al. |
| 2013/0274730 A1 | 10/2013 | Anderson et al. |
| 2013/0274731 A1 | 10/2013 | Anderson et al. |
| 2013/0289678 A1 | 10/2013 | Clark et al. |
| 2013/0289686 A1 | 10/2013 | Masson et al. |
| 2013/0296965 A1 | 11/2013 | Mokelke et al. |
| 2013/0304052 A1 | 11/2013 | Rizq et al. |
| 2013/0304054 A1 | 11/2013 | Zarins et al. |
| 2013/0310823 A1* | 11/2013 | Gelfand ............ A61M 25/0082 606/41 |
| 2013/0345670 A1 | 12/2013 | Rajagopalan et al. |
| 2014/0005591 A1 | 1/2014 | Melder et al. |
| 2014/0012251 A1 | 1/2014 | Himmelstein et al. |
| 2014/0012253 A1 | 1/2014 | Mathur |
| 2014/0018788 A1 | 1/2014 | Engelman et al. |
| 2014/0018794 A1 | 1/2014 | Anderson et al. |
| 2014/0025069 A1 | 1/2014 | Willard et al. |
| 2014/0031727 A1 | 1/2014 | Warnking |
| 2014/0039358 A1 | 2/2014 | Zhou et al. |
| 2014/0046313 A1 | 2/2014 | Pederson et al. |
| 2014/0052121 A1 | 2/2014 | Azamian et al. |
| 2014/0052122 A1 | 2/2014 | Azamian et al. |
| 2014/0058372 A1 | 2/2014 | Belson |
| 2014/0058377 A1 | 2/2014 | Deem et al. |
| 2014/0065107 A1 | 3/2014 | Lockwood et al. |
| 2014/0066883 A1 | 3/2014 | Azamian et al. |
| 2014/0066915 A1 | 3/2014 | Zhou et al. |
| 2014/0066919 A1 | 3/2014 | Azamian et al. |
| 2014/0066920 A1 | 3/2014 | Azamian et al. |
| 2014/0066921 A1 | 3/2014 | Coe et al. |
| 2014/0066923 A1 | 3/2014 | Azamian et al. |
| 2014/0066924 A1 | 3/2014 | Azamian et al. |
| 2014/0067003 A1 | 3/2014 | Vase et al. |
| 2014/0067029 A1 | 3/2014 | Schauer et al. |
| 2014/0074076 A1 | 3/2014 | Gertner |
| 2014/0081254 A1 | 3/2014 | Rudie |
| 2014/0081301 A1 | 3/2014 | Tran et al. |
| 2014/0088575 A1 | 3/2014 | Loeb |
| 2014/0088585 A1 | 3/2014 | Hill et al. |
| 2014/0094688 A1 | 4/2014 | Tegg et al. |
| 2014/0094787 A1 | 4/2014 | Reynolds |
| 2014/0094789 A1 | 4/2014 | Brannan |
| 2014/0094797 A1 | 4/2014 | Brannan |
| 2014/0110296 A1 | 4/2014 | Terzibashian |
| 2014/0114215 A1 | 4/2014 | Melder et al. |
| 2014/0121537 A1 | 5/2014 | Aeby et al. |
| 2014/0121568 A1 | 5/2014 | Weng et al. |
| 2014/0128859 A1 | 5/2014 | Lee |
| 2014/0135715 A1 | 5/2014 | Lambert et al. |
| 2014/0163372 A1 | 6/2014 | Deladi et al. |
| 2014/0163652 A1 | 6/2014 | Witzel et al. |
| 2014/0171936 A1 | 6/2014 | Govari et al. |
| 2014/0180196 A1 | 6/2014 | Stone et al. |
| 2014/0187619 A1 | 7/2014 | Pasricha et al. |
| 2014/0188103 A1 | 7/2014 | Millett |
| 2014/0194784 A1 | 7/2014 | Gertner |
| 2014/0200478 A1 | 7/2014 | Phan et al. |
| 2014/0200489 A1 | 7/2014 | Behar et al. |
| 2014/0200578 A1 | 7/2014 | Groff et al. |
| 2014/0207136 A1 | 7/2014 | De La Rama et al. |
| 2014/0213971 A1 | 7/2014 | Dolan et al. |
| 2014/0214018 A1 | 7/2014 | Behar et al. |
| 2014/0228713 A1 | 8/2014 | Thao et al. |
| 2014/0243807 A1 | 8/2014 | Mergolis |
| 2014/0243809 A1 | 8/2014 | Gelfand et al. |
| 2014/0243821 A1 | 8/2014 | Salahieh et al. |
| 2014/0249524 A1 | 9/2014 | Kocur |
| 2014/0257263 A1 | 9/2014 | Azamian |
| 2014/0257266 A1 | 9/2014 | Kasprzyk et al. |
| 2014/0271717 A1 | 9/2014 | Goshayeshgar et al. |
| 2014/0275993 A1 | 9/2014 | Ballakur |
| 2014/0276707 A1 | 9/2014 | Jaax |
| 2014/0276752 A1 | 9/2014 | Wang et al. |
| 2014/0276756 A1 | 9/2014 | Hill |
| 2014/0276764 A1 | 9/2014 | Shuman et al. |
| 2014/0276787 A1 | 9/2014 | Wang et al. |
| 2014/0276811 A1 | 9/2014 | Koblish et al. |
| 2014/0277310 A1 | 9/2014 | Beetel et al. |
| 2014/0288015 A1 | 9/2014 | Venkateswara-Rao |
| 2014/0296846 A1 | 10/2014 | Huszar et al. |
| 2014/0296902 A1 | 10/2014 | Huszar et al. |
| 2014/0303617 A1 | 10/2014 | Shimada |
| 2014/0309579 A1 | 10/2014 | Rubinsky et al. |
| 2014/0316254 A1 | 10/2014 | Eversull et al. |
| 2014/0330068 A1 | 11/2014 | Partsch et al. |
| 2014/0336639 A1 | 11/2014 | Young et al. |
| 2014/0350327 A1 | 11/2014 | Poon et al. |

(56) References Cited

U.S. PATENT DOCUMENTS

| | | |
|---|---|---|
| 2014/0350551 A1 | 11/2014 | Raatikka et al. |
| 2014/0350553 A1 | 11/2014 | Okuyama |
| 2014/0358136 A1 | 12/2014 | Kelly et al. |
| 2014/0364715 A1 | 12/2014 | Hauck |
| 2014/0364848 A1 | 12/2014 | Heimbecher et al. |
| 2014/0378962 A1 | 12/2014 | Anderson et al. |
| 2014/0378966 A1 | 12/2014 | Haverkost et al. |
| 2014/0378967 A1* | 12/2014 | Willard .............. A61B 18/1492 606/41 |
| 2014/0378968 A1 | 12/2014 | Sutermeister et al. |
| 2015/0005764 A1 | 1/2015 | Hanson et al. |
| 2015/0005766 A1 | 1/2015 | Rioux et al. |
| 2015/0011989 A1 | 1/2015 | Azamian |
| 2015/0018817 A1 | 1/2015 | Willard |
| 2015/0018818 A1 | 1/2015 | Willard et al. |
| 2015/0018819 A1 | 1/2015 | Sutermeister |
| 2015/0018820 A1 | 1/2015 | Cao et al. |
| 2015/0018821 A1 | 1/2015 | Zarins et al. |
| 2015/0018904 A1 | 1/2015 | Lafontaine |
| 2015/0025525 A1 | 1/2015 | Willard et al. |
| 2015/0025533 A1 | 1/2015 | Groff et al. |
| 2015/0025605 A1 | 1/2015 | Kaplan et al. |
| 2015/0045728 A1 | 2/2015 | Heuser |
| 2015/0045787 A1 | 2/2015 | Bloom |
| 2015/0051595 A1 | 2/2015 | Margolis |
| 2015/0057654 A1 | 2/2015 | Leung et al. |
| 2015/0057655 A1 | 2/2015 | Osypka |
| 2015/0057656 A1 | 2/2015 | Gupta et al. |
| 2015/0065783 A1 | 3/2015 | Buelna |
| 2015/0065945 A1 | 3/2015 | Zarins et al. |
| 2015/0066017 A1 | 3/2015 | Desai |
| 2015/0066023 A1 | 3/2015 | Anderson et al. |
| 2015/0066118 A1 | 3/2015 | O'Connell |
| 2015/0073409 A1 | 3/2015 | Watson et al. |
| 2015/0080875 A1 | 3/2015 | Kasprzyk et al. |
| 2015/0080882 A1 | 3/2015 | Skinner et al. |
| 2015/0080883 A1 | 3/2015 | Haverkost et al. |
| 2015/0080926 A1 | 3/2015 | Emery |
| 2015/0094787 A1 | 4/2015 | Madhavan et al. |
| 2015/0105770 A1 | 4/2015 | Amit |
| 2015/0105772 A1 | 4/2015 | Hill et al. |
| 2015/0105773 A1 | 4/2015 | Weber et al. |
| 2015/0105774 A1 | 4/2015 | Lindquist et al. |
| 2015/0112234 A1 | 4/2015 | McCaffrey et al. |
| 2015/0112326 A1 | 4/2015 | Li |
| 2015/0112328 A1 | 4/2015 | Willard et al. |
| 2015/0112329 A1 | 4/2015 | Ng |
| 2015/0112331 A1 | 4/2015 | Olson et al. |
| 2015/0119870 A1 | 4/2015 | Rudie |
| 2015/0119875 A1 | 4/2015 | Fischell |
| 2015/0119876 A1 | 4/2015 | Willard |
| 2015/0119877 A1 | 4/2015 | Jameson |
| 2015/0119878 A1 | 4/2015 | Heisel et al. |
| 2015/0119882 A1 | 4/2015 | Cao et al. |
| 2015/0126992 A1 | 5/2015 | Mogul |
| 2015/0126996 A1 | 5/2015 | Tegg |
| 2015/0126997 A1 | 5/2015 | Beetel et al. |
| 2015/0141785 A1 | 5/2015 | Hayam et al. |
| 2015/0141978 A1 | 5/2015 | Subramaniam et al. |
| 2015/0141982 A1 | 5/2015 | Lee |
| 2015/0141985 A1 | 5/2015 | Mayse et al. |
| 2015/0148794 A1 | 5/2015 | Squire et al. |
| 2015/0150624 A1 | 6/2015 | Petersohn |
| 2015/0151077 A1 | 6/2015 | Harrington |
| 2015/0157382 A1 | 6/2015 | Avitall et al. |
| 2015/0157400 A1 | 6/2015 | Gelbart et al. |
| 2015/0157401 A1 | 6/2015 | Falwell et al. |
| 2015/0157402 A1 | 6/2015 | Kunis et al. |
| 2015/0157831 A1* | 6/2015 | Crall .................. A61M 25/10 604/103.1 |
| 2015/0173830 A1 | 6/2015 | Johnson et al. |
| 2015/0190194 A1 | 7/2015 | Weber et al. |
| 2015/0190195 A1 | 7/2015 | Hanson et al. |
| 2015/0196354 A1 | 7/2015 | Haverkost et al. |
| 2015/0196356 A1 | 7/2015 | Kauphusman et al. |
| 2015/0196740 A1 | 7/2015 | Mallin et al. |
| 2015/0196783 A1 | 7/2015 | Emery et al. |
| 2015/0209107 A1 | 7/2015 | Rudie et al. |
| 2015/0216591 A1 | 8/2015 | Cao et al. |
| 2015/0223866 A1 | 8/2015 | Buelna et al. |
| 2015/0223877 A1 | 8/2015 | Behar et al. |
| 2015/0224089 A1 | 8/2015 | Saltiel |
| 2015/0230859 A1 | 8/2015 | Mauch |
| 2015/0238247 A1 | 8/2015 | Shikhman et al. |
| 2015/0238249 A1 | 8/2015 | Edmunds et al. |
| 2015/0238251 A1 | 8/2015 | Shikhman et al. |
| 2015/0251008 A1 | 9/2015 | Rezai et al. |
| 2015/0257825 A1 | 9/2015 | Kelly et al. |
| 2015/0257929 A1 | 9/2015 | Brian, III et al. |
| 2015/0265334 A1 | 9/2015 | Franke et al. |
| 2015/0265339 A1 | 9/2015 | Linquist et al. |
| 2015/0290427 A1 | 10/2015 | Warnking |
| 2015/0297281 A1 | 10/2015 | Sutermeister et al. |
| 2015/0297292 A1 | 10/2015 | Sutermeister et al. |
| 2015/0327923 A1 | 11/2015 | Just et al. |
| 2015/0335263 A1 | 11/2015 | Srivastava |
| 2015/0342491 A1 | 12/2015 | Marecki et al. |
| 2015/0342673 A1 | 12/2015 | Squire et al. |
| 2015/0342675 A1 | 12/2015 | Highsmith |
| 2015/0351652 A1 | 12/2015 | Marecki et al. |
| 2015/0359432 A1 | 12/2015 | Ehrenreich et al. |
| 2015/0359589 A1 | 12/2015 | Mauch et al. |
| 2015/0366508 A1 | 12/2015 | Chou et al. |
| 2015/0366608 A1 | 12/2015 | Weber et al. |
| 2015/0374427 A1 | 12/2015 | Goertzen et al. |
| 2016/0000498 A1 | 1/2016 | Zarins et al. |
| 2016/0008024 A1 | 1/2016 | Payne et al. |
| 2016/0008066 A1 | 1/2016 | Kaplan et al. |
| 2016/0016016 A1 | 1/2016 | Taylor et al. |
| 2016/0022353 A1 | 1/2016 | Forsyth et al. |
| 2016/0030773 A1 | 2/2016 | Burdette |
| 2016/0033144 A1 | 2/2016 | Larson |
| 2016/0045121 A1 | 2/2016 | Akingba et al. |
| 2016/0045257 A1 | 2/2016 | Fischell et al. |
| 2016/0051321 A1 | 2/2016 | Salaheih et al. |
| 2016/0051465 A1 | 2/2016 | Azamian et al. |
| 2016/0058502 A1 | 3/2016 | Clark et al. |
| 2016/0058503 A1 | 3/2016 | Tunev et al. |
| 2016/0058505 A1 | 3/2016 | Condie et al. |
| 2016/0066988 A1 | 3/2016 | Chang et al. |
| 2016/0066992 A1 | 3/2016 | Mathur |
| 2016/0074112 A1 | 3/2016 | Himmelstein et al. |
| 2016/0081746 A1 | 3/2016 | Solis |
| 2016/0095642 A1 | 4/2016 | Deno et al. |
| 2016/0095656 A1 | 4/2016 | Peled et al. |
| 2016/0106984 A1 | 4/2016 | Mathur et al. |
| 2016/0113713 A1 | 4/2016 | Ku et al. |
| 2016/0120597 A1 | 5/2016 | Azamian et al. |
| 2016/0128767 A1 | 5/2016 | Azamian et al. |
| 2016/0129223 A1 | 5/2016 | Kirschenman |
| 2016/0135878 A1 | 5/2016 | Warner et al. |
| 2016/0135879 A1 | 5/2016 | Beasley et al. |
| 2016/0143696 A1 | 5/2016 | Govari et al. |
| 2016/0175041 A1 | 6/2016 | Abunassar et al. |
| 2016/0175044 A1 | 6/2016 | Abunassar et al. |
| 2016/0184011 A1 | 6/2016 | Krishnan |
| 2016/0199116 A1 | 7/2016 | Jameson et al. |
| 2016/0199127 A1 | 7/2016 | Prutchi |
| 2016/0213262 A1 | 7/2016 | Ghaffari et al. |
| 2016/0223704 A1 | 8/2016 | Haverkost et al. |
| 2016/0249978 A1 | 9/2016 | Lee et al. |
| 2016/0256683 A1 | 9/2016 | Butera et al. |
| 2016/0262821 A1 | 9/2016 | Azamian et al. |
| 2016/0262833 A1 | 9/2016 | Rudie |
| 2016/0278853 A1 | 9/2016 | Ogle et al. |
| 2016/0287114 A1 | 10/2016 | Srivastava |
| 2016/0296747 A1 | 10/2016 | Glenn et al. |
| 2016/0331294 A1 | 11/2016 | Imran et al. |
| 2016/0331459 A1 | 11/2016 | Townley et al. |
| 2016/0332563 A1 | 11/2016 | Yin et al. |
| 2016/0367316 A1 | 12/2016 | Smith et al. |
| 2016/0374754 A1 | 12/2016 | Asirvathan et al. |
| 2016/0375235 A1 | 12/2016 | Schoenle et al. |
| 2017/0000560 A1 | 1/2017 | Mathur et al. |

(56) References Cited

U.S. PATENT DOCUMENTS

| | | |
|---|---|---|
| 2017/0007157 A1 | 1/2017 | Gross et al. |
| 2017/0007810 A1 | 1/2017 | Parsons et al. |
| 2017/0014639 A1 | 1/2017 | Preston et al. |
| 2017/0035341 A1 | 2/2017 | Nagale et al. |
| 2017/0035497 A1 | 2/2017 | Nagale et al. |
| 2017/0042613 A1 | 2/2017 | Schultheis et al. |
| 2017/0049503 A1 | 2/2017 | Cosman |
| 2017/0049513 A1 | 2/2017 | Cosman, Jr. et al. |
| 2017/0049989 A1 | 2/2017 | Kapural |
| 2017/0056087 A1 | 3/2017 | Buckley et al. |
| 2017/0056105 A1 | 3/2017 | Steinke et al. |
| 2017/0065327 A1 | 3/2017 | Joyner et al. |
| 2017/0065818 A1 | 3/2017 | Ransbury et al. |
| 2017/0086907 A1 | 3/2017 | Satake |
| 2017/0105871 A1 | 4/2017 | Nierich |
| 2017/0112564 A1 | 4/2017 | Joyner et al. |
| 2017/0128129 A1 | 5/2017 | Kelly et al. |
| 2017/0135758 A1 | 5/2017 | Danek et al. |
| 2017/0143405 A1 | 5/2017 | Rooks et al. |
| 2017/0143412 A1 | 5/2017 | O'Fallon |
| 2017/0143421 A1 | 5/2017 | Mayse et al. |
| 2017/0157366 A1 | 6/2017 | Assif et al. |
| 2017/0164999 A1 | 6/2017 | Hettel |
| 2017/0189642 A1 | 7/2017 | Masson et al. |
| 2017/0231694 A1 | 8/2017 | Mathur et al. |
| 2017/0252560 A1 | 9/2017 | Imran |
| 2017/0259057 A1 | 9/2017 | Muessig et al. |
| 2017/0296254 A1 | 10/2017 | Mitsumune et al. |
| 2017/0296264 A1 | 10/2017 | Wang |
| 2017/0311829 A1 | 11/2017 | Beeckler et al. |
| 2017/0311893 A1 | 11/2017 | Beeckler et al. |
| 2017/0312022 A1 | 11/2017 | Beeckler et al. |
| 2017/0312026 A1 | 11/2017 | Harlev et al. |
| 2017/0312029 A1 | 11/2017 | Schaer |
| 2017/0333123 A1 | 11/2017 | Liu |
| 2017/0340383 A1 | 11/2017 | Bloom et al. |
| 2017/0348049 A1 | 12/2017 | Vrba et al. |
| 2017/0354449 A1 | 12/2017 | Avitall et al. |
| 2017/0354462 A1 | 12/2017 | Dong et al. |
| 2017/0354463 A1 | 12/2017 | Mori |
| 2018/0028264 A1 | 2/2018 | Onik et al. |
| 2018/0036072 A1 | 2/2018 | Mathur et al. |
| 2018/0036073 A1 | 2/2018 | Kaplan et al. |
| 2018/0036075 A1 | 2/2018 | Gelbart et al. |
| 2018/0036076 A1 | 2/2018 | Gelbart et al. |
| 2018/0036077 A1 | 2/2018 | Gelbart et al. |
| 2018/0056074 A1 | 3/2018 | Clark et al. |
| 2018/0103992 A1 | 4/2018 | Guyuron |
| 2018/0153467 A1 | 6/2018 | Lichtenstein et al. |
| 2018/0154155 A1 | 6/2018 | Keaveney et al. |
| 2018/0177549 A1 | 6/2018 | Harrington et al. |
| 2018/0344517 A1 | 12/2018 | Nofzinger |
| 2019/0053847 A1 | 2/2019 | Tandri et al. |
| 2019/0059969 A1 | 2/2019 | Azamian et al. |
| 2019/0069942 A1 | 3/2019 | Azamian et al. |
| 2019/0069949 A1 | 3/2019 | Vrba et al. |
| 2019/0175243 A1 | 6/2019 | Keweloh |
| 2019/0223754 A1 | 7/2019 | Gunasekaran et al. |
| 2019/0274687 A1 | 9/2019 | Wang et al. |
| 2019/0307507 A1 | 10/2019 | Wang |
| 2019/0329042 A1 | 10/2019 | DiLorenzo |
| 2019/0343579 A1 | 11/2019 | Tandri et al. |
| 2019/0366130 A1 | 12/2019 | Sverdlilk et al. |
| 2019/0388132 A1 | 12/2019 | Azamian et al. |
| 2019/0388147 A1 | 12/2019 | Wang |
| 2020/0009355 A1 | 1/2020 | Wang et al. |
| 2020/0016379 A1 | 1/2020 | Wang et al. |
| 2020/0038096 A1 | 2/2020 | Schepis et al. |
| 2020/0046552 A1 | 2/2020 | Velis et al. |
| 2020/0046996 A1 | 2/2020 | Jo et al. |
| 2020/0069366 A1 | 3/2020 | Clark et al. |
| 2020/0086093 A1 | 3/2020 | Wang |
| 2020/0121357 A1 | 4/2020 | Gomez et al. |
| 2020/0197086 A1 | 6/2020 | Azamian et al. |
| 2020/0197088 A1 | 6/2020 | Vrba et al. |
| 2020/0215266 A1 | 7/2020 | Koya et al. |
| 2020/0238107 A1 | 7/2020 | Shabtay et al. |
| 2020/0253192 A1 | 8/2020 | Jiang et al. |
| 2020/0268536 A1 | 8/2020 | DiLorenzo |
| 2020/0306496 A1 | 10/2020 | Radha et al. |
| 2020/0315700 A1 | 10/2020 | Petitpierre et al. |
| 2020/0337765 A1 | 10/2020 | Smith |
| 2020/0360671 A1 | 11/2020 | Wang et al. |
| 2020/0368528 A1 | 11/2020 | Sridhar et al. |
| 2020/0368531 A1 | 11/2020 | Sridhar et al. |
| 2020/0375658 A1 | 12/2020 | Qian et al. |
| 2020/0397804 A1 | 12/2020 | Hellstrom |
| 2020/0398032 A1 | 12/2020 | Wang et al. |
| 2021/0007799 A1 | 1/2021 | Tajima et al. |
| 2021/0022948 A1 | 1/2021 | Musallam |
| 2021/0023375 A1 | 1/2021 | Holland et al. |
| 2021/0045711 A1 | 2/2021 | Brattain et al. |
| 2021/0093378 A1 | 4/2021 | Mori |
| 2021/0128051 A1 | 5/2021 | Li et al. |
| 2021/0145501 A1 | 5/2021 | Azamian et al. |
| 2021/0146136 A1 | 5/2021 | Waataja et al. |
| 2021/0205013 A1 | 7/2021 | Meyer et al. |
| 2021/0205501 A1 | 7/2021 | Bright |
| 2021/0275241 A1 | 9/2021 | Fahey et al. |
| 2021/0275784 A1 | 9/2021 | Wang |
| 2021/0275785 A1 | 9/2021 | Wang |
| 2021/0275786 A1 | 9/2021 | Wang |
| 2021/0275787 A1 | 9/2021 | Wang |
| 2021/0275810 A1 | 9/2021 | Caban |
| 2021/0301306 A1 | 9/2021 | Kaplitt et al. |
| 2021/0315638 A1 | 10/2021 | Townley et al. |
| 2021/0322718 A1 | 10/2021 | DiLorenzo |
| 2021/0322769 A1 | 10/2021 | Kim |
| 2021/0330977 A1 | 10/2021 | Sinha |
| 2021/0346625 A1 | 11/2021 | Rezai et al. |
| 2021/0369337 A1 | 12/2021 | Aklog et al. |
| 2021/0370066 A1 | 12/2021 | Caban et al. |
| 2022/0031389 A1 | 2/2022 | Fischell et al. |
| 2022/0054163 A1 | 2/2022 | Mansell |
| 2022/0096318 A1 | 3/2022 | Harper et al. |
| 2022/0104866 A1 | 4/2022 | Townley et al. |
| 2022/0151674 A1 | 5/2022 | Sharma |
| 2022/0152394 A1 | 5/2022 | Levin |
| 2022/0202483 A1 | 6/2022 | Gertner |
| 2022/0233856 A1 | 7/2022 | Gupta et al. |
| 2022/0233860 A1 | 7/2022 | Hamner et al. |
| 2022/0241590 A1 | 8/2022 | Gupta et al. |
| 2022/0249840 A1 | 8/2022 | Gupta et al. |
| 2022/0257298 A1 | 8/2022 | Fox et al. |
| 2022/0265302 A1 | 8/2022 | Thirumalai et al. |
| 2022/0265339 A1 | 8/2022 | Yin et al. |
| 2022/0296884 A1 | 9/2022 | Jeong et al. |
| 2022/0305259 A1 | 9/2022 | Gupta et al. |
| 2022/0305268 A1 | 9/2022 | Hassan et al. |
| 2022/0313995 A1 | 10/2022 | Cakmak |
| 2022/0347470 A1 | 11/2022 | Lai et al. |
| 2022/0378461 A1 | 12/2022 | Cheung et al. |
| 2022/0386935 A1 | 12/2022 | Yung et al. |
| 2023/0000564 A1 | 1/2023 | Rapoport et al. |
| 2023/0040877 A1 | 2/2023 | Reo et al. |
| 2023/0052520 A1 | 2/2023 | Mattison et al. |
| 2023/0054079 A1 | 2/2023 | Lakshmi |
| 2023/0062487 A1 | 3/2023 | Claude et al. |
| 2023/0140990 A1 | 5/2023 | Puleo et al. |
| 2023/0181245 A1 | 6/2023 | Cao et al. |
| 2023/0181251 A1 | 6/2023 | Melder et al. |
| 2023/0200637 A1 | 6/2023 | Hakimimehr et al. |
| 2023/0203582 A1 | 6/2023 | Snyder et al. |
| 2023/0218432 A1 | 7/2023 | Chabal et al. |
| 2023/0225791 A1 | 7/2023 | van der Horst |
| 2023/0233095 A1 | 7/2023 | Cezo |
| 2023/0233135 A1 | 7/2023 | Cezo et al. |
| 2023/0233251 A1 | 7/2023 | Cezo et al. |
| 2023/0255676 A1 | 8/2023 | Donovan et al. |
| 2023/0256252 A1 | 8/2023 | Brandner et al. |
| 2023/0277076 A1 | 9/2023 | Cezo |
| 2023/0277233 A1 | 9/2023 | Spranger et al. |
| 2023/0293229 A1 | 9/2023 | Barman et al. |
| 2023/0301700 A1 | 9/2023 | Nahama |

(56) References Cited

U.S. PATENT DOCUMENTS

| | | |
|---|---|---|
| 2023/0302301 A1 | 9/2023 | Sobotka et al. |
| 2023/0338083 A1 | 10/2023 | Nollert et al. |
| 2023/0338744 A1 | 10/2023 | Demazumder et al. |
| 2023/0389852 A1 | 12/2023 | Zhai |
| 2023/0414160 A1 | 12/2023 | Zhai et al. |
| 2024/0032801 A1 | 2/2024 | Coates et al. |
| 2024/0091387 A1 | 3/2024 | Berman |
| 2024/0099988 A1 | 3/2024 | Buelna |

FOREIGN PATENT DOCUMENTS

| | | |
|---|---|---|
| EP | 0643601 B1 | 8/2001 |
| EP | 1233718 B1 | 8/2002 |
| EP | 1803409 A1 | 7/2007 |
| EP | 1485034 B1 | 12/2014 |
| EP | 3023052 A1 | 5/2016 |
| EP | 3023069 A1 | 5/2016 |
| EP | 3040042 A1 | 7/2016 |
| EP | 2797535 B1 | 10/2020 |
| JP | 60-76937 | 5/1985 |
| JP | 2001/37868 | 2/2001 |
| JP | 2009/534123 | 9/2009 |
| JP | 2011-518615 | 6/2011 |
| RU | 2277381 | 6/2006 |
| RU | 2421163 | 6/2011 |
| UA | 52875 U | 9/2010 |
| WO | WO 93/02743 | 2/1993 |
| WO | WO 00/10475 | 3/2000 |
| WO | WO 00/019992 | 4/2000 |
| WO | WO 02/007601 | 1/2002 |
| WO | WO 02/70039 | 9/2002 |
| WO | 2004112883 A2 | 12/2004 |
| WO | WO 2005/023081 | 3/2005 |
| WO | WO 2006/029257 | 3/2006 |
| WO | WO 2007/015139 | 2/2007 |
| WO | WO 2007/018788 | 2/2007 |
| WO | 2007121424 A2 | 10/2007 |
| WO | 2008151001 A2 | 12/2008 |
| WO | WO 2008/153357 | 12/2008 |
| WO | WO 2009/082569 | 7/2009 |
| WO | WO 2009/090440 | 7/2009 |
| WO | WO 2009/149390 | 12/2009 |
| WO | 2010022071 A2 | 2/2010 |
| WO | WO 2010/111400 | 9/2010 |
| WO | WO 2011/046880 | 4/2011 |
| WO | WO 2011/057157 | 5/2011 |
| WO | WO 2011/060200 | 5/2011 |
| WO | WO 2009/137819 | 7/2011 |
| WO | WO 2011/101778 A1 | 8/2011 |
| WO | WO 2011/130531 | 10/2011 |
| WO | WO 2011/139589 | 11/2011 |
| WO | WO 2012/019156 | 2/2012 |
| WO | WO 2012/025245 | 3/2012 |
| WO | WO 2012/025246 | 3/2012 |
| WO | WO 2012/061159 | 5/2012 |
| WO | WO 2012/099974 | 7/2012 |
| WO | WO 2012/149205 | 11/2012 |
| WO | WO 2013/086461 | 6/2013 |
| WO | 2013111136 A2 | 8/2013 |
| WO | WO 2013/111136 | 8/2013 |
| WO | 2013134469 A1 | 9/2013 |
| WO | WO 2012/068471 | 9/2013 |
| WO | WO 2013/130655 | 9/2013 |
| WO | WO 2013/134133 | 9/2013 |
| WO | WO 2013/134479 | 9/2013 |
| WO | WO 2013/134541 | 9/2013 |
| WO | WO 2013/134543 | 9/2013 |
| WO | WO 2013/159066 | 10/2013 |
| WO | WO 2013/162722 | 10/2013 |
| WO | WO 2014/022436 | 2/2014 |
| WO | WO 2014/026055 | 2/2014 |
| WO | WO 2014/055997 | 4/2014 |
| WO | 2014091401 A2 | 6/2014 |
| WO | WO 2014/091401 | 6/2014 |
| WO | WO 2014/102756 | 7/2014 |
| WO | WO 2014/102760 | 7/2014 |
| WO | 2014176785 A1 | 11/2014 |
| WO | WO 2014/197625 | 11/2014 |
| WO | WO 2015/069446 | 5/2015 |
| WO | WO 2015/069887 | 5/2015 |
| WO | 2015119624 A1 | 8/2015 |
| WO | WO 2015/170281 | 11/2015 |
| WO | WO 2015/183952 | 12/2015 |
| WO | WO 2015/187386 | 12/2015 |
| WO | WO 2015/191938 | 12/2015 |
| WO | WO 2016/007851 | 1/2016 |
| WO | WO 2016/054379 | 4/2016 |
| WO | WO 2016/075536 | 5/2016 |
| WO | WO 2016/084081 | 6/2016 |
| WO | WO 2016/090175 | 6/2016 |
| WO | WO 2016/118934 | 7/2016 |
| WO | WO 2016/123390 | 8/2016 |
| WO | WO 2016/151595 | 9/2016 |
| WO | WO 2016/179527 | 11/2016 |
| WO | WO 2016/183468 | 11/2016 |
| WO | WO 2016/205431 | 12/2016 |
| WO | WO 2017/062753 | 4/2017 |
| WO | WO 2017/085102 | 5/2017 |
| WO | WO 2017/095689 | 6/2017 |
| WO | WO 2017/103105 | 6/2017 |
| WO | WO 2017/118986 | 7/2017 |
| WO | 2017146660 A1 | 8/2017 |
| WO | WO 2017/194557 | 11/2017 |
| WO | WO 2017/203380 | 11/2017 |
| WO | WO 2018/202877 | 11/2018 |
| WO | 2020046839 A1 | 3/2020 |
| WO | 2020250417 A1 | 12/2020 |
| WO | 2021033275 A1 | 2/2021 |
| WO | 2021097448 A1 | 5/2021 |
| WO | 2021140421 A1 | 7/2021 |
| WO | 2021242231 A1 | 12/2021 |
| WO | 2022011222 A1 | 1/2022 |
| WO | 2022221452 A1 | 4/2022 |
| WO | 2022139971 A1 | 6/2022 |
| WO | 2022169712 A1 | 8/2022 |
| WO | 2022170275 A1 | 8/2022 |
| WO | 2022204008 A1 | 9/2022 |
| WO | 2022215760 A1 | 10/2022 |
| WO | 2022237233 A1 | 11/2022 |
| WO | 2022256218 A1 | 12/2022 |
| WO | 2022266261 A1 | 12/2022 |
| WO | 2022266327 A1 | 12/2022 |
| WO | 2022269617 A2 | 12/2022 |
| WO | 2023282396 A1 | 1/2023 |
| WO | 2023283568 A1 | 1/2023 |
| WO | 2023020544 A1 | 2/2023 |
| WO | 2023025590 A1 | 3/2023 |
| WO | 2023031056 A1 | 3/2023 |
| WO | 2023031802 A1 | 3/2023 |
| WO | 2023070128 A1 | 4/2023 |
| WO | 2023097261 A1 | 6/2023 |
| WO | 2023105061 A1 | 6/2023 |
| WO | 2023167343 A1 | 9/2023 |
| WO | 2023187510 A1 | 10/2023 |
| WO | 2023201415 A1 | 10/2023 |
| WO | 2023205654 A2 | 10/2023 |
| WO | 2023221710 A1 | 11/2023 |
| WO | 2023224382 A1 | 11/2023 |
| WO | 2023225084 A1 | 11/2023 |
| WO | 2023235474 A1 | 12/2023 |
| WO | 2023240154 A2 | 12/2023 |
| WO | 2023250370 A1 | 12/2023 |
| WO | 2023250426 A1 | 12/2023 |
| WO | 2024019391 A1 | 1/2024 |
| WO | 2024042216 A1 | 2/2024 |
| WO | 2024046967 A1 | 3/2024 |
| WO | 2024056505 A1 | 3/2024 |

OTHER PUBLICATIONS

Agah, Ramtin et al., "Rate Process Model for Arterial Tissue Thermal Damage: Implications on Vessel Photocoagulation," Lasers in Surgery and Medicine, vol. 15, pp. 176-184 (1994).

(56) References Cited

OTHER PUBLICATIONS

Anderson, Erling A. et al, "Hyperinsulinemia Produces both Sympathetic Neural Activation and Vasodilation in Normal Humans," Journal of Clinical Investigation, vol. 87, pp. 2246-2252 (1991).
Atherton, Daniel S. et al., « Micro-anatomy of the Renal Sympathetic Nervous System: A Human Postmortem Histologic Study, » Clinical Anatomy, vol. 25, pp. 628-633 (2012).
Aytac, Suat K. et al., «Correlation Between the Diameter of the Main Renal Artery and the Presence of an Accessory Renal Artery, » Journal of Ultrasound in Medicine, vol. 22, pp. 433-439 (2003).
Bergman, Richard N et al., « Direct enhancement of insulin secretion by vagal stimulation of the isolated pancreas, » American Journal of Physiology, vol. 225, No. 2, pp. 481-486 (1973).
Bernal-Mizrachi, Afferent Vagal Nerve Pathway Links Hepatic Ppar Activation to Glucocorticoid-Induced Insulin Resistance and Hypertension; Cell Metabolism 5, Feb. 2007; pp. 91-102.
Berthoud, H. R. et al., « Evidence for a role of the gastric, coeliac and hepatic branches in vagally stimulated insulin secretion in the rat, Journal of the Autonomic Nervous System, vol. 7, pp. 97-110 (1983).
Berthoud, Hans-Rudolf, "Anatomy and Function of Sensory Hepatic Nerves," The Anatomical Record Part A, vol. 280A, pp. 827-835 (2004).
Borrelli, M.J. et al., « Time-Temperature Analysis of Cell Killing of BHK Cells Heated at Temperatures in the Range of 43.5° C to 57.0° C, International Journal of Radiation Oncology, Biology and Physics, vol. 19, No. 2, pp. 389-399 (Aug. 1990).
Brace, Christopher L. "Temperature-dependent dielectric properties of liver tissue measured during thermal ablation: Toward an improved numerical model," 30th Annual International IEEE EMBS Conference pp. 230-233 (2008).
Brandt, Mathias C. et al., « Renal Sympathetic Denervation Reduces Left Ventricular Hypertrophy and Improves Cardiac Function in Patients With Resistant Hypertension, » Journal of the American College of Cardiology, vol. 59, No. 10, pp. 901-909 (2012).
Brashers-Krug, G. "Understanding Oral Diabetes Medications," Retrieved Feb. 10, 2015 from https://nfb.org/images/nfb/publications/vod/vod_22_4/vodfal0712.htm (Mar. 2, 2008).
Bruce, D.G. et al., « The effects of sympathetic nervous system activation and psychological stress on glucose metabolism and blood pressure in subjects with Type 2 (non-insulin-dependent) diabetes mellitus, Diabetologia, vol. 35, pp. 835-843 (1992).
Bruinstroop, Eveline et al., "Hypothalamic neuropeptide Y (NPY) controls hepatic VLDL-triglyceride secretion in rats via the sympathetic nervous system," Diabetes, vol. 61 (5), pp. 1043-1050 (May 2012).
Buch, Eric et al., "A Novel Method to Prevent Phrenic Nerve Injury During Catheter Ablation," Heart Rhythm, vol. 4, No. 1, pp. 95-98 (Jan. 2007).
Buijs, Ruud M. et al., « The Suprachiasmatic Nucleus Balances Sympathetic and Parasympathetic Output to Peripheral Organs through Separate Preautonomic Neurons, Journal of Comparative Neurology, vol. 464, pp. 36-48 (2003).
Bunch, T. Jared et al., "Mechanisms of Phrenic Nerve Injury During Radiofrequency Ablation at thePulmonary Vein Orifice," Journal of Cardiovascular Electrophysiology, vol. 16, No. 12, pp. 1318-1325 (Dec. 2005).
Burdio, Fernando et al., "Research and development of a new RF-assisted device for bloodless rapid transection of the liver: Computational modeling and in vivo experiments," BioMedical Engineering Online, vol. 8, No. 6 (2009), available at http://www.biomeidcal-engineering-on line.com/content/8/1/6.
Cailotto, Cathy et al., "The suprachiasmatic nucleus controls the daily variation of plasma glucose via the autonomic output to the liver: are the clock genes involved?" European Journal of Neuroscience, vol. 22, pp. 2531-2540 (2005).
Cardin, Sylvain et al., "Effect of hepatic vagotomy on hormonal response to exercise in gluconeogenesis-inhibited rats," American Journal of Physiology—Regulatory Integrative Comparative Physiology, vol. 260, pp. R67-R72 (1991).

Cardin, Sylvain et al., "Involvement of the vagus nerves in the regulation of basal hepatic glucose production in conscious dogs," American Journal of Physiology—Endocrinology and Metabolism, vol. 283, op. E958-E964 (2002).
Carnethon, Mercedes R. et al., « Prospective Investigation of Autonomic Nervous System Function and the Development of Type 2 Diabetes, » Circulation, vol. 107, pp. 2190-2195 (2003).
Chang, Isaac A. et al., « Thermal modeling of lesion growth with radiofrequency ablation, BioMedical Engineering Online, vol. 3, No. 27 (2004) , available at http://www.biomeidcal-engineering-on line.com/content/3/1/27.
Chen et al., Development and application of rodent models for type 2 diabetes, Diabetes, Obesity and Metabolism, vol. 7, 2005, pp. 307-317 (2004).
Chen, J. et al., "Hepatic electrical stimulation reduces blood glucose in diabetic rats," Neurogastroenterology & Motility vol. 22, pp. 1109-e286 (2010).
Cherrington, Alan D, "Banting Lecture 1997: Control of Glucose Uptake and Release by the Liver In Vivo," Diabetes, vol. 48, DD. 1198-1214 (May 1999).
Chinushi, Masaomi et al., "Blood Pressure and Autonomic Responses to Electrical Stimulation of the Renal Arterial Nerves Before and After Ablation of the Renal Artery," Hypertension, vol. 61, pp. 450-456 (Jan. 2, 2013).
Coad, James E., "Thermal Tissue Injury and Host Response: A Pathologist Perspective," Slide Presentation (Mar. 2008).
Coate, KC et al., "Chronic Consumption of a High-Fat/High Fructose Diet Renders the Liver Incapable of Net Hepatic Glucose Uptake," Am. J. Physiolo. Endocrinol. Metab. vol. 299, pp. E887-E898 (Sep. 2010).
Coker, Robert H. et al., « Glucoregulation During Exercise: The Role of the Neuroendocrine System, » Sports Medicine, vol. 35, No. 7, pp. 575-583 (2005).
Consiglieri, Luisa et al., "Theoretical analysis of the heat convection coefficient in large vessels and the significance for thermal ablative therapies," Physics in Medicine and Biology, vol. 487, pp. 4125-4134 (2003).
Dancygier, H. "Clinical hepatology: Principles and practice of hepatobiliary diseases"; Berlin: Springer (2009).
Davies, Justin E. et al., «First-in-man safety evaluation of renal denervation for chronic systolic heart failure: Primary outcome from REACH-Pilot study, » International Journal of Cardiology (2012).
Defronzo, Ralph A., "From the Triumvirate to the Ominous Octet: A New Paradigm for the Treatment of Type 2 Diabetes Mellitus," Diabetes, vol. 58 (Apr. 2009), pp. 773-795.
Despa, F. et al., "The relative thermal stability of tissue macromolecules and cellular structure in burn injury," Burns, vol. 31, pp. 568-577 (2005).
Dicostanzo, Catherine A. et al., Aug. 16, 2005, Role of the Hepatic Sympathetic Nerves in the Regulation of Net Hepatic Glucose Uptake and the Mediation of the Portal Glucose Signal, Am J Physiol Endocrinol Metab 290:E9-E16.
Dodge, Jr., JT et al., «"Lumen diameter of normal human coronary arteries. Influence of age, sex, anatomic variation, and left ventricular hypertrophy or dilation," Circulation, vol. 86, pp. 232-246 (1992).
Doumas, Michael et al., "Renal sympathetic denervation in hypertension," Current Opinion in Nephrology and Hypertension, vol. 20, pp. 647-653 (2011).
Esler, Murray D et al., « Renal sympathetic denervation in patients with treatment-resistant hypertension (The Symplicity HTN-2 Trial): a randomised controlled trial, » Lancet, vol. 376, pp. 1903-1909 (2010).
Flaa Arnljot et al ., "Increased sympathetic reactivity may predict insulin resistance: an 18-year follow-up study," Metabolism Clinical and Experimental, vol. 57, pp. 1422-1427 (2008).
Grassi, G. et al., "Neuroadrenergic and reflex abnormalities in patients with metabolic syndrome," Diabetologia, vol. 48, pp. 1359-1365 (2005).
Guiot, Aurelie et al., "Collateral Nervous Damages After Cryoballoon Pulmonary Vein Isolation," Journal of Cardiovascular Electrophysiology, vol. 23, No. 4, pp. 346-351 (Apr. 2012).

(56) References Cited

OTHER PUBLICATIONS

Haines, David E. et al., Tissue Heating During Radiofrequency Catheter Ablation—A Thermodynamic Model, PACE, vol. 12, pp. 963-976 (Jun. 1989).
Haque, Mohammad Shahidul et al, "Role of the Sympathetic Nervous System and Insulin in Enhancing Glucose Uptake in Peripheral Tissues After Intrahypothalamic Injection of Leptin in Rats," Diabetes, vol. 48, pp. 1706-1712 (1999).
Hiatt, Jonathan R. et al., "Surgical Anatomy of the Hepatic Arteries in 1000 Cases," Annals of Surgery, vol. 220, No. 1, pp. 50-52 (1994).
Huang, W.C., et al. "Renal denervation prevents and reverses hyperinsulinemia-induced hypertension in rats." Hypertension, 32:249-254 (1998).
Huggett et al., "Impact of Type 2 Diabetes Mellitus on Sympathetic Neural Mechanisms in Hypertension," Circulation, vol. 108 (Dec. 15, 2003), pp. 3097-3101.
Imai, Junta et al., "Regulation of Pancreatic β Cell Mass by Neuronal Signals from the Liver," Science, vol. 322, pp. 1250-1254 (2008).
Inomoto, Takuya et al., "Experiences of 120 microsurgical reconstructions of hepatic artery in living related liver transplantation," Surgery, vol. 119, No. 1, pp. 20-26 (Jan. 1996).
Jackson, Patricia A, "Effect of hepatic denervation on the counterregulatory response to insulin-induced hypoglycemia in the dog," American Journal of Physiology—Endocrinology and Metabolism, vol. 279, pp. E1249-E1257 (2000).
Jones, R. M. et al., « The hepatic artery: a reminder of surgical anatomy, » Journal of the Royal College of Surgeons of Edinburgh, vol. 46, pp. 168-170 (Jun. 2001).
Kalsbeek, A et al., "Hypothalamic control of energy metabolism via the autonomic nervous system," Annals of the New York Academy of Sciences, vol. 1212, pp. 114-129 (2010).
Kalsbeek, Andries et al., "Suprachiasmatic GABAergic Inputs to the Paraventricular Nucleus Control Plasma Glucose Concentrations in the Rat via Sympathetic Innervation of the Liver," Journal of Neuroscience, vol. 24(35) pp. 7604-7613 (2004).
Kandzari, David E., Symplicity HTN Program Expanding Therapeutic Options for HTN and New Indications, Slides from Lecture presented at EuroPCR (May 2013).
Katholi, Richard K., "Renal nerves in the pathogenesis of hypertension in experimental animals and humans," Am. Physiol. Society (1983) F1-F14.
Katona, Peter G., "Biomedical engineering in heart-brain medicine: a review," Cleveland Clinic Journal of Medicine, vol. 77, Supplement 3, pp. S46-S50 (Jul. 2010).
Kimani, SM et al., "Comparative intimal-media morphology of the human splenic and common hepatic arteries," Journal of Morphological Science, vol. 28, No. 1, pp. 52-56 (2011).
King, Andrew J., "Splanchnic Circulation Is a Critical Neural Target in Angiotensin II Salt Hypertension in Rats," Journal of Hypertension, vol. 50, pp. 547-556 (2007).
Klieverik, Lars P. et al., "Effects of thyrotoxicosis and selective hepatic autonomic denervation on hepatic glucose metabolism in rats," American Journal of Physiology—Endocrinology and Metabolism, vol. 294, pp. E513-E520 (2008).
Klieverik, Lars P. et al., "Thyroid hormone modulates glucose production via a sympathetic pathway from the hypothalamic paraventricular nucleus to the liver," PNAS, vol. 106 (14), pp. 5966-5971 (2009).
Kolios, M. C. et al., « Large blood vessel cooling in heated tissues: a numerical study, Physics in Medicine and Biology, vol. 40, pp. 477-494 (1995).
Krum, Henry et al., "Catheter-based renal sympathetic denervation for resistant hypertension: a multicentre safety and proof-of-principle cohort study," Lancet, vol. 373, pp. 1275-1281 (2009).
Lambert, Gavin W. et al., "Sympathetic Nervous Activation in Obesity and the Metabolic Syndrome—Causes, consequences and therapeutic implications," Pharmacology & Therapeutics, vol. 126, pp. 159-172 (2010).
Lautt, W. Wayne et al., "Hepatic glucose balance in response to direct stimulation of sympathetic nerves in the intact liver of cats," Canadian Journal of Physiology and Pharmacology, vol. 56, pp. 1022-1028 (1978).
Lautt, W. Wayne et al., "Hepatic parasympathetic neural effect on glucose balance in the intact liver," Canadian Journal of Physiology and Pharmacology, vol. 56, pp. 679-682 (1978).
Lee, Aram J. et al., « The Road Less Traveled: Importance of the Lesser Branches of the Celiac Axis in Liver Embolotherapy, » RadioGraphics, vol. 32, pp. 1121-1132 (2012).
Lee, Bong-Ki et al., « Right Phrenic Nerve Injury Following Electrical Disconnection of the Right Superior Pulmonary Vein, » Pace, vol. 27, pp. 1444-1446 (2004).
Lee, King C. et al., "The Hepatic Vagus Nerve and the Neural Regulation of Insulin Secretion," Endocrinology, vol. 117, No. 1, pp. 307-315 (1985).
Lehmann, K. S. et al., "Ex situ quantification of the cooling effect of liver vessels on radiofrequency ablation," Langenbecks Archives of Surgery, vol. 394, pp. 475-481 (2009).
Licht, Carmilla M. M. et al., « Increased Sympathetic and Decreased Parasympathetic Activity Rather Than Changes in Hypothalamic-Pituitary-Adrenal Axis Activity Is Associated with Metabolic Abnormalities, Journal of Clinical Endocrinology and Metabolism, vol. 95, No. 5, pp. 2458-2466 (2010).
Lindfeldt, J. et al., "Hepatic sympathetic denervation potentiates glucagon-stimulated glycogenolysis and hyperinsulinaemia in the rat," Journal of the Autonomic Nervous System, vol. 19, pp. 211-217 (1987).
Liu, David M. et al., « Angiographic Considerations in Patients Undergoing Liver-directed Therapy, » Journal of Vascular Interventional Radiology, vol. 16, pp. 911-935 (2005).
Liu, Z. et al., "Computer modeling of the effect of perfusion on heating patterns in radiofrequency tumor ablation," International Journal of Hyperthermia, vol. 23, No. 1, pp. 49-58 (Feb. 2007).
Loukas, Marios et al., 2010, "A Review of the Thoracic Splanchnic Nerves and Celiac Ganglia," Clinical Anatomy, vol. 23, pp. 512-522.
Mahfoud, Felix et al., "Effect of Renal Sympathetic Denervation on Glucose Metabolism in Patients With Resistant Hypertension: A Pilot Study," Circulation, vol. 123, pp. 1940-1946 (Apr. 25, 2011 ).
Mancia, Giuseppe et al., "The sympathetic nervous system and the metabolic syndrome," Journal of Hypertension, vol. 25, No. 5, pp. 909-920 (2007).
McCuskey, Robert S., "Anatomy of Efferent Hepatic Nerves," The Anatomical Record Part A, vol. 280A, pp. 821-826 (2004).
Medtronic ATAKR® II 4802 Ablation System Technical Manual (2001).
Moore, Mary Courtney et al., "Chronic hepatic artery ligation does not prevent liver from differentiating portal vs. peripheral glucose delivery," American Journal of Physiology—Endocrinology and Metabolism, vol. 285, pp. E845-E853 (2003).
Moore, Mary Courtney et al., "Effect of hepatic denervation on peripheral insulin sensitivity in conscious dogs," American Journal of Physiology—Endocrinology and Metabolism, vol. 282, pp. E286-E296 (2002).
Nathan, David M. "Finding New Treatments for Diabetes—How Many, How Fast . . . How Good?," New England Journal of Medicine, vol. 356(5) (Feb. 1, 2007), pp. 437-440.
Niijima, Akira, "Glucose-Sensitive Afferent Nerve Fibres in the Hepatic Branch of the Vagus Nerve in the Guinea-Pig," Journal of Physiology, vol. 322, pp. 315-323 (1982).
Nobin, A. et al., "Organization and Function of the Sympathetic Innervation of Human Liver," Acta Physiologica Scandinavia suppl., vol. 452, pp. 103-106 (1977).
Nonogaki, K., "New insights into sympathetic regulation of glucose and fat metabolism," Diabetologia, vol. 43, pp. 533-549 (2000).
Okazaki, Hiroshi et al., "Modulation of Insulin Secretion by Hepatic Vagotomy in Cirrhotic Rats," Physiology & Behavior, vol. 53, pp. 521-525 (1993).
Panescu, Dorin et al., "Three-Dimensional Finite Element Analysis of Current Density and Temperature Distributions During Radio-Frequency Ablation," IEEE Transactions on Biomedical Engineering, vol. 42, No. 9, pp. 879-890 (Sep. 1995).

(56) References Cited

OTHER PUBLICATIONS

Pearce, John A. et al., "Blood vessel architectural features and their effect on thermal phenomena," Critical Reviews, vol. CR75, pp. 231-277, SPIE Optical Engineering Press (2000).
Perseghin, Gianluca et al., "Regulation of Glucose Homeostasis in Humans with Denervated Livers," The Journal of Clinical Investigation, vol. 100 No. 4, pp. 931-941 (Aug. 1997).
Pocai, Alessandro et al., "Hypothalamic KATP channels control hepatic glucose production," Nature, vol. 434, pp. 1026-1031 (2005).
Prochnau, Dirk et al., "Catheter-based renal denervation for drug-resistant hypertension by using a standard electrophysiology catheter," EuroIntervention, vol. 7, pp. 1077-1080 (Sep. 2011).
Puschel, Gerhard P., "Control of Hepatocyte Metabolism by Sympathetic and 13 Parasympathetic Hepatic Nerves," The Anatomical Record Part A, vol. 280A (2004), pp. 854-867.
Rippy, Marian K. et al., « Catheter-based renal sympathetic denervation: chronic preclinical evidence for renal artery safety, » Clinical Research in Cardiology, vol. 100, pp. 1095-1101 (2011).
Rizza, Robert, "Pathogenesis of Fasting and Postprandial Hyperglycemia in Type 2 Diabetes: Implications for Therapy," Diabetes, vol. 59 (Nov. 2010), pp. 2697-2707.
Roemer, R. B., « Optimal power deposition in hyperthermia, » International Journal of Hyperthermia, vol. 7, No. 2, pp. 317-341 (1991).
Roth, Steven M, "Endovenous Radiofrequency Ablation of Superficial and Perforator Veins," Surgical Clinics of North America, vol. 87, pp. 1267-1284 (2007).
Sacher, Frederic et al, "Phrenic Nerve Injury After Atrial Fibrillation Catheter Ablation," Journal of the American College of Cardiology, vol. 47, No. 12, pp. 2498-2503 (2006).
Schenk, Jr., Worthington G. et al., "Direct Measurement of Hepatic Blood Flow in Surgical Patients," Annals of Surgery, vol. 156, No. 3, pp. 463-469 (Sep. 1962).
Schlaich, Markus P. et al., "Renal Denervation in Human Hypertension: Mechanisms, Current Findings, and Future Prospects," Current Hypertension Reports, vol. 14, pp. 247-253 (2012).
Schlaich, Markus P. et al., "Renal denervation: a potential new treatment modality for polycystic ovary syndrome?" Journal of Hypertension, vol. 29, pp. 991-996 (2011).
Schlaich, Markus P. et al., "Renal Sympathetic Nerve Ablation: The New Frontier in the Treatment of Hypertension," Current Hypertension Reports, vol. 12, pp. 39-46 (2010).
Schlaich, Markus P. et al., "Renal Sympathetic-Nerve Ablation for Uncontrolled Hypertension," New England Journal of Medicine, vol. 361, No. 9, pp. 932-934 (Aug. 27, 2009).
Sherif, R.Z. et al., "Liver Anatomy," Surgical Clinics of North America, vol. 90, pp. 643-653 (2010).
Singh, Sheldon M. et al., "Esophageal Injury and Temperature Monitoring During Atrial Fibrillation Ablation," Circulation: Arrythmia and Electrophysiology, vol. 1, pp. 162-168 (Jun. 9, 2008).
Smith, Harold P. et al., "Radiofrequency neurolysis in a clinical model," Journal of Neurosurgery, vol. 55, pp. 246-253 (1981).
Steigerwald, Kristin et al. "Morphological assessment of renal arteries after radiofrequency catheter-based sympathetic denervation in a porcine model," Journal of Hypertension, vol. 30, No. 1, pp. 1-10 (2012).
Stiimpel, F., "Loss of regulation by sympathetic hepatic nerves of liver metabolism and haemodynamics in chronically streptozotocin-diabetic rats," Diabetologia, vol. 39, pp. 161-165 (1996).
Stovichek, GV et al., "Morphological Regularities of Adventitial Nerve Plexus Variability in Visceral Arteries on Different Stages of Human Postnatal Ontogenesis," Morphology, vol. 112, No. 5, pp. 43-48 (1997).
Stovichek, GV, "Comparative evaluation of age-related and organic characteristics of the structure of the adventitial nerve plexuses in human arteries," Archives of Anatomy, Histology and Embryology, vol. 93, No. 9, pp. 77-82 (1987).
Stovichek, GV, "Myeloarchitectonics of visceral nerves during human ontogeny," Archives of Anatomy, Histology and Embryology, vol. 80, No. 1, pp. 30-38 (1981).
Stovichek, GV, "Regularities of the Morphogenesis of Visceral Organ Nervous Connections at Different Stages of Human Postnatal Development," Morphology, vol. 125, No. 3, pp. 14-18 (2004).
Straznicky, Nora E. et al., « Neuroadrenergic Dysfunction Along the Diabetes Continuum: A Comparative Study in Obese Metabolic Syndrome Subjects, > Diabetes, vol. 61, pp. 2506-2516 (2012).
Taborsky, Jr., Gerald J. et al., "Minireview: The Role of the Autonomic Nervous System in Mediating the Glucagon Response to Hypoglycemia," Endocrinology, vol. 153, pp. 1055-1062 (2012).
Takahashi, Akira, "Effects of hepatic nerve stimulation on blood glucose and glycogenolysis in rat liver: Studies with in vivo microdialysis," Journal of the Autonomic Nervous System, vol. 61, pp. 181-185 (1996).
Takahashi, Kanji A. et al., « Fasting Induces a Large, Leptin-Dependent Increase in the Intrinsic Action Potential Frequency of Orexigenic Arcuate Nucleus Neuropeptide Y/Agouti-Related Protein Neurons, » Endocrinology, vol. 146, No. 3, pp. 1043-1047 (2005).
Tangwongsan, Chanchana, "Fluid Velocity Measurement Using Convective Heat Transfer Coefficient Measuring System," 2007 IEEE/NIH Life Science Systems and Applications Workshop, pp. 81-87 (2007).
Tavares, Fabio Luis et al., « Hepatic denervation impairs the assembly and secretion of VLDL-TAG, » Cell Biochemistry and Function, vol. 26, pp. 557-565 (2008).
Tentolouris, N. et al., "Sympathetic System Activity in Obesity and Metabolic Syndrome," Annals New York Academy of Sciences, vol. 1083, pp. 129-152 (2006).
Tentolouris, Nicholas et al., Perturbed Autonomic Nervous System Function in Metabolic Syndrome, Neuromolecular Medicine, vol. 10, pp. 169-178 (2008).
Thompson, Mary et al., "Renal Denervation Sparks Device Market Gold Rush," Elsevier Business Intelligence, Medtech Insight, vol. 24, No. 5 (May 2012).
Tungjitkusolmun, Supan et al., "Three-Dimensional Finite-Element Analyses for Radio-Frequency Hepatic Tumor Ablation," IEEE Transactions on Biomedical Engineering, vol. 49, No. 1, pp. 3-9 (Jan. 2002).
Tziafalia, Christina et al., "Echo-Doppler Measurements of Portal Vein and Hepatic Artery in Asymptomatic Patients with Hepatitis B Virus and Healthy Adults," Journal of Gastrointestinal and Liver Diseases, vol. 15, No. 4, pp. 343-346 (Dec. 2006).
Uchida, F., et al. "Effect of radio frequency catheter ablation on parasympathetic denervation: A comparison of three different ablation sites," Pace, 21:2517- 2521 (1998).
Uchida, Masfumi et al., "CT Image Fusion for 3D Depiction of Anatomic Abnormalities of the Hepatic Hilum," American Journal of Roentgenology, vol. 189, pp. W184-W191 (Oct. 2007).
Ulucakli, M. Erol, "Simulation of Radiofrequency Ablation and Thermal Damage to Tissue," IEEE Annual Northeast Bioengineering Conference, pp. 93-94 (2006).
Unger, Roger H. et al., "Glucagonocentric restructuring of diabetes: a pathophysiologic and therapeutic makeover," The Journal of Clinical Investigation, vol. 122, No. 1 (2012).
Uno, Kenji et al., « Neuronal Pathway from the Liver Modulates Energy Expenditure and Systemic Insulin Sensitivity, Science, vol. 312, pp. 1656-1659 (Jun. 16, 2006).
Valvano, J.W. et al., « Thermal Conductivity and Diffusivity of Biomaterials Measured with Self-Heated Thermistors, » International Journal of Thermophysics, vol. 6, No. 3, pp. 301-311 (1985).
Van Den Hoek, Anita M. et al., Sep. 2008, Intracerebroventricular Administration of Neuropeptide Y Induces Hepatic Insulin Resistance via Sympathetic Innervation, Diabetes, vol. 57, pp. 2304-2310.
Vaz, Mario et al., "Regional Sympathetic Nervous Activity and Oxygen Consumption in Obese Normotensive Human Subjects," Circulation, vol. 96, pp. 3423-3429 (1997).
Wada, Masahiko et al., "Hepatic denervation does not significantly change the response of the liver to glucagon in conscious dogs," American Journal of Physiology—Endocrinology and Metabolism, vol. 268, pp. E194-E203 (1995).

(56) References Cited

OTHER PUBLICATIONS

Watton, Paul N. et al., "Modelling the mechanical response of elastin for arterial tissue," Journal of Biomechanics, vol. 42, pp. 1320-1325 (2009).
Wiersma, Mariska M.L. et al., Effect of liver denervation on glucose production during running in guinea pigs, »American Journal of Physiology—Regulatory Integrative Comparative Physiology, vol. 268, pp. R72-R77 (1995).
Witkowski, Adam et al., "Effects of Renal Sympathetic Denervation on Blood Pressure, Sleep Apnea Course, and Glycemic Control in Patients With Resistant Hypertension and Sleep Apnea," Journal of Hypertension, vol. 58, pp. 559-565 (2011).
Wood, Thomas H., "Lethal Effects of High and Low Temperatures on Unicellular Organisms," Advanced Biology of Medicine and Physics, vol. 4, pp. 119-165 (1956).
Wright, Neil T., "On a Relationship Between the Arrhenius Parameters from Thermal Damage Studies," Transactions of the ASME, vol. 125, pp. 300-304 (Apr. 2003).
Xie, Hongheng et al., "Insulin resistance of skeletal muscle produced by hepatic parasympathetic interruption," American Journal of Physiology—Endocrinology and Metabolism, vol. 270, pp. E858-E863 (1996).
Xie, Hongsheng et al., "Insulin resistance of glucose response produced by hepatic denervations," Canadian Journal of Physiology and Pharmacology, vol. 71, pp. 175-178 (Feb. 1993).
Yi, Chun-Xia et al., « Pituitary Adenylate Cyclase-Activating Polypeptide Stimulates Glucose Production via the Hepatic Sympathetic Innervation in Rats, » Diabetes, vol. 59, pp. 1591-1600 (Jul. 2010).
Yi, Chun-Xia et al., «A Major Role for Perifornical Orexin Neurons in the Control of Glucose Metabolism in Rats, » Diabetes, vol. 58, Sep. 2009, pp. 1998-2005.
Yi, Chun-Xia et al., 2010, "The Role of the Autonomic Nervous Liver Innervation in the Control of Energy Metabolism," Biochimica et Biophysica Acta vol. 1802, pp. 416-431.
Yu, Nam C. et al., "Microwave Liver Ablation: Influence of Hepatic Vein Size on Heat-sink Effect in a Porcine Model," Journal of Vascular Interventional Radiology, vol. 19, pp. 1087-1092 (2008).
Zile, Michael R. et al., Effects of Autonomic Modulation, » Journal of the American College of Cardiology, vol. 59, No. 10, pp. 910-912 (2012).
Martinez Cecilia A Y.et al, Transfection of Primary CNS and PNS neurons by electroporation, Methods in Cell Biology, vol. 71, pp. 321-332 (2003).
Jiang C., Review of Basic to Clinical Studies of Irreversible Electroporation Therapy, IEEE Transactions on Biomedical Engineering, vol. 62, No. 1; Jan. 2015; pp. 4-20.
Davalos R.V.; Tissue Ablation with irreversible electroporation; Annal of Biomedical Engineering; vol. 33, No. 2, Feb. 2005; pp. 223-231.
International Search Report and Written Opinion of International Application No. PCT/US2015/063807 dated Mar. 31, 2016, 15 pp.
Adkins-Marshall et al., "Role of hepatic nerves in response of liver to intraportal glucose delivery in dogs", The American Journal of Physiology—Endocrinology and Metabolism, vol. 262, No. 5, the American Physiological Society, May 1992, pp. E679-E686, doi.org/10.1152/ajpendo.1992.262.5.E679.
Anil et al., "Feeding in Sheep During Intraportal Infusions of Short-Chain Fatty Acids in the Effect of Liver Denervation", The Journal of Physiology, vol. 298, The Physiological Society, Apr. 12, 1979, pp. 407-414, doi: 10.1113/jphysiol.1980.sp013090.
Carlson et al., "Hepatic Denervation Chronically Elevates Arterial Pressure in Wistar-Kyoto Rats", AHA Journals, American Heart Association, Inc., Feb. 6, 1998, pp. 46-51, URL: https://www.ahajournals.org/doi/10.1161/01.HYP.32.1.46.
Chida et al., "The hepatic sympathetic nerve plays a critical role in preventing Fas induced liver injury in mice", National Library of Medicine, vol. 54, No. 7, Jul. 2005, pp. 994-1002, Retrieved from the Internet on Jan. 2, 2024 from URL: https://www.ncbi.nlm.nih.gov/pmc/articles/PMC1774625/pdf/gut05400994.pdf.

Colle et al., "Transplanted Liver: Consequences of Denervation for Liver Functions", American Association for Anatomy, vol. 280, No. 1, John Wiley & Sons, Inc., Aug. 24, 2004, pp. 924-931, URL:https://anatomypubs.onlinelibrary.wiley.com/doi/pdfdirect/10.1002/ar.a.20097.
Dibona et al., "Neural Control of Renal Function", Physiological Reviews, vol. 77, No. 1, Jan. 1, 1997, pp. 75-197, URL: https://journals.physiology.org/doi/abs/10.1152/physrev.1997.77.1.75.
Dibona, "Renal Innervation and Denervation: Lessons from Renal Transplantation Reconsidered", International Society for Artificial Organs, vol. 11, No. 6, John Wiley & Sons, Inc., Dec. 1987, pp. 457-462, Retrieved from the Internet on Dec. 28, 2023 from URL: https://onlinelibrary.wiley.com/doi/abs/10.1111/j.1525-1594.1987.tb02710.x.
Dibona, "Sympathetic Nervous System and Hypertension", Recent Advances in Hypertension, American Heart Association, Inc., Dec. 27, 2012, pp. 556-560, URL: https://www.ahajournals.org/doi/pdf/10.1161/HYPERTENSIONAHA.111.00633.
Dicostanzo et al., "Role of the hepatic sympathetic nerves in the regulation of net hepatic glucose uptake and the mediation of the portal glucose signal", American Journal of Physiology—Endocrinology and Metabolism, vol. 290, No. 1, American Physiological Society, Jan. 1, 2006, pp. E9-E16, doi:10.1152/ajpendo.00184.2005.
Dolnikoff et al., "Neural mechanisms involved in the recovery from insulin hypoglycemia in dogs", Journal of the Autonomic Nervous System, vol. 8, No. 2, Elsevier, Jun. 1983, pp. 129-139, https://doi.org/10.1016/0165-1838(83)90099-1.
Erdine, "Celiac Ganglion Block", Interventional Treatment, vol. 17, No. 1, Agri, 2005, pp. 15-22, (Applicant points out, in accordance with MPEP 609.04(a), that the year of publication, 2005, is sufficiently earlier than the effective U.S. filing date, so that the particular month of publication is not an issue.).
Esler, "The Sympathetic System and Hypertension", American Journal of Hypertension, Ltd, vol. 13, No. 3, Elsevier Science, Inc., Jun. 1, 2000, pp. 99S-105S, URL: https://academic.oup.com/ajh/article/13/S4/99S/186509.
Evans, "The Place of Splanchnicectomy in the Treatment of Hypertension", Canadian Medical Association journal, vol. 64, No. 1, Jan. 1951, pp. 47-50, Retrieved from the Internet on Dec. 28, 2023 from URL: https://www.ncbi.nlm.nih.gov/pmc/articles/PMC1821460/pdf/canmedaj00652-0049.pdf.
Foss et al., "Reversal of Genetic Salt-Sensitive Hypertension by Targeted Sympathetic Ablation", Nervous System, vol. 61, No. 4, American Heart Association, Inc., Jan. 11, 2013, pp. 806-811.
Franco-Colin et al., "The effects of sympathectomy and dexamethasone in rats ingesting Sucrose", International Journal of Biological Sciences, vol. 2, No. 1, PubMed, Mar. 4, 2006, pp. 17-22, doi:10.7150/ijbs.2.17.
Gao et al., "Effects of High NaCI Diet on Arterial Pressure in Sprague-Dawley Rats with Hepatic and Sinoaortic Denervation", Japanese Journal of Physiology, vol. 55, No. 4, PubMed, Oct. 26, 2005, pp. 229-234, doi:10.2170/jjphysiol.S638.
Grimson et al., "Total thoracic and partial to total lumbar sympathectomy and celiac ganglionectomy in the treatment of hypertension", Annals of Surgery, vol. 114, No. 4, Oct. 1941, pp. 532-547, Retrieved from the Internet on Dec. 29, 2023 from URL: https://www.ncbi.nlm.nih.gov/pmc/articles/PMC1609434/.
Hayes et al., "The common hepatic branch of the vagus is not required to mediate the glycemic and food intake suppressive effects of glucagon-like-peptide-1", American Journal of Physiology—Regulatory, Integrative and Comparative Physiology, vol. 301, No. 5, PubMed, Aug. 17, 2011, pp. R1479-R1485, doi:10.1152/ajpregu.00356.2011.
Holmin et al., "A Microsurgical Method for Denervation of the Liver in the Rat", European Surgical Research, vol. 16, No. 5, 1984, pp. 288-293, (Applicant points out, in accordance with MPEP 609.04(a), that the year of publication, 1984, is sufficiently earlier than the effective U.S. filing date, so that the particular month of publication is not an issue.).

(56) References Cited

OTHER PUBLICATIONS

Xie et al., "Induction of insulin resistance by cholinergic blockade with atropine in the cat", Journal of Autonomic Pharmacology, vol. 15, No. 5, Oct. 1995, pp. 361-369, doi.org/10.1111/j.1474-8673.1995.tb00402.x.

Hoobler et al., "The Effects of Splanchuicectomy on the Blood Pressure in Hypertension A Controlled Study", vol. 4, Aug. 1951, pp. 173-183, Retrieved from the Internet on Dec. 28, 2023 from URL: https://www.ahajournals.org/doi/pdf/10.1161/01.CIR.4.2.173.

Hurr et al., "Liver sympathetic denervation reverses obesity-induced hepatic steatosis", The Journal of Physiology, vol. 597, No. 17, Jul. 6, 2019, pp. 4565-4580.

Irvine et al., "The Effect of Renal Denervation on Patients Suffering from Nephritis", The Journal of Clinical Investigation, vol. 14, No. 4, Feb. 27, 1935, pp. 443-458, URL: https://dm5migu4zj3pb.cloudfront.net/manuscripts/100000/100695/JCI35100695.pdf.

Jackson et al., "Effect of hepatic denervation on the counterregulatory response to insulin-induced hypoglycemia in the dog", American Journal of Physiology-Endocrinology and Metabolism, vol. 279, American Physiological Society, Dec. 1, 2000, pp. E1249-E1257, doi.org/10.1152/ajpendo.2000.279.6.E1249.

Jackson et al., "Effects of vagal blockade on the counterregulatory response to insulin-induced hypoglycemia in the dog", American Journal of Physiology—Endocrinology and Metabolism, vol. 273, No. 6, The American Physiological Society, Dec. 1, 1997, pp. E1178-E1188, doi.org/10.1152/ajpendo.1997.273.6.E1178.

Johns et al., "Neural Control of Renal Function", Comprehensive Physiology, vol. 1, Elsevier, Apr. 1, 2011, pp. 731-767.

Jonassen et al., "Effects of renal denervation on tubular sodium handling in rats with CBL-induced liver cirrhosis", American Journal of Physiology—Renal Physiology, vol. 284, No. 3, Nov. 19, 2002, pp. F555-F563, URL: https://journals.physiology.org/doi/full/10.1152/ajprenal.00258.2002.

Kandlikar et al., "Splanchnic sympathetic nerves in the development of mild DOCA-salt hypertension", American Physiological Society, Aug. 25, 2011, pp. H1965-H1973.

Kihara et al., "Impaired vasoreactivity to nitric oxide in experimental diabetic neuropathy", Experimental Neurology, vol. 132, No. 2, Elsevier, Apr. 1995, pp. 180-185, doi.org/10.1016/0014-4886(95)90023-3.

King et al., "Splanchnic Circulation Is a Critical Neural Target in Angiotensin II Salt Hypertension in Rats", American Heart Association, Jul. 23, 2007, pp. 547-556.

Kiuchi et al., "Combined renal and common hepatic artery denervation as a novel approach to reduce cardiometabolic risk: technical approach, feasibility and safety in a pre-clinical model", Clinical Research in Cardiology, vol. 110, Springer, Feb. 26, 2021, pp. 740-753, URL: https://link.springer.com/article/10.1007/s00392-021-01814-1.

Knuepfer et al., "Direct assessment of organ specific sympathetic nervous system activity in normal and cardiovascular disease states", Experimental physiology, vol. 95, No. 1, National Institutes of Health, Jan. 2010, pp. 31-33, Retrieved from the Internet on Jan. 2, 2024 from URL: https://www.ncbi.nlm.nih.gov/pmc/articles/PMC2856076/pdf/nihms172439.pdf.

Kraft et al., "Safety of surgical denervation of the common hepatic artery in insulin-resistant dogs", Physiological Reports, vol. 9, No. 6, John Wiley & Sons, Inc., Mar. 2021, 11 pp., Retrieved from the Internet on Dec. 28, 2023 from URL: https://physoc.onlinelibrary.wiley.com/doi/pdfdirect/10.14814/phy2.14805.

Kraft et al., "Sympathetic Denervation of the Common Hepatic Artery Lessens Glucose Intolerance in the Fat- and Fructose-Fed Dog", Diabetes, vol. 68, No. 6, American Diabetes Association, Jun. 1, 2019, pp. 1143-1155, URL: https://diabetesjournals.org/diabetes/article/68/6/1143/39704/Sympathetic-Denervation-of-the-Common-Hepatic.

Kumakura et al., "Effects of celiac superior mesenteric ganglionectomy on glucose homeostasis and hormonal changes during oral glucose tolerance testing in rats", Endrocrine Journal, vol. 60, No. 4, The Japan Endocrine Society, Dec. 12, 2012, pp. 525-531.

Lamarche et al., "Hepatic denervation reduces adrenal catecholamine secretion during insulin-induced hypoglycemia", American Journal of Pyshiology—Regulatory, Integrative and Comparative Physiology, vol. 268, No. 1, Jan. 1995, pp. R50-R57, doi.org/10.1152/ajpregu.1995.268.1.R50.

Lang et al., "Hepatic regulation of renal function", Experimental Physiology: Translation and Integration, vol. 77, No. 5, John Wiley & Sons, Inc., Sep. 1, 1992, pp. 663-673.

Lautt et al., "Afferent and Efferent Neural Roles in Liver Function", Progress in Neurobiology, vol. 21, Pergamon Press Ltd., May 23, 1983, pp. 323-348.

Lautt et al., "Hepatic parasympathetic neuropathy as cause of maturity-onset diabetes?", General Pharmacology: The Vascular System, vol. 11, No. 4, Pergamon Press Ltd., Oct. 19, 1979, pp. 343-345, doi.org/10.1016/0306-3623(80)90096-8.

Lautt et al., "Rapid insulin sensitivity test", Canadian Journal of Physiology and Pharmacology, vol. 76, No. 12, Dec. 1998, pp. 1080-1086, doi: 10.1139/cjpp-76-12-1080.

Levy et al., "Hepatic denervation alters first-phase urinary sodium excretion in dogs with cirrhosis", American Journal of Physiology—Renal Physiology, vol. 253, No. 4, Oct. 1, 1987, pp. F664-F671.

Levy et al., "Sodium excretion in dogs with low-grade caval constriction: role of hepatic nerves", American Journal of Physiology—Renal Physiology, vol. 253, No. 4, Oct. 1, 1987, pp. F672-F678.

Lindfeldt et al., "Glucose homeostasis after peri-arterial hepatic denervation in partially Hepatectomized rats", Research in Experimental Medicine, vol. 193, Springer-Verlag, Jul. 13, 1993, pp. 397-405, https://doi.org/10.1007/BF02576248.

Louis-Sylvestre et al., "Effect of liver denervation on the feeding pattern of rats", American Journal of Pyshiology—Regulatory, Integrative and Comparative Physiology, vol. 239, No. 1, The American Physiological Society, Jul. 1, 1980, pp. R66-R70, doi.org/10.1152/ajpregu.1980.239.1.R66.

Moore et al., "Effect of hepatic denervation on peripheral insulin sensitivity in conscious dogs", American Journal of Physiology—Endocrinology and Metabolism, vol. 282, Oct. 4, 2001, pp. E286-E296, doi:10.1152/ajpendo.00201.2001.

Murakami et al., "Hepatic Denervation Ameliorates Sodium and Water Retention in Experimental Cirrhosis in Rats", Digestive diseases and sciences, vol. 42, No. 11, Nov. 1997, pp. 2292-2298.

Niijima, "Blood Glucose Levels Modulate Efferent Activity in the Vegal Supply to the Rat Liver", The Journal of Physiology, vol. 364, Great Britain, Oct. 25, 1984, pp. 105-112, doi:10.1113/jphysiol.1985.sp015733.

Osborn et al., "Sympathetic Signatures of Cardiovascular Disease: A Blueprint for Development of Targeted Sympathetic Ablation Therapies", AHA Journals, vol. 59, No. 3, American Heart Association, Inc, Mar. 2012, pp. 545-547, Retrieved from the Internet on Jan. 2, 2024 from URL: https://www.ahajournals.org/doi/epub/10.1161/HYPERTENSIONAHA.111.182899.

Patarrão et al., "A new technique to assess insulin sensitivity in humans: the rapid insulin sensitivity test (RIST)", Proceedings of the Western Pharmacology Society, vol. 50, 2007, pp. 105-109, (Applicant points out, in accordance with MPEP 609.04(a), that the year of publication, 2007, is sufficiently earlier than the effective U.S. filing date, so that the particular month of publication is not an issue.).

Perseghin et al., "Regulation of Glucose Homeostasis in Humans with Denervated Livers", Glucose Metabolism and Liver Denervation, vol. 100, No. 4, The American Society for Clinical Investigation, Inc., Aug. 1997, pp. 931-941.

Xie et al., "Insulin resistance caused by hepatic cholinergic interruption and reversed by acetylcholine administration", American Journal of Physiology—Endocrinology and Metabolism, vol. 271, No. 9, Sep. 1996, pp. E587-E592, doi.org/10.1152/ajpendo.1996.271.3.E587.

Yi et al., "The role of autonomic nervous liver innervation in the control of energy metabolism", Biochimica et Biophysica Acta, vol. 1802, No. 4, Elsevier, Apr. 2010, pp. 416-431, doi:10.1016/j.bbadis.2010.01.006.

(56) References Cited

OTHER PUBLICATIONS

Office Action from U.S. Appl. No. 18/741,373 dated Aug. 15, 2024, 13 pp.
Advisory Action from U.S. Appl. No. 18/741,373 dated Apr. 2, 2025, 3 pp.
Final Office Action from U.S. Appl. No. 18/741,373 dated Feb. 10, 2025, 17 pp.

* cited by examiner

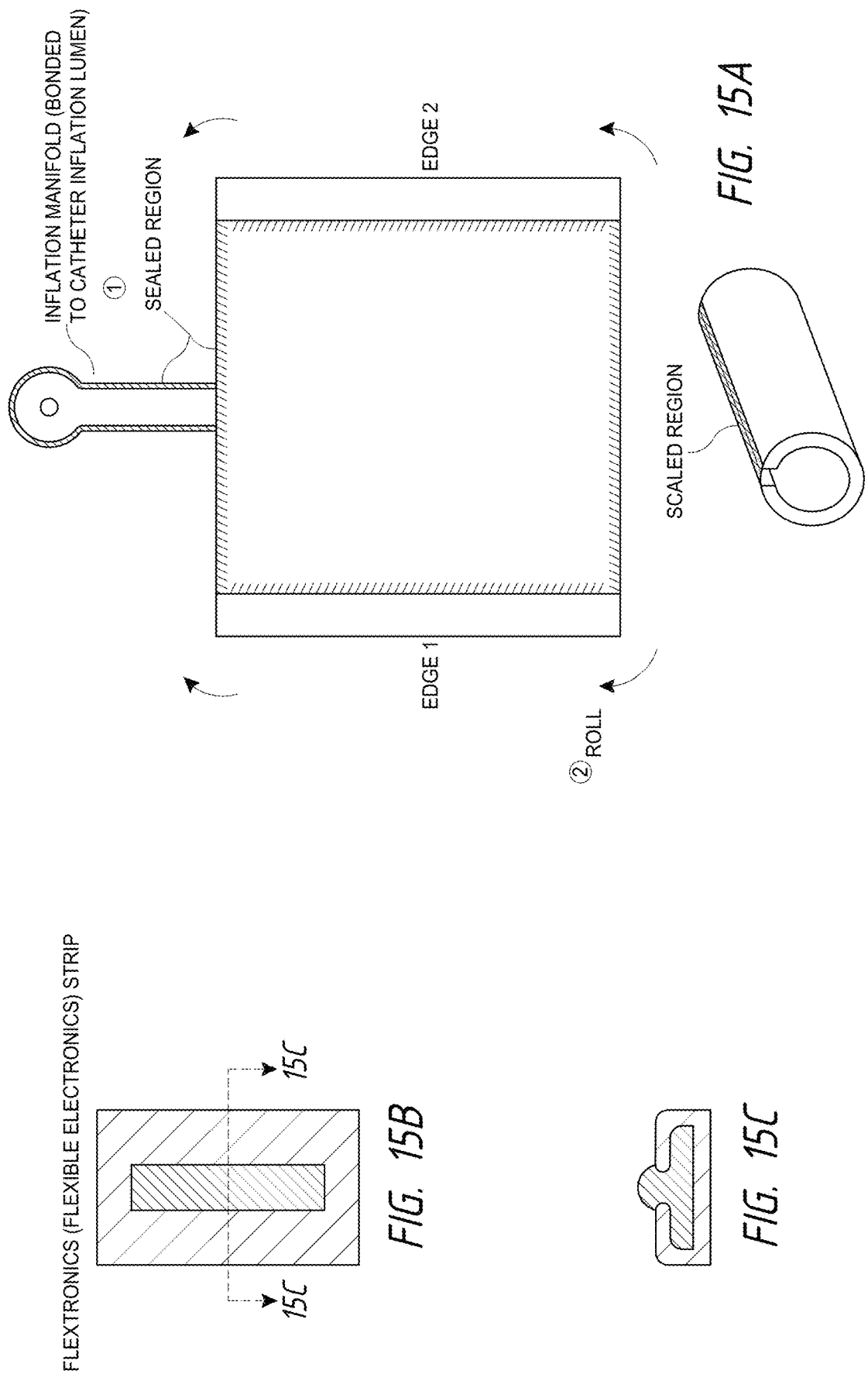

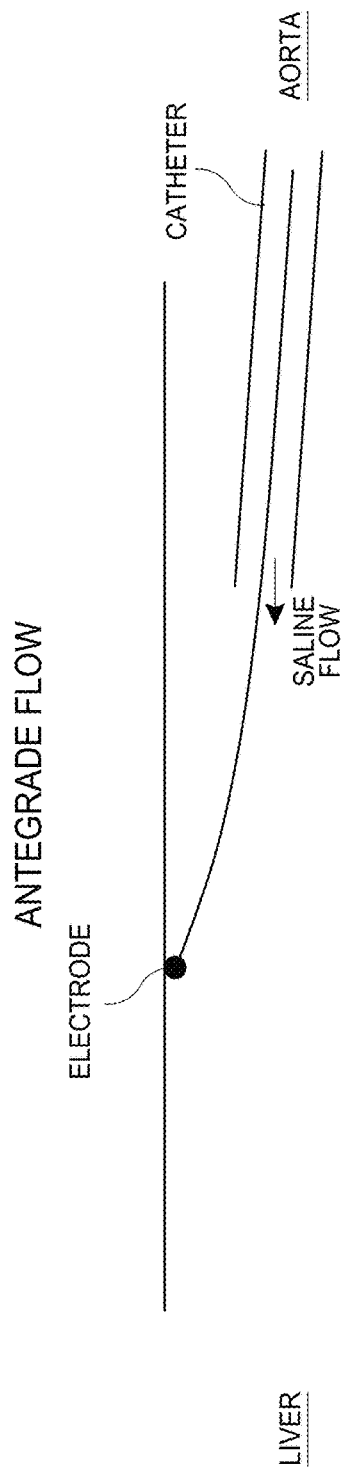
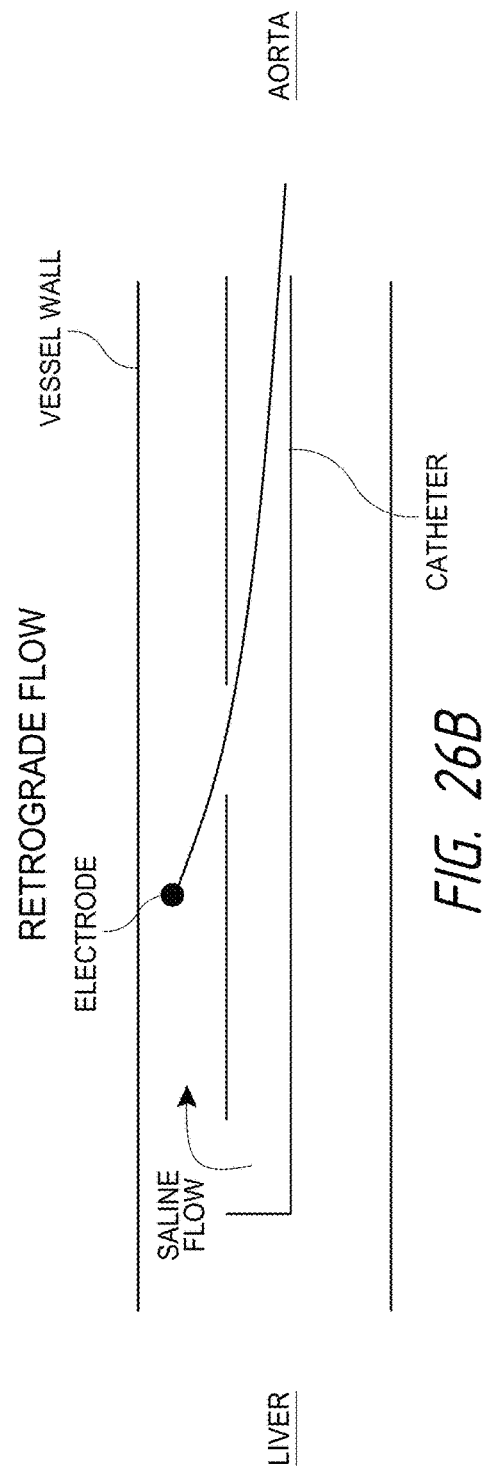
FIG. 26A
FIG. 26B

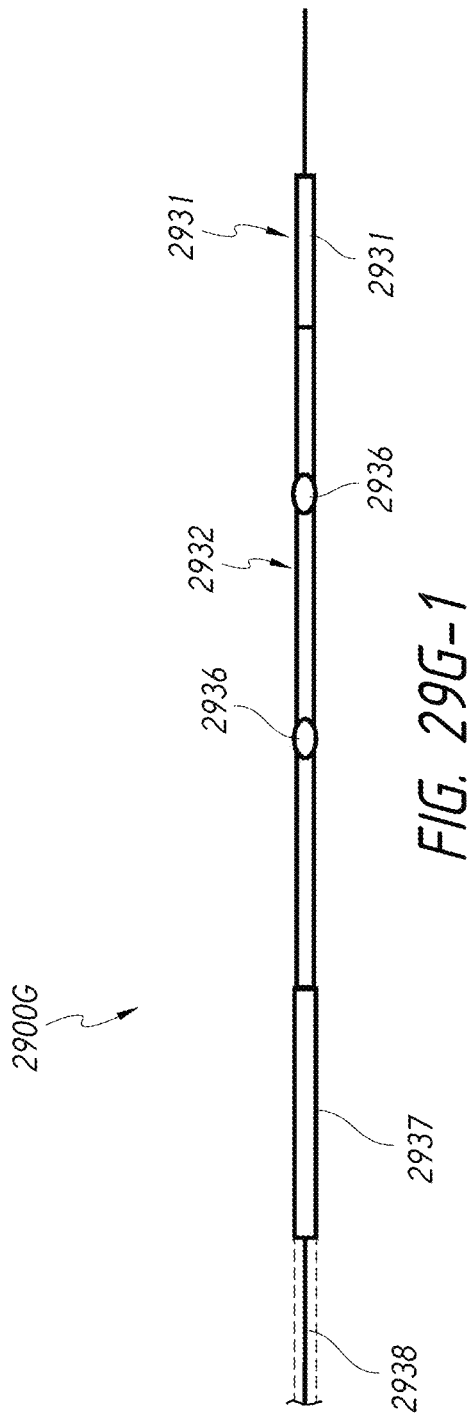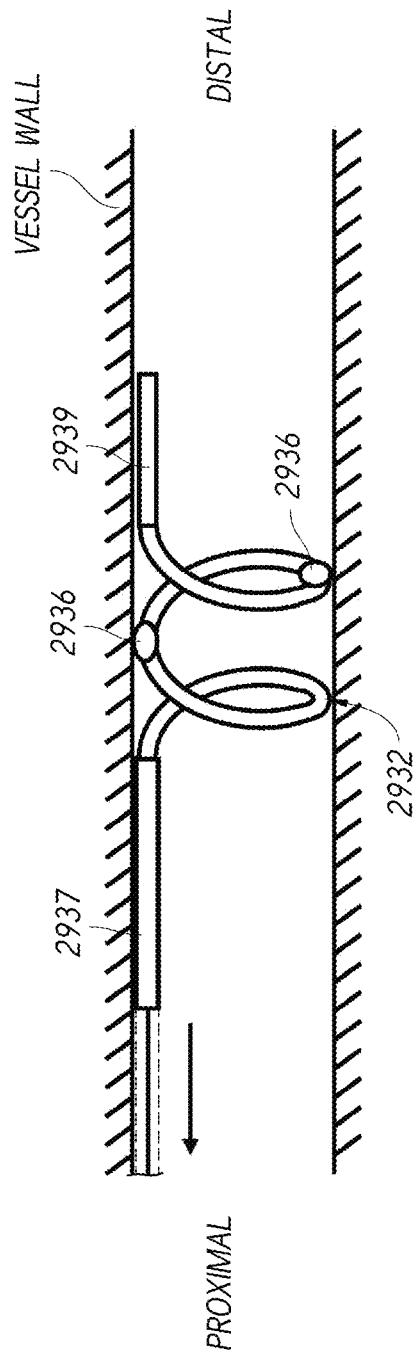
FIG. 29G-1
FIG. 29G-2

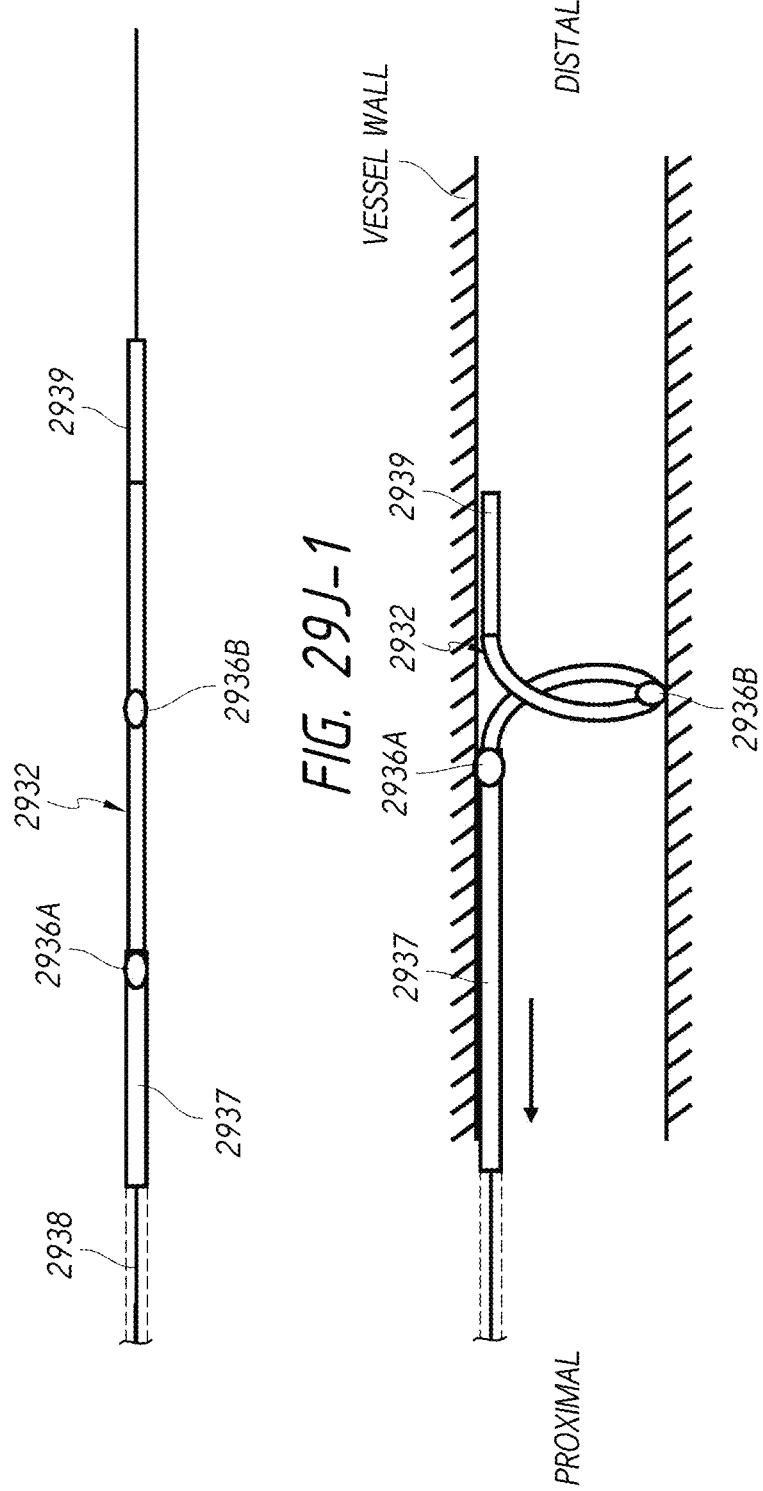

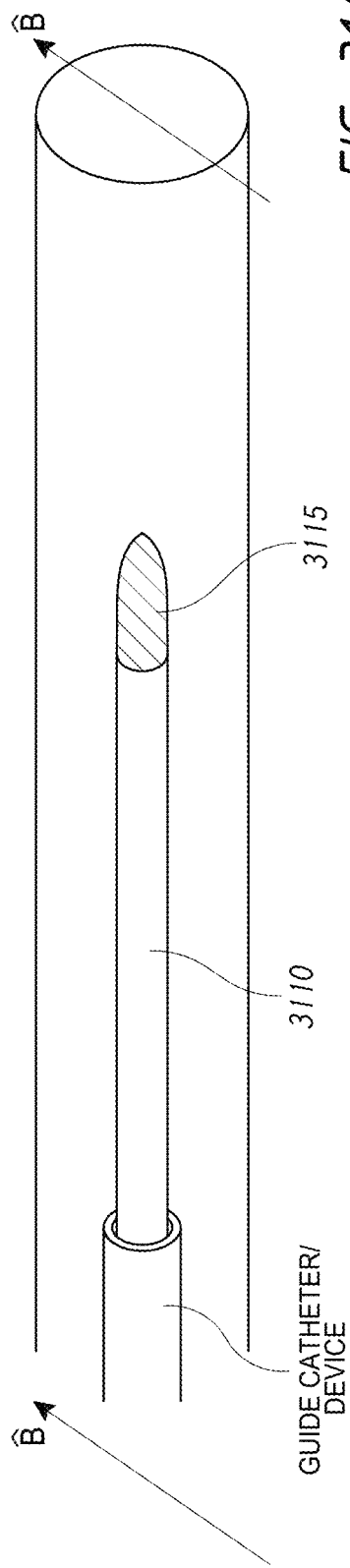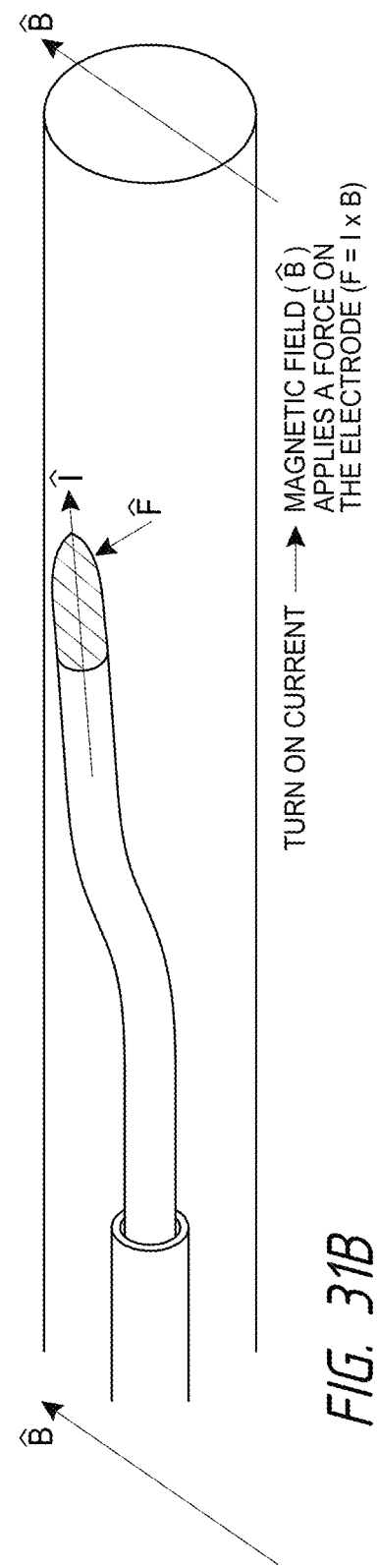

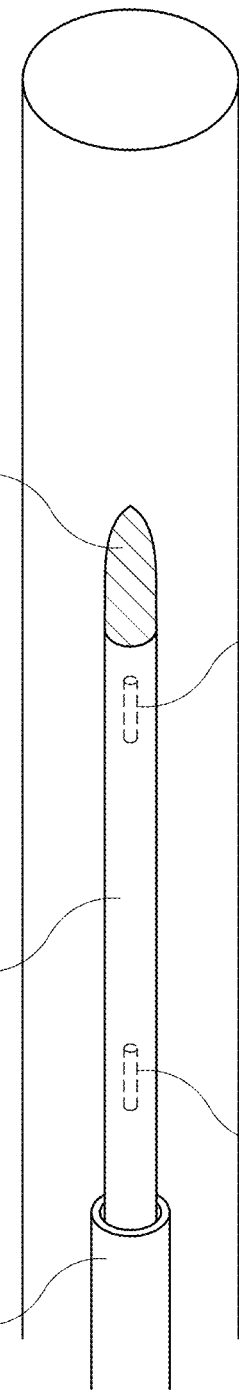
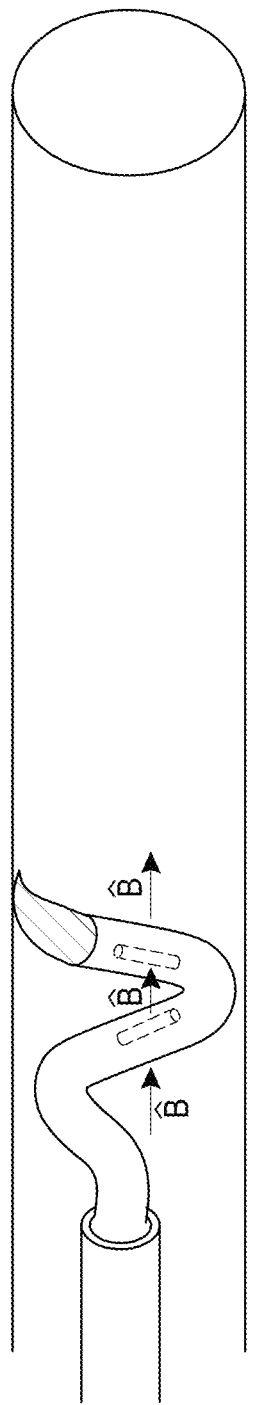

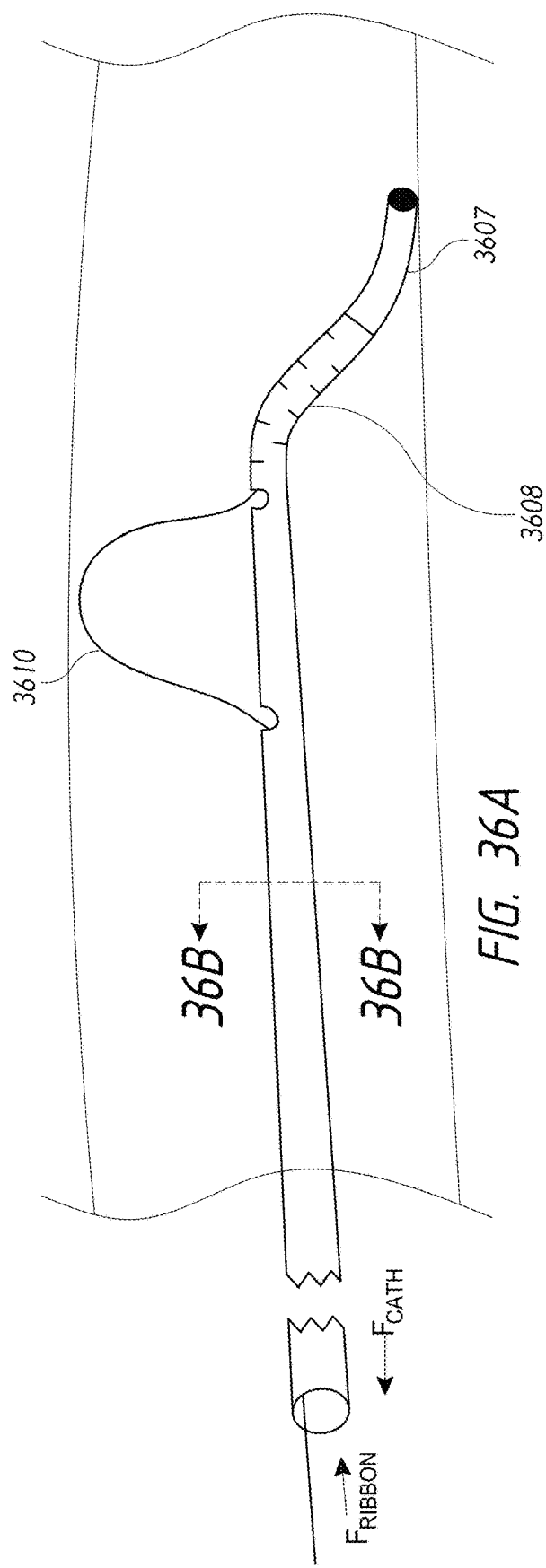
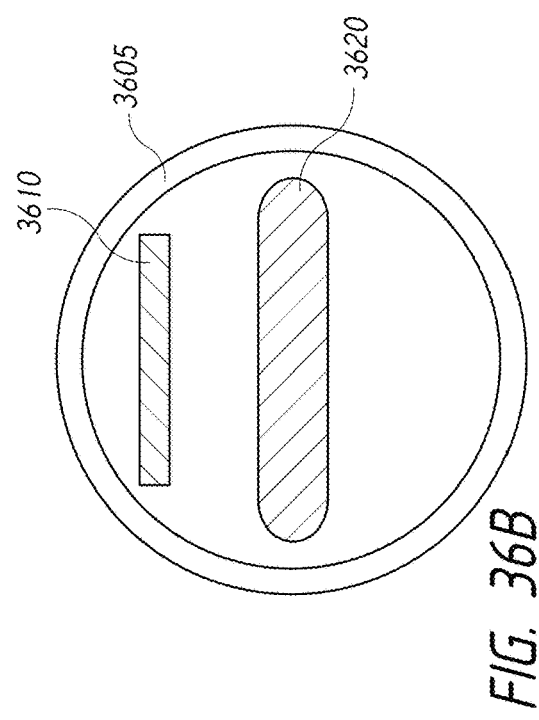
FIG. 36A
FIG. 36B

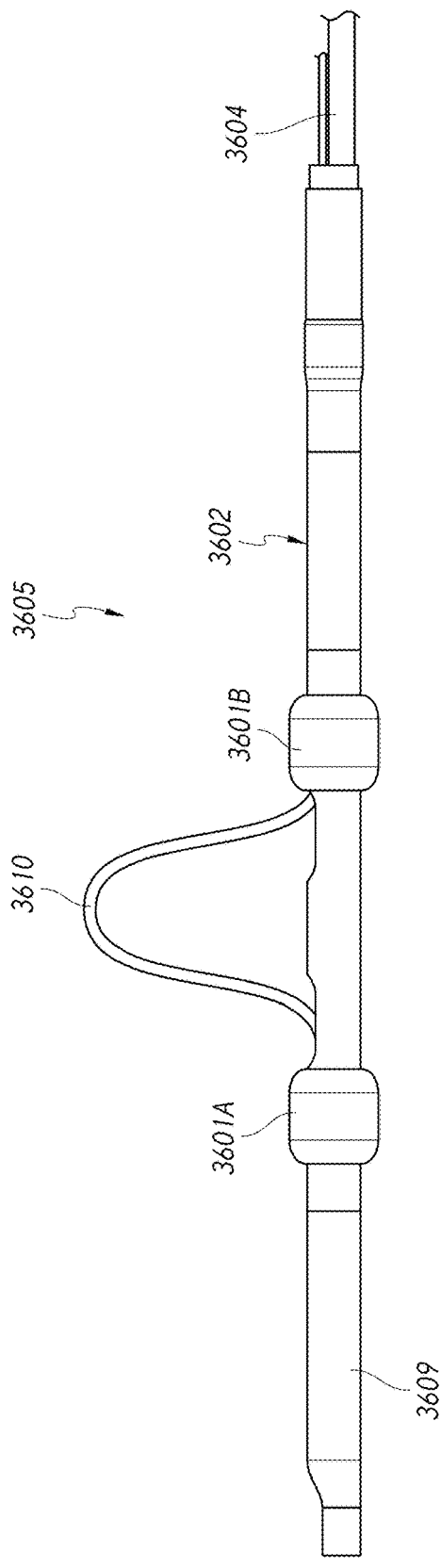
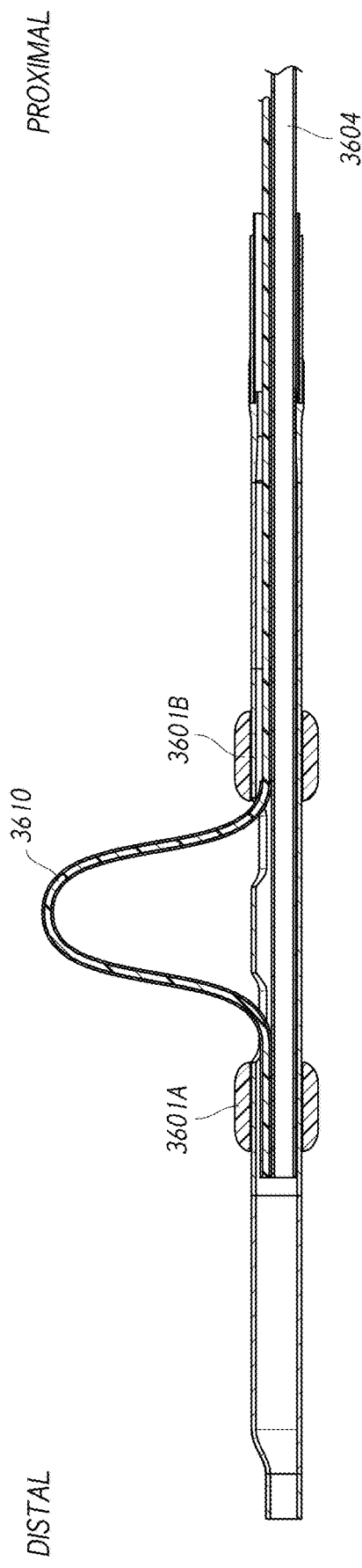
FIG. 36C
FIG. 36D

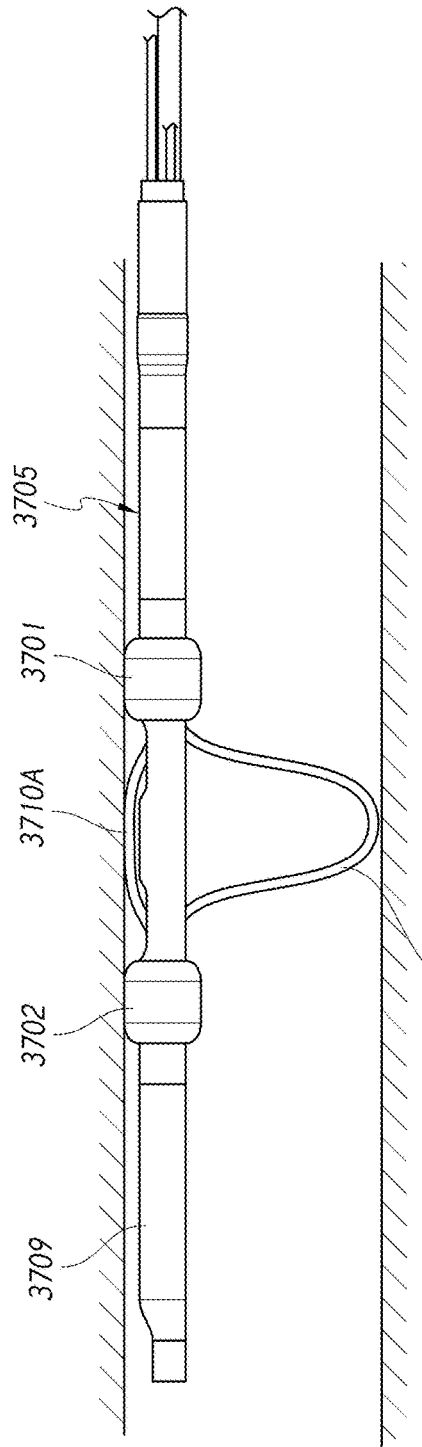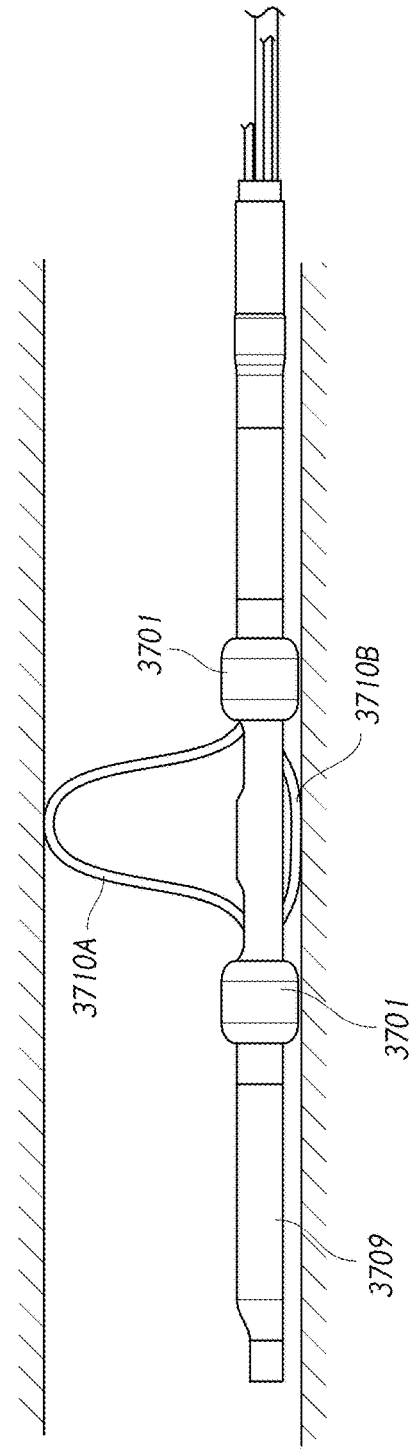

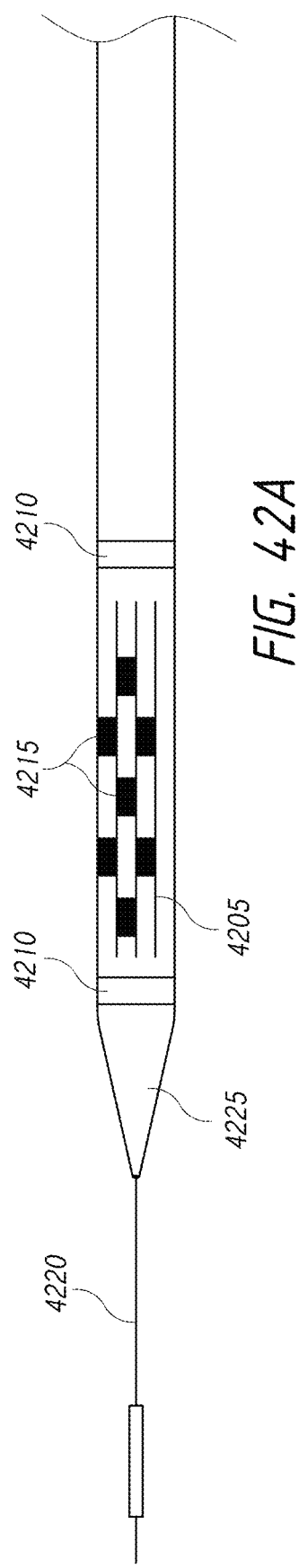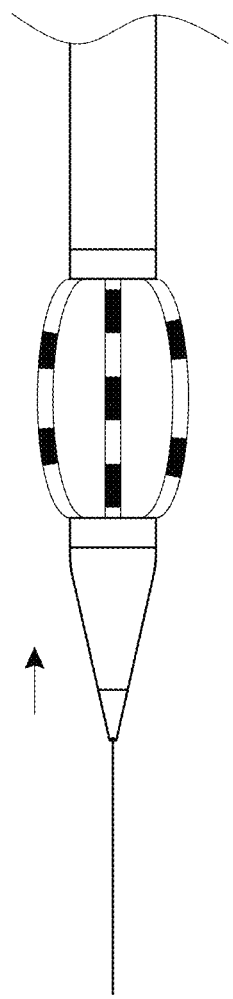

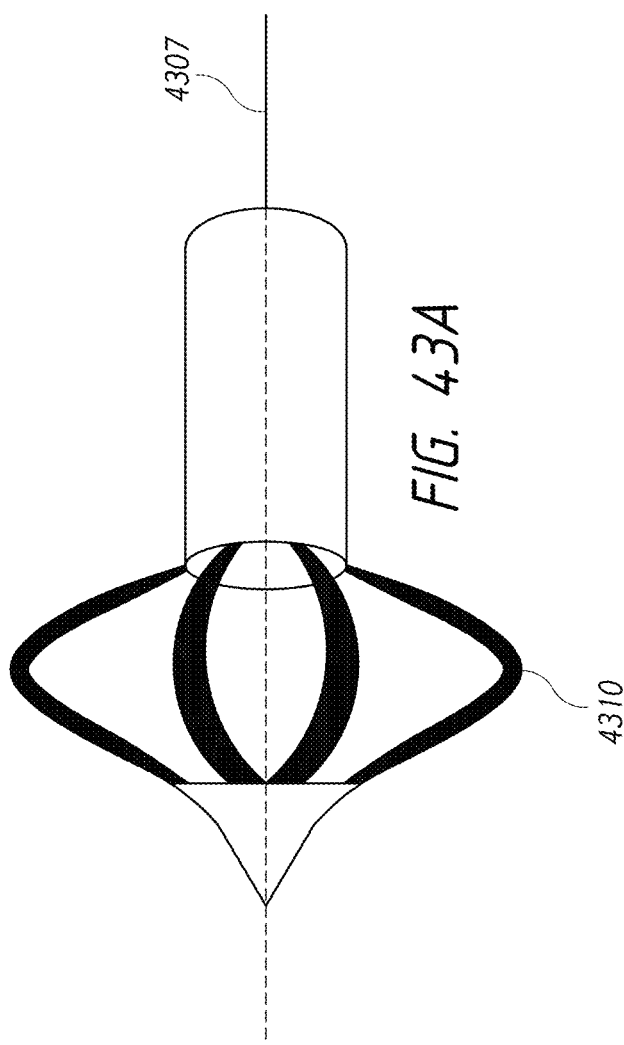
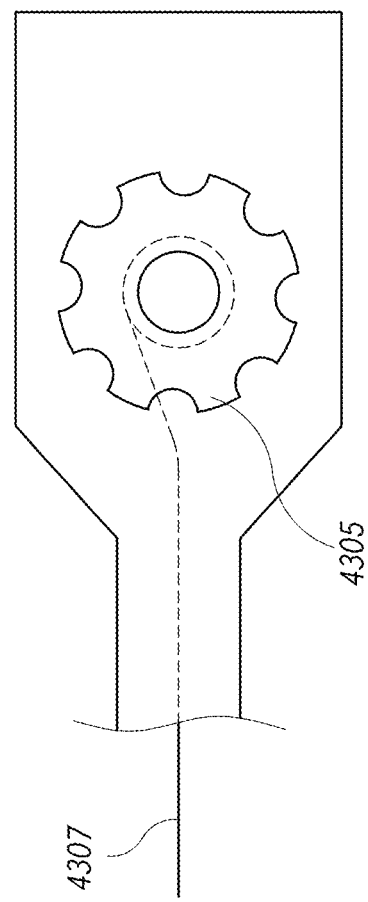

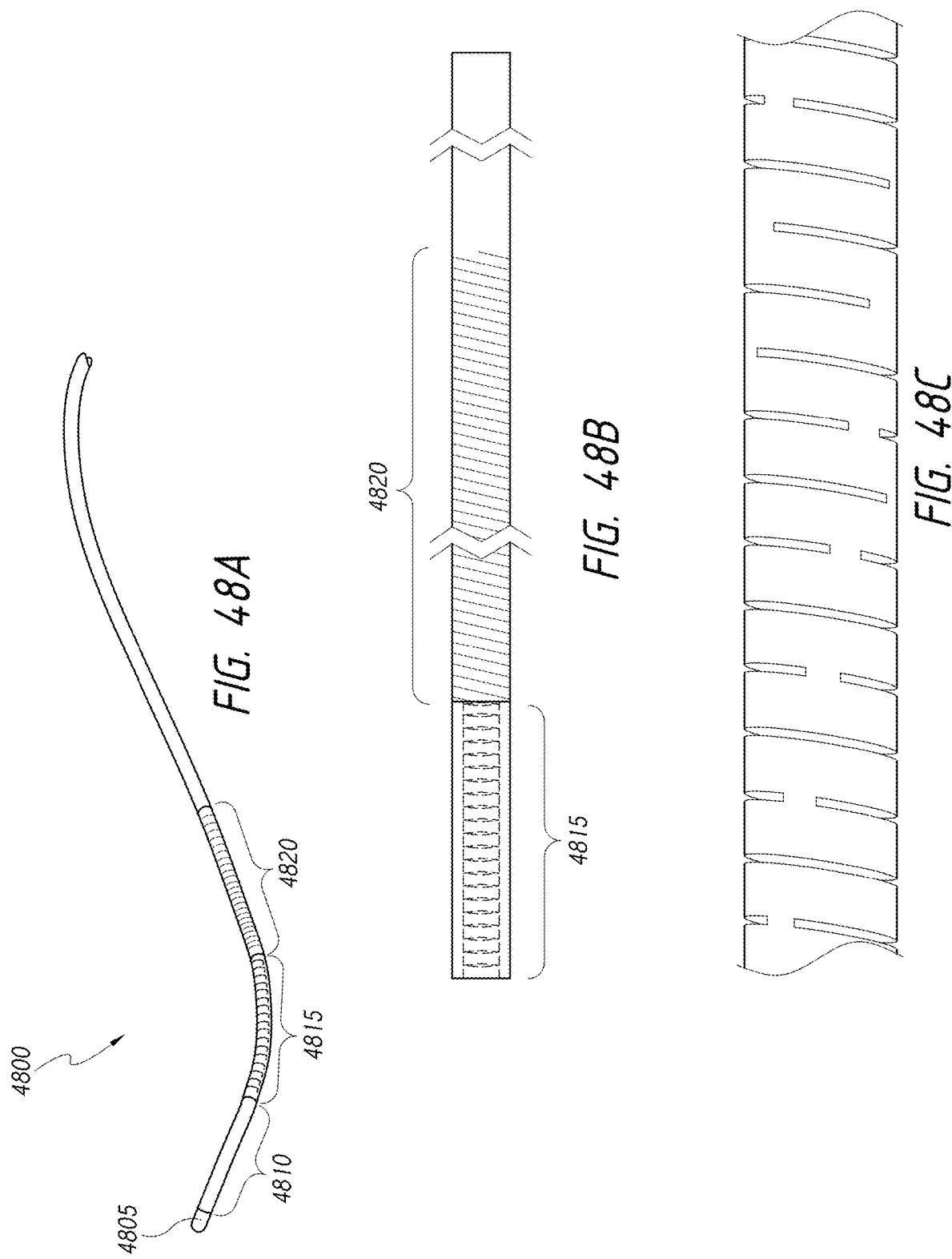

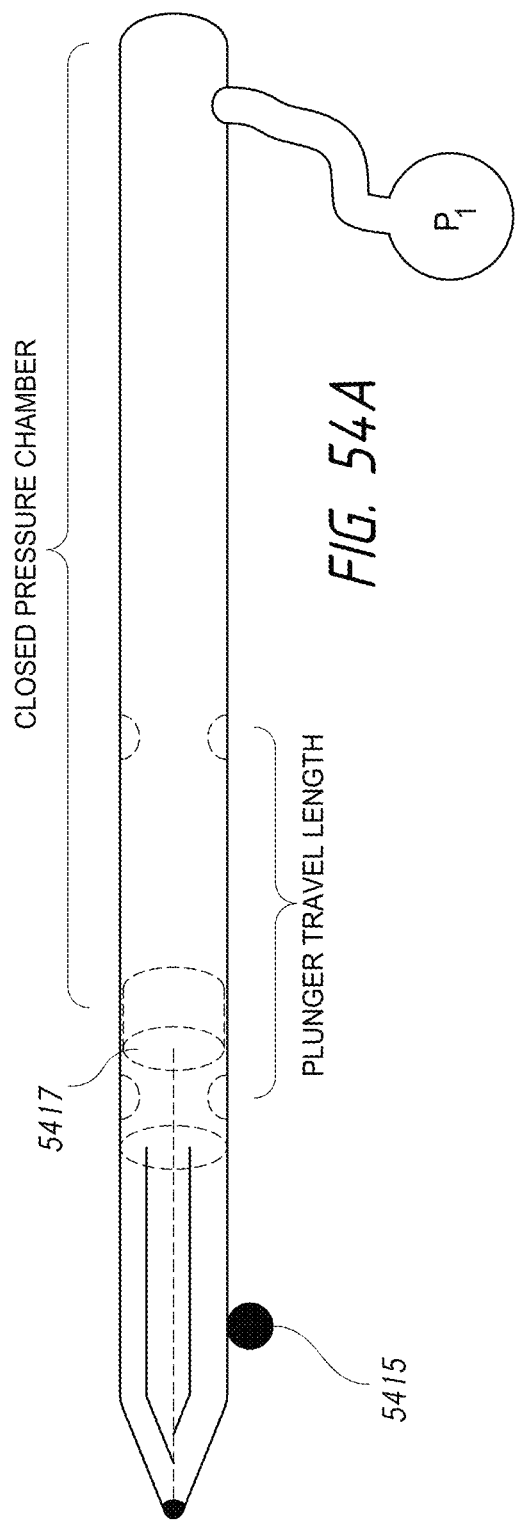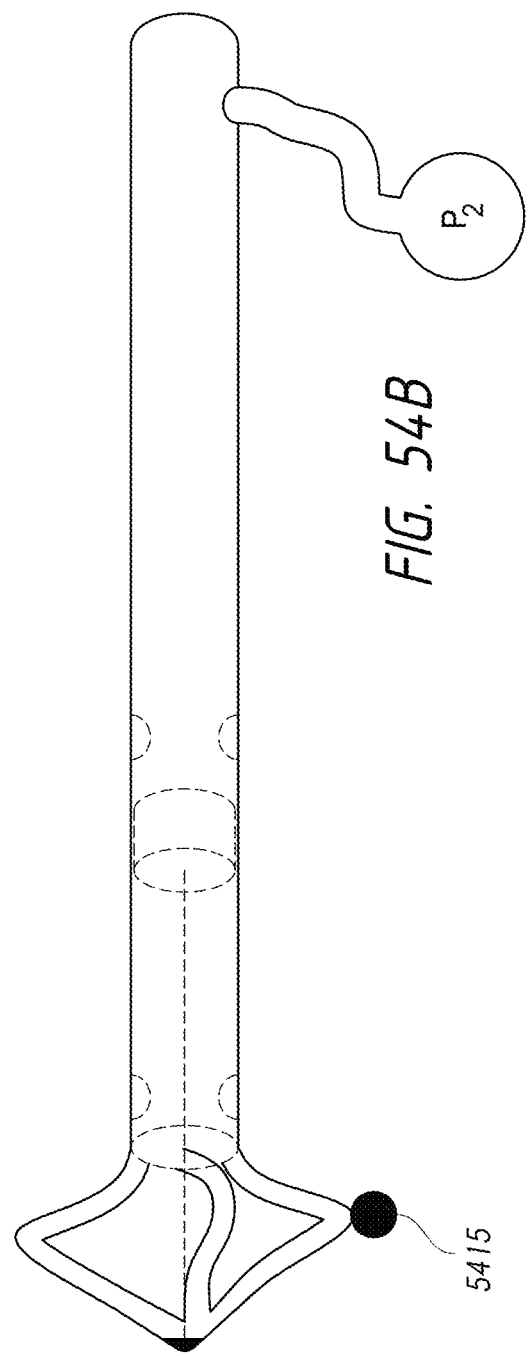

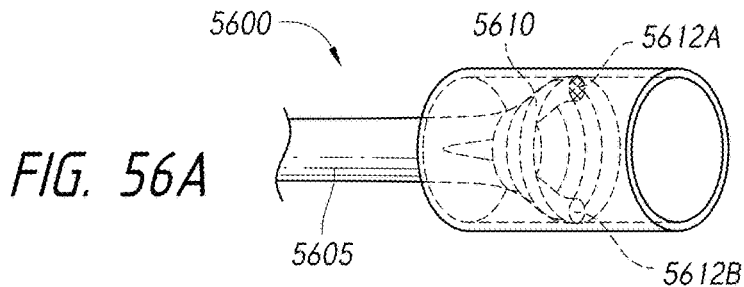
FIG. 56A
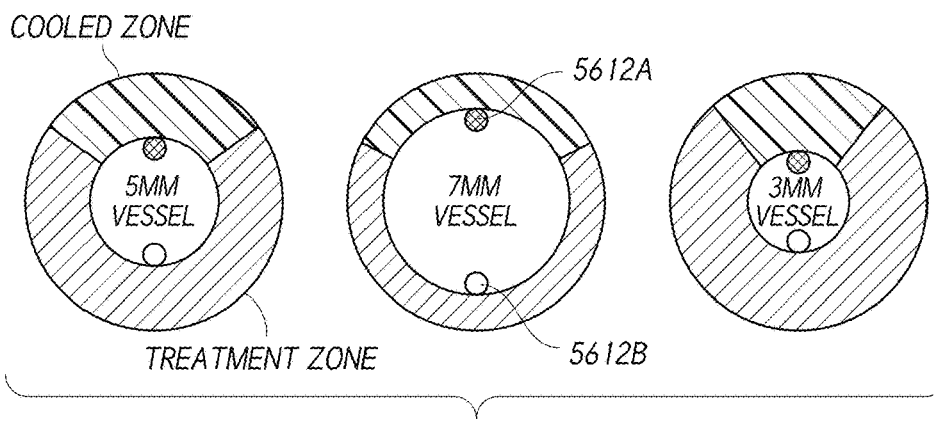
FIG. 56B
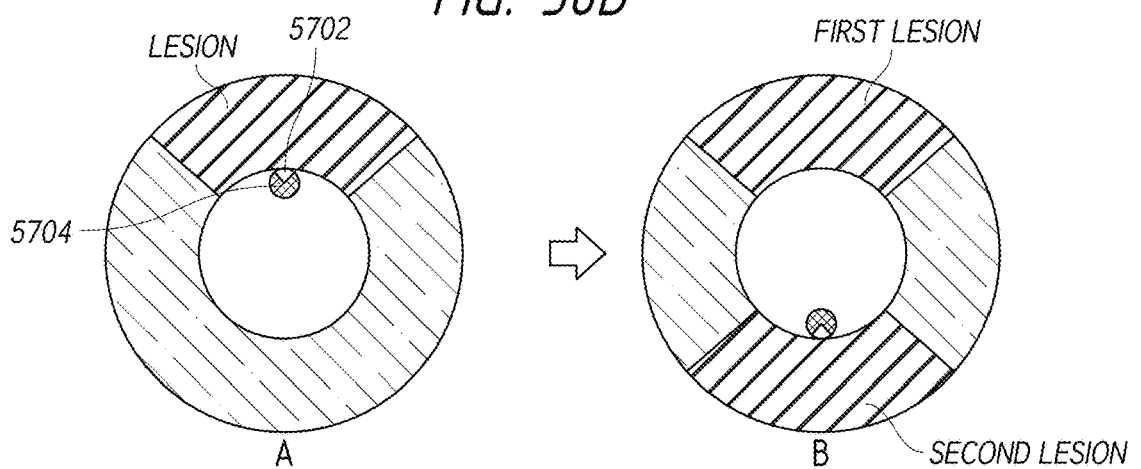
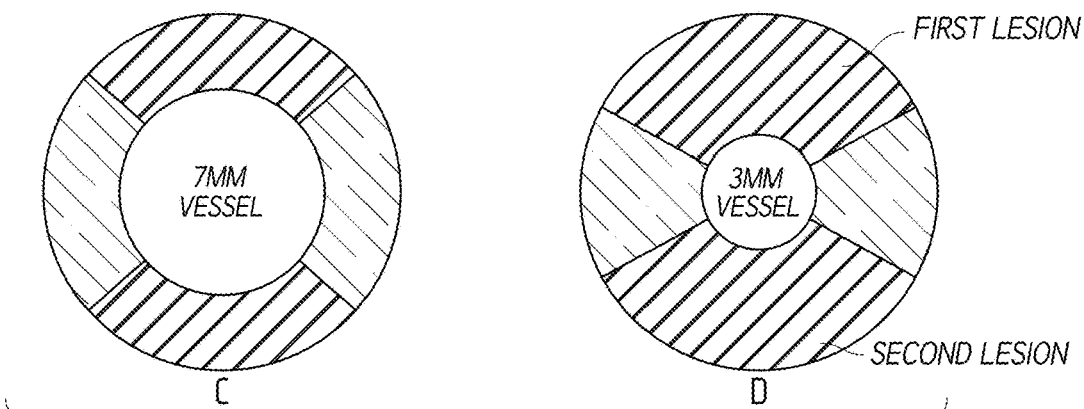
FIG. 57

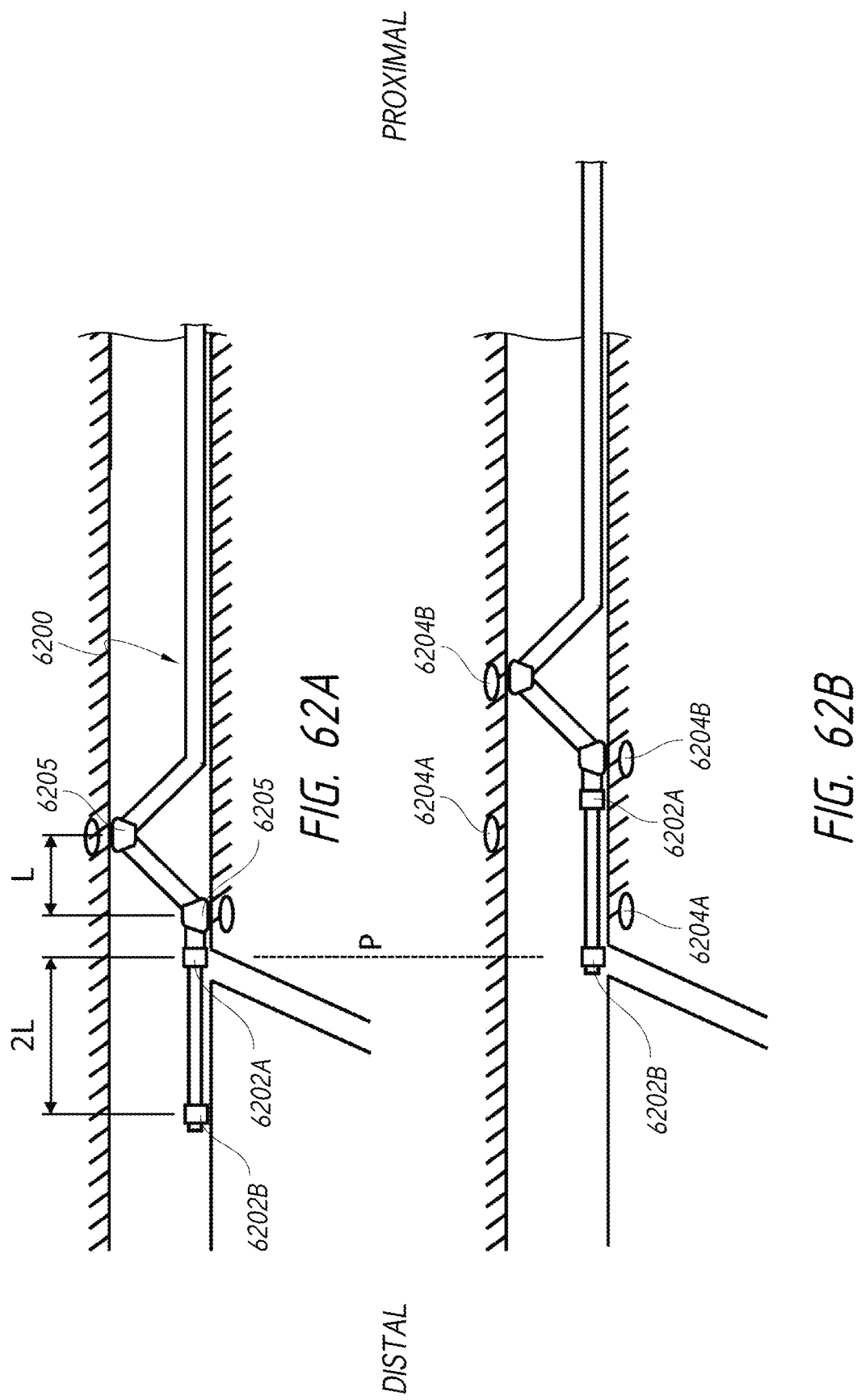

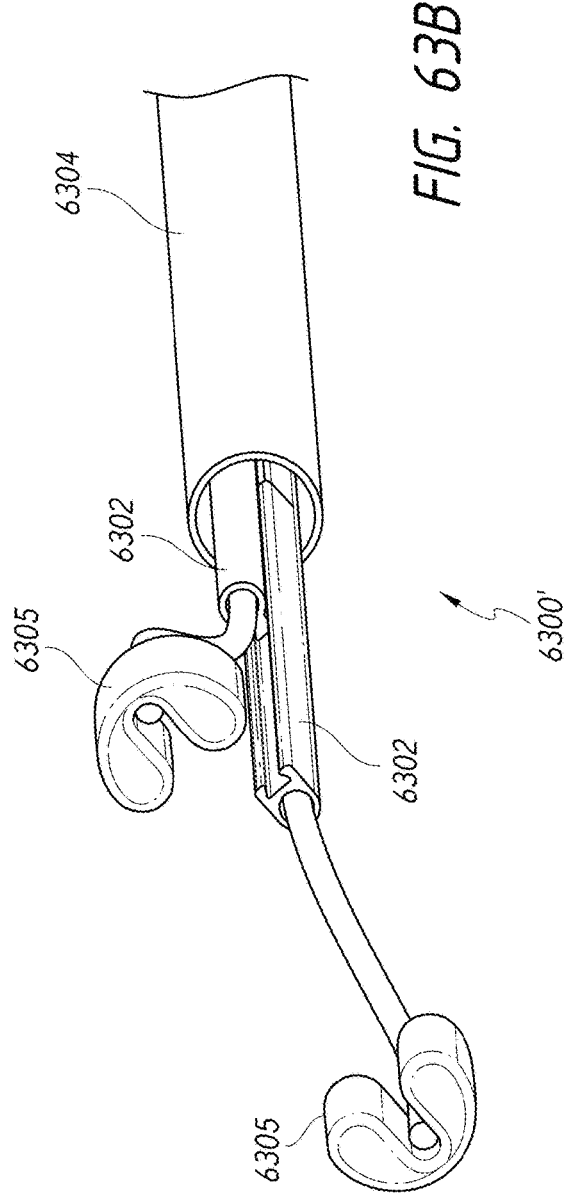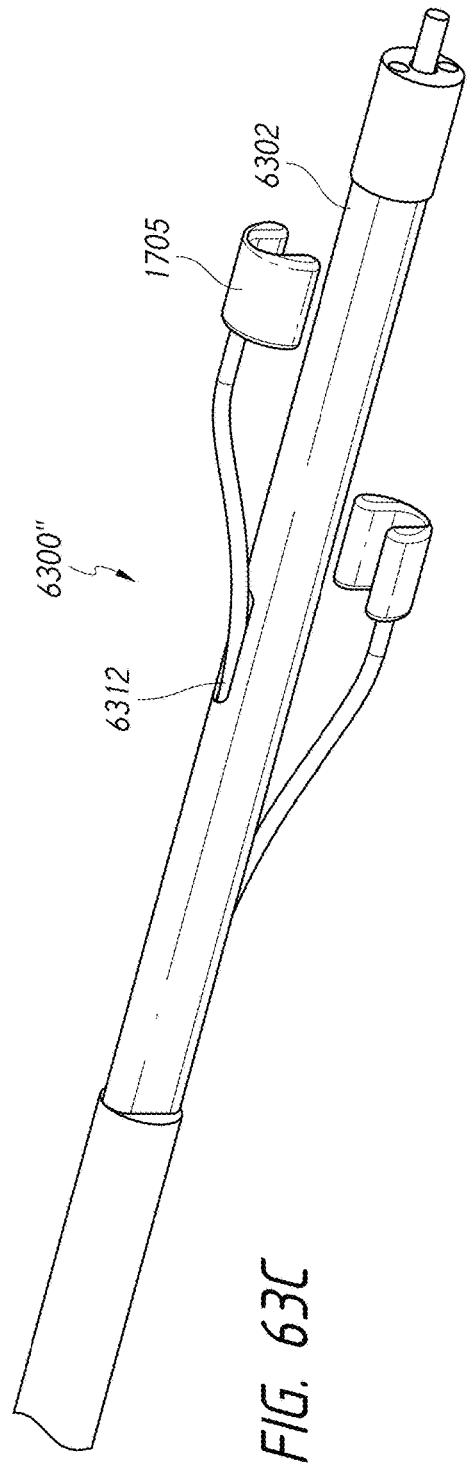

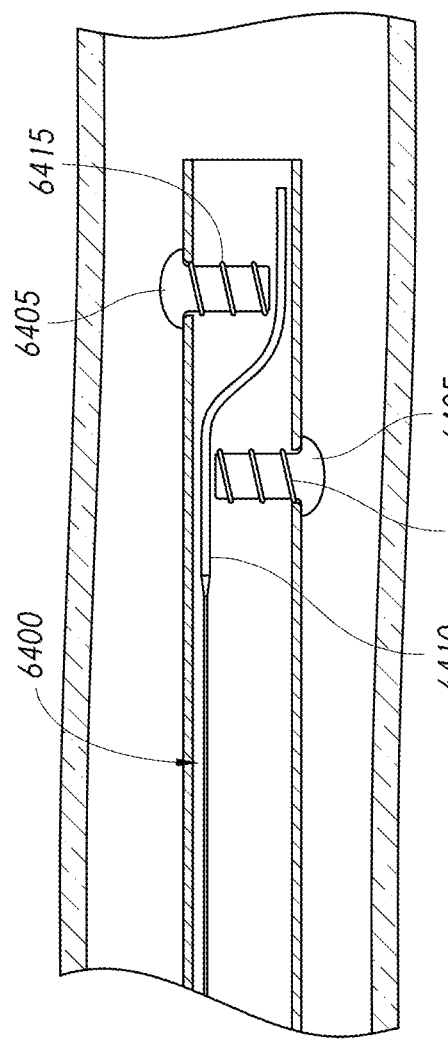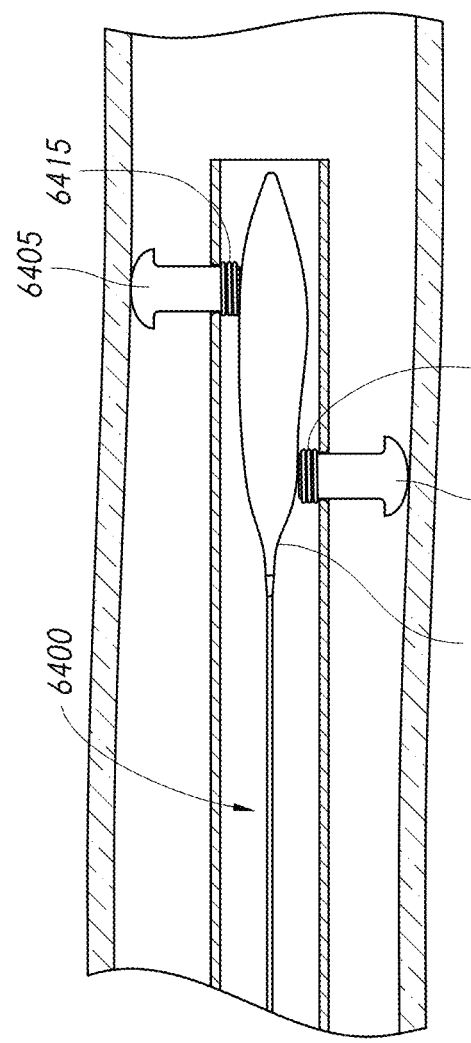

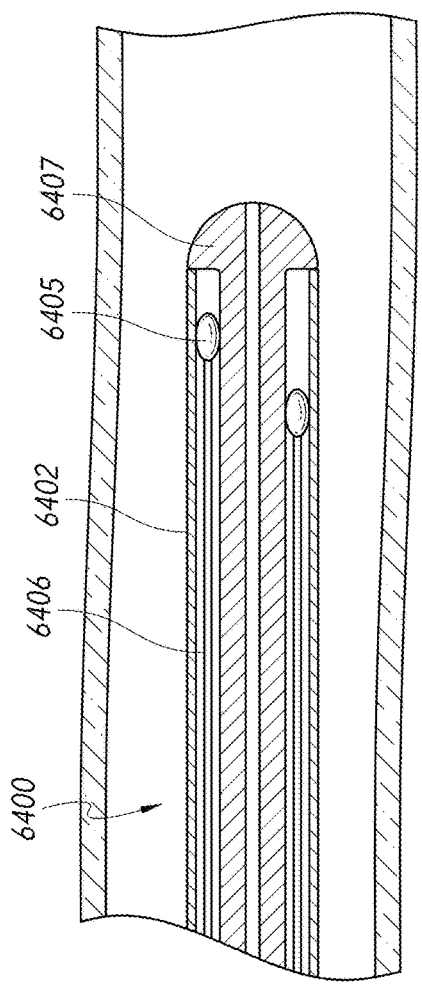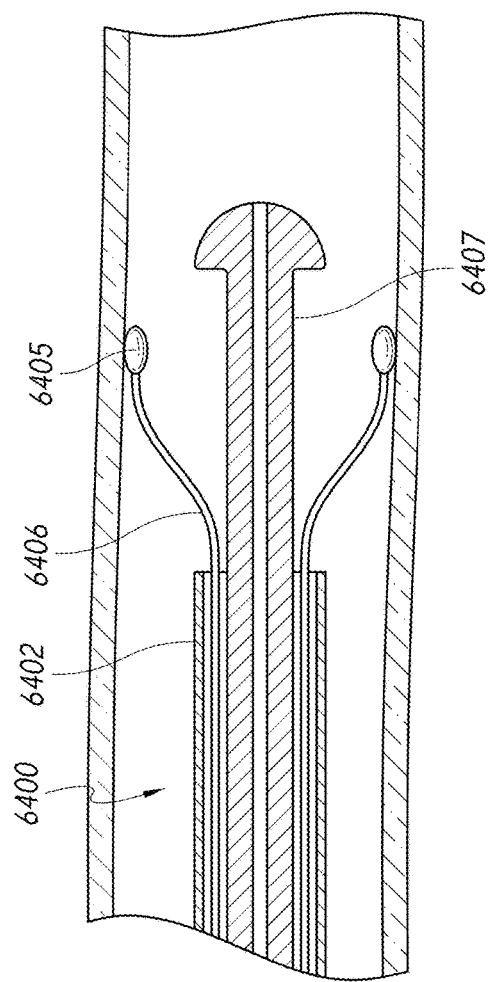

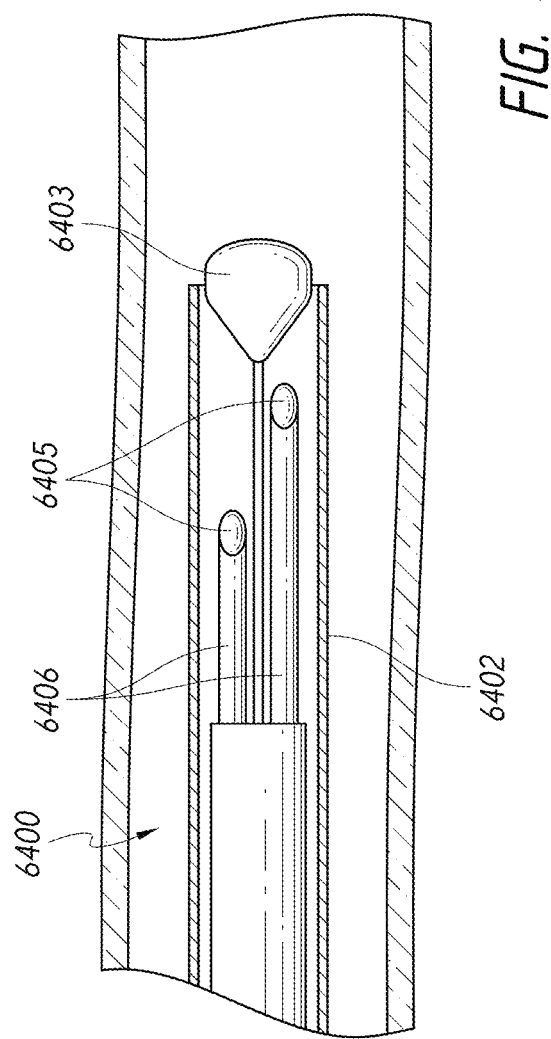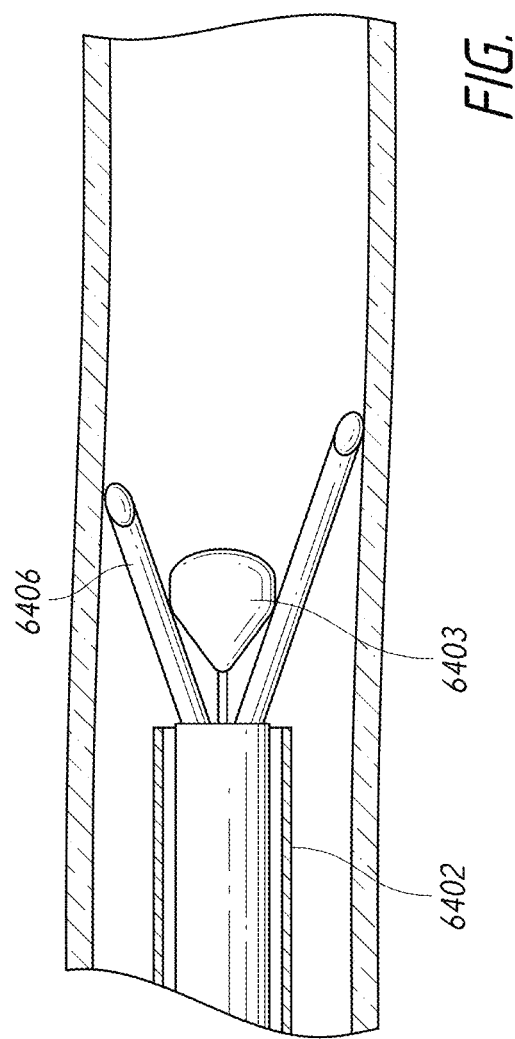

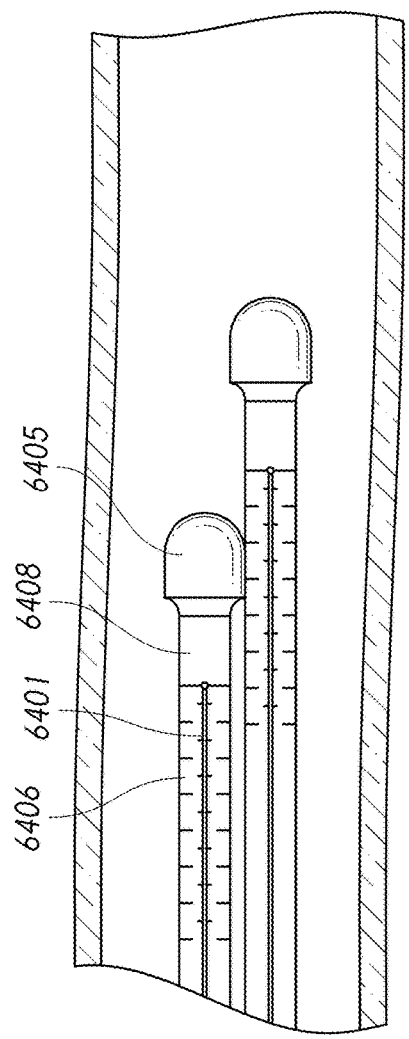
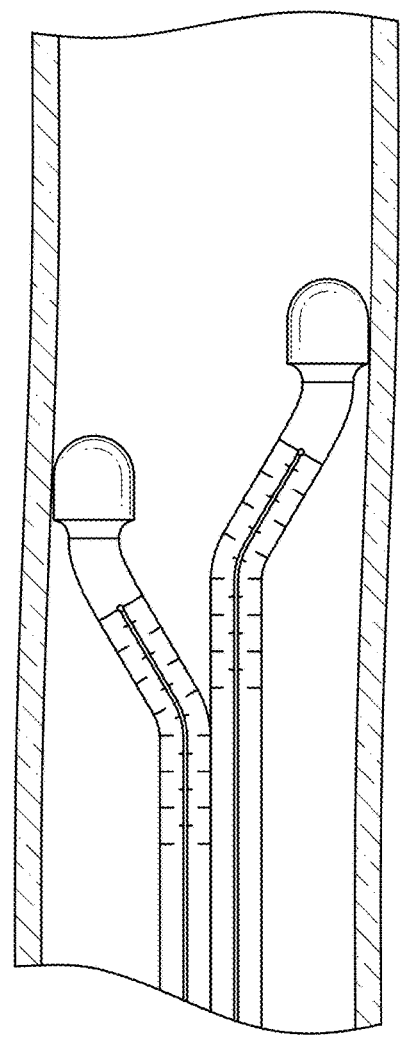
FIG. 64D-1
FIG. 64D-2

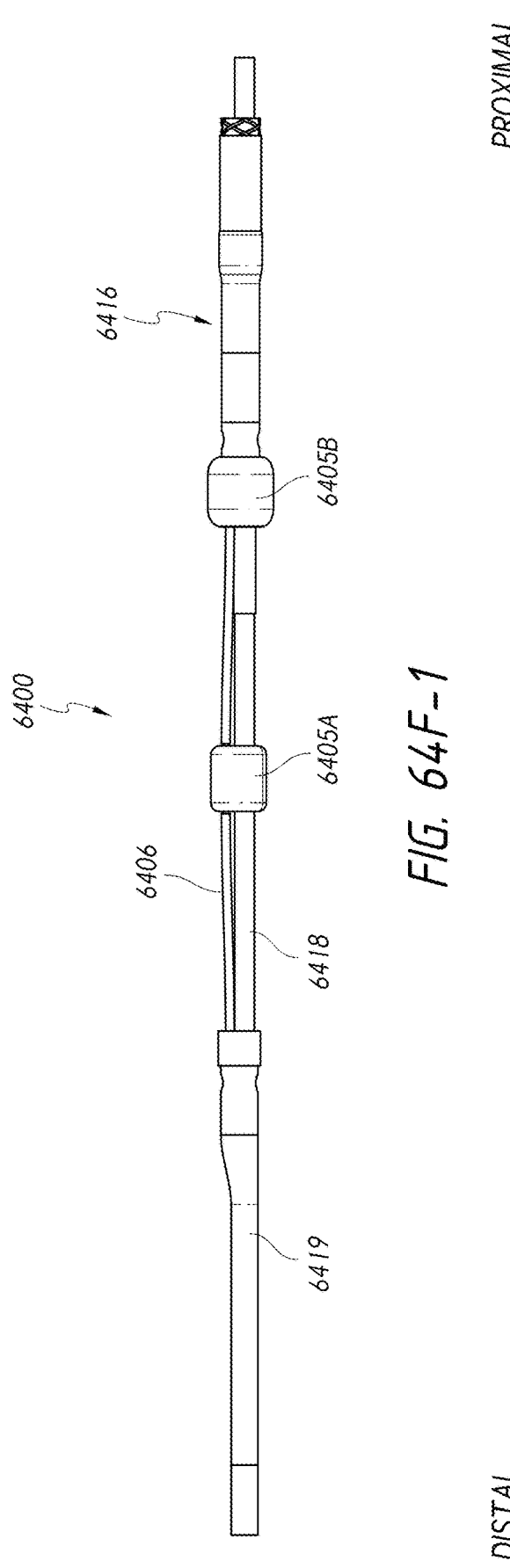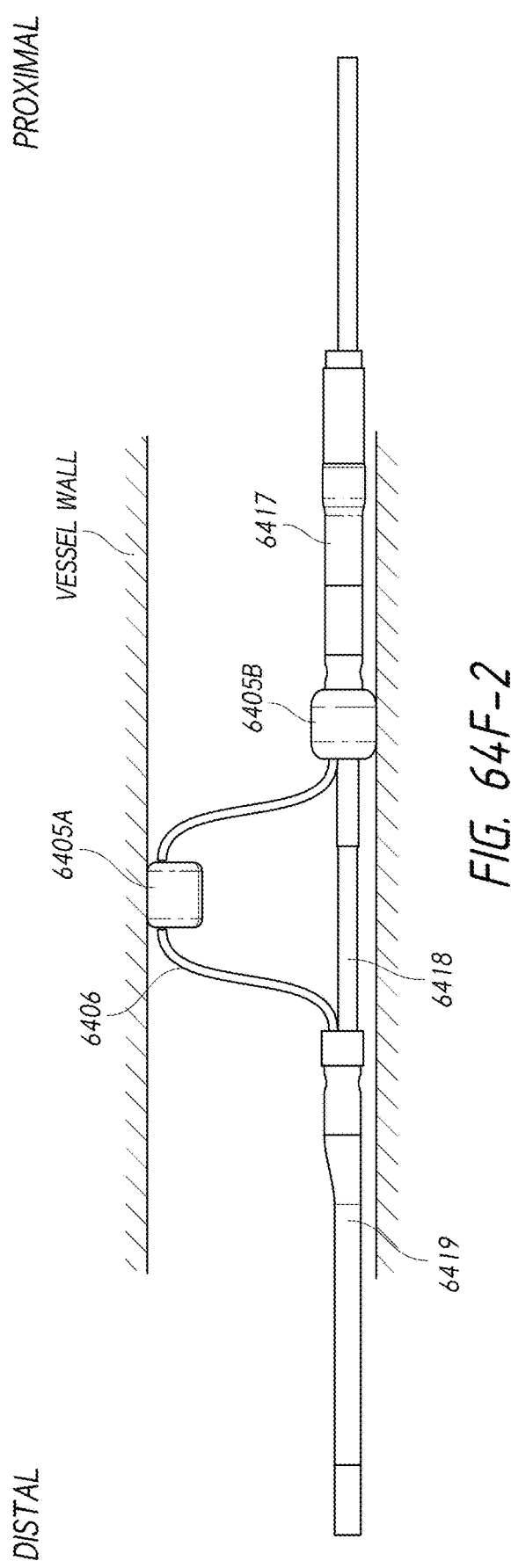

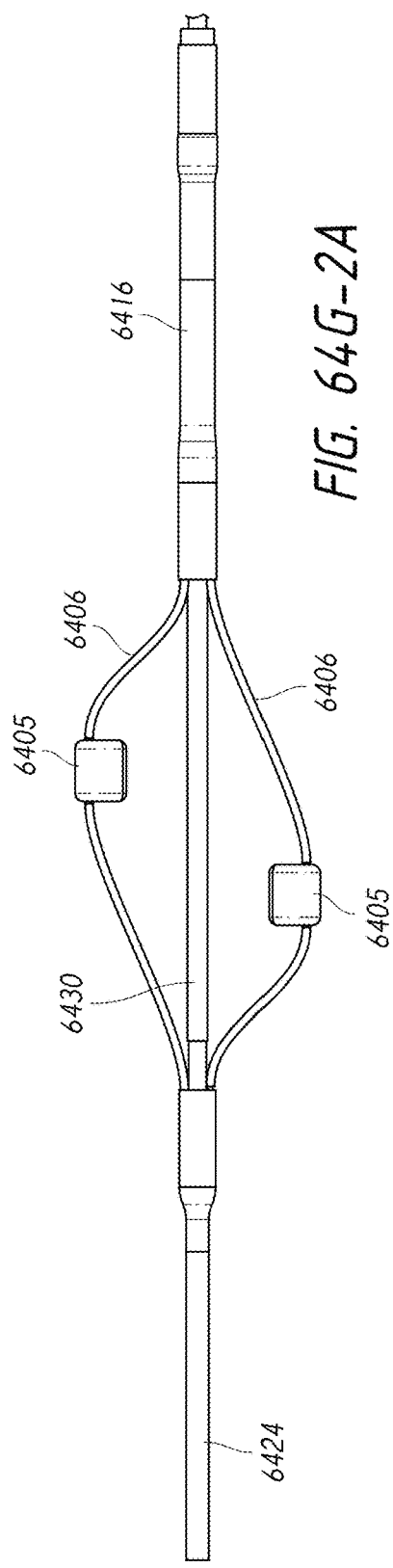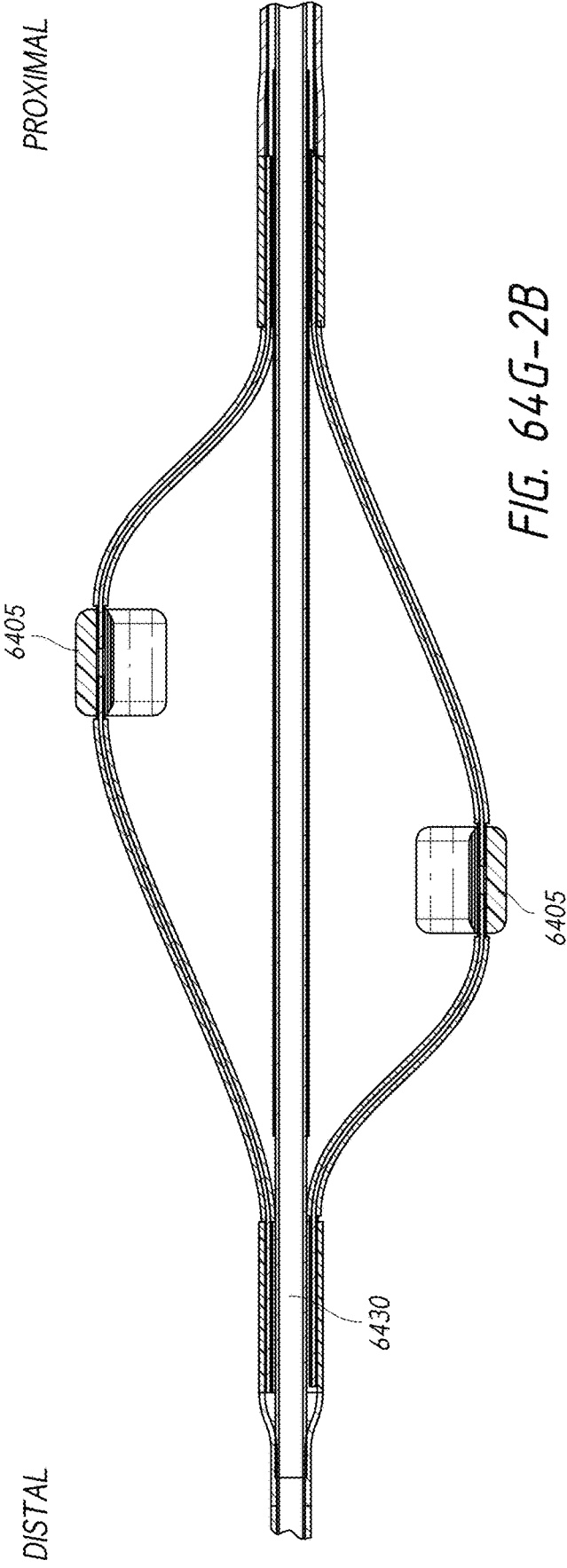

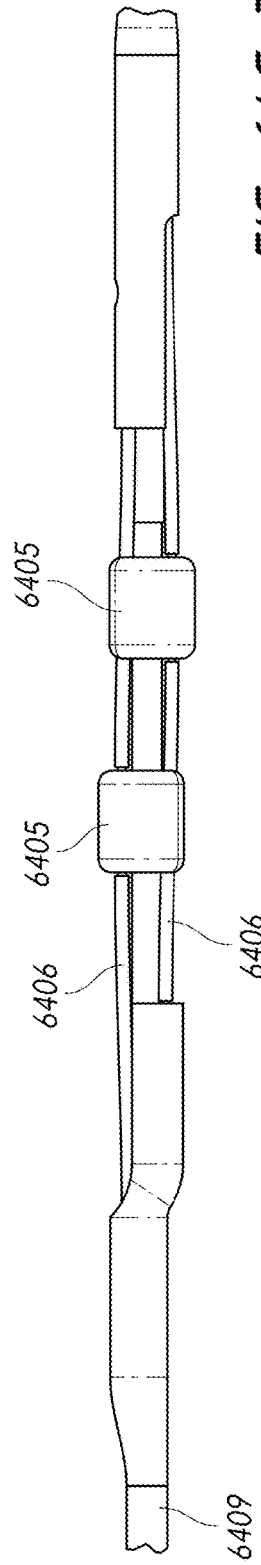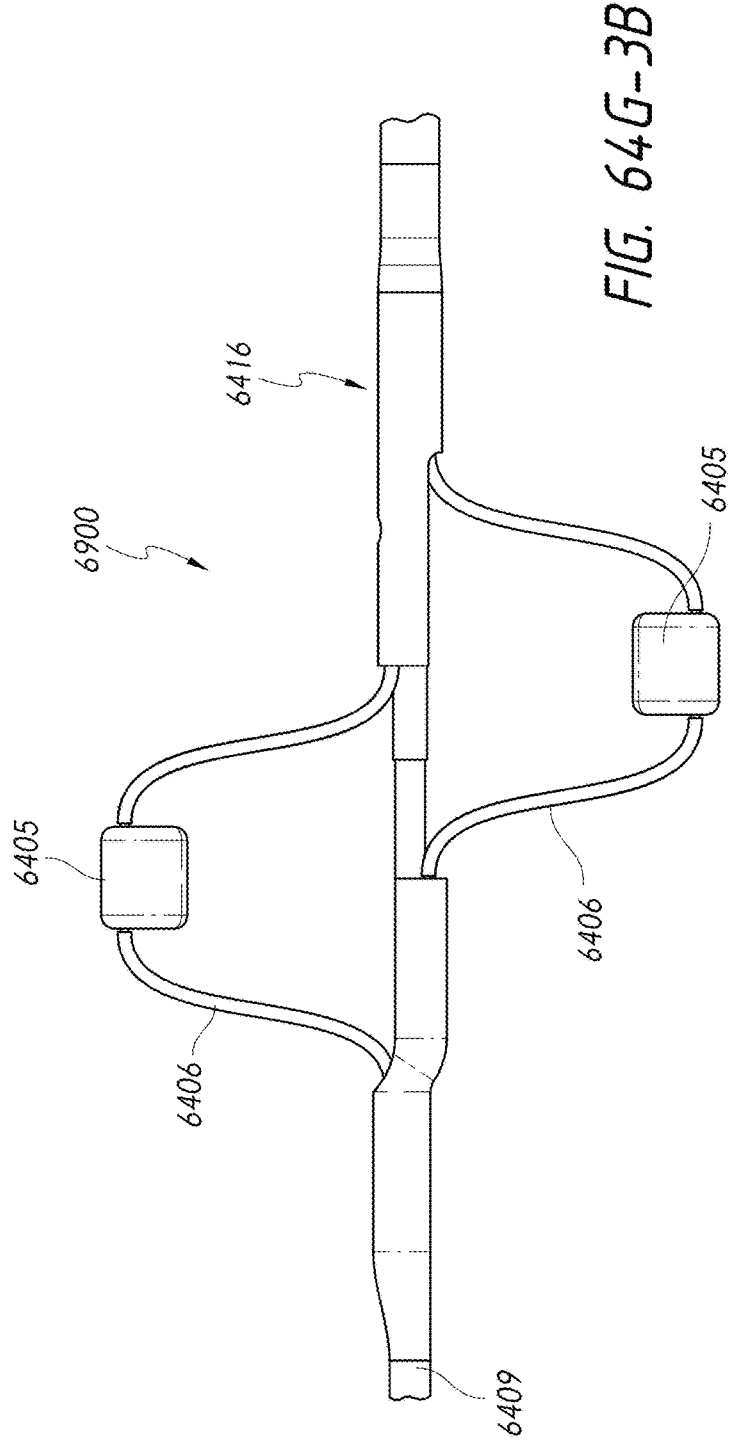

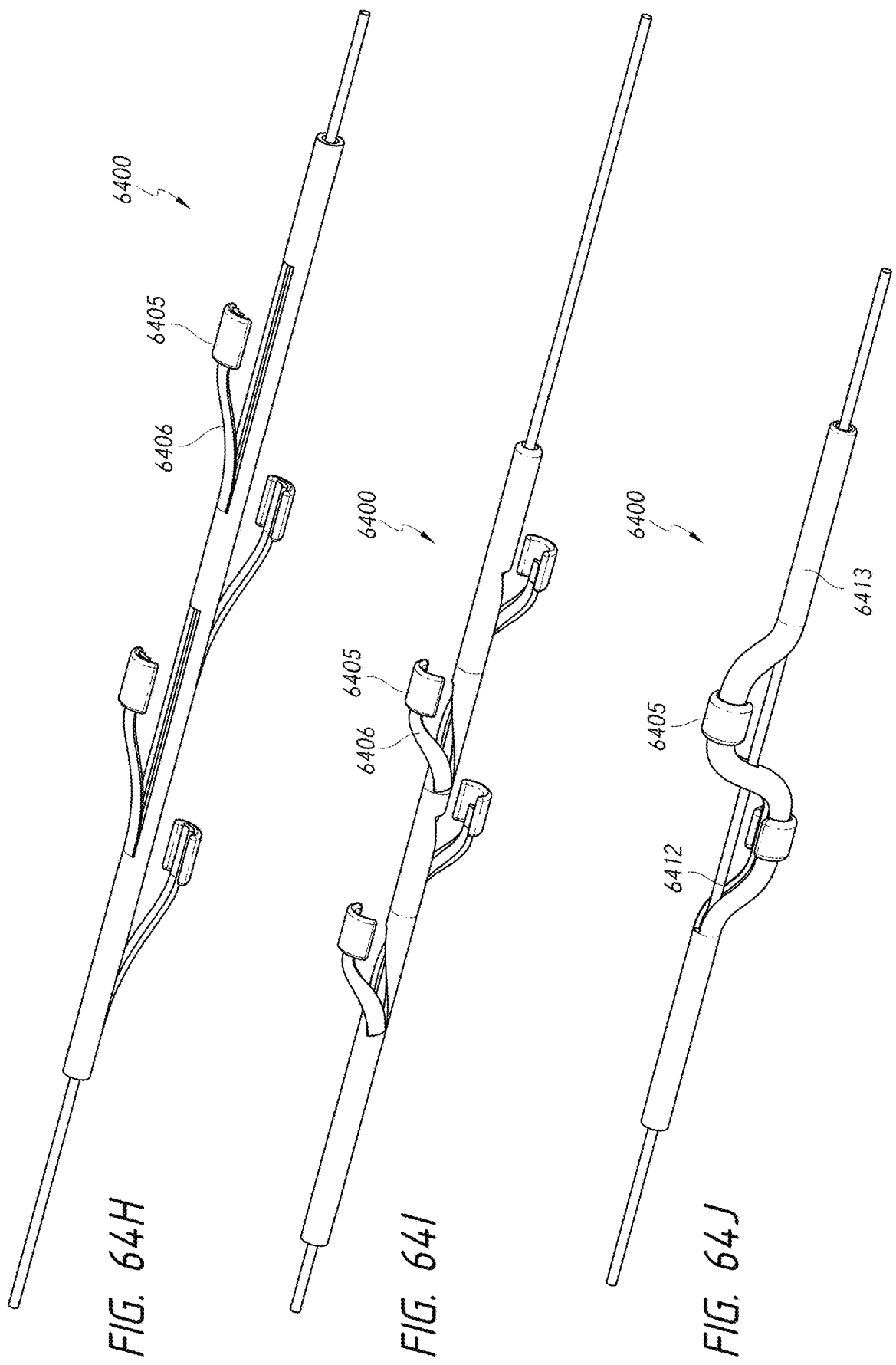

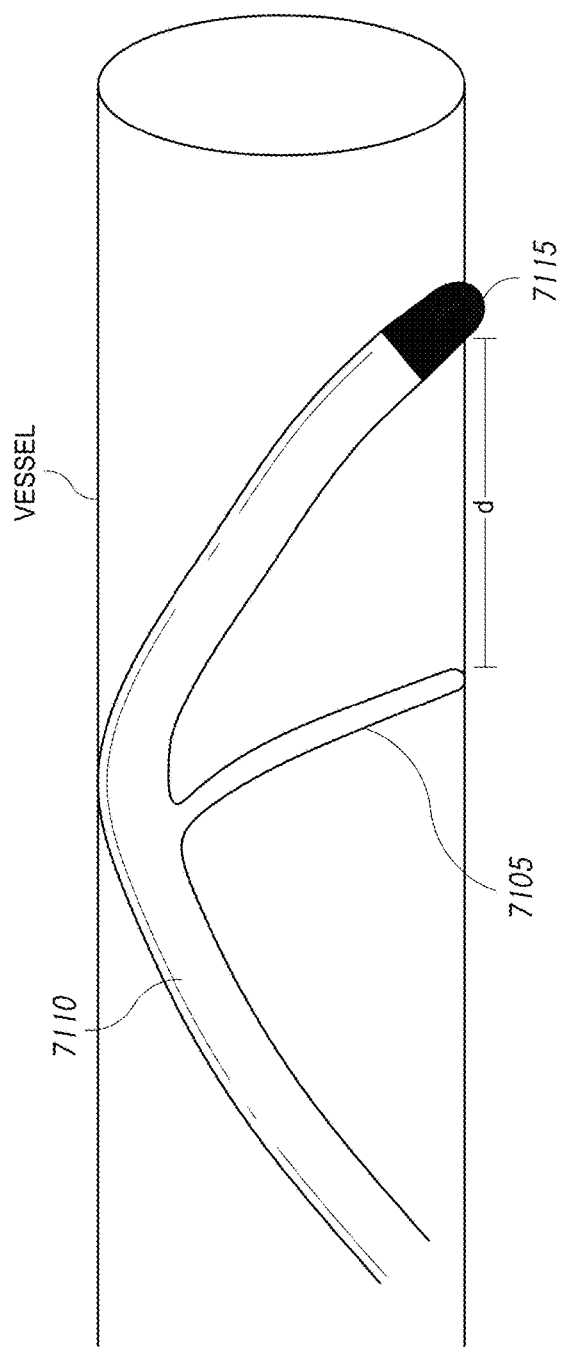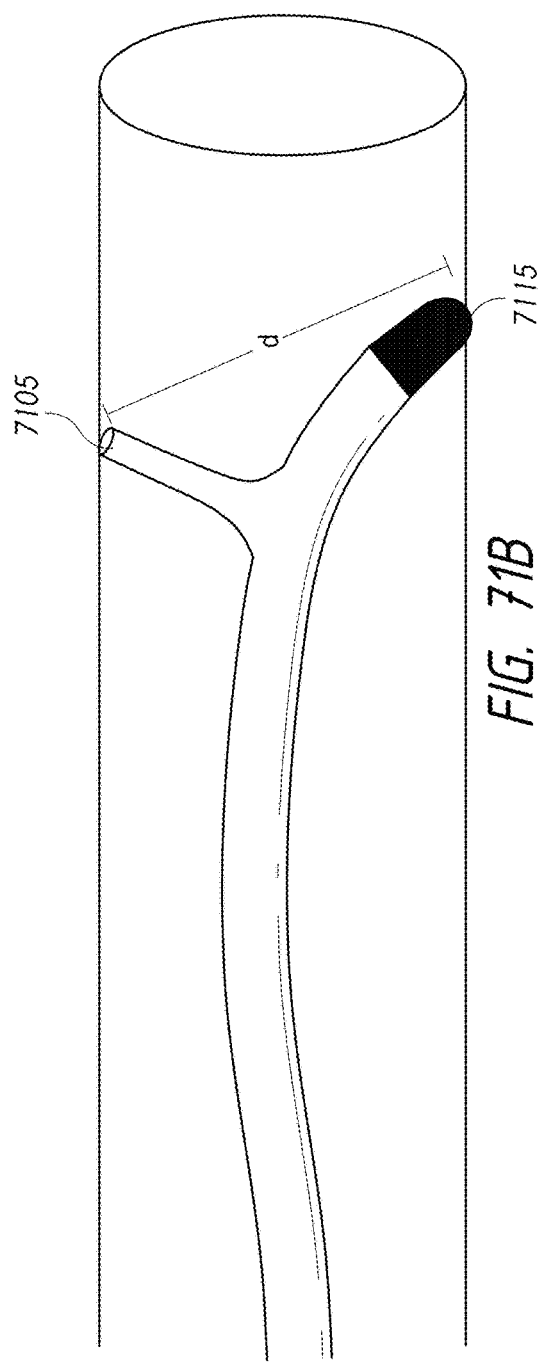
FIG. 71A
FIG. 71B

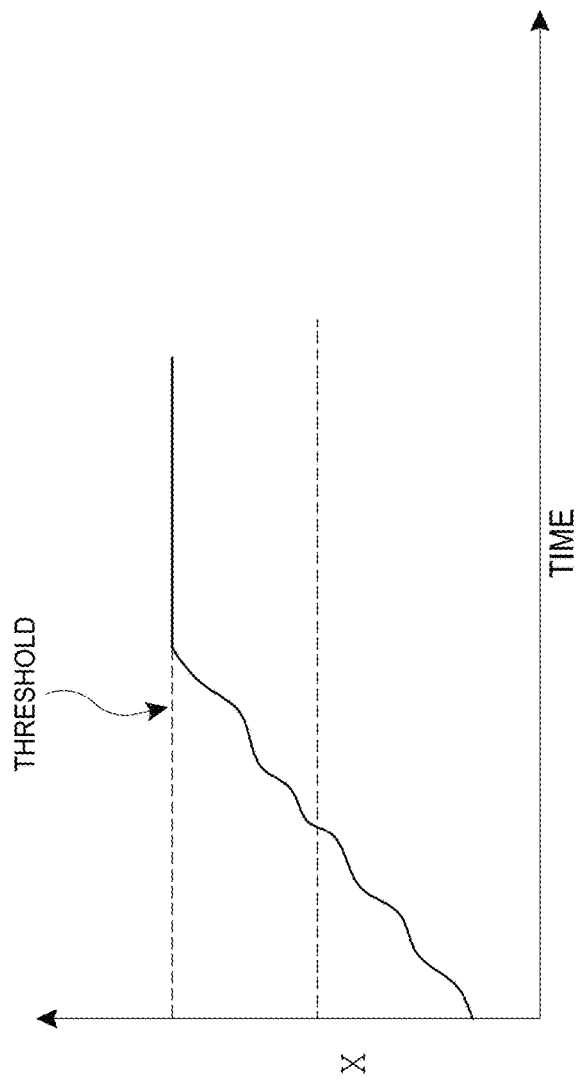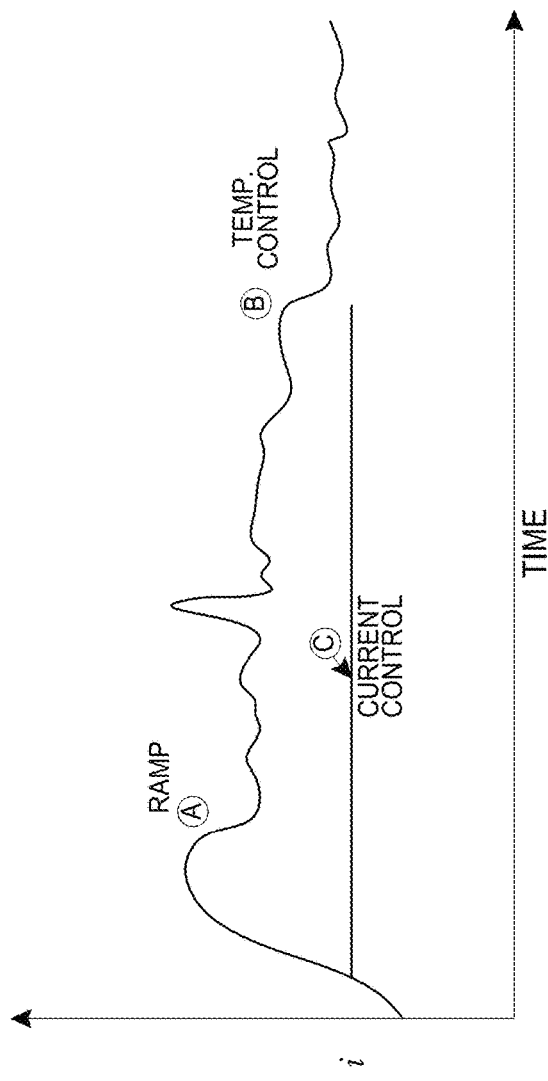
FIG. 77A
FIG. 77B

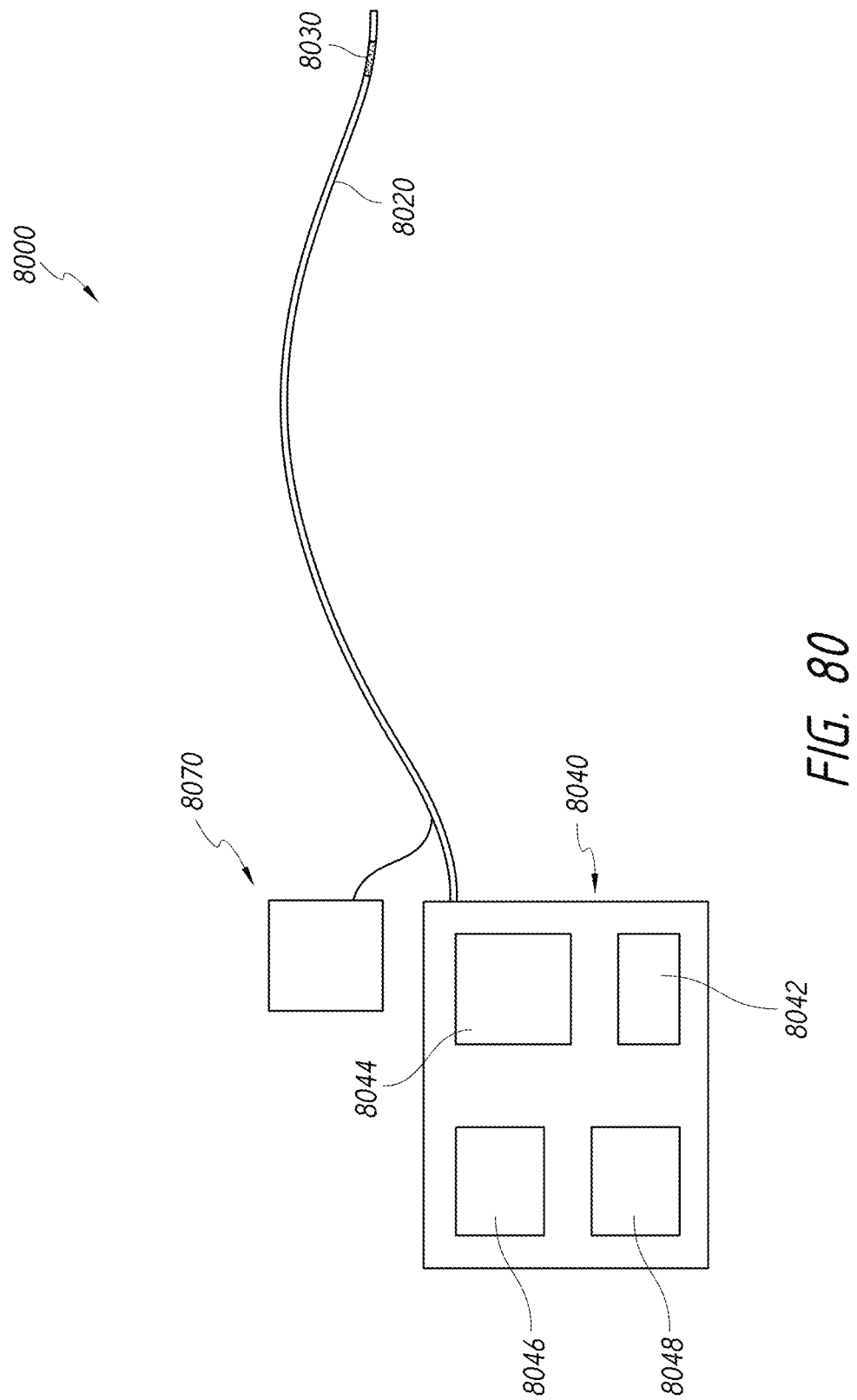

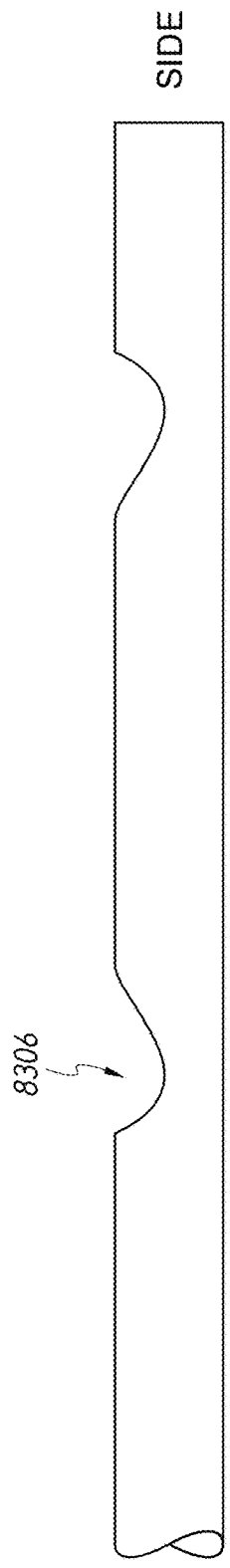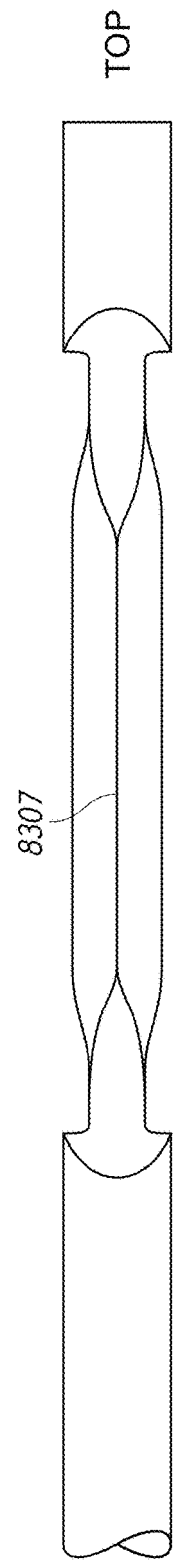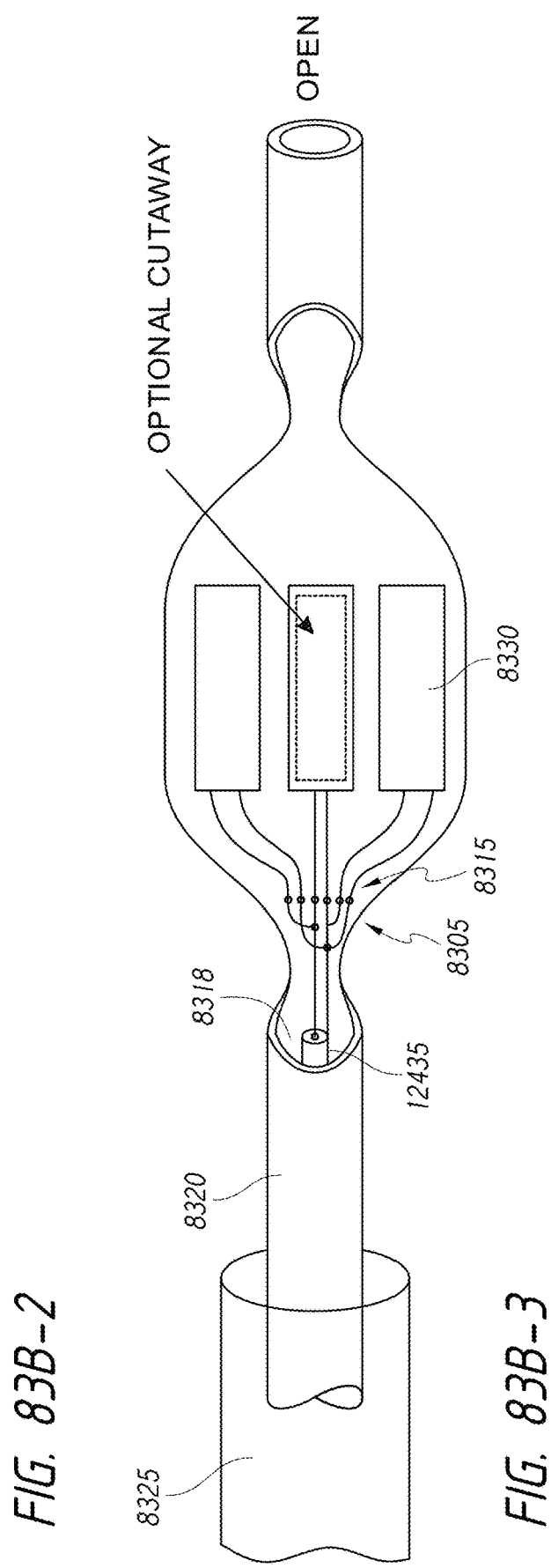
FIG. 83B-1
FIG. 83B-2
FIG. 83B-3

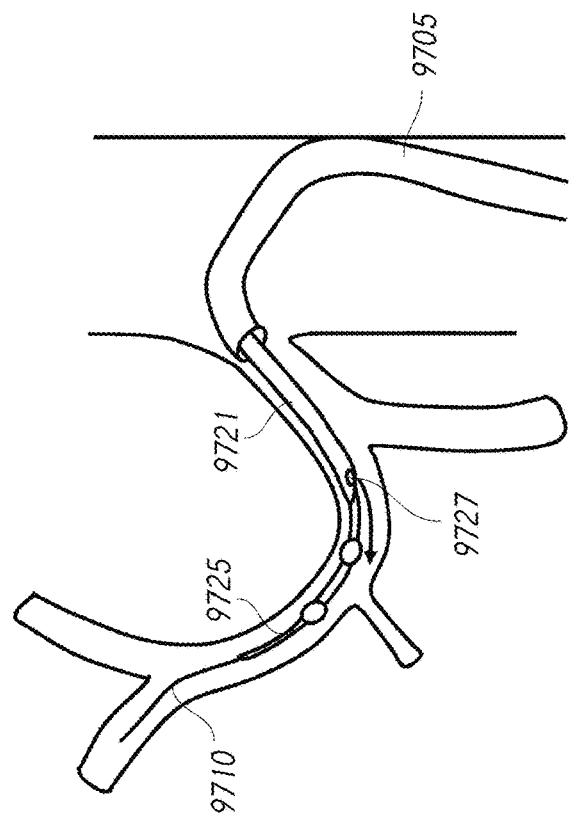
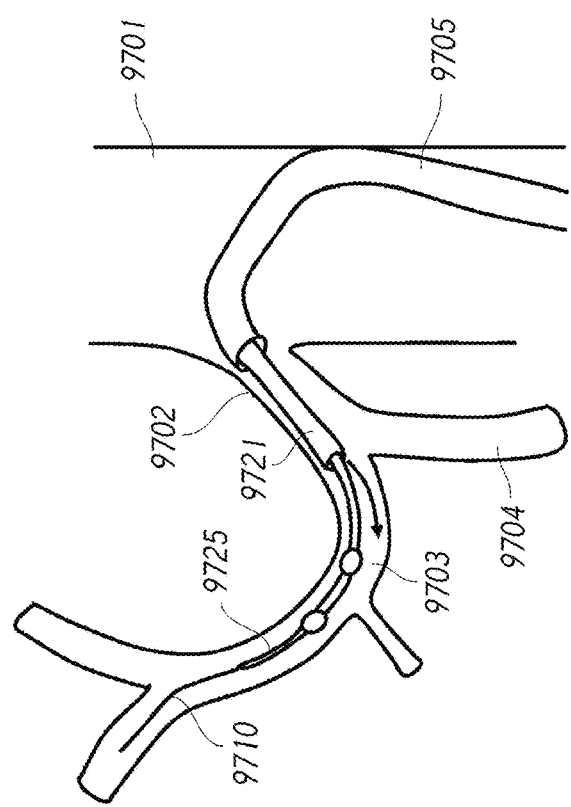
FIG. 97A
FIG. 97B

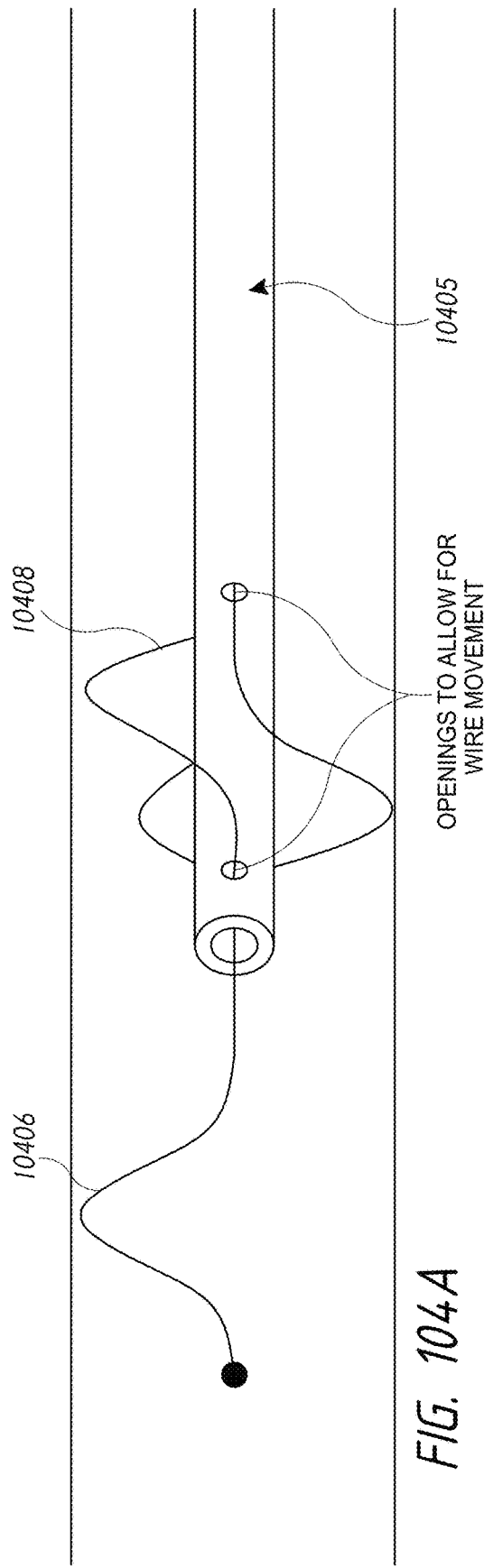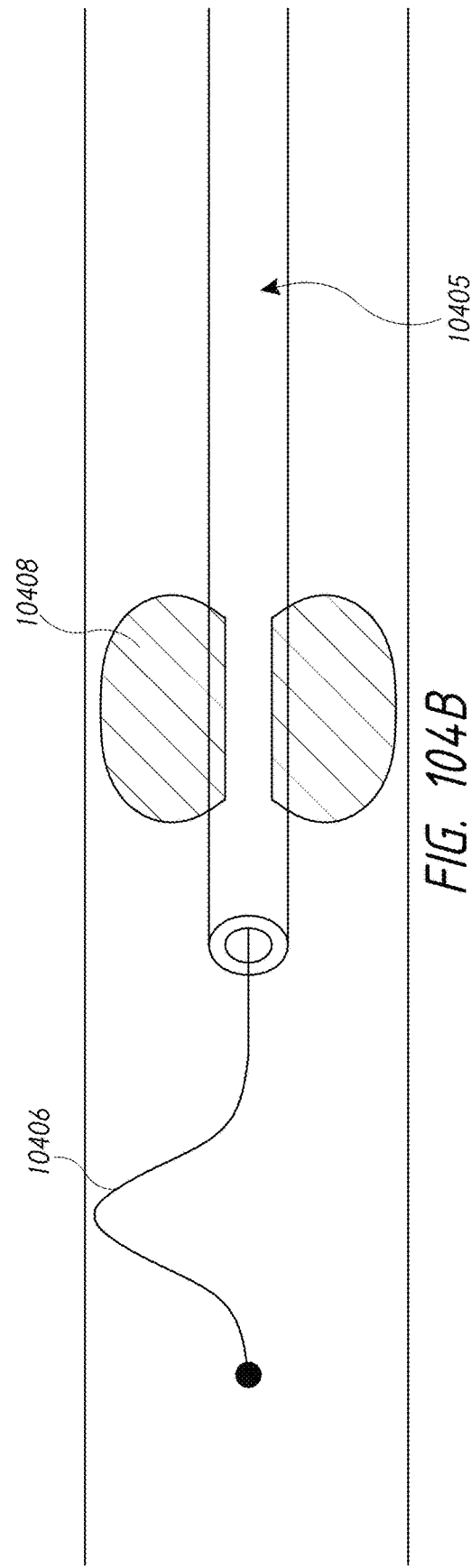

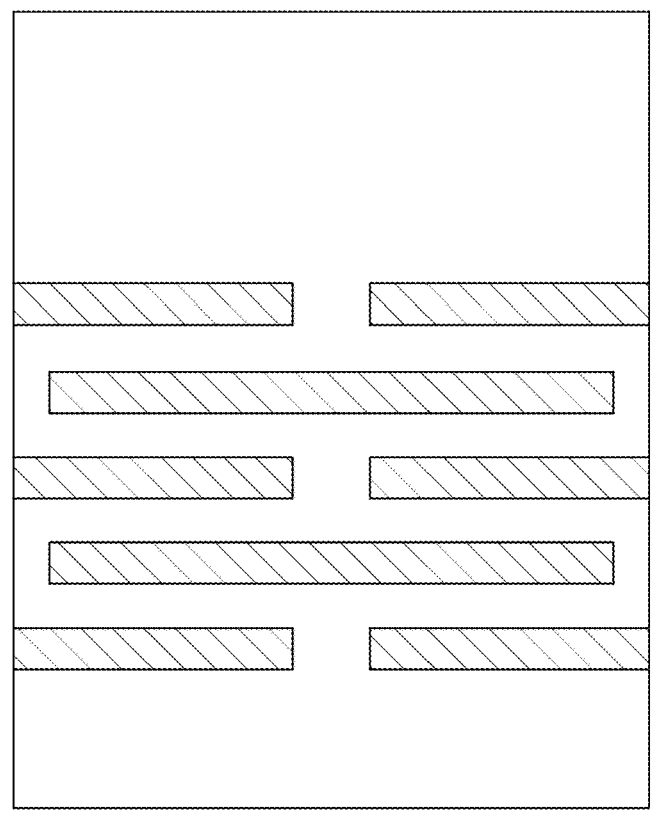
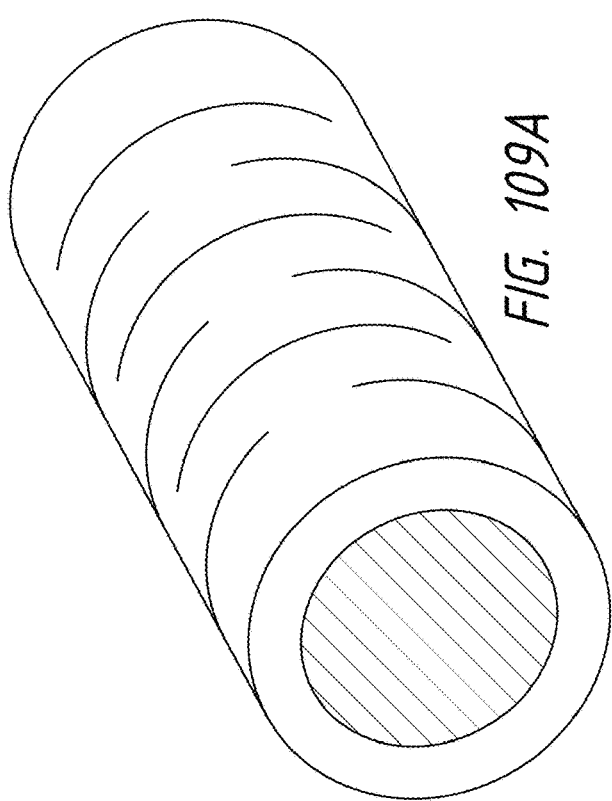

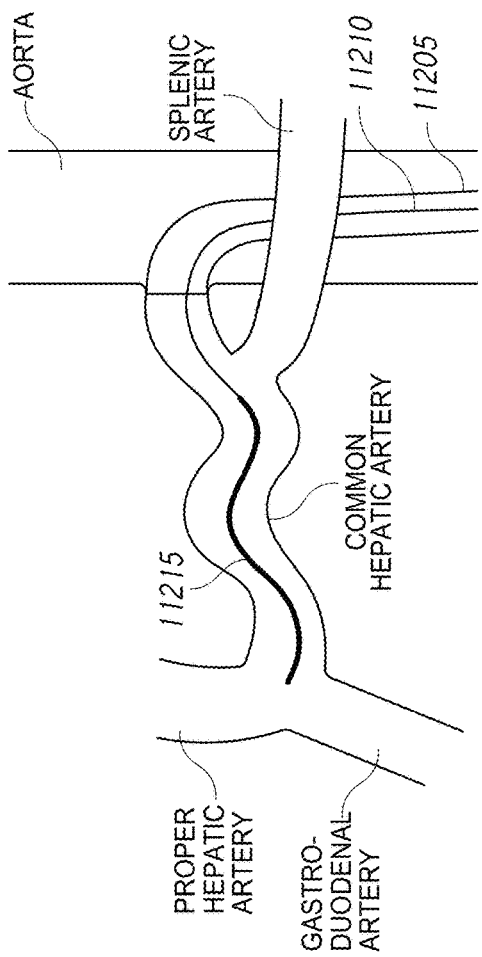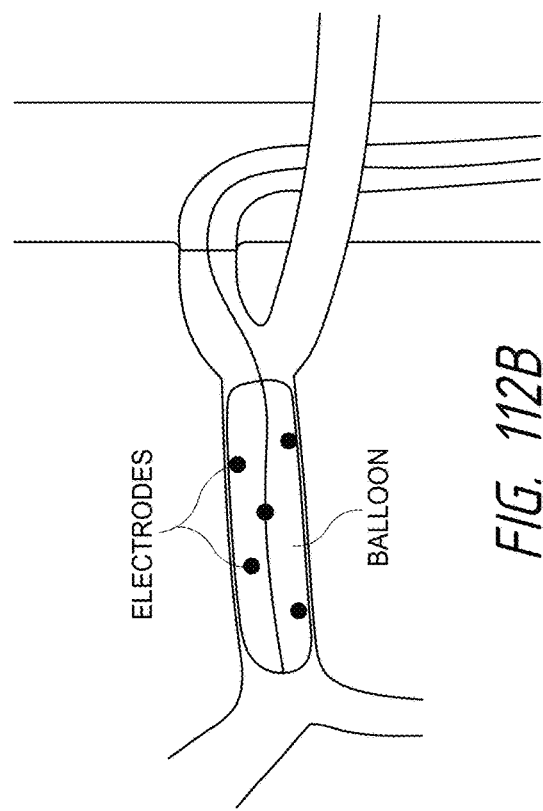

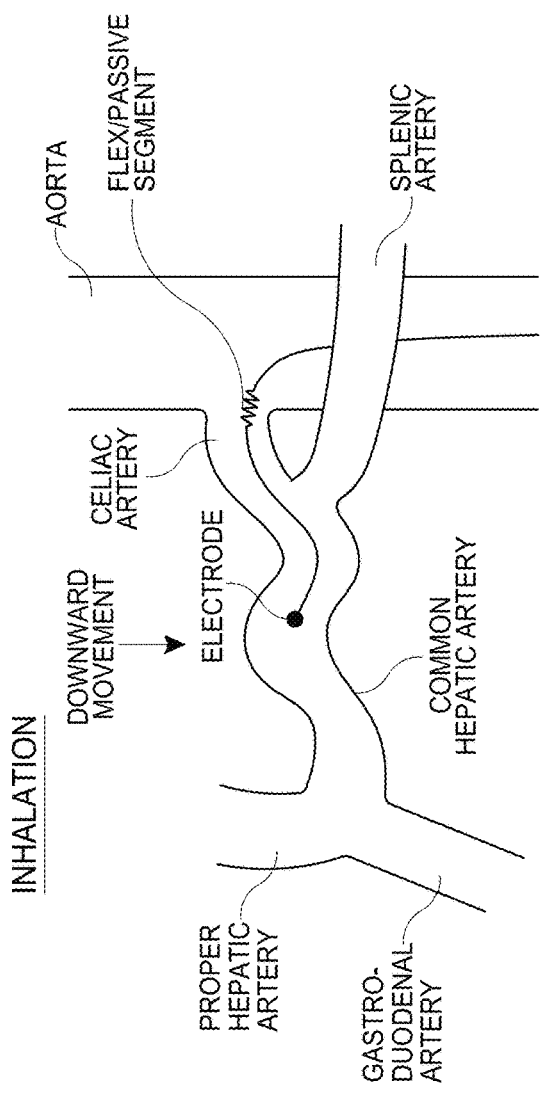
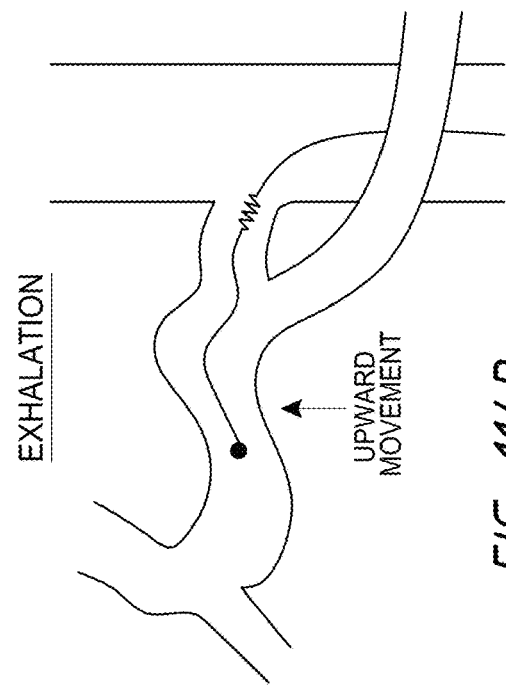
FIG. 114A
FIG. 114B

Liver norepinephrine levels

| | Lobe | Normal content | Denervated content |
|---|---|---|---|
| | | (ng/g) tissue | |
| Dog | Caudate | 248±41 | 0.9±0.4 |
| | Left central | 299±93 | 0.8±0.4 |
| | Left lateral | 376±151 | 0.4±0.2 |
| | Left posterior | 349±110 | 0.4±0.1 |
| | Quadrate | 307±104 | 28.1±12.8 |
| | Right lateral | 394±195 | 7.0±4.0 |
| | Right central | 342±135 | 0.4±0.3 |
| Pig | Left central | Estimated 72-95% effective denervation compared to dog (Vanderbilt) controls | 1.2 |
| | Right lateral | | 2.1 |
| | Left lateral | | 173.6 |
| | Right Caudate | | 269.7 |
| | Right central | | 9.5 |

FIG. 125

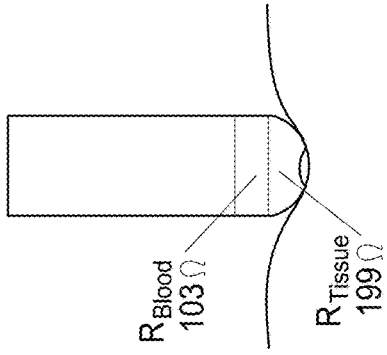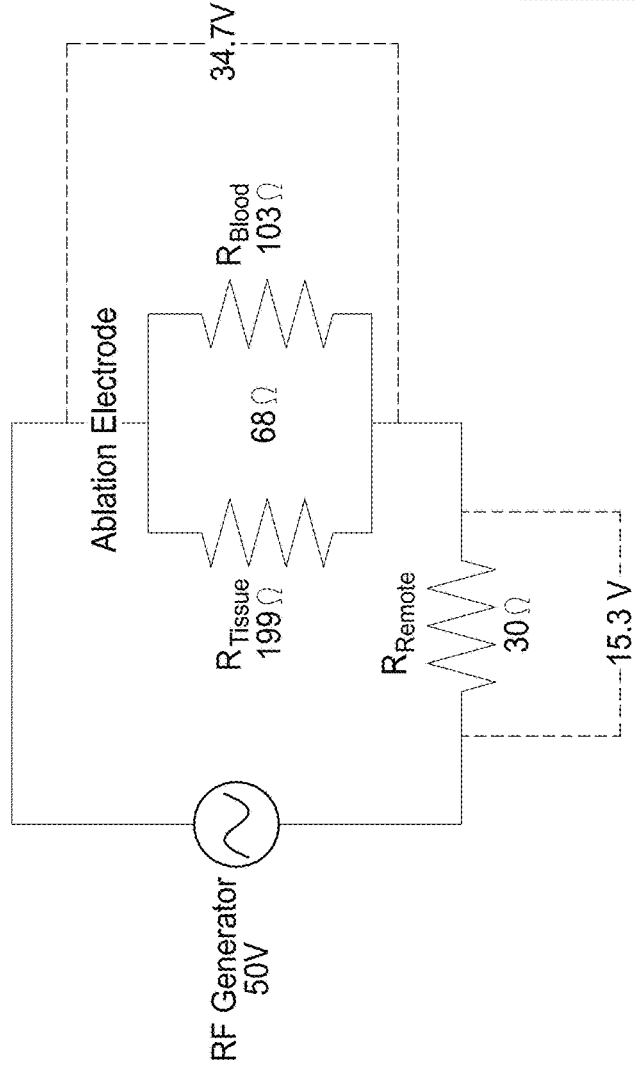
FIG. 137

SYSTEMS AND METHODS FOR MODULATING NERVES OR OTHER TISSUE

CROSS-REFERENCE TO RELATED APPLICATIONS

This application is a continuation of U.S. patent application Ser. No. 15/532,650, filed Jun. 2, 2017, which is a 371 of International Application No. PCT/US2015/063807, filed Dec. 3, 2015, which claims priority benefit of U.S. Provisional Patent Application No. 62/087,179, filed Dec. 3, 2014, and U.S. Provisional Patent Application No. 62/130,469, filed Mar. 9, 2015, each of which is incorporated herein by reference in its entirety.

FIELD

The disclosure relates generally to therapeutic tissue modulation and, more specifically, to embodiments of devices, systems and methods for therapeutically effecting neuromodulation of targeted nerve fibers of, for example, the hepatic system, to treat metabolic diseases or conditions, such as diabetes mellitus.

BACKGROUND

Chronic hyperglycemia is one of the defining characteristics of diabetes mellitus. Hyperglycemia is a condition in which there is an elevated blood glucose concentration. An elevated blood glucose concentration may result from impaired insulin secretion from the pancreas and also, or alternatively, from cells failing to respond to insulin normally. Excessive glucose release from the liver is a significant contributor to hyperglycemia. The liver is responsible for approximately 90% of the glucose production and 33% of glucose uptake, and derangements in both in type 2 diabetes contribute to hyperglycemia in the fasting and post-prandial states.

Type 1 diabetes mellitus results from autoimmune destruction of the pancreatic beta cells leading to inadequate insulin production. Type 2 diabetes mellitus is a more complex, chronic metabolic disorder that develops due to a combination of insufficient insulin production as well as cellular resistance to the action of insulin. Insulin promotes glucose uptake into a variety of tissues and also decreases production of glucose by the liver and kidneys; insulin resistance results in reduced peripheral glucose uptake and increased endogenous glucose output, both of which drive blood the glucose concentration above normal levels.

Current estimates are that approximately 26 million people in the United States (over 8% of the population) have some form of diabetes mellitus. Treatments, such as medications, diet, and exercise, seek to control blood glucose levels, which require a patient to closely monitor his or her blood glucose levels. Additionally, patients with type 1 diabetes mellitus, and many patients with type 2 diabetes mellitus, are required to take insulin every day. Insulin is not available in a pill form, however, but must be injected under the skin. Because treatment for diabetes mellitus is self-managed by the patient on a day-to-day basis, compliance or adherence with treatments can be problematic.

SUMMARY

Several embodiments described herein relate generally to devices, systems and methods for therapeutically effecting neuromodulation of targeted nerve fibers to treat various medical conditions, disorders and diseases. In some embodiments, neuromodulation of targeted nerve fibers is used to treat, or reduce the risk of occurrence of symptoms associated with, a variety of metabolic diseases. For example, neuromodulation of targeted nerve fibers can treat, or reduce the risk of occurrence of symptoms associated with, diabetes (e.g., diabetes mellitus) or other diabetes-related diseases. The methods described herein can advantageously treat diabetes without requiring daily insulin injection or constant monitoring of blood glucose levels. The treatment provided by the devices, systems and methods described herein can be permanent or at least semi-permanent (e.g., lasting for several weeks, months or years), thereby reducing the need for continued or periodic treatment. Embodiments of the devices described herein can be temporary or implantable.

In some embodiments, neuromodulation of targeted nerve fibers as described herein can be used for the treatment of insulin resistance, genetic metabolic syndromes, ventricular tachycardia, atrial fibrillation or flutter, arrhythmia, inflammatory diseases, hypertension (arterial or pulmonary), obesity, hyperglycemia (including glucose tolerance), hyperlipidemia, eating disorders, and/or endocrine diseases. In some embodiments, neuromodulation of targeted nerve fibers treats any combination of diabetes, insulin resistance, or other metabolic diseases. In some embodiments, temporary or implantable neuromodulators may be used to regulate satiety and appetite (e.g., to promote weight loss). In several embodiments, modulation of nervous tissue that innervates (afferently or efferently) the liver is used to treat hemochromatosis, Wilson's disease, non-alcoholic steatohepatitis (NASH), non-alcoholic fatty liver disease (NAFLD), and/or other conditions affecting the liver and/or liver metabolism. In some embodiments, modulation of nervous tissue that innervates (afferently or efferently) the liver (e.g., hepatic denervation) is effective for reducing whole-body sympathetic tone and resulting conditions such as hypertension, congestive heart failure, atrial fibrillation, obstructive sleep apnea, and/or renal failure, etc.

In some embodiments, sympathetic nerve fibers associated with the liver are selectively disrupted (e.g., ablated, denervated, disabled, severed, blocked, injured, desensitized, removed) to decrease hepatic glucose production and/or increase hepatic glucose uptake, thereby aiding in the treatment of, or reduction in the risk of, diabetes and/or related diseases or disorders. The disruption can be permanent or temporary (e.g., for a matter of several days, weeks or months). In some embodiments, sympathetic nerve fibers in the hepatic plexus are selectively disrupted. In some embodiments, sympathetic nerve fibers surrounding (e.g., within the perivascular space of) the common hepatic artery proximal to the proper hepatic artery, sympathetic nerve fibers surrounding the proper hepatic artery, sympathetic nerve fibers in the celiac ganglion adjacent the celiac artery, other sympathetic nerve fibers that innervate or surround the liver, sympathetic nerve fibers that innervate the pancreas, sympathetic nerve fibers that innervate fat tissue (e.g., visceral fat), sympathetic nerve fibers that innervate the adrenal glands, sympathetic nerve fibers that innervate the small intestine (e.g., duodenum), sympathetic nerve fibers that innervate the stomach (e.g., or portions thereof, such as the pylorus), sympathetic nerve fibers that innervate brown adipose tissue, sympathetic nerve fibers that innervate skeletal muscle, and/or sympathetic nerve fibers that innervate the kidneys are selectively disrupted or modulated (simultaneously or sequentially) to facilitate treatment or reduction of symptoms associated with hypertension, diabetes (e.g., diabetes mellitus), or other metabolic diseases or disorders.

In some embodiments, the methods, devices and systems described herein are used to therapeutically modulate autonomic nerves associated with any diabetes-relevant organs or tissues. For example, with respect to the pancreas and duodenum, the nerves that innervate one or both structures can be neuromodulated (e.g., ablated) in addition to or instead of the nerves that innervate the liver, wherein said neuromodulation affects one or more symptoms/characteristics associated with diabetes or other metabolic diseases or disorders. Such symptoms/characteristics include but are not limited to changes (e.g., increases or decreases) in glucose levels, cholesterol levels, lipid levels, triglyceride levels, norepinephrine levels, insulin regulation, etc. in the blood plasma or liver or other organs. The devices and methods disclosed herein with respect to hepatic modulation can be used for neuromodulating the pancreas, duodenum, stomach or other organs and structures.

In accordance with several embodiments, any nerves containing autonomic fibers are modulated, including, but not limited to, the saphenous nerve, femoral nerves, lumbar nerves, median nerves, ulnar nerves, vagus nerves, and radial nerves. Nerves surrounding arteries or veins other than the hepatic artery may be modulated such as, but not limited to, nerves surrounding the superior mesenteric artery, the inferior mesenteric artery, the femoral artery, the pelvic arteries, the portal vein, pulmonary arteries, pulmonary veins, abdominal aorta, vena cavas, splenic arteries, gastric arteries, the internal carotid artery, the internal jugular vein, the vertebral artery, renal arteries, and renal veins. Celiac arteries may also be modulated according to several embodiments herein.

In accordance with several embodiments, a therapeutic neuromodulation system is used to selectively disrupt sympathetic nerve fibers. The neuromodulation system can comprise an ablation catheter system and/or a delivery catheter system (e.g., hollow, solid, partially hollow, catheter, probe, shaft or other delivery device with or without a lumen). An ablation catheter system may use radiofrequency (RF) energy to ablate sympathetic nerve fibers to cause neuromodulation or disruption of sympathetic communication. In some embodiments, an ablation catheter system uses ultrasonic energy to ablate sympathetic nerve fibers. In some embodiments, an ablation catheter system uses ultrasound (e.g., high-intensity focused ultrasound or low-intensity focused ultrasound) energy to selectively ablate sympathetic nerve fibers. In other embodiments, an ablation catheter system uses electroporation to modulate sympathetic nerve fibers. An ablation catheter, as used herein, shall not be limited to causing ablation, but also includes devices that facilitate the modulation of nerves (e.g., partial or reversible ablation, blocking without ablation, stimulation). In some embodiments, a delivery catheter system delivers drugs or chemical agents to nerve fibers to modulate the nerve fibers (e.g., via chemoablation). Chemical agents used with chemoablation (or some other form of chemically-mediated neuromodulation) may, for example, include phenol, alcohol, or any other chemical agents that cause chemoablation of nerve fibers. In some embodiments, cryotherapy is used. For example, an ablation catheter system is provided that uses cryoablation to selectively modulate (e.g., ablate) sympathetic nerve fibers. In other embodiments, a delivery catheter system is used with brachytherapy to modulate the nerve fibers. The catheter systems may further utilize any combination of RF energy, ultrasonic energy, focused ultrasound (e.g., HIFU, LIFU) energy, ionizing energy (such as X-ray, proton beam, gamma rays, electron beams, and alpha rays), electroporation, drug delivery, chemoablation, cryoablation, brachytherapy, or any other modality to cause disruption or neuromodulation (e.g., ablation, denervation, stimulation) of autonomic (e.g., sympathetic or parasympathetic) nerve fibers. As discussed below, microwave energy or laser energy (or combinations of two, three or more energy sources) are used in some embodiments. In some embodiments, energy is used in conjunction with non-energy based neuromodulation (e.g., drug delivery).

In some embodiments, a minimally invasive surgical technique is used to deliver the therapeutic neuromodulation system. For example, a catheter system (e.g., hollow, solid, partially hollow, catheter, probe, shaft or other delivery device with or without a lumen) for the disruption or neuromodulation of sympathetic nerve fibers can be delivered intra-arterially (e.g., via a femoral artery, brachial artery, radial artery). In some embodiments, an ablation catheter system is advanced to the proper hepatic artery to ablate (completely or partially) sympathetic nerve fibers in the hepatic plexus. In other embodiments, the ablation catheter system is advanced to the common hepatic artery to ablate sympathetic nerve fibers surrounding the common hepatic artery. In some embodiments, the ablation catheter system is advanced to the celiac artery or celiac trunk to ablate sympathetic nerve fibers in the celiac ganglion or celiac plexus (e.g., including nerves downstream thereof). An ablation or delivery catheter system can be advanced within other arteries (e.g., left hepatic artery, right hepatic artery, gastroduodenal artery, gastric arteries, splenic artery, renal arteries, etc.) in order to disrupt targeted sympathetic nerve fibers associated with the liver or other organs or tissue (such as the pancreas, fat tissue (e.g., visceral fat of the liver), the adrenal glands, the stomach, the small intestine, gall bladder, bile ducts, brown adipose tissue, skeletal muscle), at least some of which may be clinically relevant to diabetes. In several embodiments, neuromodulation (e.g., denervation, stripping, stimulation) of the celiac ganglion or modulation of celiac ganglion activity facilitates treatment of hypertension.

In some embodiments, a therapeutic neuromodulation or disruption system is delivered intravascularly through the venous system. For example, the therapeutic neuromodulation system may be delivered either through the portal vein or through the inferior vena cava. In some embodiments, the neuromodulation system is delivered percutaneously to the biliary tree to modulate or disrupt sympathetic nerve fibers.

In other embodiments, the neuromodulation system is delivered translumially or laparoscopically to modulate or disrupt sympathetic nerve fibers. For example, the neuromodulation system may be delivered translumially either through the stomach, or through the duodenum.

In some embodiments, minimally invasive surgical delivery (e.g., laparoscopic) of the neuromodulation system is accomplished in conjunction with image guidance techniques. For example, a visualization device such as a fiberoptic scope can be used to provide image guidance during minimally invasive surgical delivery of the neuromodulation system. In some embodiments, fluoroscopic, computerized tomography (CT), radiographic, optical coherence tomography (OCT), intravascular ultrasound (IVUS), Doppler, thermography, and/or magnetic resonance (MR) imaging is used in conjunction with minimally invasive surgical delivery of the neuromodulation system. In some embodiments, radiopaque markers are located at a distal end of the neuromodulation system to aid in delivery and alignment of the neuromodulation system.

In some embodiments, an open surgical procedure is used to access the nerve fibers to be modulated. In some embodiments, any of the modalities described herein, including, but not limited to, RF energy, ultrasonic energy, HIFU, thermal energy, light energy, electrical energy other than RF energy, drug delivery, chemoablation, cryoablation, steam or hotwater, ionizing energy (such as X-ray, proton beam, gamma rays, electron beams, and alpha rays) or any other modality are used in conjunction with an open surgical procedure to modulate or disrupt sympathetic nerve fibers. Neuromodulation via microwave energy and laser energy are also provided in some embodiments and discussed herein. In other embodiments, nerve fibers are surgically cut (e.g., transected) to disrupt conduction of nerve signals or otherwise cause nerve injury.

In some embodiments, a non-invasive (e.g., transcutaneous) procedure is used to modulate or disrupt sympathetic nerve fibers (e.g., nerves that innervate the liver, nerves within or surrounding the hepatic arteries, the celiac arteries, the gastroduodenal artery, the splenic artery, nerves that innervate the pancreas, and/or nerves that innervate the duodenum). In some embodiments, any of the modalities described herein, including, but not limited, to RF energy, ultrasonic energy, HIFU energy, radiation therapy, light energy, infrared energy, thermal energy, steam, hot water, magnetic fields, ionizing energy, other forms of electrical or electromagnetic energy or any other modality are used in conjunction with a non-invasive procedure to modulate or disrupt sympathetic nerve fibers.

In accordance with some embodiments, the neuromodulation system is used to modulate or disrupt sympathetic nerve fibers at one or more locations or target sites. For example, an ablation catheter system (e.g., comprising an ablation device or methodology described herein, for example ultrasound, RF, cryo, etc.) may perform ablation in a circumferential or radial pattern, and/or the ablation catheter system may perform ablation at a plurality of points linearly spaced apart along a vessel length. In other embodiments, an ablation catheter system performs ablation at one or more locations in any other pattern capable of causing disruption in the communication pathway of sympathetic nerve fibers (e.g., spiral patterns, zig-zag patterns, multiple linear patterns, etc.). The pattern can be continuous or non-continuous (e.g., intermittent). The ablation may be targeted at certain portions of the circumference of the vessels (e.g., half or portions less than half of the circumference). In some embodiments, modulation of (e.g., thermal injury or damage to) the vessel wall is non-circumferential. Ablation or other treatment may be performed in one quadrant, two quadrants, three quadrants or four quadrants of the vessel. In one embodiment, ablation or other treatment is not performed in more than two quadrants of the vessel. In other embodiments, ablation or other treatment is performed in sectors of other increments such as 2, 3, 5 or 6 sections. In some embodiments, the sector may span a radial distance of 90 degrees to 120 degrees. In other embodiments, the sector may span a radial distance of 120 degrees to 240 degrees. In various embodiments, the sectors are radially disposed in increments of approximately 90, 120, 144, or 180 degrees in order to achieve the desired effect.

In accordance with embodiments of the invention disclosed herein, therapeutic neuromodulation to treat various medical disorders and diseases includes neural stimulation of targeted nerve fibers. For example, autonomic nerve fibers (e.g., sympathetic nerve fibers, parasympathetic nerve fibers) may be stimulated to treat, or reduce the risk of occurrence of, diabetes (e.g., diabetes mellitus) or other conditions, diseases and disorders.

In some embodiments, parasympathetic nerve fibers that innervate the liver are stimulated. In some embodiments, parasympathetic nerve fibers that innervate the pancreas, fat tissue (e.g., visceral fat of the liver), the adrenal glands, the stomach (e.g., or portions thereof such as the pylorus), the kidneys, brown adipose tissue, skeletal muscle, and/or the small intestine (e.g., duodenum) are stimulated. In accordance with some embodiments, any combination of parasympathetic nerve fibers innervating the liver, the pancreas, fat tissue, the adrenal glands, the stomach, the kidneys, brown adipose tissue, skeletal muscle, and the small intestine are stimulated to treat, or alleviate or reduce the risk of occurrence of the symptoms associated with, diabetes (e.g., diabetes mellitus) or other conditions, diseases, or disorders. In some embodiments, the organs or tissue are stimulated directly either internally or externally. For example, modulation of tissue (or components of tissue, such as cells, receptors, baroreceptors, etc.) may be accomplished by several embodiments described herein, and may occur with or without modulation of nerves.

In some embodiments, a neurostimulator is used to stimulate sympathetic or parasympathetic nerve fibers. In some embodiments, the neurostimulator is implantable. In accordance with some embodiments, the implantable neurostimulator electrically stimulates parasympathetic nerve fibers. In some embodiments, the implantable neurostimulator chemically stimulates parasympathetic nerve fibers. In still other embodiments, the implantable neurostimulator uses any combination of electrical stimulation, chemical stimulation, or any other method capable of stimulating parasympathetic nerve fibers.

In other embodiments, non-invasive neurostimulation is used to effect stimulation of parasympathetic nerve fibers. For example, transcutaneous electrical stimulation may be used to stimulate parasympathetic nerve fibers. Other energy modalities can also be used to affect non-invasive neurostimulation of parasympathetic nerve fibers (e.g., light energy, ultrasound energy).

In some embodiments, neuromodulation of targeted autonomic nerve fibers treats diabetes (e.g., diabetes mellitus) and related conditions by decreasing systemic glucose. For example, therapeutic neuromodulation of targeted nerve fibers can decrease systemic glucose by decreasing hepatic glucose production. In some embodiments, hepatic glucose production is decreased by disruption (e.g., ablation) of sympathetic nerve fibers. In other embodiments, hepatic glucose production is decreased by stimulation of parasympathetic nerve fibers.

In some embodiments, therapeutic neuromodulation of targeted nerve fibers decreases systemic glucose by increasing hepatic glucose uptake. In some embodiments, hepatic glucose uptake is increased by disruption (e.g., ablation) of sympathetic nerve fibers. In other embodiments, hepatic glucose uptake is increased by stimulation of parasympathetic nerve fibers. In some embodiments, triglyceride or cholesterol levels are reduced by the therapeutic neuromodulation.

In some embodiments, disruption or modulation of the sympathetic nerve fibers of the hepatic plexus has no effect on the parasympathetic nerve fibers surrounding the liver. In some embodiments, disruption or modulation (e.g., ablation or denervation) of the sympathetic nerve fibers of the hepatic plexus causes a reduction of very low-density lipoprotein (VLDL) levels, thereby resulting in a beneficial effect on lipid profile. In several embodiments, the invention comprises neuromodulation therapy to affect sympathetic drive and/or triglyceride or cholesterol levels, including high-density lipoprotein (HDL) levels, low-density lipoprotein (LDL) levels, and/or very-low-density lipoprotein (VLDL) levels. In some embodiments, denervation or ablation of sympathetic nerves reduces triglyceride levels, cholesterol levels and/or central sympathetic drive. For example, norepinephrine levels may be affected in some embodiments.

In other embodiments, therapeutic neuromodulation of targeted nerve fibers (e.g., hepatic denervation) decreases systemic glucose by increasing insulin secretion. In some embodiments, insulin secretion is increased by disruption (e.g., ablation) of sympathetic nerve fibers (e.g., surrounding branches of the hepatic artery). In other embodiments, insulin secretion is increased by stimulation of parasympathetic nerve fibers. In some embodiments, sympathetic nerve fibers surrounding the pancreas may be modulated to decrease glucagon levels and increase insulin levels. In some embodiments, sympathetic nerve fibers surrounding the adrenal glands are modulated to affect adrenaline or noradrenaline levels. Fatty tissue (e.g., visceral fat) of the liver may be targeted to affect glycerol or free fatty acid levels. In some embodiments, insulin levels remain the same or increase or decrease by less than ±5%, less than 10%, less than ±2.5%, or overlapping ranges thereof. In some embodiments, insulin levels remain constant or substantially constant when a portion of the pancreas is ablated, either alone or in combination with the common hepatic artery or other hepatic artery branch. In various embodiments, denervation of nerves innervating the liver (e.g., sympathetic nerves surrounding the common hepatic artery) does not affect a subject's ability to respond to a hypoglycemic event.

In accordance with several embodiments of the invention, a method of decreasing blood glucose levels within a subject is provided. The method comprises forming an incision in a groin of a subject to access a femoral artery and inserting a neuromodulation device (e.g., catheter, ultrasound catheter, etc.) into the incision. In some embodiments, the method comprises advancing the neuromodulation device from the femoral artery through an arterial system to a common or proper hepatic artery and causing a therapeutically effective amount of energy to thermally inhibit neural communication along a sympathetic nerve in a hepatic plexus surrounding the common or proper hepatic artery to be delivered intravascularly by the ablation catheter to the inner wall of the proper hepatic artery, thereby decreasing blood glucose levels within the subject. Other incision or access points may be used as desired or required. In some embodiments, the neuromodulation device (e.g., hollow, solid, partially hollow, catheter, probe, shaft or other delivery device with or without a lumen) is a focused or unfocused ultrasound ablation catheter.

In some embodiments, the neuromodulation device (e.g., hollow, solid, partially hollow, catheter, probe, shaft or other delivery device with or without a lumen) is a radiofrequency (RF) ablation catheter comprising one or more electrodes. In some embodiments, the neuromodulation catheter is a high-intensity focused ultrasound ablation catheter. In some embodiments, the neuromodulation catheter is a cryoablation catheter. The method can further comprise stimulating one or more parasympathetic nerves associated with the liver to decrease hepatic glucose production or increase glucose uptake.

In accordance with several embodiments, a method of treating a subject having diabetes or symptoms associated with diabetes is provided. The method can comprise delivering an RF ablation catheter (e.g., hollow, solid, partially hollow, catheter, probe, shaft or other delivery device with or without a lumen) to a vicinity of a hepatic plexus of a subject and disrupting neural communication along a sympathetic nerve of the hepatic plexus by causing RF energy to be emitted from one or more electrodes of the RF ablation catheter. In some embodiments, the RF ablation catheter is delivered intravascularly through a femoral artery to a location within the proper or common hepatic artery branch. In some embodiments, the RF energy is delivered extravascularly by the RF ablation catheter.

In some embodiments, disrupting neural communication comprises permanently disabling neural communication along the sympathetic nerve of the hepatic plexus. In some embodiments, disrupting neural communication comprises temporarily inhibiting or reducing neural communication along the sympathetic nerve of the hepatic plexus. In some embodiments, disrupting neural communication along a sympathetic nerve of the hepatic plexus comprises disrupting neural communication along a plurality of sympathetic nerves of the hepatic plexus.

The method can further comprise positioning the RF ablation catheter in the vicinity of the celiac plexus of the subject and disrupting neural communication along a sympathetic nerve of the celiac plexus by causing RF energy to be emitted from one or more electrodes of the RF ablation catheter. In some embodiments, the method comprises positioning the RF ablation catheter in the vicinity of sympathetic nerve fibers that innervate the pancreas and disrupting neural communication along the sympathetic nerve fibers by causing RF energy to be emitted from one or more electrodes of the RF ablation catheter, positioning the RF ablation catheter in the vicinity of sympathetic nerve fibers that innervate the stomach and disrupting neural communication along the sympathetic nerve fibers by causing RF energy to be emitted from one or more electrodes of the RF ablation catheter, and/or positioning the RF ablation catheter in the vicinity of sympathetic nerve fibers that innervate the duodenum and disrupting neural communication along the sympathetic nerve fibers by causing RF energy to be emitted from one or more electrodes of the RF ablation catheter. In some embodiments, drugs or therapeutic agents can be delivered to the liver or surrounding organs or tissues.

In accordance with several embodiments, a method of decreasing blood glucose levels within a subject is provided. The method comprises inserting an RF, ultrasound, etc. ablation catheter (e.g., hollow, solid, partially hollow, catheter, probe, shaft or other delivery device with or without a lumen) into vasculature of the subject and advancing the RF ablation catheter to a location of a branch of a hepatic artery (e.g., the proper hepatic artery or the common hepatic artery). In one embodiment, the method comprises causing a therapeutically effective amount of RF, ultrasound, etc. energy to thermally inhibit neural communication within sympathetic nerves of a hepatic plexus surrounding the common or proper hepatic artery to be delivered intravascularly by the ablation catheter to the inner wall of the proper hepatic artery, thereby decreasing blood glucose levels within the subject. In some embodiments, the delivery of the therapeutically effective amount of RF, ultrasound, etc. energy to the common or proper hepatic artery also comprises delivery of energy sufficient to modulate (e.g., ablate, denervate) nerves of the pancreas and/or duodenum, which may provide a synergistic effect. In various embodiments, blood glucose levels decrease by 30-60% (e.g., 40-50%, 30-50%, 35-55%, 45-60% or overlapping ranges thereof) from a baseline level.

In one embodiment, the therapeutically effective amount of RF energy at the location of the inner vessel wall of the target vessel or at the location of the target nerves is in the range of between about 100 J and about 1 kJ (e.g., between about 100 J and about 500 J, between about 250 J and about 750 J, between about 300 J and about kJ, between about 500 J and 1 kJ, or overlapping ranges thereof). In one embodiment, the therapeutically effective amount of RF energy has a power between about 0.1 W and about 14 W (e.g., between about 0.1 W and about 10 W, between about 0.5 W and about 5 W, between about 3 W and about 8 W, between about 2 W and about 6 W, between about 5 W and about 10 W, between about 8 W and about 12 W, between about 10 W and about 14 W, or overlapping ranges thereof). The ranges provided herein can be per electrode, per energy delivery location, or total energy delivery. The RF, ultrasound, etc. energy may be delivered at one location or multiple locations along the target vessel or within multiple different vessels. In some embodiments, the RF, ultrasound, etc. energy is delivered sufficient to cause fibrosis of the tissue surrounding the nerves, thereby resulting in nerve dropout.

In one embodiment, the RF ablation catheter (e.g., hollow, solid, partially hollow, catheter, probe, shaft or other delivery device with or without a lumen) comprises at least one ablation electrode. The RF ablation catheter may be configured to cause the at least one ablation electrode to contact the inner wall of the hepatic artery branch and maintain contact against the inner wall with sufficient contact pressure while the RF energy is being delivered. In one embodiment, the RF ablation catheter comprises a balloon catheter configured to maintain sufficient and continuous contact pressure of the at least one electrode against the inner wall of the hepatic artery branch. In one embodiment, the RF ablation catheter comprises an actuatable (e.g., steerable, articulatable, expandable) distal tip configured to maintain sufficient contact pressure of the at least one electrode against the inner wall of the hepatic artery branch. In various embodiments, the sufficient contact pressure may range from about 0.1 $g/mm^2$ to about 100 $g/mm^2$ (e.g., between about 0.1 $g/mm^2$ and about 10 $g/mm^2$). In some embodiments, the RF ablation catheter comprises at least one anchoring member configured to maintain sufficient and continuous contact of the at least one electrode against the inner wall of the hepatic artery branch. The actuatable distal tip and/or anchoring member may comprise one or more flexible portions, one or more expandable members (e.g., balloons, ribbons, cages, baskets, wires, struts), one or more steerable or articulatable members, one or more pre-curved shape memory portions, or combinations of the same. Expandable members may be self-expandable, mechanically expandable, pneumatically expandable, inflatable, or otherwise expandable.

In accordance with several embodiments, a method of treating a subject having diabetes or symptoms associated with diabetes is provided. In one embodiment, the method comprises delivering an RF ablation catheter to a vicinity of a hepatic plexus within a hepatic artery branch (e.g., proper hepatic artery, common hepatic artery or adjacent or within a bifurcation between the two). In one embodiment, the RF ablation catheter comprises at least one electrode. The method may comprise positioning the at least one electrode in contact with an inner wall of the hepatic artery branch. In one embodiment, the method comprises disrupting neural communication of sympathetic nerves of the hepatic plexus surrounding the hepatic artery branch by applying an electric signal to the at least one electrode, thereby causing thermal energy to be delivered by the at least one electrode to heat the inner wall of the hepatic artery branch. Non-ablative heating, ablative heating, or combinations thereof, are used in several embodiments.

In one embodiment, disrupting neural communication comprises permanently disabling neural communication of sympathetic nerves of the hepatic plexus. In one embodiment, disrupting neural communication comprises temporarily inhibiting or reducing neural communication along sympathetic nerves of the hepatic plexus. In some embodiments, the method comprises positioning the RF ablation catheter in the vicinity of the celiac plexus of the subject and disrupting neural communication along sympathetic nerves of the celiac plexus, positioning the RF ablation catheter in the vicinity of sympathetic nerve fibers that innervate the pancreas and disrupting neural communication along the sympathetic nerve fibers, positioning the RF ablation catheter in the vicinity of sympathetic nerve fibers that innervate the stomach and disrupting neural communication along the sympathetic nerve fibers, and/or positioning the RF ablation catheter in the vicinity of sympathetic nerve fibers that innervate the duodenum and disrupting neural communication along the sympathetic nerve fibers by causing RF energy to be emitted from the at least one electrode of the RF ablation catheter. In several embodiments, a feedback mechanism is provided to facilitate confirmation of neuromodulation and to allow for adjustment of treatment in real time. In one embodiment, ultrasound elastography, ultrasound sonography, echo decorrelation, Doppler ultrasound, magnetic resonance elastography, and/or computed tomography is used to track progress or status of neuromodulation (e.g., ablation) procedures or methods (such as the methods described herein).

In accordance with several embodiments, a method of treating a subject having diabetes or symptoms associated with diabetes (e.g., high blood glucose or triglyceride levels) is provided. In one embodiment, the method comprises delivering a neuromodulation catheter within a hepatic artery to a vicinity of a hepatic plexus of a subject and modulating nerves of the hepatic plexus by causing RF, ultrasound, etc. energy to be emitted from one or more electrodes of the neuromodulation catheter. In one embodiment, the step of modulating the nerves of the hepatic plexus comprises denervating sympathetic nerves of the hepatic plexus and/or stimulating parasympathetic nerves of the hepatic plexus. In one embodiment, the sympathetic denervation and the parasympathetic stimulation are performed simultaneously. In one embodiment, the sympathetic denervation and the parasympathetic stimulation are performed sequentially. In one embodiment, sympathetic nerves are modulated without modulating parasympathetic nerves surrounding the same vessel or tissue.

In accordance with several embodiments, an apparatus configured for hepatic neuromodulation is provided. In one embodiment, the apparatus comprises a balloon catheter configured for intravascular placement within one or more hepatic artery branches or adjacent artery branches. In one embodiment, the balloon catheter comprises at least one expandable balloon and a bipolar electrode pair. In one embodiment, at least one of the bipolar electrode pair is configured to be positioned to be expanded into contact with an inner wall of the hepatic artery branch upon expansion of the at least one expandable balloon. In one embodiment, the bipolar electrode pair is configured to deliver a thermal dose of energy configured to achieve hepatic denervation. The at least one expandable balloon may be configured to maintain sufficient contact pressure (e.g., continuous contact pressure) between the at least one electrode of the bipolar electrode pair and the inner wall of the hepatic artery branch. In some embodiments, the balloon catheter comprises two expandable balloons, each having one electrode of the bipolar electrode pair disposed thereon. In one embodiment, the balloon catheter comprises a single expandable balloon and the bipolar electrode pair is disposed on the expandable balloon. In one embodiment, the balloon comprises a cooling fluid within a lumen of the balloon.

In accordance with several embodiments, an apparatus configured for hepatic neuromodulation is provided. In one embodiment, the apparatus comprises a catheter comprising a lumen and an open distal end and a steerable shaft configured to be slidably received within the lumen of the catheter. In one embodiment, at least a distal portion of the steerable shaft comprises a shape memory material having a pre-formed shape configured to cause the distal portion of the steerable shaft to change in linear shape (e.g., bend) to contact a vessel wall upon advancement of the distal portion of the steerable shaft out of the open distal end of the catheter. In one embodiment, a distal end of the steerable shaft comprises at least one electrode that is configured to be activated to deliver a thermal dose of energy configured to achieve denervation of a branch of a hepatic artery or other target vessel. In one embodiment, the shape memory material of the steerable shaft is sufficiently resilient to maintain sufficient and continuous contact pressure between the at least one electrode and an inner wall of the branch of the hepatic artery during a hepatic denervation procedure. The outside diameter at a distal end of the catheter may be smaller than the outside diameter at a proximal end of the catheter to accommodate insertion within vessels having a small inner diameter. In various embodiments, the outside diameter at the distal end of the catheter is between about 1 mm and about 4 mm (e.g., 1 mm-3 mm, 1 mm, 2 mm, 3 mm, 4 mm, less than or equal to 3 mm). In one embodiment, the at least one electrode comprises a coating having one or more windows. For embodiments to be used in the hepatic arteries, the steerable shaft of the catheter can be actuated to have multiple bends (e.g., two, three, or more bends) configured to conform to two or more bends in the hepatic artery branches or neighboring arteries. In some embodiments, one or more portions of the catheter are pre-curved to have a particular bend shape. In some embodiments, one of the multiple bends is pre-formed and one of the multiple bends is actuated during delivery. In some embodiments, an energy delivery device (e.g., catheter) comprises a distal portion constructed of shape memory material and a lumen configured to receive a guidewire. The shape memory material may be heat- or shape-set so as to cause a distal end of the energy delivery device (which may include an energy delivery element such as an electrode) to contact an inner wall of a target vessel. A guidewire may retain the distal portion of the energy delivery device in a straight or substantially straight alignment until the distal portion is positioned in a desired position within the target vessel. When the guidewire is withdrawn from the lumen of the energy delivery device, the shape-memory distal portion deforms to the heat- or shape-set configuration so as to cause the distal end of the energy delivery device to contact the inner wall of the target vessel.

In accordance with several embodiments, a neuromodulation kit is provided. In one embodiment, the kit comprises a neuromodulation catheter configured to be inserted within a vessel of the hepatic system for modulating nerves surrounding the hepatic artery. In one embodiment, the kit comprises a plurality of energy delivery devices configured to be inserted within the lumen of the neuromodulation catheter. In one embodiment, each of the energy delivery devices comprises at least one modulation element at or near a distal end of the energy delivery device. In one embodiment, each of the energy delivery devices comprises a distal portion comprising a different pre-formed shape memory configuration. The at least one modulation element may be configured to be activated to modulate at least a portion of the nerves surrounding the hepatic artery to treat symptoms associated with diabetes.

In several embodiments, the invention comprises modulation of the nervous system to treat disorders affecting insulin and/or glucose, such as insulin regulation, glucose uptake, metabolism, etc. In some embodiments, nervous system input and/or output is temporarily or permanently modulated (e.g., decreased). Several embodiments are configured to perform one or a combination of the following effects: ablating nerve tissue, heating nerve tissue, cooling the nerve tissue, deactivating nerve tissue, severing nerve tissue, cell lysis, apoptosis, and necrosis. In some embodiments, localized neuromodulation is performed, leaving surrounding tissue unaffected. In other embodiments, the tissue surrounding the targeted nerve(s) is also treated.

In accordance with several embodiments, methods of hepatic denervation are performed with shorter procedural and energy application times than renal denervation procedures. In several embodiments, hepatic denervation is performed without causing pain or mitigates pain to the subject during the treatment. In accordance with several embodiments, neuromodulation (e.g., denervation or ablation) is performed without causing stenosis or thrombosis within the target vessel (e.g., hepatic artery). In embodiments involving thermal treatment, heat lost to the blood stream may be prevented or reduced compared to existing denervation systems and methods, resulting in lower power and shorter treatment times. In various embodiments, the methods of neuromodulation are performed with little or no endothelial damage (e.g., less than 20% ablation of) to the target vessels. In several embodiments, energy delivery is delivered substantially equally in all directions (e.g., omnidirectional delivery). In various embodiments of neuromodulation systems (e.g., catheter-based energy delivery systems described herein), adequate electrode contact with the target vessel walls is maintained, thereby reducing power levels, voltage levels, vessel wall or tissue thermal injury, and treatment times.

In accordance with several embodiments, a method for thermally-induced hepatic neuromodulation is provided. The method comprises inserting a neuromodulation catheter (e.g., RF ablation catheter) into vasculature of a subject. In one embodiment, the neuromodulation catheter is configured to form a first bend to conform to, or be positioned to correspond with, a first anatomical bend of a first hepatic artery portion or a first artery branching into or out from a hepatic artery and is configured to form a second bend to conform to a second anatomical bend of a second hepatic artery portion or a second artery branching into or out from the hepatic artery. The first bend and/or second bend may be formed by mechanical actuation, magnetic actuation, material actuation, pneumatic actuation, hydraulic actuation, inflation, self-expansion, or the like. In one embodiment, the neuromodulation catheter, the first bend and/or second bend is pre-bent or pre-curved. Although several catheters and other access/delivery devices are disclosed herein that are designed (e.g., in shape, size, flexibility, etc.) for the hepatic artery, such catheters and other access/delivery devices can also be used for other arteries and vessels, and in particular, other arteries and vessels that are tortuous. In addition, although devices may be described herein as neuromodulation catheters or devices and described with respect to modulation (e.g., ablation) of nerves, the catheters or other devices may be used to modulate other types of tissue (e.g., tissue lining an organ or vessel, muscle tissue, endothelial tissue, submucosal tissue).

In some embodiments, the neuromodulation catheter is advanced to a location within a hepatic artery of the vasculature or to a location upstream of the hepatic artery (e.g., within the aorta or celiac trunk or axis). The first bend may be formed and/or aligned with a first anatomical bend (e.g., an acute bend between the aorta or celiac trunk and the common hepatic artery, or a first bend within the common hepatic artery). The second bend may be formed and/or aligned with a second anatomical bend (e.g., an acute bend between the common hepatic artery and the proper hepatic artery or gastroduodenal artery, or a second bend within the common hepatic artery). In some embodiments, the neuromodulation catheter is activated or otherwise caused to intravascularly deliver a therapeutically effective amount of energy (e.g., RF energy, thermal energy, ultrasound energy) to an inner wall of the hepatic artery to modulate (e.g., denervate, ablate, injure, stimulate) one or more sympathetic nerves of a hepatic plexus.

In one embodiment, the neuromodulation catheter comprises an RF ablation catheter having at least one electrode. The RF ablation catheter may advantageously be configured to maintain sufficient contact pressure of the at least one electrode against an inner arterial wall of the hepatic artery while RF energy is being delivered. In one embodiment, the RF ablation catheter comprises a balloon catheter configured to maintain the sufficient contact pressure of the at least one electrode against the inner arterial wall of the hepatic artery. In one embodiment, the RF, ultrasound, etc. ablation catheter comprises an actuatable distal portion configured to conform to the first anatomical bend and the second anatomical bend during said advancing of the RF, ultrasound, etc. ablation catheter to a location within a hepatic artery. In one embodiment, the actuatable distal portion comprises shape memory material configured to form the first bend and the second bend. In one embodiment, the actuatable distal portion is configured to be mechanically expanded by one or more pull wires to form the first bend and the second bend. In one embodiment, the first bend and the second bend together from an S-shape.

In one embodiment, the sufficient contact pressure is between about 0.1 $g/mm^2$ and about 100 $g/mm^2$ (e.g., between about 0.1 $g/mm^2$ and about 10 $g/mm^2$, between about 5 $g/mm^2$ and about 20 $g/mm^2$, between about 1 $g/mm^2$ and about 50 $g/mm^2$, or overlapping ranges thereof). In one embodiment, the therapeutically effective amount of RF energy is in the range of between about 300 J and about 1.5 kJ (e.g., about 300 J to about 1 kJ) per target location or total for all target locations. The therapeutically effective amount of RF energy may have a power level between about 0.1 W and about 14 W (e.g., between about 0.1 W and about 10 W, between about 3 W and about 8 W, between about 3 W and about 10 W) per target location.

In some embodiments, the method comprises providing cooling to a portion of the common hepatic artery that is or is not being targeted by the RF energy or to the at least one electrode. In one embodiment, cooling comprises infusing saline within the catheter or within the blood flow adjacent the at least one electrode. In one embodiment, cooling comprises obstructing flow upstream of the at least one electrode to increase the arterial flow rate past the at least one electrode, thereby providing convective cooling due to increased blood flow. In some embodiments, flow is diverted or channeled toward the at least one electrode (e.g., from a center of the vessel toward a wall of the vessel).

In accordance with several embodiments, a device for thermally-induced hepatic neuromodulation is provided. The device comprises a catheter body having a proximal end and a distal end and a lumen extending from the proximal end to the distal end. In one embodiment, the catheter body is configured for percutaneous, intravascular placement within a hepatic artery branch. The device may comprise an actuatable portion at the distal end of the catheter body and at least one electrode disposed on the actuatable portion. In some embodiments, the actuatable portion is configured to provide stabilization of the catheter within the hepatic artery branch and to facilitate contact of the at least one electrode with an inner arterial wall of hepatic artery branch. The at least one electrode or transducer may be configured to be activated to deliver thermal energy sufficient to achieve modulation (e.g., denervation, ablation, stimulation) of at least a portion of the hepatic artery branch (e.g., a segment of the common hepatic artery having a length of 30 mm or less, 24 mm or less, 20 mm or less, or between 20 mm and 30 mm). The at least one electrode or transducer may be repositioned and activated at multiple positions along the length of and/or around the circumference of the hepatic artery branch. The at least one electrode or transducer may comprise one or more monopolar electrodes or one or more bipolar electrode pairs. In embodiments involving multiple electrodes or transducers, modulation at different locations or positions may be performed simultaneously or sequentially. In some embodiments, a neuromodulation device consists or consists essentially of only two electrodes or transducers. In some embodiments, a neuromodulation device consists or consists essentially only of four electrodes or transducers. In various embodiments, the electrodes or transducers advantageously facilitate ablation of only two quadrants or sections of the vessel wall instead of all four quadrants. In some embodiments, electrodes or transducers are positioned to maintain 180-degree offset between the electrodes or transducers and to provide spacing between the electrodes or transducers along the length of the vessel, as desired or required. Other numbers of electrodes or transducers (e.g., three electrodes, five electrodes, etc.) and other circumferential offsets (e.g., 30 degrees, 45 degrees, 60 degrees, 72 degrees, 90 degrees, 120 degrees) may be used in other embodiments. In various embodiments, the electrodes or transducers may be spaced circumferentially (or radially) and/or axially (or longitudinally) and may be independently adjustable to adjust circumferential and/or axial spacing of the electrodes (and treatment sites) depending on the vessel, patient, or treatment parameters.

In one embodiment, the actuatable portion comprises an inflatable balloon. In one embodiment, the actuatable portion comprises a deflectable bend segment having a preformed bend shape such that the distal end of the catheter body bends off-axis relative to a longitudinal axis of the proximal portion of the catheter body. In one embodiment, the actuatable portion comprises shape memory material having one or more pre-formed bend shapes. In one embodiment, the actuatable portion comprises one or more flexible bend segments configured to be actuated by one or more pull wires to form one or more bend shapes to conform to anatomical bends within the hepatic artery branch or to facilitate access to the hepatic artery branch. In one embodiment, the actuatable portion comprises one or more flexible ribbon wires or cables configured to be expanded outward to contact the inner arterial wall of the hepatic artery branch at a target location with the at least one electrode disposed on at least one of said one or more flexible ribbon wires or cables. The actuatable portion may comprise a plurality of independently actuatable members. In various embodiments, the actuatable portion(s) comprises one or more of the following: shape-memory material, flexible bend segments, ribbon wires or cables, expandable members, and inflatable members. In one embodiment, the device comprises an outer sheath and the catheter body (e.g., probe or shaft) is configured to be delivered within a lumen of the outer sheath and is translatable relative to the outer sheath. In one embodiment, the outer sheath is deflectable. In one embodiment, articulation of a first bend segment is controlled by a first pull wire and articulation of a second bend segment is controlled by a second pull wire. In one embodiment, a first flexible bend segment is configured to conform to a first arterial bend upon actuation and a second flexible bend segment is configured to conform to a second arterial bend. The first bend segment and the second segment may together form an S-shape upon actuation. In one embodiment, the device comprises an obstruction element configured to be positioned adjacent the at least one electrode to increase arterial flow past the electrode, thereby facilitating cooling of the at least one electrode. The at least one electrode may comprise a plurality of electrodes configured to deliver thermal energy to multiple locations within the hepatic artery branch simultaneously or sequentially. The target locations may be spaced apart along a length of a target segment of the hepatic artery (e.g., segment of less than 30 mm length, 20 mm to 30 mm length, less than 24 mm length, etc.). In some embodiment, an apparatus for neuromodulation includes an elongate body having a proximal end and a distal end that is configured for percutaneous, intravascular placement within a tortuous artery. The apparatus may also include an actuatable portion at the distal end of the elongate body. The apparatus may include at least one electrode disposed on the actuatable portion that is configured to provide stabilization within the tortuous artery and configured to facilitate contact of the at least one electrode with an inner wall of the tortuous artery. In one embodiment, the at least one electrode is configured to be activated to deliver thermal energy sufficient to achieve denervation of at least a portion of the tortuous artery. The actuatable portion may comprise one or more flexible bend segments configured to be actuated by one or more pull wires to form one or more bend shapes to conform to anatomical bends within the artery or to facilitate access to the tortuous artery, wherein a first flexible bend segment is configured to conform to a first arterial bend upon actuation, and wherein a second flexible bend segment is configured to conform to a second arterial bend upon actuation. In some embodiments, articulation of the first flexible bend segment is controlled by a first pull wire and articulation of the second flexible bend segment is controlled by a second pull wire. The apparatus may further include an outer sheath, wherein the elongate body is configured to be delivered within a lumen of the outer sheath and is translatable relative to the outer sheath. The elongate body may include a lumen configured to track a guidewire to facilitate access. In one embodiment, the elongate body comprises a third and/or fourth bend. In one embodiment, the elongate body further comprises a pre-formed bend shape.

In accordance with several embodiments, a method for thermally-induced hepatic neuromodulation is provided to decrease blood glucose and/or triglyceride levels within a subject. In one embodiment, the method comprises identifying a subject having a metabolic disorder and inserting an RF ablation catheter into vasculature of the subject. In one embodiment, the method comprises advancing the RF ablation catheter to a location within a common hepatic artery of the vasculature. The location may be within the common hepatic artery between a branch of the celiac artery and a branch of the common hepatic artery. In one embodiment, the RF ablation catheter is used to intravascularly deliver a therapeutically effective amount of RF energy to an inner wall of the common hepatic artery to ablate one or more sympathetic nerves of a hepatic plexus, thereby decreasing blood glucose and/or triglyceride levels within the subject. In one embodiment, the RF ablation catheter consists, consists essentially of or comprises two electrodes. The RF ablation catheter may advantageously be configured to maintain sufficient contact pressure of at least one of the two electrodes (e.g., an active electrode) against the inner wall of the common hepatic artery while the RF energy is being delivered. In one embodiment, the ablation catheter comprises a balloon catheter configured to maintain the sufficient contact pressure of the at least one electrode against the inner wall of the common hepatic artery. In one embodiment, the ablation catheter comprises a steerable distal tip configured to maintain sufficient contact pressure of the at least one electrode against the inner wall of the common hepatic artery. The sufficient contact pressure may be between about 5 g/mm$^2$ and about 100 g/mm$^2$ or between about 0.1 g/mm$^2$ and about 10 g/mm$^2$. In one embodiment, the RF energy is caused to be delivered to an anterior 180° arc of the inner wall of the common hepatic artery, thereby ablating sympathetic nerves without ablating parasympathetic nerves. In some embodiments, the ablation catheter comprises a force sensor or transducer for measuring the contact force of the at least one electrode against the inner wall of the common hepatic artery.

In one embodiment, a method for thermally-induced hepatic neuromodulation to decrease blood glucose and/or triglyceride levels within a subject is provided. The method comprises delivering an RF ablation catheter comprising two electrodes to a vicinity of a hepatic plexus within a hepatic artery branch, positioning at least one of the two electrodes in contact with an inner wall of the hepatic artery branch and disrupting neural communication of sympathetic nerves of the hepatic plexus surrounding the hepatic artery branch by applying an electric signal to the at least one electrode, thereby causing thermal energy to be delivered by the at least one electrode to heat the inner wall of the hepatic artery branch. The hepatic artery branch may be the proper hepatic artery or the common hepatic artery. In various embodiments, disrupting neural communication comprises permanently disabling neural communication of sympathetic nerves of the hepatic plexus or temporarily inhibiting or reducing neural communication of sympathetic nerves of the hepatic plexus. In one embodiment, the method comprises positioning the RF ablation catheter in the vicinity of the celiac plexus of the subject and disrupting neural communication of sympathetic nerves of the celiac plexus by causing RF energy to be emitted from the at least one electrode of the RF ablation catheter.

In one embodiment, a method for thermally-induced hepatic neuromodulation to decrease blood glucose and/or triglyceride levels within a subject comprises delivering a neuromodulation catheter within a hepatic artery to a vicinity of a hepatic plexus of a subject; and modulating nerves of the hepatic plexus by using said catheter to deliver energy to the hepatic plexus sufficient to modulate one or more nerves within the hepatic plexus to decrease at least one of blood glucose levels or triglyceride levels in said subject. In one embodiment, modulating the nerves of the hepatic plexus comprises denervating sympathetic nerves of the hepatic plexus without denervating parasympathetic nerves of the hepatic plexus. In one embodiment, modulating the nerves of the hepatic plexus comprises denervating sympathetic nerves of the hepatic plexus and stimulating parasympathetic nerves of the hepatic plexus.

In accordance with several embodiments, a device for hepatic neuromodulation is provided. In one embodiment, the device comprises a catheter body having a proximal end and a distal end and a lumen extending from the proximal end to the distal end and the catheter body is configured for percutaneous, intravascular placement within a hepatic artery branch. In one embodiment, the device comprises an articulatable portion at the distal end of the catheter body and at least one articulation member (e.g., wire) extending from the proximal end of the body and being coupled to the articulatable portion. The at least one articulation wire may be configured to bend the articulatable portion at the distal end of the catheter body. In one embodiment, the articulatable portion and/or a region distal to the articulatable portion comprises one or more RF electrodes, wherein at least one of the RF electrodes is configured to be activated to deliver RF energy sufficient to achieve denervation of the hepatic artery branch, thereby decreasing blood glucose and/or triglyceride levels within the subject. In one embodiment, the distal portion of the catheter body comprises a deflectable bend segment having a preformed bend shape such that the distal end of the catheter body bends off-axis relative to a longitudinal axis of the proximal portion of the catheter body such that the articulatable portion and the deflectable bend segment facilitate treatment within variable and tortuous anatomy of or leading to the hepatic artery (such as the celiac artery branching off the abdominal aorta). In one embodiment, the articulatable portion is configured to apply and maintain contact pressure between the at least one active RF electrode and an inner arterial wall of the hepatic artery branch, thereby facilitating continuous contact as the hepatic artery branch moves in response to diaphragm motion. In one embodiment, the contact pressure is between about 5 $g/mm^2$ and about 100 $g/mm^2$ and the RF energy configured to be delivered to achieve denervation of the hepatic artery branch is between about 100 J and about 2 kJ (e.g., between about 100 J and 1 kJ, between 500 J and 1.5 kJ, between 1 kJ and 2 kJ, or overlapping ranges thereof).

In one embodiment, the catheter body has a length sufficient to extend from a radial or femoral artery to the hepatic artery branch and the distal end of the catheter body has an outside diameter sized to fit within the hepatic artery branch. In some embodiments, the catheter body has a length sufficient to extend from a femoral artery or a radial artery to an arterial branch supplying the pancreas, duodenum, stomach, liver, or other gastrointestinal organs. In one embodiment, the device comprises an outer sheath and the catheter body is configured to be delivered within a lumen of the outer sheath and is translatable relative to the outer sheath. In one embodiment, the deflectable bend segment of the catheter body is configured to transition to the preformed bend shape upon retraction of the outer sheath or upon advancement of the distal end of the catheter body out of the outer sheath. In one embodiment, the outer sheath is deflectable. In one embodiment, the device comprises two radiopaque markers positioned along the distal end of the catheter body configured to be used to adjust the contact pressure. In one embodiment, the articulatable portion comprises a plurality of independently controllable bending segments. In one embodiment, the preformed bend shape of the deflectable bend segment is configured to correspond to a bend between a celiac artery or aorta and a common hepatic artery. Various embodiments of RF ablation catheters and methods of use provide decreased ablation times and decreased lumenal injury while providing heat to ablate nerves.

In accordance with several embodiments, a device for hepatic neuromodulation is provided. In one embodiment, the device comprises a catheter body having a proximal end and a distal end and a lumen extending from the proximal end to the distal end and the catheter body is configured for percutaneous, intravascular placement within a hepatic artery branch. In one embodiment, the device comprises an articulatable portion at the distal end of the catheter body comprising two independently controllable bending segments configured to be individually articulated by two articulation members (e.g., wires) extending from the proximal end of the catheter body to the two independently controllable bending segments. In one embodiment, the two independently controllable bending segments together comprise two or more electrodes, wherein at least one of the RF electrodes is configured to be activated to deliver RF energy sufficient to achieve denervation of the hepatic artery branch, thereby decreasing blood glucose and/or triglyceride levels within the subject. In one embodiment, articulation of a first bending segment of the two independently controllable bending segments is controlled by a first articulation wire and wherein articulation of a second bending segment of the two independently controllable bending segments is controlled by a second articulation wire. The first bending segment may be configured to articulate to conform to a first arterial bend, and wherein the second bending segment is configured to conform to a second arterial bend.

In accordance with several embodiments, a device for thermally-induced hepatic neuromodulation is provided. In one embodiment, the device comprises a catheter body having a proximal end and a distal end and a lumen extending from the proximal end to the distal end and the catheter body is configured for percutaneous, intravascular placement within a hepatic artery branch. In one embodiment, the catheter body has a length sufficient to extend from a femoral artery to the hepatic artery branch and the distal end of the catheter body has an outside diameter sized to fit within the hepatic artery branch. The distal end of the catheter body may comprise a deflectable bend segment having a preformed bend shape such that the distal end of the catheter body bends off-axis relative to a longitudinal axis of the proximal portion of the catheter body. The deflectable bend segment and/or a region distal to the bend segment may comprise one or more electrodes, wherein at least one of the RF electrodes is configured to be activated to deliver RF energy sufficient to achieve denervation of the hepatic artery branch. In one embodiment, the deflectable bend segment is configured to apply and maintain contact pressure between the at least one active RF electrode and an inner arterial wall of the hepatic artery branch, thereby facilitating continuous contact as the hepatic artery branch moves in response to diaphragm motion and thereby facilitating treatment within variable and tortuous anatomy of the hepatic artery. In one embodiment, the device comprises an outer sheath and the catheter body is configured to be delivered within a lumen of the outer sheath and is translatable relative to the outer sheath. The deflectable bend segment may be configured to transition to the preformed bend shape upon retraction of the outer sheath or upon advancement of the distal end of the catheter body out of the outer sheath.

In accordance with several embodiments, an apparatus for hepatic neuromodulation is provided that includes a shaft comprising a proximal end, a distal end and a lumen and an electrode positioned at a distal tip of the distal end of the shaft. In one embodiment, the shaft comprises a first region, a second region and a third region. The first region may comprise a resiliently deformable region proximal to the electrode, the second region may comprise an articulatable region proximal to the resiliently deformable region and the third region may comprise a torsionally rigid region proximal to the articulatable region. In some embodiments, at least one of the first region, the second region and the third region is configured to navigate a tortuosity of a hepatic artery. The apparatus may include a pull wire extending from a distal end of the articulatable region to the proximal end of the shaft, the pull wire configured to articulate the electrode at the distal tip toward an inner wall of the hepatic artery and maintain a consistent contact force of the electrode against the inner wall, wherein the electrode is configured to be activated to deliver energy sufficient to achieve denervation of at least a portion of the hepatic artery. In one embodiment, the diameter of the electrode is equal to the length of the electrode. In one embodiment, the torsionally rigid region is flexible and the torsionally rigid region is torsionally rigid in at least one direction. The articulatable region may be configured to provide a cantilever support to facilitate maintenance of the consistent electrode contact force. The length of the articulatable region may be between 0.5 and 2 cm. In one embodiment, the shaft comprises a hypotube and the torsionally rigid region comprises an interrupted spiral cut pattern that varies along a length of the torsionally rigid region. In one embodiment, the articulatable region comprises a spine cut pattern and/or is configured to provide 180-degree articulation.

In accordance with several embodiments, a neuromodulation catheter is provided. The catheter comprises a first end, a second end and a lumen extending from the first end to the second end. In one embodiment, the catheter comprises a balloon disposed at the distal end. The balloon may be disposed about substantially the entire circumference of the catheter (e.g., between 80% and 90%, between 75% and 85%, between 85% and 95%, or overlapping ranges thereof). In one embodiment, the catheter comprises an electrode disposed at a region of the catheter not covered by the balloon. Inflation of the balloon may be effective to occlude a portion of the cross-sectional area of an artery or other vessel into which the catheter is placed, thereby increasing the blood flow velocity around the electrode. In one embodiment, the electrode is configured to deliver energy sufficient to cause denervation of one or more sympathetic nerves surrounding the artery or other vessel. In some embodiments, an apparatus adapted for neuromodulation of nerves surrounding a vessel lumen comprises a tubular shaft comprising a first end, a second end and a lumen extending from the first end to the second end. The apparatus may comprise a balloon positioned at the distal end of the shaft, the balloon configured to transition from a deflated configuration to an inflated configuration through introduction of fluid through the lumen of the shaft. When in the inflated configuration, the balloon may be disposed around between 85% and 95% of a circumference of the shaft. The apparatus may comprise an electrode positioned at a location of the shaft that is not covered by the balloon. In the inflated configuration the balloon may occlude a portion of a cross-sectional area of a vessel, thereby increasing blood flow velocity around the electrode. In one embodiment, the electrode is configured to deliver energy sufficient to cause denervation of one or more sympathetic nerves surrounding the vessel. In some embodiments, the apparatus comprises a plurality of electrodes positioned along a length of the shaft that is not covered by the balloon.

In accordance with several embodiments, a neuromodulation device configured for intravascular hepatic neuromodulation comprises an elongated shaft having a proximal end and a distal end, a first electrode deployment arm coupled to the distal end of the elongated shaft, a first electrode coupled to a distal end of the first electrode deployment arm, a second electrode deployment arm coupled to the distal end of the elongated shaft, and a second electrode coupled to a distal end of the second electrode deployment arm. The first electrode deployment arm and the second electrode deployment arm are positioned 180 degrees apart from each other about the circumference of the elongated shaft and the first electrode deployment arm and the second electrode deployment arm are configured to cause the first electrode and the second electrode to contact a vessel wall when in a deployed configuration. In one embodiment, the neuromodulation device includes two and only two electrode deployment arms each having one electrode and does not include more than two electrodes. In another embodiment, the neuromodulation device includes four and only four electrode deployment arms each having one electrode and does not include more than four electrodes. In some embodiments, two electrodes are advantageous because 180 degree offset may be maintained and vessels having short lengths (e.g., common hepatic artery having a length of about 30 mm) may be modulated. In another embodiment, four electrodes are advantageous because of one or more of the following benefits: (i) increased vessel lengths may be treated while still maintaining 90-degree or 180 degree offset; (ii) ability to place multiple electrodes in shortest vessel length while controlling radial or circumferential spacing between two electrodes, (iii) increased ability to adjust electrode placement characteristics in difficult anatomy (e.g., tortuous, short length, severe tapers); allows operator to work around side branches or focal disease sites; (iv) allows operator to perform treatments in multiples of two; (v) reduces treatable territory lost in the vessel due to incomplete treatment (e.g., ablation) cycles; and/or (vi) maintains the ability to radially and/or longitudinally offset space between sets of treatments (e.g., ablations). In some embodiments using four electrodes, treatment may be better controlled (e.g., radial and/or length spacing between electrode pairs may be controlled) and the number of treatment sites or catheter placements may be reduced to perform four treatments (e.g., ablations) compared to devices having more than four electrodes. Using only two electrodes or only four electrodes is viable in several embodiments due to, for example, the increased efficiency of the electrodes and the treatment parameters used. If two electrodes are used, the two electrodes may comprise monopolar electrodes or a bipolar electrode pair. If four electrodes are used, the four electrodes may comprise monopolar electrodes or two bipolar electrode pairs. In some embodiments, a neuromodulation device configured for intravascular hepatic neuromodulation comprises an elongated shaft having a proximal end and a distal end, a first electrode deployment arm coupled at its distal end to the distal end of the elongated shaft, a first electrode coupled to a proximal end of the first electrode deployment arm, a second electrode deployment arm coupled at its distal end to the distal end of the elongated shaft, and a second electrode coupled to a proximal end of the second electrode deployment arm.

In some embodiments, the electrode deployment arms are coupled to the elongated shaft in a manner such that the electrodes are brought into contact with the vessel wall at positions spaced apart along a length of a blood vessel when in the deployed configuration. In some embodiments, the electrodes are each mounted on a pivot configured to facilitate an orientation that is in substantial alignment with the vessel wall. In one embodiment, the electrode deployment arms comprise shape memory material such that the electrode deployment arms are configured to automatically transition to the deployed configuration upon retraction of a sheath covering the elongated shaft. In one embodiment, the electrode deployment arms are steerable. For example, the electrode deployment arms may be collectively actuated by a single pullwire extending along the length of the elongated shaft or individually actuated by separate pullwires. In one embodiment, the elongated shaft comprises a lumen configured to receive a guidewire for providing trackability of the elongated shaft over the guidewire.

In some embodiments, the electrodes comprise curved electrodes (e.g., having a half-cylindrical shape). In some embodiments, the electrodes do not comprise spherical electrodes or flat electrodes. In one embodiment, the neuromodulation device comprises an inner core member disposed within a lumen of the shaft. The distal end of the inner core member may comprise a deployment member configured to deploy the electrode deployment arms to the deployed configuration. For example, the inner core member may be translatable relative to the elongated shaft. Upon retraction of the inner core member in a proximal direction, the deployment member on the distal end of the inner core member may be configured to mechanically separate the electrode deployment arms and cause them to transition to the deployed configuration. In various embodiments, the electrode deployment arms comprise a flexible or "soft" segment proximal of an electrode attachment point configured to enable a pivot of the electrode such that the contact surface (e.g., side) of the electrode is at least substantially parallel with the vessel wall. In several embodiments, the electrode deployment arms are configured to provide uniform contact force on the vessel wall by the electrodes.

In accordance with several embodiments, a neuromodulation device configured for intravascular hepatic neuromodulation comprises or consists essentially of an elongated shaft having a proximal end and a distal end, a first electrode positioned at the distal end of the elongated shaft and a second electrode positioned proximal to the first electrode at the distal end of the elongated shaft (the first electrode and second electrode each comprise a rounded contact surface, an electrode shaft; and a control element) and an expansion member positioned within the elongated shaft. The expansion member is configured to cause the first electrode and the second electrode to transition between (i) a non-deployed configuration in which the rounded contact surfaces of the first electrode and the second electrode are substantially flush with an outer surface of the elongated shaft and the electrode shafts are disposed within the elongated shaft and (ii) a deployed configuration in which the rounded contact surfaces of the first electrode and the second electrode are brought into contact with a vessel wall as a result of the electrode shafts being advanced radially outward of the elongated shaft. The control element is configured to limit a maximum outward force of the electrode on a vessel wall and to cause the electrode to return to the non-deployed configuration once the expansion member is returned to a non-expanded state. The first electrode and the second electrode are positioned such that the rounded contact surfaces of the first electrode and the second electrode are 180 degrees apart from each other about the circumference of the elongated shaft.

In various embodiments, the expansion member comprises an inflatable balloon or a mechanically-actuated scaffold. The control element may comprise a coil spring disposed about the electrode shafts of the first electrode and the second electrode. The control element may comprise other mechanisms configured to restore the electrode shafts to a non-deployed configuration and to limit the outward force exerted by the electrodes on the vessel wall. In one embodiment, the elongated shaft comprises a lumen configured to receive a guidewire for providing trackability of the elongated shaft over the guidewire. In one embodiment, the elongated shaft is steerable.

In one embodiment, the invention comprises a system that includes an elongated shaft configured to be intravascularly advanced to a location within a blood vessel configured to facilitate modulation of nerves that innervate the liver, pancreas and/or duodenum (e.g., within a common hepatic artery). The distal end of the elongated shaft includes two or four radiofrequency electrodes offset (e.g., by 90 or 180 degrees) about the circumference of the elongated shaft. The electrodes are configured to transition between a non-deployed state in which they are substantially flush with the outer surface of the elongated shaft and a deployed state in which the electrodes are caused to contact and maintain contact with a vessel wall. The elongated shaft also includes a deployment, or expansion member, configured to cause the electrodes to transition to the deployed state in which they are in contact with the vessel wall. The deployment, or expansion, member may be configured to cause the electrodes to maintain contact with a uniform or consistent force or pressure. The electrodes may be optionally curved or otherwise shaped or conformable to enhance surface area contact or otherwise facilitate contact with a target site (such as a vessel wall). Additionally, the system may be controllably deployed using pull wires, retraction of a sheath or other cover, inflatable members such as balloons, or mechanically actuated expansion members such as scaffolds.

In accordance with several embodiments, a tissue modulation device (e.g., neuromodulation device adapted for intravascular hepatic neuromodulation) having differentially-oriented electrodes comprises an elongated shaft having a proximal end portion and a distal end portion. The elongated shaft comprises a guidewire lumen extending from the proximal end portion to the distal end portion. The tissue modulation device further comprises a first monopolar electrode positioned along the elongated shaft and a shape-set portion located along the distal end portion of the elongated shaft. The shape-set portion is adapted to transition between a delivery configuration in which a guidewire extends distal to the shape-set portion within the guidewire lumen and a deployed configuration upon retraction of the guidewire proximal to the shape-set portion. In this embodiment, the shape-set portion comprises a second monopolar electrode. The shape-set portion may be adapted such that it forms a non-helical shape in the deployed configuration. The second monopolar electrode may be positioned at a position along a length of the non-helical shape of the shape-set portion such that the second monopolar electrode contacts a vessel wall of a vessel (e.g., common hepatic artery, renal artery) at a first location and such that second monopolar electrode (e.g., a longest aspect or dimension) is oriented substantially perpendicular to a longitudinal axis of the elongated shaft when the shape-set portion is in the deployed configuration. In this embodiment, the first monopolar electrode is adapted to contact the vessel wall at a second location spaced apart axially and offset circumferentially from the first location when the shape-set portion is in the deployed configuration. In some embodiments, the first location and the second location are on opposite sides of the vessel wall. In other embodiments, the first location and the second location are in different quadrants of the vessel wall.

In one embodiment, the first monopolar electrode is positioned proximal to the shape-set portion. In another embodiment, the first monopolar electrode is positioned distal to the shape-set portion. Some embodiments include a third monopolar electrode positioned either proximal or distal to the shape-set portion (e.g., on the opposite side of the shape-set portion as the first monopolar electrode). The electrode(s) positioned proximal or distal of the shape-set portion may be cylindrical electrodes having a longitudinal axis oriented in parallel with a longitudinal axis of the elongated shaft. In one embodiment, a longest aspect or dimension of the electrode(s) are oriented in parallel with a longitudinal axis of the elongated shaft. The electrode on the shape-set portion (e.g., the second monopolar electrode) may comprise a cylindrical shape or a trapezoidal shape or may comprise a slotted or nested configuration (such as a "horseshoe" shape or a U-shape) to facilitate a reduction in outer profile as the electrode is nested around a partial circumference of the shape-set portion. In some embodiments, the non-helical shape-set portion, when in the deployed configuration, comprises a longitudinal axis that transitions from a first orientation that is in parallel with a longitudinal axis of the elongated shaft to a second orientation that is perpendicular to the longitudinal axis of the elongated shaft and then back to the first orientation that is parallel with the elongated shaft. The non-helical shape-set portion may double back or loop on itself such that at least a first length of the shape-set portion that is distal of a second length of the shape-set portion in an undeployed configuration is proximal of the second length in a deployed configuration.

The shape-set portion may comprise more than one monopolar electrode. For example, two monopolar electrodes may be spaced apart from each other on the shape-set portion and positioned such that, when in the deployed configuration, the two electrodes are circumferentially offset by between 90 degrees and 210 degrees (e.g., between 90 degrees and 120 degrees, between 110 degrees and 140 degrees, between 120 degrees and 160 degrees, between 150 degrees and 180 degrees, between 170 degrees and 200 degrees, between 180 degrees and 210 degrees, overlapping ranges thereof or any value of or within the recited ranges, such as 90 degrees or 180 degrees). The two monopolar electrodes may be positioned such that the two electrodes are circumferentially offset and come into contact at opposite sides of the vessel wall or at different quadrants of the vessel wall when in the deployed configuration.

The electrodes along the elongated shaft (whether on the shape-set portion or proximal or distal to the shape-set portion) may be positioned such that they are spaced apart axially by between 3 mm and 8 mm (e.g., between 3 and 5 mm, between 4 and 7 mm, between 5 and 8 mm, overlapping ranges thereof or any value of or within the recited ranges, such as 4 mm or 6 mm) when in the deployed configuration.

In some embodiments, the tissue modulation device (e.g., neuromodulation device) comprises one or more lesion spacing indicators positioned along the distal end portion of the elongated shaft (e.g., distal of the distal-most electrode) to facilitate controlled spacing of lesion zones. The lesion spacing indicators may be positioned on a distal extension extending beyond the shape-set portion. In one embodiment, the device consists of two spaced-apart lesion indicators. In another embodiment, one of the electrodes functions as one of the spaced-apart lesion-spacing indicators. The lesion-spacing indicators may comprise radiopaque markers visible under fluoroscopy or other imaging technique. The lesion-spacing indicators may be spaced apart at a distance equal to the distance between the first monopolar electrode and the second monopolar electrode when the shape-set portion is in the deployed configuration or at a distance that is twice the distance between the first monopolar electrode and the second monopolar electrode when the shape-set portion is in the deployed configuration. Other distances may be used as desired and/or required.

In some embodiments, the deployment of the shape-set portion is not triggered by retraction of a guide wire but instead is triggered by retraction of an outer sheath. In other embodiments, the shape-set portion is replaced with a deflectable portion that does not comprise shape-memory or heat-set material and is deployed by one or more actuation members (e.g., pull-wires) or movement of two portions of the elongated shaft with respect to each other to form a three-dimensional curve or other configuration.

In accordance with several embodiments, a tissue modulation device (e.g., neuromodulation device adapted for intravascular hepatic neuromodulation) comprises an elongated shaft comprising a proximal end portion and a distal end portion and a balloon positioned at the distal end portion, the balloon being configured to transition from a non-inflated delivery configuration to an inflated deployment configuration. In this embodiment, the balloon comprises a plurality of electrode arrays positioned along an outer surface of the balloon, each of the electrode arrays comprising a plurality of spaced-apart electrodes. In this embodiment, each of the electrode arrays is configured to be connected to a generator by separate connection wires such that each of the electrode arrays is individually controllable (e.g., activated or deactivated). The plurality of electrode arrays are arranged to form a spiral pattern along the outer surface of the balloon. When in the inflated deployment configuration, at least one of the plurality of electrode arrays is adapted to be in contact with a vessel wall (e.g., a common hepatic artery, proper hepatic artery, gastroduodenal artery, splenic artery, celiac artery, renal artery).

In some embodiments, a size of each of the plurality of electrode arrays in its longest aspect is less than or equal to a characteristic length of thermal conduction in body tissue. In some embodiments, the plurality of spaced-apart electrodes in each array or group of electrodes are closely-spaced such that the electrodes are positioned within a region or area having a longest aspect or dimension that is no more than 6 mm (e.g., when the electrode array consists of four electrodes). In various embodiments, each electrode array consists of between two and eight spaced-apart electrodes (e.g., two, three, four, five, six, seven, eight electrodes). Each electrode array may have the same number of electrodes or some electrode arrays may have different numbers of electrodes than others. In various embodiments, the number of electrode arrays or groups ranges from two to eight (e.g., two, three, four, five, six, seven, eight arrays or groups). However, more than eight arrays or groups may be present in other embodiments.

In some embodiments, the electrode arrays are coupled to the outer surface of the balloon by an adhesive. In some embodiments, the electrode arrays are coupled to a flexible substrate. The balloon may comprise a coating covering an entire outer surface of the balloon except for active electrode areas of the electrodes or covering a substantial portion of the outer surface of the balloon and/or electrodes other than the active electrode areas. In some embodiments, a portion of the connection wires spanning from the first electrode to the last electrode in at least one of the plurality of electrode arrays forms a zig-zag pattern. Each of the electrode arrays disposed on the outer surface of the balloon may form the zig-zag pattern of connection wires to reduce overall spacing and to avoid folds of the balloon in a non-inflated configuration (e.g., to reduce overall profile). In some embodiments, the device comprises one or more lesion spacing indicators positioned along the distal end portion of the elongated shaft to facilitate controlled spacing of lesion zones. The lesion spacing indicator(s) (e.g., radiopaque markers) may be positioned on a distal extension distal of the balloon.

In accordance with several embodiments, a tissue modulation device (e.g., neuromodulation device adapted for intravascular hepatic neuromodulation) comprises an outer tube and an inner tube concentrically positioned within and longitudinally moveable with respect to the outer tube, the inner tube having a length to extend beyond a distal end of the outer tube. The device further comprises a first deployment arm having a proximal end and a distal end, the proximal end being coupled to a distal end portion of the outer tube and the distal end being coupled to a distal end portion of the inner tube, the first deployment arm being adapted to transition between a delivery configuration and a deployed configuration upon movement of the inner tube with respect to the outer tube. The first deployment arm comprises a first electrode positioned at a location along a length of the first deployment arm such that the first electrode is adapted to contact a vessel wall at a first location when the first deployment arm is in the deployed configuration.

In some embodiments, the device comprises a second deployment arm having a proximal end and a distal end, the proximal end being coupled to a distal end portion on an opposite side of the outer tube as the first deployment arm and the distal end being coupled to a distal end portion of the inner tube on an opposite side of the inner tube as the first deployment arm. The first deployment arm is adapted to transition between a delivery configuration and a deployed configuration upon movement of the inner tube with respect to the outer tube and wherein, when in the deployed configuration, the first deployment arm and the second deployment arm expand outward on opposite sides of a circumference of the inner tube. In one embodiment, the second deployment arm comprises a second electrode positioned at a location along a length of the second deployment arm such that the second electrode is adapted to contact a vessel wall at a second location on an opposite side of a circumference of the vessel wall as the first location when the second deployment arm is in the deployed configuration.

In some embodiments, the first electrode is positioned at a midpoint along the length of the first deployment arm. In embodiments comprising two deployment arms each comprising an electrode, the location of the second electrode may be at a midpoint of the length of the second deployment arm to match the location of the first electrode on the first deployment arm. In other embodiments comprising two deployment arms, the location of at least one of the first electrode and the second electrode is not at a midpoint of the lengths of the first and/or second deployment arms, such that the first and second electrodes are configured to be spaced apart axially along a length of the vessel wall when the first and second deployment arms are in their deployed configurations. For example, the location of the first electrode and the location of the second electrode may be asymmetrical. In one embodiment, neither the first electrode nor the second electrode is positioned at a midpoint of the length of the respective deployment arm.

In embodiments comprising one or two deployment arms, one or more electrodes may also be positioned along the distal end portion of the outer tube proximal to the deployment arm(s) and/or may be positioned along a distal end portion of the inner tube distal to the deployment arm(s). In some embodiments, the device comprises a distal extension coupled to and extending beyond a distal end of the inner tube, the distal extension comprising a lumen adapted to receive a guide wire to facilitate trackability. The electrodes may comprise nested or slotted electrodes to reduce overall profile. For example, the nested or slotted electrodes may comprise a half-cylinder shape, a U-shape, a horseshoe shape or other parabolic or curved shape.

In some embodiments, the device comprises a second deployment arm having a proximal end and a distal end, the proximal end being coupled to a distal end portion of the outer tube and the distal end being coupled to a distal end portion of the inner tube, the first deployment arm being adapted to transition between a delivery configuration and a deployed configuration upon movement of the inner tube with respect to the outer tube and wherein, when in the deployed configuration, the first deployment arm and the second deployment arm expand outward so as to contact the vessel wall. In this embodiment, the second deployment arm comprises a second electrode positioned at a location along a length of the second deployment arm such that the second electrode is adapted to contact the vessel wall at a second location in a different quadrant along the circumference of the vessel wall as the first location when the second deployment arm is in the deployed configuration (for example, the second location and the first location are spaced apart circumferentially by at least ninety degrees). In some embodiments, the second location and the first location are spaced apart circumferentially by about 180 degrees. In some embodiments, the second location and the first location are spaced apart circumferentially by between 120 degrees and 210 degrees (e.g., between 120 and 150 degrees, between 140 and 180 degrees, between 180 and 210 degrees, overlapping ranges thereof or any value of or within the recited ranges). In some embodiments, the device comprises one or more lesion spacing indicators (e.g., radiopaque markers) positioned along the neuromodulation device to facilitate controlled spacing of lesion zones as described herein in connection with other embodiments. The lesion spacing indicator(s) may be positioned distal of the first electrode.

In accordance with several embodiments, a tissue modulation device (e.g., a neuromodulation device configured for intravascular hepatic neuromodulation) comprises or consists essentially of an elongated shaft having a proximal end portion and a distal end portion, a first electrode deployment arm coupled to the distal end of the elongated shaft, a first electrode coupled to a distal end of the first electrode deployment arm, a second electrode deployment arm coupled to the distal end of the elongated shaft proximal to a location of a coupling of the first electrode deployment arm to the distal end of the elongated shaft and a second electrode coupled to a distal end of the second electrode deployment arm, wherein the first electrode deployment arm and the second electrode deployment arm are positioned on opposite sides about the circumference of the elongated shaft and wherein the first electrode deployment arm and the second electrode deployment arm are configured to cause the first electrode and the second electrode to contact a vessel wall at positions on opposite sides of the vessel wall when in a deployed configuration.

In some embodiments, the first electrode deployment arm and the second electrode deployment arm are coupled to the elongated shaft in a manner such that the first electrode and the second electrode are brought into contact with the vessel wall at positions spaced apart along a length of a blood vessel when in the deployed configuration. In some embodiments, at least one of the first electrode and the second electrode is mounted on a pivot configured to facilitate an orientation that is in substantial alignment with the vessel wall. The electrode deployment arms may comprise shape memory material such that the electrode deployment arms are configured to automatically transition to the deployed configuration upon retraction of a sheath covering the elongated shaft or upon retraction of a guidewire from a guidewire lumen of the elongated shaft. In some embodiments, the electrode deployment arms are steerable (for example, both actuated together by a single pullwire or other actuation member or individually by separate pullwires or actuation members). The electrodes may comprise curved, nested or slotted electrodes. For example, the electrodes may comprise a half-cylinder shape, a U-shape, a horseshoe shape or other parabolic or curved shape. In some embodiments, the device comprises an inner core member disposed within a lumen of the elongated shaft, a distal end of the inner core member comprising one or more deployment members configured to deploy the first electrode deployment arm and the second electrode deployment arm to the deployed configuration. In one embodiment, the inner core member is translatable relative to the elongated shaft, and wherein, upon retraction of the inner core member in a proximal direction, the deployment member on the distal end of the inner core member is configured to mechanically separate the first electrode deployment arm and the second electrode deployment arm and cause them to transition to the deployed configuration.

In some embodiments, the first electrode deployment arm and the second electrode deployment arm comprise a flexible segment proximal of an electrode attachment point configured to enable a pivot of the electrode such that the side of the electrode is at least substantially parallel with the vessel wall. In some embodiments, the elongated shaft comprises a first slot sized to house the first electrode deployment arm in a non-deployed configuration and a second slot sized to house the second electrode deployment arm in a non-deployed configuration. The first slot and the second slot may be straight, curved or helical. In one embodiment, the first slot and the second slot are curved or helical and the first electrode deployment arm and the second electrode deployment arm are adapted to have a curved or helical configuration when in a deployed configuration. In various embodiments, the first electrode deployment arm and the second electrode deployment arm are configured to provide uniform contact force on the vessel wall by the first electrode and the second electrode. The tissue modulation device may also comprise one or more lesion spacing indicators (e.g., radiopaque markers) positioned along the distal end portion of the elongated shaft to facilitate controlled spacing of lesion zones as described herein in connection with other embodiments. The lesion spacing indicator(s) may be positioned distal of the first electrode. In embodiments consisting of two spacing indicators positioned distal of the first electrode, the lesion spacing indicators may be spaced apart at a distance equal to the distance between the first electrode and the second electrode when the first electrode deployment arm and the second electrode deployment arm are in the deployed configuration or at a distance equal to twice the distance between the first electrode and the second electrode when the first electrode deployment arm and the second electrode deployment arm are in the deployed configuration.

In accordance with several embodiments, a tissue modulation device a tissue modulation device (e.g., a neuromodulation device adapted for intravascular hepatic neuromodulation) comprises or consists essentially of an elongated shaft having a proximal end and a distal end, a first electrode deployment arm coupled to the distal end of the elongated shaft, a first electrode coupled to a distal end of the first electrode deployment arm, a second electrode deployment arm coupled to the distal end of the elongated shaft, a second electrode coupled to a distal end of the second electrode deployment arm, a third electrode deployment arm coupled to the distal end of the elongated shaft, a third electrode coupled to a distal end of the third electrode deployment arm, a fourth electrode deployment arm coupled to the distal end of the elongated shaft, a fourth electrode coupled to a distal end of the fourth electrode deployment arm, wherein the first electrode deployment arm and the second electrode deployment arm are positioned 180 degrees apart from each other about the circumference of the elongated shaft, wherein the third electrode deployment arm and the fourth electrode deployment arm are positioned 180 degrees apart from each other about the circumference of the elongated shaft, wherein the first electrode deployment arm and the third electrode deployment arm are positioned in the same quadrant about the circumference of the elongated shaft, wherein the second electrode deployment arm and the fourth electrode deployment arm are positioned in the same quadrant about the circumference of the elongated shaft, and wherein the four electrode deployment arms are configured to cause the four electrodes to contact a vessel wall when in a deployed configuration.

In some embodiments, the second electrode deployment arm is spaced proximally of the first electrode deployment arm, the third electrode deployment arm is spaced proximally of the second electrode deployment arm, and the fourth electrode deployment arm is spaced proximally of the third electrode deployment arm such that the four electrodes contact the vessel wall at spaced-apart locations along the length of the vessel when in the deployed configuration. Any or all of the four electrodes may be mounted on a pivot configured to facilitate an orientation that is in substantial alignment with the vessel wall. In some embodiments, the four electrode deployment arms comprise shape memory material such that the electrode deployment arms are configured to automatically transition to the deployed configuration upon retraction of a sheath covering the elongated shaft. In some embodiments, the four electrode deployment arms are steerable (e.g., actuated together by a single pullwire or other actuation member or individually actuated by separate pullwires or actuation members). In some embodiments, the elongated shaft comprises a lumen configured to receive a guidewire for providing trackability of the elongated shaft over the guidewire. The electrodes may comprise curved, nested or slotted electrodes. For example, the electrodes may comprise a half-cylinder shape, a U-shape, a horseshoe shape or other parabolic or curved shape. In some embodiments, the electrode deployment arms comprise a flexible segment proximal of an electrode attachment point configured to enable a pivot of the electrode such that the side of the electrode is at least substantially parallel with the vessel wall. In various embodiments, the first electrode deployment arm and the second electrode deployment arm are configured to provide uniform contact force on the vessel wall by the first electrode and the second electrode. The tissue modulation device may also comprise one or more lesion spacing indicators (e.g., radiopaque markers) positioned along the distal end portion of the elongated shaft to facilitate controlled spacing of lesion zones as described herein in connection with other embodiments. The lesion spacing indicator(s) may be positioned distal of the distal-most deployment arm.

In accordance with several embodiments, a tissue modulation device a tissue modulation device (e.g., a neuromodulation device adapted for intravascular hepatic neuromodulation) comprises or consists essentially of an elongated shaft comprising a proximal end portion and a distal end portion, wherein the distal end portion comprises a first electrode a second electrode spaced apart distally from the first electrode, a first slot between the first electrode and the second electrode, and a first mechanical deflection member configured to be contained within the first slot in an undeployed configuration and to expand outward from the first slot in a deployed configuration. In the deployed configuration, at least a portion of the first mechanical deflection member contacts a vessel wall so as to cause the first electrode and the second electrode to contact the vessel wall on an opposite side of a circumference of the vessel wall as a contact location of the first mechanical deflection member. The first mechanical deflection member may comprise a ribbon member.

In some embodiments, the device further comprises a first actuation wire coupled to a proximal end of the first mechanical deflection member and configured to cause the first mechanical deflection member to transition between the undeployed configuration and the deployed configuration by advancement and retraction of the first actuation wire, wherein the first actuation wire extends from the proximal end portion of the neuromodulation device to the proximal end of the first mechanical deflection member. In some embodiments, the electrodes comprise cylindrical monopolar electrodes. In other embodiments, the first electrode and the second electrode comprise a bipolar electrode pair. The device may comprise a distal extension distal to the second electrode. The distal extension may comprise a pair of spaced-apart lesion spacing indicators (e.g., radiopaque markers). In one embodiment, one of the electrodes may act as one of the pair of spaced-apart lesion spacing indicators. The pair of spaced-apart lesion indicators may be spaced apart at a distance equal to the distance between the first electrode and the second electrode or at a distance equal to twice the distance between the first electrode and the second electrode. Other distances may be used depending on treatment vessel length or diameter.

In some embodiments, the tissue modulation device further comprises a second slot positioned on an opposite side of a circumference of the distal end portion as the first slot and a second mechanical deflection member configured to be contained within the second slot in an undeployed configuration and to expand outward from the second slot in a deployed configuration, wherein the second mechanical deflection member is configured to expand outward in a direction substantially opposite an expansion direction of the first mechanical deflection member. The second mechanical deflection member may comprise a ribbon member. In these embodiments, the device further comprises a second actuation wire coupled to a proximal end of the second mechanical deflection member and configured to cause the second mechanical deflection member to transition between the undeployed configuration and the deployed configuration by advancement and retraction of the second actuation wire, wherein the second actuation wire extends from the proximal end portion of the neuromodulation device to the proximal end of the second mechanical deflection member.

In accordance with several embodiments, a method of ablating nerves surrounding a blood vessel having a controlled lesion spacing pattern comprises inserting a neuromodulation device within the blood vessel. The neuromodulation device comprises a first electrode and a second electrode spaced apart distal of the first electrode along a distal end portion of the neuromodulation device and at least one lesion spacing indicator positioned distal of the second electrode. The method further comprises causing the first electrode to contact an inner wall of the blood vessel at a first contact location and the second electrode to contact the inner wall of the blood vessel at a second contact location, wherein the first contact location and the second contact location are spaced apart axially from each other by a separation distance. The method further comprises causing the first electrode and the second electrode to deliver radiofrequency energy to the inner wall of the blood vessel while at the contact locations. The method also comprises repositioning the neuromodulation device axially within the blood vessel using the at least one lesion spacing indicator and causing the first electrode to contact the inner wall of the blood vessel at a third contact location and the second electrode to contact the inner wall at a fourth contact location, wherein the third contact location and the fourth contact location are spaced apart axially from each other by the separation distance. The neuromodulation device may then be removed from the blood vessel.

In some embodiments, the first location and the second location are in different quadrants of the inner wall of the blood vessel with respect to each other and the third location and the fourth location are in different quadrants of the inner wall of the blood vessel with respect to each other. The first location and the third location may be in the same quadrant and the second location and the third location may be in the same quadrant. For example, the neuromodulation device may be adapted to deflect or otherwise change configurations such that one of the first and second electrodes is in contact with the vessel wall at a first quadrant while the other of the first and second electrodes is in contact with the vessel wall at a second quadrant different from the first quadrant. In some embodiments, the first and second electrodes are configured to come into contact with the vessel wall in quadrants on opposite sides of the vessel wall (e.g., contact locations spaced apart by about 180 degrees). In some embodiments, the first contact location and the second contact location are spaced apart circumferentially by between 120 degrees and 210 degrees. In some embodiments, the first contact location and the second contact location are spaced apart circumferentially by about 90 degrees.

In other embodiments, the first location and the second location are in the same quadrant and the third location and the fourth location are in the same quadrant. For example, the first and second electrodes may be positioned into contact with an inner wall of the blood vessel in a first quadrant and activated to form spaced apart lesion zones in the first quadrant and then the neuromodulation device may be retracted or advanced by a distance using the at least one spacing indicator and the first and second electrodes may be positioned into contact with an inner wall of the blood vessel in a second quadrant different from the first quadrant (e.g., on an opposite side of the vessel circumference).

In some embodiments, the at least one lesion spacing indicator is spaced apart axially from the second electrode by a distance that is equal to the separation distance. In other embodiments, the at least one lesion spacing indicator is spaced apart axially from the second electrode at distance that is twice the separation distance. In embodiments where two spaced-apart lesion spacing indicators positioned distal to the second electrode are used, a proximal lesion spacing indicator may be positioned adjacent the second electrode (e.g., within 2 mm, within 1 mm) and the spacing between the two spaced-apart lesion spacing indicators may be equal to or twice the separation distance. In some embodiments, repositioning the neuromodulation device axially within the blood vessel comprises aligning a distal one of the two lesion spacing indicators with a position of a proximal one of the two lesion spacing indicators prior to repositioning. The separation distance may be between 3 mm and 8 mm (e.g., 3 mm, 4 mm, 5 mm, 6 mm, 7 mm, 8 mm).

In accordance with several embodiments, a neuromodulation system adapted for tissue contact sensing and modulation of tissue comprises a neuromodulation device including an elongated shaft having a proximal end portion and a distal end portion and an electrode assembly positioned at the distal end portion of the elongated shaft. In one embodiment, the electrode assembly comprises an inner electrode element and an outer electrode element separated by an insulation layer, wherein the inner electrode element is concentric within the outer electrode element. The electrode assembly is adapted to apply common mode signals to the inner electrode element and the outer electrode element to cause delivery of radiofrequency power sufficient to ablate tissue and to apply differential mode sensing signals between the inner electrode element and the outer electrode element to generate tissue contact sensing measurements to be received by a processing device adapted to determine a level of tissue contact based on the tissue contact sensing measurements.

The tissue contact sensing measurements may comprise bipolar contact impedance measurements between the inner electrode member and the outer electrode member and/or temperature measurements obtained by one or more thermocouple leads within the inner electrode member. In some embodiments, the system comprises a processing device configured to receive the tissue contact sensing measurements and to determine whether contact exists or a level of tissue contact based on the received tissue contact sensing measurements. The processing device may be configured (e.g., specifically programmed) to generate an output indicative of the level of tissue contact. In some embodiments, the common mode signals have a frequency range between 400 kHz and 650 kHz (e.g., between 400 kHz and 500 kHz, between 450 kHz and 600 kHz, between 550 kHz and 650 kHz, overlapping ranges thereof or any value of or within the recited ranges). In some embodiments, the differential mode sensing signals have a frequency outside the frequency range of the common mode signals. For example, the differential mode sensing signals have a frequency between 800 kHz and 20 MHz (e.g., between 800 kHz and 1 MHz between 1 MHz and 10 MHz, between 5 MHz and 15 MHz, between 10 MHz and 20 MHz, overlapping ranges thereof or any value of or within the recited ranges). In several embodiments, a ratio of a contact surface area of the outer electrode to a contact surface are of the inner electrode is between 5:1 and 25:1 (e.g., between 5:1 and 10:1, between 10:1 and 25:1, between 10:1 and 20:1, between 15:1 and 25:1, overlapping ranges thereof or any value of or within the recited ranges).

In accordance with several embodiments, a neuromodulation device adapted for tissue contact sensing and modulation of nerves or other tissue comprises an elongated shaft comprising a proximal end portion and a distal end portion and an electrode positioned at the distal end portion of the elongated shaft. The electrode is adapted to apply signals to cause delivery of radiofrequency power sufficient to ablate target tissue. The electrode comprises an optical window or side port extending from a contact surface of the electrode to a position within an inner core of the electrode. The neuromodulation device further comprises an optical sensor comprising at least one illumination fiber and at least one sensing fiber. A distal end of the at least one illumination fiber and a distal end of the at least one sensing fiber are positioned within the optical window within the inner core of the electrode. A proximal end of the at least one illumination fiber is configured to be coupled to an illumination source and a proximal end of the at least one sensing fiber is configured to be coupled to a detector.

In some embodiments, the optical window and/or the distal ends of the at least one illumination fiber and the at least one sensing fiber are filled, covered or coated with optical adhesive. In some embodiments, the optical adhesive has a refractive index adapted to improve transmission of incident and reflected light into the target tissue. A system may be provided that comprises the neuromodulation device and a contact sensing unit comprising the illumination source and the detector. The contact sensing unit may be positioned within the elongated shaft or may be a separate, standalone component configured to be positioned external to a body of the subject. In some embodiments, the contact sensing unit is within a same housing as the power or energy source (e.g., RF generator). The system may also comprise a processing device configured to generate an output indicative of tissue contact based on information received from the detector.

In accordance with several embodiments, the systems, devices and methods disclosed herein provide consistent disruption of nerves that innervate organs that influence glucose production and/or storage regardless of anatomical variation between subjects. In some embodiments, an ultrasound system adapted for hepatic neuromodulation comprises a generator and an ultrasound catheter. The generator may be configured to activate the ultrasound catheter to deliver acoustic energy sufficient to modulate tissue (e.g., nerves) of one or more organs that influence glucose production and/or storage (such as the liver, pancreas, small intestine, stomach, etc.).

In one embodiment, the ultrasound catheter comprises a proximal end portion, a distal end portion, and an elongate member extending between the proximal end portion and the distal end portion. The elongate member and the distal end portion may be specifically designed and adapted (e.g., configured) to navigate tortuous vasculature to be positioned in a hepatic artery (e.g., a common hepatic artery, a proper hepatic artery, a left hepatic artery, a right hepatic artery) or other artery or blood vessel. The ultrasound catheter comprises at least one ultrasound transducer positioned at the distal end portion. The ultrasound catheter may comprise one, two, three, four, five, six, or any number of transducers.

In one embodiment, the ultrasound system is adapted to sense or visualize adjacent dense structures from a location within a hepatic artery or other blood vessel and then modulate (e.g., ablate) an identified area of interest, such as an area of high nerve concentration or density caused by the proximity of the adjacent dense structure. In various embodiments, the at least one ultrasound transducer is adapted to (a) provide imaging data to the generator to determine distances to one or more adjacent dense structures and (b) to deliver acoustic energy sufficient to modulate nerves. A single ultrasound transducer may be adapted to provide both diagnostic (e.g., imaging, sensing, visualization, localization, etc.) capabilities and tissue modulation (e.g., nerve ablation) capabilities. In some embodiments, one or more ultrasound transducers are adapted for diagnostic purposes and one or more ultrasound transducers are adapted for tissue modulation purposes. For example, the diagnostic transducers may operate in a first range of frequencies adapted for diagnostic purposes (e.g., 5-60 MHz) and the tissue modulation transducers may operate in a second range of frequencies adapted for tissue modulation (e.g., 0.5-40 MHz). In some embodiments, diagnostic purposes may be accomplished at lower frequencies, while tissue modulation may be accomplished at higher frequencies. In one embodiment, the same range of frequencies may be used for diagnostic and tissue modulation.

In some embodiments, the locations of energy delivery within a hepatic artery are selected based on the determined distances to the one or more adjacent dense structures or the locations of the one or more adjacent dense structures determined from images or data obtained by the ultrasound catheter that are overlaid on anatomical images. In some embodiments, areas of close proximity to adjacent dense structures are likely to have a high nerve density or concentration due to the limited space between the adjacent dense structure and the hepatic artery or other blood vessel. Operators may deliver energy at locations having a distance to an adjacent dense structure that is below a threshold level (e.g., within 1 cm, within 9 mm, within 8 mm, within 7 mm, within 6 mm, within 5 mm). In some embodiments, there may be a minimum threshold level (e.g., 2 mm, 3 mm, 4 mm, 5 mm) so as to avoid damage to the adjacent dense structure if it is a dense structure that is not desired to be ablated or otherwise thermally damaged.

The generator may be adapted to operate in a diagnostic mode or a treatment mode. The energy delivered by the ultrasound transducer(s) in either the diagnostic mode or the treatment mode may be focused ultrasound (e.g., high-intensity focused ultrasound) or unfocused ultrasound. An operator may be able to toggle between the operational modes through interface with the generator (e.g., a touchscreen interface or physical buttons or switches). In some embodiments, the generator is adapted to display the determined distances or images of the adjacent dense structures on a display of the graphical user interface.

The generator may be adapted to adjust a frequency of the energy being delivered by the at least one ultrasound transducer based on the mode of operation. In one embodiment, the generator is adapted to adjust one or more parameters of treatment (e.g., power level, intensity level, duration, target temperature, frequency) of the at least one ultrasound transducer based on the imaging data or other feedback received when the generator is in the diagnostic mode.

In some embodiments, the ultrasound catheter comprises a structure adapted to center the at least one transducer within the hepatic artery or to maintain an offset (e.g., a minimum distance) between the inner wall of the hepatic artery and a contact surface of the at least one transducer.

In some embodiments, the ultrasound catheter comprises one or more cooling or heat transfer structures adapted to prevent overheating of the at least one transducer. In one embodiment, the elongate member of the ultrasound catheter comprises a lumen and wherein the ultrasound catheter is adapted to be delivered over a guidewire received in at least a portion of the lumen (e.g., a majority of the portion within the subject, the distal-most portion, or a portion distal to the at least one transducer).

In various embodiments, the at least one transducer comprises at least one of a resonant cavity transducer, a heat pipe configuration, or acoustic mirrors or lenses to facilitate cooling, to control power distribution or focal targets, to improve efficiency or operation of the transducer(s), and to increase power without increasing size of the transducer(s). In some embodiments, the ultrasound catheters comprise structures or mechanisms adapted to increase circumferential coverage and decrease axial coverage during energy delivery while maintaining a reduced profile for introduction to facilitate access to hepatic vasculature or surrounding vasculature. In some embodiments, the ultrasound catheters comprise flexible circuits. In some embodiments, the ultrasound catheters are adapted to pivot a longest dimension of the at least one transducer from a position generally parallel to a length of the hepatic artery to a position that is generally parallel to the circumference of the hepatic artery, thereby increasing circumferential area of modulation while decreasing axial length of modulation.

In accordance with several embodiments, a method of modulating nerves in a manner to reduce glucose production comprises identifying one or more locations along a hepatic artery within a specified distance from an adjacent dense structure using one or more ultrasound transducers adapted for imaging and delivering energy sufficient to modulate nerves to reduce a blood glucose level using the one or more ultrasound transducers. In one embodiment, a single ultrasound transducer is adapted for imaging and for delivering energy sufficient to modulate nerves. In other embodiments, the one or more transducers comprises a first one or more transducers adapted for imaging and a second one or more ultrasound transducers adapted for delivering energy to modulate nerves. The energy sufficient to modulate nerves may be sufficient to denervate or ablate the nerves in several embodiments.

In some embodiments, the method comprises confirming modulation of the nerves (e.g., using a sensing wire coupled to a radiofrequency electrode on the ultrasound catheter). In some embodiments, impedance of the tissue may be monitored to determine whether the tissue in contact with the electrode has been ablated or not. In some embodiments, the ultrasound catheter is adapted to deliver both ultrasound energy using the ultrasound transducer(s) and radiofrequency energy using one or more radiofrequency electrodes.

In some embodiments, one or more parameters of the energy delivery (e.g., power level, intensity level, duration, target temperature, frequency) are adjusted based on imaging data received by the one or more ultrasound transducers or based on impedance measurements obtained by one or more radiofrequency electrodes. In various embodiments, the method comprises adjusting an orientation of the one or more ultrasound transducers to adjust a treatment area within the hepatic artery (e.g., to increase circumferential coverage while reducing axial coverage). In some embodiments, the method comprises cooling the one or more ultrasound transducers (for example, with cooling balloons, with circulating fluid, and/or with heat plate configurations).

In accordance with several embodiments, a method of delivering energy sufficient to ablate nerves innervating the liver to reduce a glucose level comprises delivering radiofrequency energy to a target location sufficient to increase a temperature of tissue to a temperature proximate an ablation threshold using at least one electrode of an energy delivery device and delivering acoustic energy to the target location sufficient to raise the temperature above the ablation threshold using at least one ultrasound transducer of the energy delivery device. In some embodiments, the frequency of the radiofrequency energy is between 400 kHz and 60 MHz (e.g., between 400 kHz and 600 kHz, between 500 kHz and 750 kHz, between 600 kHz and 900 kHz, between 700 kHz and 1 MHz, between 1 MHz and 10 MHz, between 10 MHz and 60 MHz, or overlapping ranges thereof) and wherein the frequency of the acoustic energy is between 0.5 MHz and 60 MHz (e.g., between 0.5 MHz and 5 MHz, between 1 MHz and 10 MHz, between 2 MHz and 8 MHz, between 10 MHz and 40 MHz, between 15 MHz and 30 MHz, between 20 MHz and 60 MHz, between 30 MHz and 50 MHz, and overlapping ranges thereof). In one embodiment, the at least one electrode is connected in series with the at least one ultrasound transducer. In another embodiment, the at least one electrode is connected in parallel with the at least one ultrasound transducer. In another embodiment, the at least one electrode also serves as an electrode for the at least one ultrasound transducer. In one embodiment, the method comprises confirming ablation of the tissue at the target location using the at least one electrode of the energy delivery device. The at least one electrode may be the same electrode as the energy delivery electrode or a separate sensing electrode coupled directly to a generator. In one embodiment, the at least one electrode may be an electrode coupled to the ultrasound transducer.

In one embodiment, a method of modulating nerves in a manner to reduce glucose production comprises identifying one or more locations along a vessel and delivering energy sufficient to modulate nerves in or surrounding said vessel to directly or indirectly reduce a glucose level using one or more ultrasound transducers. The modulation may be performed invasively (e.g., within the subject's body) or non-invasively (e.g., from a source external to a subject's body). In one embodiment, a method of treating diabetes comprises identifying one or more locations along a vessel and delivering energy sufficient to modulate nerves in or surrounding said vessel to directly or indirectly reduce a glucose level using one or more ultrasound transducers.

In various embodiments, an ultrasound system adapted for neuromodulation to reduce blood glucose levels by treating nerves located in or surrounding a vessel comprises an ultrasound device comprising a proximal end portion, a distal end portion, and an elongate member extending between the proximal end portion and the distal end portion. The elongate member and the distal end portion are configured to navigate tortuous vasculature to be positioned in the vessel. The ultrasound device comprises at least one ultrasound transducer positioned at the distal end portion. The at least one ultrasound transducer is adapted to deliver acoustic energy sufficient to modulate nerves of the vessel. In one embodiment, the frequency of the ultrasound transducer is between 2 MHz and 40 MHz (e.g., between 2 MHz and 20 MHz, between 10 MHz and 40 MHz) and the ultrasound transducer is adapted to deliver energy between 0.5 mm and 10 mm from an internal surface of the vessel. In some embodiments, ablation of nerves occurs 0.5-5 mm, 1-6 mm, 0.1-10 mm, 1-3 mm, or 2-4 mm from a vessel surface (inner or outer), and overlapping ranges thereof. The vessel may be a hepatic artery. In some embodiments, the transducer comprises multiple (e.g., two to ten or more) transduction elements in a linear or radial pattern. The transducer may be configured for electronic or phase focusing, or mechanical focusing. In one embodiment, the transducer is configured for delivering unfocused ultrasound. In some embodiments, the ultrasound system comprises an imaging transducer on the ultrasound device or on a separate device. The ultrasound system may be used to treat diabetes or other metabolic conditions.

Although some embodiments summarized above are described with respect to hepatic neuromodulation, the embodiments herein also contemplate neuromodulation or tissue modulation of regions other than the liver or hepatic vessels. For example, the catheters, devices and systems described herein may also be used for renal denervation (e.g., by modulating the nerves in one or both renal arteries), for glucose or lipid regulation by modulating the nerves that innervate the pancreas, kidney, duodenum, jejunum and/or stomach, for cardiac ablation, for pulmonary tissue or vessel ablation or neuromodulation, as well as other targets and indications described herein. The devices and systems summarized above may be used within vessels other than a hepatic artery, such as a renal artery, a gastroduodenal artery, a celiac artery or a splenic artery. For example, the devices and systems may be used within one or more renal arteries or veins and may be suitable for treating hypertension or other conditions associated with modulation of nerves surrounding the renal vessels. As another example, the devices and systems may be used within a gastroduodenal artery, celiac artery or vessel innervating the pancreas and the neuromodulation device may be suitable for treating one or more symptoms of diabetes. As another example, the devices and systems may be used within a vessel and may be configured to cause modulation of nerves surrounding the vessel sufficient to alter sympathetic tone.

For purposes of summarizing the disclosure, certain aspects, advantages, and novel features of embodiments of the invention have been described herein. It is to be understood that not necessarily all such advantages may be achieved in accordance with any particular embodiment of the invention disclosed herein. Thus, the embodiments disclosed herein may be embodied or carried out in a manner that achieves or optimizes one advantage or group of advantages as taught or suggested herein without necessarily achieving other advantages as may be taught or suggested herein. The methods summarized above and set forth in further detail below describe certain actions taken by a practitioner; however, it should be understood that they can also include the instruction of those actions by another party. Thus, actions such as "delivering a neuromodulation catheter within a hepatic artery" include "instructing the delivery of a neuromodulation catheter within a hepatic artery." With respect to the drawings, elements from one figure may be combined with elements from the other figures.

BRIEF DESCRIPTION OF THE DRAWINGS

FIGS. 11A-11C, 12A-12E, 13A, 13B, 14, 15A-15C, 16A, 16B, 17A, 17B, 18 and 19A-19C illustrate embodiments of balloon catheters.

FIGS. 22A-22C, 23A-23C, 24, 25, 26A, 26B, 27A-27D and 28 illustrate devices and methods configured to provide increased cooling for electrode catheters.

FIGS. 29A, 29B, 29C-1, 29C-2, 29D, 29E, 29F, 29G-1, 29G-2, 29H, 29I, 29J-1, 29J-2, 29K, 29L-1, 29L-2, 29M-1, 29M-2, 29M-3, 29M-4, 29N-1, 29N-2 and 29O illustrate embodiments of radiofrequency energy delivery devices for neuromodulation.

FIGS. 31A-34F illustrate embodiments of radiofrequency energy delivery devices for neuromodulation.

FIGS. 35-47B illustrate embodiments of devices and methods for increasing catheter and/or electrode stabilization of electrode catheters within target vessels.

FIGS. 48A-48E illustrate an embodiment of a radiofrequency energy delivery catheter configured for hepatic denervation.

FIGS. 51A-54B illustrate embodiments of devices and methods for increasing catheter and/or electrode stabilization of electrode catheters within target vessels.

FIGS. 56A-62B illustrate embodiments of systems and methods configured to control lesion formation.

FIGS. 63A-1 to 63C illustrate various embodiments of deployment sleeve systems for use in deploying multiple electrodes.

FIGS. 64A-1 to 64K illustrate various embodiments of multi-electrode energy delivery devices.

FIGS. 71A and 71B illustrate schematic embodiments of a catheter having a cooled electrode and a thermocouple to provide temperature feedback at a distance from the cooled electrode.

FIGS. 77A and 77B illustrate embodiments of an energy delivery algorithm based on blood flow measurement.

FIG. 80 illustrates an embodiment of an energy delivery system.

FIGS. 83A and 83B-1 to 83B-3 illustrate embodiments of a distal portion of an ultrasound energy delivery device including a foldable flexible circuit.

FIGS. 97A and 97B illustrate embodiments of a vascular access system comprising a guide sheath or captive sleeve.

FIGS. 100-110 illustrate embodiments of catheter systems and associated methods configured to provide catheter stabilization.

FIGS. 112A-118 illustrate embodiments of neuromodulation catheters configured to provide catheter stabilization within tortuous vasculature or within vasculature subject to movement during respiration.

FIGS. 123A-1, 123A-2, 123B and 124 illustrate graphs of data from hepatic denervation studies, in accordance with embodiments of the invention.

FIG. 125 illustrates the effect on liver norepinephrine levels following a hepatic denervation procedure during an animal study.

FIG. 137 illustrates components of impedance in an embodiment of an endovascular ablation procedure.

DETAILED DESCRIPTION

I. Introduction and Overview

Figure 1A:
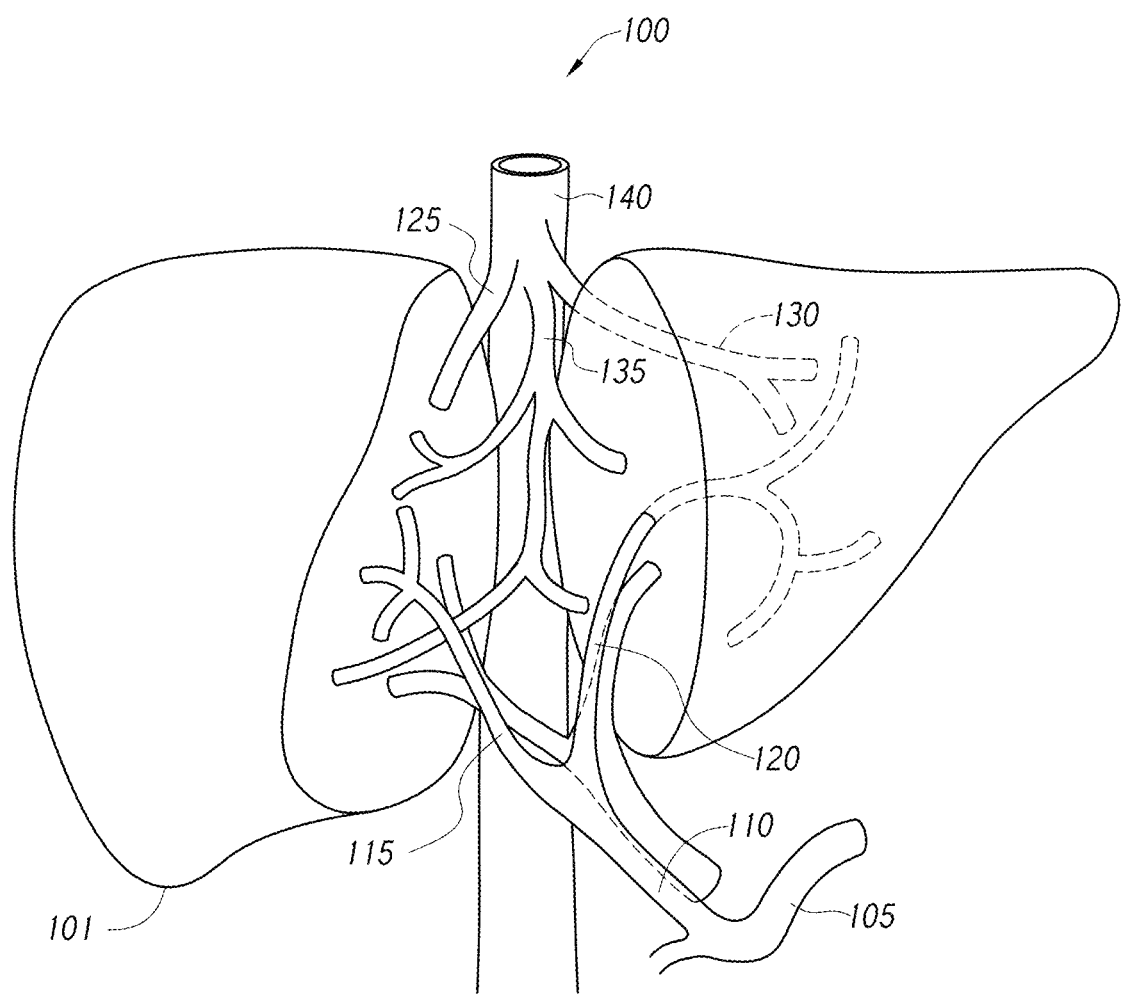
FIG. 1A illustrates the anatomy of a target treatment location including the liver and hepatic blood supply, in accordance with an embodiment of the invention.

Embodiments of the invention described herein are generally directed to therapeutic neuromodulation of targeted nerve fibers to treat, or reduce the risk of occurrence or progression of, various metabolic diseases, conditions, or disorders, including but not limited to diabetes (e.g., diabetes mellitus). While the description sets forth specific details in various embodiments, it will be appreciated that the description is illustrative only and should not be construed in any way as limiting the disclosure. Furthermore, various applications of the disclosed embodiments, and modifications thereto, which may occur to those who are skilled in the art, are also encompassed by the general concepts described herein. Although several figures set forth below are described with respect to hepatic neuromodulation, the embodiments herein also contemplate neuromodulation or tissue modulation of regions other than the liver or hepatic vasculature. For example, the catheters, devices and systems described herein may also be used for renal denervation (e.g., by modulating the nerves in one or both renal arteries), for glucose or lipid regulation by modulating the nerves that innervate the pancreas, duodenum, jejunum and/or stomach, for cardiac ablation, for pulmonary tissue or vessel ablation or neuromodulation, as well as other targets and indications described herein.

The autonomic nervous system includes the sympathetic and parasympathetic nervous systems. The sympathetic nervous system is the component of the autonomic nervous system that is responsible for the body's "fight or flight" responses, those that can prepare the body for periods of high stress or strenuous physical exertion. One of the functions of the sympathetic nervous system, therefore, is to increase availability of glucose for rapid energy metabolism during periods of excitement or stress, and to decrease insulin secretion.

The liver can play an important role in maintaining a normal blood glucose concentration. For example, the liver can store excess glucose within its cells by forming glycogen, a large polymer of glucose. Then, if the blood glucose concentration begins to decrease too severely, glucose molecules can be separated from the stored glycogen and returned to the blood to be used as energy by other cells. The liver is a highly vascular organ that is supplied by two independent blood supplies, one being the portal vein (as the liver's primary blood supply) and the other being the hepatic artery (being the liver's secondary blood supply).

The process of breaking down glycogen into glucose is known as glycogenolysis, and is one way in which the sympathetic nervous system can increase systemic glucose. In order for glycogenolysis to occur, the enzyme phosphorylase must first be activated in order to cause phosphorylation, which allows individual glucose molecules to separate from branches of the glycogen polymer. One method of activating phosphorylase, for example, is through sympathetic stimulation of the adrenal medulla. By stimulating the sympathetic nerves that innervate the adrenal medulla, epinephrine is released. Epinephrine then promotes the formation of cyclic AMP, which in turn initiates a chemical reaction that activates phosphorylase. An alternative method of activating phosphorylase is through sympathetic stimulation of the pancreas. For example, phosphorylase can be activated through the release of the hormone glucagon by the alpha cells of the pancreas. Similar to epinephrine, glucagon stimulates formation of cyclic AMP, which in turn begins the chemical reaction to activate phosphorylase.

Another way in which the liver functions to maintain a normal blood glucose concentration is through the process of gluconeogenesis. When the blood glucose concentration decreases below normal, the liver will synthesize glucose from various amino acids and glycerol in order to maintain a normal blood glucose concentration. Increased sympathetic activity has been shown to increase gluconeogenesis, thereby resulting in an increased blood glucose concentration.

The parasympathetic nervous system is the second component of the autonomic nervous system and is responsible for the body's "rest and digest" functions. These "rest and digest" functions complement the "fight or flight" responses of the sympathetic nervous system. Stimulation of the parasympathetic nervous system has been associated with decreased blood glucose levels. For example, stimulation of the parasympathetic nervous system has been shown to increase insulin secretion from the beta-cells of the pancreas. Because the rate of glucose transport through cell membranes is greatly enhanced by insulin, increasing the amount of insulin secreted from the pancreas can help to lower blood glucose concentration. Neuromodulation (e.g., denervation or stimulation) of sympathetic and/or parasympathetic nerves surrounding other organs or tissues (such as the pancreas, small intestine, duodenum, and/or portions of the stomach) may also be performed in combination with modulation of nerves innervating the liver to treat diabetes or the symptoms associated with diabetes (e.g., high blood glucose levels, high triglyceride levels, high cholesterol levels, low insulin secretion levels). Several embodiments described herein are adapted to modulate (e.g., ablate, stimulate, etc.) the parasympathetic system alone or in conjunction with the sympathetic system. In some embodiments, one system is activated and the other deactivated. Alternatively, both systems can be activated or deactivated. In some embodiments, stimulation of the parasympathetic nerves innervating the pancreas is combined with denervation of sympathetic nerves innervating the liver to treat diabetes or the symptoms associated with diabetes (e.g., high blood glucose levels, high triglyceride levels, high cholesterol levels, low insulin secretion levels). Stimulation and/or denervation of sympathetic and/or parasympathetic nerves surrounding other organs or tissues (such as the pancreas, duodenum and/or portions of the stomach) may also be performed in combination.

FIG. 1A illustrates a liver 101 and vasculature of a target hepatic treatment location 100. The vasculature includes the common hepatic artery 105, the proper hepatic artery 110, the right hepatic artery 115, the left hepatic artery 120, the right hepatic vein 125, the left hepatic vein 130, the middle hepatic vein 135, and the inferior vena cava 140. In the hepatic blood supply system, blood enters the liver by coursing through the common hepatic artery 105, the proper hepatic artery 110, and then either of the left hepatic artery 120 or the right hepatic artery 115. The right hepatic artery 115 and the left hepatic artery 120 (as well as the portal vein, not shown) provide blood supply to the liver 101, and directly feed the capillary beds within the hepatic tissue of the liver 101. The liver 101 uses the oxygen provided by the oxygenated blood flow provided by the right hepatic artery 115 and the left hepatic artery 120. Deoxygenated blood from the liver 101 leaves the liver 101 through the right hepatic vein 125, the left hepatic vein 130, and the middle hepatic vein 135, all of which empty into the inferior vena cava 140.

Figure 1B:
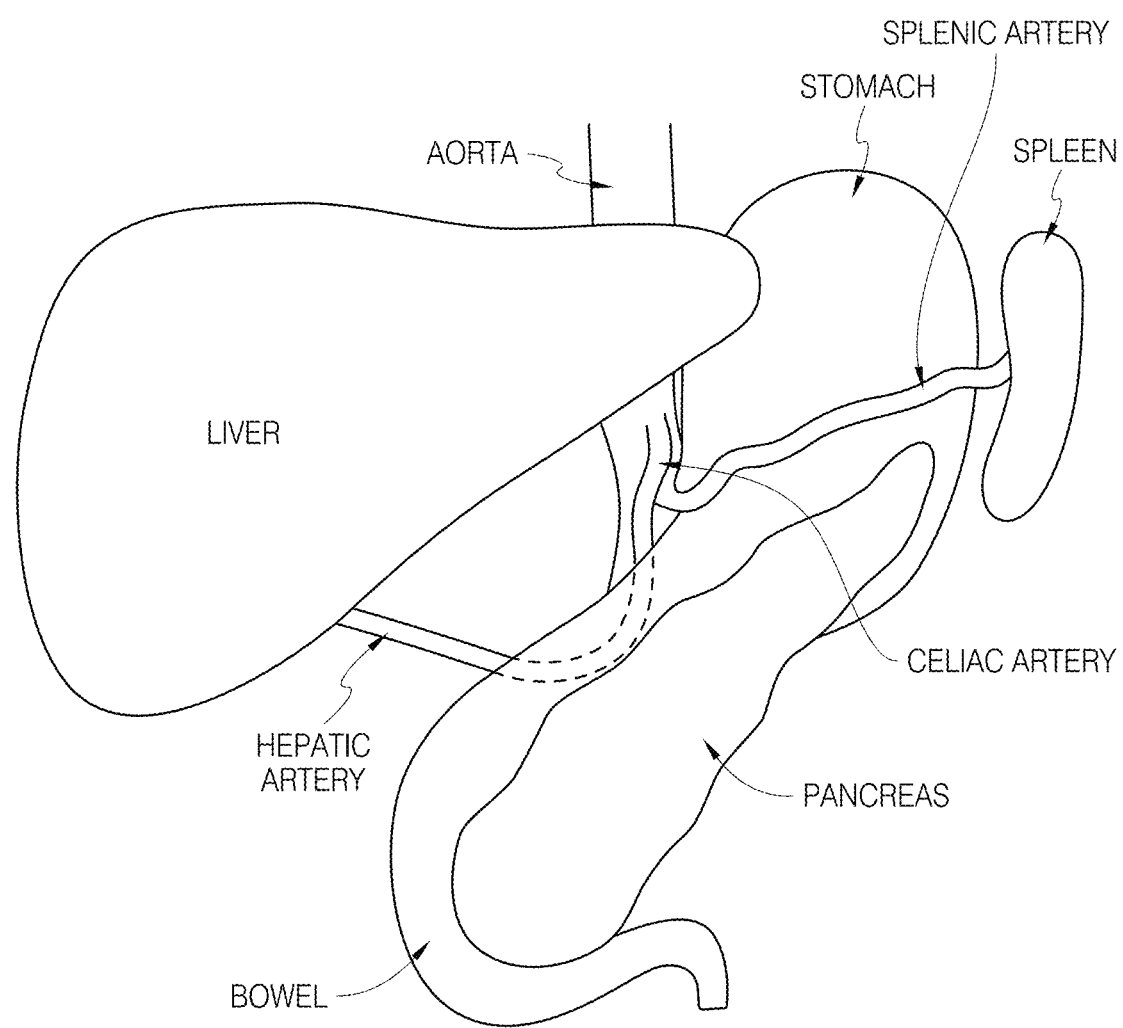
FIG. 1B illustrates the anatomy of a target treatment location including the liver and hepatic blood supply, in accordance with an embodiment of the invention.

FIG. 1B illustrates a liver 101 and target vasculature of hepatic neuromodulation methods and systems to treat diabetes or symptoms associated with diabetes or glucose production. The target vasculature may include a hepatic artery 105, which branches off from a celiac artery 210 originating at the abdominal aorta 205. The hepatic artery 105 supplies blood to the liver. The splenic artery 235 is also illustrated, which also branches off from the celiac artery 210 to provide blood to the spleen 145. Other organs or dense structures positioned adjacent the hepatic artery 105 may include the pancreas 150, the stomach 155, and portions of the bowel 160 (including the small intestine). As will be discussed in further detail below, systems and methods may be provided to identify locations along the hepatic artery 105 that are in close proximity to adjacent structures (e.g., organs) which may influence glucose production and to modulate tissue at or near the identified locations (e.g., delivering energy using radiofrequency, ultrasound or microwave energy delivery devices sufficient to modulate nerves that innervate the liver and/or other adjacent structures that may influence glucose production (such as the pancreas 150, stomach 155, and/or small intestine 160)). The modulation provided may be sufficient to reduce glucose levels (e.g., blood glucose levels), lipid levels, cholesterol levels, etc. In various embodiments, portions of multiple adjacent structures (e.g., organs) may be denervated or otherwise modulated (either from a single location or from multiple locations along a portion of the hepatic artery 105 or arteries connected or adjacent to the hepatic artery 105, such as the celiac artery 210, splenic artery 235, and gastroduodenal artery). Several embodiments of the invention are particularly advantageous in that disruption of sympathetic nerves that innervate organs that influence glucose production and storage may be performed consistently regardless of anatomical variations between subjects.

Figure 1C:
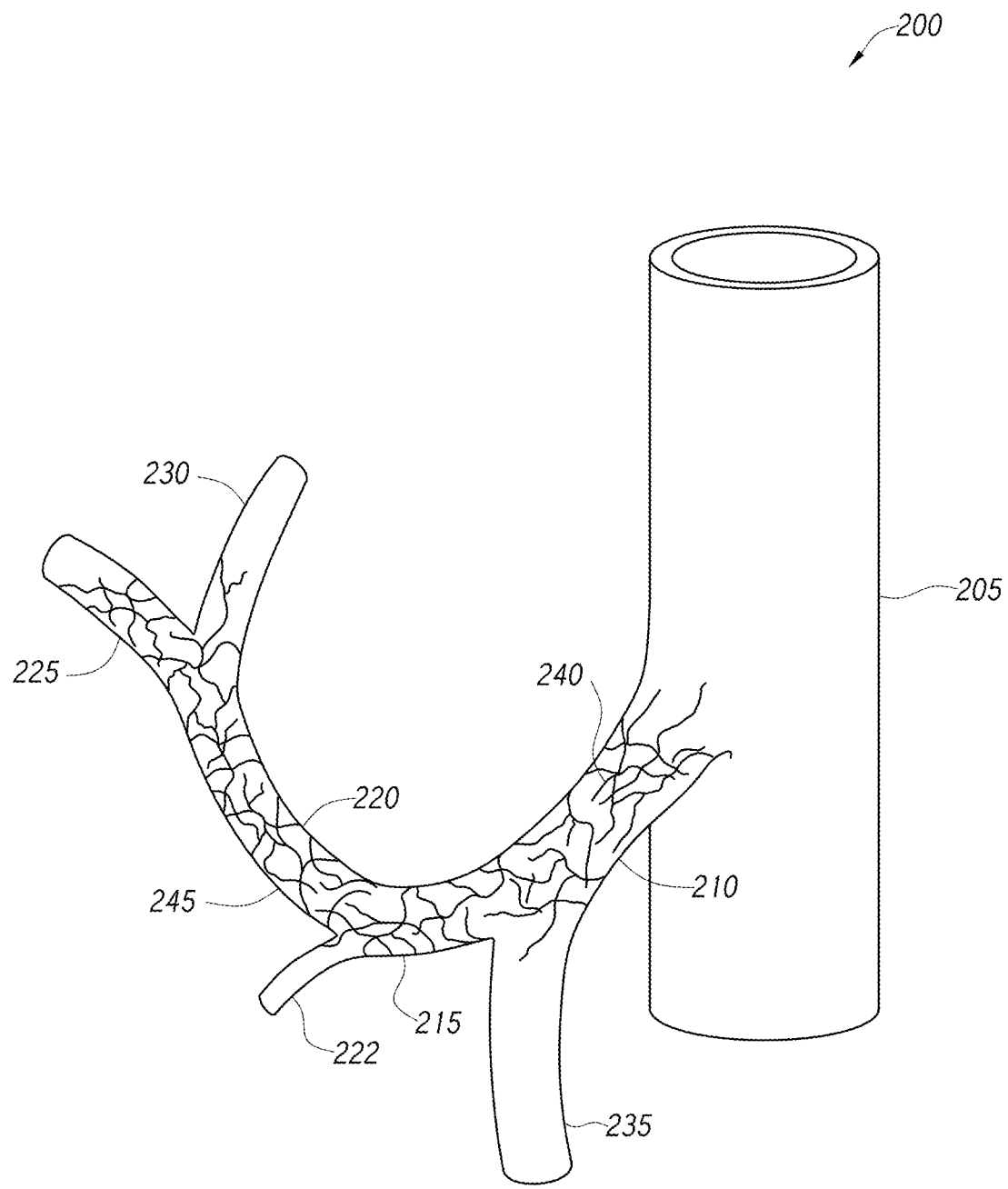
FIG. 1C illustrates various arteries supplying blood to the liver and its surrounding organs and tissues and nerves that innervate the liver and its surrounding organs and tissues.

FIG. 1C illustrates various arteries surrounding the liver and the various nerve systems 200 that innervate the liver and its surrounding organs and tissue. The arteries include the abdominal aorta 205, the celiac artery 210, the common hepatic artery 215, the proper hepatic artery 220, the gastroduodenal artery 222, the right hepatic artery 225, the left hepatic artery 230, and the splenic artery 235. The various nerve systems 200 illustrated include the celiac plexus 240 and the hepatic plexus 245. Blood supply to the liver is pumped from the heart into the aorta and then down through the abdominal aorta 205 and into the celiac artery 210. From the celiac artery 210, the blood travels through the common hepatic artery 215, into the proper hepatic artery 220, then into the liver through the right hepatic artery 225 and the left hepatic artery 230. The common hepatic artery 215 branches off of the celiac trunk, or artery 210. The common hepatic artery 215 gives rise to the gastric and gastroduodenal arteries. The nerves innervating the liver may include portions of the celiac plexus 240 and the hepatic plexus 245. The celiac plexus 240 wraps around the celiac artery 210 and continues on into the hepatic plexus 245, which wraps around the proper hepatic artery 220, the common hepatic artery 215, and may continue on to the right hepatic artery 225 and the left hepatic artery 230. In some anatomies, the celiac plexus 240 and hepatic plexus 245 adhere tightly to the walls (and some of the nerves may be embedded in the adventitia) of the arteries supplying the liver with blood, thereby rendering intra-to-extra-vascular neuromodulation particularly advantageous to modulate nerves of the celiac plexus 240 and/or hepatic plexus 245. In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements. In some embodiments where radiofrequency energy is used, low-power or low-energy (e.g., less than 10 W of power output and/or less than 1 kJ of energy delivered to the inner wall of the target vessel or to the target nerves) intravascular energy delivery may be used because the nerves are tightly adhered to or within the outer walls of the arteries supplying the liver with blood (e.g., hepatic artery branches).

With continued reference to FIGS. 1A, 1B, and 1C, the hepatic plexus 245 is the largest offset from the celiac plexus 240. The hepatic plexus 245 is believed to carry primarily afferent and efferent sympathetic nerve fibers, the stimulation of which can increase blood glucose levels by a number of mechanisms. For example, stimulation of sympathetic nerve fibers in the hepatic plexus 245 can increase blood glucose levels by increasing hepatic glucose production. Stimulation of sympathetic nerve fibers of the hepatic plexus 245 can also increase blood glucose levels by decreasing hepatic glucose uptake. Therefore, by disrupting (e.g., blocking, terminating, denervating, ablating) sympathetic nerve signaling in the hepatic plexus 245, blood glucose, triglyceride, norepinephrine, lipid (e.g., lipoprotein), and/or cholesterol levels can be decreased or reduced. In some embodiments, blood glucose levels are reduced from baseline by 10-80% (e.g., 10-20%, 20-30%, 30-40%, 40-50%, 50-60%, 60-70%, 70-80%, 30-60%, 40-70%, 20-50%, or overlapping ranges thereof). Triglyceride, norepinephrine, lipid and/or cholesterol levels may also be reduced by similar amounts.

In several embodiments, any of the regions (e.g., arteries, nerves) identified in FIGS. 1A, 1B, and 1C may be modulated according to embodiments described herein. Alternatively, in one embodiment, localized therapy is provided to the hepatic plexus, while leaving one or more of these other regions unaffected. In some embodiments, multiple regions (e.g., of organs, arteries, nerve systems) shown in FIGS. 1A, 1B, and 1C may be modulated in combination (simultaneously or sequentially), which may provide one or more synergistic effects. For example, in some embodiments, methods of metabolic neuromodulation treatment involve forming ablation lesions in the common hepatic artery as well as in the celiac, splenic and/or other portions or branches of the hepatic artery (e.g., proper hepatic artery, left hepatic artery, right hepatic artery) to facilitate denervation of complementary metabolic organs and structures (e.g., pancreas, stomach, duodenum) in addition to the liver, even in the instance of a shortened common hepatic artery and/or unusual branch vessel anatomy. In some embodiments, if a subject has a short common hepatic artery (e.g., less than 30 mm), ablation of other vessels or portions of the hepatic artery may be desired and/or required to achieve an effective treatment. In other embodiments, treatment of complementary metabolic organs and structures by delivering energy in the celiac artery, splenic artery, gastroduodenal artery and/or other portions of the hepatic artery (e.g., proper hepatic artery, right hepatic artery, left hepatic artery) may advantageously provide one or more synergistic effects. Although several access/delivery devices are described herein that are configured for (e.g., in shape, size, flexibility, etc.) the hepatic artery, such access/delivery devices can also be used for other arteries and vessels, and in particular, other tortuous vasculature. In addition, although devices may be described herein as neuromodulation catheters or devices and described with respect to modulation (e.g., ablation) of nerves, the catheters or other devices may be used to modulate other types of tissue (e.g., tissue lining an organ or vessel, muscle tissue, endothelial tissue, connective tissue, submucosal tissue).

Figure 2A:
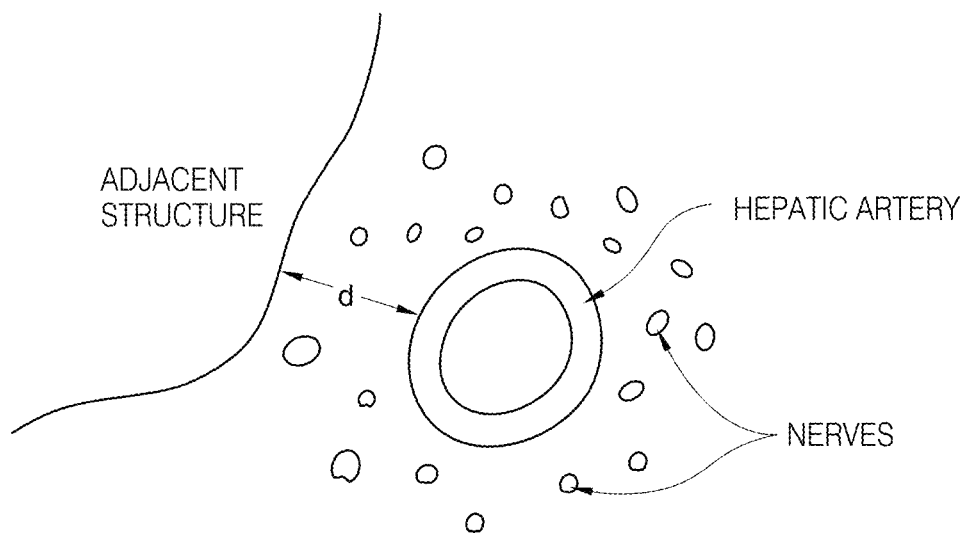
FIGS. 2A and 2B illustrate examples of distribution of nerves surrounding a hepatic artery, as influenced by presence of an adjacent dense structure.
Figure 2B:
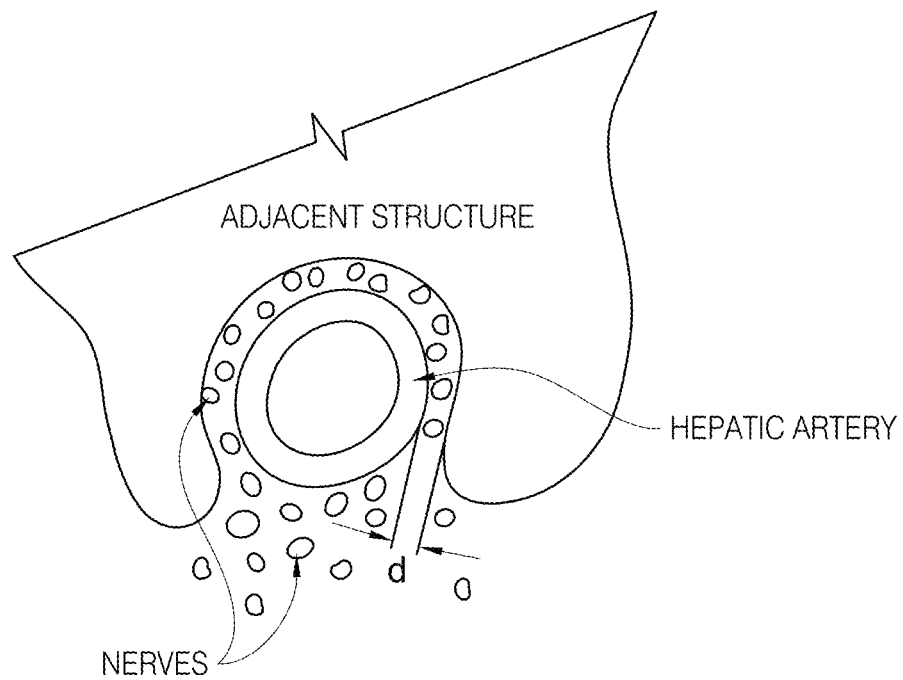

Sympathetic nerves may be distributed around the hepatic artery (or other arteries, such as the celiac artery, the splenic artery, the gastroduodenal artery), and several embodiments of the invention are adapted to treat these vessels. The hepatic artery passes by many adjacent structures from its origin at the celiac artery to its termination at the liver. The distance that the nerves are away from the hepatic artery or the density of nerves can be influenced by the proximity of adjacent dense structures, such as the liver, pancreas, stomach, small intestine). In accordance with several embodiments, it may be advantageous to modulate tissue at locations along the hepatic artery that are in sufficiently close proximity (e.g., less than 1 cm away from the inner wall of the hepatic artery) to adjacent dense structures (e.g., liver, pancreas, stomach, small intestine, muscle, and/or connective tissue). For example, locations along the hepatic artery that are close to adjacent structures may be associated with highly dense concentrations of nerves, the modulation of which could reduce glucose levels or provide other effects associated with treatment of diabetes in an efficient and effective manner. FIG. 2A illustrates a schematic representation of distribution of nerves 165 surrounding a hepatic artery 105 with limited adjacent structure 170 influence (e.g., where the adjacent dense structure 170 is greater than 1 cm away from the inner wall of the hepatic artery 105) and FIG. 2B illustrates a schematic representation of distribution of nerves 165 surrounding a hepatic artery 105 with significant adjacent structure 170 influence (e.g., wherein the adjacent dense structure 170 is less than 1 cm away from the inner wall of the hepatic artery 105). As can be seen, the distribution of nerves 165 in FIG. 2B is very highly concentrated around the hepatic artery 105 due to the limited space between the hepatic artery 105 and the adjacent structure 170. The illustrated example may represent an area of the hepatic artery 105 that is generally encapsulated by the pancreas.

The anatomy of the vascular branches distal of the celiac plexus may be highly disparate between subjects. In accordance with several embodiments, systems and methods are provided to identify locations along the hepatic artery 105 where the hepatic artery 105 is in close proximity to (e.g., less than 1 cm, less than 5 mm from) an adjacent dense structure 170 and to provide energy to the identified locations in a manner that disrupts the nerves 165 surrounding the hepatic artery 105 (e.g., nerves 165 between the medial layer of the hepatic artery 105 and the adjacent dense structure 170). In some embodiments, the locations where the hepatic artery 105 is in close proximity to an adjacent dense structure 170 are matched with locations determined to be ideal candidates for neuromodulation (e.g., locations having a proper vessel diameter, sufficient treatment length without much tortuosity, etc.).

Figure 3:
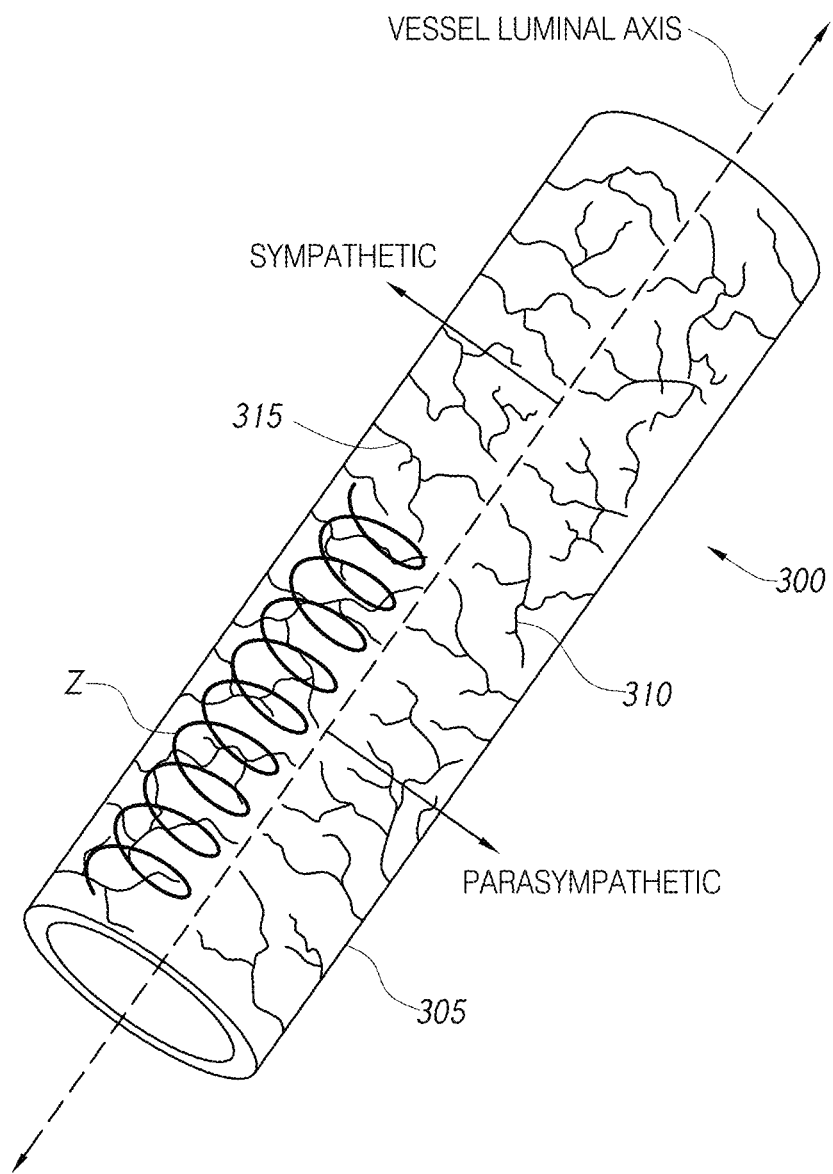
FIG. 3 illustrates a schematic drawing of a common hepatic artery and nerves of the hepatic plexus.

FIG. 3 is a schematic illustration of the nerve fibers of the hepatic plexus 300. A portion of the common hepatic artery 305 (or, alternatively, the proper hepatic artery) is shown with the hepatic plexus 300 wrapping around the artery. Some of the nerve fibers of the hepatic plexus may be embedded within the perivascular space (e.g., adventitia) of the common hepatic artery 305 (or proper hepatic artery), or at least tightly adhered to or within the outer vascular walls. As shown, there is a vessel lumenal axis that follows the center of the artery lumen. The hepatic plexus 300 is comprised of parasympathetic nerves 310 and sympathetic nerves 315. In some anatomies, the parasympathetic nerves 310 tend to course down one half of the circumference of an artery and the sympathetic nerves 315 tend to course down the other half of the artery.

As shown in FIG. 3, the portion of the common hepatic artery 305 is roughly cylindrical, with parasympathetic nerves 310 innervating approximately a 180° arc of the cylinder, and the sympathetic nerves of the hepatic plexus 315 innervating the opposite approximately 180° arc of the cylinder. In some anatomies, there is very little overlap (if any) between the parasympathetic nerves 310 and the sympathetic nerves 315 of the hepatic plexus. Such discretization may be advantageous in embodiments where only sympathetic nerves 315 or parasympathetic nerves 310 of the hepatic plexus are to be modulated. In some embodiments, modulation of the sympathetic nerves 315 of the hepatic plexus may be desirable while modulation of the parasympathetic nerves 310 of the hepatic plexus may not be desirable (or vice-versa).

In some embodiments, only selective regions of the perivascular space (e.g., adventitial layer) of target vasculature is modulated. In some subjects, parasympathetic and sympathetic nerves may be distributed distinctly on or within the adventitial layer of blood vessels. For example, using an axis created by the lumen of a blood vessel, parasympathetic nerves of the hepatic plexus may lie in one 180 degree arc of the adventitia while sympathetic nerves may lie in the other 180 degree arc of the adventitia, such as shown in FIG. 3. Generally, the sympathetic nerve fibers tend to run along the anterior surface of the hepatic artery, while the parasympathetic nerve fibers are localized toward the posterior surface of the hepatic artery. In these cases, it may be advantageous to selectively disrupt either the sympathetic or the parasympathetic nerves by modulating nerves in either the anterior region or the posterior region, respectively.

In some subjects, sympathetic nerve fibers may run along a significant length of the hepatic artery, while parasympathetic nerve fibers may join toward the distal extent of the hepatic artery. Research has shown that the vagus nerve joins the liver hilus near the liver parenchyma (e.g., in a more distal position than the nerves surrounding the hepatic arterial tree). As the vagal nerves are parasympathetic, the nerves surrounding the hepatic artery proximally may be predominantly sympathetic. In accordance with several embodiments, modulation (e.g., ablation) of the proper hepatic artery towards its proximal extent (e.g., halfway between the first branch of the celiac artery and the first branch of the common hepatic artery) is performed when it is desired to disrupt sympathetic nerves in the hepatic plexus. Ablation of the proximal extent of the hepatic artery could advantageously provide the concomitant benefit of avoiding such critical structures as the bile duct, pancreas and portal vein (which approaches the hepatic artery as it courses distally towards the liver), in accordance with one embodiment of the invention.

In one embodiment, only the anterior regions of the hepatic artery are selectively modulated (e.g., ablated). In one embodiment, approximately 180 degrees of the arterial circumference (which may include the corresponding adventitial layer) is ablated. In some embodiments, it is desirable to ablate in the range of about 60o to about 240°, about 80° to about 220°, about 100° to about 200°, about 120° to about 180°, about 140 to about 160°, or overlapping ranges thereof. In some embodiments, the portion of the vessel wall not being targeted opposite the portion of the vessel wall being targeted is actively cooled during the modulation procedure (e.g., as described, for example, in connection with FIGS. 56A and 56B). Such cooling may decrease collateral injury to the nerve fibers not intended for treatment. In many embodiments, cooling is not used.

In embodiments in which only selective portions of the vessel wall are to be treated, a zig-zag, overlapping semicircular, spiral, lasso, or other pattern of ablation may be used to treat only selective regions of nerve tissue in the adventitia or other perivascular space. An example of a spiral ablation pattern Z, in accordance with one embodiment, is shown in FIG. 3. In some embodiments, one or more ablation electrodes having an inherent zig-zag, spiral or other pattern are used. In some embodiments, a single point ablation electrode (regardless of electrode pattern) is advanced longitudinally and circumferentially about substantially 180 degrees of the vessel circumference to ablate in a zig-zag, spiral or other pattern, thereby selectively ablating only approximately 180 degrees of the vessel wall and the accompanying nerve tissues. In some embodiments, other patterns of electrode configurations are used. In some embodiments, other patterns of ablation electrode movement (regardless of inherent conformation) are used. In some embodiments, lesion zones are created that do not overlap with each other. In various embodiments, lesion zones are spaced apart axially and/or radially.

In some embodiments, where only selective regions of the vessel wall are to be modulated (e.g., ablated or stimulated) it may be helpful to have a high degree of device (e.g., catheter) control, stability and/or precision. To achieve the control necessary for a high degree of precision, a guide catheter may be used to engage the osteum of a nearby branch (e.g., the branch of the common hepatic artery off of the celiac artery, or celiac trunk) to provide a constant reference point from which to position an energy delivery (e.g., ablation) catheter. Alternatively, the catheter (e.g., probe) could also be anchored in other branches, either individually or simultaneously, to further improve control and/or stabilization. Simultaneous anchoring may be achieved by means of a compliant, inflatable balloon (e.g., having a shape and size configured to match an osteum or another portion of a particular vessel), which may substantially occlude the vascular lumen (e.g., osteum), thereby anchoring the catheter and providing increased stability. Such an approach may obviate the need for angiography to map the course of treatment, including the concomitant deleterious contrast agent and x-ray exposure, because treatment guidance can be performed relative to a reference angiogram, with distance of the neuromodulation catheter from the guide catheter measured outside of the patient. In some embodiments, the inflatable balloon may have a size and shape configured to engage multiple ostia or to be anchored in multiple branches (simultaneously or sequentially). In some embodiments, occlusion of a vessel results in increased arterial blood flow at a target location, thereby providing more effective convective cooling. In one embodiment, a balloon catheter is configured to deliver a controlled amount of energy within a defined region of an arterial wall irrespective of low and/or variable flow within the artery (e.g., hepatic artery).

The anatomy of the vascular branches distal of the celiac plexus may be highly disparate between subjects and variations in the course of the sympathetic and parasympathetic nerves tend to be associated predominantly with branches distal of the celiac plexus, rather than being associated with any specific distance distally along the hepatic artery. In some embodiments, a neuromodulation location is selected based on a position relative to the branching anatomy rather than on any fixed distance along the hepatic artery in order to target the sympathetic nerve fibers; for example, within the common hepatic artery and about 1 cm-6 cm (e.g., about 2 cm-3 cm, or substantially at the midpoint of the common hepatic artery) from the branching of the celiac axis or 1 mm-1 cm (e.g., 1 mm, 2 mm, 3 mm, 4 mm, 5 mm, 6 mm, 7 mm, 8 mm, 9 mm, 1 cm) from the branching of the splenic artery or from the branching of the gastroduodenal artery.

Parasympathetic and sympathetic nerve fibers tend to have opposing physiologic effects, and therefore, in some embodiments, only the sympathetic nerve fibers and not the parasympathetic nerve fibers are disrupted (e.g., denervated, ablated) in order to achieve the effects of reducing endogenous glucose production and increasing hepatic and peripheral glucose storage. In some embodiments, only the parasympathetic nerve fibers and not the sympathetic nerve fibers are stimulated in order to achieve the effects of reducing endogenous glucose production and increasing hepatic and peripheral glucose storage. In some embodiments, the sympathetic nerve fibers are denervated while the parasympathetic nerve fibers are simultaneously stimulated in order to achieve the effects of reducing endogenous glucose production and increasing hepatic and peripheral glucose storage. In some embodiments, the denervation of the sympathetic nerve fibers and the stimulation of the parasympathetic nerve fibers are performed sequentially.

In accordance with several embodiments, methods of therapeutic neuromodulation for preventing or treating disorders (such as diabetes mellitus) comprise modulation of nerve fibers (e.g., the sympathetic nerve fibers of the hepatic plexus). In one embodiment, neuromodulation decreases hepatic glucose production and/or increases hepatic glucose uptake, which in turn can result in a decrease of blood glucose levels, triglyceride levels, lipid levels, norepinephrine levels, and/or cholesterol levels. Disruption of the nerve fibers can be effected by ablating, denervating, severing, destroying, removing, desensitizing, disabling, reducing, crushing or compression, or inhibiting neural activity through, blocking, or otherwise modulating (permanently or temporarily) the nerve fibers or surrounding regions. In some embodiments, the disruption is carried out using one or more energy modalities that are delivered for example, intravascularly, extravascularly, or noninvasively (e.g., transcutaneously) from an extracorporeal location. Energy modalities include, but are not limited to, acoustic or sound energy such as ultrasonic energy, unfocused ultrasound, focused ultrasound such as high-intensity or low-intensity focused ultrasound, microwave energy, radiofrequency (RF) energy, thermal energy (e.g., cryoenergy, heat provided by a hot fluid or gas, such as steam), electrical energy, infrared energy, laser energy, phototherapy or photodynamic therapy (e.g., in combination with one or more activation agents), plasma energy, ionizing energy delivery (such as X-ray, proton beam, gamma rays, electron beams, and alpha rays), mechanical energies delivered by cutting or abrasive elements, cryoablation, and chemical energy or modulation (e.g., chemoablation), or any combination thereof. In some embodiments, the disruption of the sympathetic nerve fibers is carried out by chemicals or therapeutic agents (for example, via drug delivery), either alone or in combination with an energy modality. In various embodiments different energy modalities may be used in combination (either simultaneously or sequentially).

In some embodiments, a catheter system is configured to extravascularly and selectively disrupt target nerves. In some embodiments, a catheter is advanced through a cardiovascular system to the target site. The catheter may be passed transluminally to the extravascular space or may create a virtual space between the vascular media and adventitia of the vessel. In some embodiments, the catheter, once positioned at the desired location is activated to selectively modulate or disrupt the target nerve or nerves. The selective disruption may be accomplished or performed through chemo-disruption, such as supplying any type of nerve destroying agent, including, but not limited to, neurotoxins or other drugs detrimental to nerve viability. In some embodiments, selective disruption is performed through energy-induced disruption, such as thermal or light ablation (e.g., radiofrequency ablation, ultrasound ablation, or laser ablation). In one embodiment, a camera or other visualization device (e.g., fiberoptic scope) is disposed on a distal end of the catheter to ensure that nerves are targeted and not surrounding tissue. If a target location is adjacent the branch between the common hepatic artery and the proper hepatic artery, a less acute catheter bend may be required due to the angulation between the bifurcation of the common hepatic artery and the proper hepatic artery. In some embodiments, the catheter comprises a side port, opening or window, thereby allowing for delivery of fluid or energy to denervate or ablate nerves with the longitudinal axis of the catheter aligned parallel or substantially parallel to the target vessel portion. In some embodiments, the catheter or probe is inserted percutaneously and advanced to the target location for extravascular delivery of energy or fluid.

In accordance with several embodiments disclosed herein, the invention comprises modulation of nerve fibers instead of or in addition to nerve fibers in the hepatic plexus to treat diabetes or other metabolic conditions, disorders, or other diseases. For example, sympathetic nerve fibers surrounding (e.g., within the intima, media, perivascular space (e.g., adventitia) of the common hepatic artery proximal to the proper hepatic artery or other branch of the hepatic artery, sympathetic nerve fibers surrounding the celiac artery (e.g., the celiac ganglion or celiac plexus, which supplies nerve fibers to multiple organs including the pancreas, stomach, and small intestine), sympathetic nerve fibers that innervate the pancreas, sympathetic nerve fibers that innervate the adrenal glands (e.g., the renal plexus or suprarenal plexus), sympathetic nerve fibers that innervate the gut, bowel, stomach or small intestine (e.g., the duodenum or jejunum), sympathetic nerve fibers that innervate brown adipose tissue, sympathetic nerve fibers that innervate skeletal muscle, the vagal nerves, the phrenic plexus or phrenic ganglion, the gastric plexus, the splenic plexus, the splanchnic nerves, the spermatic plexus, the superior mesenteric ganglion, the lumbar ganglia, the superior or inferior mesenteric plexus, the aortic plexus, or any combination of sympathetic nerve fibers thereof may be modulated in accordance with the embodiments herein disclosed. In some embodiments, instead of being treated, these other tissues are protected from destruction (e.g., ablation or denervation) during localized neuromodulation of the hepatic plexus. In some embodiments, one or more sympathetic nerve fibers (for example, a ganglion) can be removed (for example, pancreatic sympathectomy). The nerves (sympathetic or parasympathetic) surrounding the various organs described above may be modulated in a combined treatment procedure (either simultaneously or sequentially), which may provide one or more synergistic effects.

In some embodiments, modulation of the nerves (e.g., sympathetic denervation) innervating the stomach results in reduction of ghrelin secretion and greater satiety, decreased sympathetic tone leading to increased motility and/or faster food transit time, thereby effecting a "neural gastric bypass." In some embodiments, modulation of the nerves (e.g., sympathetic denervation) innervating the pylorus results in decreased efferent sympathetic tone, leading to faster transit time and effecting a "neural gastric bypass." In some embodiments, modulation of the nerves (e.g., sympathetic denervation) innervating the duodenum results in disrupted afferent sympathetic activity leading to altered signaling of various receptors and hormones (e.g., gut hormones, GLP-1, gastric inhibitory peptide (GIP), cholecystokinin (CCK), peptide YY (PYY), 5-hydroxytryptamine (5-HT)), thereby causing increased insulin secretion and insulin sensitivity, and/or decreased efferent sympathetic tone leading to faster transit time, thereby effecting a "neural duodenal bypass."

In some embodiments, modulation of the nerves (e.g., sympathetic denervation) innervating the pancreas results in decreased efferent sympathetic tone, thereby causing increased beta cell insulin production and beta cell mass, and decreased alpha cell glucagon production. In some embodiments, modulation of the afferent sympathetic nerves innervating the liver results in reflexive decreased sympathetic tone to the pancreas, gastrointestinal tract, and/or muscle. In some embodiments, modulation of the afferent sympathetic nerves innervating the liver results in an increase in a hepatokine hormone with systemic effects (e.g., hepatic insulin sensitizing substance). In some embodiments, stimulation of the common hepatic branch of the vagus nerves could result in similar effects.

Several embodiments of the invention are particularly advantageous because they include one, several or all of the following benefits: (i) consistent and maintained contact with vessel walls; (ii) fewer treatment locations due to increased efficacy; (iii) ability to effectively treat a short vessel length such as the common hepatic artery; (iv) reduction in blood glucose, cholesterol and/or triglyceride levels, (v) reduction in lipid and/or norepinephrine levels in the liver, pancreas, and/or duodenum; (vi) confirmation of treatment efficacy; (vii) denervation of multiple organs or tissue structures from a single location; (viii) effective denervation of nerves in a perivascular region while maintaining minimal heating of, or thermal injury to, the inner vessel wall; (ix) higher likelihood of successful neuromodulation due to modulation of areas of high nerve density; (x) increased likelihood of modulation having an effect on glucose production due to modulation of areas of high nerve density or concentration; and/or (xi) increased circumferential vessel coverage with reduced axial vessel length coverage.

II. Types of Neuromodulation

A. Mechanical Neuromodulation

The selective modulation or disruption of nerve fibers may be performed through mechanical or physical disruption, such as, but not limited to, cutting, severing, ripping, tearing, transecting, or crushing. Several embodiments of the invention comprise disrupting cell membranes of nerve tissue. Several embodiments involve selective compression of the nerve tissue and fibers. Nerves being subjected to mechanical pressure, such as, but not limited to, selective compression or crushing forces may experience effects such as, but not limited to, ischemia, impeded neural conduction velocity, and nervous necrosis. Such effects may be due to a plurality of factors, such as decreased blood flow.

In several embodiments, many of the effects due to selective compression or mechanical crushing forces are reversible. Beyond using mechanical compression to selectively and reversibly modulate neural response, mechanical compression may be used to permanently modulate neural response through damage to select myelin sheaths and individual nerve fascicles. In some embodiments, the level of neural modulation is tuned by modulating the mechanical compressive forces applied to the nerve. For example, a large compressive force applied to a nerve may completely inhibit neural response, while a light compressive force applied to the same nerve may only slightly decrease neural response. In some embodiments, a mechanical compressive force or crushing force may be applied to a nerve, such as a sympathetic nerve in the hepatic plexus, with a removable crushing device. In some embodiments, the removable crushing device is removed and replaced with a stronger or weaker removable crushing device depending on the individual needs of the subject (e.g., the strength of the removable crushing device being keyed to the needed neural response levels). The ability of such removable crushing devices to be fine-tuned to selectively modulate neural response is advantageous over the binary (e.g., all or nothing) response of many types of neural ablation.

In various embodiments, the compressive or crushing forces necessary to compress or crush nerves or cause ischemia within the hepatic artery or other vessels may range from about 1 to about 100 $g/mm^2$, from about 1 $g/mm^2$ to about 10 $g/mm^2$, from about 3 $g/mm^2$ to about 5 $g/mm^2$ (e.g., 8 $g/mm^2$), from about 5 $g/mm^2$ to about 20 $g/mm^2$, from about 10 $g/mm^2$ to about 50 $g/mm^2$, from about 20 $g/mm^2$ to about 80 $g/mm^2$, from about 50 $g/mm^2$ to about 100 $g/mm^2$, or overlapping ranges thereof. These compressive forces may be effected by the various embodiments of mechanical neuromodulation devices or members described herein.

Figure 4A:
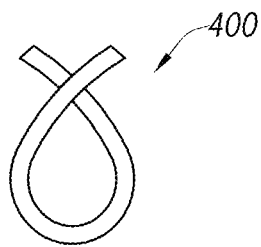
FIGS. 4A-4C, 5A and 5B, 6 and 7 illustrate embodiments of compression members configured to facilitate modulation of nerves.
Figure 4B:
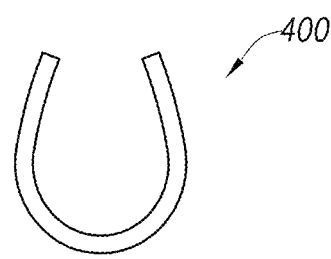
Figure 4C:
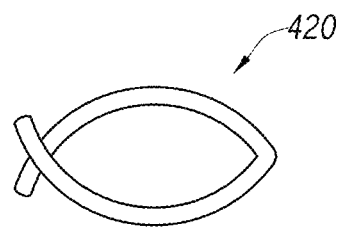

FIGS. 4A-4C, 5A, 5B, 6 and 7 illustrate various embodiments of mechanical neuromodulation devices or members. FIGS. 4A-4C illustrate embodiments of a shape memory compression clip 400. In some embodiments, the shape memory compression clip 400 is used to mechanically compress target nerves. In some embodiments, the shape memory compression clip 400 is removable. FIG. 4A illustrates a resting conformation of the shape memory compression clip 400. FIG. 4B illustrates a strained conformation of the shape memory compression clip 400, which looks like a capital "U" in the illustrated embodiment The shape memory compression clip 400 may be applied to a nerve, such as a nerve of the hepatic plexus by forcibly placing the shape memory compression clip 400 in its strained conformation, placing the target nerve in the bottom well of the shape memory compression clip 400, and then allowing the shape memory compression clip 400 to return to its resting conformation, thereby applying the desired compressive forces to the target nerve by causing it to be crushed or pinched. FIG. 4C illustrates an alternative embodiment of a shape memory compression clip 420 in which the bottom well forms an acute bend instead of being curvate when in a resting shape. The compression clip 400, 420 may be allowed to return to a resting configuration through either removal of external forces biasing the compression clip in a strained configuration (e.g., utilizing superelastic properties of shape memory materials) or heating the compression clip above a transition temperature, thereby allowing the compression clip to assume a native or resting configuration in an austenitic phase above the transition temperature.

In some embodiments, mechanical compressive forces are held at substantially constant levels after application. In some embodiments, the shape memory compression clip 400 may be tailored to the anatomy of different target nerves.

In some embodiments, the shape memory compression clip 400 varies in size or shape to compensate for anatomical variance. In some embodiments, varying sizes or shapes of shape memory compression clips may be used, in addition to compensating for anatomical variance, to selectively apply varying levels of compressive stresses to the target nerve (e.g., smaller clip or stronger material for higher forces and larger clip or weaker material for smaller forces). In one embodiment, the shape memory material is nitinol. In various embodiments, the shape memory material is a shape memory polymer or any other appropriate material having shape memory material properties. In some embodiments, compression members comprise simple spring clips or any other devices capable of applying a substantially constant force. In some embodiments, a compression member is configured to clamp the entire artery and the nerves in the adventitial layer, thereby applying the desired compressive forces to both the target nerves and the artery around which the target nerves travel.

Applying compressive, occlusive or collapsing forces to hepatic arteries is uniquely feasible, in some embodiments, because the liver is supplied with blood from both the hepatic arteries, around which many of the target nerves described herein may travel, as well as the portal vein. If at least one of the hepatic arteries is clamped (for the purpose of applying compressive forces to the nerves in its adventitia), the liver would lose the blood supply from that artery, but would be fully supplied by the portal vein, thereby leaving the liver viable and healthy.

In some embodiments, mechanical compressive forces are variable across time following application. In some embodiments, the mechanical compressive forces are varied according to a pre-set duty cycle, thereby titrating the effects of the neuromodulation. One or more embodiments may comprise a transcutaneous delivery of energy to a circuit coupled to a compression member (e.g., a nitinol clip) having a transition between martensitic and austenitic states at a specific temperature induced by a temperature that is substantially different from body temperature. In several embodiments, a variance in temperature is provided through, but is not limited to: a thermocouple (e.g., a Peltier junction) thermally coupled to the compression member to which the circuit may apply power, or a heating element thermally coupled to the compression member to which the circuit may apply resistive power, thereby altering the physical conformation of the compression member and varying (either increasing or decreasing depending on the power applied) the compressive forces generated by the compression member. In one embodiment, the compression member itself acts as a resistive element and the circuit is coupled directly to the compression member to apply resistive power to the compression member, thereby altering the physical conformation of the compression member and varying (either increasing or decreasing depending on the power applied) the compressive forces generated by the compression member. Other embodiments combine the compression member with a thermocouple or other temperature-measurement device to allow the selective application of electric power to vary the compressive stresses created by the compression member.

Figure 5A:
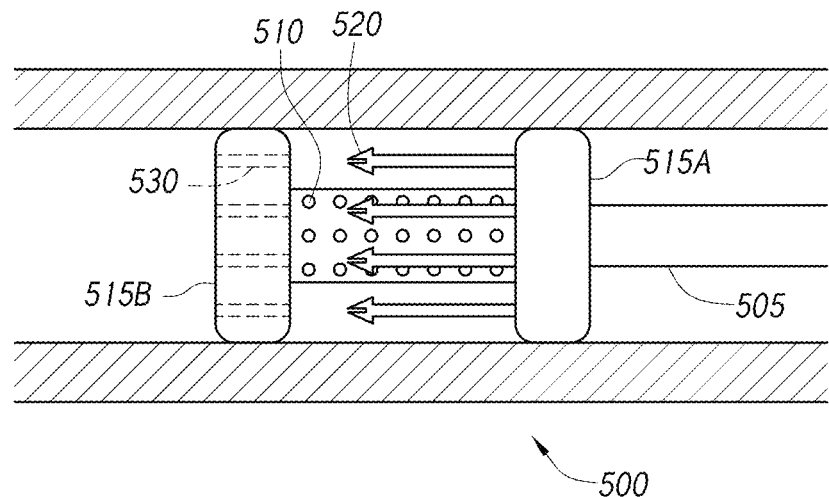
Figure 5B:
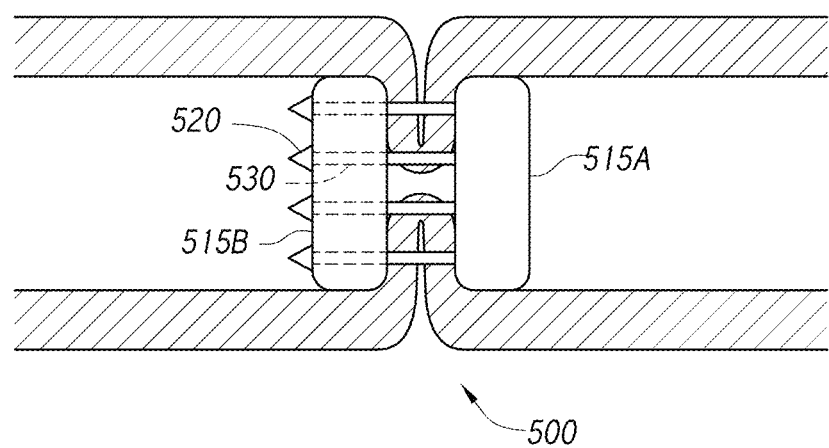

FIGS. 5A and 5B illustrate another embodiment of a compression device. FIG. 5A illustrates a catheter-based vascular wall compression system 500 including a vascular wall clamp 515 in an open conformation. The catheter-based vascular wall compression system 500 includes a detachable insertion catheter 505, suction holes 510, an engagement portion 515A of the vascular wall clamp 515, an anchoring mechanism 520, a receiving portion 515B of the vascular wall clamp, and an anchoring mechanism accepting portion 530. In operation, the vascular wall clamp 515 may be inserted into the target vessel on the distal end of the detachable insertion catheter 505. In one embodiment, the receiving portion 515B of the vascular wall clamp 515 is located at the distal end of the detachable insertion catheter 505, while the engagement portion 515A of the vascular wall clamp 515 is located slightly proximal to the receiving portion 515B. The surface of the detachable insertion catheter 505 between the receiving portion 515B and the engagement portion 515A may include a plurality of suction holes 510.

In further operation, once the vascular wall clamp 515 is placed at the desired target location, the suction holes 510, in one embodiment, create a vacuum, or suction, which brings the walls of the target vessel in substantially direct apposition to the surface of the detachable insertion catheter portion that includes the plurality of suction holes 510. While maintaining suction, and therefore the position of the vessel wall in apposition to the detachable insertion catheter 505, the engagement portion 515A is moved toward the receiving portion 515B (or vice versa), thereby pinching the vascular wall which remained in direct apposition to the detachable insertion catheter between the receiving portion 515B and the engagement portion 515A.

The anchoring mechanism 520, which is attached to the engagement portion 515A engages the anchoring member accepting portion 530 of the receiving portion 515B, thereby securing the receiving portion 515B to the engagement portion 515A and clamping the vascular wall portion that remains in direct apposition to the detachable insertion catheter 505 between the receiving portion 515B and the engagement portion 515A. Once the receiving portion 515B has fully engaged with the engagement portion 515A, the detachable insertion catheter 505 may be disengaged from the vascular wall clamp 515 and removed by the same path it was inserted.

FIG. 5B illustrates the vascular wall clamp 515 in a closed conformation. In FIG. 5B, the anchoring mechanism 520, which is attached to the engagement portion 515A of the vascular wall clamp 515 has engaged the anchoring member accepting portion 530 of the receiving portion 515B of the vascular wall clamp 515, thereby clamping a portion of the vascular wall between the receiving portion 515B and the engagement portion 515A. FIG. 5B shows that the detachable insertion catheter 505 has already been removed.

In some embodiments, the engagement portion 515A and the receiving portion 515B of the vascular wall clamp 525 both include a hollow center. In these embodiments, when the detachable insertion catheter 505 is removed, the hole at the center of the engagement portion 515A of the vascular wall clamp 515 and the hole at the center of the receiving portion 515B of the vascular wall clamp 525 creates a patent lumen between the receiving portion 515B and the engagement portion 515A, thereby allowing continued blood flow from one side to the other. In some embodiments, the detachable insertion catheter 505 is attached to either the engagement portion 515A or the receiving portion 515B of the vascular wall clamp 515 by means of a threaded portion, which may be unthreaded once the receiving portion 515B and engagement portion 515A have engaged, and the detachable insertion catheter 505 is no longer needed.

In some embodiments, the vascular wall clamp 515 is inserted to the target anatomy using an over-the-wire approach. In some embodiments, the detachable insertion catheter 505 is hollow and has suction holes 510 in communication with an internal hollow lumen of the detachable insertion catheter 505. The suction holes 510 may be a series of small openings, a screen, or any other structure which allows a lower pressure area to be created between the receiving portion 515B and the engagement portion 515A of the vascular wall clamp 515 to bring the vessel wall and perivascular tissue in substantially direct apposition with the detachable insertion catheter 505. In some embodiments, the vascular wall clamp 515 is deployed by pulling proximally on the detachable insertion catheter 505, thereby bringing the distal receiving portion 515B of the vascular wall clamp 525 into engagement with the proximal engagement portion 515A of the vascular wall clamp 515, thereby compressing and/or severing arterial and nerve tissue captured therein. In some embodiments, rotation of the catheter 505 is effective to disengage the catheter 505 from the vascular wall clamp 515. In some embodiments, removal of the detachable insertion catheter 505 from the vascular wall clamp 515 leaves a patent lumen permitting blood flow to the liver.

In some embodiments, the engagement mechanism 520 comprises at least one spear-shaped clip and the engagement accepting portion 530 comprises at least one hole aligned to accept the at least one spear shaped clip and to engage the at least one spear shaped clip engagement mechanism 520 as it enters the at least one hole engagement accepting portion 530 and snaps into place. In some embodiments, the engagement mechanism 520 and engagement accepting portion 530 are simply magnets which hold the receiving portion 515B of the vascular wall clamp 515 and the engagement portion 515A of the vascular wall clamp 515 together. In still other embodiments, the engagement mechanism 520 and the engagement accepting portion 530 are any structures that allow the engagement portion 515A to engage the receiving portion 515B and remain in that engaged conformation. In some embodiments, the vascular wall clamp 515 comprises a biologically inert material with decreased thrombogenicity, such as Teflon®.

Figure 6:
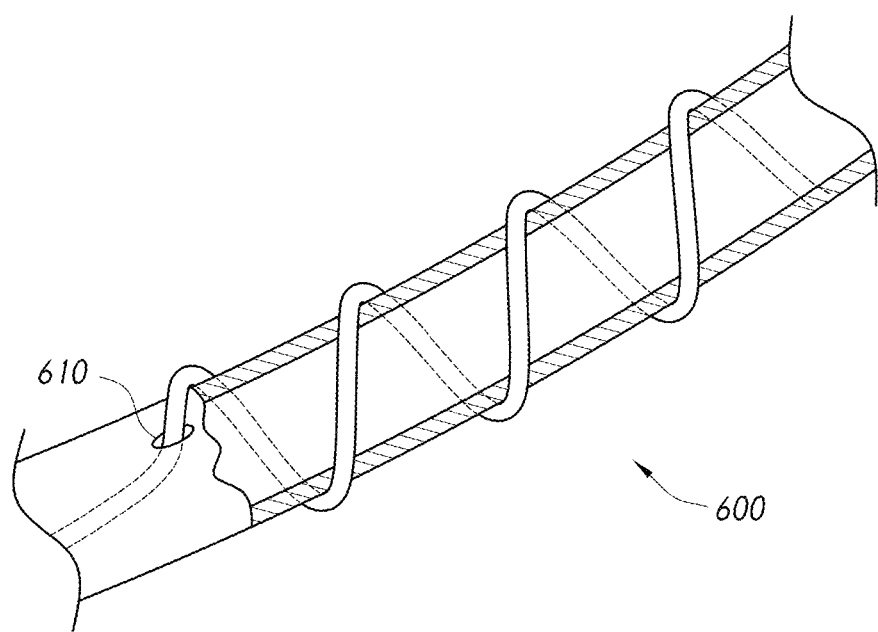

FIG. 6 illustrates an embodiment of an extravascular compression coil 600 inserted within a vessel. In operation, the extravascular compression coil 600 may be advanced through a hole in the vascular wall 610 in a spiraling intra-vascular to extra-vascular manner into the vessel adventitia, thereby placing the extravascular compression coil 600 around the target vessel. In some embodiments, the extravascular compression coil 600 has the effect of compressing the nerves located within the vascular wall of the target vessel. In some embodiments, to prevent or inhibit occlusion and stenosis, an intravascular stent is subsequently placed within the lumen of the target vessel, thereby both propping open the vessel for continued flow and providing a resilient surface against which the target nerves may be compressed.

In embodiments where stenosis is of particular concern, a stent is placed in the target vessel after treatment to retain patency. In some embodiments, the placement of a stent within the lumen of the target vessel provides the added benefit of compressing the vascular wall to a higher degree, thereby disrupting the target nerves even more. In some embodiments, a stent is placed in the portal vein due to the risk of portal vein stenosis from hepatic arterial ablation procedures. In some embodiments, to protect the portal vein from possible stenosis, anal cooling is used because the gut venous flow travels to the portal system (in some embodiments, anal cooling has the direct result of cooling the portal vein and decreasing the likelihood of stenosis due to treatment of the hepatic artery).

In some embodiments, magnets may be delivered separately into the portal vein and hepatic artery. Upon placement of the two magnets, opposite poles of the two magnets will attract each other and subsequently mate, thereby resulting in substantial compression of the nerves disposed between the two magnets. The force created by the mating of the two magnets may be selectively modulated by increasing or decreasing the strength of magnets used for any given patient morphology, as desired or required.

Figure 7:
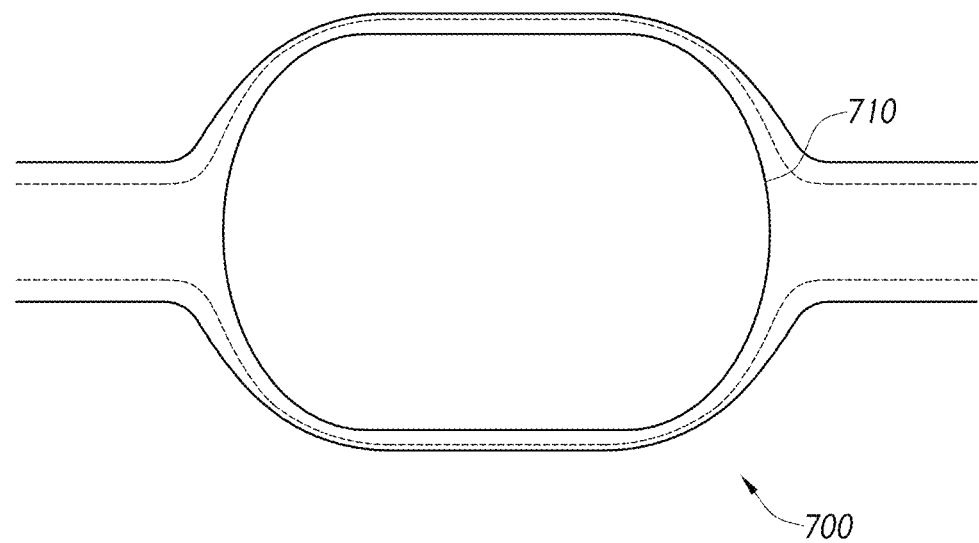

FIG. 7 illustrates an embodiment of a fully occluding balloon 700 inserted within a target blood vessel. In operation, a fully occluding balloon 710 is inserted into a target vessel, inflated and used to expand or stretch the vascular lumen to sufficiently stretch the surrounding nerves to either the point of ischemia or physical disruption. The fully occluding balloon 710 may be removed after physical disruption or after the target nerves have been destroyed due to ischemia. Alternatively, the fully occluding balloon 710 may be left in place permanently because, as discussed previously, the liver is supplied by blood from the portal vein as well, rendering the hepatic artery at least somewhat redundant. In some embodiments, the level of balloon compression is adjusted in an ambulatory fashion, thereby allowing for titration of the neuromodulation effect.

In some embodiments, rather than using a fully occluding balloon 710, a non-occluding balloon or partially occluding balloon is inserted into a target vessel, inflated, and used to expand or stretch the vascular lumen to sufficiently stretch the surrounding nerves to the point of ischemia or physical disruption. The non-occluding or partially occluding balloon may have similar structural features as the fully occluding balloon 710, but may include at least one hollow lumen (e.g., a central lumen) to allow for continued blood flow after placement. In some embodiments, the level of balloon compression can be adjusted in an ambulatory fashion, thereby allowing for titration of the neuromodulation effect.

In some embodiments, similar to the occlusion techniques described above, a balloon catheter may be inserted into the target vessel and then filled with a fluid which is infused and withdrawn at a specific frequency (e.g., pressurized in an oscillating fashion), thereby causing mechanical disruption of the nerve fibers surrounding (e.g., within a wall of, such as within the intima, media or adventitia of) the target vessel (e.g., hepatic artery). In some embodiments, the fluid used to fill the balloon catheter may be a contrast agent to aid in visualization of the arterial structure (and thereby limiting the amount of contrast agent used in the procedure).

In some embodiments, a fluid is injected into the interstitial space surrounding the vasculature around which the target nerve lies, thereby applying compressive forces to the nerve bundle which surrounds the vessel(s). In some embodiments, the fluid is air. In some embodiments, the fluid is any noble gas (e.g., heavy gas), including but not limited to: helium, neon, argon, krypton, and xenon. In some embodiments, the fluid is nitrogen gas. In some embodiments, the fluid is any fluid capable of being injected to apply the desired compressive forces. In some embodiments, the fluid is injected by a catheter inserted transluminally through a blood vessel in substantially close proximity to the target site (e.g., location where nervous compression is desired). In some embodiments, the fluid is injected by a needle or trocar inserted transdermally through the skin and surrounding tissues to the target site. Any method of fluid injection may be used to deliver the requisite amount of fluid to the target site in order to create compressive forces that are applied to the target nerve, such as nerves of the hepatic plexus.

In some embodiments, a target vessel is completely transected, thereby causing a complete and total physical disruption of the vessel wall and the surrounding nerves in the adventitial tissues. The target vessel may then be re-anastamosed, thereby allowing continued perfusion through the vessel. The nerve tissue either does not reconnect, or takes a significant amount of time to do so. Therefore, all neural communication surrounding the transected vessel may temporarily or permanently the disrupted. In some embodiments, a cutting device is advanced in a catheter through the subject's vasculature until it reaches a target vessel. The cutting device may then be twisted along the axis of the target vessel to cut through the target vessel from the inside out. In some embodiments, an expandable element, such as a balloon catheter, is inserted into the vessel to compress the vessel wall and provide a controlled vessel thickness to permit transection. A rotational cutter may then be advanced circumferentially around the expandable element to effect transection of the vessel and the nerves disposed within the adventitia of the vessel. In one embodiment, the target vessel is transected during open surgery.

Re-anastomoses of vessels could be achieved using any of several methods, including laser, RF, microwave, direct thermal, or ultrasonic vessel sealing. In some embodiments, thermal energy may be delivered through an expandable element to effect anastomosis of the vessel under the mechanical pressure provided by the expandable element. The combination of pressure, time, and temperature (e.g., 60° C., 5 seconds, and 120 psi in one embodiment) may be an effective means to seal vessels such as the hepatic arteries.

B. Energy-Based Neuromodulation
1. Radiofrequency

In some embodiments, a catheter system comprises an ablation device coupled to a generator (for example, pulse-generating device or power generator). For example, the ablation device may be an ablation catheter. The ablation catheter may have a proximal end portion and a distal end portion. In some embodiments, the distal end portion of the ablation catheter comprises one or more electrodes (e.g., one electrode, two electrodes, three electrodes, four electrodes, five electrodes, six electrodes, more than six electrodes). In some embodiments, the ablation catheter consists of only two electrodes. In other embodiments, the ablation catheter consists of only four electrodes. The one or more electrodes can be positioned on an external surface of the ablation catheter or can extend out of the distal end portion of the ablation catheter. In some embodiments, the electrodes comprise monopolar electrodes. In some embodiments, the electrodes comprise one or more active electrodes and one or more return electrodes that cooperate to form bipolar electrode pairs. In some embodiments, the distal end portion of the ablation catheter comprises at least one bipolar electrode pair and at least one monopolar electrode. One or more electrically conductive wires (for example, thermo-couple wires) may connect one or more electrodes located at the distal end of the ablation catheter to the generator (for example, pulse-generating device). In some embodiments, multiple electrodes can extend from the ablation catheter on multiple wires or deployment arms to provide multiple energy delivery locations or points within a vessel (e.g., a hepatic artery, a renal artery) or other body lumen or within an organ (e.g., pancreas, stomach, small intestine).

In some embodiments, the generator (for example, pulse-generating device) applies power or delivers electrical (e.g., radiofrequency (RF)) signals or pulses to the electrodes located at or near the distal end portion of the ablation catheter. The electrodes may be positioned to deliver RF energy in the direction of sympathetic nerve fibers in the hepatic plexus to cause ablation due to thermal energy. In some embodiments, the electrodes are positioned on top of reflective layers or coatings to facilitate directivity of the RF energy away from the ablation catheter. In various embodiments, the electrodes are curved or flat. The electrodes can be dry electrodes or wet electrodes. In some embodiments, a catheter system comprises one or more probes with one or more electrodes. For example, a first probe can include an active electrode and a second probe can include a return electrode. In some embodiments, the distal ends of the one or more probes are flexible. The ablation catheter can comprise a flexible distal end portion. Variable regions of flexibility or stiffness along a catheter length are provided in some embodiments. In various embodiments, a first flexible portion is actuated to have a first bend shape configured to conform to a first anatomical bend (e.g., a first bend of a hepatic artery branch) and a second flexible portion is actuated to have a second bend shape configured to conform to a second anatomical bend (e.g., a second bend of a hepatic artery branch).

In one embodiment, a pair of bipolar electrodes is disposed at a location that is substantially tangential to the inner lumen of the hepatic artery, each individual electrode having an arc length of 20 degrees, with an inter-electrode spacing of 10 degrees. In one embodiment, the arc length and electrode spacing are configured to deliver thermal energy to a region within 1-3 mm of a hepatic artery lumen. The edges of the two electrodes may have radii sufficient to reduce current concentrations. In some embodiments, the two electrodes are coated with a thin layer of non-conductive material to reduce current concentrations such that energy is delivered to target tissue via capacitive coupling. The arc length and spacing of the bipolar electrodes may be varied to alter the shape of the energy delivery zones and thermal lesions created by the delivery of energy from the electrodes.

In some embodiments, peripheral active or grounding conductors are used to shape an electric field. In one embodiment, a grounding needle is positioned perivascularly to direct ablative current towards nerves within the perivascular space. In a non-invasive embodiment to accomplish the same effect, high ion content material is infused into the portal vein. In another embodiment, a shaping electrode is positioned within the portal vein using percutaneous techniques such as employed in transjugular intrahepatic portosystemic (TIPS) techniques. In one embodiment, a second shaping electrode is positioned in the biliary tree endoscopically.

In some embodiments, a plurality of electrodes are spaced apart longitudinally with respect to a center axis of the ablation catheter (e.g., along the length of the ablation catheter). In some embodiments, a plurality of electrodes are spaced apart radially around a circumference of the distal end of the ablation catheter. In some embodiments, a plurality of electrodes are spaced apart both longitudinally along a longitudinal axis of the ablation catheter and radially around a circumference of the ablation catheter from each other. In various embodiments, the electrodes are positioned in various other patterns (e.g., spiral patterns, checkered patterns, zig-zag patterns, linear patterns, randomized patterns).

One or more electrodes can be positioned so as to be in contact with the inner walls (e.g., intima) of the blood vessel (e.g., common hepatic artery or proper hepatic artery) at one or more target ablation sites adjacent the autonomic nerves to be disrupted or modulated, thereby providing intravascular energy delivery. In some embodiments, the electrodes are coupled to expandable and collapsible structures (e.g., self-expandable or mechanically expandable) to facilitate contact with an inner vessel wall. The expandable structures can comprise coils, springs, prongs, tines, scaffolds, wires, stents, balloons, cages, baskets and/or the like. The expandable electrodes can be deployed from the distal end of the catheter or from the external circumferential surface of the catheter. The catheter can also include insulation layers adjacent to the electrodes or active cooling elements. In some embodiments, cooling elements are not required. In some embodiments, the electrodes can be needle electrodes configured to penetrate through a wall of a blood vessel (e.g., a hepatic artery) to deliver energy extravascularly to disrupt sympathetic nerve fibers (e.g., the hepatic plexus). For example, the catheter can employ an intra-to-extravascular approach using expandable needle electrodes having piercing elements. The electrodes can be disposable or reusable.

In some embodiments, the catheter includes electrodes having a surface area of about 2 to about 5 mm$^2$, 5 to about 20 mm$^2$, about 7.5 to about 17.5 mm$^2$, about 10 to about 15 mm$^2$, overlapping ranges thereof, less than about 5 mm$^2$, greater than about 20 mm$^2$, 4 mm$^2$, or about 12.5 mm$^2$. In some embodiments, the catheter relies only on direct blood cooling. In some embodiments, the surface area of the electrodes is a function of the cooling available to reduce thrombus formation and endothelial wall damage. In some embodiments, lower temperature cooling is provided. In some embodiments, higher surface areas are used, thereby increasing the amount of energy delivered to the perivascular space, including surface areas of about 5 to about 120 mm$^2$, about 40 to about 110 mm$^2$, about 50 to about 100 mm$^2$, about 60 to about 90 mm$^2$, about 70 to about 80 mm$^2$, overlapping ranges thereof, less than 5 mm$^2$, or greater than 120 mm$^2$. In some embodiments, the electrodes comprise stainless steel, copper, platinum, gold, nickel, nickel-plated steel, magnesium, or any other suitably conductive material. In some embodiments, positive temperature coefficient (PTC) composite polymers having an inverse and highly non-linear relationship between conductivity and temperature are used. In some embodiments, PTC electrodes (such as the PTC electrodes described in U.S. Pat. No. 7,327,951, which is hereby incorporated herein by reference) are used to control the temperature of RF energy delivered to the target tissue. For example, PTC electrodes may provide high conductivity at temperatures below 60° C. and substantially lower conductivity at temperatures above 60° C., thereby limiting the effect of energy delivery to tissue above 60° C.

a. Hydrogel-Coated Electrode Catheters

Figure 8:
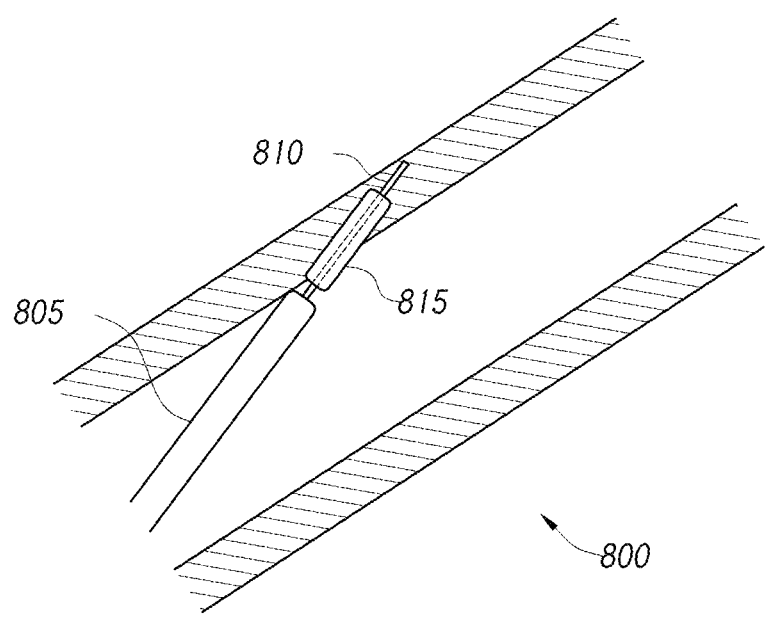
FIGS. 8 and 9 illustrate embodiments of electrode catheters.

FIG. 8 illustrates a self-repairing ablation catheter 800. The self-repairing ablation catheter 800 comprises a catheter body 805, a needle electrode 810, and a vascular wall plug 815. In one embodiment, the needle electrode 810 is placed at or near the distal end of the catheter body 805 and used to heat tissue (which may result in nerve ablation). The vascular wall plug 815 may be placed around the needle electrode 810 such that when the needle electrode 810 is pushed into or through the vascular wall, the vascular wall plug 815 is pushed into or through the vascular wall as well. Upon retracting the self-repairing ablation catheter 800, the needle electrode 810 fully retracts in some embodiments, leaving the vascular wall plug 815 behind, and thereby plugging or occluding the hole left by the needle electrode 810.

In embodiments used to modulate (e.g., ablate) extravascularly, the vascular wall plug 815 may comprise a hydrogel jacket or coating disposed on the needle electrode 810. In some embodiments, the vascular wall plug 815 is glued or otherwise adhered or fixed in a frangible manner at its distal end to the needle electrode 810, yet may be sufficiently thin so it does not prevent or inhibit smooth passage of the needle electrode 810 as it is advanced into the perivascular space. In some embodiments, once the proximal end of the vascular wall plug 815 passes out of the guiding lumen, it cannot be pulled proximally. Therefore, upon ablation completion, removal of the needle electrode 810 from the perivascular space places the hydrogel jacket in compression in the hole made by the needle electrode 810 in the vessel wall, thereby forming a plug which prevents or reduces the likelihood of vessel leakage or rupture. In some embodiments, the vascular wall plug 815 is made of a hydrogel that swells when exposed to tissues, such as polyvinyl alcohol, or a thrombogenic material, such as those employed during interventional radiology procedures to coil off non-target vessels.

Figure 9:
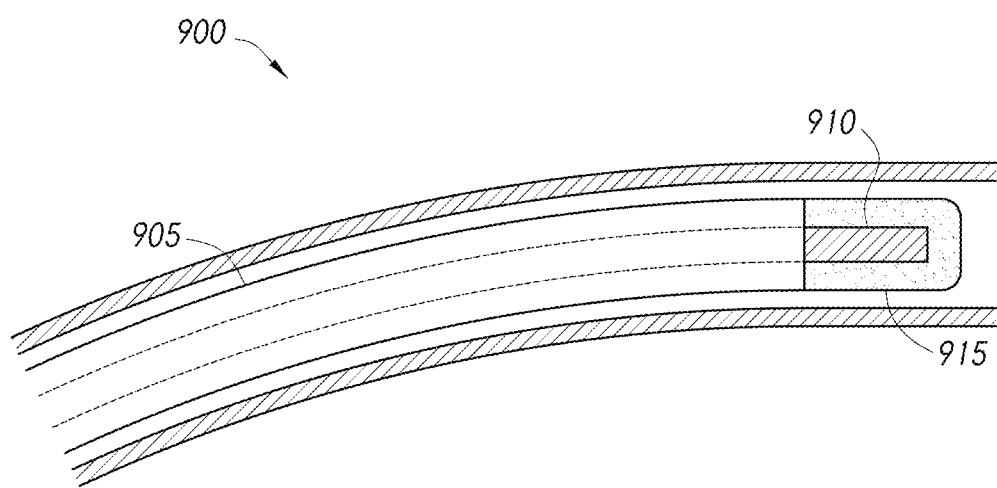

FIG. 9 illustrates an embodiment of a hydrogel-coated electrode catheter 900. The hydrogel-coated electrode catheter 900 includes a catheter body 905, an ablation electrode 910, and a hydrogel coating 915. In one embodiment, the ablation electrode 910 is attached to the distal end of the catheter body 905 and the hydrogel coating 915 coats the electrode 910.

In some embodiments, the hydrogel coating 915 is a previously-desiccated hydrogel. Upon insertion into the target anatomy, the hydrogel coating 915 on the ablation electrode 910 may absorb water from the surrounding tissues and blood. Ions drawn in from the blood (or included a priori in the hydrogel coating 915) may impart conductive properties to the hydrogel coating 915, thereby permitting delivery of energy to tissue. In accordance with several embodiments, the hydrogel-coated electrode catheter 900 requires less cooling during ablation, as the hydrogel coating resists desiccation. A smaller catheter size may also be used, as construction requirements and number of components may be reduced. In some embodiments, the electrode impedance replicates native tissue impedance for better impedance matching. In some embodiments, temperature measurements at the surface of the hydrogel-coated electrode are possible.

b. Balloon Catheters

Energy delivery catheters may comprise balloon catheters configured to modulate nerves or other tissue. In some embodiments, a balloon catheter comprises a catheter body and a distal balloon. The catheter body comprises a lumen configured to continuously infuse saline or other fluid into the balloon. The distal balloon comprises one or more hydrogel portions spaced around the circumference of the distal balloon. In one embodiment, if saline is used, any water that vaporizes from the surface of the distal balloon is replenished by diffusion from the balloon lumen, thereby preventing or inhibiting free saline to travel into the vessel interface and reducing any undesired effects of saline infusion.

In accordance with several embodiments, the branches of the forks between the common hepatic artery, the proper hepatic artery and the gastroduodenal artery are advantageously simultaneously or sequentially targeted (e.g., with RF energy) because sympathetic nerves supplying the liver and pancreas are generally tightly adhered to or within the walls of these arteries. Forks between other arteries or vessels may similarly be simultaneously or sequentially be targeted (e.g., with RF energy). In some embodiments, coiled electrodes opposing the artery walls are used.

Figure 10A:
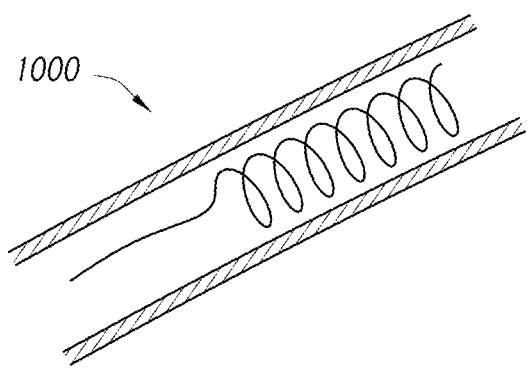
FIGS. 10A and 10B illustrate embodiments of ablation coils.

FIG. 10A illustrates an embodiment of a single ablation coil 1000 device. The single ablation coil device 1000 may be inserted into target vasculature and activated to ablate the nerves within or surrounding the vasculature. To ablate a vascular fork, it may be necessary to insert the single ablation coil 1000 into one branch of the fork (e.g., proper hepatic artery branch) and ablate that branch, then insert the single ablation coil 1000 into the other branch of the fork (e.g., gastroduodenal artery branch or left or right hepatic artery branch) and ablate that branch.

Figure 10B:
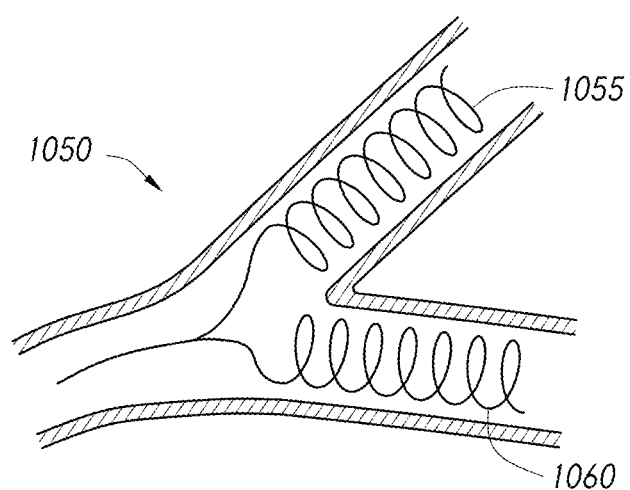

FIG. 10B illustrates a forked ablation coil device 1050. The forked ablation coil device 1050 comprises two ablation coils, a first ablation coil 1055 and a second ablation coil 1060. In accordance with several embodiments, the forked ablation coil device 1050 allows an entire vascular fork to be ablated simultaneously. In operation, the forked ablation coil device 1050 may be inserted to the target vasculature by overlapping the first ablation coil 1055 and the second ablation coil 1060 (effectively creating a single double helix coil). Once the target fork is reached, the first ablation coil 1055 and the second ablation coil 1060 may be separated and the first ablation coil 1055 inserted into a first branch of the target fork and the second ablation coil 1060 inserted into a second branch of the target fork. The branches of the target vessel fork (and the nerves within or surrounding the vessels of the fork branches) may then be simultaneously ablated.

In some embodiments, the coiled electrodes (e.g., ablation coil device 1000 or forked ablation coil device 1050) are created out of a memory material, such as nitinol or any other shape memory material. In some embodiments, energy may be delivered by the one or more coiled electrodes in a manner so as not to cause nerve ablation (temporary or permanent). In some embodiments, the thermal dose delivered may modulate nerves without causing ablation. The ablation coils may be delivered by one or more catheters. The ablation coils may be coupled to a catheter such that the ablation coils may be removed or repositioned following ablation of a target location. Balloon electrodes or other ablation elements may be used instead of ablation coils. In some embodiments, a single balloon with multiple electrodes may be used instead of the coiled electrodes. A portion of the balloon with an electrode may be positioned in each of the branches. In other embodiments, each of the branches may be occluded with an occlusion member and fluid may be infused to create a wet electrode effect for ablation.

In some embodiments, energy is delivered between two ablation elements positioned to span a vessel bifurcation in a bipolar manner, thereby concentrating delivery of energy and denervation between the ablation elements in a bifurcation region where a higher density of nerve fibers may exist.

Figure 11A:
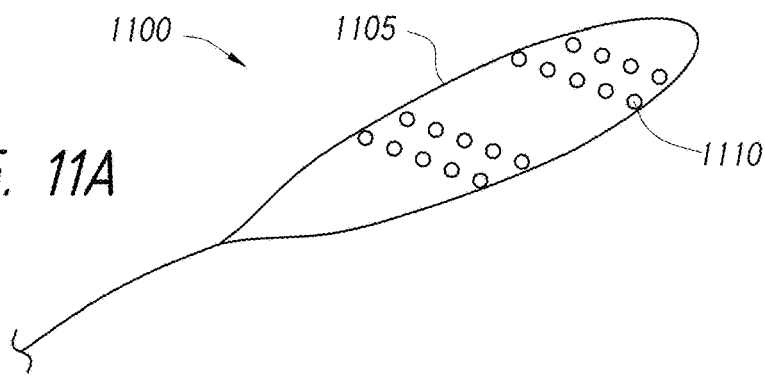
Figure 11B:
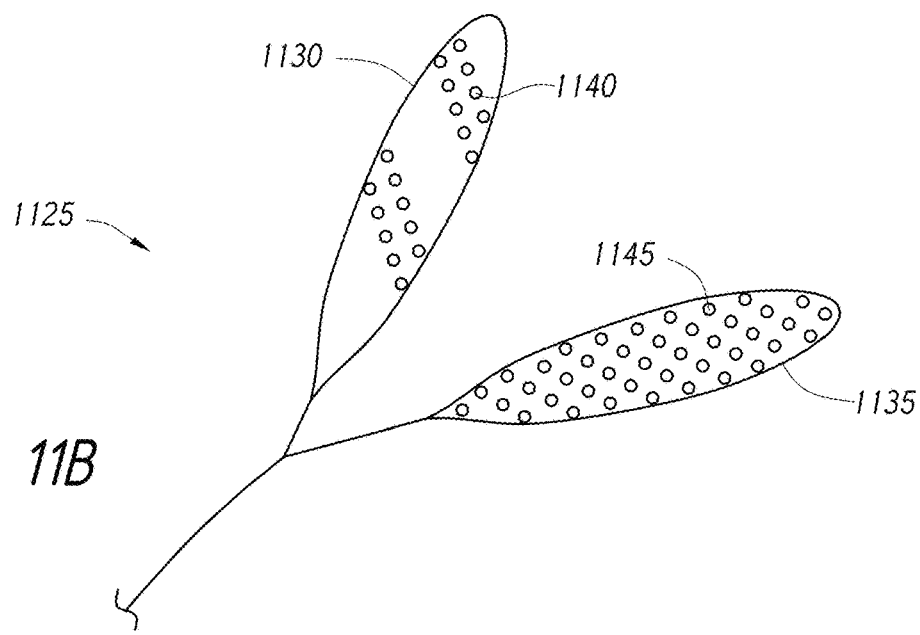
Figure 11C:
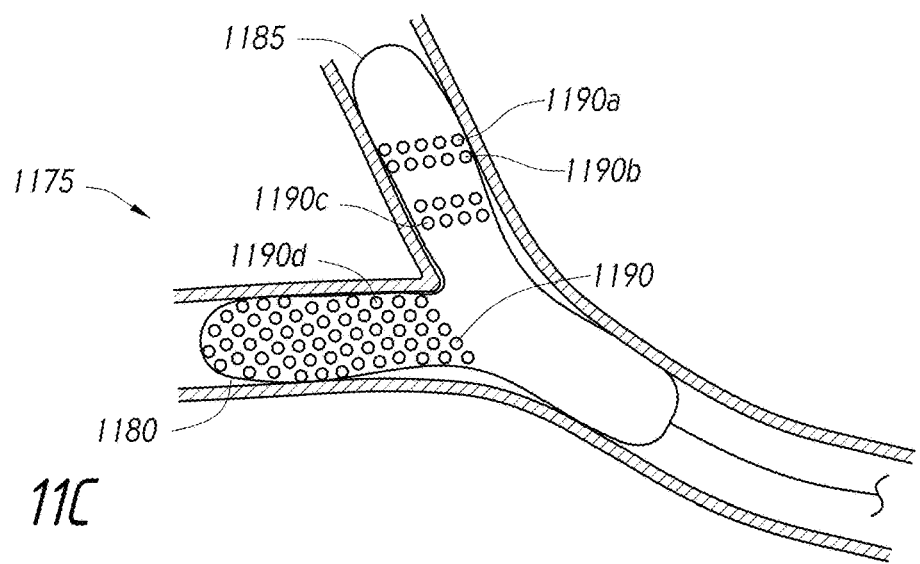

FIGS. 11A-11C illustrate embodiments of balloon ablation catheters. FIG. 11A illustrates an embodiment of a single balloon ablation catheter 1100, FIG. 11B illustrates an embodiment of a forked double balloon ablation catheter 1125, and FIG. 11C illustrates an embodiment of a forked balloon ablation catheter 1175. In various embodiments, a balloon ablation catheter comprises a bipolar balloon catheter.

The single balloon ablation catheter 1100 of FIG. 11A comprises an electrode balloon 1105 having at least one electrode 1110 (e.g., one electrode, two electrodes, three electrodes, four electrodes, five to ten electrodes, ten to twenty electrodes, or more than twenty electrodes). The electrode patterns and configurations shown in FIGS. 11A-11C illustrate various embodiments of electrode patterns and configurations; however, other patterns and configurations may be used as desired or required. In some embodiments, a high dielectric constant material may be used in the place of at least one electrode. The single balloon ablation catheter 1100 may be inserted into target vasculature and then inflated and used to ablate the vasculature (and thereby ablate the nerves within or surrounding the vessel, such as within the perivascular space). To ablate a vascular fork, it may be necessary to insert the single balloon ablation catheter 1100 into one branch of the fork and ablate that branch, then retract the single balloon ablation catheter 1100 from that branch and insert the single balloon ablation catheter 1100 into the other branch of the fork and ablate that branch.

The forked two balloon ablation catheter 1125 of FIG. 11B includes a first electrode balloon 1130 and a second electrode balloon 1135. The first electrode balloon 1130 includes at least a first electrode 1140, and the second electrode balloon 1135 includes at least a second electrode 1145. In several embodiments, the forked two balloon ablation catheter 1125 allows an entire vascular fork (e.g., all branches) to be ablated simultaneously. In operation, the forked two balloon ablation catheter 1125 is inserted into the vasculature and advanced to the target fork. Once the target fork is reached, the left electrode balloon 1130 and the right electrode balloon 1135 may be inflated and the left electrode balloon 1130 inserted into the left branch of the target fork and the right electrode balloon 1135 inserted into the right branch of the target fork (or vice versa). The target fork may then be simultaneously ablated. As discussed above, the first balloon and the second balloon can comprise a plurality of electrodes, or in some embodiments, at least one of the electrodes is replaced with a high dielectric constant material. The one or more electrodes may be individually connected to a generator via one or more leads or thermocouple wires. By selectively and/or sequentially activating one or more electrode pair simultaneously, energy delivery to the surrounding tissue can be uniquely directed toward target anatomy with respect to balloon position. For example, referring now to FIG. 11C, energy could be directed between electrode 1190A and electrode 1190B in order to create a focused lesion within the vessel wall, or between electrode 1190C and 1190D to focus energy delivery at the vessel bifurcation.

The forked balloon ablation catheter 1175 of FIG. 11C includes a single balloon which has a left fork 1180 and a right fork 1185 with at least one balloon electrode 1190. In some embodiments, the forked balloon ablation catheter 1175 comprises at least one balloon electrode for each balloon fork. The electrodes can be spaced and distributed along the balloon to facilitate positioning of at least one balloon electrode in each branch of the target fork. The forked balloon ablation catheter 1175 operates in the same manner as the forked double balloon ablation catheter 1125; however, it may advantageously allow for more effective ablation of the crotch of the vascular fork. In some embodiments, the balloon of the forked balloon ablation catheter 1175 is substantially the shape of the target fork or is configured to conform to the shape of the target fork. In some embodiments, the forked balloon ablation catheter 1175 is configured to be used in vessels having forks with three or more branches (such as the fork between the common hepatic artery, proper hepatic artery and the gastroduodenal artery). In some embodiments, each of the branches of the vessel fork may be occluded with an occlusion member and fluid may be infused to form a wet electrode for ablation. In various embodiments, the bifurcation devices described herein are used to modulate nerves at the bifurcation of the common hepatic artery and the gastroduodenal artery or the bifurcation of the proper hepatic artery into the right and left hepatic arteries.

An electrode balloon may be used to ablate (or otherwise modulate) target vasculature. In some embodiments, the electrode balloon is inserted via a catheter and inflated such that the balloon is in contact with substantially all of the fork intimal walls. In some embodiments, the electrode balloon is substantially oval. A two-step approach may be used to ablate the entire surface of the fork: first, the balloon can be put in place in one branch of the fork (e.g., the proper hepatic artery branch), inflated, and then used to ablate; second, the balloon can be retracted and then advanced into the other fork (e.g., the gastroduodenal artery branch or right or left hepatic artery branch), inflated, and then used to ablate. In some embodiments, the electrode balloon comprises ablation electrodes on an external surface in sufficient density that simultaneous ablation of the entire intimal wall in contact with the electrode balloon is possible. In some embodiments, the ablation electrodes on the surface of the electrode balloon are arranged in a predetermined pattern. In some embodiments, the ablation electrodes on the surface of the electrode balloon are activated simultaneously. In some embodiments, the ablation electrodes on the surface of the electrode balloon are individually addressable (e.g., actuatable), thereby allowing selective areas to be ablated as desired. In some embodiments, at least one electrode on the electrode balloon is an ablation electrode and at least one electrode on the electrode balloon is a sensing electrode (used, for example, to sense impedance, temperature, etc.).

In some embodiments, the electrode balloon comprises a proximal electrode and a distal electrode configured to be individually actuatable and configured to be used in a stimulation mode, ablation mode, and/or sensing mode. The proximal electrode and distal electrode may be positioned in two different branches (e.g., the proximal electrode in the proper hepatic artery and the distal electrode in the gastroduodenal artery). The electrode balloon may be deployed from a guide catheter positioned in the common hepatic artery. In one embodiment, the proximal electrode is stimulated and the distal electrode is sensed and if the correct territory is identified (e.g., nerve fibers emanating to the proper hepatic artery but not the gastroduodenal artery), then the proximal electrode may be activated for ablation. The electrode balloon may be used to map and selectively ablate or otherwise treat various vessel portions.

In some embodiments, a round electrode balloon may be used to selectively ablate only a select area. In some embodiments, the round electrode balloon has approximately the same electrode properties as described above, including electrode density, and the presence of at least one ablation electrode. In some embodiments, the round electrode balloon comprises at least one sensor electrode or temperature-measurement device (e.g., thermocouple).

In some embodiments, a dielectric ablating balloon is used. The dielectric ablating balloon may have the same shape characteristics as do the other electrode balloon embodiments described herein. In some embodiments, the dielectric ablating balloon comprises at least one piece of a high conductivity material on its outer surface. In some embodiments, use of the dielectric ablating balloon comprises advancing the dielectric ablating balloon into position in the target vessel through methods described herein and inflating the dielectric ablating balloon so that its outer surface is proximate to the intimal walls of the target vessel. In some embodiments, a microwave generator is then placed near the surface of the body of the subject and microwaves are directed from the microwave generator toward the dielectric ablating balloon within the subject such that the microwaves interact with the at least one piece of a high conductivity material to create heat in a manner such that the heat created thermally ablates the region (e.g., vessel wall surface) proximate to the at least one high conductivity material. In some embodiments, the dielectric ablating balloon comprises a plurality of (e.g., two, three, four or more than four) pieces or portions of high conductivity material on its outer surface.

Figure 12A:
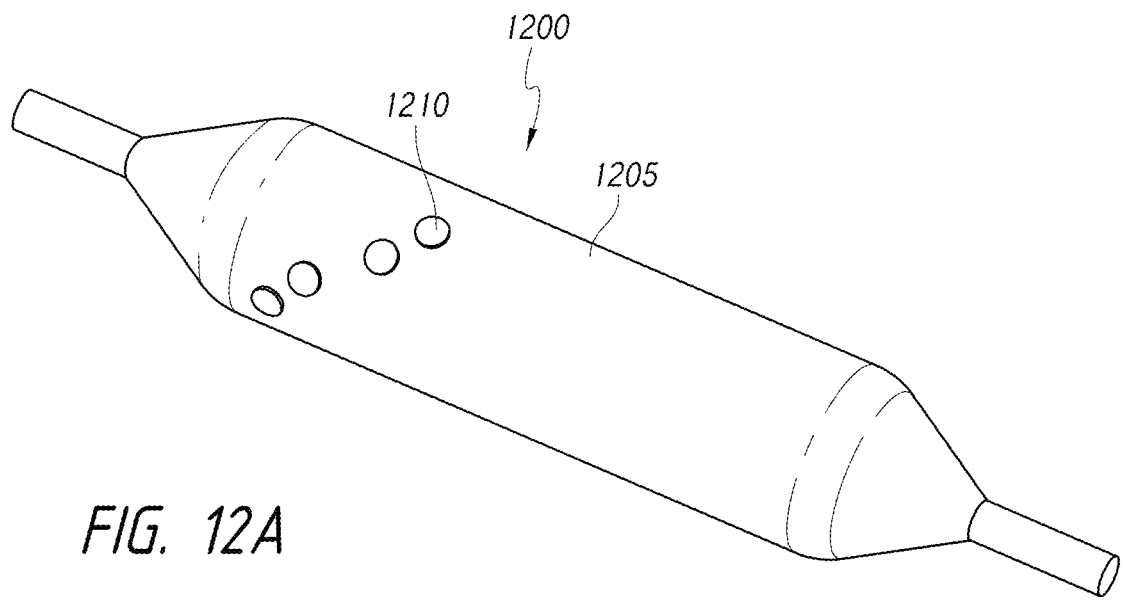

FIG. 12A illustrates a schematic representation of an embodiment of a radiofrequency energy delivery device 1200 comprising a balloon 1205. The balloon 1205 is adapted to be partially or substantially occlusive and comprises multiple electrodes 1210 positioned at one or more locations along the outer surface of the balloon 1205. The balloon 1205 may be sized to cover the entire length of the vessel (e.g., common hepatic artery) to be treated (e.g., ablated or denervated) or may be shorter in order to treat a portion of the vessel. In one embodiment, the balloon 1205 is 5 mm in diameter by 20 mm long; however other balloons may range from 3 mm to 8 mm (e.g., 3 mm, 3.5 mm, 4 mm, 4.5 mm, 5 mm, 5.5 mm, 6 mm, 6.5 mm, 7 mm, 7.5 mm, 8 mm) in diameter and from 10 mm to 40 mm (e.g., from 10 mm to 20 mm, from 15 mm to 25 mm, from 20 mm to 30 mm, from 25 mm to 35 mm, from 30 mm to 40 mm) in length as desired or required based on vessel length. The electrode area may range from 1 $mm^2$ to 6 $mm^2$ (e.g., from 1 $mm^2$ to 3 $mm^2$, from 2 $mm^2$ to 4 $mm^2$, from 3 $mm^2$ to 6 $mm^2$). The electrodes 1210 may be comprised of a single electrode element or member or may be comprised of one or more arrays of a plurality of separate electrode elements (e.g., clusters or groups of four electrodes). For example, at least one array of electrode elements may be proximate an area of tissue in thermal communication such that RF power delivered via the electrodes 1210 acts to heat a substantially continuous volume of tissue. The electrodes 1210 may be from 0.5 mm to 3 mm in diameter (e.g., from 0.5 mm to 1 mm, from 1 mm to 1.5 mm, from 1.5 mm to 2 mm, from 2 mm to 2.5 mm, from 2.5 mm to 3 mm, overlapping ranges thereof, or any value of or within the recited ranges). The at least one array of electrodes may be linear, zig zag, curved, rectangular, polygonal, or circular. Other shapes and patterns may also be used as desired or required. The size of the electrode array may be from 0.1 mm to 3 mm (e.g., from 0.1 mm to 0.5 mm, from 0.3 mm to 1 mm, from 0.5 mm to 1.5 mm, from 0.8 mm to 2 mm, from 1 mm to 3 mm, from 1.5 mm to 3 mm, overlapping ranges thereof, or any value of or within the recited ranges) in its narrowest aspect and from 1 mm to 5 mm (from 1 mm to 3 mm, from 2 mm to 4 mm, from 3 mm to 5 mm, overlapping ranges thereof, or any value of or within the recited ranges) in its longer aspect. In some embodiments the electrode array may be from 10 mm to 20 mm in its longest aspect. The individual electrodes 1210 comprising the array may be from 0.1 mm to 2 mm (e.g., from 0.1 mm to 0.5 mm, from 0.3 mm to 1 mm, from 0.5 mm to 1.5 mm, from 0.8 mm to 2 mm, overlapping ranges thereof, or any value of or within the recited ranges) in their narrowest aspect and from 0.5 mm to 5 mm (e.g., from 0.5 mm to 2.5 mm, from 2 mm to 4 mm, from 3 mm to 5 mm, overlapping ranges thereof, or any value of or within the recited ranges) in their longest aspect. In some embodiments the longest aspect of the electrode elements may be from 5 mm to 20 mm. In some embodiments, 0.5 W-3 W (e.g., 0.5 W, 1 W, 1.5 W, 2 W, 2.5 W, 3 W) of RF power may be delivered though the electrode or electrodes.

Figure 12B:
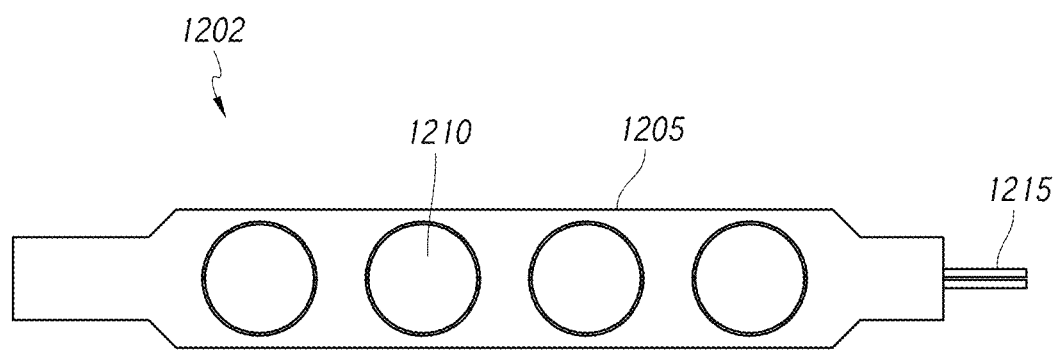
Figure 12C:
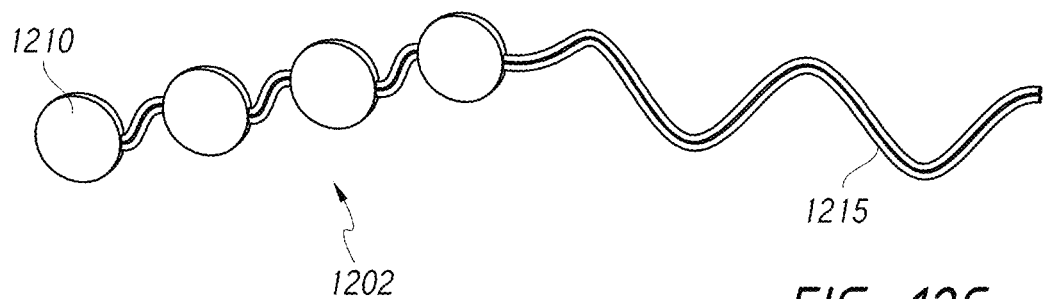

In various embodiments, electrodes or arrays may be affixed to the balloon 1205 along with one or more connecting wires 1215. Two embodiments of electrode arrays with connecting wires are illustrated in FIGS. 12B and 12C. In accordance with various embodiments, the connecting wires 1215 supply RF current to the electrode(s) 1210. In some embodiments, the connecting wires 1215 carry a signal for measuring the temperature. In some embodiments, the connecting wires 1215 carry both RF current for ablation or other treatment and signals to measure temperature. In some embodiments, the connecting wires 1215 form a thermocouple (e.g. bifilar thermocouple). The balloon 1205 may consist of two, three, four, five, six or more than six electrode arrays. Each array may consist of two, three, four, five, six, seven, eight or more than eight electrodes.

Figures 1, 12D:
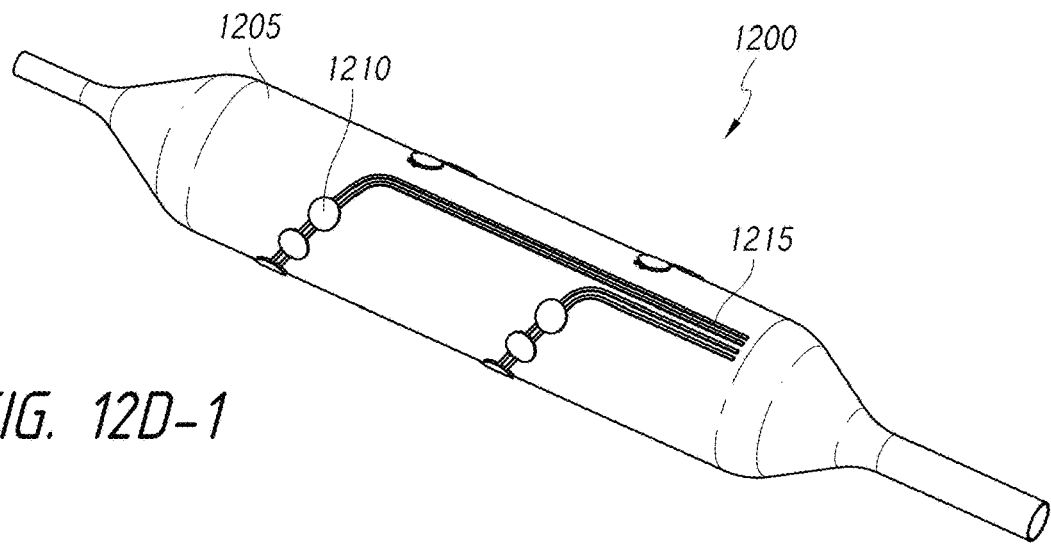

In some embodiments, the electrodes 1210 together with their one or more connecting wires 1215 are affixed to the balloon with adhesives such as epoxy, cyanoacrylate, silicone, acrylic, polyamide, polyurethane, pressure sensitive adhesive, and hot melt adhesives. In one embodiment, the entire balloon and electrode assembly, except for active electrode areas, may be encapsulated in a coating. In another embodiment, the coating covers only portions of the balloon and electrode assembly. FIG. 12B illustrates an embodiment of an electrode array 1202 comprising an adhesive body 1220 that is adapted to be adhered to the balloon 1205. In other embodiments, the electrodes may be attached directly to the balloon 1205. FIG. 12C illustrates an electrode array having a zig-zag arrangement with the connecting wires 1215 coupled between each individual electrode. The zig-zag arrangement may advantageously reduce the spacing between the electrodes and reduce the overall size or array occupied by the electrode array while maintaining a generally spiral pattern. In some embodiments, the electrodes of the electrode array are affixed to a flexible substrate. In some embodiments, the electrodes, connecting wires and flexible substrate together comprise a flex circuit. FIG. 12D illustrates an embodiment of a balloon catheter 1200 having a plurality of electrode arrays 1202 comprising electrodes 1210 and connecting wires 1215 arranged in a spiral pattern around the outer surface of the balloon 1205. The connecting wires 1215 may be coupled to a source of RF power or energy (such as a generator). Each electrode array or group of electrodes may have separate connecting wires such that each electrode array or group is individually controllable by an RF power source.

In accordance with several embodiments, a balloon of a balloon electrode catheter includes at least one group of diagonally or circumferentially oriented electrodes formed of a plurality of electrode elements connected in parallel, where the size of the electrode group in its longest aspect is less than or equal to a characteristic length of thermal conduction or diffusion in tissue. Larger lesions require more power, therefore greater electrode surface area is required to keep current density within acceptable levels (for example, >3 mm$^2$). However, large electrodes (for example, >1.5 mm in a largest aspect) degrade flexibility, trackability and foldability of balloons. Circumferential or diagonal orientation of electrodes may further interfere with balloon folding; however, the electrodes may be positioned so as to be arranged around folds. In accordance with several embodiments, closely-spaced electrode arrays as illustrated and described in connection with FIGS. 12A-12C create locally inhomogeneous current density near the electrodes (e.g., near field) and current density evens out at farther distances from the electrode (e.g., far field). In addition, thermal conduction within the tissue tends to even out temperature within the near field. When electrodes are closely spaced and the length of the electrode is not too long, current density distribution over the electrode surface is predictable and a single temperature measurement can represent the temperature of the entire electrode. For example, temperature may still vary, but in a predictable fashion. In accordance with several embodiments, "closely-spaced" means that the total electrode area is in a region that is no more than 6 mm in its longest aspect.

Figures 2, 12D:
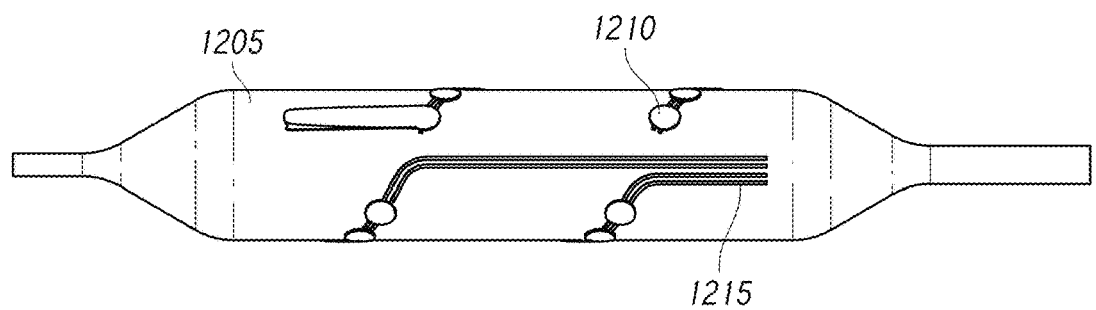
Figure 12E:
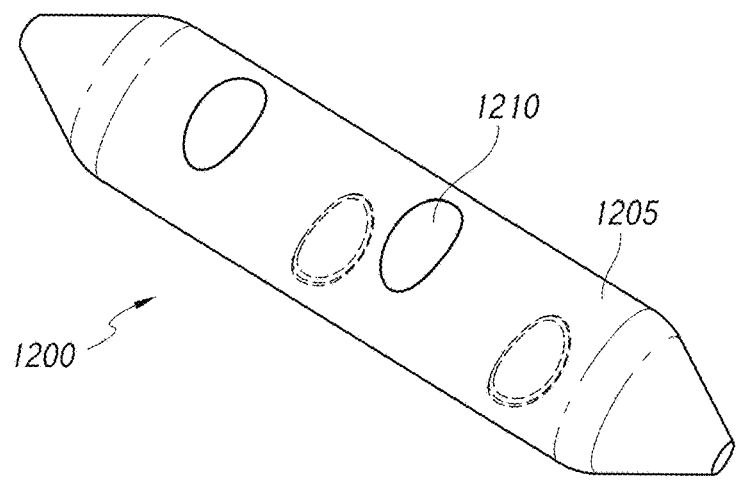

FIG. 12E illustrates an embodiment of a balloon 1205 of a balloon catheter 1200 comprising four individual electrode members offset by 180 degrees from each other and spaced apart longitudinally along the surface of the balloon 1205 so as to provide a desired ablation or treatment pattern designed to provide increased perivascular treatment while reducing vessel wall injury or damage. In some embodiments, the electrodes 1205 exhibit a circumferential aspect ratio. In some embodiments, the array of electrodes is oriented in a diagonal direction with respect to the axis of the artery or other body lumen, thereby increasing the circumferential extent of the lesion while avoiding interference between the electrodes 1210 when the balloon 1205 is in a collapsed, deflated configuration. Greater frequency and extent of ablated tissue increases the degree of neuromodulation or other tissue modulation (e.g., ablation, denervation). The degree of circumferential orientation to the electrode of an electrode array is reflected by the shape of the lesion created by the heating generated by the electrode. Staggered, oblique lesions can advantageously be packed tightly (for example, spaced apart by between 2 mm and 8 mm, e.g., 2 mm, 3 mm, 4 mm, 5 mm, 6 mm, 7 mm, 8 mm) along the vessel to increase the circumferential coverage of the lesion without overlapping lesions.

The electrodes of the balloon catheters (e.g., balloon catheters 1200) may be circular, rectangular or oblong. In some embodiments, the electrodes may be disk shaped. In one embodiment, the electrodes may be comprised of metals selected from a list including, without limitation, gold, platinum, stainless steel, layered composites of gold or platinum, gold or platinum plated base metals such as copper, stainless steel, nickel. In some embodiments, the connecting wires 1215 are continuous with the electrode(s) 1210. In other embodiments, the connecting wires 1215 may be attached to the electrode(s) 1210 by means such as welding, soldering, crimping, or swaging.

In some embodiments, the balloon material is of a low compliance material selected from a list of materials comprising, without limitation: PET, polyester, polyolefin, nylon, high durometer polyurethane and polyether block amide. In some embodiments, the balloon material is comprised of a compliant material such as low durometer polyurethane, kraton, latex, silicone, and/or thermoplastic elastomer.

In some embodiments, lower power and longer duration ablations are used for ablation procedures involving occlusion within the hepatic arteries than for ablation procedures in other arteries, such as the renal arteries. Such treatment may be uniquely possible because of the liver's dual source blood supply (as described above). Balloon ablation of the hepatic vessels (e.g., common hepatic artery) may employ full occlusion for a substantial period of time, not previously possible or not previously attempted in other locations for safety reasons (e.g., to avoid potential stroke due to ischemia). In some embodiments, balloons may be inflated and used for ablation in the range of about 1 to about 10 minutes, about 10 minutes to about 20 minutes, about 20 minutes to about 60 minutes, about 15 minutes to about 45 minutes, about 10 minutes to about 40 minutes, about 15 minutes, about 20 minutes, about 25 minutes, about 30 minutes, about 35 minutes, about 40 minutes, about 45 minutes, about 50 minutes, about 55 minutes, about 60 minutes. Longer ablation times may have several advantages in accordance with several embodiments. First, longer exposure times mean that lower treatment temperatures may be used because tissue and nerve death is a function of both temperature and time. In some embodiments, temperatures are used in the ranges of about 30° C. to about 80° C., about 40° C. to about 70° C., or about 50° C. to about 60° C. In one embodiment, temperatures greater than 45° C. and less than 60° C. are used.

In some embodiments, the vessel (e.g., arterial) lumen is simultaneously protected by infusing a low temperature coolant through the balloon cavity (thereby keeping the intima cool) while focusing RF energy and thermal heating at the level of the adventitia or perivascular space (where the target nerves are located). Second, balloon occlusion may facilitate improved contact and contact pressure between the electrodes disposed on the outside of the balloon and the arterial wall. Third, balloon occlusion may compress the tissues of the vessel wall and thereby reduce the distance from the electrode(s) to the target nerves, which improves the efficiency of thermal energy delivery to the target nerves. Fourth, less contrast/imaging agent may be required by using a balloon catheter because an occluding device is reliably and accurately positioned (and maintains that position once in place), and serves as a reliable marker of device and therapy placement. Additionally, when a balloon engages the vascular wall, heating of the blood is avoided entirely (because energy is transferred directly from the electrode(s) to the vessel wall without directly contacting the blood), thereby reducing the risk of vapor bubble formation or thrombosis (e.g., clot formation).

Figure 13A:
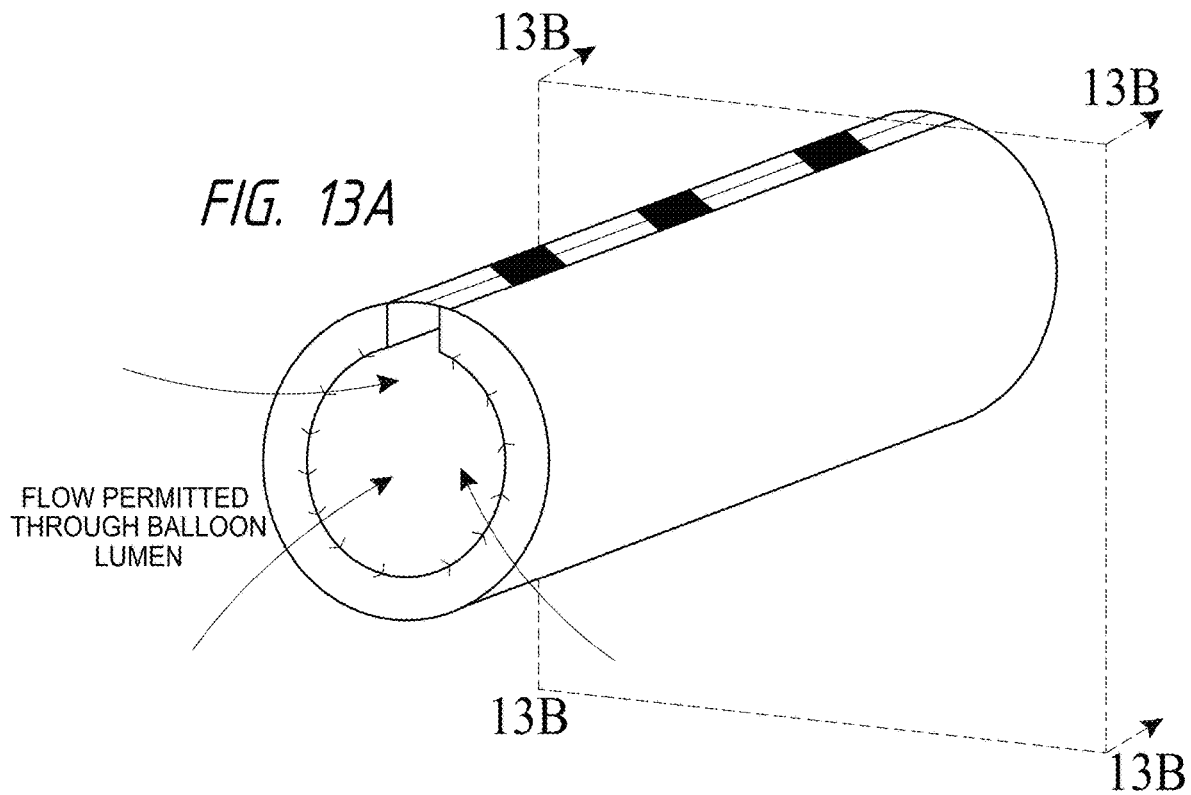
Figure 13B:
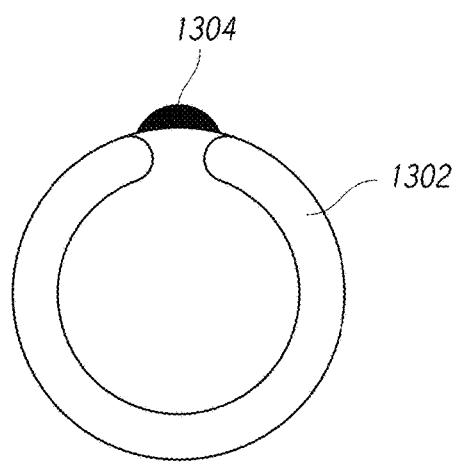

An embodiment of a balloon catheter is illustrated in FIGS. 13A and 13B. The balloon catheter may advantageously be configured to provide flow to cool one or more electrodes without having or without requiring the electrode(s) in contact with blood. In some embodiments, the balloon is a c-shaped balloon as shown in FIGS. 13A and 13B, having an inflatable region 1302 about a substantial portion of the balloon circumference and a small non-inflatable region 1304 (e.g., "webbed region") comprising less than $1/18$ (or alternatively, less than $1/10$, less than $1/12$, less than $1/14$, less than $1/16$, less than $1/20$, less than $1/22$, less than $1/24$, less than $1/25$) of the total circumference of the balloon in order for the balloon to maintain a substantially circular shape upon inflation. A plurality of electrodes may be disposed along the longitudinal axis of the balloon on the non-inflatable webbed region, configured to deliver RF energy to the hepatic artery or other target vessel or tissue. The c-shaped balloon of the design illustrated in FIG. 13 defines a lumen upon inflation that may permit the flow of blood therethrough. In one embodiment, a thin membrane of the webbed region provides electrical isolation to ensure that the applied RF energy is delivered substantially to the target tissue (and hence to the nerves surrounding the hepatic artery or other target vessel or tissue) and not lost to the blood. In one embodiment, the balloon design illustrated in FIGS. 13A and 13B advantageously provides the ability for the blood to cool the electrode by means of the limited thermal insulation offered by the thin membrane of the webbed region, thereby increasing the effective power that can be delivered to the target tissue.

Figure 14:
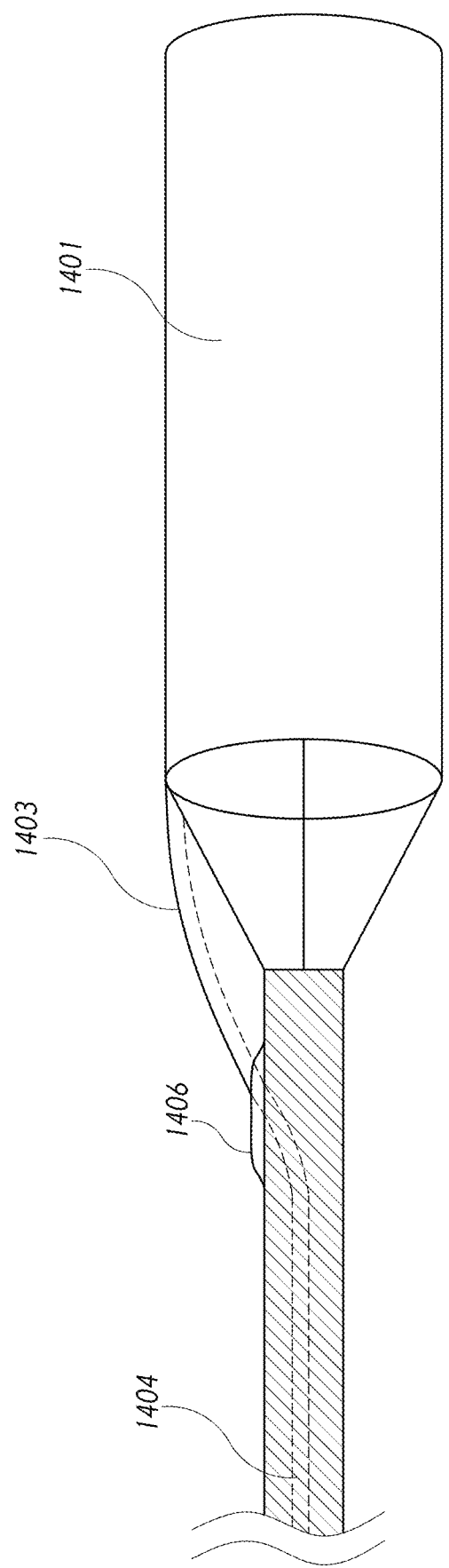

FIG. 14 illustrates how the c-shaped balloon electrode design of FIGS. 13A and 13B could be attached to an interventional catheter. In one embodiment, the inflatable region 1402 of the c-shaped balloon is in fluidic communication with an inflation manifold 1403, which may be disposed proximally toward a shaft of the interventional catheter. The inflation manifold 1403 can define a lumen 1404 terminating in a flange 1406 configured for attachment to the catheter. The flange 1406 of the inflation manifold 1403 may be adhered to a side-exiting lumen disposed along a portion of or substantially the entire length of the catheter using suitable adhesion means (e.g., UV cured adhesives, RF welding, adhesives, heat sealing), thereby permitting fluidic communication between the catheter lumen and the inflatable region of the c-shaped balloon 1401. In order to structurally attach the c-shaped balloon 1401 to the catheter, a plurality of struts may be provided. In one embodiment, the struts are formed of a resilient material such as nitinol and biased towards a position that would tend to expand the balloon into a cylindrical shape. The struts may be joined to the catheter and c-shaped balloon using any suitable means. In one embodiment, the struts are overmolded into the catheter and glued to the balloon 1401.

An exemplary method for fabricating the c-shaped balloon and electrode is highlighted in FIGS. 15A-15C. The balloon may be fabricated using two pieces of flat or substantially flat stock material (e.g., polyurethane sheet of about 0.003" in thickness). The two layers may be bonded using suitable techniques in the regions illustrated (e.g., RF welding, adhesives, heat sealing, etc.), and then rolled and sealed into a cylinder to form the non-inflatable webbed region. In one embodiment, the webbed region 1504 is formed using flexible electronics manufacturing techniques (e.g., "Flextronics"), where the electrode is laminated between two dielectric layers, such as polyimide. The Flextronics strip can then be adhered to each edge of the thin film balloon structure to form the cylindrical, c-shaped balloon.

Figure 16B:
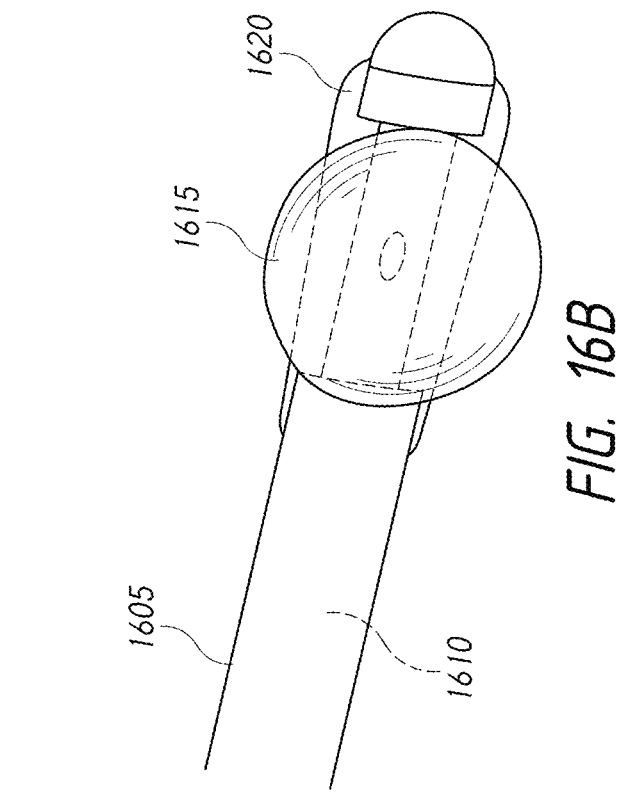
Figure 16A:
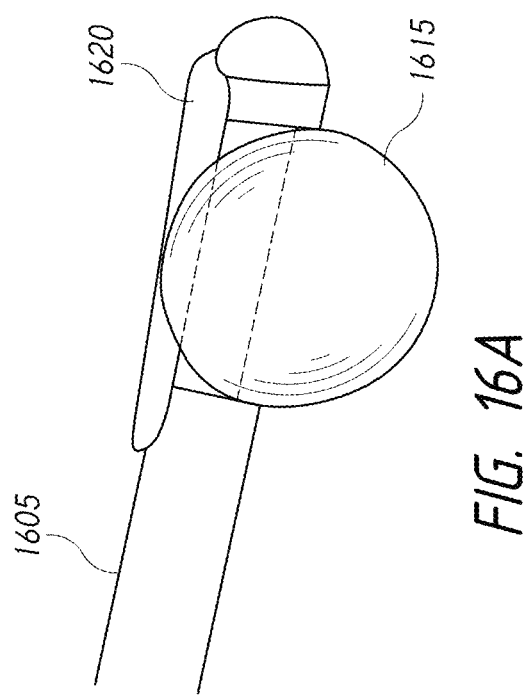

FIGS. 16A and 16B illustrate an embodiment of a balloon catheter 1600 configured to deliver RF energy. In one embodiment, the catheter is comprised of a polymeric shaft 1605 having a lumen 1610 disposed along a portion or substantially the entire length in communication at a proximal end portion with a pressure source (e.g., capable of creating between 0-600 mmHg within a balloon at a distal end of the catheter). In one embodiment, the lumen 1610 exits through a transverse surface of the shaft 1605 near the distal tip of the shaft 1605. As shown, a balloon 1615 is disposed about the lumen exit and a portion of the shaft. In various embodiments, the balloon 1615 is disposed about a substantial (e.g., greater than 30%, greater than 40%, greater than 50%, greater than 60%, about 40%, about 50%, about 60%, about 70%, about 80%, or about 90%, of the circumference of the shaft 1605.

In one embodiment, the balloon 1615 is disposed about the entire circumference of the shaft 1605 not covered by an electrode or other energy delivery member. In one embodiment, the balloon 1615 is expandable to a diameter of 1 mm to 8 mm (e.g., 1 mm to 5 mm, 1 mm to 4 mm, 2 mm to 5 mm, 3 mm to 8 mm, 1 mm to 6 mm, 4 mm to 8 mm, or overlapping ranges thereof) and is disposed about a length of 5 mm to 30 mm (e.g., 5 mm to 20 mm, 5 mm to 15 mm, 10 mm to 20 mm, 10 mm to 30 mm, 5 mm to 25 mm, 15 mm to 25 mm, 20 mm to 30 mm, or overlapping ranges thereof) along a distal portion of the shaft 1605. In one embodiment, substantially opposite the balloon 1615 an electrode (e.g., half-cylindrical electrode) or other energy delivery member 1620 is bonded or otherwise affixed to the shaft and in electrical communication with a wire (e.g., thermocouple wire) through either the lumen or routed along an exterior surface of the catheter 1600, which is connected to an RF generator and a thermocouple (e.g., type T thermocouple)

reading circuit to permit the delivery of RF energy and assessment of electrode or tissue temperature. In one embodiment, the electrode 1620 is positioned within 1 cm of the distal tip of the catheter 1600. The electrode 1620 is advantageously flush or substantially flush with the catheter surface, in one embodiment.

Figure 17B:
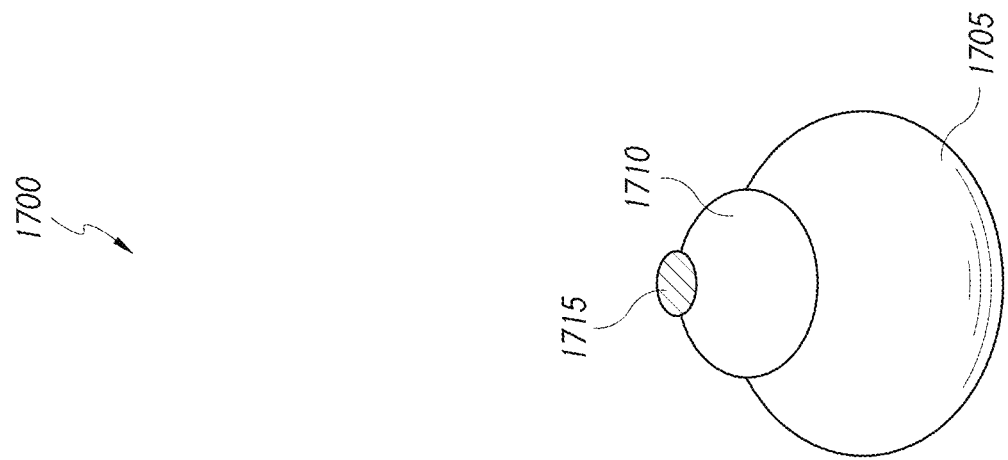
Figure 17A:
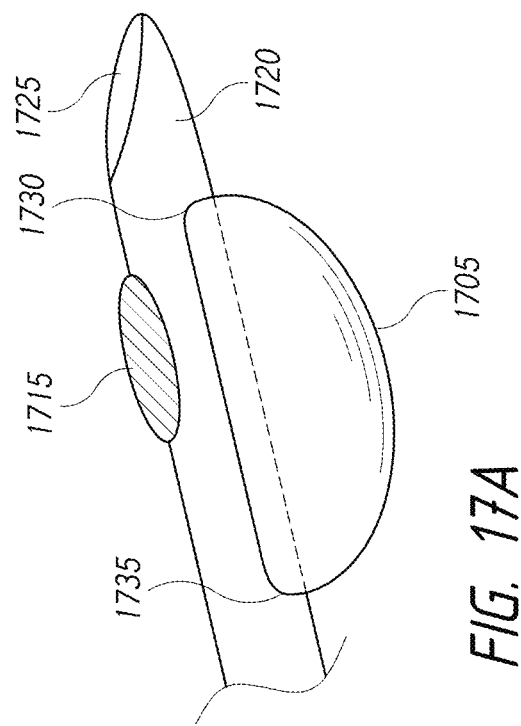

FIGS. 17A and 17B illustrate another arrangement of the balloon catheter of FIGS. 13A and 13B. In one embodiment, an energy delivery catheter 1700 includes a perfusion balloon 1705 enabling occlusion of a vessel lumen and redirection of the blood flow through a perfusion lumen 1710. The perfusion lumen 1710 provides a constant diameter flow pathway which directs the blood flow over an exposed electrode surface within the perfusion lumen 1710, thereby allowing for a more predictable cooling effect. The catheter embodiments described herein may be used in conjunction with an over-the-wire, rapid exchange or steerable catheter approach.

At the distal end of the catheter 1700, an atraumatic, flexible tip 1720 is incorporated on or adjacent to a distal opening 1725 of the perfusion lumen 1710. In one embodiment, proximal to the distal tip 1720 is a balloon attachment region 1730, where the perfusion balloon 1705 is attached to the perfusion lumen 1710. The balloon attachment region 1730 may advantageously be optimized to provide a smooth flexibility transition. In various embodiments, the perfusion balloon 1705 is attached by adhesive or thermal joining or bonding methods and materials. The balloon attachment region 1730 may encompass the full or partial circumference of the perfusion lumen 1710 and/or guide wire lumen. The balloon material may be a compliant or non-compliant type. The balloon 1705 can be made of a single material or incorporate layers of different materials or grades of the same material. Similarly, the balloon 1705 can be formed of a polymer blend.

The shape of the balloon 1705 may be tapered or non-concentric. Cross sectional shapes may range from round to crescent shaped. In accordance with several embodiments, the balloon 1705 is formed and attached to the perfusion lumen 1710 such that it occludes the natural vessel lumen and maintains electrode contact with the vessel wall. The balloon diameter in the expanded state can range from about 2 mm to about 10 mm, (e.g., from 2 mm to 8 mm, from 3 mm to 6 mm, from 4 mm to 10 mm, and overlapping ranges thereof).

In some embodiments, at least one electrode 1715 resides within the length of the perfusion lumen 1710. The electrode 1715 may be placed or positioned such that the exterior side of the electrode 1715 is able to contact the vessel wall and the internal side (e.g., the side exposed within the perfusion lumen 1710) is flush or within the lumen formed by the internal diameter of the perfusion lumen 1710. The one or more electrodes 1715 are connected via conductive wires to an external energy source, such as an RF generator. The electrodes 1715 may be individually controlled or jointly controlled to deliver energy independently or simultaneously at the same or different levels.

Proximal to the electrode location is a second balloon attachment point or region 1735. Materials and joining methods may advantageously be selected to optimize the flexibility transition. Cross-sectionally at the attachment point or region 1735, the balloon 1705, the perfusion lumen 1710, an inflation lumen, a guide wire lumen, and/or conductive wires are contained. Proximal to the second balloon attachment point or region 1735 is a perfusion lumen exit or opening (not shown). The length of the perfusion lumen 1710 can range from about 5 mm to about 80 mm (e.g., 5 mm to 40 mm, 10 mm to 50 mm, 20 mm to 60 mm, 30 mm to 80 mm, 5 mm to 20 mm, or overlapping ranges thereof). The balloon length may generally be shorter than the length of the perfusion lumen 1710. The perfusion lumen 1710 may be insulated from the electrode 1715 by an insulation layer to avoid direct contact of the electrode 1715 with the blood, as described in connection with FIGS. 90A and 90B.

Proximal or corresponding with the perfusion lumen proximal opening the catheter construction may be optimized for flexibility, torque and push force capability while maintaining a lumen or lumens for balloon inflation, guide wire containment, and/or conductive wire pathways.

In some embodiments, a handle or manifold (not shown) is located proximally on the shaft that enables conductive wire connections to the energy source (e.g., RF generator), attachment to a balloon inflation device, and/or access to a guide wire lumen and/or a mechanism to deflect the distal steerable segment.

In a rapid exchange embodiment, a guide wire port may be located 10 to 20 cm proximal of the distal tip. In one embodiment, the guide wire port is constructed to maintain a flexibility transition that is kink resistant while efficiently transferring push force to the distal assembly. Proximal to the guide wire port, the shaft maybe be constructed of a hypotube that is sheathed in polymer and includes an inflation lumen and protects the conductive wires.

In some embodiments, the shaft proximal to the proximal perfusion lumen opening comprises an inflation lumen, a lumen containing the shielded conductive wires, a guide wire lumen, a pull wire, and/or a polymer that encapsulates or sheaths the aforementioned lumens. The polymer encasement or sheath may be an extruded or deposition formed tube or a thermoplastic that has been reflowed to reduce profile. In some embodiments, the catheter is steerable and contains a pull wire assembly that can deflect the distal assembly, as described elsewhere in the disclosure.

Balloon ablation catheter systems may be advantageous for denervating nerves surrounding (e.g., within a wall of, such as within the intima, media or adventitia of) the hepatic artery branches in that the hepatic artery branches (e.g., common hepatic artery) can be occluded by one or more balloons and then coolant can be circulated in the region of the ablation (e.g., through a lumen of a balloon). In various embodiments, balloon ablation catheters advantageously facilitate both higher power net energy through larger electrode surface area (enabled, for example, by large electrode sizes that can be included on a balloon) and increased deposition time (which may be permitted by the ability to occlude flow to the hepatic artery for longer periods of time). In some embodiments, the risk of damage to the endothelial wall is mitigated by the flow of coolant even with an increase in energy density through higher power. Accordingly, higher power energy delivery (e.g., about 40 to 50% higher power) may be used than denervation systems used for denervation of other vessels or organs without risk of damage to the endothelial region of the hepatic artery due to maintained less than hyperthermic temperatures up to 1 mm from the lumen of the hepatic artery.

In some embodiments, an actively-cooled balloon catheter is used to ablate target vasculature. A pump sufficient to deliver high flow coolant to the cooling element may be used to facilitate the active cooling. In several embodiments, the range of drive pressures to deliver an appropriate flow rate (e.g., between about 100 and 500 mL/min) of coolant into a 4 to 6 Fr balloon catheter to maintain an appropriate temperature is between about 25 and about 150 psi. The flow rate may be adjusted on the basis of the actual temperature inside the balloon. In some embodiments, the desired coolant temperature in the balloon is between about 5° C. and about 10° C. In some embodiments, temperature-measurement devices (e.g., thermocouples) are included inside the balloon to constantly monitor the coolant temperature. The pump output may be increased or decreased based on the difference between the desired temperature and the actual temperature of the coolant.

Figure 18:
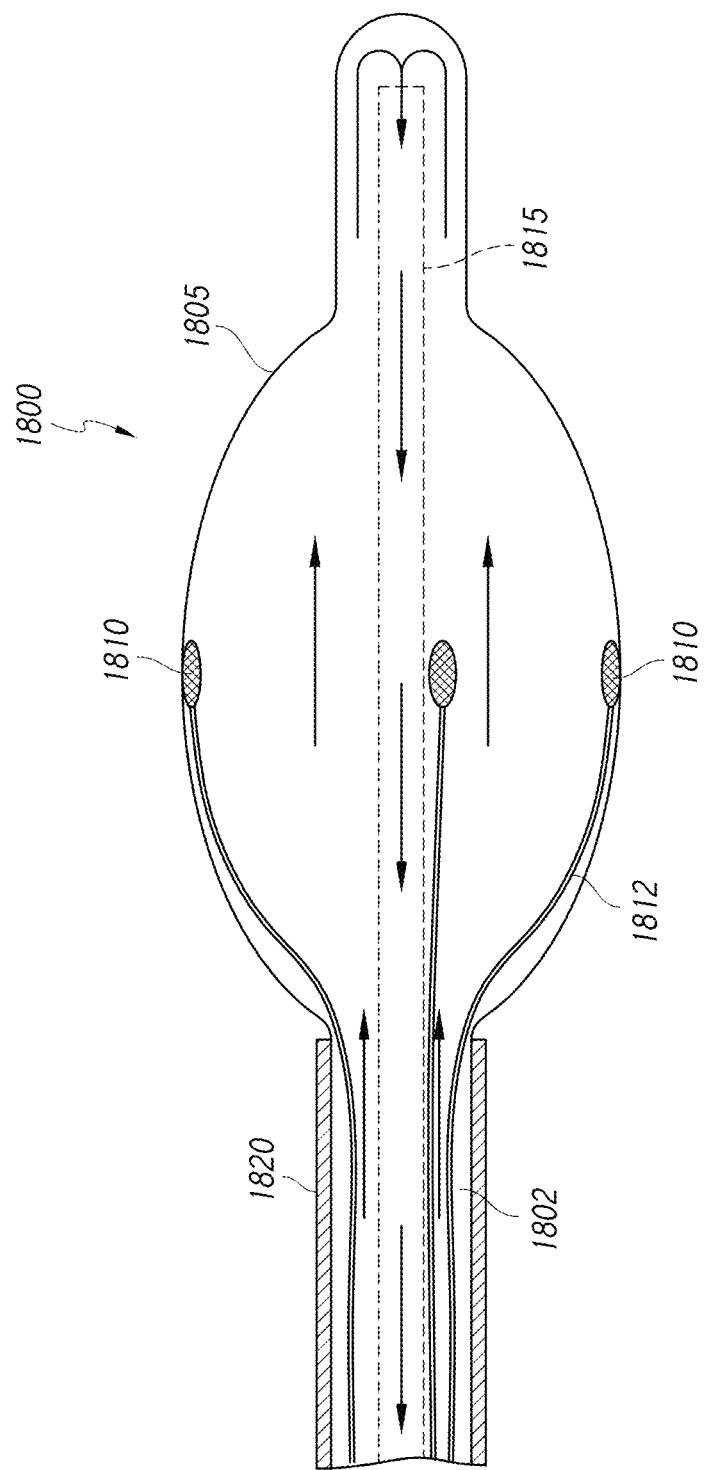

FIG. 18 illustrates an embodiment of an actively-cooled balloon catheter 1800. The balloon catheter comprises a main shaft 1802 having a lumen, a balloon 1805 coupled to a distal end of the main shaft 1802 and in fluid communication with the lumen, a plurality of electrodes 1810 disposed around the circumference of the balloon 1805, electrode leads 1812 coupled to the electrodes 1810 and extending to a proximal end of the main shaft 1802, and an outlet tube 1815. Nonconductive coolant solution may be pumped into an inlet of the balloon 1805 by a pump (not shown) and the nonconductive coolant solution may exit the balloon 1805 through the outlet tube 1815. The main shaft 1802 may comprise an insulating sheath or cover 1820 to prevent or inhibit heat transfer. The nonconductive coolant solution may advantageously provide cooling to the electrodes 1810 on the balloon 1805, while also shielding adjacent tissues from RF energy.

Figures 19A, 19B, 19C:
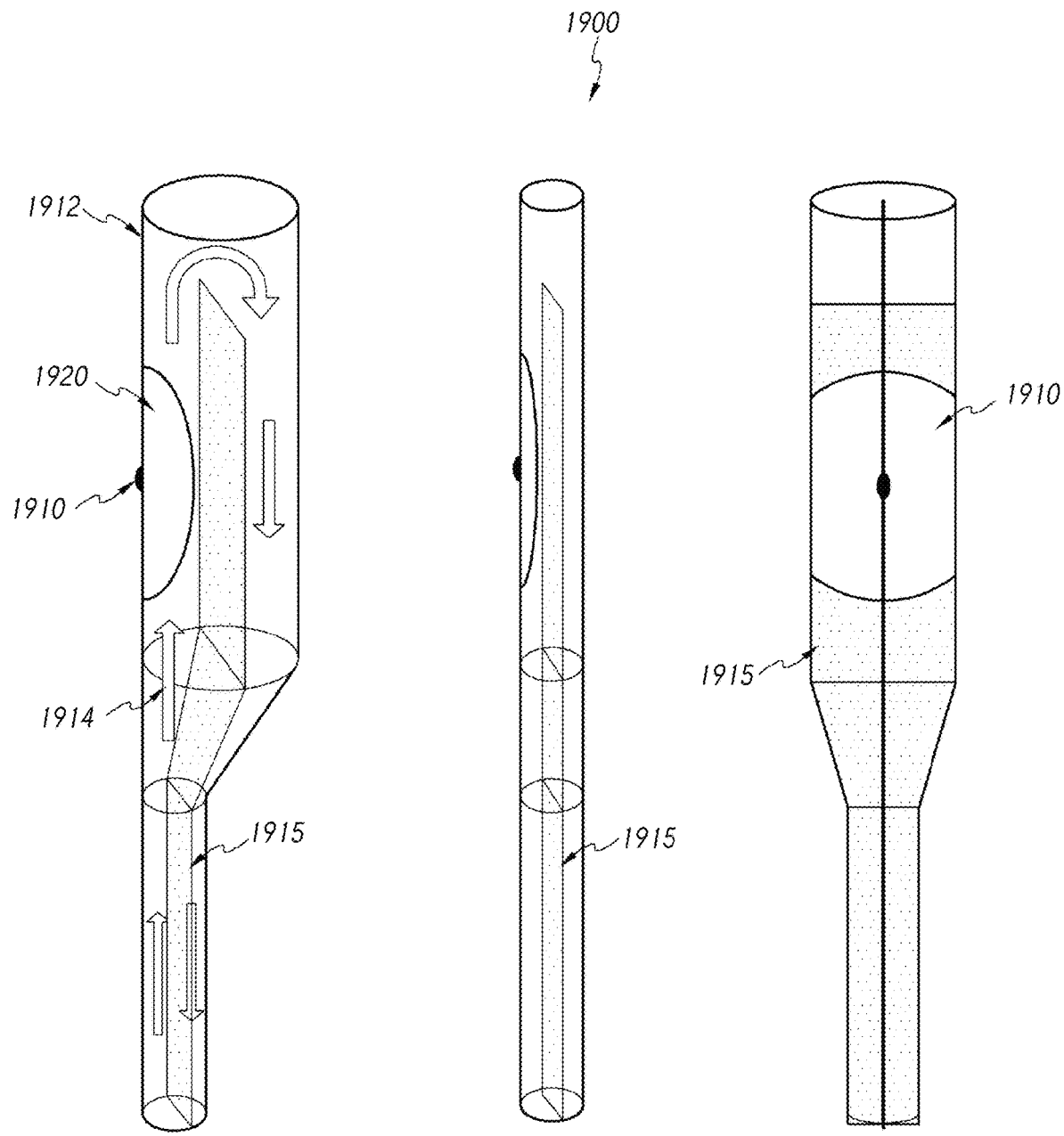

FIGS. 19A-19C illustrate a distal end portion of another embodiment of a balloon catheter 1900 configured to provide cooling to an electrode 1910 of the balloon catheter 1900. In the illustrated embodiment, the balloon catheter 1900 is a tube comprising a balloon 1912 that expands when infused with coolant, pulling taut an internal diaphragm 1915 which directs the flow 1914 (illustrated by arrows) of the coolant from at least one inlet to at least one outlet. A circular surface centered on the electrode 1910 may comprise a heat conducting surface 1920, while the rest of the catheter 1900 may comprise a heat-insulating material configured to prevent or inhibit warming of the coolant 1914 while traveling to a target ablation area. When the cooling balloon 1912 is infused with coolant, the balloon 1912 expands, thereby pressing the electrode 1910 and the cooling balloon 1912 against the vessel wall. In one embodiment, the coolant cools the vessel wall at the target ablation area, thereby preventing against or reducing the likelihood of excessive vessel wall damage.

In some embodiments, the neuromodulation catheter (e.g., ablation catheter) designs described herein advantageously provide effective modulation of nerves innervating branches of the hepatic artery or other vessel without causing, or at least minimizing endothelial damage, if desired. For example, the catheters described herein can occlude the hepatic artery (e.g., using a balloon) and then circulate coolant in the region of the ablation (e.g., within the lumen of the balloon). In some embodiments, the catheters provide the unique advantage of both higher power net energy offered through larger electrode surface area (which may be enabled by the larger electrode sizes that can be manufactured on a balloon) and increased deposition time (which may be permitted by the ability to occlude flow to the hepatic artery for longer periods of time). In accordance with several embodiments, the increase in energy density through higher power mitigates the risk of damage to the endothelial wall by the flow of coolant within the balloon.

Figure 20:
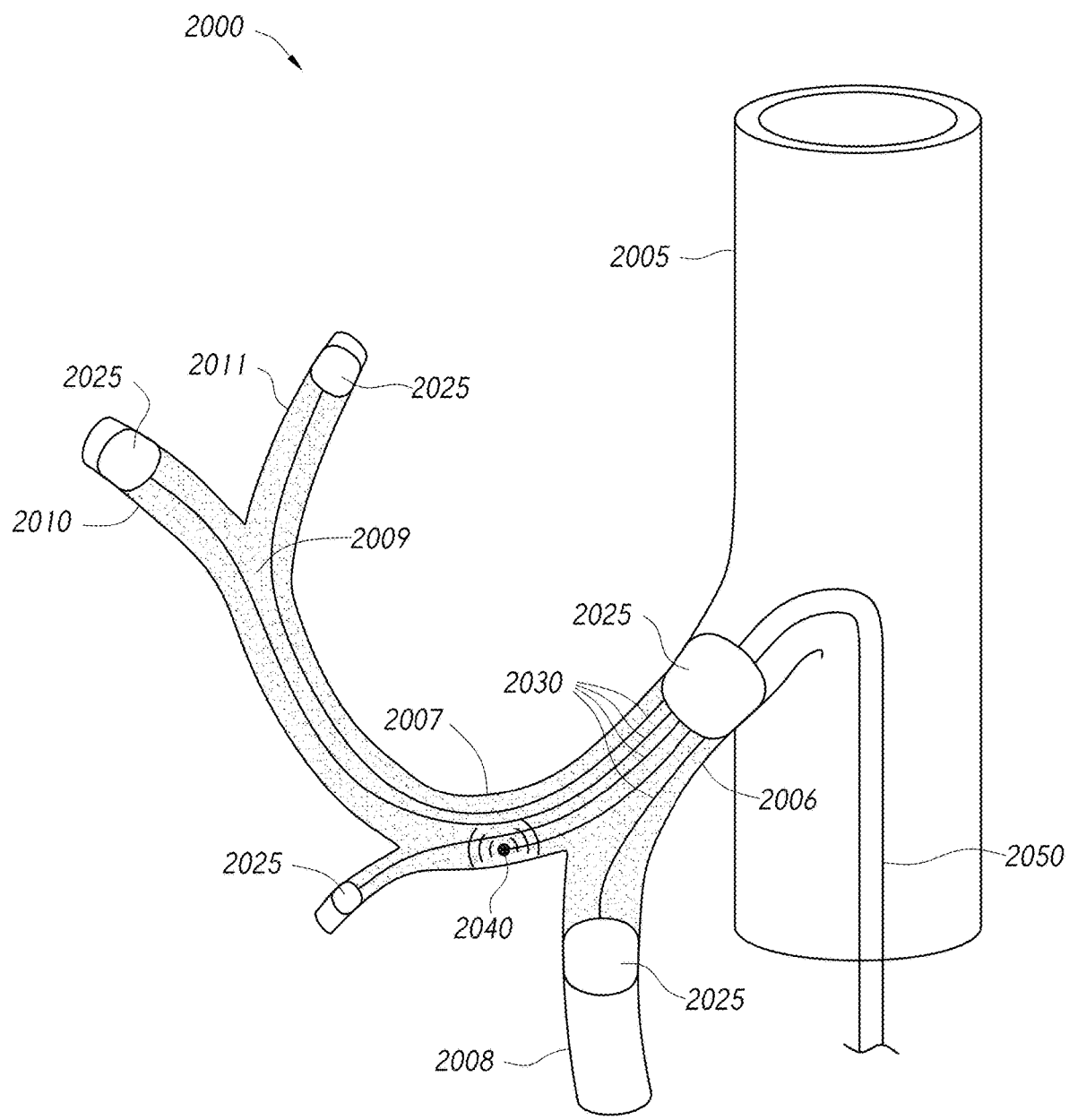
FIG. 20 illustrates an embodiment of a balloon-based volume ablation catheter system.

FIG. 20 is an embodiment of a balloon-based volume ablation system 2000, which can be used, for example, in the celiac, common hepatic, and proper hepatic arteries. In the illustrated embodiment, the balloon-based volume ablation system 2000 comprises a plurality of occlusive balloons 2025, a plurality of balloon guide wires 2030, a catheter 2050, and an electrode 2040. FIG. 20 also illustrates the abdominal aorta 2005, the celiac artery 2006, the common hepatic artery 2007, the splenic artery 2008, the proper hepatic artery 2009, the right hepatic artery 2010, and the left hepatic artery 2011 as an example of a target treatment site. In operation, the balloon-based volume ablation system 2000 may be inserted to the target treatment site through the abdominal aorta 2005 and into the celiac artery 2006. Individual occlusive balloons 2025 may then be advanced into subsequent vessels, such as the splenic artery 2008, the right hepatic artery 2010 and the left hepatic artery 2011. When the appropriate occlusive balloons 2025 have been placed such that they define the desired volume of vasculature to be ablated, the occlusive balloons 2025 may be inflated, thereby occluding the vessels in which they have been placed. In one embodiment, the target volume is then filled with saline and the electrode 2040 is activated to deliver electrical energy to heat the entire target volume simultaneously. The electrode 2040 may be configured to deliver sufficient energy to the target volume to ablate all or at least a portion of the nerves of the vessels within the target treatment site. Upon completion, the occlusive balloons 2025 may be deflated and the entire balloon-based volume ablation system 2000 may be retracted.

In some embodiments, it may be advantageous to simultaneously ablate a region of nerves innervating a portion of all, or a subset of all, arteries arising from the celiac artery (such as the left gastric artery, the splenic artery, the right gastric artery, the gastroduodenal artery, and the hepatic artery). In some embodiments, ablation is achieved by using balloon catheters or other occlusion members deployed from a guide catheter within the celiac artery or abdominal aorta to block off or occlude portions of vessels not to be ablated (the target volume may be adjusted by inflating balloons or placing occlusion members upstream and downstream of the desired volume, thereby creating a discrete volume), filling the target volume with saline solution through a guide catheter, and applying RF or other energy to the saline to thereby ablate the tissues surrounding the target volume in a manner that maintains vessel patency with hydraulic pressure while also providing for direct cooling of the endothelial surfaces of the vessels through circulation of chilled saline. In some embodiments, the described "saline electrode" system is used to pressurize the target arteries with saline. The contact pressure of the saline electrode system against the arterial walls can be assessed by measurement of the arterial diameter on angiography and utilizing the pre-defined relationship between arterial diameter and fluid pressure or by using one or more pressure sensors, which in one embodiment, are included as a component of the saline electrode system. The saline electrode system may advantageously facilitate omnidirectional delivery of energy.

In some embodiments, hypertonic (e.g., hyperosmolar) saline is used in the ablation of the target volume. Using hypertonic saline may cause "loading" of the endothelial cells with ions, effectively increasing their conductivity. The loading of the endothelial cells with ions may have one or more of the following effects: decreasing ion friction in the endothelial lining (and other cells affected along the osmosis gradient, such as those in the media); reducing the heat deposited in the endothelial cell locations; preventing or inhibiting significant thermal damage to the endothelial cells; and increasing current density as a result of the increased conductivity in the region near the electrode, which may advantageously increase the efficiency of heating deeper in the vessel wall where the target nerves may be located. In one embodiment, "loading" of the vessel reduces the impact of the bile duct and/or portal vein structures on an ablation profile shape.

Saline slug electrodes, such as the embodiment described in FIG. 20, can be configured to circulate chilled fluid with constant infusion to maintain constant temperature at a lumen surface. In some embodiments, the difference between the inlet and outlet coolant flow can be measured to gauge the amount of energy delivered. Because a saline slug is by definition conformable to any shape or size lumen, the use of multiple compliant balloons (which may lead to delamination of the electrodes mounted on the respective balloons, is not required to accommodate variations in lumen size of various blood vessels. In accordance with several embodiments, the saline electrodes described herein advantageously provide improved electrode contact independent of device design, function, or operator variability. In several embodiments, the saline slug electrode employs catheter designs that interventional cardiologists are familiar with using in practice on a daily basis (e.g., balloons), whereas only electrophysiologists may be comfortable and trained using "point electrode" ablation catheters.

In several embodiments, by precisely controlling the convective heat transfer coefficient (h) in saline slug electrode (or metal electrode) configurations (e.g., by precisely controlling flow rate within the slug region), energy delivery can be interrupted, and by measuring the thermal decay (time constant) at a point within the slug, the depth of ablation can be assessed, where a longer time constant generally corresponds to a larger depth of ablation.

Figure 21:
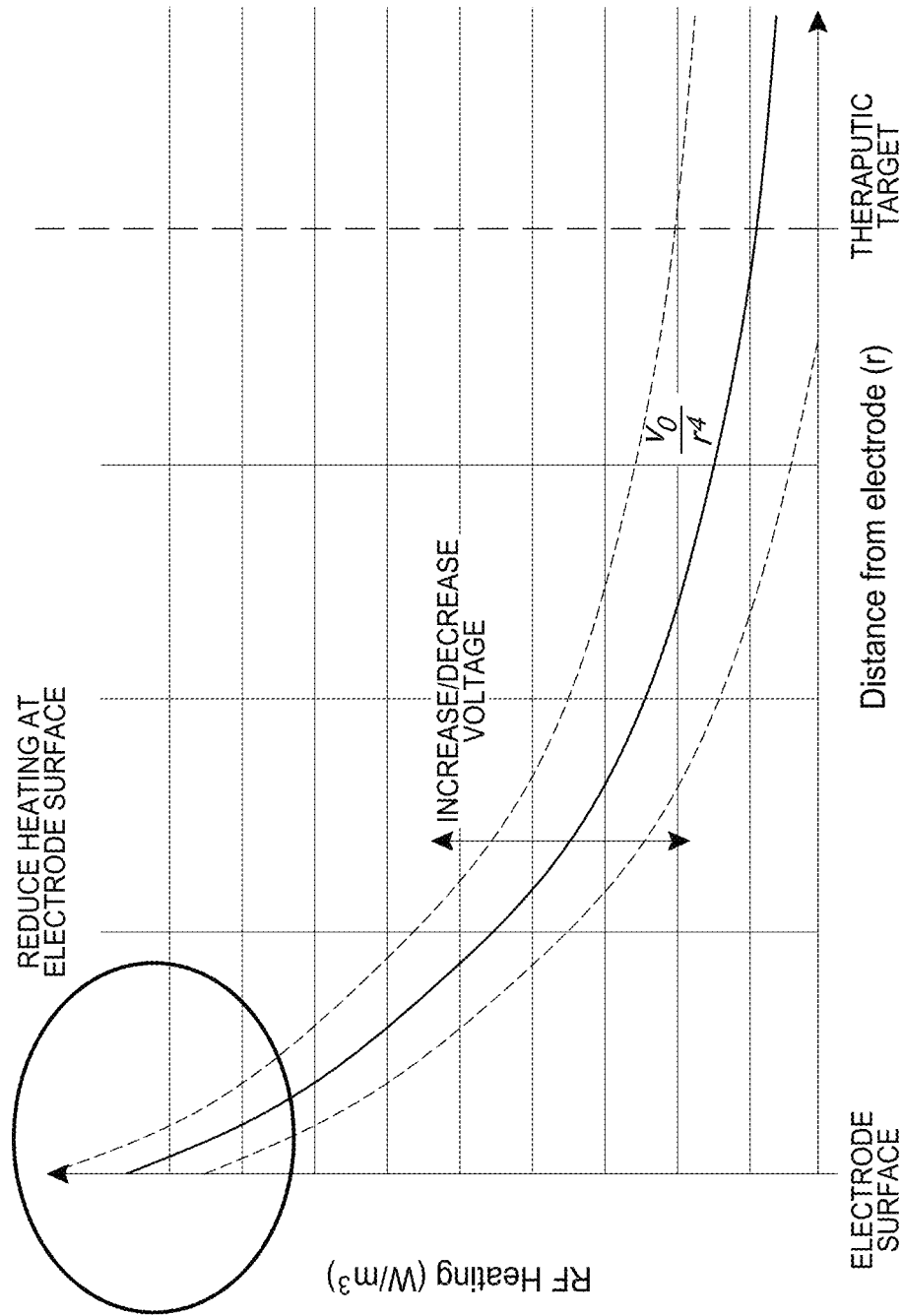
FIG. 21 illustrates a graph of RF heating versus distance from the electrode.

In accordance with several embodiments, electrode and vessel wall temperature are carefully monitored and controlled during vessel ablation. Depth of ablation may be monitored. In several embodiments, temperatures at the arterial wall are limited or reduced to avoid vessel spasm, thrombus formation, and stenosis. The ability to affect the convective cooling of the electrode and contacted tissue can be particularly advantageous in various embodiments. Electrode temperature can affect the depth of the lesion. In some embodiments, a main mechanism affecting electrode cooling is convective cooling from blood flow past the electrode and contacted vessel wall. Ablation of the renal artery has a flow rate of 550 mL/min. Flow through the common hepatic artery is ~100-200 mL/min (e.g., 150 mL/min), which is much slower than typical flow rates in renal arteries (~550 mL/min), where ablations have been performed with minimal or no electrode cooling. Because of the low and/or variable flow rate within the hepatic arteries, methods and systems aimed at increasing electrode cooling are provided herein. FIG. 21 illustrates an example of challenges of endovascular ablation given the reduced flow rates in the common hepatic artery. FIG. 21 illustrates a plot of the reduction in RF heating as the distance from the electrode surface increases. In some embodiments, reduced heating at the electrode surface requires a reduction in overall power, which can result in reduced heating at the therapeutic target (e.g., hepatic nerves, renal nerves or other peripheral nerves).

Figure 22A:
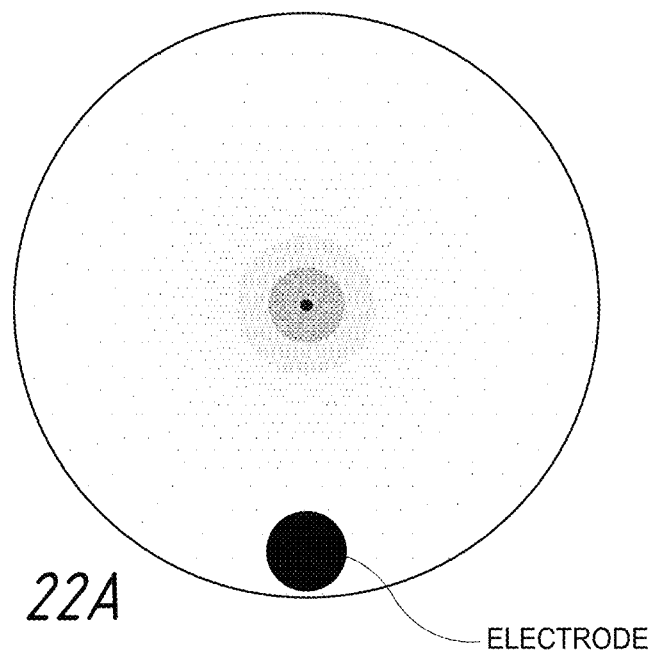
Figure 22B:
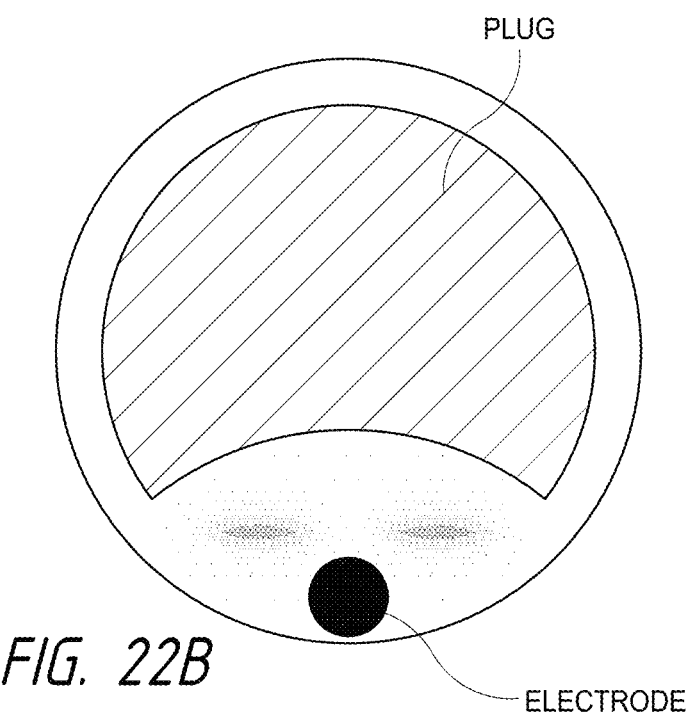
Figure 22C:
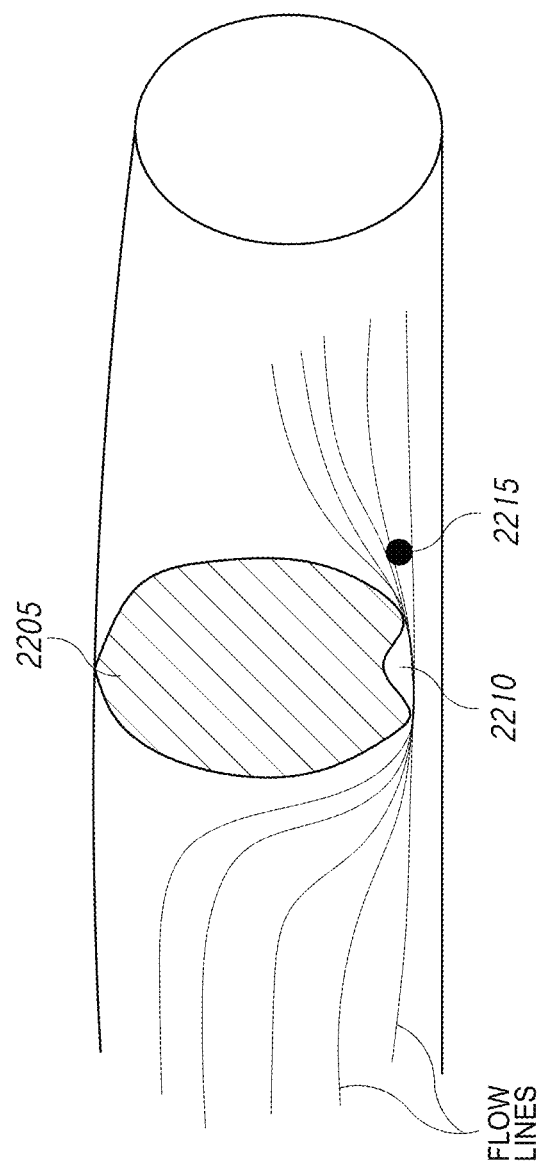

In one embodiment, the mass flow rate around the electrode and contacted tissue at the therapeutic target is increased, as illustrated, for example, in FIGS. 22A-22C. For example, by reducing the cross-sectional area around the electrode (e.g., by partially occluding a vessel using a plug or other obstruction or occlusion device), the average flow velocity increases and the peak velocity flow line is moved closer to the electrode and contacted tissue, as shown in the transverse cross-section in FIG. 22B and in FIG. 22C. The shading in FIGS. 22A and 22B illustrates fluid velocity—the darker the shading, the higher the flow velocity. As shown, by at least partially occluding flow, the blood flow adjacent to the electrode is increased over unobstructed or unoccluded flow. FIG. 22C illustrates a longitudinal cross-section view of an obstruction or occluding element 2205 within a blood vessel (e.g., hepatic artery). The obstruction or occluding element 2205 may have an opening or notch or indentation 2210 that is at least substantially aligned with an electrode 2215. The obstruction or occluding element 2205 with the aligned opening 2210 may cause flow line density downstream of the electrode 2215 to be more dense than upstream of the electrode 2215. The increased blood flow may result in increased cooling of the electrode 2215.

In one embodiment, the obstruction element (e.g., balloon) is effective to apply a reaction force as close to the electrode as possible (in a direction perpendicular to the surface defined by the contact of the electrode and the tissue surface, in one embodiment). In one embodiment, the balloon is disposed directly opposite the electrode. In order to limit motion of a balloon within the artery as an artifact of diaphragmatic motion, the balloon may be comprised of materials having higher coefficients of friction between the balloon and arterial components, such as endothelial tissue. In one embodiment, the balloon is comprised of silicone.

In various embodiments, the balloon is configured to occlude at least 50% of the arterial cross-sectional area. Suitable ranges may include 50-60%, 50-70%, 50-80%, 60-80%, and 70-90% occlusion, or overlapping ranges thereof. In some embodiments, the power required to reach a target electrode temperature is higher when the vessel lumen is substantially occluded compared to the unoccluded configuration, increasing the efficiency of energy delivery.

Figure 23A:
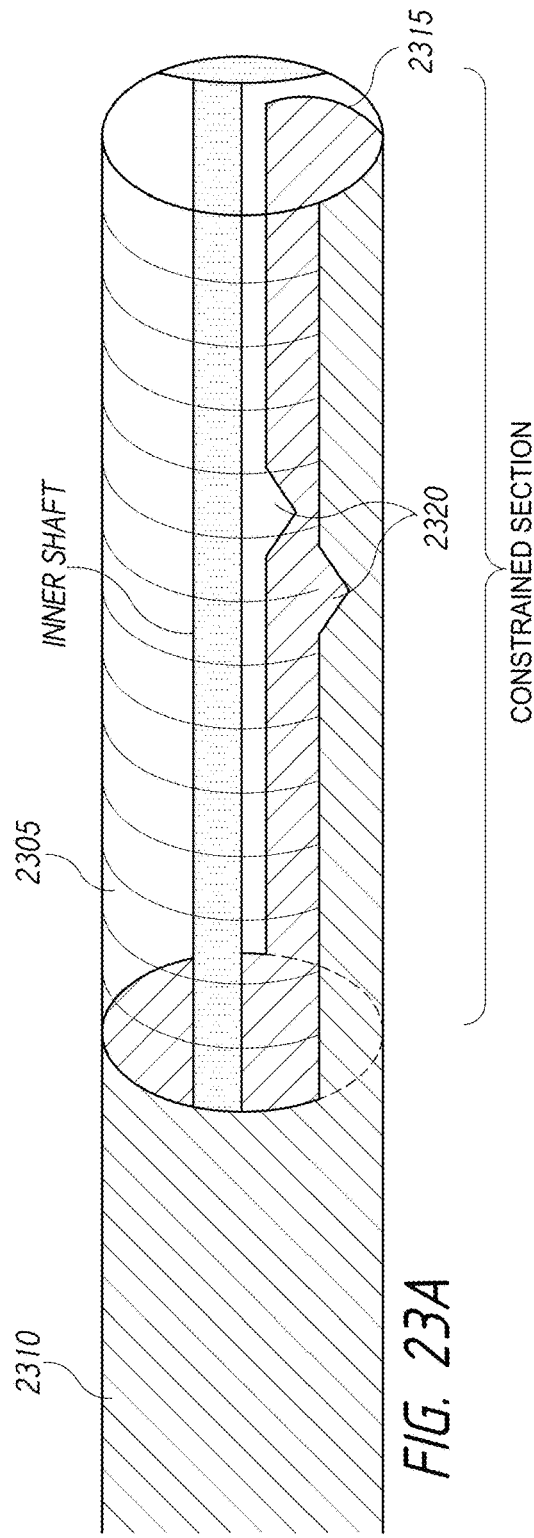
Figure 23C:
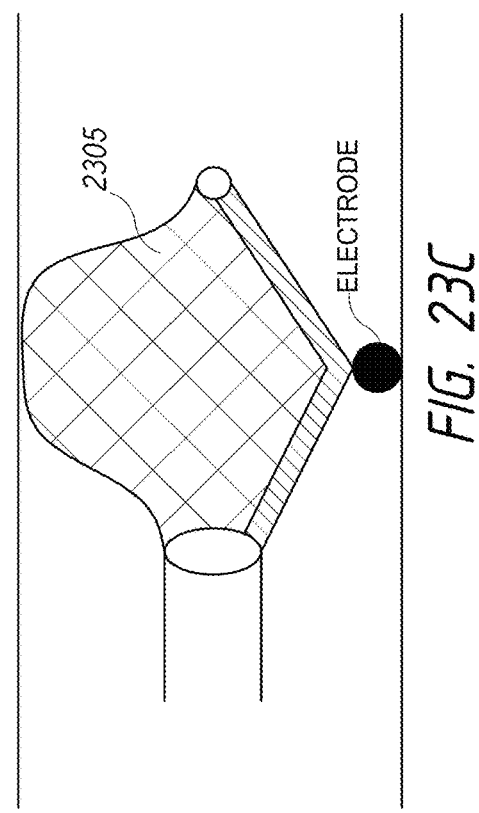
Figure 23B:
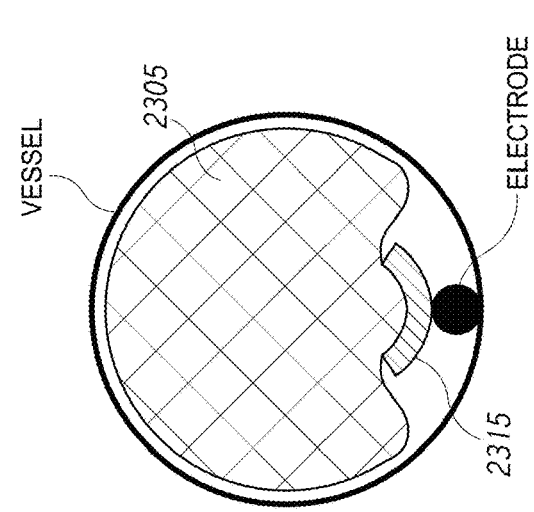

Referring now to FIGS. 23A-23C, one embodiment of an occlusive or obstruction element is a compliant balloon 2305 (e.g., made of silicone, polyurethane, or other suitable compliant material) bonded to a distal end of a catheter shaft 2310 and to a distal point of the overall catheter (e.g., which includes an electrode or other activation member). In one embodiment, a portion of the balloon's circumferential arc 2315 is constrained by a less compliant material (e.g., PEBAX, Nylon, PE, Nitinol, stainless steel, or other suitably less compliant material) that spans a significant distance of the balloon's axial length. In some embodiments, the constrained section or portion of the catheter is an extension of the catheter shaft 2310 and may be constructed so that it can bend. In the illustrated embodiment, the constrained section incorporates physical design elements, such as notches or flexure-like regions 2320 to permit bending.

As shown in FIG. 23B, during inflation of the balloon 2305, the balloon material would expand evenly until it hit the vessel wall everywhere except near the constrained section. In some embodiments, although the constrained section would move out radially, the constrained section would still restrict the compliant balloon 2305, thereby creating a gap between the vessel (e.g., artery) wall and the balloon 2305 on either side of the constrained section arc 2315. The size of this gap may be pressure dependent (as it is related to the expansion of the compliant balloon). In some embodiments, the gap size is characterized as a function of balloon pressure by experimentation where the compliant balloon (with a constrained arc) is expanded within a semi-compliant tube and the cross-sectional area is measured visually or as a function of fluid resistance.

In various embodiments, the cross-section of the gap is advantageously smaller than the natural vessel cross-section, thereby increasing the fluid velocity at that cross-section. In some embodiments, the midpoint of the cross-section (e.g., region of highest velocity flow lines) would be moved closer to the constrained arc 2315.

In some embodiments, when the balloon 2305 is inflated, it expands evenly, except around the strip of catheter material, where it has to bend (requiring more pressure to stretch the material in that area). Through a range of pressures, the balloon 2305 may expand to press against the opposing vessel wall while leaving a gap around the electrode. In various embodiments, this pressure range could be experimentally defined.

In one embodiment, the balloon 2305 is inflated by a syringe at the proximal end of the catheter. The physician or other clinician may self-inflate the balloon, using his/her tactile sense (and potentially a pressure gauge in the syringe), and adjust the applied pressure. In one embodiment, the pressure is limited by a release valve or by a set volume placed in the syringe before inflating the balloon. In one embodiment, the balloon becomes the mechanism for applying the electrode force, and this mechanism has tactile feedback (e.g., the syringe). The balloon may be filled with cold fluid to enhance the overall cooling effect.

In various embodiments, the electrode(s) are bonded (e.g., physically with an overmold, chemically with adhesive, or other suitable bonding method) onto the constrained section. The wire(s) from the electrode(s) may run outside, within or inside the constrained section. In one embodiment, the constrained section is made of a thin, flexible circuit with wire(s) and electrode(s) embedded within the circuit encasing material.

In various embodiments, capacitive coupling or resistive heating catheter devices are used to deliver thermal energy. In one embodiment, a capacitive coupling catheter device comprises a balloon comprising a bipolar electrode pair arranged in a capacitive coupling configuration with an insulation layer between the two electrodes. In one embodiment, the insulation layer coats the two electrodes. In one embodiment, the balloon comprises a non-conductive balloon filled with saline that is capacitively coupled to the target tissue through the dielectric layer formed by the substantially non-conductive balloon membrane. The capacitive coupling catheter device may advantageously not require direct electrode contact with the target tissue, thereby reducing current density levels and edge effects required by other devices. Capacitive coupling devices or methods similar to those described in U.S. Pat. No. 5,295, 038, incorporated herein by reference, may be used. A return electrode path may also be provided.

In one embodiment, a resistive heating energy delivery catheter comprises a balloon catheter having a resistive heating element disposed thereon. For example, the balloon catheter may comprise spiral resistive heater that wraps around the balloon. Instead of inducing RF currents in the vascular tissue, DC or AC/RF currents can be used to generate heat in the balloon catheter itself and the heat can be transmitted to the surrounding vascular tissue (e.g., hepatic arterial tissue) by conduction.

c. Electrode Cooling

Figure 24:
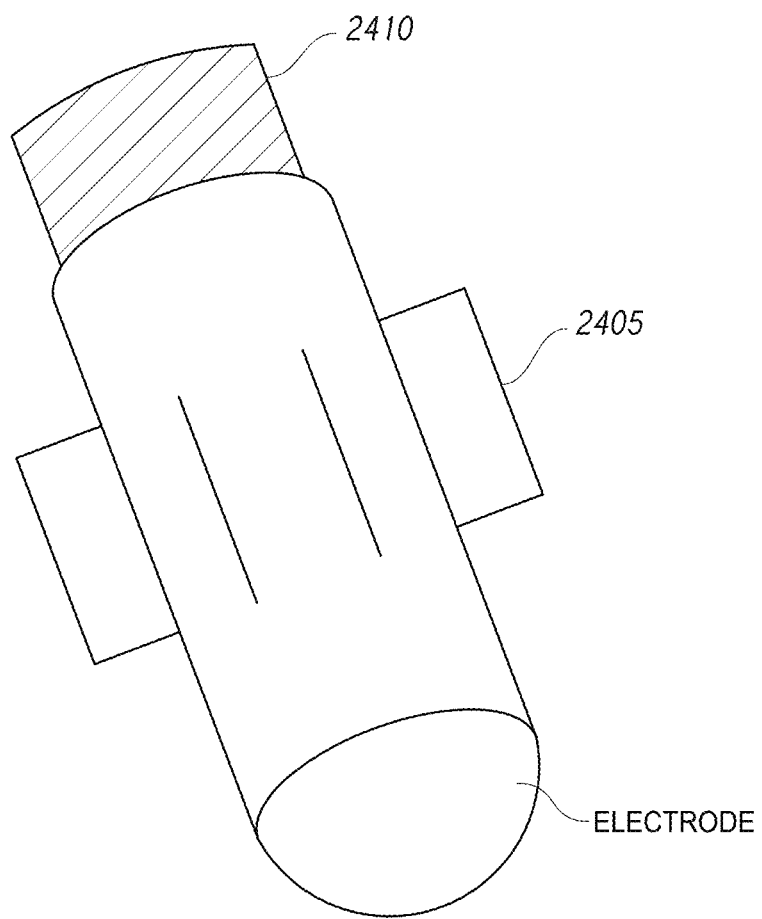

In accordance with several embodiments, the surface area of the electrode or a region in thermal proximity to the electrode can be increased. The increased temperatures can be achieved by increasing the length or diameter of the electrode, as convective cooling according to Newton's law is proportional to the surface area. In one embodiment, increasing the surface area of the electrode is achieved by adding fins 2405 or thermally connecting the electrode to another section of the catheter 2410 (as illustrated in FIG. 24). In various embodiments, the finned region of the catheter 2410 might either be in direct electrical communication with the electrode or electrically isolated from the electrode by means of a thin dielectric layer. In accordance with several embodiments, electric insulation (for example a thin 0.001" layer of polyimide) does not substantially reduce the thermal communication between the finned region and the electrode because the rate of thermal conduction through a thin material is greater than that through a thicker material.

In various embodiments, instead of fins, the surface of the electrode can also be microstructured, for example bead-blasted, microfractured, or etched. In some embodiments, small solder bumps are welded or riveted onto the surface of the electrode. In one embodiment, gold or other radiopaque material solder bumps are particularly advantageous to increase the radiopacity of the electrode.

Figure 25:
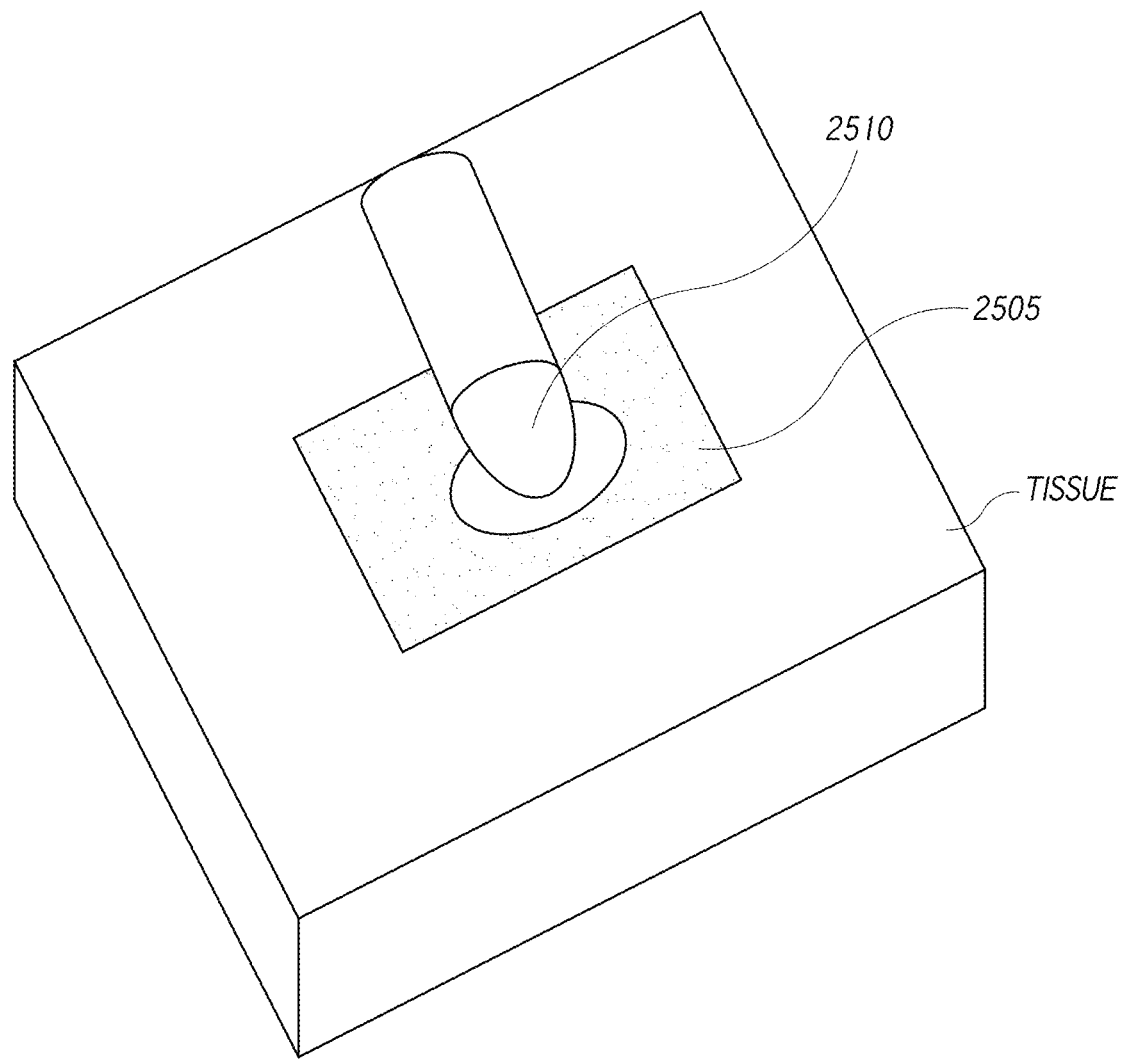

In one embodiment, electrode cooling is increased by effectively increasing the surface area of the lumen of the vessel (as opposed to increasing the surface area of the electrode), thereby increasing the heat transfer rate from the tissue to the blood. In an embodiment shown in FIG. 25, increasing the heat transfer rate from the tissue to the blood is achieved by placing a thermally conductive pad 2505 in contact with the tissue surrounding the electrode 2510. For example, a stent or ring may be deployed before the ablation energy dosage. The deployable stent or ring may place a thermally conductive structure (e.g., "pad") around the ablation site. In one embodiment, the pad 2505 is a pre-formed structure comprised of gelatin, hydrogel, or other high thermal conductivity material. In order to prevent or inhibit non-targeted ablation of tissue, it may be necessary to electrically insulate the pad 2505 from the electrode. Electrical insulation may be achieved by leaving space between the electrode 2510 and the conductive pad 2505 (thereby preventing or inhibiting contact between the pad 2505 and the electrode 2510) through accurate placement of the electrode 2510 or a placement-guiding mechanism such as a funnel. Electrical insulation may also be achieved by placing a thin layer of an electrical insulator on the surface of the pad 2505 exposed to the electrode 2510. The layer of electrical insulation may also be attached to the catheter between the electrode 2510 and the pad 2505.

In accordance with various embodiments, it would be advantageous for the pad to have a large surface area. Fins, as shown and described in FIG. 24, are one way to increase the surface area and to increase heat dissipation.

In some embodiments, an ablation region is precooled using cold infusion techniques (e.g., iced saline infused directly into the vessel) or using a chilled balloon. In some embodiments, blood flow may also be restricted during pre-cooling to increase residence time and achieve desired heat transfer. The pre-cooling of the ablation region may advantageously lower the initial temperature for the ablation and allow more power to be delivered locally, thereby enabling steeper temperature gradients and deeper, tighter lesions. The pre-cooling may also result in lower conductivity in the cooled region, further concentrating power into locally heated regions. In one embodiment, a balloon having one or more electrodes is inserted to a target ablation site within a blood vessel or organ (e.g., within a common hepatic artery). Coolant may be circulated through the balloon for a period of time (e.g., 20-60 seconds, 30-50 seconds, 20-40 seconds, 30 seconds) prior to initiating ablation via the one or more electrodes. In some embodiments, the pre-cooling of the target ablation site may advantageously allow for delivery of ablative energy at a higher power level than if the target ablation site was not precooled, thereby enabling deeper, more narrow lesions to be formed.

In one embodiment, electrode and/or tissue cooling is increased by decreasing the temperature of the blood in order to increase heat conduction by increasing the temperature delta between the blood and the electrode and surrounding tissue. In several embodiments, electrode and/or tissue cooling is achieved by placing thermoelectrics on the catheter and proximal to the electrode. Using the Peltier effect, a current driven through a junction of two different conductors can be used to remove heat from (cool) the junction. Because the catheter is inserted into the hepatic artery in an antegrade fashion, blood flows along the catheter towards the electrode (or ablation site). In one embodiment, the region of the catheter proximal to the electrode is upstream of the ablation (other site and the blood could be cooled along the catheter before it reaches the ablation site. In one embodiment, multiple thermoelectric coolers (e.g., the MD03 series or MDL06 series) are placed in the catheter proximal to the electrode and used to cool the blood. Since increasing the thermal conductance of the thermoelectric sites improves the efficiency of the thermoelectric elements, the thermoelectric elements may be placed to maximize or increase surface area (e.g., fins), minimize or otherwise reduce wall thickness, and/or maximize or increase location near the max velocity flow lines. In some embodiments, cold fluid injections upstream of the ablation site are used instead of thermoelectrics to achieve the same goal of reducing the blood temperature at the ablation site.

In some embodiments, a saline hyperphysiologic flow catheter is used to increase fluid flow within a target artery (e.g., common hepatic artery). FIGS. 26A and 26B illustrate schematic embodiments of a saline hyperphysiologic flow catheter. FIG. 26A illustrates an embodiment of a saline hyperphysiologic flow catheter configured to provide increased antegrade flow control at the electrode-vessel contact location (e.g., of about 500 mL/min). FIG. 26B illustrates an embodiment of a saline hyperphysiologic flow catheter configured to provide increased retrograde or reverse flow past the electrode-vessel contact location. In one embodiment, the vessel flow may be partially or completely stopped proximally or distally of the electrode and/or lower power can be used. The saline flow may cause flow within the vessel to be increased by two, three, four, five, six times or more. In one embodiment, a flow sensor is placed at a distal tip of the catheter to provide feedback of the convective cooling rate so that a desired temperature can be achieved.

Figure 27A:
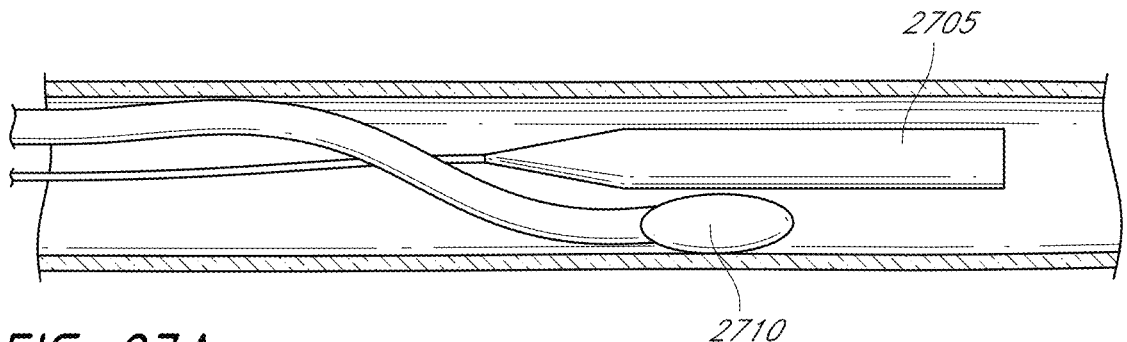
Figure 27B:
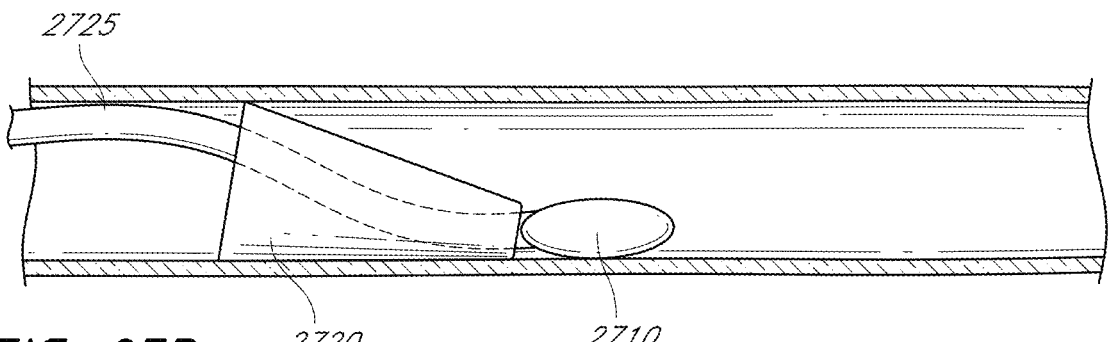
Figure 27C:
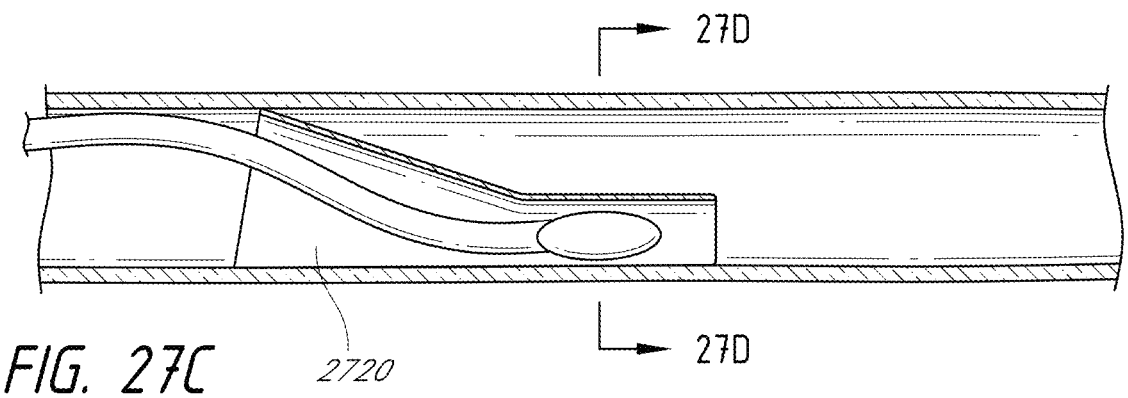
Figure 27D:
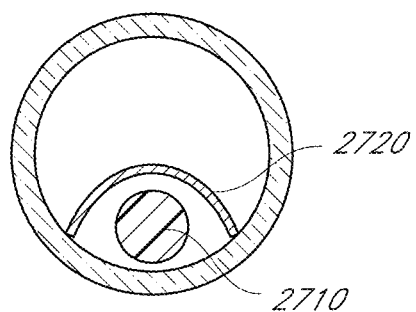

In accordance with several embodiments, redirecting high velocity blood flow from a higher-flow region (e.g., center) of the vessel to the vessel wall (or to an electrode in contact with the vessel wall) increases the removal of heat generated during ablation. FIGS. 27A-27D Illustrate embodiments of devices configured to redirect or divert high velocity blood flow from the center of a vessel toward an electrode in contact with the vessel wall. FIG. 27A illustrates an embodiment of an inflatable cone 2705, which can be placed above an electrode 2710 to redirect flow toward the electrode 2710. In one embodiment, the inflatable cone 2705 may be introduced into and delivered to the location through a separate catheter. The cone 2705 can be inflated to give room for blood flow around the cone 2705 and may be positioned in the center of the vessel, thereby resulting in a laminar high velocity flow along the walls of the vessel, and thereby cooling the electrode 2710 and vessel lumen. FIGS. 27B-27D illustrate an embodiment of a funnel 2720 configured to divert flow toward an electrode 2710 at a distal end of a catheter 2725 (e.g., probe or shaft). FIG. 27D is a cross-section view of FIG. 27C. The funnel 2720 may be affixed or coupled to the catheter 2725 by a joint or hinge at a location near the electrode 2710 (however, other coupling techniques may be used as desired and/or required). The funnel 2720 may be configured to collect higher blood flow at the center of the vessel and divert the flow directly across the electrode 2710. In some embodiments, the funnel 2720 comprises a flexible material. The cooling provided by the increased blood flow may facilitate formation of deeper lesions without causing charring or spasm, may reduce the likelihood of excessive superficial injury, and may provide more control over ablations. In one embodiment, flaps may capture and divert flow over the electrode to enhance cooling and direct the electrode toward an upstream location in the vessel (e.g., artery). The flaps may enable the electrode to be directed by the flow against the vessel wall, thereby enhancing or enabling wall contact. In one embodiment, a proximal catheter shaft can be extremely flexible to enable traversing extreme tortuosity. The flow-directed wall contact may enable electrode contact in situations where there is a desire to neuromodulate (e.g., ablate) on tight bends. In one embodiment, a "cup" may be created for blood capture, thereby enabling flow directed tracking and flow directed wall contact.

In accordance with several embodiments, branches of a main vessel other than those leading to a target vessel (e.g., the common hepatic artery) are partially or completely occluded to increase blood flow to the target vessel. For example, the left gastric artery and splenic artery (which branch off of the abdominal aorta upstream of the origin of the common hepatic artery) may be occluded temporarily during treatment of a common hepatic artery to increase blood flow through the common hepatic artery, thereby increasing electrode cooling and reducing the likelihood of spasms, notching and charring. In some embodiments, the partial or total occlusion of the branch vessels may be provided by a guide catheter. The guide catheter may be modified to add extensible and adjustable plates that may be retracted during insertion and removal of the guide catheter and deployed upon advancement of the guide catheter to an appropriate location adjacent a target vessel (e.g., within the abdominal aorta adjacent an origin of the common hepatic artery). Once the guide catheter is in position, the plates may be deployed and positioned to occlude a portion or the entire entrance to the branch arteries upstream of the target artery, thereby increasing flow into the target artery, which in turn increases the cooling of the electrode and of the arterial wall.

Figure 28:
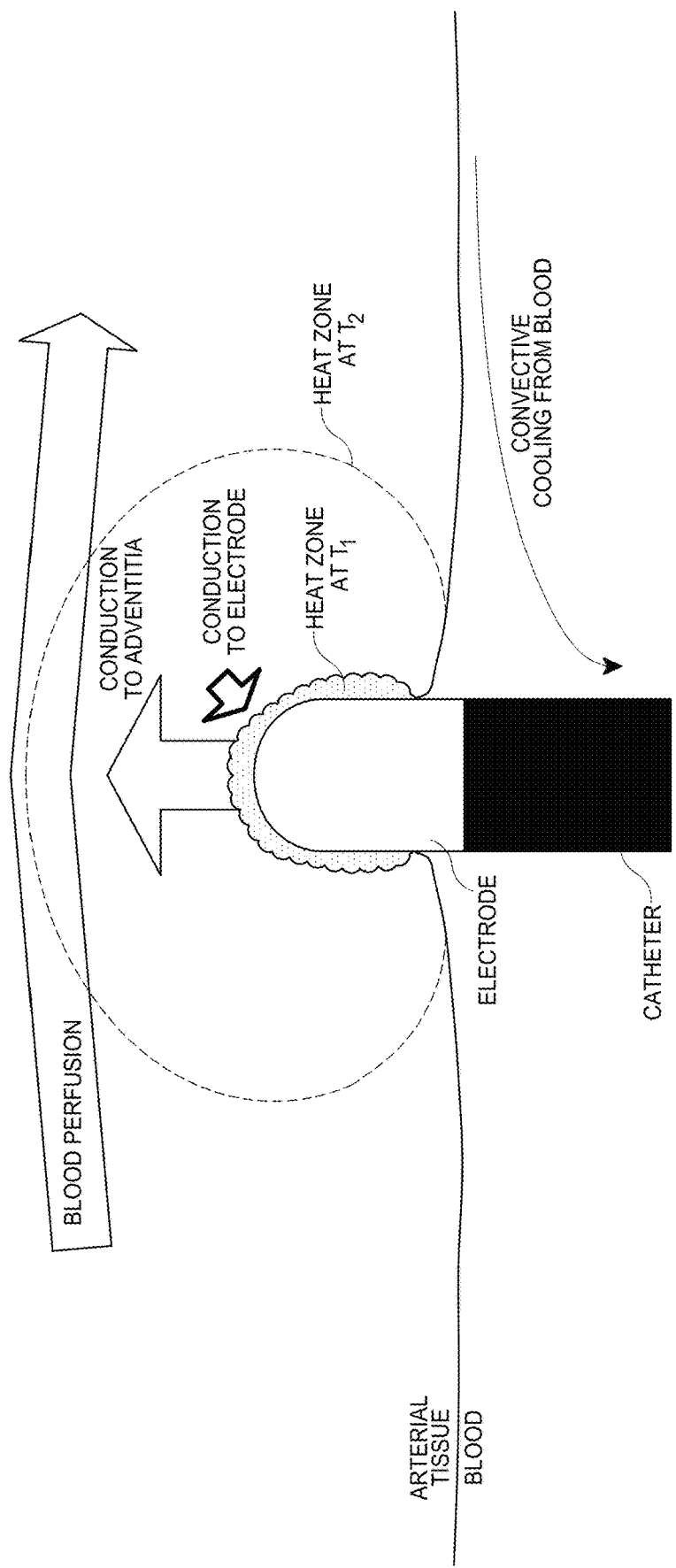

In accordance with some embodiments, buried and/or shielded electrode designs are used to prevent or inhibit cooling. FIG. 28 illustrates an example of burying the electrode to substantially shield the electrode from cooling by blood flow within the artery, thereby increasing electrical aperture. In some embodiments, the electrode can be pushed against or into the media of the arterial wall to create a "false lumen" between the intima and the media to shield the electrode from blood flow. In one embodiment, a flat or substantially flat electrode can be used that is placed such that the electrode is parallel or substantially parallel to the vessel wall, thereby shielding the electrode from cooling due to blood flow. In one embodiment, the electrode comprises a finger-like electrode with a hemisphere covered with insulation to prevent or inhibit blood cooling.

d. Deflectable, Steerable, Deployable or Expandable Structures

Figure 29A:
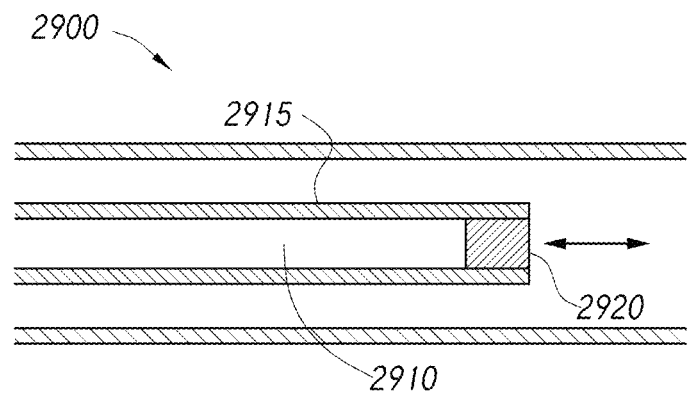
Figure 29B:
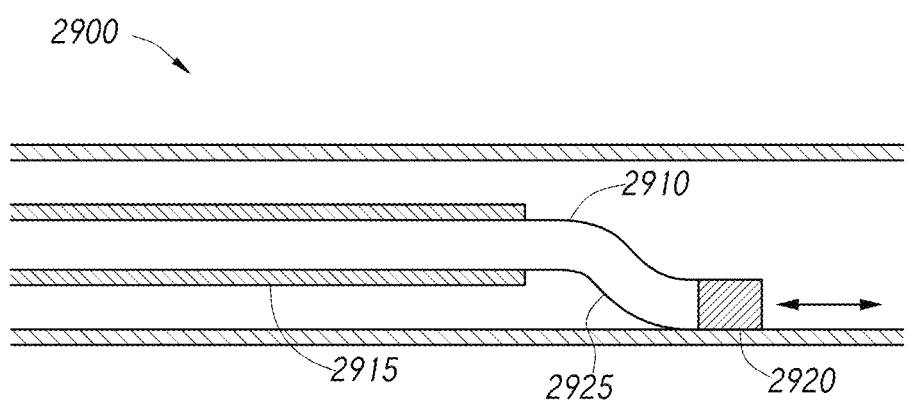

The hepatic artery anatomy is generally more tortuous and variable than anatomies of other vessels in other areas. Maintaining good contact of electrodes or other energy delivery elements in the tortuous hepatic artery anatomy can be difficult and may require the use of different catheter devices than existing catheter devices for nerve ablation. FIGS. 29A and 29B illustrate an embodiment of a low-profile ablation catheter 2900 that may advantageously facilitate contact of electrodes or other energy delivery elements with the inner walls of arteries of the tortuous hepatic vascular anatomy. The low-profile ablation catheter 2900 comprises an inner electrode member 2910 and an outer sheath 2915. The inner electrode member 2910 may comprise a reversibly deflectable, pre-shaped cylindrical shaft comprising resilient (e.g., shape memory) material and at least one electrode 2920. In one embodiment, the outer sheath 2915 comprises a guide catheter having a lumen. The inner electrode member 2910 may be configured to be delivered within the lumen of the outer sheath 2915 and to be translatable relative to the outer sheath 2915 such that the inner electrode member 2910 may be advanced out of a distal end of the outer sheath 2915 and retracted back in. In one embodiment, the inner electrode member 2910 assumes a generally deflected (e.g., off-axis) configuration when advanced out of the distal end of the outer sheath 2915, as shown in FIG. 29B. In this unconstrained state, the distal end of the inner electrode member 2910 deviates from a longitudinal axis defined by the proximal portion of the electrode. When the inner electrode member 2910 is retracted within the outer sheath 2915, the inner electrode member 2910 is resiliently deformed to assume a substantially straight shape defined by the substantially straight shape of the lumen of the outer sheath 2915, as shown in FIG. 29A. In some embodiments, when the inner electrode member 2910 is advanced out of the distal end of the outer sheath 2915, the distal end portion of the inner electrode member 2910 deflects to contact a vessel wall (e.g., arterial wall). The shape of the distal end of the inner electrode member 2910 in the unconstrained state may be pre-formed to ensure contact with the vessel wall.

In some embodiments, the outer sheath 2915 has a diameter of less than about 4 mm, less than about 3 mm, less than about 2 mm, or less than about 1 mm. In some embodiments, the inner electrode member 2910 comprises a shaft formed, at least partly, of memory material such as a nickel titanium alloy material. The inner electrode member 2910 may have an outer cross-sectional dimension that is substantially equal to the outside diameter of the outer sheath 2915 or may have an outer cross-sectional dimension that is smaller or larger than the outside diameter of the outer sheath 2915. In some embodiments, when the inner electrode member 2910 is slid out of the outer sheath 2915 past a pre-formed step 2925 at or near its distal end, the step 2925 at or near the distal end places the surface of the distal end of the inner electrode member 2910 away from the natural axis of the outer sheath 2915. In some embodiments, the step 2925 near the distal end of the inner electrode member 2910 places the surface of the inner electrode member 2910 between about the same plane as the outer surface of the outer sheath 2915 and about double the diameter from the center of the outer sheath 2915 to the outer surface of the outer sheath 2915. In some embodiments, the outer sheath 2915 is deflectable.

In some embodiments, the magnitude of the off-axis deflection created in the step 2925 near the distal end is tailored to satisfy varying anatomic requirements (e.g., larger step near the distal end for larger blood vessels and smaller step near the distal end for smaller blood vessels). In some embodiments, the inner electrode member 2910 is interchangeable and may be replaced with a different inner electrode member with different size parameters. The different sizes of inner electrode members or electrode members with different pre-formed shapes may be provided in a kit and an appropriate inner electrode member may be selected after evaluating patient anatomy (for example, by CT, fluoroscopy, or ultrasound imaging methods). In some embodiments, the inner electrode member 2910 is rotated within the catheter body.

In some embodiments, the at least one electrode 2920 of the inner electrode member 2910 comprises one or more monopolar, bipolar or multipolar electrodes (the addition of additional pre-shaped electrodes may enable bipolar and multi-polar RF energy delivery). Any combination of electrodes may be incorporated into the design of the inner electrode member 2910 to create a catheter with any desired properties.

In some embodiments, the shaft of the inner electrode member 2910 comprises an insulation member to prevent or inhibit heat transfer away from or electrically insulate portions of the inner electrode member 2910. In some embodiments, the insulation member is a tubing, coating or heat shrink comprised of polyamide, polytetrafluoroethylene, polyetheretherketone, polyethylene, or any other high dielectric material. The insulation member may comprise one or more openings to expose portions of the distal end portion of the inner electrode member 2910. In some embodiments, the insulation member is used to define specific electrode geometries by selective removal of the insulation member in whatever geometry is desired. In other embodiments, the inner electrode member 2910 comprises a shape memory polymer or shape-biased polymer with one or more electrode leads disposed therein. In one embodiment, the low-profile ablation catheter 2900 comprises a catheter coextruded with a shape memory electrode spine, where the extruded catheter provides electrical insulation. In one embodiment, the at least one electrode 2920 comprises a spherical electrode. In one embodiment, the distal end of the inner electrode shaft comprises a series of electrodes.

In some embodiments, the low-profile ablation catheter 2900 comprises a radial window or slot in a side portion near the distal end of the ablation catheter. In one embodiment, the distal end of the inner electrode member 2910 is configured to be deployed out of the radial window or slot. In one embodiment, the lumen of the ablation catheter 2900 comprises a ramp leading up to the radial window or slot to direct the distal end of the inner electrode member out of the radial window or slot.

In accordance with several embodiments, the low-profile ablation catheter 2900 advantageously provides a device that comprises a low profile (e.g., small outer cross-sectional dimension) and uses the same mechanism to actuate the electrode deflection as well as the electrode itself, thereby reducing the number of distinct components. The inner electrode 2910 of the low-profile ablation catheter 2900 may also advantageously be at least partially deployed to facilitate navigation by providing a variety of tip curvature options for "hooking" vascular branches or navigating tortuous vessels during catheter insertion. In accordance with several embodiments, the low-profile ablation catheter 2900 advantageously facilitates solid and continuous contact with the vessel wall, thereby allowing for substantially constant voltage to maintain a desired electrode tip temperature.

FIGS. 29C-29K Illustrate various embodiments of energy delivery devices configured to facilitate maintained contact of an energy delivery member (e.g., an electrode) against a vessel wall (e.g., a wall of a common hepatic artery) despite motion due to respiration or blood flow.

Figures 1, 29C:
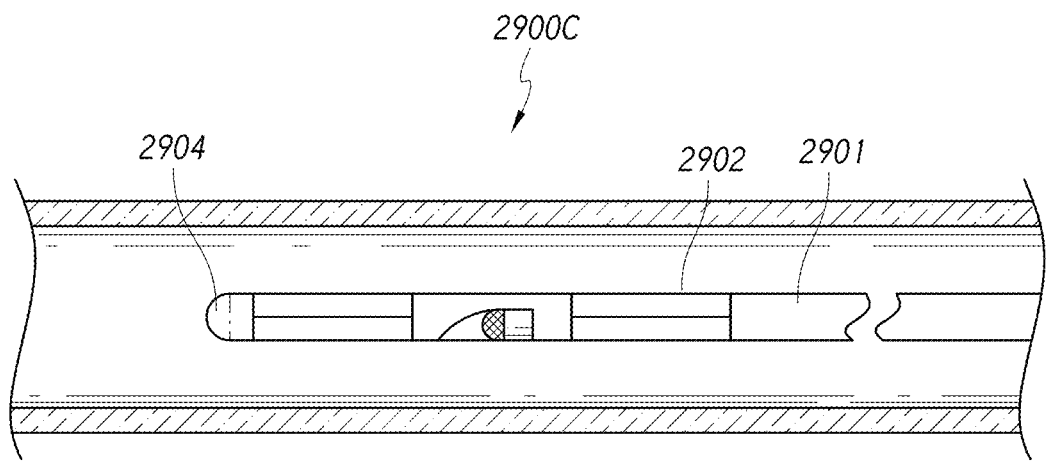
Figures 2, 29C:
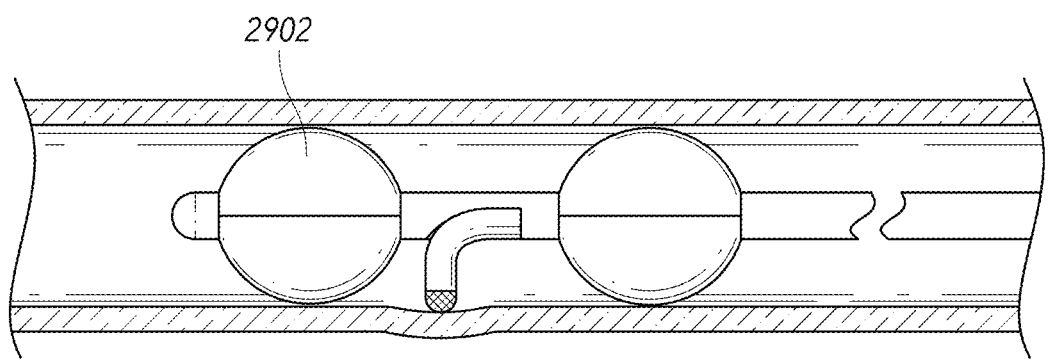

FIGS. 29C-1 and 29C-2 illustrate an embodiment of an ablation catheter system 2900C comprising a shaft 2901 having one or more expandable intravascular structures 2902 configured to expand into contact with a vessel wall upon expansion. The ablation catheter system 2900C may advantageously be used to provide vessel centering for embodiments involving an electrode-tipped catheter. In some embodiments, the expandable structures 2902 allow for minimal restriction to blood flow while supporting an electrode 2904 for a controlled vertical presentation to a desired treatment site. The expandable intravascular structures 2902 may comprise a scaffold, frame, cage or basket formed of multiple lobes or tines constructed from a flexible, durable and/or flex resilient material (such as Nitinol, Inconel or other shape memory materials). In one embodiment, expansion of the structures 2902 from the unexpanded state to the expanded state involves compression, or foreshortening, by way of a pull wire being retracted. As shown in the illustrated embodiment, the shaft 2901 may comprise two expandable intravascular structures 2902. The electrode-tipped catheter may comprise a cylindrical probe or tube having an electrode tip 2904 that is advanced through a lumen of the shaft 2901 and out of a port or side opening 2903 of the shaft 2901. In one embodiment, the electrode tip 2904 is advanced through the lumen of the shaft 2901 until it reaches a deflection ramp positioned between (e.g., at the midpoint between) the expandable intravascular structures 2902 that forces the electrode tip 2904 out of the port or side opening 2903 of the shaft 2901 at a 90 degree angle relative to the longitudinal axis of the shaft 2901 until the electrode tip 2904 contacts the vessel wall.

Figure 29D:
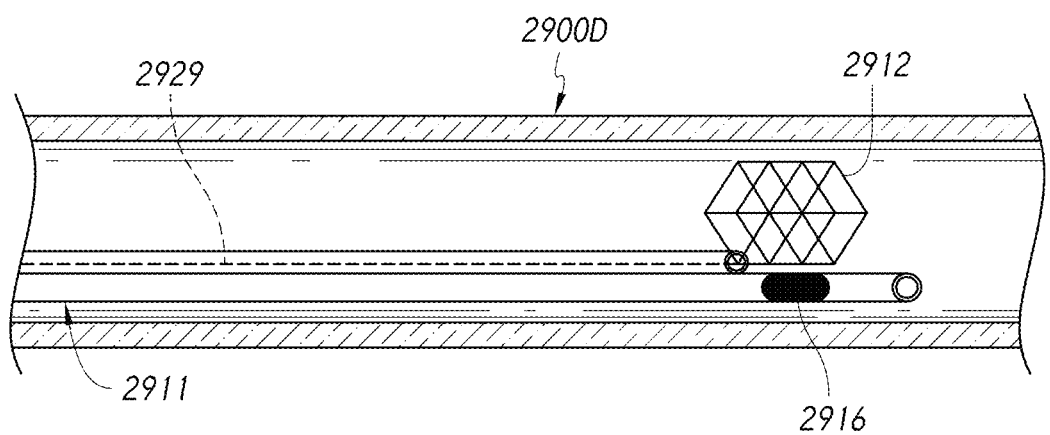

FIG. 29D illustrates an embodiment of an ablation catheter system 2900D comprising a dual-lumen catheter 2911. A distal end of the dual-lumen catheter 2911 comprises an expandable structure 2912 and an electrode 2916. In the illustrated embodiment, the expandable structure 2912 is mechanically expanded by a pull-wire 2914 extending from a proximal end of one of the lumens to the expandable structure 2912 at the distal end. The expandable structure 2912 may advantageously comprise a scaffold or basket having an open pattern that facilitates free, unrestricted flow of blood while the scaffold or basket is in an expanded state. The expandable structure 2912 may have a configuration that enables the structure 2912 to be deployed and secured within any of a number of target vessels having different diameters (e.g., for the purpose of creating a lesion) without the influence of movement due to respiration or blood flow (e.g., piston-like axial movement), thereby providing consistent and focused electrode wall contact during energy delivery. As an example embodiment of a method of use, an operator may place the dual-lumen catheter 2911 in a target vessel, advance it to a target site within the target vessel, and deploy the expandable structure 2912 using the mechanical pull-wire 2914. Energy may be delivered via the electrode 2916. Once the energy cycle is complete, the expandable structure 2912 may be retracted and the catheter 2911 may be withdrawn or moved to a different target site. In some ablative embodiments, the improved precision of lesion creation and minimization of axial lesion extension reduces likelihood of lesion overlap and improves vascular safety profile.

Figure 29E:
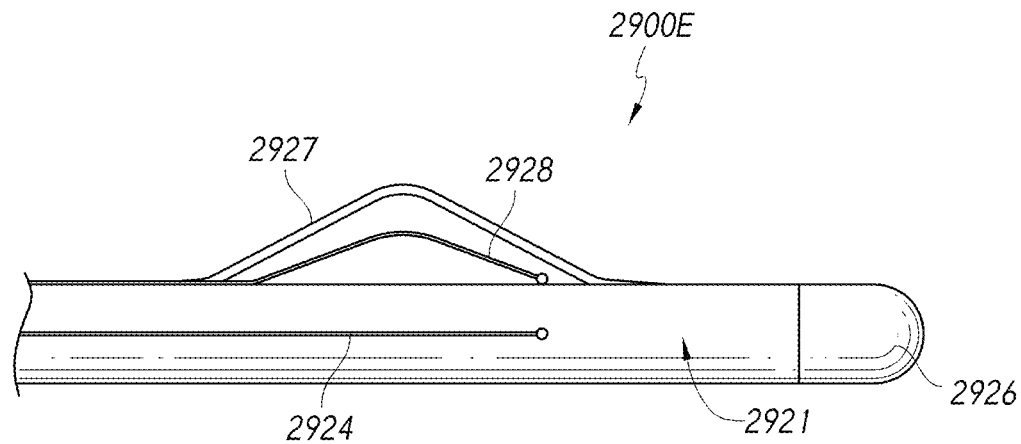

FIG. 29E illustrates an embodiment of a radiofrequency energy delivery catheter 2900E that is configured to harness the energy of blood flow through a vessel to facilitate maintained contact of an electrode against the vessel wall. The catheter 2900E comprises a deflectable shaft segment 2921, a pull wire 2924, a distal tip electrode 2926, an elastic membrane 2927 and a push wire 2928 configured to expand the elastic membrane 2927. As actuation of the deflectable shaft segment 2921 occurs upon pulling of the pull wire 2924, the same action pushes the push wire 2928, thereby expanding the elastic membrane 2927. The elastic membrane 2927 extends around a portion (e.g., 180 degrees of the shaft circumference) of the deflectable shaft segment 2921, and forms a "sail" that takes advantage of the force provided by blood flow to provide increased electrode contact force and stability. The design of catheter 2900E may minimize or otherwise reduce shaft profile by eliminating actuation structures. In some embodiments, the push wire 2928 and the pull wire 2924 are actuated independently.

In accordance with several embodiments, energy delivery devices (e.g., catheters) comprise a distal portion constructed of shape memory material and a lumen configured to receive a guidewire. The shape memory material may be heat or shape set so as to cause an electrode positioned on the distal portion of the energy delivery device to contact an inner wall of a target vessel. A guidewire may retain the distal portion of the energy delivery device in a straight or substantially straight alignment until the distal portion is positioned in a desired position within the target vessel. When the guidewire is withdrawn from the lumen of the energy delivery device, the shape-memory distal portion deforms to the heat- or shape-set configuration so as to cause an electrode of the energy delivery device to contact the inner wall of the target vessel. In some embodiments, energy delivery devices (e.g., catheters may have one or more pre-formed configuration portions configured to transition to a pre-formed configuration upon being advanced out of a sheath or introducer catheter and one or more pre-formed configuration portions configured to transition to a pre-formed configuration upon removal or withdrawal of a guidewire.

Figure 29F:
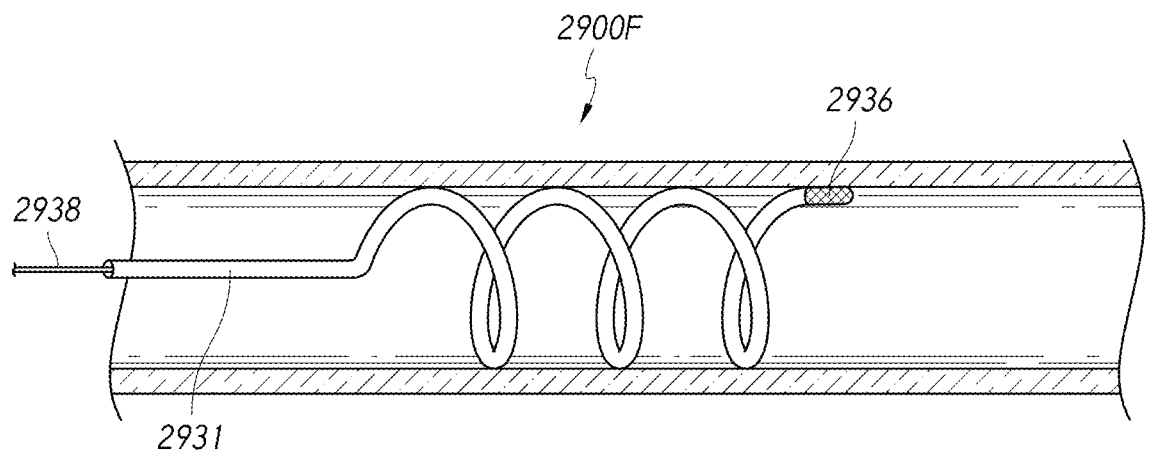

FIG. 29F illustrates an embodiment of an RF energy delivery system 2900F comprising a device (e.g., catheter) 2931 having a tip electrode 2936 and a guidewire 2938. The distal portion of the catheter 2931 is shape set during manufacture to have a pre-formed pigtail (e.g., spiral or corkscrew) shape. The distal portion of the catheter 2931 remains in a straight or substantially straight shape as it is advanced to a target location over the guidewire. Upon retraction of the guidewire, the distal portion of the catheter 2931 assumes the pre-formed pigtail shape, thereby causing contact of the distal portion of the catheter 2931 at multiple locations along the length and circumference of the vessel wall, including at the electrode tip 2936. Re-insertion of the guidewire straightens the distal portion of the catheter 2931 and facilitates removal of the catheter 2931.

FIGS. 29G-1 and 29G-2 illustrate another embodiment of an RF energy delivery system 2900G for neuromodulation or other tissue modulation. The energy delivery system 2900G comprises an over-the wire treatment catheter 2931 and a guidewire 2938. The treatment catheter 2931 of FIGS. 29G-1 and FIGS. 29G-2 comprises two electrodes 2936 on a shape-set portion 2932 and a lumen sized and adapted to receive the guidewire 2938. The shape-set portion 2932 is coupled to a proximal portion 2937 and a distal portion 2939 of a main shaft of the treatment catheter 2931. The distal portion 2939 may comprise an extension to facilitate trackability over the guidewire 2938.

As described above in connection with FIG. 29F, a portion of the catheter 2931 of FIGS. 29G-1 and 29G-2 is shape set during manufacture to have a preformed pigtail (e.g., spiral or corkscrew) shape. The shape-set portion 2932 of the treatment catheter 2931 remains in a straight or substantially straight configuration as it is advanced to a target location over the guidewire 2938. Once the treatment catheter is positioned at the target location, the guidewire 2938 may be retracted or withdrawn, which allows the shape-set portion 2932 of the treatment catheter 2931 to "spring" into a three-dimensional curve (as shown in the deployed configuration of FIG. 29G-2), thereby causing the electrodes 2936 on the shape-set portion 2932 to contact an inner vessel wall at multiple spaced-apart locations along the length and circumference of the vessel wall. Re-insertion of the guidewire 2938 straightens the shape-set portion 2932 and facilitates removal of the treatment catheter 2931. The three dimensional curve can be spiral-shaped, as shown. The spiral may have varying pitch and or diameter or may be helical, of uniform diameter and pitch. The shape-set portion 2932 may be formed by incorporating a shaped elastic member, such as from a metal or metal alloy (e.g., nitinol), or may be formed with a thermoplastic material using heat shaping techniques. The shape-set portion 2932 may be formed by heat-setting or pre-stressing methods or techniques.

The shape-set portion 2932 may comprise two or more electrodes (e.g., two, three, four, more than four). In the case where two electrodes are included, the electrodes 2936 can be positioned at approximately 180 degrees of circumferential angular separation on the shape-set portion 2932, as shown in FIG. 29G-2. The 180 degree offset puts the electrodes 2936 longitudinally spaced, but at opposing sides when deployed within a treatment vessel. The electrodes 2936 may be positioned in any manner along the shape-set portion, as desired and/or required. In various embodiments, the positioning of the electrodes 2936 and the shape of the three-dimensional curve are configured such that a first electrode contacts the vessel wall in an axial or longitudinal orientation (e.g., as determined by a longest aspect of the first electrode) and the second electrode contacts the vessel wall in an oblique orientation (offset perpendicularly with respect to a longitudinal axis of the vessel or catheter shaft), as shown in FIG. 29G-2. For example, the first electrode and the second electrode may be differentially oriented 90 degrees or substantially perpendicular to each other. In one embodiment, the three-dimensional curve is non-helical. The non-helical curve or shape-set portion 2932 may be configured to transition from a proximal longitudinal portion connected to a proximal portion of the catheter shaft to a proximal oblique portion to a central longitudinal portion to a distal oblique portion and then back to a distal longitudinal portion connected to a distal portion of the catheter shaft, as shown in FIG. 29G-2. In the illustrated embodiment, a first electrode is positioned on the central longitudinal portion and a second electrode is positioned on the distal oblique portion. The contact portions of the longitudinal and oblique portions may be configured to be 180 degrees offset from each other. In some embodiments, the second electrode may be positioned on the proximal oblique portion or electrodes may be positioned on each of the proximal and distal oblique portions, with each of the obliquely-oriented electrodes being offset by 180 degrees from the axially-oriented electrode. In some embodiments, electrodes may be positioned on one or both of the proximal and distal longitudinal portions or on the catheter shaft adjacent the proximal and distal longitudinal portions, in addition to or instead of on the middle longitudinal portion. The electrodes 2936 may be configured to be spaced apart axially by 2 mm, 3 mm, 4 mm, 5 mm, 6 mm.

Figure 29H:
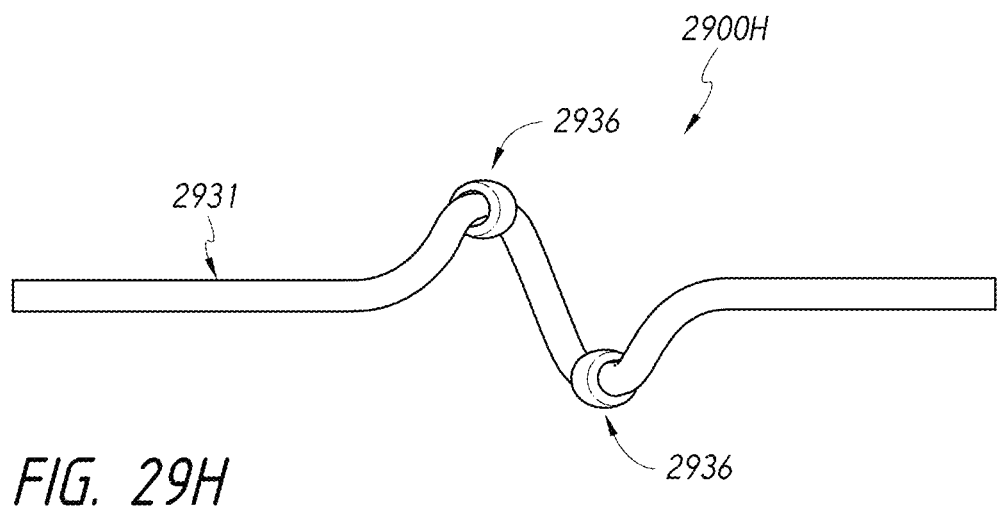

FIG. 29H illustrates an embodiment of a catheter shaft 2931 adapted to form a helical configuration along a portion of the length of the catheter shaft 2931. The catheter shaft 2931 comprises two electrodes 2936 positioned at spaced-apart locations along the helical portion so as to contact a vessel wall at locations spaced apart axially and circumferentially (e.g., 180 degrees apart). In some embodiments, one or more electrodes are located on non-deflectable (for example, non-helical) portions of the shaft proximal and/or distal of the deflectable portion of the shaft. In one embodiment, a catheter shaft consists of a single electrode on a deflectable (for example, shape memory, steerable via pull-wire) portion and one or more electrodes on a main, non-deflectable portion of the shaft.

Figure 29I:
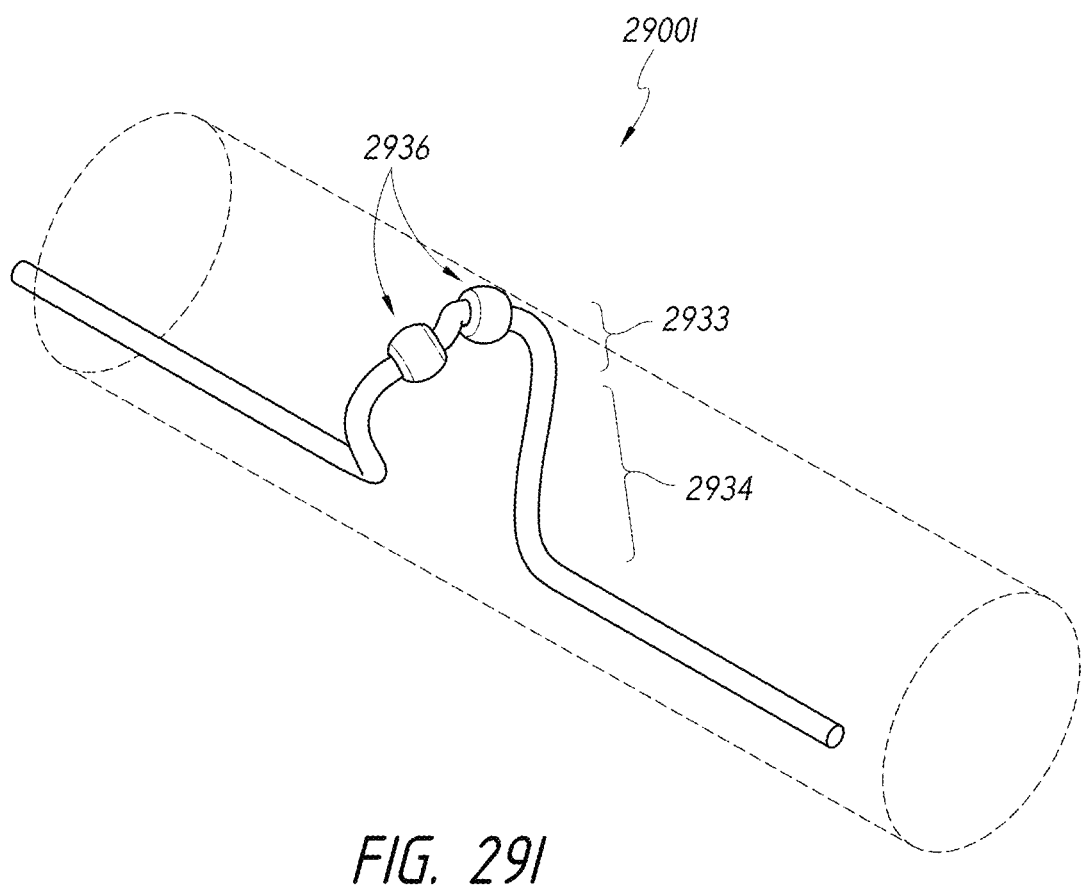

FIG. 29I illustrates an embodiment of a catheter shaft comprising two electrode members 2936 on a flexible, deflectable portion of the catheter shaft. The catheter shaft may also comprise one or more electrodes positioned at locations along the non-deflectable main shaft portion. In some embodiments, flush contact may be achieved by two spaced-apart electrode portions on the deflectable portion due to variability in the flexibility and/or material of the catheter shaft. The deflectable portion may comprise sub-portions or lengths having varying degrees of flexibility. For example sub-portions 2933 immediately adjacent (proximal and distal of) the electrodes 2936 may comprise a more-flexible portion than sub-portion 2934 extending from sub-portion 2933 to a non-deflectable main shaft portion. The various sub-portions of the deflectable portion may be specifically adapted and designed to cause the electrodes 2936 to contact the vessel wall in a straight, flush or substantially straight or flush manner.

In some embodiments, one or more additional electrodes may be positioned along the main shaft portion proximal and/or distal of the deflectable portion. The electrodes 2936 may comprise cylindrical or non-cylindrical electrodes (e.g., slotted, C-shaped, D-shaped electrodes). The deflectable portion may comprise shape-memory material (heat-set thermoplastic or a shape-memory metal or metal alloy) or may be controlled by one or more pullwires or other actuation members.

FIGS. 29J-1 and 29J-2 illustrate another embodiment of a self-deploying treatment catheter 2931. As with the embodiment of FIGS. 29G-1 and 29G-2, the treatment catheter 2931 comprises a shape-set portion 2932 configured to transition to a three dimensional shaped configuration upon retraction of an internal guidewire 2938. However, in this embodiment, the proximal electrode 2936A is not on the shape-set portion 2932, but positioned on the proximal portion 2937 of the main shaft. The distal electrode 2936B may be mounted on the shape-set portion 2932 such that when the shape-set portion 2932 is in its deployed configuration (FIG. 29J-2), the distal electrode 2936B is on the opposing side of the vessel. The shape-set portion 2932 may comprise a non-helical shape. For example, in one embodiment, the shape-set portion comprises a proximal longitudinal portion connected to a proximal portion of the catheter shaft, which transitions to a central oblique portion and then back to a distal longitudinal portion. The contact portions of the longitudinal and oblique portions may be configured to be 180 degrees offset from each other. As shown in FIGS. 29J-1 and 29J-2, the proximal electrode 2936A on the main catheter shaft is axially oriented or aligned (e.g., parallel with the longitudinal axis of the catheter or vessel) and the distal electrode 2936B is obliquely oriented or aligned (e.g., offset perpendicularly with respect to a longitudinal axis of the vessel or catheter shaft). As shown, the proximal electrode 2936A and the distal electrode 2936B may also be positioned so as to contact the vessel wall at locations offset circumferentially (e.g., 180 degrees offset). In one embodiment, an electrode may be positioned on the distal portion 2939 of the catheter shaft, either instead of or in addition to the proximal electrode 2936A. The shape-set portion 2932 may be formed by heat-setting or pre-stressing methods or techniques.

In accordance with several embodiments, the electrode(s) may advantageously be positioned on a side of a low-profile catheter (e.g., probe or shaft), thereby providing a longer segment of electrode contact with the vessel wall than a tip electrode. The side placement may allow for reduced catheter dimensions for equivalent energy delivery.

Figure 29K:
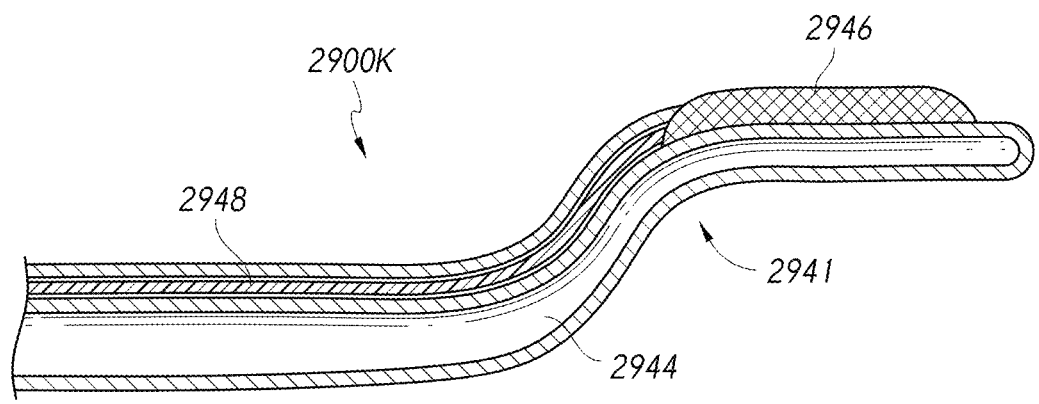

FIG. 29K illustrates an embodiment of an energy delivery catheter (e.g., shaft or probe) 2900K comprising a distal end portion 2941 having a pre-formed bend shape and comprising a side electrode 2946. The energy delivery catheter 2900K may comprise (1) a core wire 2944 having the pre-formed bend shape that is configured to transition to the pre-formed bend shape upon being advanced out of a sheath or catheter or (2) a hollow sheath having the pre-formed bend shape that is configured to be advanced over a guidewire and then "deployed" upon retraction of the guidewire. In some embodiments, the catheter 2900K comprises an insulating and/or protective layer between the core wire 2944 and the electrode 2946 and the electrode lead wire(s) 2948.

Figures 1, 29L:
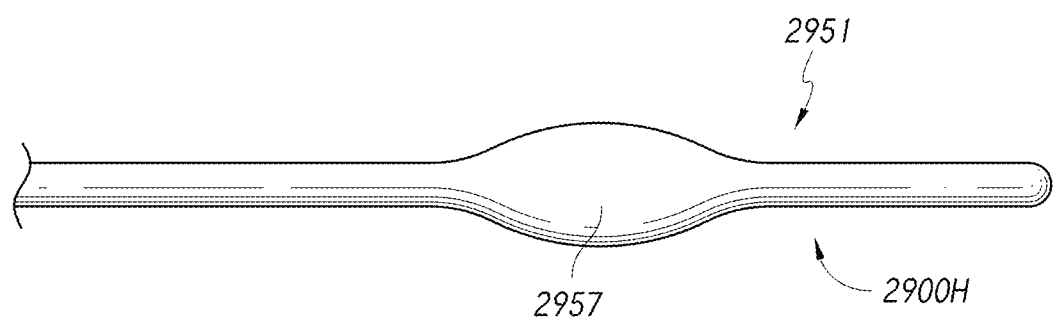
Figures 2, 29L:
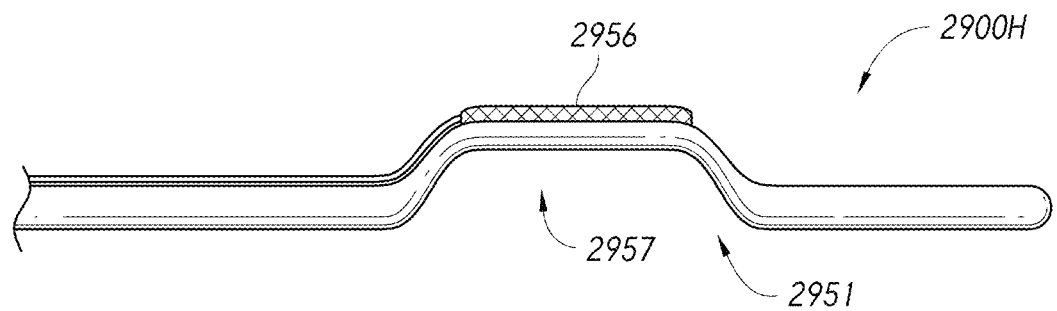

FIGS. 29L-1 and 29L-2 illustrate an embodiment of an energy delivery catheter (e.g., shaft, probe, or wire) 2900L comprising a distal end portion 2951 having a pre-formed bend shape and comprising a side electrode 2956. FIG. 29L-1 illustrates that a segment 2957 of the energy delivery catheter is flattened. The side electrode 2956 is positioned at a distance from a distal terminus of the distal end portion 2951 at the location of the flattened segment 2957. FIG. 29L-2 illustrates the pre-formed bend shape of the distal end portion 2951 that is heat- or shape-set during manufacture. The pre-formed bend shape facilitates contact of the side electrode 2956 with a vessel wall upon being advanced out of an outer sheath (e.g., guide extension catheter or guide catheter).

Figures 1, 29M:
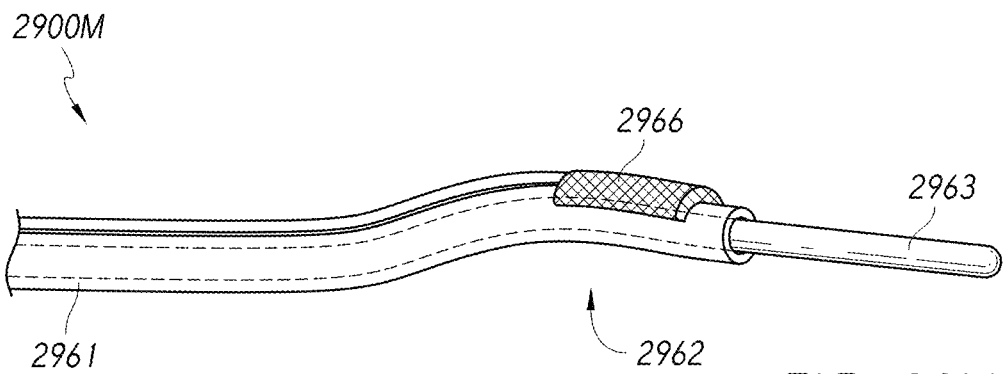
Figures 2, 29M:
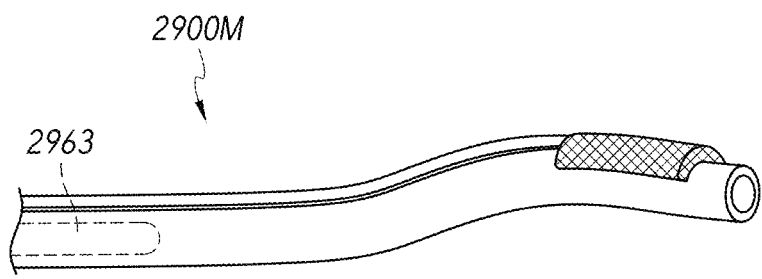
Figures 3, 29M:
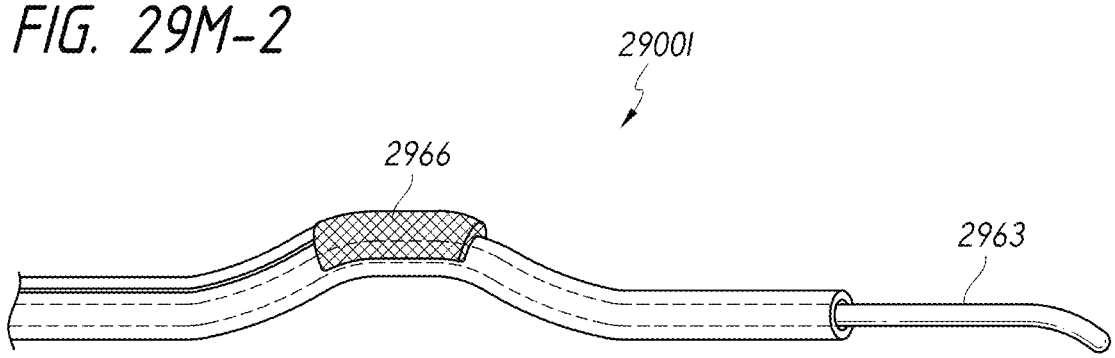
Figures 4, 29M:
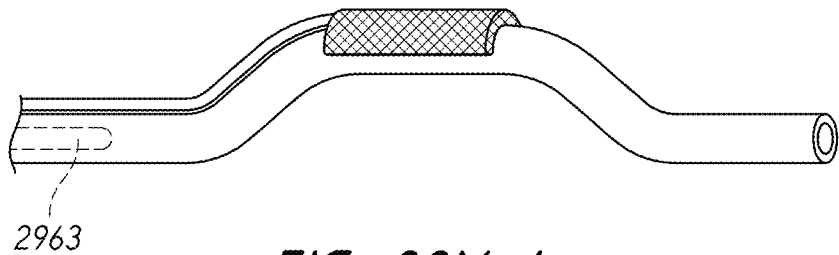

FIGS. 29M-1 to 29M-4 illustrate embodiments of an energy delivery system 2900M comprising a catheter 2961 having a distal end portion 2962 with a pre-formed bend shape or configuration and a side electrode 2966 and a guidewire 2963 (e.g., 0.014" wire). The distal end portion 2962 remains in a substantially straight configuration while being advanced over the guidewire 2963 and transitions to a "cobra-head" configuration upon retraction of the guidewire 2963, thereby causing the side electrode 2966 to contact the vessel wall. The side electrode 2966 is positioned at or near a distal terminus in FIGS. 29M-1 and 29M-2 and at a location spaced from the distal terminus in FIGS. 29M-3 and 29M-4. The guidewire 2963 can be re-advanced to straighten the distal end portion 2962 to facilitate removal of the catheter 2961.

Figures 1, 29N:
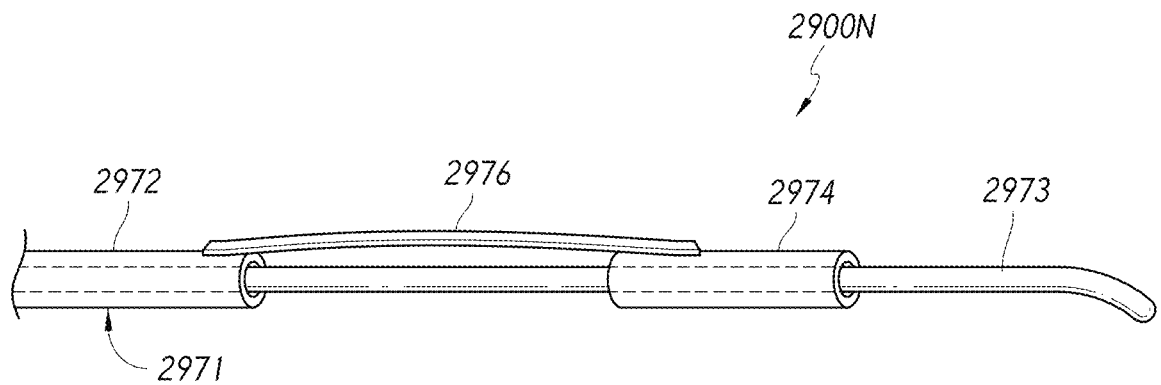
Figures 2, 29N:
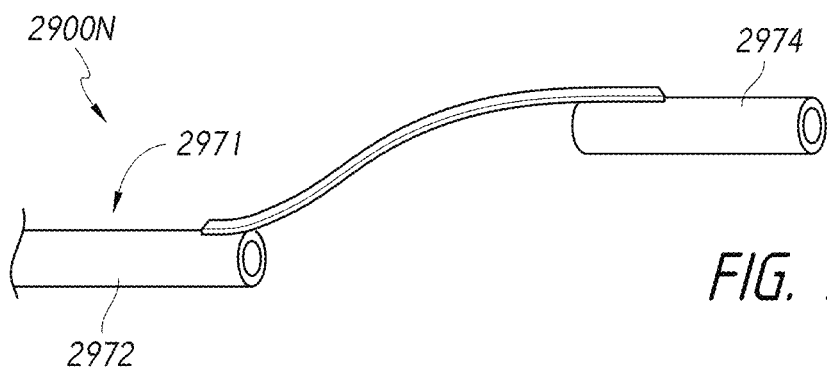

FIGS. 29N-1 and 29N-2 illustrate embodiments of an energy delivery system 2900N comprising a low-profile catheter 2971 and a guidewire 2973. The catheter 2971 comprises a main shaft 2972, a distal shaft tip 2974 and an electrode 2976. The proximal end of the electrode 2976 is coupled to the distal portion of the main shaft 2972 and the distal end of the electrode 2976 is coupled to the proximal portion of the distal shaft tip 2974. The catheter 2971 is advanced over the guidewire 2973 to a target treatment site within a target vessel. The guidewire 2973 may then be retracted, allowing the electrode 2976 to transition to a configuration in which the electrode 2976 contacts the vessel wall. The embodiment of the energy delivery system 2900N advantageously provides for lower profile at the electrode location.

Figure 29O:
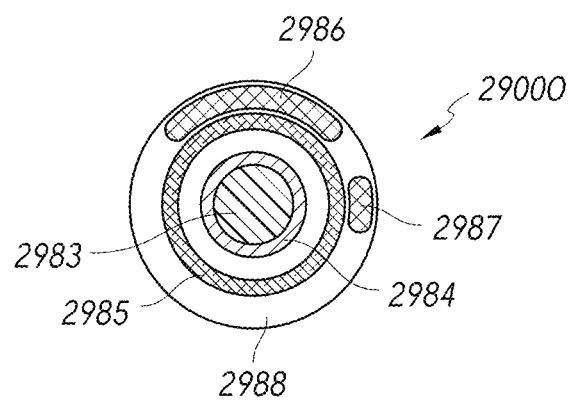

FIG. 29O illustrates a cross-section view of an embodiment of an energy delivery catheter 2900O. The catheter 2900O may be delivered over a guidewire 2983 such that at least a portion of the catheter 2900O having a shape-memory configuration remains in a substantially straight configuration. The catheter 2900O may comprise a central lumen 2984 configured to receive the guidewire 2983, a braided wall 2985 formed of shape-memory material (e.g., nitinol) extending along all or a portion of the catheter length, and an electrode 2986 and a temperature-measurement device 2987 (e.g., thermistor, thermocouple) embedded in an outer layer 2988 of the catheter 2900O.

Figure 30:
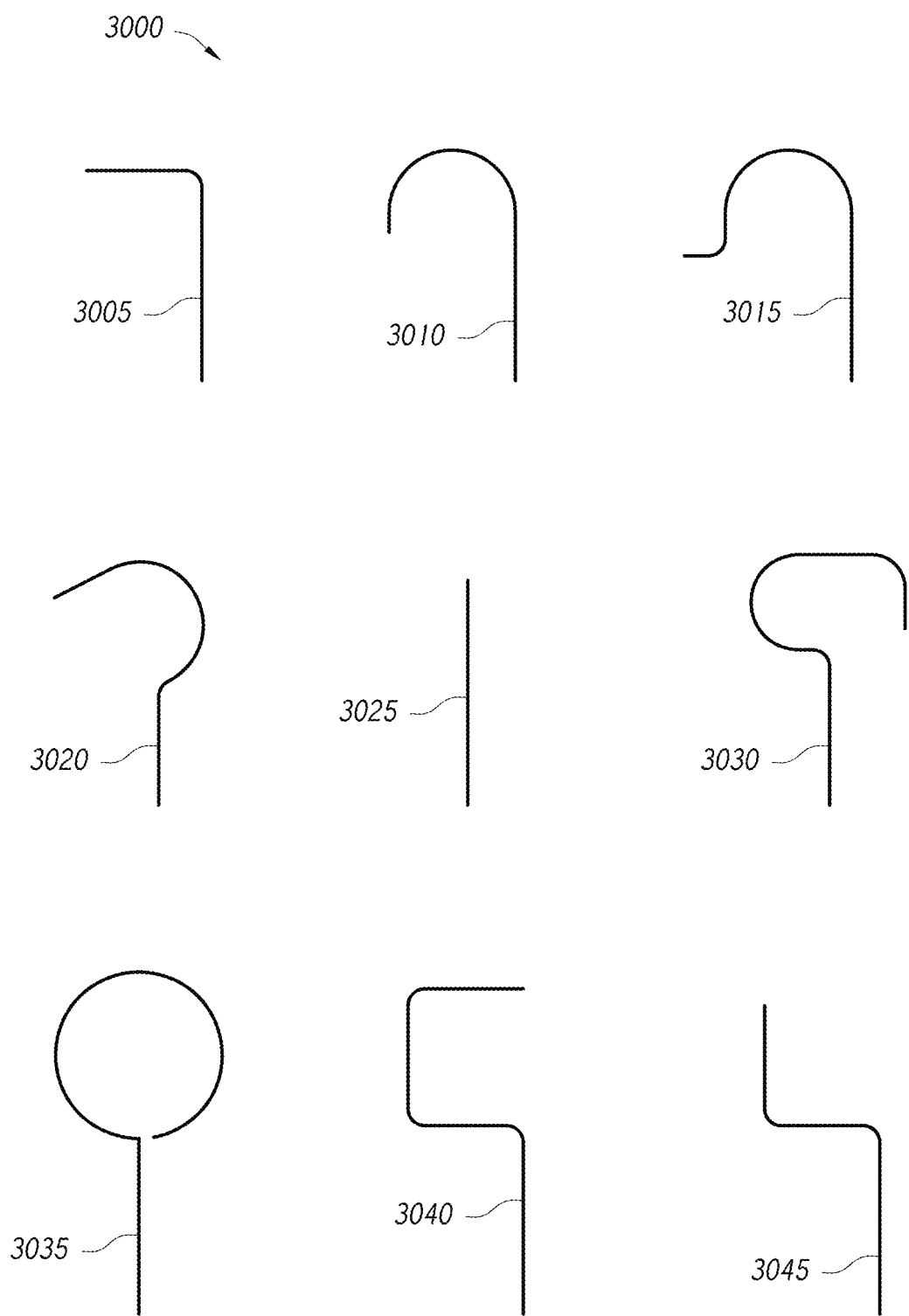
FIG. 30 illustrates several embodiments of catheter distal tip electrode and guide wire shapes.

FIG. 30 illustrates various embodiments of distal tip electrode and guide wire shapes 3000. The distal tip electrode and guide wire shapes 3000 may include an "L" shaped tip 3005, a "J" shaped tip 3010, a "shepherds crook"-shaped tip 3015, a "hook" shaped tip 3020, a "line" shaped tip 3025, a "key" shaped tip 3030, a "circle" shaped tip 3035, a "square hook" shaped tip 3040, or a "step" shaped hook 3045. A spiral-shaped tip (such as shown in FIG. 10A) may also be used. In one embodiment, a lasso-shaped tip is used. The lasso-shaped tip may have a similar configuration to the "circle" shaped tip 3035 but with the "circle"- or "lasso"-shaped tip portion being oriented substantially perpendicular to the straight line portion. The various shapes illustrated in FIG. 30 may advantageously be selected from and used in conjunction with the low-profile ablation catheter 2900 or other catheter devices to facilitate contact of electrodes or other energy delivery elements with the inner walls of arteries of the tortuous hepatic vascular anatomy (e.g., based on the particular vascular anatomy of the subject being treated or the particular vessels being treated). Any of the shapes 3000 shown in FIG. 30 may comprise a plurality of electrodes arranged in different patterns. The various distal tip shapes or designs may be provided in a kit and can increase the ability to treat the wide variety of hepatic artery anatomies or other target anatomies between subjects.

In some embodiments, the distal tip electrode itself, or a guide wire, may be partially or fully extended from an insertion catheter, to aid in navigation, thereby providing for a variety of tip curvature options for "hooking" vascular branches during catheter insertion. In some embodiments, shape-memory electrodes may be interchangeable by a clinician-user. For example, the clinician may select the most appropriate shape conformation for the patient's unique anatomy from a kit of different shaped devices, rather than being bound to a single device conformation or configuration. In one embodiment, the particular shape is selected based on angiography or other imaging modalities of the target treatment region. The various shaped tips may advantageously be selected to optimize the ability for the one or more electrodes or energy delivery elements to contact the target vessel due to the tortuosity and variability of the vascular anatomy at and/or surrounding the target vessel. The electrode assembly may also include a sensing element, such as a thermal sensing element (e.g., thermistor or thermocouple) to permit measurement of tissue temperatures and energy delivery during the treatment. The sensing element may provide feedback regarding confirmation of denervation or blocking of nerve conduction and/or regarding the contact force applied to the vessel wall and whether or not the contact force is sufficient to enable effective neuromodulation.

In accordance with several embodiments, once a particular shape is selected, forces (F) can be applied to the proximal end of the electrode to adjust the contact force F' against a vessel wall. In some embodiments, the degree of strain of the electrode distal portion is proportional to the force applied to the vessel wall. Radiopaque markers may be placed along the length of the inner electrode 1410 and the relative angle (between lines drawn between two of the radiopaque markers can be designed such that $F'=f(\phi(F))$. A clinician may then adjust the force on the proximal end of the electrode to achieve the desired contact force.

In some embodiments, electrode contact force and/or electrode articulation is provided through the use of electromagnetic elements disposed within the neuromodulation catheter (e.g., ablation catheter). As shown in FIGS. 31A and 31B, an embodiment of an ablation catheter device is comprised of at least an electrode 3115, a flexible shaft 3110, and a segment that is capable of carrying current and that is significantly close to the electrode to effect movement of the electrode in response to an applied magnetic field. In some embodiments, the ablation catheter device is positioned in a vessel and a magnetic field is applied through the vessel (for example, applied external to the patient). When the current is turned on, an electro-magnetic force is applied to the current-carrying segment per the Lorentz force law: $F=I\times B$. The location of the magnetic field may be moved so that the direction of the force (and hence the location of the applied force within the vessel) can be adjusted. The magnitude and the current or magnetic field may be adjusted to adjust the magnitude of the force. The direction of the current and magnetic field can be used to adjust the magnitude of the force, as the magnitude of a cross product is dependent on direction of the crossed vectors. In various embodiments, one or more current-carrying segments, one or more electrodes and/or one or more flexible catheter segments may be used.

Figure 32A:
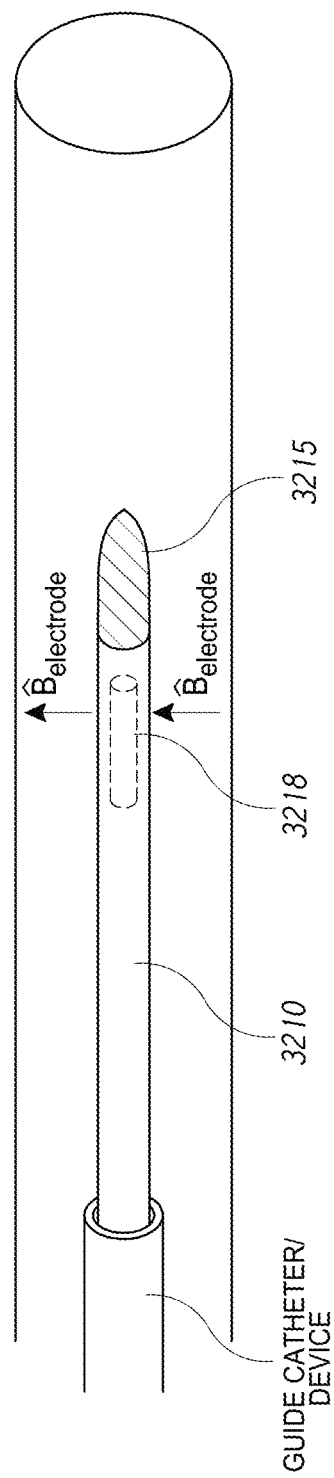
Figure 32B:
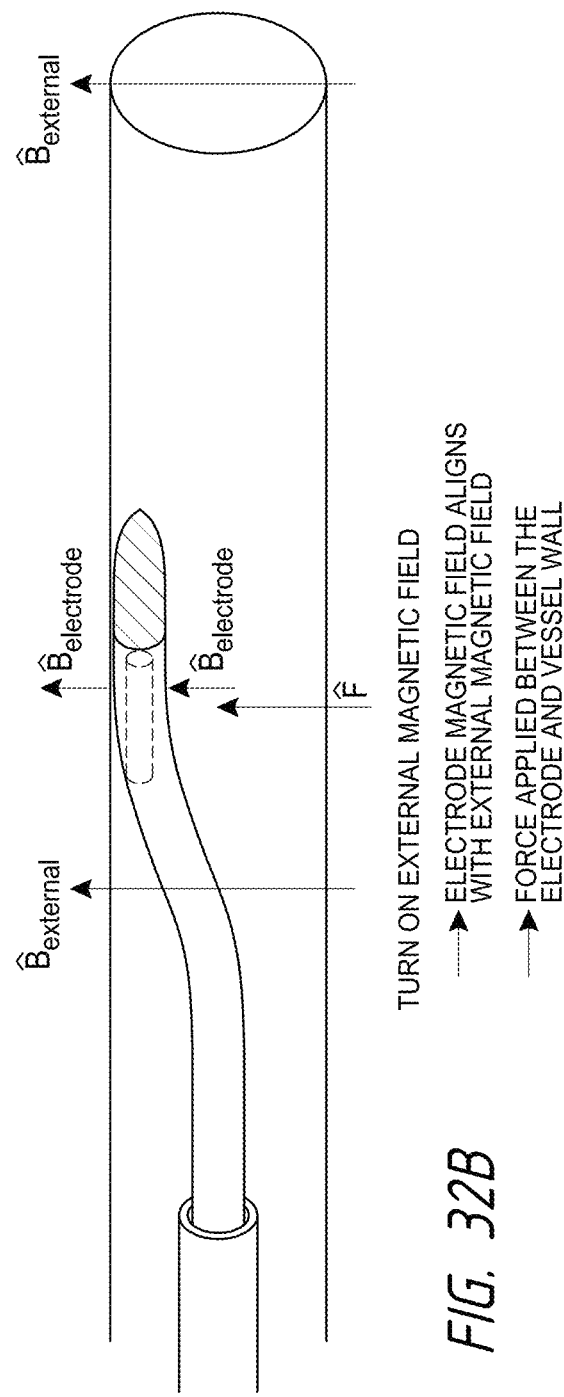

In one embodiment, shown in FIGS. 32A and 32B, a neuromodulation device (e.g., ablation catheter) is comprised of at least an electrode 3215, a flexible shaft 3210, and a segment or element 3218 that is capable of carrying a magnetic field (for example, a ferromagnetic material) and that is significantly close to the electrode to effect movement of the electrode in response to one or more applied magnetic fields. The ablation catheter device may be positioned in a vessel at a particular location and a magnetic field may then be applied through the vessel in conjunction with application of the magnetic field of the magnetic segment, thereby causing the opposite poles of the magnetic fields to attract. The location and/or direction of the magnetic fields may be moved to adjust the direction of the force. The magnitude of the magnetic fields may be adjusted to adjust the magnitude of the force. In various embodiments, the number of magnetic field-carrying segments may vary (e.g., one, two, three, four or more) and/or the number of electrodes and flexible catheter segments may vary (e.g., one, two, three, four or more). In some embodiments, the magnetic segment 3218 comprises a ferromagnet and/or electro-magnet.

With reference to FIGS. 33A and 33B, in some embodiments, a neuromodulation device (e.g., ablation catheter) is comprised of at least an electrode 3315, a flexible shaft 3310, and two segments or elements 3318 that are capable of carrying a magnetic field and that are significantly close to the electrode to effect movement of the electrode in response to one or more applied magnetic fields. In some embodiments, the two magnetic segments are configured to generate magnetic fields having opposite poles. The device may be positioned in a vessel at a particular target location. Magnetic fields may be applied through the magnetic segments, causing the opposite poles of the magnetic fields of the two magnetic segments to attract (e.g., magnetic fields align), thereby leading to at least one bending moment in the flexible shaft. As shown in FIG. 33B, multiple bends can be created in the distal portion of the catheter. The location and/or direction of the magnetic fields may be moved to adjust the direction of the force and/or bending moment(s). The magnitude of the magnetic fields may be adjusted to adjust the magnitude of the force and/or bending moment(s). In various embodiments, the number of magnetic field-carrying segments may vary (e.g., one, two, three, four or more) and/or the number of electrodes and flexible catheter segments may vary (e.g., one, two, three, four or more). In some embodiments, one or more of the magnetic segment comprises a ferromagnet and/or electro-magnet.

The embodiments illustrated in and described in connection with FIGS. 31 through 33 may advantageously allow a force to be applied directly to a segment of the ablation catheter device that is significantly close to the electrode(s), thereby improving control of the electrode(s) and control of the electrode-vessel force when the ablation catheter device is placed in a tortuous or otherwise difficult-to-navigate anatomy.

In some embodiments, a catheter having an outer diameter substantially matching the target vessel's inner diameter is used, thereby minimizing mechanical and footprint requirements for precise targeting. A catheter may be selected from a kit of catheters having various outside diameter dimensions based on a measured inner diameter of the target vessel. In some embodiments, the outside diameter of a catheter can be modified using spacers provided in a procedure kit. The catheter may be advanced through the patient's vasculature (the inner diameter of which may decrease as the target location nears). Once the catheter is advanced to the target vessel location, it may then advantageously engage the vessel wall with substantially uniform contact pressure about its circumference. In some embodiments, because application of energy to the entire circumference of the vessel is undesirable (due to the risk of stenosis) any of the designs herein disclosed that employ selective electrode placement or electrode "windows" are used, thereby allowing the delivery of energy in discrete locations about the vessel wall.

Figure 34A:
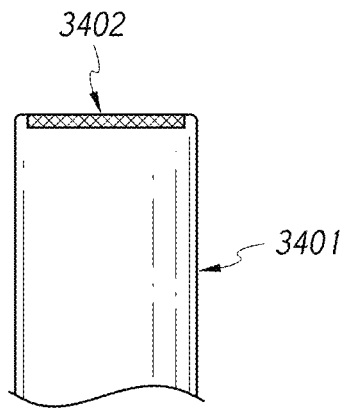
Figure 34B:
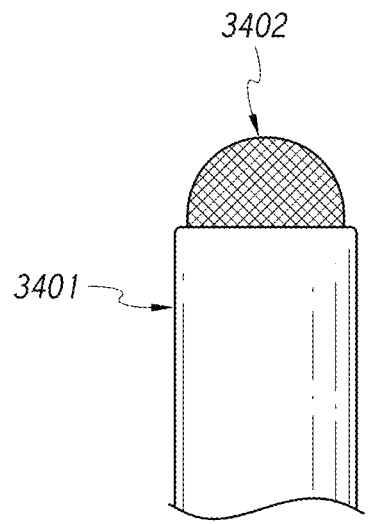
Figure 34C:
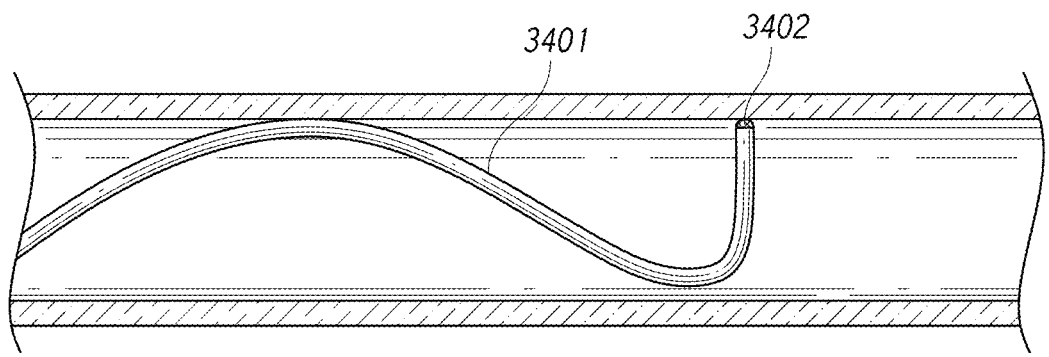

Turning to FIGS. 34A-34C, embodiments of an RF electrode ablation catheter (e.g., probe) 3400 are illustrated. The RF ablation catheter 3400 may comprise a tip electrode 3402 configured to contact a vessel wall provide more focused, more directed energy delivery to a target ablation site, thereby reducing circumferential heating of extraneous tissues and surrounding blood. The RF ablation catheter 3400 in FIG. 34A comprises a flat plate electrode and the RF ablation catheter 3400 in FIG. 34B comprises a semi-sphere electrode. With reference to FIG. 34C, the distal-most portion 3401 of the RF ablation catheter 3400 may be actuated to position a contact surface of the tip electrode flush or substantially flush with the vessel wall (e.g., such that the a longitudinal axis of the distal-most portion 3401 is perpendicular or substantially perpendicular to the vessel wall) by cantilevering off the opposite vessel wall (e.g., via one or more pull-wires and one or more flexible, steerable and/or shape-memory deformable portions of a main shaft 3402 of the RF ablation catheter 3400).

Figure 34D:
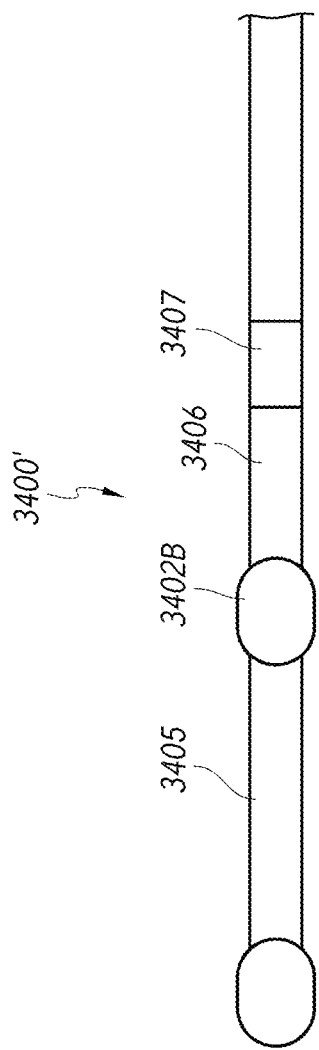
Figure 34E:
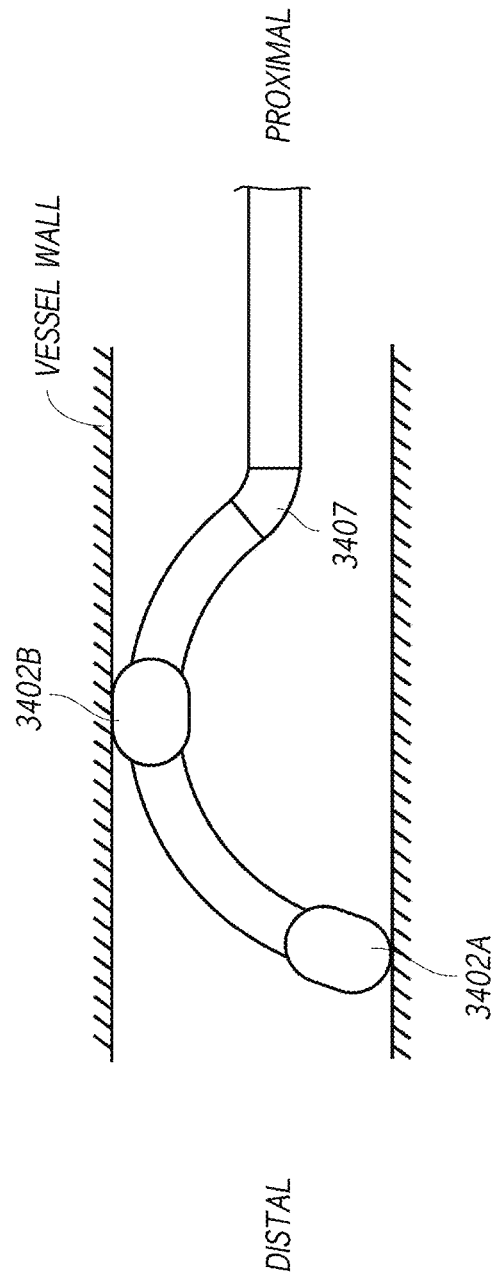

FIGS. 34D and 34E illustrate an embodiment of an RF treatment catheter 3400' comprising two electrodes 3402. A distal deflection region 3405 extends between the two electrodes 3402 and a proximal deflection region 3406 extends proximal of the proximal electrode 3402B. The deflection regions 3405, 3406 may be constructed of an articulating structure actuated by an internal deflection wire (not shown). The RF treatment catheter 3400' can be navigated to a treatment vessel (e.g., common hepatic artery) utilizing techniques described herein. When the electrodes 3402 are in a desired treatment position, the distal deflection segment 3405 is actuated into a curved shape, which presses the distal electrode 3402A toward a quadrant of the vessel lumen, thereby urging the proximal electrode 3402B to the opposite quadrant (side) of the vessel lumen (as shown in FIG. 34D). A flexible region 3407 extends proximal to the proximal deflection region 3406 to allow the catheter shaft further proximal to extend generally parallel to the vessel lumen rather than be forcibly apposed to the opposite wall. Distal and/or proximal electrodes 3402 may further include rounded surfaces, as shown, to maintain consistent and uniform contact with the vessel lumen, even when the electrodes 3402 are not lying parallel to the lumen surface. With both electrodes 3402 in the longitudinally spaced and diametrically opposed position, two treatment zones can be created without longitudinal or rotational manipulation of the catheter. Three or more treatment zones can be created with longitudinal manipulation and reactivation of the treatment catheter 3400'. The electrodes 3402 may be activated simultaneously or sequentially, or a single electrode may be activated. In some embodiments, the distal electrode 3402A is configured to contact the vessel wall in an oblique or generally perpendicular orientation and the proximal electrode 3402B is adapted to contact the vessel wall in a parallel orientation.

In one embodiment, the treatment catheter 3400' is of a "non-over-the-wire" design. In this embodiment, a wire lumen is not provided, and the distal electrode may simply have a closed off distal surface. Delivery of such a non-over-the-wire embodiment may be performed through a guide catheter positioned at the ostium of the celiac artery, or through a guide catheter positioned deeper, for example at the ostium of the common hepatic artery. The treatment catheter 3400' could alternatively be positioned in other vessel segments, and catheter delivery could be performed by placement of a guide catheter at the ostium of any appropriate vessel.

Figure 34F:
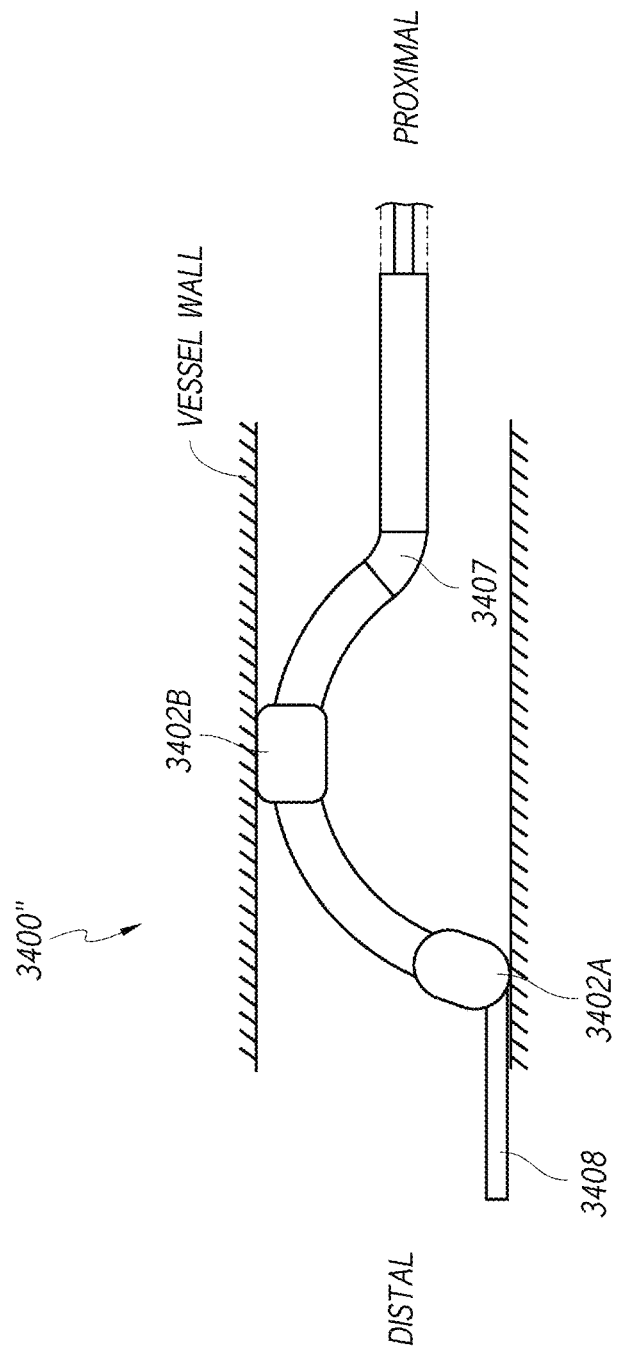

The embodiment of the RF treatment catheter 3400' illustrated in FIGS. 34D and 34E can also be of a "self-deploying" design. For example, instead of having active deflection regions, such regions can be pre-curved to attain the desired shape shown in FIG. 34E. The RF treatment catheter 3400" may comprise a lumen configured to receive a guide wire 3408. When utilized with an internal guide wire 3408 (as shown in FIG. 34F), the RF treatment catheter 3400" is relatively straight when the guide wire 3408 is advanced distally of the deflection regions. Upon retraction of the guide wire 3408, the "deployment" regions elastically self-deflect to the curved condition, thereby placing the electrodes 3402 in the spaced and opposing configuration. In use, the RF treatment catheter 3400" would be relatively straight due to the presence of the guide wire 3408. Once in a desired position, the guide wire 3408 may be retracted to allow the distal portion of the RF treatment catheter 3400" to take on the serpentine shape, which may place the electrodes 3402 against the vessel lumen for activation. The guide wire 3408 may be readvanced to reposition the catheter 3400" for subsequent treatments, or withdrawal of the catheter 3400" from the subject.

Figure 35:
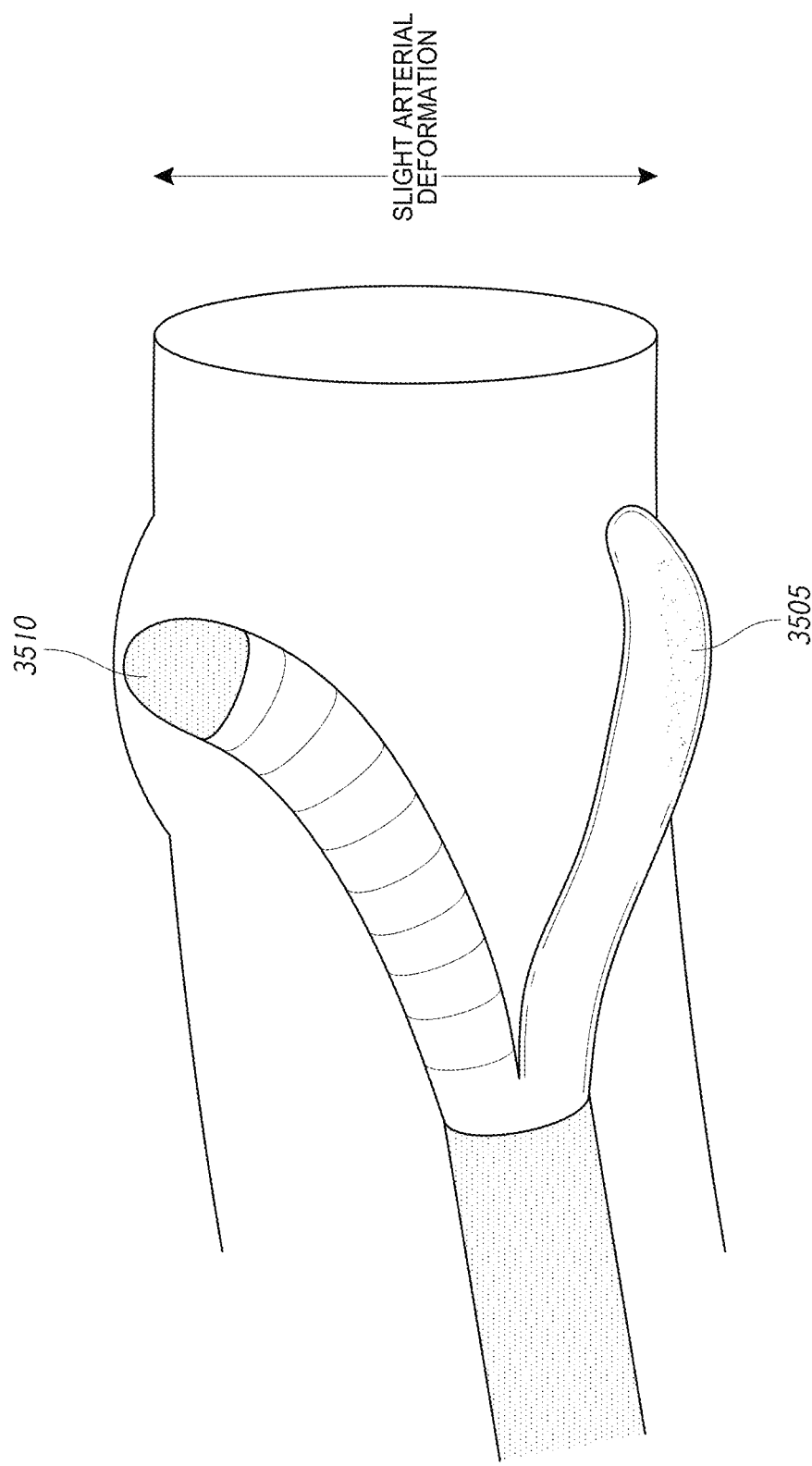

FIGS. 35, 36A, 36B, 37A, 37B, 38, 39, 40, 41A, 41B, 41C, 41D, 42A, 42B, 43A, 43B, 44, 45A, 45B, 46A, 46B, 47A, 47B, 53A, 53B, and 54A-54C illustrate embodiments of electrode catheters or catheter modifications configured to provide enhanced catheter stabilization and/or electrode contact with vessel walls at therapeutic target locations (e.g., within hepatic arteries). FIG. 35 illustrates one embodiment of an electrode catheter with a retractable stabilization segment 3505 configured to anchor to the inner wall of a vessel (e.g., artery), in the opposite direction of the electrode 3510. To provide friction, the stabilization segment 3505 may comprise an anti-slip surface. In one embodiment, the stabilization segment 3505 only protrudes or is deployed once in place so that the friction does not significantly affect the ability to insert the catheter. In one embodiment, the anti-slip surface is achieved by modifying the outer layer of silicone so that it is no longer smooth but has an array of longitudinal and transversal small size dents. The extensible stabilization segment 3505 presses into the arterial wall without poking a hole in it, as its tip extends parallel to the arterial wall, in order to distribute the stress on a larger surface. In one embodiment, the catheter with the stabilization segment causes at least a slight vessel (e.g., arterial) deformation as a result of the stabilization forces.

Because of the tortuous anatomy of the hepatic arteries or vasculature leading to the hepatic arteries or other vasculature, it may be difficult to apply a repeatable force to the electrode of an RF electrode catheter at various locations along the length of the artery. Cantilever flex catheters are catheters that apply a bending moment along a distal section of the catheter by compressing the inner arc with a pull wire. The bending moment moves the catheter tip towards the vessel wall. In order for the bending moment to apply a force through the catheter tip and into the vessel wall, a reactionary force must be applied at another section of the catheter. This reactionary force is likely between the catheter and vessel wall opposite of the catheter distal tip and through a segment of the catheter proximal to the distal tip. With tortuous anatomy and sharp bends, this "reaction force" may not be repeatable. Several embodiments of the devices, systems and methods described herein are configured to provide a repeatable and/or continuous contact force. In several embodiments of catheters and methods of use described herein, pulsatile contact is advantageously provided.

In one embodiment, instead of applying a moment at the distal tip and relying on a reaction force between the vessel and a proximal segment of the catheter, one could use a wire or ribbon to apply the reaction force closer to the bending moment and cantilevered tip. The objective is to create a reaction force (or multiple reaction forces) as close to the electrode contact as possible, thereby anchoring the distal region of the catheter relative to the vessel wall to provide a reaction moment against the flex mechanism (e.g., cantilever flex catheter) that applies the electrode into the vessel wall with a bending moment. Referring now to FIG. 36A, two openings are made in a cantilever flex catheter 3605 opposite of the location where the bending moment is applied (e.g., where a pull wire is attached to the catheter shaft) and a ribbon 3610 is threaded through these openings so that the ribbon 3610 is outside of the catheter 3605 between these two openings. The ribbon may 3610 be fixed to a point in the catheter 3605 that is distal to the most distal opening and able to be pushed at the proximal end of the catheter. When the ribbon 3610 is pushed, it moves out of the proximal opening and creates a loop. This loop is enlarged until it presses against the wall of the vessel opposite of the bending moment. An optional additional feature that may be added to reduce slack in the system (since the ribbon is being pushed, it will want to fill all of the empty space in the catheter) is a divider 3620 that runs along the length of the catheter 3605 and rests near the midpoint of the cross-section, as shown in FIG. 36B. Because the divider is at the cross-sectional midpoint in some embodiments, the divider would not significantly affect the catheter's flexibility towards and away from the ribbon 3610; therefore, the divider 3620 could run through the distal flex section 3608 without affecting the bending moment.

In various embodiments, modifications and improvements to the catheter of the sort described in connection with FIG. 36A may be made. For example, in one embodiment, instead of using a pull wire to create the bending moment at the catheter tip 3607, the ribbon 3610, which is pushed along the outer arc of the catheter 3605, could place the outer arc of the flex region in tension and create the bending moment. This embodiment would simplify the design by reducing the redundant pull wire.

In accordance with several embodiments, RF electrode treatment catheters may have one or more deployment segments that do not themselves carry the electrodes. FIG. 36C illustrates an embodiment of an RF electrode treatment catheter 3605 comprising two electrodes 3601. The electrodes 3601 are fixedly coupled to a main catheter shaft 3602 and a deflection segment 3610 extends between the two electrodes 3601 and is configured to deploy radially outward from a slot 3603 in the main catheter shaft 3602. Because the electrodes 3601 are fixedly coupled to the main catheter shaft 3602, their longitudinal position will remain stable, independent of the radial extent that the deployment segment 3610 is deployed. The deployment segment 3610 may be of a ribbon configuration, such as a metallic ribbon. The deployment segment 3610 may be deployed radially by advancing a proximal portion relative to the proximal catheter shaft. Alternatively, as best seen in FIG. 36D (which is a cross-section of FIG. 36C), the deployment segment 3610 may be deployed by relative retraction of an inner catheter 3604, to which a distal end of the deployment segment 3610 is coupled or secured.

The deployment segment 3610 may also have a pre-set shape in a radially extended shape, and can be "held" in a pre-deployment shape generally parallel to the catheter shaft 3602 during tracking of the treatment catheter 3605 to a treatment site. Once at or near the treatment site, the deployment segment 3610 can be allowed to self-deploy by relative advancement of a proximal portion relative to the proximal catheter shaft. A combination of self-deployment and active deployment is also contemplated. For example, the deployment segment 3610 may be pre-shaped to self-deploy to a certain radial distance from the catheter shaft 3602, but further relative advancement of the proximal portion of the deployment segment 3610 may extend it further radially.

Figure 61A:
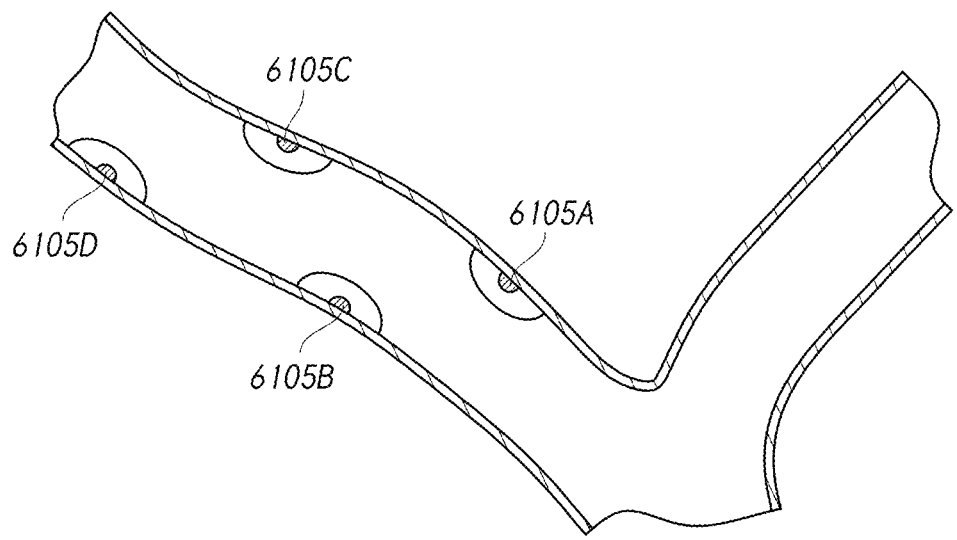

As both electrodes 3601 are mounted on the catheter shaft 3602, when the deployment segment 3610 is deployed, both electrodes 3601 will be on the same side of the vessel lumen. If both electrodes 3601 are activated simultaneously, two longitudinally spaced treatment zones will be created on one side of the vessel. If it is desired to create two longitudinally spaced treatment zones, but on opposite sides of the vessel, a single electrode may be activated (for example, the distal electrode). After that, the catheter 3605 may be rotated by torquing 180 degrees, then re-deploying the deployment segment 3610, and then activating a single electrode (for example, the proximal electrode). In one embodiment, this approach is referred to as a "leapfrog" approach. If it is desired to create more than two treatment zones, the catheter 3605 may be advanced or withdrawn to another longitudinal position, and the same steps above repeated. In some implementations, a total of 4 longitudinally-spaced treatment zones, alternating on opposite sides of the vessel lumen may be desired, as shown in FIG. 61A. Such a pattern of treatment zones can be created with the embodiment of FIG. 36C, by initially placing the catheter 3605 at a first location, deploying the deployment segment 3610 and energizing both the distal and proximal electrodes 3601. Then, the catheter 3605 is advanced or withdrawn a distance of approximately half the distance between the electrodes 3601, rotated, deployed, and both electrodes 3601 activated. In some embodiments, the catheter 3605 comprises a distal extension 3609 to facilitate trackability.

Figure 37A:
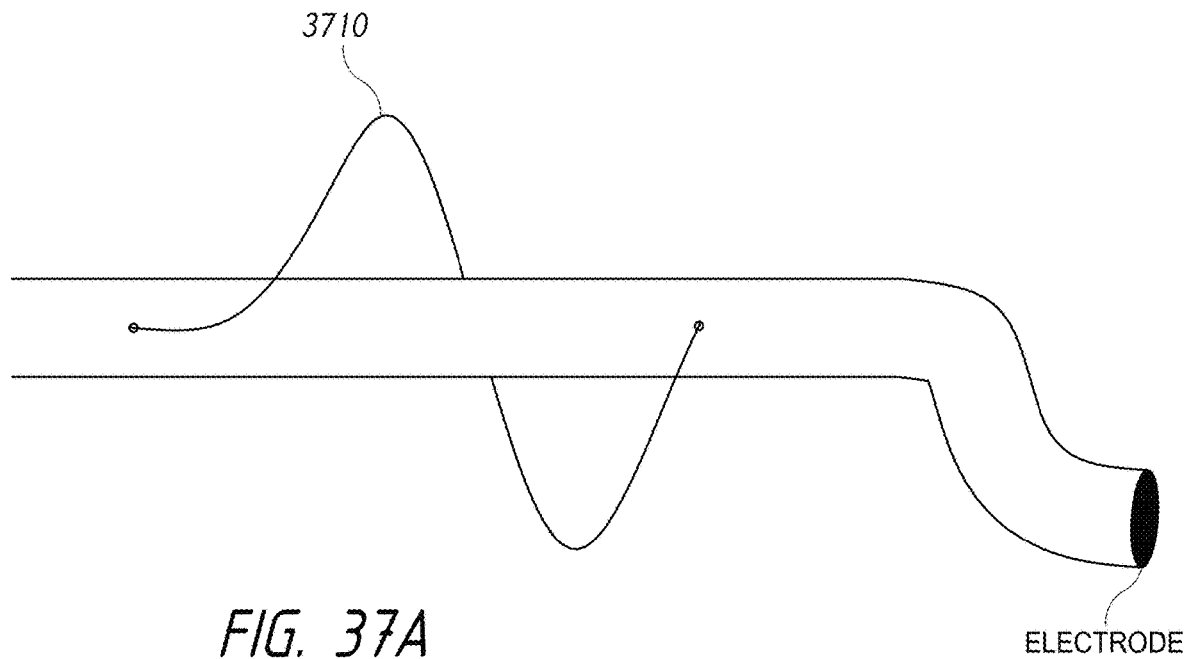
Figure 37B:
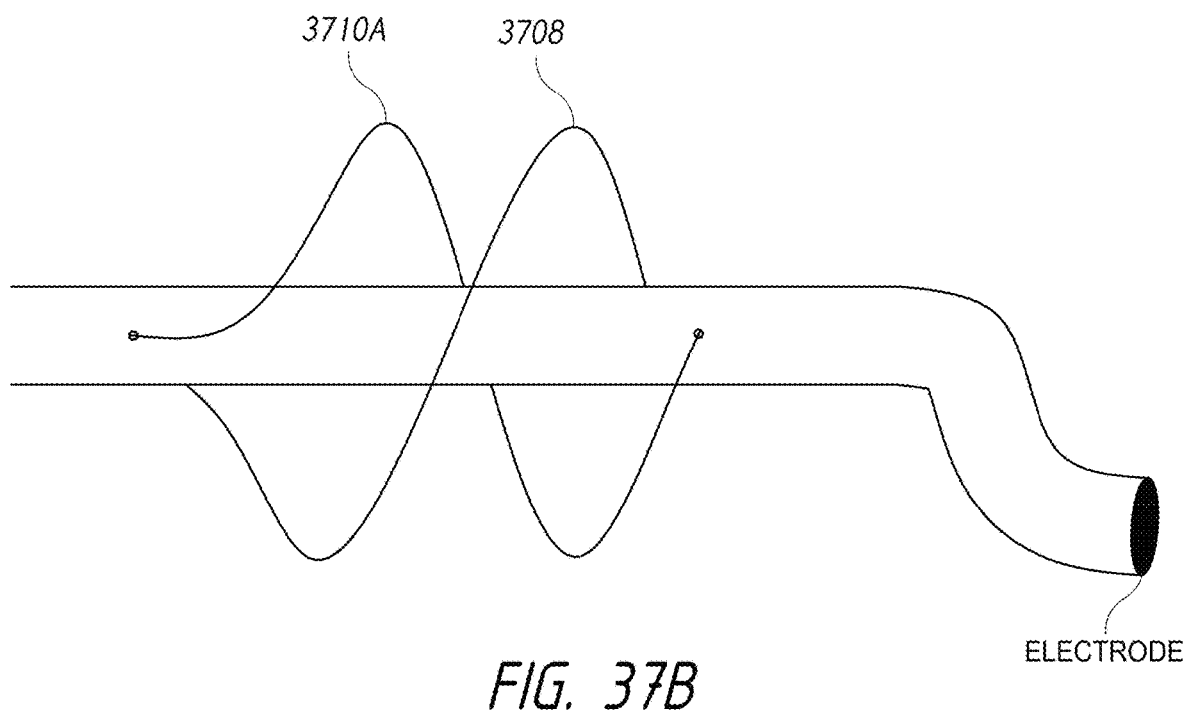

In some embodiments, multiple ribbons 3710 could be used as shown in FIGS. 37A-37D. These embodiments increase the number of contact points and increase catheter stability. In one embodiment, a balloon could be used alone or in combination with the one or more ribbons. FIGS. 37C and 37D illustrate an embodiment of an RF electrode treatment catheter 3705 similar to the RF treatment catheter 3605 of FIGS. 36C and 36D; however, the embodiment of the RF treatment catheter 3705 of FIGS. 37C and 37D comprises two deployment segments (upper deployment segment 3710A and lower deployment segment 3710B). This embodiment facilitates treatment of opposite sides of the vessel (e.g., formation of lesion zones offset by 180 degrees) without having to torque or rotate the RF electrode treatment catheter 3705. For example, the catheter 3705 may be advanced to a first treatment position and the upper deployment segment 3710A may be deployed to a deployed configuration such that the electrodes 3701 contact the vessel wall on the opposite side of the vessel. The lower deployment segment 3710B remains in an undeployed configuration. One or both of the electrodes 3701 may then activated to deliver energy to the vessel wall. In embodiments where ablative energy is delivered, one or two lesion zones may be formed at the first treatment position (depending on whether the electrodes are monopolar or bipolar and whether one or both electrodes are activated). The upper deployment segment 3710A is then transitioned to an undeployed configuration. The catheter 3705 may then be advanced or retracted to a second treatment position spaced longitudinally, or axially, from the first treatment position and the lower deployment segment 3710B may be deployed to a deployed configuration such that the electrodes 3701 contact the vessel wall on the opposite side of the vessel. One or both of the electrodes 3701 may then activated to deliver energy to the vessel wall. In embodiments where ablative energy is delivered, one or two lesion zones may be formed at the second treatment position (depending on whether the electrodes are monopolar or bipolar and whether one or both electrodes are activated) that are circumferentially offset from the lesion zone(s) created at the first treatment position. The embodiment of the RF electrode treatment catheter 3705 may be used to form 4 longitudinally-spaced treatment zones, alternating on opposite sides of the vessel lumen, as shown in FIG. 61A. In some embodiments, the catheter 3705 comprises a distal extension 3709 to facilitate trackability.

In one embodiment, instead of providing multiple contact points in a line along the circumference, one could create contact points (also shown in FIGS. 37A and 37B) that contact the vessel at different locations along the vessel's length and/or circumference. Creating multiple points separated by a distance may enable these points to resist a torque (because their applied force is separated by a distance).

The "ribbon" is not limited to a specific material or geometric configuration. For example, metallic, polymer, or shape memory materials may be used. In some embodiments, flat wires (ribbons) could be replaced with wires or any other geometry (e.g., cylindrical, triangular, rectangular, diamond).

In accordance with several embodiments, applying the "reaction force" closer to the bending moment and cantilevered tip reduces the length required to apply the electrode force when compared to a standard cantilever flex catheter, which may advantageously improve the repeatability of the applied "electrode force" in tortuous vessels. Moving reaction forces or contact points towards the electrode may also increase the stability near the electrode and reduce electrode movement during use. Increasing the normal force applied to the vessel may also increase the stability of the catheter electrode in the target anatomy.

Figure 38:
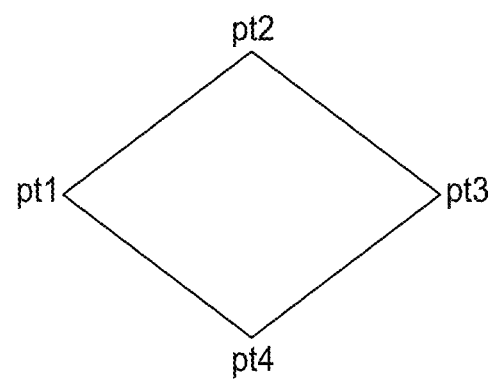
Figure 39:
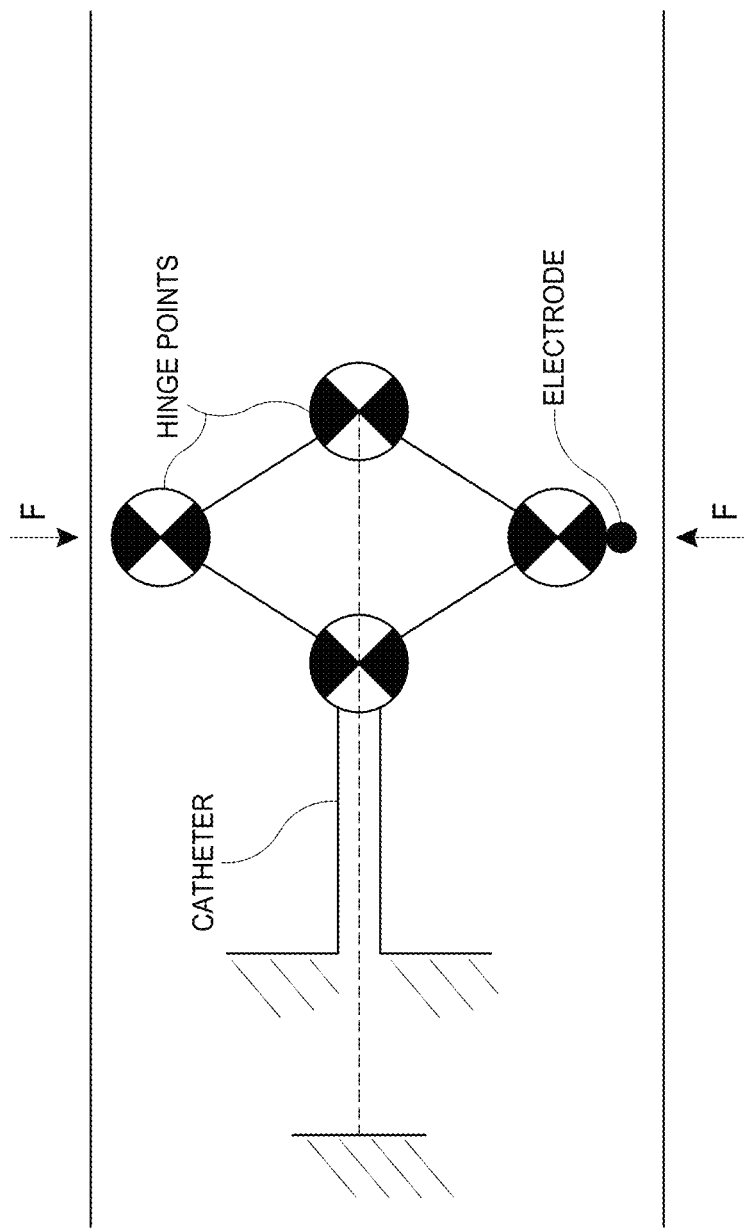

In some embodiments, instead of applying a moment at the distal tip of the catheter and relying on a reaction force between the vessel and a proximal segment of the catheter, one could apply the reaction force perpendicular to the electrode force (also interchangeably referred to as the catheter tip force). Referring now to FIG. 38, a structure comprising four hinge points connected by members resembling a square or parallelogram could be disposed at the distal end of a catheter. Assuming the members connecting these points have a constant length, if two opposite hinge points are pulled towards each other (e.g., pt1 and pt3) the other pair of opposite points will move away from each other (e.g., pt2 and pt4). In one embodiment, this opposing motion could be achieved by fixing pt1 against the distal end of a catheter and pulling pt3 towards pt1. The electrode can be placed at one of the other hinge points (pt2 or pt3) and both of these hinge points can apply a force against the vessel wall, as illustrated in FIG. 39.

Figure 40:
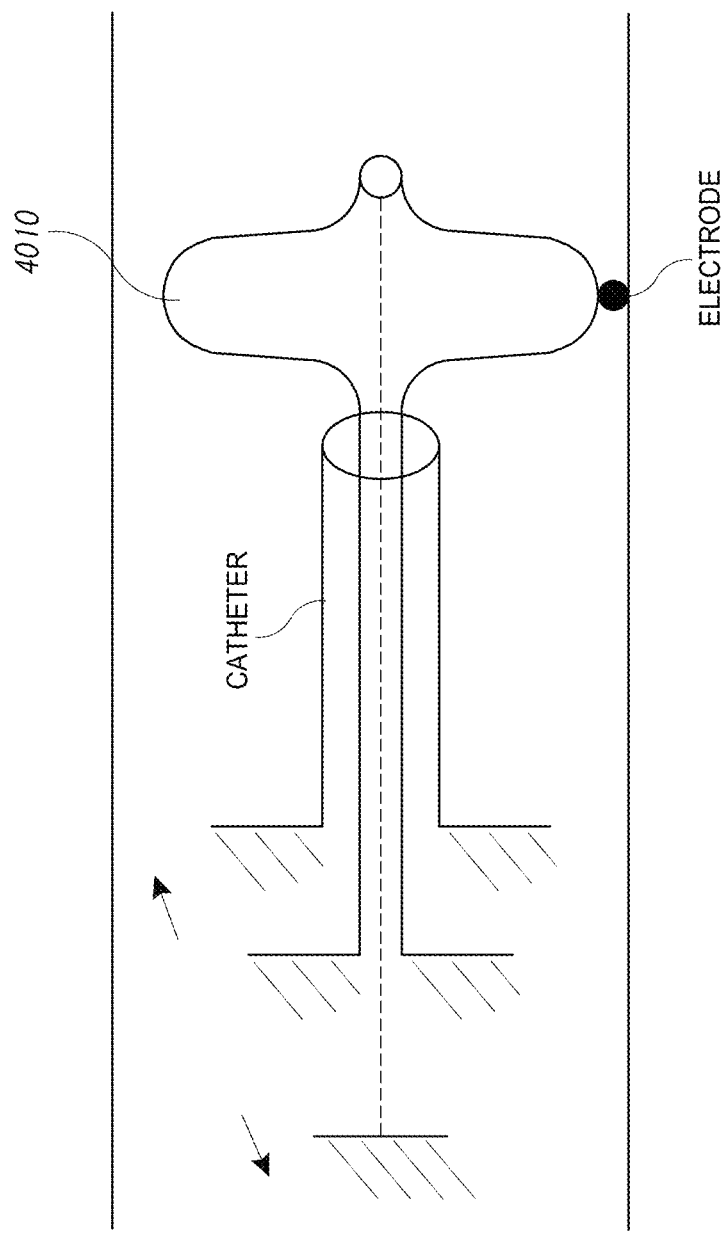

In one embodiment, as shown in FIG. 40, the hinge points comprise flexures (e.g., thin, flexible segments connecting larger segments) or the members and opposite hinge points (pt2 and pt4) could be replaced by a flexible, continuous length of wire or ribbon, forming "virtual" or "living" hinges. Using flexible ribbons 4010 may eliminate the need for explicit hinge points (pt2 and pt4) and it would also eliminate the need for explicit hinges at pt1 and pt3. Instead, pt1 could be an opening in the catheter and pt3 could be the bond point for the ribbons. In this embodiment, the electrode can be fixed on at least of one of the ribbons in a location substantially in contact with the vessel wall.

In accordance with several embodiments, the "reaction force" vector is opposite of (180 degrees from) the "electrode force" and the "reaction force" is applied at the same segment of the vessel as the "electrode force," thereby reducing the length required to apply the electrode force when compared to a cantilever flex catheter, and thereby improving the repeatability of the applied "electrode force" in tortuous vessels. Moving reaction forces or contact points towards the electrode may also increase the stability near the electrode and reduce electrode movement during use.

In another preferred embodiment illustrated in FIGS. 42A and 42B, a plurality of ribbons may be formed by cutting slits 4205 through the wall of a tube formed of flexible electronics, or electronic devices mounted on flexible plastic substrate, such as polyimide. For example, two layers of polyimide having a plurality of copper or silver leads (preferably at least one) embedded between the two layers can be rolled into a tube structure, defining a cylindrical structure. A plurality of openings (preferably at least one) can be cut into the polyimide layer comprising the outer surface of the cylinder to define individual electrodes 4215 that can be connected to a generator, including but not limited to an electrosurgical (RF) generator in either a monopolar or bipolar or multipolar fashion. To define the ribbons described previously, slits 4205 can be cut along substantially the longitudinal axis of the tube. The tube structure can be mounted on a catheter as shown in FIGS. 42A and 42B, with marker bands 4210 (e.g., radiopaque marker bands) defining the proximal and distal extents of the tube structure. In one embodiment, the ribbon or wire or like device (such as a thin nitinol ribbon) is jacketed with polyimide in a manner to provide the substrate to mount the flexible electronics. The nitinol or other higher modulus material, may provide integrity to an expandable structure while it is in the expanded and unexpanded states. In one embodiment, a guidewire housing is disposed at the distal end of the catheter, in communication with a lumen extending through substantially the entire length of the catheter. In one embodiment, the catheter device is passed or introduced over a locking guidewire 4220 containing a detent feature designed to interface with the guidewire housing, such that moving the guidewire and the catheter in opposite directions creates a compression force on the tube structure that causes expansion of the ribbons. The detent may be designed such that upon exceeding a maximum detent force, the locking guidewire 4220 is retracted into the guidewire housing. In this manner, this maximum contact force applied to tissue can be limited; for example, the detent force (and hence the force applied to tissue) can be controlled by varying the dimensional interference defined by an outer dimension of the detent feature and an inner dimension of the guidewire housing.

One particular advantage of the embodiment of the flexible circuit design described above is the ability to isolate the delivery of energy from the blood flow while still achieving the beneficial effects of convective cooling from the blood. Because of the high dielectric properties of flex circuit materials such as polyimide, polyether ether ketone (PEEK) or polyester, only a thin layer of material may be required to electrically isolate any one of the plurality of electrodes from the arterial blood flow, effectively limiting the amount of energy "lost" to the blood, and providing a more repeatable and measurable titration of electrical and thermal energy to the target tissues surrounding the artery. In some embodiments, the thin construction of the electrical isolation layer permits enhanced heat transfer from the electrode, through the isolation layer, and to the arterial blood to limit the temperature of the electrode, thereby advantageously allowing for higher power energy delivery, deeper ablations, and reduced treatment times, for example.

Referring now to FIGS. 43A and 43B, the force applied to the vessel wall may also be limited by a torque limiter 4305 in the handle of the catheter to deploy one or more ribbons of an expandable structure 4310. For example, the pull wire 4307 might be wrapped around the capstan of a torque-wrench mechanism having a pre-defined torque slip value.

In yet other embodiments, modifications and improvements to the catheter of the sort described in FIGS. 40-43 are provided. For example, in one embodiment, instead of using two ribbons (one to apply the electrode force, the other to apply the reaction force), multiple ribbons are used to apply the reaction force (e.g., 3, 4, 5, 6 or more contact points against the vessel wall). The "ribbon" is not limited to a specific material or geometric configuration. In various embodiments, metallic, polymer, or shape memory materials may be used. In some embodiments, flat wires (ribbons) could be replaced with wires or any other geometry (e.g., cylindrical, triangular, rectangular, diamond).

Figure 41B:
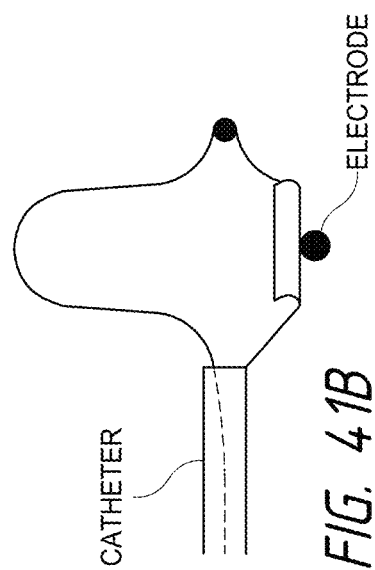
Figure 41A:
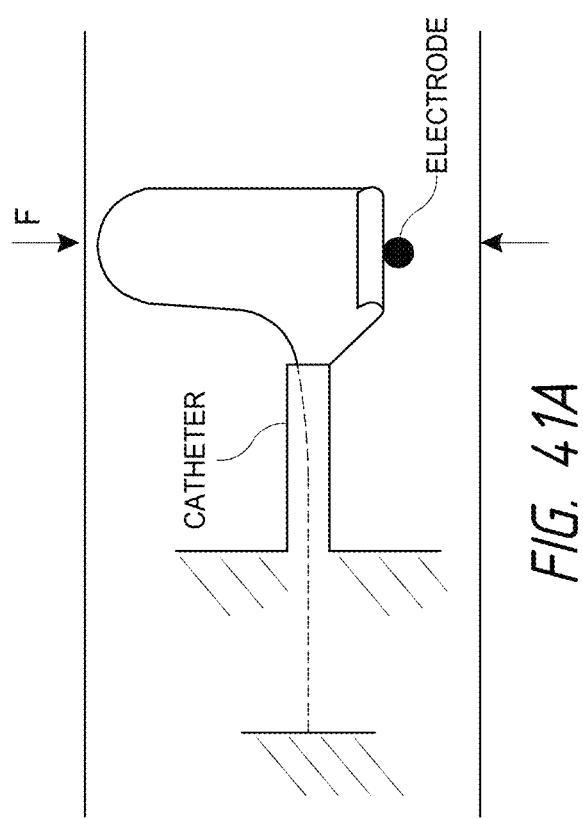

In various embodiments, a stage could be used to support the electrode, as illustrated in FIGS. 41A and 41B. The stage may be connected to pt1 (catheter end) with a flexible ribbon and it can act like pt3 (distal connection point for the other ribbon). In one embodiment, the stage could be connected to pt1 (catheter end) and a separate pt3 (distal connection point for the other ribbon) with a flexible ribbon.

Figure 44:
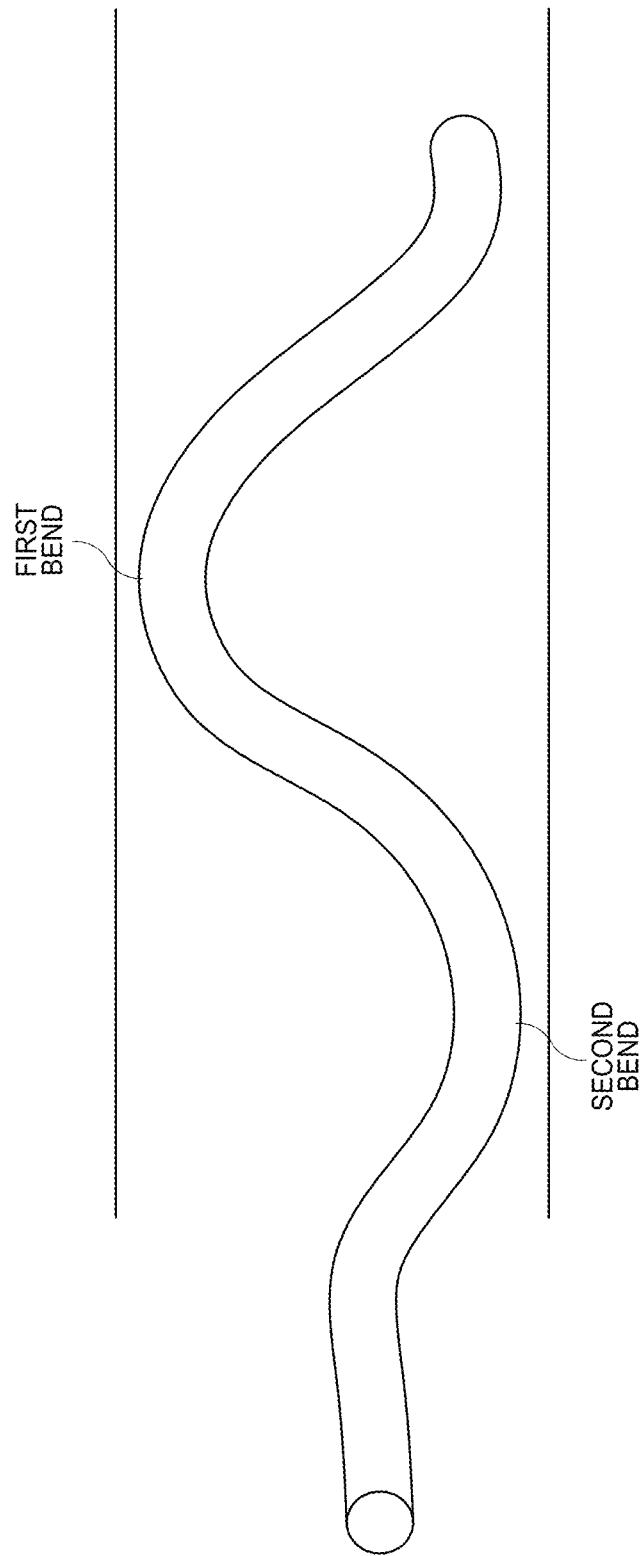

In one embodiment, instead of applying a moment at a distal tip of the steerable catheter and relying on a reaction force between the vessel and a segment of the steerable catheter, one could force the catheter to bend at specific locations (e.g., creating an s-curve) and/or apply larger reaction forces at multiple locations. Referring now to FIG. 44, multiple bending moments can be provided that force the catheter into the vessel and apply a force through the electrode to the vessel wall. The electrode(s) may advantageously be disposed at locations in contact with the vessel wall.

Figure 45A:
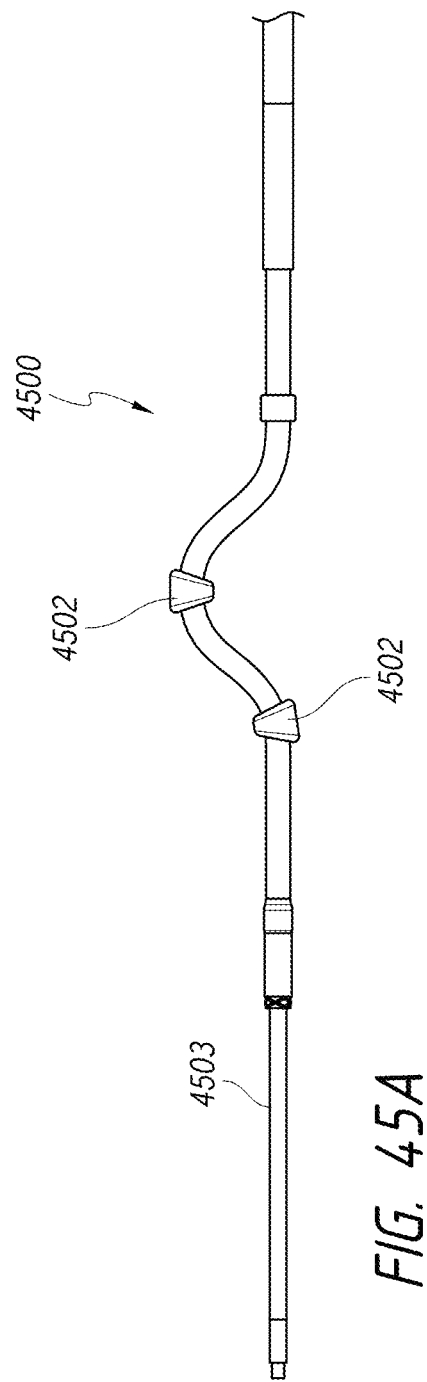

FIG. 45A illustrates an embodiment of a "self-deploying" catheter 4500 adapted to transition to a shape to facilitate contact of two electrodes 4502 spaced apart along a length of the catheter 4500 at treatment locations on opposite sides (e.g., 180 degrees apart) of a vessel wall. As shown, a distal portion of the catheter is shaped into a generally serpentine shape. The serpentine or otherwise curved shape extends laterally away from a generally longitudinal axis, creating an apex which defines a span dimension. Two electrodes 4502 may be positioned in the distal portion, one at or near the distal end of the curve, and one at or near the apex. The catheter 4500 may further include a guide wire lumen for use with a guide wire 4503. The lumen may be extended distally with a distal extension 4504, as shown, distal of the distal electrode to enhance trackability of the catheter. The distal extension 4504 may transition in lateral stiffness, being more flexible in the distal direction. In use, the guide wire may be retracted once the electrodes 4502 are in a desirable location so as not to hinder the deflection or create electrical anomalies during subsequent electrical activation of the electrodes 4502. It may be desirable for the stiffness of the extension 4504, even near the distal electrode, to be low enough to allow for the extension to flex easily away from the vessel wall when the catheter is in its deflected state. The distal extension 4504 may also incorporate kink resisting structures, such as a coil or braid to prevent kinking near the distal electrode. The distal extension 4504 may be constructed of an elastomeric material, such that if it does kink near the distal electrode, it can recover after the deflection is reversed.

Figure 45B:
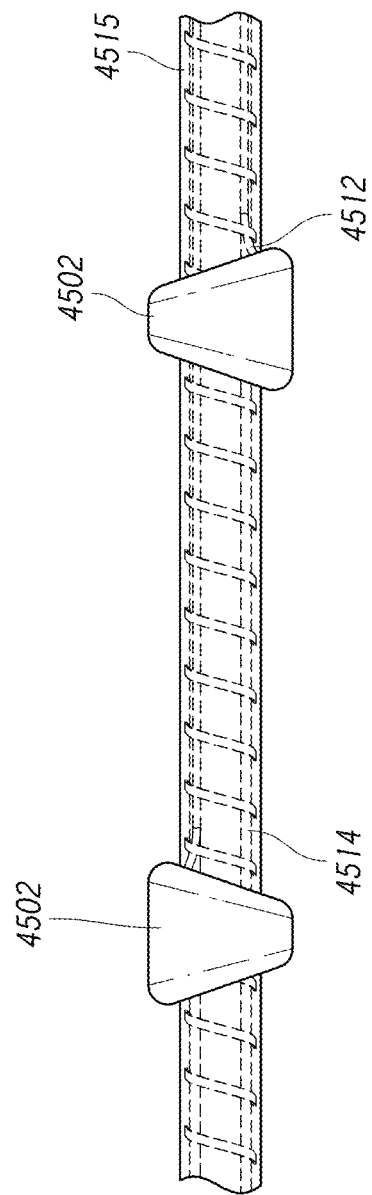

One or both of the electrodes 4502 may have a generally trapezoidal side profile, as shown in FIG. 45B. In order for the guide wire lumen to remain patent (e.g., not kinked or crimped), the serpentine shape preferably has smooth curves and not sharp curves. If the span desired for the serpentine shape is relatively large in comparison to the longitudinal spacing, the length of the electrodes 4502 is preferably relatively short to maximize the available length of the distal portion of the catheter 4500 to take on the serpentine shape. However, it may still be desirable for the electrodes to present a relatively large surface area to the contact the vessel wall. In accordance with one embodiment, a trapezoidal shape allows for reducing the impact on the serpentine shape of the catheter while presenting a relatively large surface to the treatment vessel lumen. Any embodiments of treatment catheters or devices including electrodes described herein may incorporate a trapezoidal shape for one or more of the electrodes.

One or both electrodes 4502 may be configured with an inner cavity or hole to facilitate mounting of the electrode 4502 to the catheter shaft while retaining a substantially cylindrical outer aspect. In some embodiments, this cavity or hole may be placed eccentrically so that the contact surface of the electrode lies farther from the catheter axis. FIG. 45B also shows additional elements that may be incorporated into any of the embodiments of treatment catheters or devices having electrodes described herein. Each electrode may have a lead wire 4512 connecting to it. One or both electrodes 4502 may have thermocouples or other temperature sensors connected to them. If an electrode has a temperature sensor connected to it, one of the lead wires of the sensor may actually be used to power the electrode as well. Additionally, an internal lumen for use with a guide wire may be provided. The lumen may be formed from an internal tube 4514. One or more electrodes may be mechanically coupled or secured to an outer tube 4515. A coil structure 4516 between the inner tube 4514 and the outer tube 4515 may be provided for some or all the length of the catheter to provide kink resistance, and may also be preshaped in the serpentine shape. FIG. 45B shows the distal portion of the treatment catheter 4500 in a straight configuration, such as when an internal guide wire (not shown) is present.

Figure 46A:
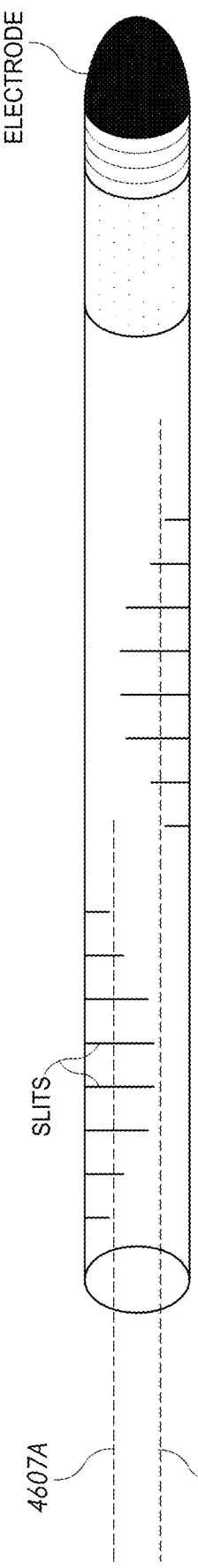
Figure 46B:
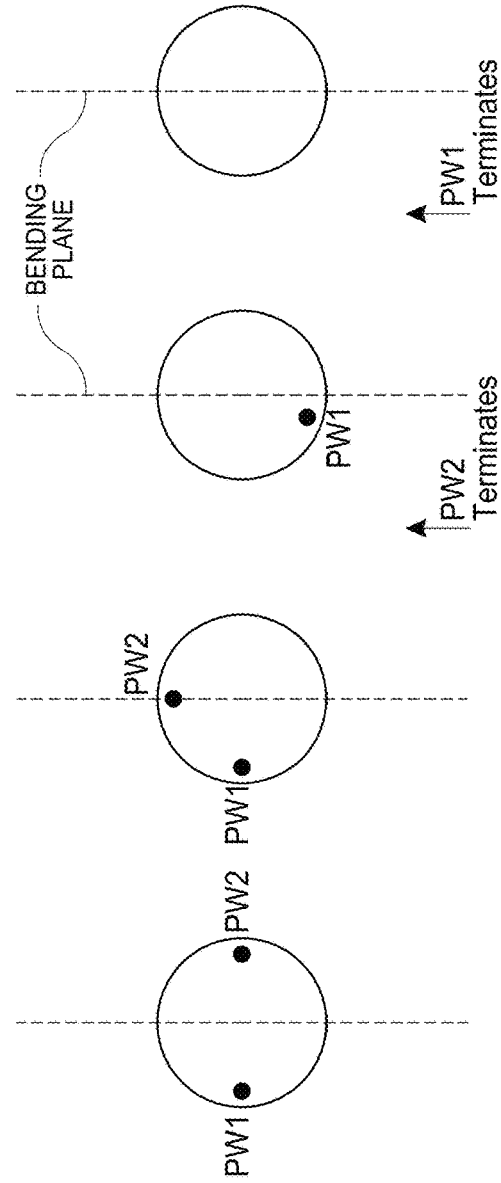
Figure 47A:
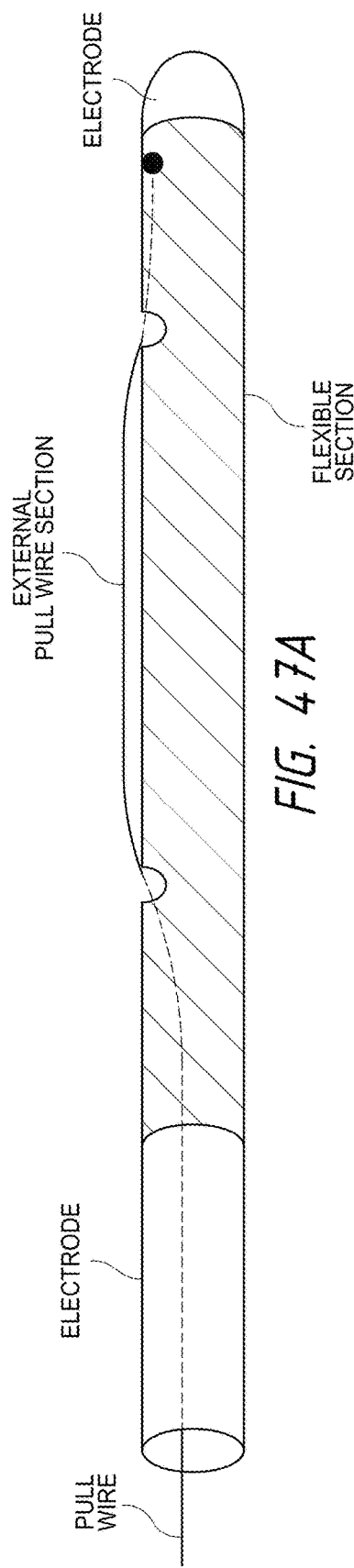
Figure 47B:
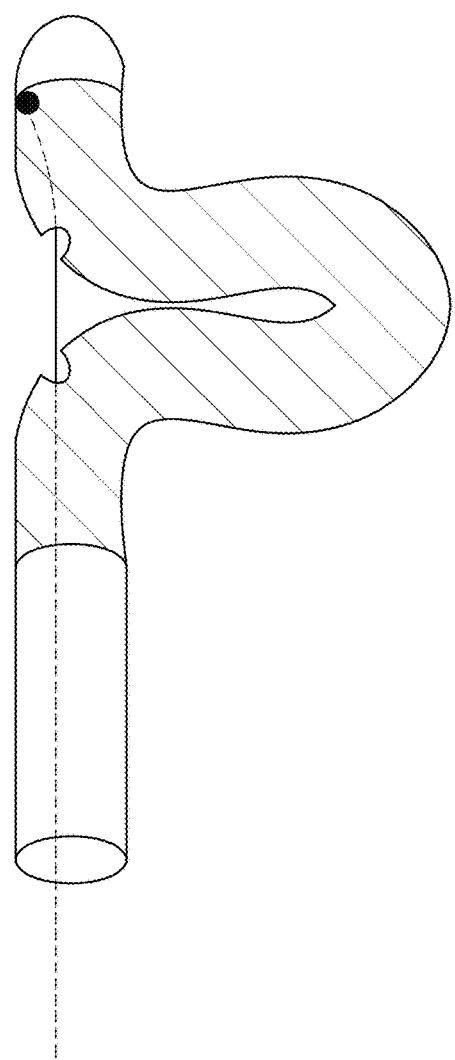

FIGS. 46A and 46B illustrate one embodiment of a catheter having an s-curve (e.g., having two bends). A hypotube-supported catheter may be laser cut (as shown in FIG. 46A) to create two highly flexible sections close to the distal tip and the electrode. In one embodiment, the two sections are separated by a distance and are offset by 180 degrees or about 180 degrees, such that the two sections bend opposite of each other and within the same plane. For example, the two sections can facilitate 180-degree articulation of the catheter. In one embodiment, two pull wires 4607A, 4607B run down the length of the catheter (see FIG. 46B), perpendicular to the bending plane until they each reach their corresponding flexible section. Through a pull wire's flex section, the pull wire runs in the bending plane and along the catheter wall with the flex cuts. The pull wire may then be bonded to the catheter shaft (e.g., just distal to its flex cuts). Orienting the pull wires in this manner may advantageously prevent or inhibit opposing forces from each pull wire that would otherwise resist multi-segment, multi-direction flexing.

In various embodiments, modifications and improvements to the device (e.g., catheter) of the sort described in FIGS. 40-43 may be made. For example, some embodiments may comprise one or more of the following:
1. Instead of using two pull wires, one pull wire could be used to cause both bending moments (e.g., compression of the inner arc length of each bend). Causing both bending moments with a single pull wire can be performed, for example, by placing the pull wire in a spiral pattern along the inside of the catheter and orienting the pull wire with the flex cuts or, alternatively, one pull wire could run loosely within the catheter until the location of the flex cuts, where the pull wire would enter through loops connected to each of the flex cut sections.

2. Instead of using the single pull wire to compress the inner arc length of each bend, one pull wire could pass outside of the catheter through a hole, extend outside of the catheter lumen along a section of the catheter length, and then re-enter the catheter lumen through a second hole (see, for example, FIGS. 47A and 47B). In one embodiment, the pull wire is fixed distal to both holes and can be pulled by a mechanism proximal to both holes. The catheter may have a flexible region at least extending proximally and distally from the holes. Upon pulling the pull wire, the two holes may move towards each other, thereby causing the catheter to bend in an arc away from the holes.
3. Multiple flex sections (>1, >2, >3, >4) could be used to improve stability and apply force through the electrode with more repeatability.
4. Instead of bending in one plane (because the flex cuts are oriented 180 degrees apart), the catheter could bend in multiple (e.g., two, three, four or more) planes. In one embodiment, the catheter bends into a helical shape (e.g., a pigtail or corkscrew shape).
5. In one embodiment, the catheter could be cut or configured so that pulling a distal point of a pull wire would cause the catheter to elastically collapse into a coil or helical shape. Once the tension in the pull wire is released, the catheter may elastically straighten out.

FIGS. 48A-48C illustrate embodiments of a catheter 4800 having a longitudinal axis and an internal lumen disposed about a substantial portion of the longitudinal axis. In the illustrated embodiment, an electrode 4805 is disposed at a distal tip or towards the distal end of the catheter 4800, with a resiliently deformable region 4810 disposed proximal to the electrode 4805, a deflectable or articulatable region 4815 disposed proximal to the resiliently deformable region 4810, and a torsionally-rigid but flexible region 4820 (torsionally rigid in at least one rotational direction) disposed proximal to the deflectable region 4815. The remaining length of the catheter 4800 (proximal solid tubing portion 4825) may be substantially torsionally and flexually rigid. The catheter 4800 may comprise a hypotube with the resiliently deformable region 4810 and the deflectable region 4815 having a spine cut pattern and the torsionally-rigid but flexible region 4820 having a spiral cut pattern (interrupted or continuous).

Figure 49:
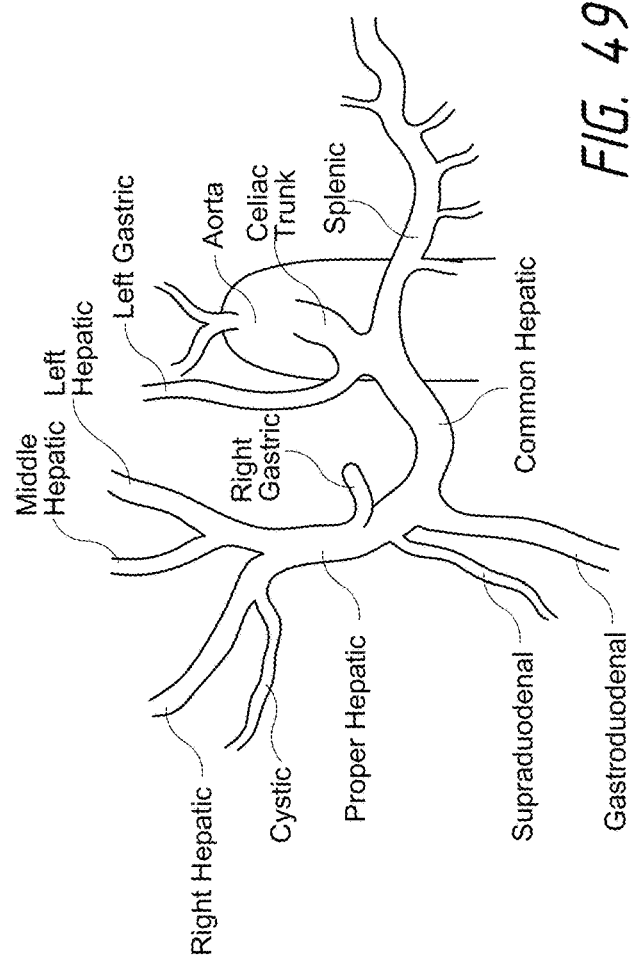
FIG. 49 is a schematic illustration of arterial branches that may be targeted by the methods, devices and systems described herein.

The dimensional characteristics of each catheter region may be tailored to the specific anatomy targeted for the neuromodulation. For example, the catheter 4800 may be used to access any portions of the arteries illustrated in FIG. 49. In one embodiment, the catheter 4800 is configured to access and modulate nerves surrounding (e.g., within a wall of, such as within the intima, media or adventitia of, or within the perivascular space around) the common hepatic artery. Treatment of the common hepatic artery can be particularly difficult due to the tortuosity and routing variance of the vasculature in this region. In one embodiment, the diameter of the electrode 4805 is 2 mm (6 Fr) with a length of 2 mm, though other combinations of electrode diameter (e.g., 0.5-1 mm, 1-1.25 mm 1-1.5 mm, 1.5-2 mm, 2-2.5 mm, 2.5-3 mm) and length (e.g., 0.5-1 mm, 1-1.25 mm, 1-1.5 mm, 1.5-2 mm, 2-2.5 mm, 2.5-3 mm) may be desirable. In order to provide and maintain an effective contact force (such as the contact forces and pressures described herein) and cantilever support, the length of the resiliently deformable region 4810, in one embodiment, is covered with a reflow polymer (e.g., 40D Pebax® of 35D Hytrel®, 0.042"OD×0.038" ID and between 0.250" and 0.350" in length (or alternatively, 30 mm±1 mm in length)). In one embodiment, the catheter 4800 is configured to repeatably apply an effective contact force or pressure (e.g., 0.1-100 $g/mm^2$, 0.1-10 $g/mm^2$, 5-20 $g/mm^2$) to the inner wall of the common hepatic artery. The resiliently deformable region 4810 may be designed to provide the cantilever support to provide a consistent and effective contact force or pressure. The catheter 4800 may be used to deliver 8-14 Watts of power (e.g., 8 W, 10 W, 12 W) for 1 to 4 minutes (e.g., 1 minute, 90 seconds, 2 minutes, 150 seconds, 3 minutes) to deliver energy between 480 J to 2520 J (e.g., about 1 kJ, about 1500 J, about 2000 J) at each ablation or heating location.

Figure 50:
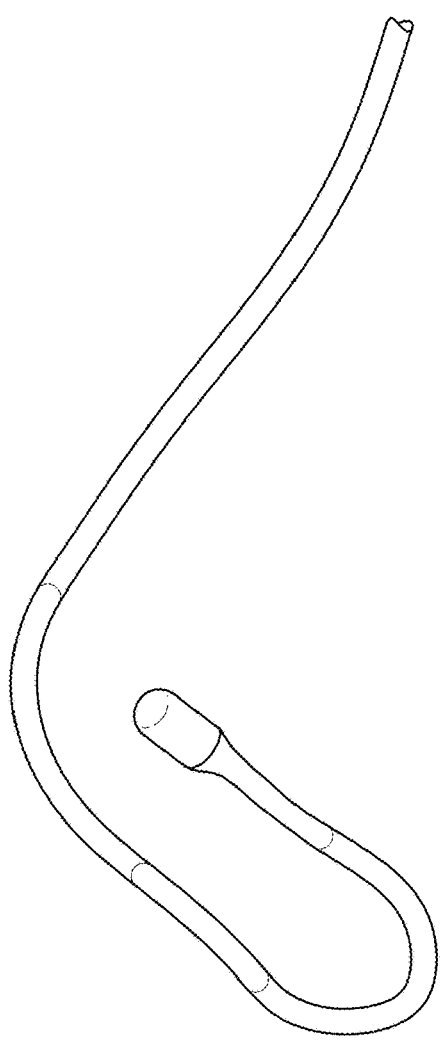
FIG. 50 illustrates an embodiment of a catheter configured to facilitate 180° articulation within vasculature.

In order to facilitate contact in the tortuous anatomy of the common hepatic artery or other arterial branches, increased ranges of deflection may be required in some embodiments, in contrast to relatively straight vascular beds such as the renal artery, where 90 degrees (by definition) is the minimum required deflection required to deflect a line off of its longitudinal axis to a point directly perpendicular to the longitudinal axis. In regions of increased vascular curvature or tortuosity (such as the vasculature proximate or within the common hepatic artery), the required deflection angle may be 90 degrees plus an amount proportional to the radius of curvature of the vessel. For example, in one embodiment, the deflectable or articulatable region 4815 is capable of 180 degrees of deflection, as shown in FIG. 50. The 180 degree deflection may advantageously improve the coupling of reaction forces between the electrode to tissue contact surface (defining an electrode to tissue contact force/pressure) and deflectable region segment to tissue contact surface. The coupling of reaction forces can serve to prevent or inhibit motion of the distal catheter region within the hepatic artery during diaphragmatic motion. In some embodiments, in order to ensure that the deflectable region 4815 can reliably remain wholly within the length of the common hepatic artery, thereby providing the appropriate contact force or pressure, the length of the deflectable region 4815 plus the resiliently deformable region 4810 is less than 2 cm or other length corresponding to the mean common hepatic artery length (which, from studies has been determined to be 27 mm±8.5 mm) minus one standard deviation, thereby ensuring that the majority of common hepatic artery anatomies will be accessible by the catheter 4800. In some embodiments, this combined length is between 0.5 and 2 cm. The length of the deflectable region 4815, in some embodiments, is between about 0.4 inches and 0.5 inches. In one embodiment, a pull wire can be coupled to a distal end of the deflectable or articulatable region 4815 to effect deflection, articulation, or steerability.

One embodiment of the torsionally-rigid yet flexible or floppy section 4820 is shown in FIG. 48C. The section 4820 may advantageously include interrupted spiral cuts in a hypotube (e.g., stainless steel hypotube) to permit flexural bending for entrance into the tortuous anatomy of the celiac axis and common hepatic artery. In some embodiments, the length of the region 4820 is at least 5±3 cm in order to permit catheter access to a wide range of variable celiac and common hepatic anatomies found in human subjects. The embodiment illustrated in FIG. 48C, owing to its spiral cut hypotube design, is advantageously torsionally-rigid in at least one direction (or in a preferred direction), as the spiral is wound when rotated in the counter-clockwise direction and is measurably stiffer from a torsional perspective. Other tubing cut designs are possible, including continuous spiral cut and those with a) opposing double interrupted helix cuts (torsionally rigid in both directions), b) a pattern of holes drilled through a transverse axis of the tube, offset along the longitudinal axis of the tube by an angle (for example, 180 degrees), and other patterns. In one embodiment, the cut pattern is a spiral cut having a pitch or spine width of between 0.012" and 0.015" (e.g., 012", 0.013", 0.014", 0.015"). In one embodiment, the cut pattern is uniform along the entire length. In one embodiment, the cut pattern varies along its length, as shown in FIG. 48A. In one embodiment, the cut pattern includes a highly flexible interrupted spiral cut pattern along a first distal portion (e.g., 8.5 cm) and a transition (either an abrupt or gradual transition) to a less flexible, wider-pitch interrupted spiral cut pattern along a second proximal portion (11.5 cm). For example, the pitch of the first distal portion can be 0.015" and then gradually transition to a 0.220" inch pitch. In some embodiments, the transition between the torsionally rigid yet flexible region 4820 and the solid tubing proximal region 4825 is supported by a thermoset heat shrink material (e.g., PET heat shrink tubing) to reduce the chance of kinking the catheter in this region. In one embodiment, the width of the cuts is 0.002"; however, the width may range from about 0.001" to about 0.005", from about 0.0015" to about 0.0025", from about 0.002" to about 0.004", or overlapping ranges thereof.

The catheter 4800 may advantageously be configured to have sufficient push efficiency to push the distal tip and electrode through at least two tight bends of about 0.5 cm radius. The catheter length of any of the catheters described herein (including the catheter 4800) may range from 50 cm to 150 cm (e.g., 50 cm to 100 cm, 80 cm to 120 cm, 90 cm to 130 cm, 100 cm, 110 cm, 120 cm) in various embodiments. In one embodiment, the catheter 4800 has a length of 110 cm. In one embodiment, the catheter 4800 comprises a smooth, low-friction material such as polytetrafluoroethylene (PTFE). The kink radius of the catheter 4800 may be less than 0.5 cm. The length of the electrode 4805 can be less than 0.25 inches. In various embodiments, the outer diameter of the catheter 4800 is less than 8 Fr, less than 7 Fr, 6 Fr or less, or less than 5 Fr. The electrode 4805 is advantageously flush or substantially flush with the catheter surface, in one embodiment. In some embodiments, the electrode 4805 has sufficient torque efficiency provided by the catheter 4800 to be configured to contact the inner wall of a vessel at four points (or fewer or more than four points as desired or required) around the circumference of the vessel (e.g., 4 points 90 degrees apart) after navigating through two or more tight (approximately 0.5 cm) bends. In various embodiments, the catheter 4800 is configured to deliver energy at multiple locations without having to reposition the catheter. The catheter 4800 may be introduced within vasculature through a vascular access system that includes a guide sheath or a guide catheter and (optionally) a guide extender. In some embodiments, a temperature-measurement device (e.g., thermocouple) is bonded to the electrode 4805 by soldering, spot welding and/or an adhesive.

Figure 48D:
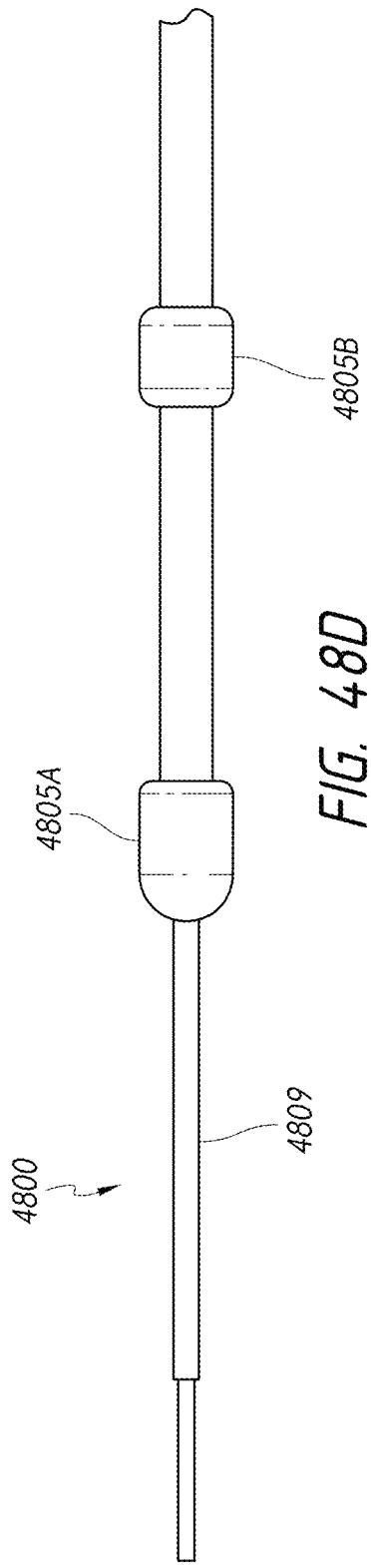
Figure 48E:
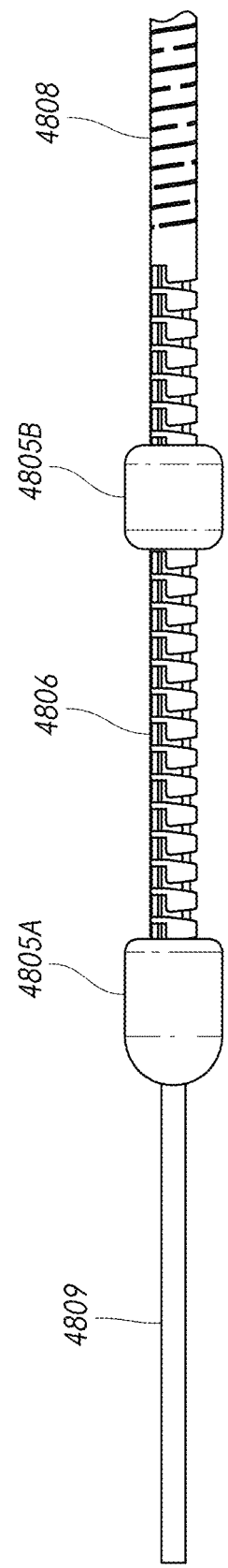

FIGS. 48D and 48E illustrate another embodiment of a catheter 4800 configured to provide uniform and consistent contact by multiple electrodes 4805 positioned along a length of a distal end portion of the catheter 4800. The catheter 4800 of FIGS. 48D and 48E consists of two electrodes; however, other embodiments may include more than two electrodes (e.g., three, four, five, six or more than six electrodes). The catheter 4800 comprises a distal electrode 4805A and a proximal electrode 4805B spaced proximal to the distal electrode. A deflection mechanism activated with an internal pull wire may be incorporated.

Referring to FIG. 48E, an embodiment of an internal structure to effect deflection is shown. The catheter shaft may comprise segmented stiffness, or segments having varying degrees of flexibility or stiffness, to effect the distal deflection. The primary structural element of the catheter shaft may be a tube such as a hypotube, wherein a pattern is cut or etched. The deflectable portion 4806 of the treatment catheter 4800 may incorporate a slotted pattern with a spine on the side that becomes the outer portion of the curved deflected portion. The deflectable portion 4806 may have a uniform degree of flexibility determined by the spacing and width of the slots as well as the material of the shaft. Proximal of the deflectable portion 4806 is a relatively flexible region 4808 which may be formed by cutting a spiral pattern into the tube. The relatively flexible region 4808 comprises a different slot or slit pattern than the deflectable portion 4806 and may be less flexible than the distal length of the deflectable portion 4806. The variable flexibility of the catheter lengths and the positioning of the two electrodes 4805 may be adapted so as to cause both of the electrodes 4805 to be positioned against a vessel wall at spaced-apart locations.

As illustrated, both electrodes 4805 are positioned on the deflectable portion 4806, with the distal electrode 4805 positioned at a distal end of the deflectable portion 4806 and the proximal electrode positioned at a proximal end of the deflectable portion 4806. In some embodiments, both electrodes 4805 are positioned so that a side of the electrode is flush or generally parallel to a vessel wall surface. In other embodiments, the distal electrode 4805A may be positioned in generally perpendicular or an oblique contact with the vessel wall at a first location while the proximal electrode 4805B is positioned in generally parallel contact with the vessel wall at a second location. The electrodes 4805 may comprise monopolar electrodes each separately adapted to apply power or energy to the vessel wall. In other embodiments, the proximal electrode 4805B is not positioned on the deflectable portion 4806 but is positioned on the relatively flexible portion 4808 portion. The catheter shaft may be reinforced with stainless steel and/or polyimide.

In some embodiments, the catheter 4800 comprises a guidewire lumen that is extended distally with a distal extension 4809 extending distal of the distal electrode 4805A to enhance trackability of the catheter 4800. The distal extension 4809 may transition in lateral stiffness, being more flexible in the distal direction. In use, the guide wire may be retracted once the electrodes 4805 are in a desirable location, so as not to hinder the deflection or create electrical anomalies during subsequent electrical activation of the electrodes 4805. It may be desirable for the stiffness of the distal extension 4809, even near the distal electrode 4805A, to be low enough to allow for the extension 4809 to flex easily away from the vessel wall when the catheter is in its deflected state. The distal extension 4809 may also incorporate kink resisting structures, such as a coil or braid to prevent kinking near the distal electrode 4805A. The distal extension 4809 may be constructed of an elastomeric material, such that if it does kink near the distal electrode 4805A, it can recover after the deflection is reversed. In some embodiments, the catheter 4800 comprises an outer sheath or covering 4811.

In accordance with several embodiments, forcing the catheter to oppose the electrode force (the secondary s-bend) would reduce the length required to apply the electrode force and would improve the repeatability of the applied "electrode force" in tortuous vessels. Moving reaction forces or contact points towards the electrode may also increase the stability near the electrode and reduce electrode movement during use. Increasing the normal force applied to the vessel may also increase the stability of the catheter electrode in the target anatomy and increase the amount of energy delivered to target nerves surrounding (e.g., within a wall of, such as within the intima, media or adventitia of) the hepatic artery (e.g., common or proper hepatic artery or other arteries, veins or other vessels or organs). In accordance with several embodiments, directing the path of the pull wire as described herein provides a predictable bending direction for a given rotational catheter orientation.

In one embodiment, instead of applying a moment at the distal tip of the catheter and relying on a reaction force between the vessel and a segment of the catheter, one could apply the reaction force perpendicular to the electrode force (previously referred to as the catheter tip force), and instead of applying the force at one point, or multiple discrete points, it could be applied around the circumference of the vessel. For example, a balloon or stent-like member could be used to apply reaction forces and electrode forces to the circumference of the vessel. As an alternative, a "reverse" Tuohy Borst-type mechanism could be used. A Tuohy Borst is an example of a seal mechanism where a compressible polymer shaped like a thick hollow cylinder is placed within a cylindrical sleeve and compressed from either end of the sleeve. The compression can cause the compressible hollow cylinder to collapse on itself and reduce its inner diameter. Looking at the inverse, one could place a compressible hollow cylinder over a rod and compress it, thereby causing its outer diameter to expand. In one embodiment, creating longitudinal cuts in the material exaggerates this mechanism.

Figure 51B:
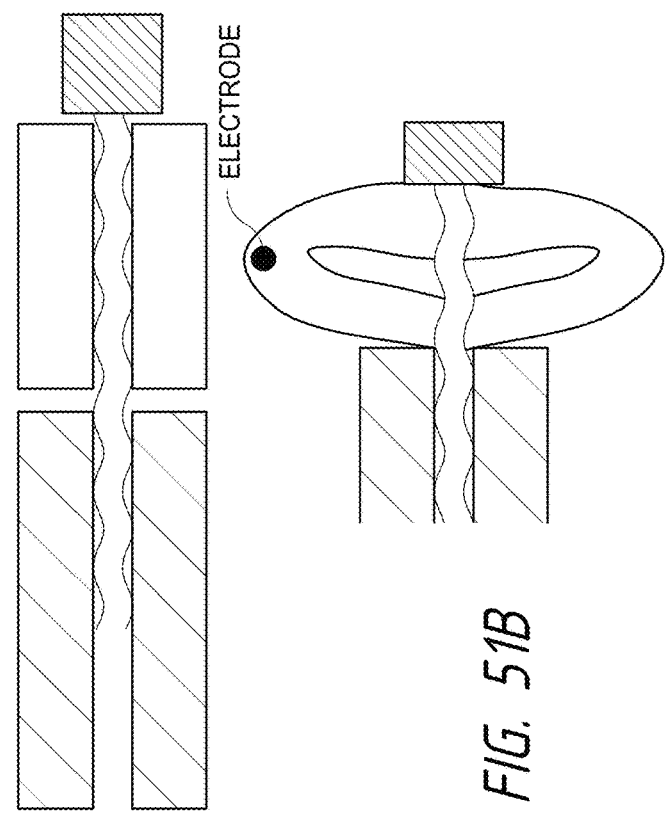
Figure 51A:
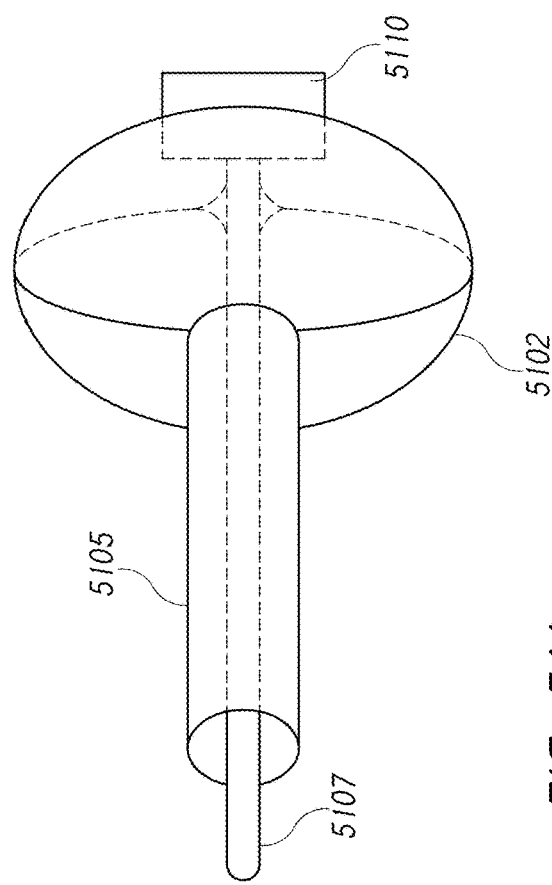

Referring now to FIGS. 51A and 51B, a cylinder 5102 of a soft and flexible material (e.g., low Young's modulus material such as silicone or polyurethane) is placed between a catheter shaft 5105 and a distal plug 5110, with a pull rod or pull wire 5107 running through the center of the material. In some embodiments, one or more electrodes are disposed near or at the mid-point of the longitudinal length of the cylinder such that the electrode(s) are exposed beyond the outer surface of the cylinder and are subsequently brought into contact with the vessel wall upon expansion of the cylinder. The electrode(s) may be fixed to the cylinder using an over-molding process or bonded to the cylinder with adhesive. In various embodiments, the wire(s) connected to the electrode(s) run along the outer surface of the cylinder, through the cylinder material (over-molded onto the wires), or inside the cylinder. In one embodiment, the wire(s) are replaced with a flexible, printed circuit. Pulling the distal plug 5110 relative to the catheter shaft 5105 causes the cylinder material to be deformed outward and brings the electrodes into contact with the vessel wall. In some embodiments, creating longitudinal cuts in the material exaggerates this mechanism.

Figure 52C:
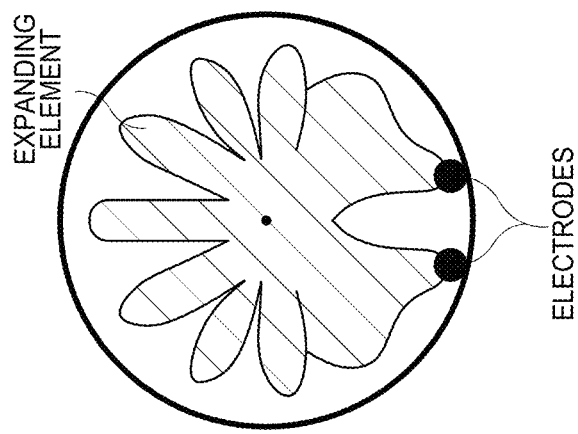
Figure 52B:
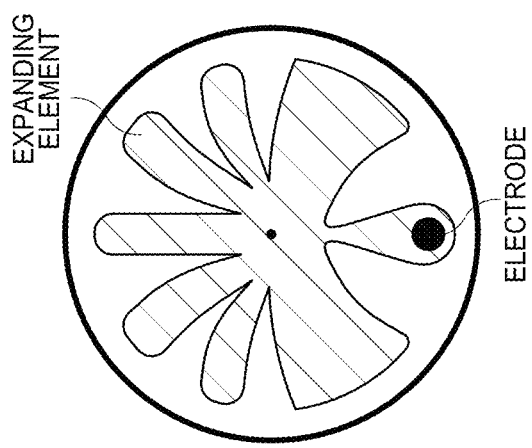
Figure 52A:
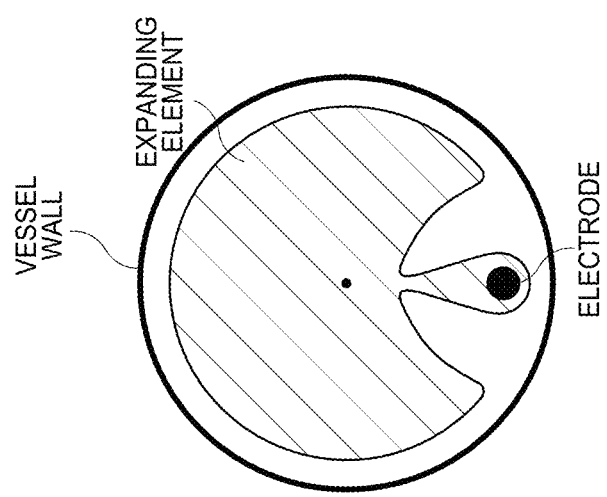
Figure 53A:
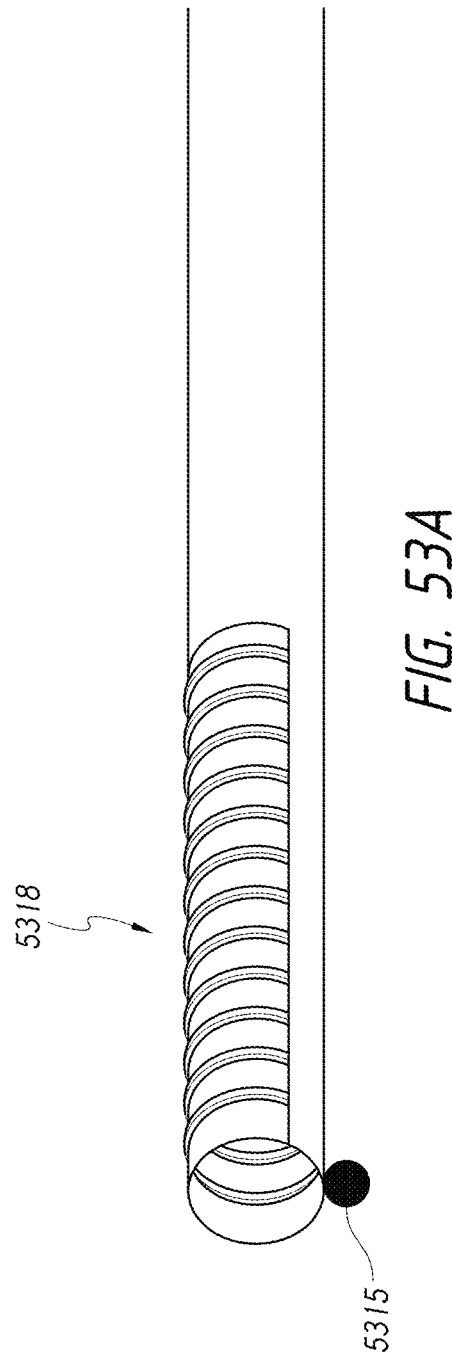
Figure 53B:
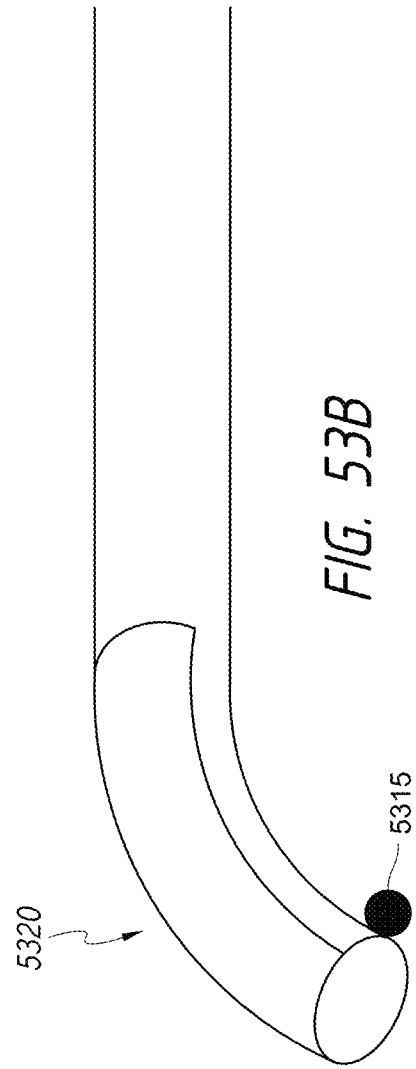

Applying the reaction force around a circumference in the same plane as the electrode force may reduce the length required to apply the electrode force and improve the repeatability of the applied "electrode force" in tortuous vessels. Moving reaction forces or contact points towards the electrode may also increase the stability near the electrode and reduce electrode movement during use. Increasing the normal force applied to the vessel may increase the stability of the catheter electrode in the target anatomy. As compared to the balloon or stent, a slit, "reverse Tuohy Borst" may enable the designer to direct blood flow to particular areas and control the mass flow rate through those areas, as illustrated in FIGS. 52A-52C.

In the case of denervating the common hepatic artery, unique vessel tortuosity (e.g., multiple acute turns or bends) can make force or torque transfer from the proximal end of the device to the distal end difficult. For example, torque may initially be lost due to translation of a catheter shaft until it contacts a tortuous vessel wall, and a pull wire locked in one plane of the catheter shaft can cause straightening or bending of the shaft through bends in that plane, leading to a loss of force along those bends prior to the flexing of the distal segment intended for articulation. Several embodiments described herein advantageously use a form of energy that does not experience a loss as it travels through tortuous bends.

In some embodiments, mechanism other than pull wires can be used to actuate structures such as cantilever flex catheters as described herein. For example, hydraulic or pneumatic means can be utilized to effect bending of a flex catheter, as illustrated, for example, in FIGS. 53A and 53B. In some embodiments, a neuromodulation device (e.g., ablation catheter) is comprised of at least an electrode 5315, a flexible shaft, and a segment 5318 that is adjacent to the electrode (e.g., located at the distal end portion of the device) and that is exposed to a medium surrounding the shaft and/or to a fluid within the shaft. In one embodiment, the segment 5318 comprises a compliant balloon 5320 made of a material with a low elastic modulus (e.g., silicone or polyurethane) or a balloon made of a less compliant material (e.g., Nylon, PET, silicone, etc.) and processed to have circumferential ribs or folds (e.g., similar to a bendable straw). When the internal pressure is greater than the external pressure, the balloon may expand axially. If one side is constrained, the expansion can cause the balloon and constrained segment to bend towards the constrained segment or vessel wall.

Referring now to FIGS. 54A and 54B, in one embodiment, a neuromodulation device (e.g., ablation catheter) is comprised of at least an electrode 5415, a flexible shaft, an articulating (e.g., expandable) section in communication with a plunger 5417, and two pressure chambers separated by a seal or plunger. In one embodiment, at least one chamber is filled with a compressible fluid or is filled with a non-compressible fluid and is also in communication with another chamber such as a syringe. In one embodiment, the plunger 5417 is driven by changing the pressure on either side of the plunger 5417, thereby transferring energy into the articulating section that is in communication with the plunger 5417. The articulating section illustrated in FIGS. 54A and 54B may be similar in structure and/or operation to the structure and/or operation of the expanding structure illustrated in and described in connection with FIGS. 42A, 42B, and 43A.

e. Controlled Lesion Formation

Figure 55A:
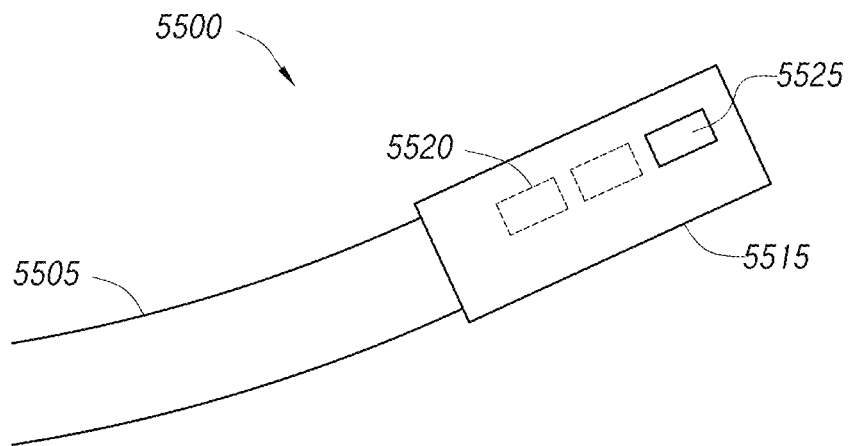
FIGS. 55A and 55B illustrate an embodiment of a windowed ablation catheter.
Figure 55B:
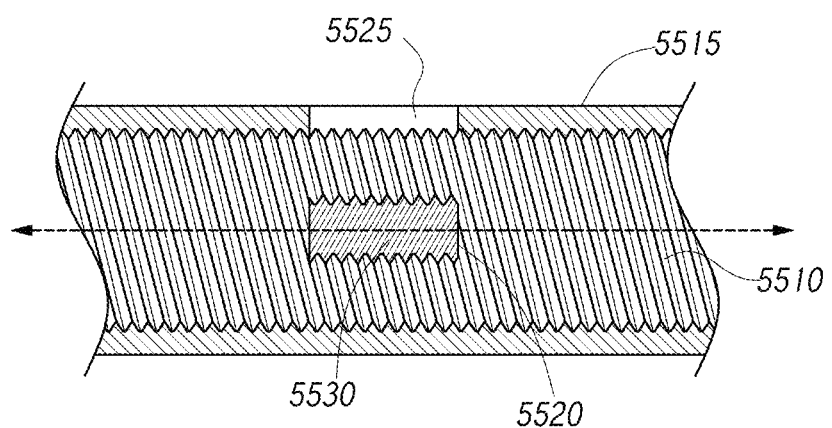

FIGS. 55A and 55B illustrate an embodiment of a windowed ablation catheter 5500. The windowed ablation catheter 5500 comprises a catheter body 5505, an inner sleeve 5510 having a first window 5520 and at least one ablation electrode 5530 and an outer sleeve 5515 having a second window 5525. FIG. 55A shows a view of the distal end of the windowed ablation catheter 5500 and FIG. 55B shows a detailed cut-away view of the distal end of the windowed ablation catheter 5500.

In some embodiments, the ablation electrode 5530 is disposed within a lumen of the inner sleeve 5510. The inner sleeve 5510 is rotatably received within the outer sleeve 5515 such that the outer sleeve 5515 is rotatable about the inner sleeve 5510. Energy can be delivered by the catheter by aligning the second window 5525 of the outer sleeve 5515 with the first window 5520 of the inner sleeve 5510 by rotating the inner sleeve 5510 with respect to the outer sleeve 5515, or vice-versa. In one embodiment, the inner sleeve 5510 comprises a dielectric covering to provide insulation.

In some embodiments, when the first window 5520 of the inner sleeve 5510 and the second window 5525 of the outer sleeve 5515 overlap, the ablating electrode 5530 is exposed to the outside of the outer sleeve 5515 (which may be placed against the wall of the target vessel). In one embodiment, energy only reaches the wall of the target vessel when the first window 5520 and the second window 5525 overlap, or are at least partially aligned. The degree of overlap may be controlled by the rotation or translation of the inner sleeve 5510 relative to the outer sleeve 5515. In one embodiment, the catheter is inserted by a user, the inner sleeve 5510 is turned based on user control, and the outer sleeve 5515 is turned based on user control, thereby allowing selective application of energy generated by the at least one ablation electrode to substantially any portion of the target vessel.

In some embodiments, the inner sleeve 5510 comprises multiple openings spaced along the length of the inner sleeve 5510 at different locations. For example, the inner sleeve 5510 may have openings spaced linearly along the axis of the inner sleeve 5510 and openings rotated about the axis of the inner sleeve 5510. In one embodiment, the openings of the inner sleeve 5510 define a spiral pattern. As shown in FIG. 55B, the external surface of the inner sleeve 5510 and the internal surface of the outer sleeve 5515 may be threaded such that the inner sleeve 5510 is translated with respect to the outer sleeve 5515 by rotation of the outer sleeve 5515 relative to the inner sleeve 5510. In some embodiments, relative rotation of the outer sleeve 5515 with respect to the inner sleeve 5510 serves to both translate and rotate window 5525 of the outer sleeve 5515, sequentially exposing vascular tissue to the ablation electrode 5535 through each of the openings of the inner sleeve 5510. In accordance with several embodiments, a windowed ablation catheter as described herein may facilitate creation of a spiral lesion along a length of the vessel wall. By selectively creating openings in the inner sleeve 5510, and rotating the outer sleeve 5515 with respect to the inner sleeve 5510, substantially any pattern of ablation along a helical path may be created.

To improve ablation catheter-vascular wall contact and thereby improve treatment efficacy, some embodiments include a window on the distal tip of the ablation catheter, or incorporated into one or more of the electrode windows, to provide suction (or vacuum pressure). The suction provided to the lumen wall places the artery in direct contact with the device to thereby achieve more efficient and less damaging ablation.

In accordance with several embodiments, the common hepatic artery is a target of ablation using an RF electrode catheter. For some subjects, a length of the common hepatic artery may limit the number of possible ablation sites. In some embodiments, minimizing the size of the lesions created along the longitudinal length of the common hepatic artery increases the number of ablation sites available within the vessel. In order to decrease the width of the lesions parallel to the vessel longitudinal axis while maintaining sufficient depth of the lesions and maximizing a surface of the electrode exposed to blood flow or cooling fluid for cooling, the electrode(s) of the RF electrode catheter may be constructed to have a diameter that is greater than or equal to its length. For example, if the electrode is generally 6 French in diameter (0.080 inches), then the length of the electrode may be 0.080 inches or less.

In accordance with several embodiments, consistency in lesion size is desired without being dependent on variations in vessel size, which may vary for the same target vessel across different subjects. For example, the inner diameter of the common hepatic artery may vary from 3 mm to 7 mm. In addition, overlap in lesion formation may be undesirable. Overlap in lesion formation can be difficult to avoid or prevent if a target treatment length is sufficiently short (e.g., due to patient anatomy) and multiple spaced-apart lesions are required to be formed along the vessel length.

For situations where there is an intrinsic limit in the number of ablations that can be performed at a defined spacing due to patient-specific anatomy limitations, a target vessel may be stretched out while being ablated. In one embodiment, the target vessel may be stretched by placing a spring in the vessel during ablation to stretch the vessel to a desired length and then may be removed upon completion of ablation. In one embodiment, a balloon is inserted within the vessel and expanded to straighten and thus stretch the vessel. The balloon may be a balloon of a balloon ablation catheter. In some embodiments, the length and the area of the vessel may be increased by the balloon, resulting in no increase in resistance of the vessel. In accordance with several embodiments, stretching of the vessel enables more lesions to be formed across the length of the target vessel or a portion of the target vessel at a given spacing, thereby resulting in potential greater effectiveness of therapy. In some embodiments, because cells are stretched by the vessel stretching while tissue conductivity remains constant, the energy plume or cone targets fewer cells within the vessel wall while still reaching the same density of nerve fibers within or surrounding the vessel wall (e.g., within the adventitia).

Turning to FIGS. 56A and 56B, a metabolic neuromodulation system 5600 configured to provide consistency in lesion size regardless of vessel diameter while utilizing a single energy protocol is illustrated. In one embodiment, the metabolic neuromodulation system 5600 advantageously allows for a single ablation protocol to be developed for a full range of vessel diameters that ensures a desired circumferentiality (e.g., 60-80% of vessel circumference) while reducing the risk of lesion tail overlap between spaced-apart lesions (e.g., reduces the risk of complete circumferentiality due to overlapping lesion zones). In some embodiments, the metabolic neuromodulation system 5600 may allow for reduction in the number of lesions necessary to ensure full circumferential treatment in multiple different planes. The metabolic neuromodulation system 5600 comprises a single disposable catheter 5605 with a mechanically-deployable scaffold 5610 having two opposing contact points 5612A and 5612B. The scaffold 5610 may be mechanically expanded and retracted by a mechanical pull wire (not shown). In one embodiment, the scaffold 5610 comprises a funnel-shaped basket. An electrode may be positioned at the second contact point 5612B to deliver energy for the purpose of ablation and a cooling tip may be positioned at the first contact point 5612A 180 degrees opposed to the second contact point 5612B to facilitate creation of a cooled tissue zone for the purpose of preventing or inhibiting lesion circumferentiality. In accordance with several embodiments, the size of the cooled tissue zone would differ based upon vessel diameter, but would be sufficient to prevent or inhibit full circumferentiality of the lesion. In one embodiment, the cooling tip may be facilitated by continuously infusing cooled liquid through a lumen of the catheter 5605. The cooling tip may be directed toward the vessel wall adjacent to the electrode contact area. In this manner, the tissues adjacent to the electrode contact point may be cooled before, during, and/or after the electrode is energized or activated. In embodiments that employ modalities other than RF, the cooling tip may also be used. In embodiments that employ cryotherapy (such as cryoablation), warming elements/fluids may be introduced instead.

In some embodiments, the cooling tip of the catheter 5605 advantageously creates a cooled zone that is 180 degrees in opposition to the site of ablation during energy delivery to ensure that the "tails" of the C-shaped lesions do not touch or overlap, regardless of vessel diameter. The circumferential extent of the cooled zone can be variable as long as it is cool enough to prevent or inhibit lesion formation across the entire vessel circumference regardless of vessel size. In some embodiments, the cooled zone prevents at least 10% of the vessel circumference from being ablated regardless of vessel diameter. In some embodiments, the cooled zone prevents at least 20% of the vessel circumference from being ablated regardless of vessel diameter. FIG. 56B schematically illustrates treatment zones 5625 and cooled zones 5630 for vessels having diameters of 3 mm, 5 mm and 7 mm.

FIG. 57 schematically illustrates a metabolic neuromodulation system configured to provide controlled circumferentiality of lesions, thereby allowing for creation of two opposing lesions in the same plane while preventing or reducing the likelihood of circumferentiality or overlap of the two lesions. The neuromodulation system may comprise a single disposable catheter having an energy source 5702 (e.g., electrode) surrounded by shielding material or a shielding structure 5704 configured to cause directional energy delivery that creates an asymmetric lesion. The neuromodulation system may include instructions stored on a non-transitory computer-readable medium that, upon execution by a processor or other computing device, cause delivery of an energy protocol that allows for the creation of two opposing lesions in the same plane while ensuring that lesion borders do not touch or overlap across a range of representative vessel inner diameters (e.g., 3 mm-7 mm). FIG. 57 schematically illustrates examples of lesions formed for vessels having inner diameters of 3 mm (FIG. 57D), 5 mm (FIG. 57B) and 7 mm (FIG. 57C).

The embodiments illustrated in FIGS. 56A,B and 57 may allow for (1) increased lesion-to-length ratio without increase in risk, (2) a single ablation protocol to be developed for a full range of vessel diameters that ensures optimal (e.g., 50-80%) circumferentiality while eliminating or reducing the likelihood of risk of lesion tail overlap, (3) improved predictability of lesion circumferentiality regardless of vessel diameter, and (4) patients with smaller vessel (e.g., common hepatic artery) lengths to be treatment candidates. Other devices may also be configured to provide like performance across variable patient anatomy.

Figure 58:
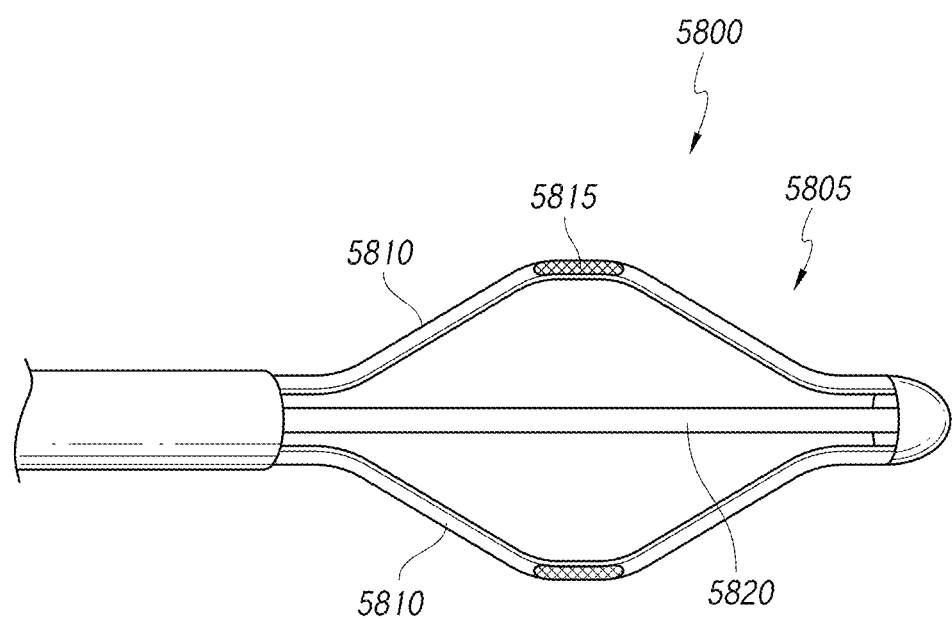

FIG. 58 illustrates an embodiment of an intravascular RF ablation catheter 5800 configured to prevent or reduce the likelihood of circumferentiality due to formation of multiple lesions within a single cross-sectional slice around a vessel wall. In one embodiment, the RF ablation catheter 5800 may provide assurance that energy is delivered in a manner that does not involve heating or ablation of more than 75% of the adventitia in any cross-sectional slice of the vessel. The RF ablation catheter 5800 comprises an expandable frame or scaffold 5805 configured to contact the vessel wall at spaced-apart locations around a circumference of the vessel. The expandable frame or scaffold 5805 comprises two treatment members or loops 5810 spaced 180 degrees apart from each other having electrodes 5815 positioned at vessel contact points along the members and two cooling members or loops 5820 spaced 180 degrees apart from each other and spaced 90 degrees apart from the two treatment members or loops 5810 having the electrodes 5815. The total number of members or loops of the expandable frame or scaffold 5805 may vary (e.g., 2, 4, 8) and the number of treatment members or loops 5810 and the number of cooling members or loops 5820 may vary. For example, the expandable frame or scaffold 5805 may comprise three treatment members or loops 5810 and one cooling member or loop 5820. The members or loops may comprise flexible splines, tines, arms, or the like. The expandable frame or scaffold may form a basket-like scaffold. The members or loops may be spaced in a uniform manner or a non-uniform manner. The treatment members and cooling members may alternate consecutively or may not alternate consecutively. In some embodiments, the catheter 5800 comprises one or more expandable members. The expandable member may be constructed of members that expand in a basket form. In the expanded form, the members may contact the vessel wall. The individual members of the basket can include at least one cooling channel configured to cool the vessel wall and at least one member with one or more RF electrodes that transfer RF energy into the vessel wall via contact. Multiple cooling members or electrode members can be configured to effect the desired ablation result. In one embodiment, the expandable member comprises a balloon that is expanded with cooling fluid and electrodes mounted on the surface of the balloon or an expandable basket that include RF electrodes mounted thereon. In various embodiments, the cooling fluid may be contained within the cooling members or released from the cooling members toward the vessel wall.

In accordance with several embodiments, lesions may be coordinated and positioned to provide continuous oblique circumferential lesions without creating a circumferential lesion at any one location or cross-sectional slice. In some embodiments, both the position and the extent of the lesions are controlled. The lesions may be placed 180 degrees apart and displaced axially along the vessel length. In some embodiments, the circumferential and axial extent of the lesion are controlled so that the margins of the lesions just intersect at a location 90 degrees on either side of the energy delivery element (e.g., electrode) positions. In some embodiments, a reference electrode may be positioned between the lesions to measure temperature or impedance to detect lesion intersection. In some embodiments, lesions are spaced between 1-50 mm apart (e.g., 1, 5, 10, 12, 15, 20, 25, 50 mm, and overlapping ranges thereof). Lesions may be overlapping or non-overlapping. In one embodiment, multiple foci or ablation sites, which may or may not overlap, are created to generate lines of thermal injury. The foci or sites can be spaced at 0.2 mm to 20 mm apart (e.g., 0.2 mm to 2 mm, 5 mm to 15 mm, 10 mm to 20 mm, 1 mm to 12 mm, or overlapping ranges thereof). In some embodiments, lesions are non-circumferential. In some embodiments, lesions are circumferential, including off-set circumferential, partially circumferential, and fully circumferential. In various embodiments, lesions may be spaced between 1 to 15 times the electrode diameter. For example, for electrodes having diameters of 1 or 2 mm, the electrodes may be spaced from 1 mm to 30 mm apart (e.g., 1 to 12 mm, 5 to 15 mm, 10 to 20 mm, and overlapping ranges thereof). Lesion spacing may be adjusted based on vessel diameter. The number of ablations may also vary based on vessel diameter.

Because catheter tip temperature and impedance alone may be poor indicators of tissue temperature or lesion size, tip temperature and impedance may both be measured during ablation in order to monitor lesion development and/or to confirm lesion formation, thereby providing confirmation of denervation of target nerves.

Initially, tip temperature increases and impedance decreases. Tissue conductivity increases with temperature up to a certain threshold (e.g., approximately 80 degrees Celsius). Above this threshold temperature, tissue may begin to contract and desiccate and impedance may start to increase instead of decrease. The decoupling of temperature and impedance may be used as an indication of lesion formation to confirm denervation. If impedance begins to increase without a corresponding decrease in tip temperature, this may be used as an end point or as confirmation of lesion formation. The time of decoupling of temperature and impedance may also be used as feedback to trigger other changes in an energy delivery protocol, such as decreasing power or increasing cooling.

Figure 59:
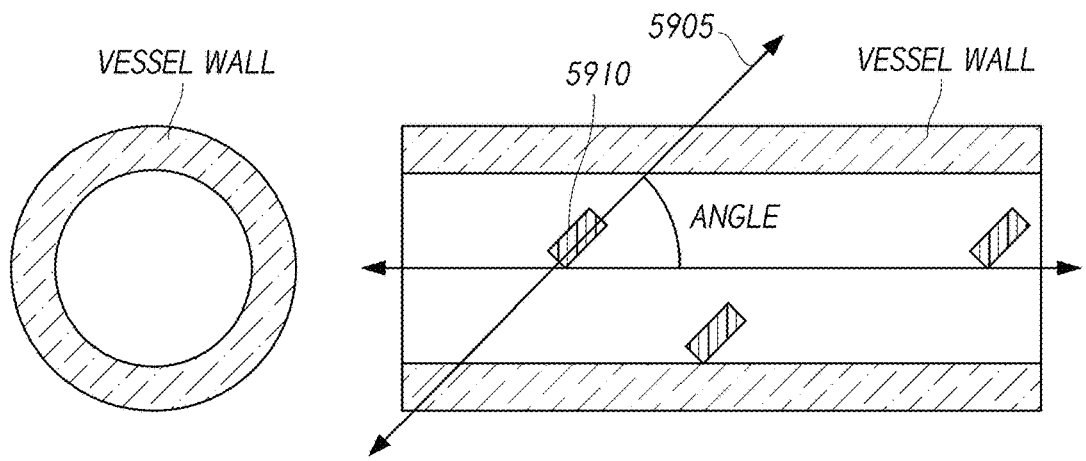

Turning to FIG. 59, a shaft or frame of an RF ablation catheter may be configured to ensure that a longitudinal axis 5905 of an electrode 5910 is not in the same plane as the vessel longitudinal axis 5915. For such a configuration, the longest dimension of the lesion created by the electrode may not be parallel to the vessel longitudinal axis 5915, as schematically illustrated in FIG. 59. In one embodiment, in order to orient an electrode 5910 off the vessel longitudinal axis 5915 for a catheter having a single distal electrode, a shaft of the catheter may be configured to form a spiral on the distal end, which may tilt the electrode 5910 out of the vessel's longitudinal plane. Alternatively, a pre-shaped shaft can be employed that shifts from a relatively straight to a non-straight orientation with the insertion or removal of a mandrel or guidewire. For multiple electrode catheter approaches, a basket or scaffold comprising a plurality of electrodes disposed around the basket or scaffold may, when actuated, be configured to hold the electrodes off axis.

Figure 60:
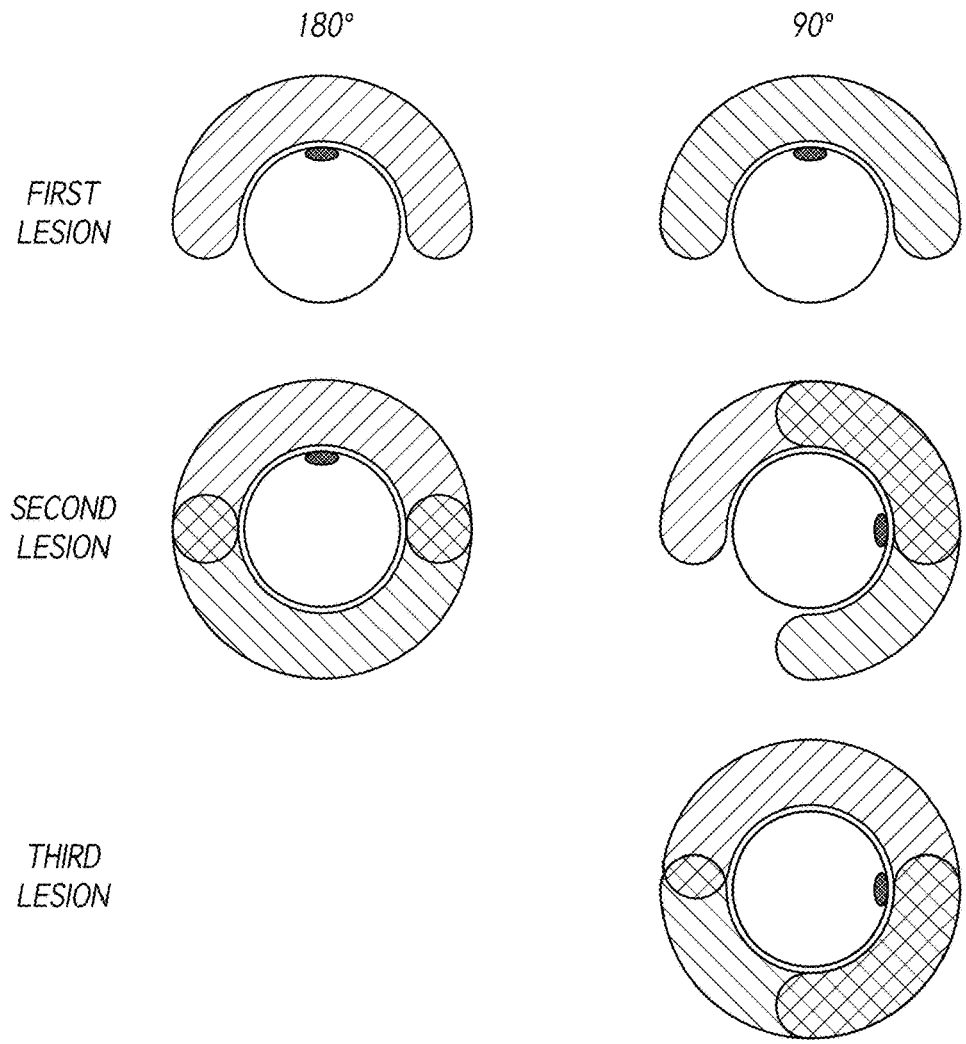

In some embodiments, complete circumferential ablation of a vessel may be prevented or inhibited by spacing ablation sites radially at 90 degree intervals as opposed to at 180 degree intervals. FIG. 60 schematically illustrates ablation performed at 180 degree intervals and at 90 degree intervals. As shown, even if the 180 degree intervals are spaced apart axially along the length of the vessel, the "tails" of the ablation lesions could potentially overlap on both sides of the vessel (assuming that each ablation forms a lesion that extends around 180 degrees of the vessel circumference), thereby forming a complete circumferential lesion. When 90 degree intervals are used, there may potentially be overlap between adjacent lesions but the risk of complete vessel circumferentiality of the overall lesion composed of the multiple lesions is reduced. A single or multi-point RF ablation catheter may facilitate radial spacing of ablation sites by approximately 90 degrees and longitudinal spacing of at least one electrode length. In some embodiments, radial spacing of the ablation sites by 90 degrees causes less than complete circumferential ablation of the vessel (e.g., 75%-95%, 70%-90%, 65%-80%, 75%-90%, or overlapping ranges thereof). In some embodiments, treatment sites (e.g., ablation sites) may be spaced 120 degrees apart circumferentially (for example, if the energy delivery device includes three electrodes).

In accordance with several embodiments, the systems and methods described herein advantageously increase the perivascular ablation size and nerve impact while decreasing vascular wall injury and adjacent structure involvement. For example, for RF electrode embodiments, the electrode shape and energy delivery parameters may be designed to maximize or increase the perivascular ablation area and nerve impact while minimizing vascular wall injury and adjacent structure involvement. In various embodiments, an energy delivery device consisting essentially of a single electrode is used. In other embodiments, an energy delivery device consisting essentially of two and only two electrodes is used. In some embodiments, an energy delivery device consisting essentially of four and only four electrodes is used. In other embodiments, an energy delivery device consisting essentially of three and only three electrodes is used. In yet other embodiments, an energy delivery device consisting essentially of five and only five electrodes is used.

Figure 61B:
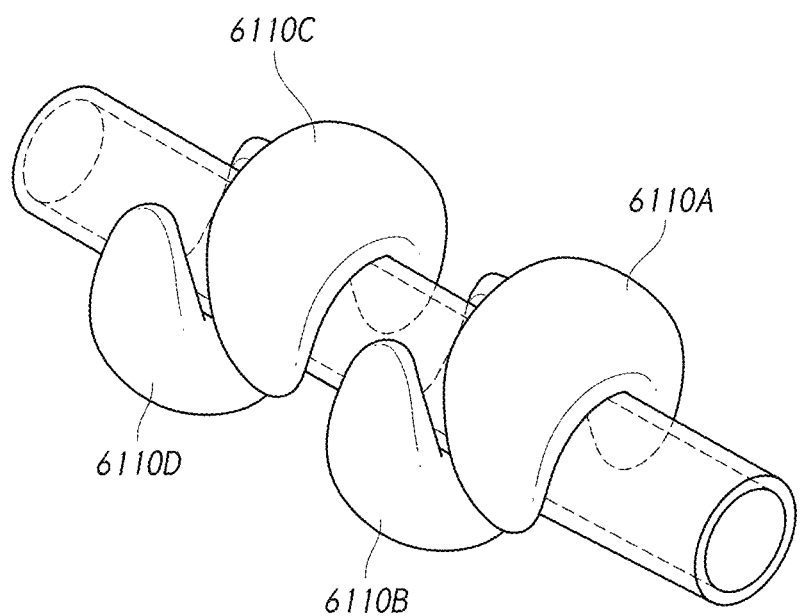

With reference to FIG. 61A and FIG. 61B, ablation patterns may advantageously increase the overall perivascular ablation volume while maintaining little to no thermal damage or endothelialization (e.g., less than 20% mean maximum circumference of vessel injury, no internal elastic lamina disruption, no arterial dissection, and/or no clinically significant neointimal formation, no long-term vascular stenosis, no circumferential vessel wall injury) to the portions of the vessel wall in contact with an ablation member (e.g., electrode, transducer). FIG. 61A illustrates one embodiment of an ablation pattern comprising four spaced-apart ablation locations 6105A-6105D. The ablation locations are spaced apart at an equal distance X and each ablation location is offset by 180 degrees from the next location. In some embodiments, the spacing between the locations is determined by a minimum threshold and the spacing does not necessarily have to be equal (just above the minimum threshold spacing). The minimum threshold spacing (between center points of lesion zones) may be between 2 and 8 mm (e.g., between 2 and 4 mm, between 3 and 6 mm, between 4 and 8 mm, between 3 and 7 mm, 2 mm, 3 mm, 4 mm, 5 mm, 6 mm, 7 mm, 8 mm, overlapping ranges thereof or any value of or within the ranges). In some embodiments, the minimum threshold spacing depends on anatomical limitations of target vessel length. For example, for the common hepatic artery, spacing is 4 mm or 6 mm in accordance with several embodiments. The spacing described with respect to FIG. 61A may be used for spacing of electrodes in any of the embodiments described herein. For devices having deployed configurations, the spacing may be the spacing when the devices are in the deployed configuration in contact with a vessel wall.

FIG. 61B illustrates a schematic representation of the lesion zones 6110A-D formed by ablation at the four locations shown in FIG. 61A. As shown, the combination of the spacing and 180-degree offset increases perivascular lesion blending to provide larger circumferential perivascular injury along the vessel length, thereby increasing the likelihood of efficacy, while avoiding circumferential vessel wall injury. Factors of electrode size, power, duration and level of contact may also contribute to efficacy. In accordance with several embodiments, the individual ablation point and subsequent lesion zone is influenced by the electrode size and shape, the energy algorithm applied by the ablation system, vessel diameter, vessel wall thickness, and blood flow rates. The spacing between the ablation points facilitates the blending or separation of the individual lesion zones in the vessel wall and the perivascular space. In accordance with several embodiments, increasing the space between ablation points reduces (e.g., minimizes) lesion zone blending while decreasing the space between ablation points increases (e.g., maximizes) lesion zone blending. When creating a lesion zone for disruption of nerves surrounding a vessel it is desirous to reduce (e.g., minimize) the lesion zone within the vessel wall and increase (e.g., maximize) the lesion zone in the perivascular space. Optimization of lesion zone blending increases the likelihood of a 360 degree (or near 360 degree) circumferential perivascular lesion zone while reducing the likelihood of circumferential vessel wall injury along the length of the treated vessel, thereby avoiding vascular stenosis. The frequency of 360 degree circumferential perivascular ablation zones along the length of the vessel can be increased while holding the vessel wall injury constant by reducing the distance between the ablation points from 8 mm or more (e.g., 8 mm, 9 mm, 10 mm, 11 mm, 12 mm) to 6 mm or less (e.g., 6 mm, 5 mm, 4 mm, 3 mm, 2 mm) within a vessel diameter range while holding the electrode diameter and length (e.g., electrode area of between 3 mm$^2$ and 16 mm$^2$ (e.g., between 3 mm$^2$ and 6 mm$^2$, between 4 mm$^2$ and 8 mm$^2$, between 4 mm$^2$ and 10 mm$^2$, between 6 mm$^2$ and 8 mm$^2$, between 8 mm$^2$ and 12 mm$^2$, between 10 mm$^2$ and 16 mm$^2$, 4 mm$^2$, 6 mm$^2$, 8 mm$^2$, 10 mm$^2$, overlapping ranges thereof or any value of or within the recited ranges) and energy algorithm constant (e.g., from 500 J/ablation point to 2000 J/ablation point, from 500 J/ablation point to 1000 J/ablation point, 1000 J/ablation point to 2000 J/ablation point, 500 J/ablation point, 1000 J/ablation point, 1200 J/ablation point, 1600 J/ablation point, 2000 J/ablation point). In accordance with several embodiments, the pattern (including point spacing, electrode size, energy algorithm, circumferential offset) is configured to produce ratios of circumferential perivascular injury to circumferential vessel wall injury of greater than or equal to 2:1 (e.g., 5:1, 4:1, 3:1, 2:1). In some embodiments, the pattern may also include level of contact (such as indentation depth or contact force). For example, indentation depth may range from 0-1 mm (e.g., 0.1 mm to 0.3 mm, 0.2 mm to 0.4 mm, 0.3 mm to 0.6 mm, 0.4 mm to 0.8 mm, 0.6 mm to 1 mm, overlapping ranges thereof or any value of or within the recited ranges). Contact force may range from 1 to 15 grams of force (gmf) (e.g., between 1 and 5 gmf, between 5 and 10 gmf, between 10 and 15 gmf, overlapping ranges thereof or any value of or within the recited ranges). In some embodiments, each ablation point is offset by 180 degrees. In other embodiments, the circumferential offset is between 90 and 180 degrees (e.g., between 90 and 130 degrees, between 100 and 140 degrees, between 110 and 160 degrees, between 130 and 180 degrees, overlapping ranges thereof or any value of or within the recited ranges).

One embodiment of a treatment configuration in a treatment vessel, such as the common hepatic artery, is to treat two or more zones (e.g., two, three, four, five, six, more than six) that are longitudinally and/or rotationally spaced from each other. In some instances it may be advantageous to treat two or more zones wherein adjacent zones are both longitudinally and rotationally spaced from each other, such as shown in FIG. 61A. Such a series of treatment zones may be created with single electrode embodiments, by manipulations of the electrode both longitudinally and rotationally. In some cases it may be desirable to include two or more electrodes that tend to align along opposing quadrants (or sides) of the lumen of treatment vessel. This may be particularly beneficial if multiple non-overlapping treatment zones, such as described in FIG. 61A, are desired.

In various embodiments, the electrode(s) is/are approximately 0.5 mm to 5 mm in diameter (e.g., 0.5 mm, 1 mm, 1.5 mm, 2 mm, 2.5 mm, 3 mm, 3.5 mm, 4 mm, 4.5 mm, 5 mm or any diameter within the recited range). The electrode(s) may have a length of between 1 mm and 4 mm (e.g., 1.0 mm, 1.1 mm, 1.2 mm, 1.3 mm, 1.4 mm, 1.5 mm, 1.6 mm, 1.7 mm, 1.8 mm, 1.9 mm, 2.0 mm, 2.1 mm, 2.2 mm, 2.3 mm, 2.4 mm, 2.5 mm, 2.6 mm, 2.7 mm, 2.8 mm, 2.9 mm, 3 mm, 3.1 mm, 3.2 mm, 3.3 mm, 3.4 mm, 3.5 mm, 3.6 mm, 2.7 mm, 3.8 mm, 3.9 mm, 4.0 mm), between 2.5 mm and 3.0 mm, between 2.6 mm and 2.9 mm, between 2.7 mm and 3.0 mm, between 3.0 mm and 3.5 mm, between 3.5 mm and 4.0 mm, between 2.0 mm and 2.5 mm, or overlapping ranges thereof. In some embodiments, the ratio of electrode length to electrode diameter is 1:1, 1.2:1, 1.3:1, 1.4:1, 1.5:1, 1.6:1, 1.7:1, 1.8:1, 1.9:1, or 2:1. In some embodiments, the electrode(s) comprise cylindrical (e.g., rounded) or non-cylindrical (e.g., curved, slotted) electrodes.

In one embodiment, an electrode catheter consists essentially of a single rounded electrode at a distal tip of a deflectable or steerable catheter shaft. The electrode may be coupled to a flexible shaft segment that enables, in a deflected shaft state, for the side of the electrode to generally lay in parallel with the vessel wall to provide a stable contact area. The diameter of the electrode may enable a consistent and large contact area with the vessel wall, thereby minimizing the ability of the operator to bury the electrode into the vessel wall. The vessel contact area and the remaining surface area may advantageously allow for effective energy transmission into the vessel wall while maintaining a controlled tip temperature with an energy algorithm that steps energy up to 10 watts and monitors electrode temperature to modulate energy delivery during the treatment cycle. The energy delivery parameters may fall within the ranges of those described herein.

In accordance with several embodiments, the systems and methods described herein utilize a single electrode, two electrodes or four electrodes having a size and shape and energy delivery parameters that affect on average 5-30% (e.g., 5-10%, 10-15%, 15-20%, 20-25%, 25%-30% or overlapping ranges thereof) of the vessel wall circumference (e.g., common hepatic artery wall circumference) and between 40% and 80% (e.g., 40-60%, 45-55%, 50-60%, 60-85%, or overlapping ranges thereof) of perivascular circumference at depths of about 5 mm, thereby impacting a large number of nerves per ablation (by achieving larger ablation zones) while using fewer total ablations within the patient's artery to achieve a desired treatment effect. Because the length of the common hepatic artery is only 30 mm on average, embodiments targeting the common hepatic artery the number of ablations that can be performed over the length of the common hepatic artery is constrained. Accordingly, it is advantageous to reduce the number of ablations and increase the effectiveness of the ablations when targeting this anatomy while still reducing or limiting damage to the vessel wall. In accordance with several embodiments, RF ablation catheters described herein maintain proper contact conditions to initiate or complete energy cycles required for successful ablations, thereby reducing the number of ablation cycles or placement locations despite the constrained vessel length.

FIGS. 62A and 62B illustrate an embodiment of a treatment catheter 6200 and positioning method that incorporates use of lesion spacing indicators 6202 to aid in the positioning of the treatment catheter 6200 when it is desired to position the treatment catheter 6200 at multiple locations to create multiple treatment zones, for example as shown in FIGS. 61A and 61B. The lesion spacing indicators and technique described could be incorporated into any embodiment of neuromodulation device (e.g., treatment catheter, ablation catheter or device) described herein, whereby the neuromodulation device (e.g., treatment catheter) would be repositioned to create multiple treatment zones 6204. The treatment catheter 6200 includes multiple electrodes 6205 (in this case, two electrodes) that, when in the deployed configuration, are longitudinally spaced by a separation distance of L, and contact the vessel on opposing sides of the vessel (e.g., offset by about 180 degrees). The treatment catheter 6200 may include two lesion spacing indicators 6202, and may be secured on the distal end portion of the treatment catheter 6200 distally of the electrodes 6205. The spacing of the lesion spacing indicators 6202 may be of a predetermined relationship to the longitudinal spacing (when deployed) of the electrodes 6205. In this case, the spacing of the lesion spacing indicators 6202 is twice the length L (or 2L). As shown, the treatment catheter 6200 includes one electrode on a deflectable portion and one electrode on a non-deflectable portion; however, in other embodiments, both electrodes 6205 may be positioned along a deflectable portion or along a non-deflectable portion.

In use, the treatment catheter 6200 can be positioned within a desired treatment vessel with the aid of fluoroscopic angiographic imaging. Once positioned at a desired first location within the vessel (for example as shown in FIG. 62A), the electrodes 6205 are activated to create a first set of treatment zones 6204A, such as lesion zones, at contact locations of the electrodes 6205 with the vessel wall. The treatment catheter 6200 is re-positioned to a second location (in this case withdrawn) by positioning the distal lesion spacing indicator 6202B where the proximal lesion spacing indicator 6202A was previously. Once deployed, the electrodes 6205 are activated a second time to create a second set of treatment zones 6204B (as shown in FIG. 62B). In this manner, four relatively equally spaced treatment zones, on alternating opposing sides of the vessel are created.

When the treatment catheter is in the first position (e.g., the position shown in FIG. 62A), it may also be advantageous if a corresponding anatomic landmark is noted on the fluoroscopic or angiographic image (for example, a side branch adjacent the proximal marker 6202A). If a "roadmap" is created from this first angiographic image, the treatment catheter 6200 can be repositioned to the second location with only the use of fluoroscopic imaging "on top" of the roadmap, without the need of additional contrast delivery. The radiopaque markers 6202 can also be useful in the case of digital subtraction angiography. In this embodiment, a ghost image of the lesion spacing indicators 6202 can be created when the treatment catheter 6200 is in its first location. Repositioning to the second location can be accomplished without need of additional contrast delivery.

While two lesion spacing indicators, such as radiopaque marker bands, distal of the electrodes 6205 have been described, it is contemplated that the lesion spacing indicators could also be proximal of the electrodes, one of the electrodes 6205 could also be used as one of the lesion spacing indicators, as long as the electrode is fluoroscopically visible. Portions of the catheter shaft that incorporate radio dense materials could also be used.

In the above embodiment in which two electrodes when deployed are in a longitudinally spaced arrangement, but on opposing sides of the vessel, the lesion indicator spacing is advantageously twice the electrode spacing. However, in some embodiments in which the deployed electrodes may be longitudinally spaced, but on the same side of the vessel, the spacing between the lesion spacing indicators is advantageously equal to the spacing or half the spacing between the electrodes. The spacing between the electrodes may vary depending on vessel diameter. In other embodiments, the first two lesion zones 6204A are on the same side of the vessel and the second two lesion zones 6204B are on the opposite side of the vessel, with the treatment catheter 6200 being rotated to the opposite side of the vessel and positioned such that the distal electrode is positioned axially between the first two lesion zones 6204A, as may be determined by a spacing between and positioning of the lesion spacing indicators.

In accordance with several embodiments, controlled electrode deployment is desired to achieve consistent electrode positioning, contact force and orientation. Various means for controllably releasing and recovering multiple elastic or deformable electrode support members are described herein. In several embodiments, the means for controllable releasing and recovering electrodes functions even when an electrode is very close to (e.g., within 5 mm) a distal terminus of a guide catheter. In some embodiments the orientation of an electrode deployment arm and/or an electrode deployment sheath may be reversed to permit an electrode to be positioned proximate to a distal terminus of a guide catheter. In several embodiments, an actuation coupling element is provided to actuate the electrode deployment arms or sheath from the distal direction.

Figures 1, 2, 63A:
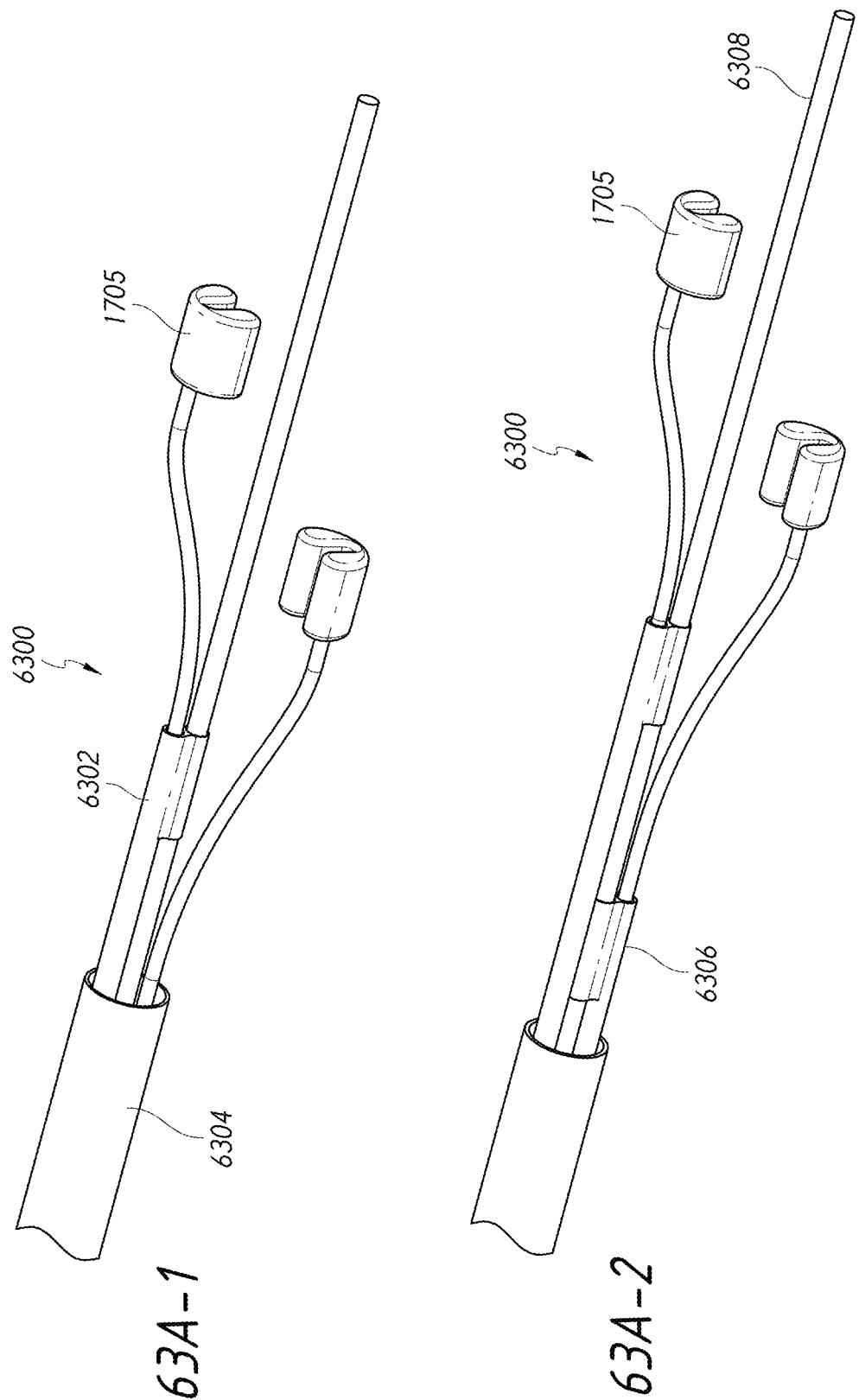

For example, FIGS. 63A to 63C illustrate various embodiments of deployment sleeve systems for providing multiple electrodes deployed laterally along a shaft without increasing profile. One or more electrodes 6305 may be mounted on elastic flexural elements that may be deployed to contact a vessel wall. FIGS. 63A-1 and 63A-2 illustrate embodiments of coaxial electrode deployment sleeve systems 6300. The deployment sleeve system 6300 of FIG. 63A-1 comprises a single inner sleeve 6302 and a coaxial outer sleeve 6304 that are independently adjustable to control electrode deployment. The first electrode deployment arm is coupled to a common support element 6308 by a rail member. The second electrode deployment arm is not surrounded by an inner sleeve and is deployed by retraction of the outer sleeve 6304. The deployment sleeve system 6300 of FIG. 63A-2 comprises two inner sleeves 6302 slidably coupled to the common support element 6308 by rail sections 6306. The common support element 6308 may be a guide wire. FIG. 63B illustrates an embodiment of a dovetail electrode deployment sleeve system 6300'. The deployment sleeve system 6300' comprises two inner sleeves 6302 that are independently advanceable within the outer sleeve 6304. The two inner sleeves 6302 are coupled to each other in a dovetail manner. The two inner sleeves can be translated with respect to each other to position the electrodes 6305 such that they are spaced apart axially along the length of the vessel or such that they are aligned axially along the length of the vessel but offset by 180 degrees. FIG. 63C illustrates an embodiment of a side-hole sleeve deployment system 6300". The sleeve 6302 may have a plurality of side holes 6312 designed to allow for deployment and recovery of a plurality of electrodes (as illustrated) or may have a single side hole for deployment and recover of a single electrode. For embodiments involving multiple electrodes or electrode deployment members, the electrodes may be independently adjustable to provide offset spacing circumferentially and/or axially. In some embodiments, the sleeve(s) and/or guide wires may be formed to permit nesting of electrodes and the electrodes may be slotted to nest over the sleeve or guide wire. The orientation of the various embodiments illustrated in FIGS. 63A-63C may be reversed to facilitate treatment of sites very close to a distal terminus of a guide catheter.

In one embodiment, a deployment sleeve is actuated by hydraulic pressure. For example, the sleeve may comprise a rolling membrane. An electrode on the hydraulic sleeve may be recovered by mechanical tension after hydraulic deployment.

f. Multi-Electrode Devices

FIGS. 64A to 64K illustrate various embodiments of multi-electrode energy delivery devices. As illustrated, the energy delivery devices may consist essentially of two electrodes or four electrodes. In various embodiments, the electrodes and the energy delivery parameters are designed such that more than two or more than four electrodes, respectively are not required to achieve successful modulation of nerves (e.g., denervation or ablation of nerves in the perivascular area of the hepatic arteries, such as the common hepatic artery, the proper hepatic artery, the right hepatic artery, the left hepatic artery). In accordance with several embodiments, the energy delivery devices provide uniform contact characteristics, thereby achieving consistent ablation performance with maximal contact customization per catheter placement.

FIGS. 64A to 64D illustrate undeployed and deployed states of embodiments of multi-electrode delivery devices. FIGS. 64A-1 and 64A-2 illustrate undeployed and deployed configurations of a distal portion of a multi-electrode catheter 6400 having two button electrodes 6405. The button electrodes 6405 may be radially deployed mechanically or hydraulically from the catheter surface by expelling the electrode shafts outward as a result of an expansion member 6410 within the catheter shaft. The expansion member 6410 may be a balloon, an expandable mechanical scaffold or frame or other expandable member or structure that, upon expansion or other actuation, expels the electrodes 6405 to a deployed state against the vessel wall. The expansion member 6410 provides a uniform outward pressure on the electrodes 6405. The electrodes 6405 comprise a coil spring 6415 or another control element (e.g., compression and/or tension member) surrounding the electrode shaft surface contained within the catheter shaft in the un-deployed state. The coil springs or other control elements (e.g., force limiting and/or force restoration structures) may advantageously limit the maximum outward force an electrode can project and enable the electrode to return to the un-deployed state once the internal expansion member is returned to the non-actuated (e.g., unexpanded) state. The multi-electrode catheter may be an over-the-wire catheter or a steerable catheter. The multi-electrode catheter 6400 may advantageously provide one or more of the following benefits: (i) simultaneous and balanced electrode deployment; (ii) reduces the exposed length of catheter beyond a guide catheter or sheath tip required for electrode deployment against the vessel wall; and/or (iii) enables the ability to independently limit the electrode contact force.

Some embodiments of multi-electrode delivery devices comprise pairs of electrode deployment arms placed along a catheter shaft. The electrodes can be deployed by a number of mechanisms, such as (1) a retractable sheath which releases the deployment arms to self-expand into the deployed state, (2) a retractable tip that mechanically separates and radially expands the deployment arms to ensure electrode contact with the vessel; and/or (3) pullwire-activated deployment arms that include structures that elastically deform into a predetermined shape enabling contact of the electrodes with the vessel wall.

FIGS. 64B-1 and 64B-2 illustrate undeployed and deployed configurations of an embodiment of a multi-electrode catheter 6400 having a retractable sheath 6402 to facilitate deployment of multiple electrodes 6405. The multiple electrodes 6405 are coupled to ends of individual deployment arms 6406 that include structures that elastically deform into a predetermined shape, thereby enabling contact of the electrodes 6405 with the vessel wall. The electrode deployment arms 6406 may comprise shape memory material that automatically transitions to a preformed shape upon retraction of the retractable sheath 6402. As shown, the multi-electrode catheter may comprise a core member 6407 having a distal tip sized to interface with the distal end of the retractable sheath 6402. The core member 6407 includes a central lumen to facilitate over-the-wire advancement. In other embodiments, the core member 6407 does not include a central lumen. The retractable sheath 6402 and the core member 6407 may be independently controlled and moved with respect to each other.

FIGS. 64C-1 and 64C-2 illustrate undeployed and deployed configurations of an embodiment of a multi-electrode catheter 6400 having a retractable catheter tip 6403 configured to mechanically separate and radially expand electrode deployment arms 6406 to facilitate uniform electrode contact with the vessel wall. Similar to multi-electrode catheter of FIG. 64B, the multi-electrode catheter of FIG. 64C comprises a retractable sheath 6402. However, the electrode deployment arms 6406 in this embodiment are not automatically deployed upon retraction of the retractable sheath 6402 or actuated by a pullwire. In the illustrated embodiment, the electrode deployment arms are separated and expanded outward toward the vessel wall by retraction of the catheter tip 6403 in a proximal direction. The catheter tip 6403 may be coupled to an inner member (e.g., wire, tether, shaft) that may be pulled in a proximal direction. The orientation of the various embodiments illustrated in FIGS. 64A-64C may be reversed to facilitate treatment of sites very close to a distal terminus of a guide catheter.

FIGS. 64D-1 and 64D-2 illustrate undeployed and deployed configurations of an embodiment of a multi-electrode catheter 6400 having multiple pullwire-activated electrode deployment arms 6406 that include structures that elastically deform into a predetermined shape, thereby enabling uniform contact of the electrodes 6405 with the vessel wall. The electrode deployment arms 6406 comprise biased slotted hypotubes or microtubes. In the illustrated embodiment, a distal segment of the electrode deployment arms 6406 have slots or slits configured to cause the distal end of the electrode deployment arms 6406 to elastically deform into a predetermined shape. The electrode deployment arms 6406 each comprise a "soft", or flexible, segment 6408 just proximal of the electrode attachment point designed to enable a pivot of the electrode such that the side of the electrode is at least substantially parallel with the vessel wall. In accordance with several embodiments, the soft segment 6408 may advantageously limit the maximum force the electrode can exert on the vessel in the fully deployed state. The electrode deployment arms may be collectively actuated by a single pullwire 6401 or individually actuated by separate pullwires 6401.

Figure 64E:
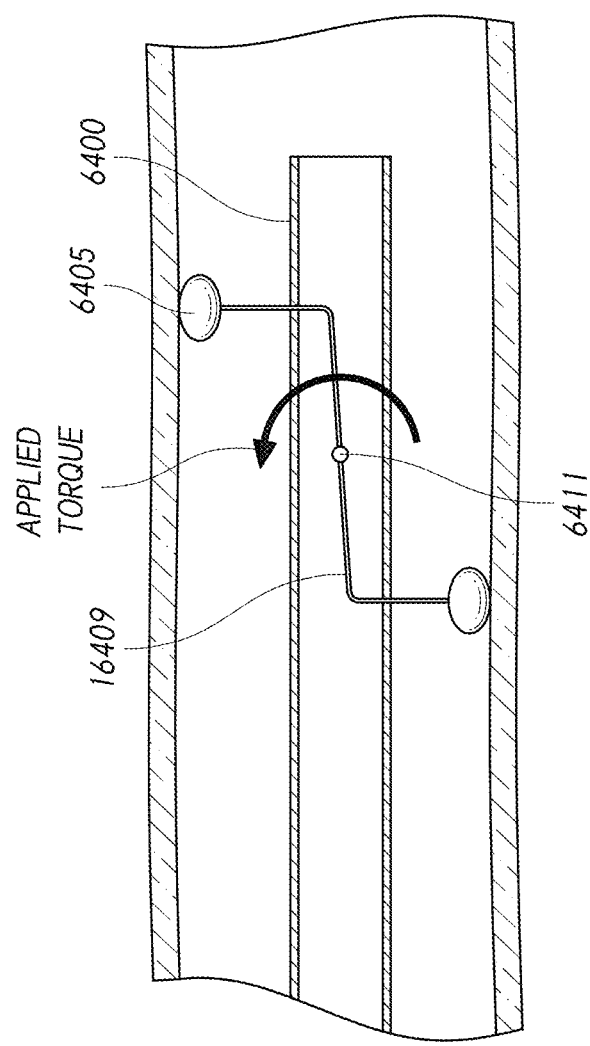

FIG. 64E illustrates an embodiment of a multi-electrode catheter 6400 configured to provide uniform and consistent contact by the multiple electrodes. The multi-electrode catheter 6400 is an over-the wire catheter comprising a lever arm 6409 having a central pivot point 6411 and two electrodes 6405, one electrode positioned at each end of the lever arm 6409. Torque is applied by any one or more torque application mechanisms. In various embodiments, the torque application mechanism may convert linear motion to rotational motion. Such mechanisms may include but are not limited to one or more of the following: pulley, rack and pinion, Scotch Yoke, Crank shaft, ball screw, lead screw, and/or cam follower. In some embodiments, the linear to rotational mechanism is comprised of an elongate tube or shaft having a helical groove or slot and a rotational element providing a pin, the pin being adapted to slide within the slot or groove. In other embodiments the torque application mechanism may convert rotational motion in a first direction into rotational motion in a second direction. Such mechanisms include but are not limited to one or more of the following: worm gears, spiral gears, beveled gears and/or a twisted belt or chain. In some embodiments, the gear is a pin gear. The central pivot point may advantageously enable electrode deployment and catheter centering at the deployment site, as well as the ability to independently limit the electrode contact force with a single deployment mechanism. The multi-electrode catheter 6400 may comprise more than one lever arm 6409 in other embodiments.

Figures 4, 64F:
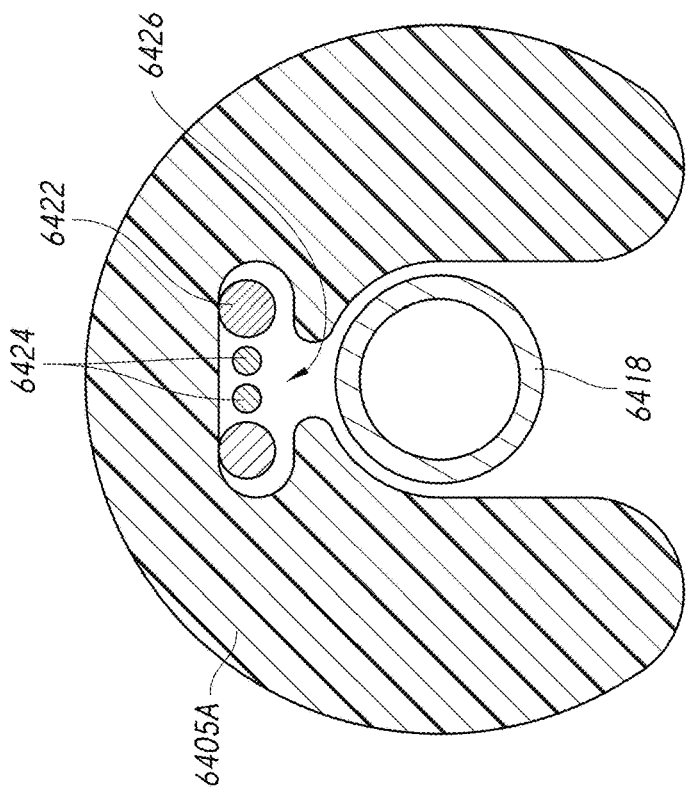
Figures 3, 64F:
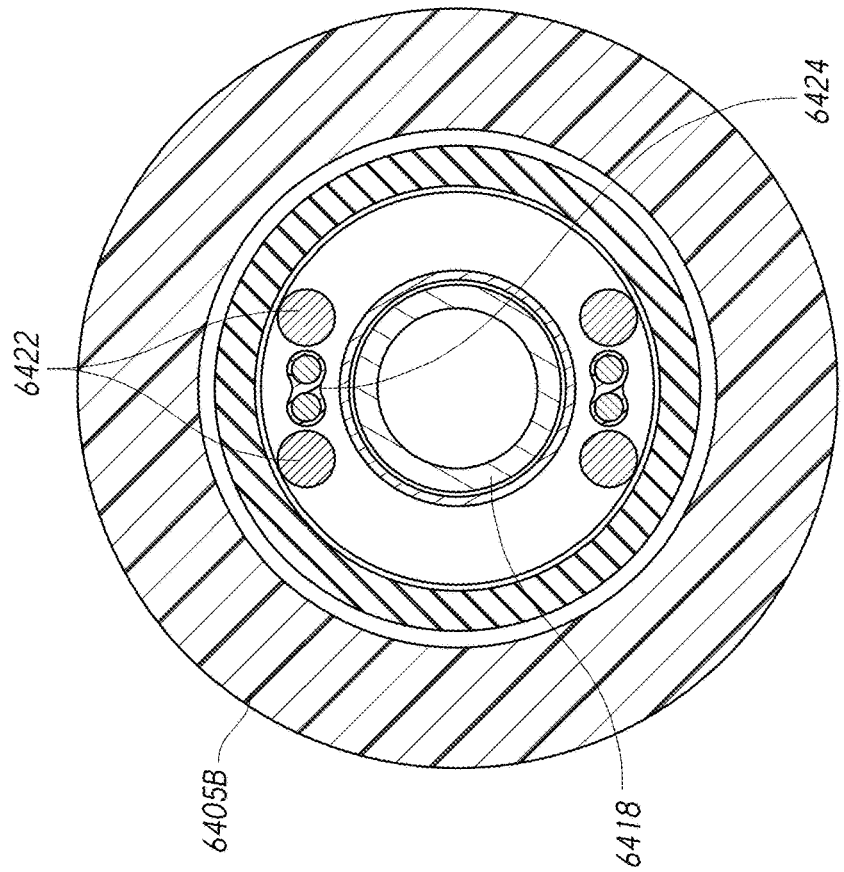

FIGS. 64F-1 to 64F-4 illustrate an embodiment of a neuromodulation device (e.g., treatment catheter) 6400 comprising two electrodes 6405 which may be actively deployed to create two longitudinally displaced treatment zones at opposing sides of a treatment vessel (e.g., a "bowstring" design). In a deployed configuration, as shown in FIG. 64F-2, the treatment catheter 6400 comprises a deployment segment 6406 including (e.g., carrying) a first electrode 6405A configured to be brought into contact at a first location on a first side of a vessel wall. The deployment segment 6406 also urges the adjacent distal and proximal portions of the catheter shaft 6416 against the opposite side of the vessel wall. A second electrode 6405B may be coupled or secured to the catheter shaft 6416 on the proximal portion 6417, and is therefore brought into contact against the vessel wall on the opposing quadrant of the vessel from the first electrode 6405A. The distal portion 6419 of the catheter shaft 6416 is also urged against this opposing quadrant which tends to keep the treatment catheter 6400 oriented along the axis of the blood vessel. The deployment may be controlled by retraction (e.g., by longitudinal actuation) of an inner tube 6418 relative to the remainder of the catheter shaft 6416. The inner tube 6418 may also serve to provide a lumen for use with a guide wire.

The deployment segment 6406 may comprise a ribbon-like cross section, which may provide structural stability as it is deployed outwards. As seen in FIG. 64F-3, the elements that make up the deployment segment 6406 may comprise a ribbon composite including two laterally-displaced outer structural wires 6422, with inner sensor and/or power leads 6424 (e.g., bifilar thermocouple such as a T-type thermocouple comprising copper and constantan leads, optical fibers, other temperature-measurement device leads and/or other sensor or power conductor leads) in between. The outer structural wires 6422 may comprise nitinol, stainless steel or other metallic, metallic alloy or shape-memory materials. In one embodiment, the diameter of the outer structural wires 6422 is 0.006 inches; however, other diameters may be used as desired and/or required (e.g., from 0.0004 inches to 0.0010 inches, from 0.0005 inches to 0.0015 inches, from 0.0008 inches to 0.0012 inches, overlapping ranges thereof or any value of or within the recited ranges). The inner leads may optionally be encased in an insulation covering or jacket comprised of one or more polymeric materials such as polyimide, PTFE, perfluoroalkoxy alkane (PFA), polyurethane, Nylon and/or the like. Where the deployment segment 6406 connects to the first electrode 6405A (as shown in FIG. 64F-4), the energizing lead (which may be one of the leads for the thermocouple, if included) is electrically connected to the electrode 6405A, by suitable connection means, such as by soldering or welding. In some embodiments, the structural wires 6422 comprise generally planar structural elements of electrically insulated metal or metallic alloy (e.g., polyimide laminate, thermoplastic reflow insulation). In various embodiments, the ribbon composite structure optionally comprises an outer covering (not shown) surrounding the outer structural wires and the inner sensor and/or power wires. The outer covering may comprise polyimide tape, Pebax®, coextruded polymers (inside hot melt adhesive), and/or adhesives used to bond everything together.

The first electrode 6405A may have a generally "horseshoe" or U-shape, as seen in FIG. 64F-4. The opening allows for the electrode 6405A to be nested around the inner tube 6418 during placement of the treatment catheter 6400 within the vasculature, when the treatment catheter is undeployed (FIG. 64F-1). Upon deployment, the first electrode 6405A can move laterally away from the inner tube 6418. In some embodiments, the first electrode 6405A comprises a keyhole 6426 within which the deployment segment 6406 can securely reside. Such a keyhole 6426 provides good mechanical connection to the first electrode 6405A. The second electrode 6405A may have a similar shape as the first electrode 6405B or may have a cylindrical shape that extends around a full circumference of the catheter shaft 6416.

The multi-electrode catheters 6400 of FIGS. 64B to 64E may advantageously provide one or more of the following benefits: (i) simultaneous and balanced electrode deployment of an electrode pair; (ii) centers the catheter during electrode deployment; (iii) reduces the exposed length of catheter beyond a guide catheter or sheath tip required for electrode deployment against the vessel wall; and/or (iv) enables the ability to independently limit the electrode contact force. The electrode deployment arms 6406 may be designed to space the electrodes along a single circumferential cross-section at a single position along the length of the vessel wall or at different positions along the length of the vessel wall. The electrodes 6405 may be activated simultaneously or sequentially.

Figures 1, 64G:
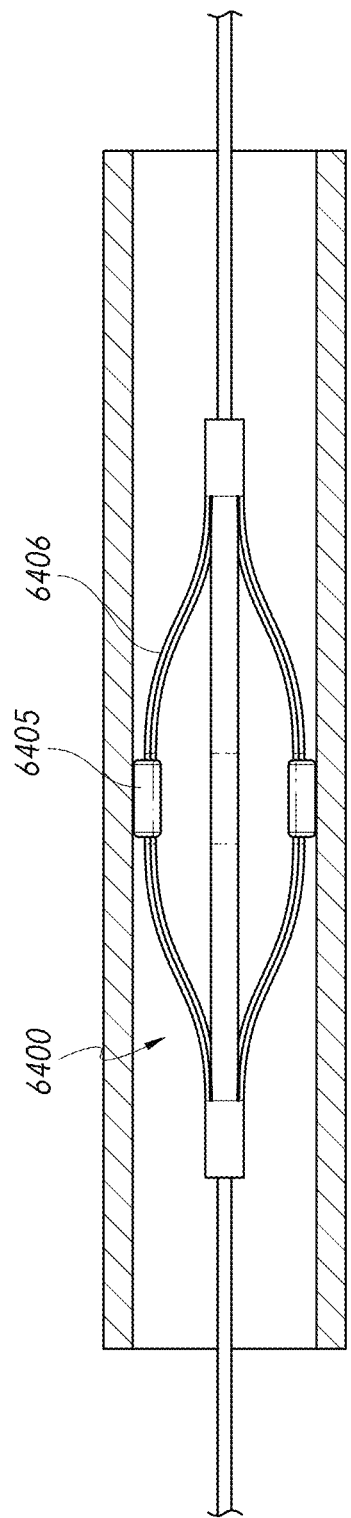

FIGS. 64G-1, 64G-2, 64G-3, 64G-4, 64G-5, 64G-6, 64H and 64I illustrate various embodiments of multi-electrode catheters 6400 having multiple cantilevered tines or electrode deployment arms 6406 configured to provide controlled self-expanding electrode deployment of multiple electrodes 6405 along the catheter shaft without increasing profile. The deployment arms 6406 may comprise free-floating distal ends that do not connect back to the main catheter shaft (as shown for example in FIGS. 64H and 64I). In some embodiments, the multi-electrode catheters 6400 comprise closed configurations of deployment arms in which the deployment arms are connected to the main shaft at both ends (such as shown in FIGS. 64G and 64J)). The number of deployment arms may vary (for example, 2, 3, 4 or more arms). Each deployment arm may consist of a single electrode or multiple electrodes positioned along the length of the deployment arm. For closed configurations, each electrode may be positioned at a central portion of the length of the deployment arm (as shown, for example, in FIG. 64G-1) or the electrodes may be positioned at axially offset positions along the length (as shown, for example, in FIG. 64G-2) of the deployment arms to facilitate lesion formation at locations spaced apart along a length of a vessel. If monopolar, the multiple electrodes may be activated simultaneously or sequentially. The cantilevered tines may be deployed from straight axial slots (as shown for example in FIG. 64H) or curved slots (as shown for example in FIG. 64I). As shown, the multi-electrode catheters 6400 may comprise a central lumen to facilitate advancement over a guidewire. The multi-electrode catheters may consist of two electrodes or four electrodes in various embodiments. The electrodes may be configured to be deployed at various positions spaced along the length of the vessel (e.g., 0.4 cm, 0.5 cm, 0.6 cm, 0.7 cm, 0.8 cm, 0.9 cm, 1 cm, 1.1 cm, 1.2 cm, 1.3 cm, 1.4 cm, 1.5 cm, 1.6 cm, 1.7 cm, 1.8 cm, 1.9 cm, 2 cm, less than 0.4 cm or more than 2 cm apart). The electrodes may comprise rounded electrodes (e.g., cylindrical, slotted, half-cylinder, C-shaped, D-shaped electrodes) configured to match the curvature of the vessel wall to facilitate increased surface contact with the vessel wall. The electrodes may also comprise keyhole slots as described above in connection with FIG. 64F-4. The orientation of the various embodiments illustrated in FIGS. 64G-64 may be reversed to facilitate treatment of sites very close to a distal terminus of a guide catheter. The deployment arms or segments described herein may be pull-actuated or push-actuated.

FIG. 64G-2A illustrates an embodiment of a treatment catheter 6400 having two deployable electrodes 6405 mounted on two deployment arms or segments 6406 on opposite sides of the treatment catheter 6400. The distal ends of each deployment segment 6406 may be secured within the treatment catheter 6406 at the same longitudinal location. The proximal portions of each deployment segment 6406 may emanate from the same longitudinal location on the catheter shaft 6416. The electrodes 6405 may be located asymmetrically along the deployment segments 6406. For example, a first electrode may be mounted to its deployment segment 6406 more distally, while a proximal electrode is mounted more proximally, as shown in FIG. 64G-2A.

The deployment segments 6406 may have a uniform cross section, or may have a non-uniform cross section, as is the case in FIG. 64G-2A. Each deployment segment 6406 may have a different bending stiffness that extends distal of the electrode as compared to proximal of the electrode 6405. In this manner, the deployment segment 6406 may deploy in an eccentric fashion, as shown in FIG. 64G-2A for example. The different bending stiffness may be achieved, for example, by reducing the dimension of a portion of the deployment segment 6406.

The deployment segments 6406 may be actuated by advancing a proximal portion of each deployment segment in a distal direction relative to the catheter shaft 6416. The deployment segments 6406 may be actuated simultaneously or sequentially. As seen in the cross-sectional view of FIG. 64G-2A (FIG. 64G-2B), the proximal portions of the deployment segments 6406 may both be coupled or secured to a longitudinally movable element 6430 (such as a tubular sleeve) that also includes or contains the electrical lead wires that connect to the electrodes 6405 via the deployment segments 6406. The treatment catheter 6400 may include a distal extension 6424 as described elsewhere herein to facilitate guidewire trackability.

Figures 3C, 64G:
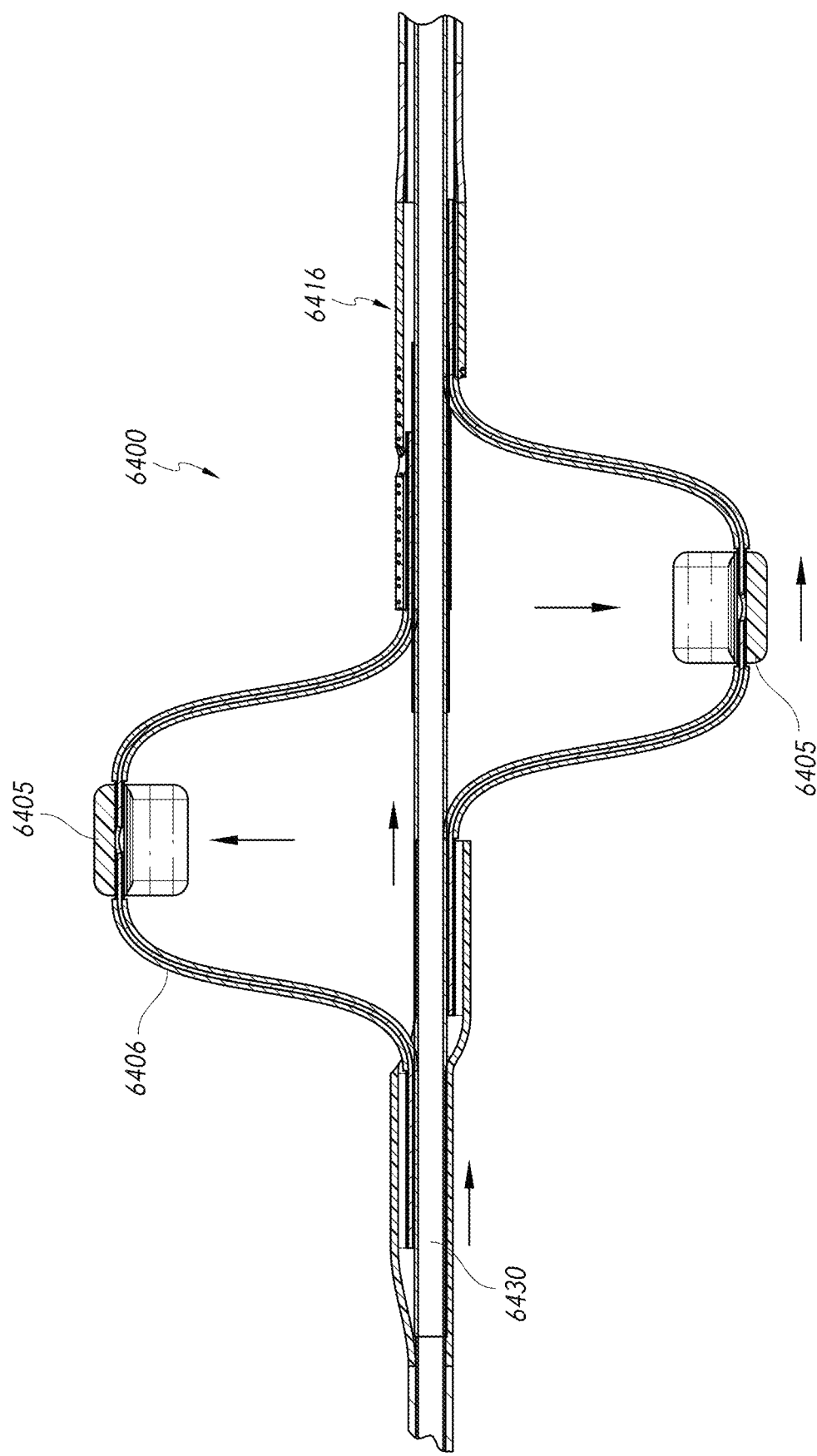
Figures 4, 64G:
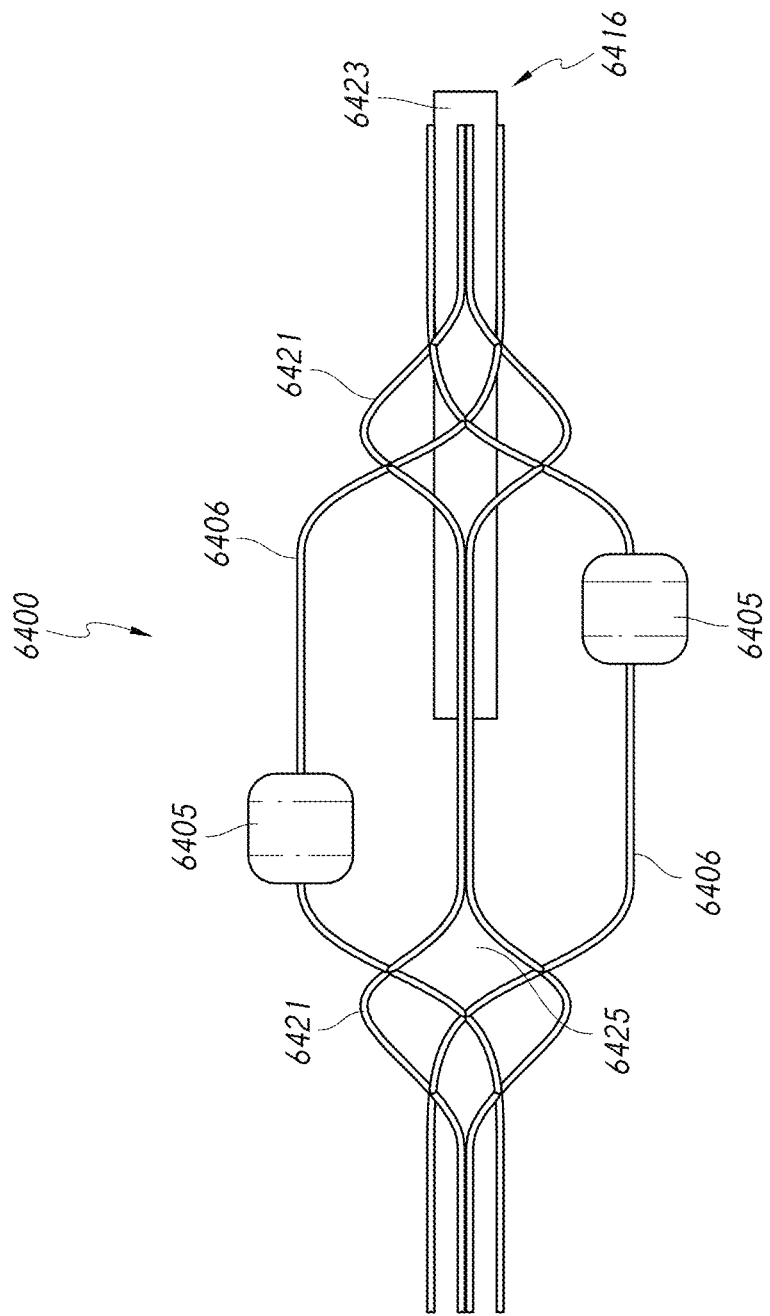

FIGS. 64G-3A to FIGS. 64G-3C illustrate an embodiment of a deployable multi-electrode treatment catheter 6400. The treatment catheter 6400 comprises two offset deployment arms or segments 6406, each comprising an electrode 6405 (e.g., a "double bowstring" design). Each deployment segment 6406 is configured to extend laterally away from the catheter shaft 6416. The deployment segments 6406 may be positioned at 180 degrees apart, such that when they are in contact with the vessel wall they are on generally opposite sides. Other angular orientations are contemplated, as well as more than two deployment segments along the length of the catheter shaft or more than one electrode per deployment segment.

As with the embodiment described in connection with FIGS. 64F-1 to 64F-4, the electrodes 6405 of FIGS. 64G-3A to FIGS. 64G-3C may be "horseshoe" or U-shaped such that when in the undeployed condition (as shown in FIGS. 64G-3B), the electrodes 6405 can nest around the shaft 6416 of the treatment catheter 6400. Other slotted or nested shapes or configurations are also contemplated. The method of deployment of the electrodes 6405 may include a longitudinally moveable inner tube 6430 relative to the outer tube of the proximal catheter shaft, as can be seen in the cross-sectional view of FIG. 64G-3C. Movement (e.g., retraction) of the inner tube 6430 may retract the distal connections of the deployment segments 6406, thereby causing the electrodes 6405 to deploy radially outward. In accordance with several embodiments, while both electrodes 6405 also move in a retrograde fashion as they move radially outward, the longitudinal spacing between them remains relatively constant, advantageously resulting in the longitudinal spacing being consistent across a wide range of vessel diameters. The deployment segments 6406 may be of a composite ribbon-like construction, similar to the construction described in FIG. 64F-3. In some embodiments, the catheter 6400 comprises a distal extension 6419 to facilitate trackability.

In various embodiment, the electrodes 6405 may be supported between stent-like support structures providing expansion and stabilization of the electrodes 6405, said support structures being connected by substantially axial connectors that control the axial spacing of the electrodes 6405 substantially independent of vessel diameter. Stent-like support structures may be braid, zig zag, serpentine, sinusoidal, pinwheels, tessellated or non-tessellated designs. Supports may be comprised of PEEK fiber, insulated metal or a combination of the two.

FIG. 64G-4 illustrates an embodiment of a deflectable portion of an RF electrode treatment catheter 6400. The deflectable portion comprises two deployment segments 6406 each comprising an electrode 6405. The electrodes are positioned so as to be offset longitudinally and circumferentially (e.g., 180 degrees offset) when in the deployed configuration as shown. The deployment segments 6406 are configured to be actuated by a braid guide assembly 6421 of wires. In one embodiment, a proximal portion of the braid guide assembly 6421 is coupled to an outer tube 6423 of the catheter shaft 6416 and a distal portion of the braid guide assembly 6421 is coupled to an inner tube 6425 within the catheter shaft 6416, with the inner tube 6425 being moveable with respect to the outer tube 6423, or vice-versa.

Figures 5, 64G:
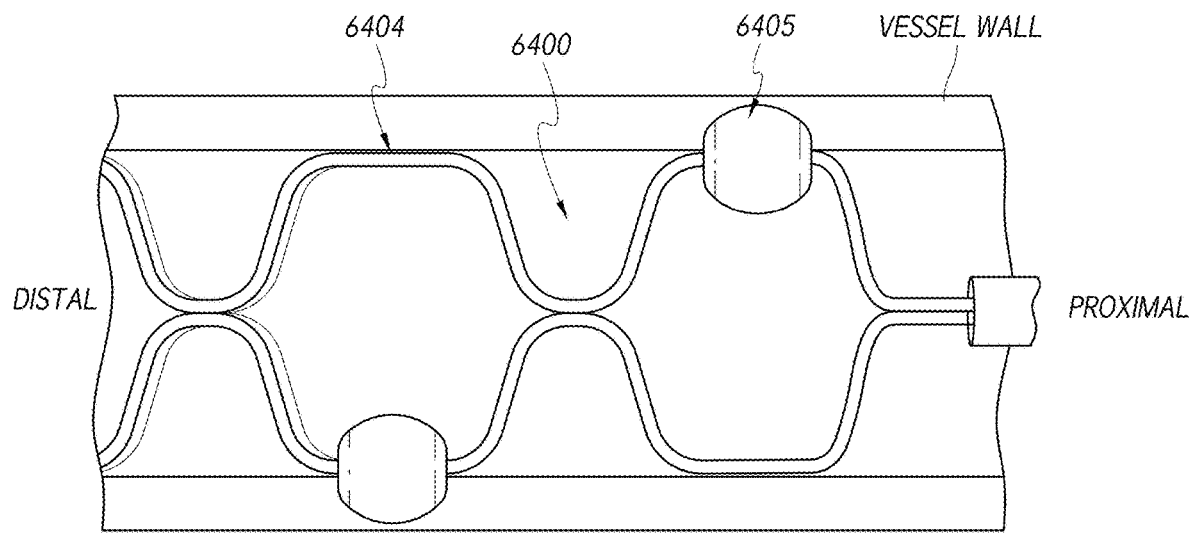
Figures 6, 64G:
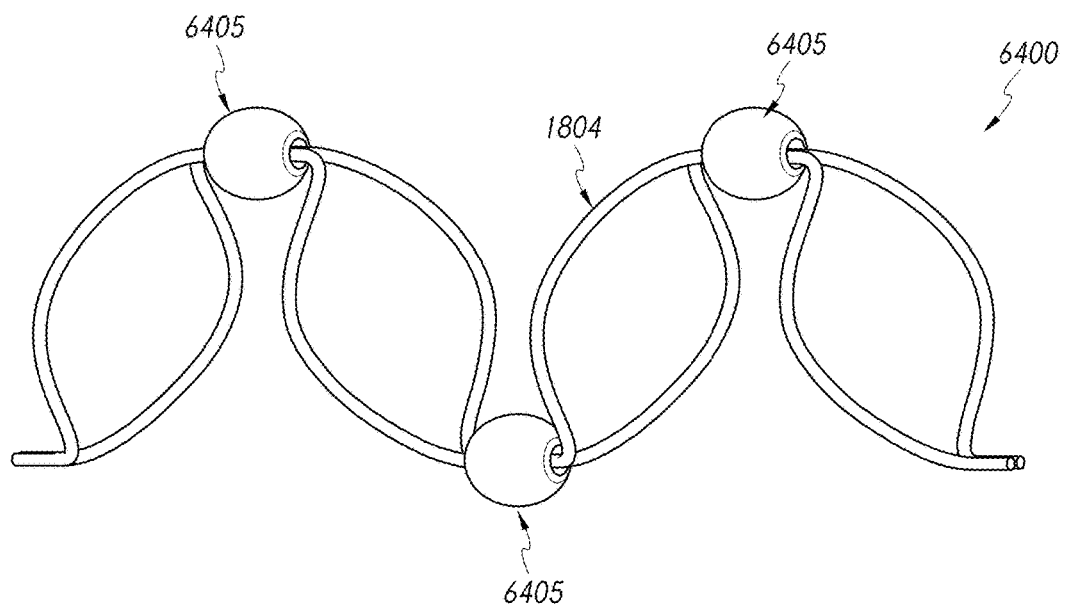

FIGS. 64G-5 and 64G-6 illustrate embodiments of multi-electrode catheters 6400 comprising frames or scaffolds 6404 having multiple electrodes 6405 positioned along the length of the frames or scaffolds 6404. The frame or scaffold 6406 of FIG. 64G-5 comprises a planar frame 6404 having electrodes 6405 aligned along the same plane but spaced 180 degrees apart from each other and spaced apart axially along the length of the frame 6404. Only a portion of the frame 6404 is illustrated. It should be appreciated that the frame 6404 may include additional electrodes following the same alternating 180-degree pattern (for example, four total electrodes). The electrodes 6405 illustrated in FIG. 64G-5 are monopolar electrodes. In an alternative embodiment, the electrodes 6405 comprise a first electrode (e.g., active electrode) of a bipolar electrode pair and corresponding second electrodes (e.g., return electrodes) may be positioned on the frame 6404 on the strut opposite the first electrodes. In some embodiments, the frame 6404 can be non-planar (for example, the frame 6404 may have a helical or spiral configuration. In some embodiments, the frame 6404 can have a configuration similar to a stent.

The frame 6404 of FIG. 64G-6 comprises two continuous wires extending through a lumen of each of the electrodes 6405. The wires are adapted to cause the electrodes 6405 to contact a vessel wall at axially spaced-apart locations that are offset circumferentially by 180 degrees. The portions of the wires between the electrodes may be sized and shaped so as to deploy outward and to contact the vessel wall to provide support to maintain contact of the electrodes 6405 with the vessel wall.

In some embodiments, the electrodes 6405 of the frames 6404 are offset at other than 180 degrees (for example 120 degrees, 90 degrees). The frames 6404 may comprise shape-memory metallic alloy material or other self-expandable material adapted to cause the electrodes 6405 to be placed into effective contact with a vessel wall inside any vessel having a diameter of between 3 mm and 10 mm upon exiting a sheath or sleeve and transitioning to a pre-formed shape. The frames 6404 may also be adapted to be recaptured within the sheath or sleeve for repositioning at another location in the vessel or for removal from the body. The strut or cell pattern of the frames 6404 are provided as examples; the patterns may vary as desired and/or required. The electrodes 6405 may comprise generally cylindrical electrodes as shown or non-cylindrical electrodes (slotted, D-shaped, C-shaped).

Figure 64K:
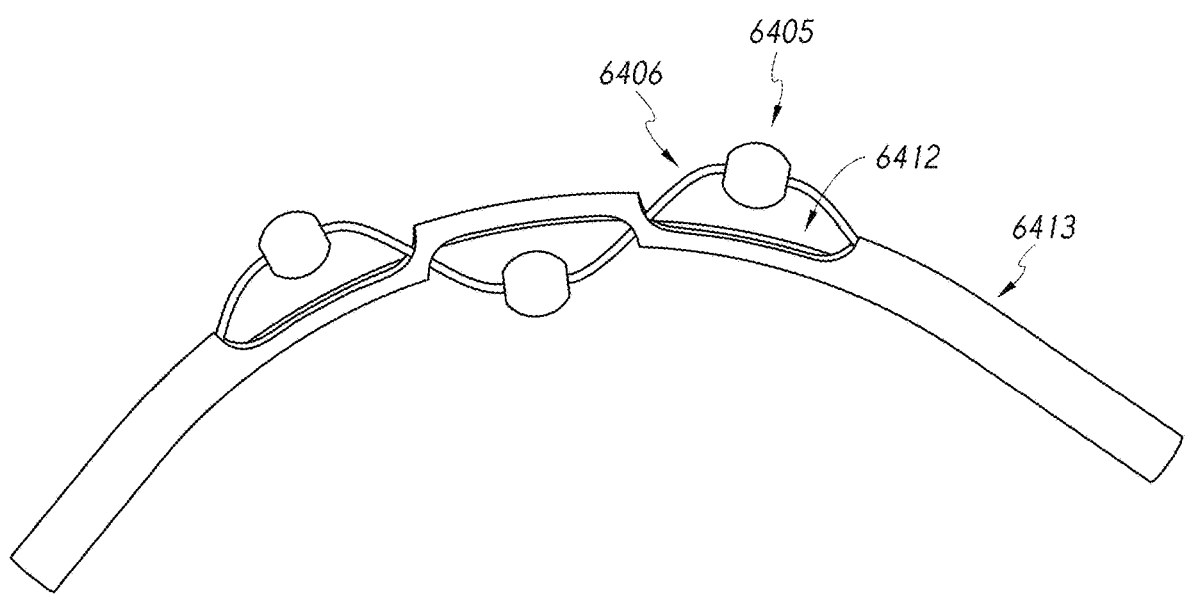

FIGS. 64J and 64K illustrate embodiments of a multi-electrode catheter 6400 comprising slots 6412 positioned along the length of the catheter shaft 6413 to permit deformation of a portion of the catheter shaft 6413 to deploy the multiple electrodes 6405 in a serpentine fashion at various locations along the length of a vessel wall. The multi-electrode catheter 6400 may comprise or consist essentially of two electrodes (as shown in FIG. 64J), three electrodes (as shown in FIG. 64K), four electrodes, six electrodes, or eight electrodes. In some embodiments, the electrodes 6405 are configured to be positioned 180 degrees apart from each other (as shown in FIGS. 64G-1, 64G-2, 64G-3, 64G-4, 64J and 64K). In various embodiments, the electrodes 6405 advantageously facilitate ablation of only two quadrants of the vessel wall instead of all four quadrants. If monopolar, the multiple electrodes may be activated simultaneously or sequentially. The multi-electrode catheters 6400 of FIGS. 64G to 64K may advantageously provide one or more of the following benefits: (i) low profile, (ii) large electrode surface and curvature, (iii) lateral deployment, (iv) low force, (v) controlled flexibility; and/or (vi) effective denervation of nerves in a perivascular region while maintaining minimal heating of, or thermal injury to, the inner vessel wall.

Figure 65:
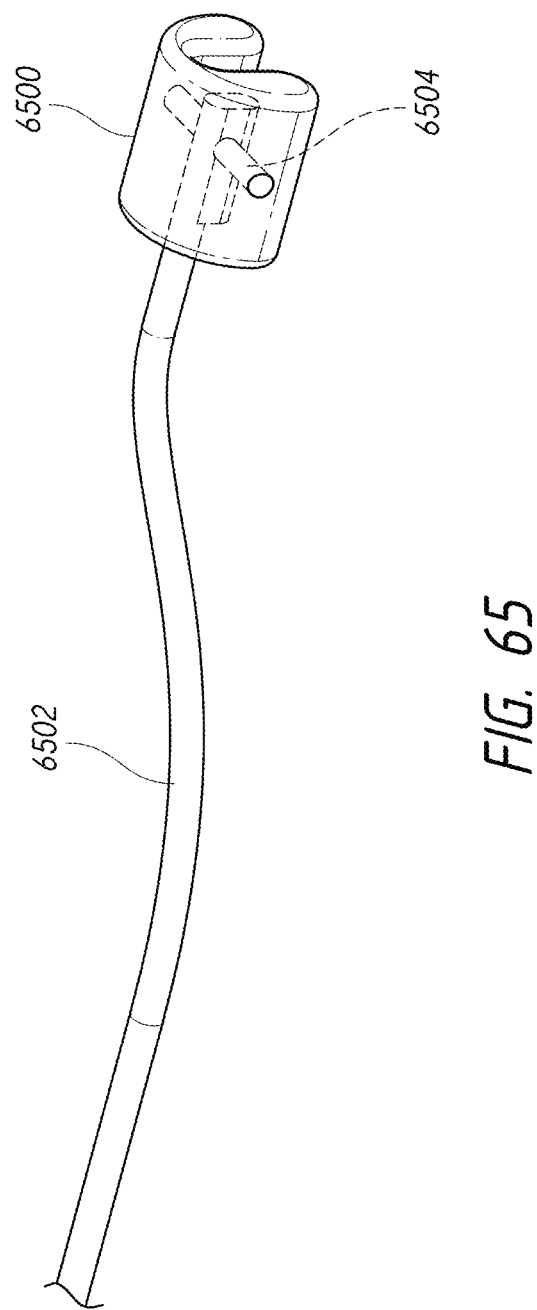
FIG. 65 illustrates an embodiment of a pivoting electrode.

FIG. 65 illustrates an embodiment of a pivoting electrode 6500 on a distal end of a shaft or electrode deployment arm 6502. The pivoting electrode 6500 is mounted on a pivot 6504 configured to facilitate an orientation that is in substantial alignment with the vessel wall. The pivoting electrode 6500 comprises an elongate electrode that provides increased surface area compared to a spherical electrode of comparable thickness. In the illustrated embodiment, the pivot DD04 comprises a pin. The pin may be substantially at the center of the electrode 6500. The pivot 6504 may be formed of a highly flexible polymer or gel. In some embodiments, the pivot 6504 may comprise a fiber or thread. In some embodiments, the pivot 6504 may comprise a ball and socket joint.

The pivoting electrode 6500 may be substantially cylindrical (e.g., a half cylinder). In one embodiment, the electrode 6500 has substantially spherical ends. One end and/or a side of the electrode 6500 may be slotted to permit access to the pivot 6504. In some embodiments, the electrode 6500 is attached to the shaft 6502 using a saddle, stirrup or clevis arrangement. If a clevis fastener is used, the clevis may be on the electrode or the shaft.

The pivot 6504 may be skew to the central longitudinal axis of the shaft 6502 to correct for helical deformation of the deflected catheter shaft. The pivot 6504 may provide a restricted range of motion. In some embodiments, the pivot 6504 provides substantially zero moment or torque within its range of motion. In some embodiments, the pivot 6504 provides a specified moment or torque within its range of motion. The pivoting electrode 6500 may be incorporated into any of the electrode-based devices or systems described herein. The pivoting electrode 6500 may advantageously provide one or more of the following benefits: (i) uniform electrode contact in a desired orientation despite possible deformation of the vessel by a catheter or variations in vascular anatomy, (ii) increased electrode surface contact, (iii) consistent lesion size, (iv) reduced superficial vessel wall injury by reducing electric current and cooling variations, (v) increased catheter lengths, trackability and steerability; and/or (vi) not dependent on apposition force to achieve reorientation that may not be consistent with different vessel geometry.

g. RF Energy Delivery Parameters

In some embodiments, an RF energy delivery system delivers RF energy waves of varying duration. In some embodiments, the RF energy delivery system varies the amplitude of the RF energy. In other embodiments, the RF energy delivery system delivers a plurality of RF wave pulses. For example, the RF energy delivery system may deliver a sequence of RF pulses. In some embodiments, the RF energy delivery system varies the frequency of RF energy. In other embodiments, the RF energy delivery system varies any one or more parameters of the RF energy, including, but not limited to, duration, amplitude, frequency, and total number of pulses or pulse widths. For example, the RF energy delivery system can deliver RF energy selected to most effectively modulate (e.g., ablate or otherwise disrupt) sympathetic nerve fibers in the hepatic plexus. In some embodiments, the frequency of the RF energy is maintained at a constant or substantially constant level.

In some embodiments, the frequency of the RF energy is between about 50 kHz and about 20 MHz, between about 100 kHz and about 2.5 MHz, between about 400 kHz and about 1 MHz, between about 50 kHz and about 5 MHz, between about 100 kHz and about 10 MHz, between about 500 kHz and about 15 MHz, less than 50 kHz, greater than 20 MHz, between about 3 kHz and about 300 GHz, or overlapping ranges thereof. Non-RF frequencies may also be used. For example, the frequency can range from about 100 Hz to about 3 kHz. In some embodiments, the amplitude of the voltage applied is between about 1 volt and 1000 volts, between about 5 volts and about 500 volts, between about 10 volts and about 200 volts, between about 20 volts and about 100 volts, between about 1 volt and about 10 volts, between about 5 volts and about 20 volts, between about 1 volt and about 50 volts, between about 15 volts and 25 volts, between about 20 volts and about 75 volts, between about 50 volts and about 100 volts, between about 100 volts and about 500 volts, between about 200 volts and about 750 volts, between about 500 volts and about 1000 volts, less than 1 volt, greater than 1000 volts, or overlapping ranges thereof.

In some embodiments, the current of the RF energy ranges from about 0.5 mA to about 500 mA, from about 1 mA to about 100 mA, from about 10 mA to about 50 mA, from about 50 mA to about 150 mA, from about 100 mA to about 300 mA, from about 250 mA to about 400 mA, from about 300 to about 500 mA, or overlapping ranges thereof. The current density of the applied RF energy can have a current density between about 0.01 mA/cm$^2$ and about 100 mA/cm$^2$, between about 0.1 mA/cm$^2$ and about 50 mA/cm$^2$, between about 0.2 mA/cm$^2$ and about 10 mA/cm$^2$, between about 0.3 mA/cm$^2$ and about 5 mA/cm$^2$, less than about 0.01 mA/cm$^2$, greater than about 100 mA/cm$^2$, or overlapping ranges thereof. In some embodiments, the power output of the RF generator ranges between about 0.1 mW and about 100 W, between about 1 mW and 100 mW, between about 1 W and 10 W, between about 1 W and 15 W, between 5 W and 20 W, between about 10 W and 50 W, between about 25 W and about 75 W, between about 50 W and about 90 W, between about 75 W and about 100 W, or overlapping ranges thereof. In some embodiments, the total RF energy dose delivered at the target location (e.g., at an inner vessel wall, to the media of the vessel, to the adventitia of the vessel, or to the target nerves within or adhered to the vessel wall) is between about 100 J and about 2000 J, between about 150 J and about 500 J, between about 300 J and about 800 J (including 500 J), between about 500 J and about 1000 J, between about 800 J and about 1200 J, between about 1000 J and about 1500 J, and overlapping ranges thereof. In some embodiments, the impedance ranges from about 10 ohms to about 600 ohms, from about 100 ohms to about 300 ohms, from about 50 ohms to about 200 ohms, from about 200 ohms to about 500 ohms, from about 300 ohms to about 600 ohms, and overlapping ranges thereof. In some embodiments, power is provided between 8 W and 14 W (e.g., 10 W, 12 W) for between 30 seconds and 3 minutes (e.g., 1 minute, 90 seconds, 2 minutes, 150 seconds) to provide a total energy delivery of between 240 J and 2520 J (e.g., 1200 J-10 W for 2 minutes, 1500 J-12 W for 2 minutes). Electrode(s) may be coupled (e.g., via wired or wireless connection) to an energy source (e.g., generator) even if the generator is not explicitly shown or described with each embodiment. The various treatment parameters listed herein (e.g., power, duration, energy, contact force/pressure, electrode size, pulsing, resistance, etc.) may be used for any of the embodiments of devices (e.g., catheters) or systems described herein.

In various embodiments, the generator comprises stored computer-readable instructions that, when executed, provide specific treatment (e.g., custom energy algorithm) to treat specific vessels selected by an operator. Accordingly, the generator facilitates delivery of RF energy having different treatment parameters using a single RF energy delivery device configured to provide similar or consistent performance across varying patient anatomy (e.g., one-size-fits-all). The generator may comprise safety controls tailored to environment: vessel size, flow, resistance, and/or other structures. The stored computer-readable instructions (e.g., software, algorithms) may be customized to deliver optimized lesion depth and/or may comprise pre-programmed operator-independent treatment algorithms. In some embodiments, a pre-programmed treatment course, which may include one or more parameters (such as power, treatment duration, number of target locations, spacing of target locations, energy, pulsed or non-pulsed, etc.) is provided. The pre-programmed treatment course may be based on vessel dimensions (e.g., diameter, segment length, wall thickness, age of patient, weight of patient, etc.). In one embodiment, a preconfigured or predetermined course of neuromodulation (e.g., ablation) may be performed (e.g., automatically or manually) to modulate (e.g., ablate) one or more nerves. The predetermined treatment course or profile may comprise a full or partial route of treatment or treatment points. The route may extend around a partial circumference of a blood vessel (e.g., 270 degrees, 220 degrees, 180 degrees, 90 degrees, or 60 degrees) or around the entire circumference.

For example, in some patients a target modulation (e.g., ablation) location (such as the common hepatic artery) may not be long enough to allow for complete modulation (e.g., ablation) of target nerves. In some embodiments, it may be desirable to treat multiple vessels adjacent to or that are portions of the hepatic artery vasculature (e.g., celiac, splenic, common hepatic, proper hepatic arteries) using a single energy delivery device. In some embodiments, an operator may select a vessel to be treated and the generator may automatically adjust the energy delivery parameters (e.g., select a pre-determined energy algorithm) based on the selected vessel. For example, different vessels may have different flow characteristics and different diameters. Accordingly, different energy profiles (e.g., varying power and/or time) may be associated with the different vessels to achieve a desired overall energy output. In ablation embodiments, the different energy profiles provide the same volume and/or circumferential arc of lesion for the various different vessels. The delivery of energy may be controlled manually or automatically according to a preconfigured energy profile determined by a controller, processor or other computing device (e.g., based on execution of instructions stored in memory) within the generator. For example, if the nominal vessel diameter (e.g., common hepatic artery) is greater than an adjacent vessel diameter, the power level and time can be adjusted lower as there will be a greater area of contact between the vessel wall and electrode surface. In some embodiments, the allowable temperature target or limit may be adjusted higher to compensate for a lower capacity of the blood flow to remove heat from the electrode. If the adjacent artery is larger, then power may be increased to modulate (e.g., ablation) a larger area in a single cycle. In some embodiments, a tendency towards more modulation (e.g., ablation) sites in the larger adjacent vessel may be employed.

The RF energy can be pulsed or continuous. The voltage, current density, frequencies, treatment duration, power, and/or other treatment parameters can vary depending on whether continuous or pulsed signals are used. For example, the voltage or current amplitudes may be significantly increased for pulsed RF energy. The duty cycle for the pulsed signals can range from about 0.0001% to about 100%, from about 0.001% to about 100%, from about 0.01% to about 100%, from about 0.1% to about 100%, from about 1% to about 10%, from about 5% to about 15%, from about 10% to about 50%, from about 20% to about 60% from about 25% to about 75%, from about 50% to about 80%, from about 75% to about 100%, or overlapping ranges thereof. The pulse durations or widths of the pulses can vary. For example, in some embodiments, the pulse durations can range from about 10 microseconds to about 1 millisecond; however, pulse durations less than 10 microseconds or greater than 1 millisecond can be used as desired and/or required. In accordance with some embodiments, the use of pulsed energy may facilitate reduced temperatures, reduced treatment times, reduced cooling requirements, and/or increased power levels without risk of increasing temperature or causing endothelial damage due to heating. In some embodiments involving use of a catheter having a balloon, the balloon can be selectively deflated and inflated to increase lumen wall cooling and enhance the cooling function that pulsed energy provides.

Figure 66:
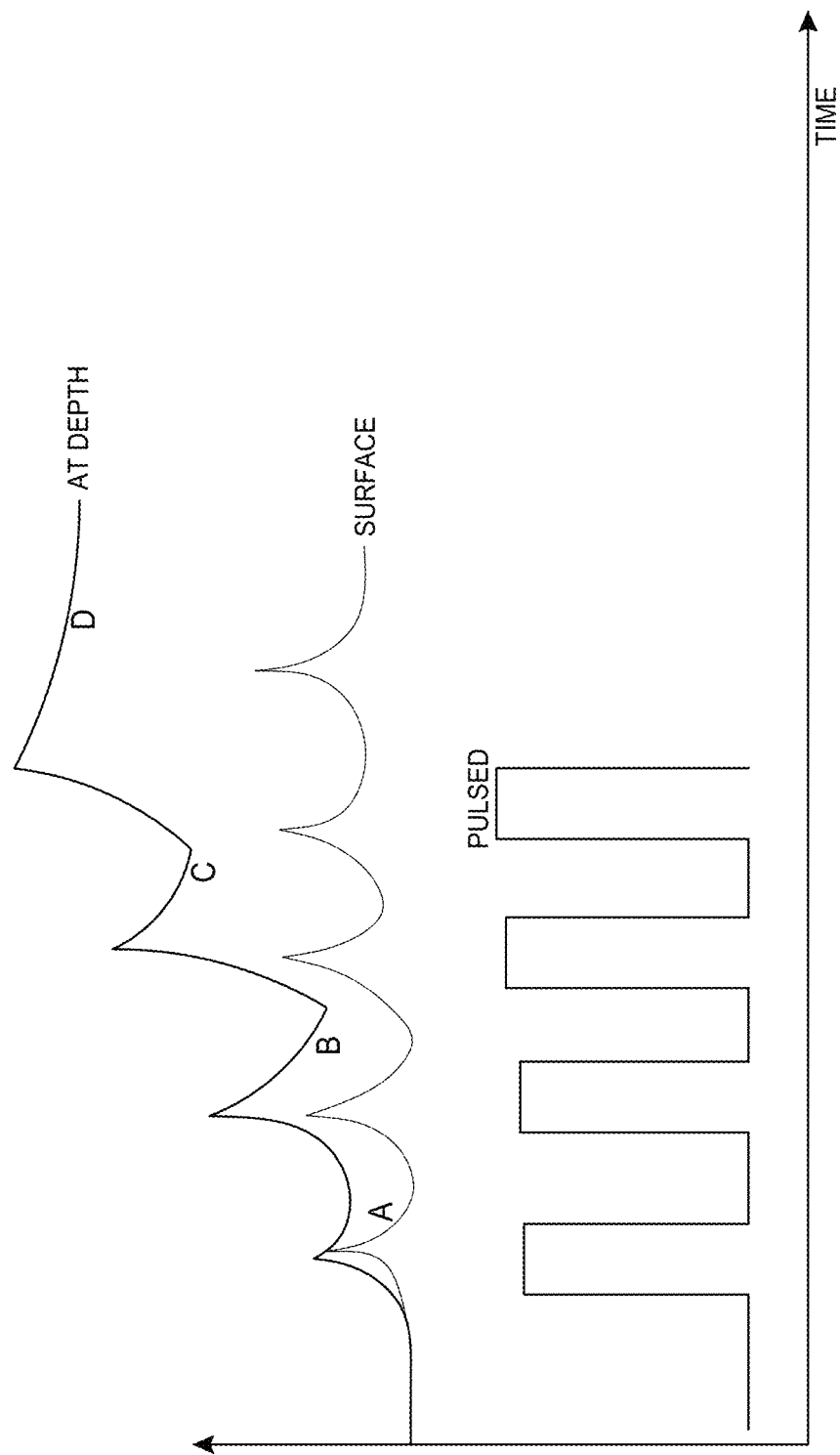
FIG. 66 illustrates a graph demonstrating the use of pulsed therapy, in accordance with an embodiment of the invention.

In some embodiments, the RF energy is pulsed based, at least in part, on the sensed tissue impedance or temperature, as shown, for example, in FIG. 66. For example, RF power can be delivered until a second temperature reaches a predefined value greater than a first temperature, at which point RF power may temporarily be interrupted. Because tissues near the arterial lumen cool faster than the target tissue (e.g., about 3, 3.5, 4, 4.5, 5 mm from the arterial lumen), in some embodiments, the temporary interruption tends to concentrate heat at the location of the target tissue, as shown in FIG. 55. In several embodiments, a similar result can be obtained by pulsing RF energy based, at least in part, on tissue impedance. In one embodiment, each subsequent cooling period (A, B, C, and then D) is longer than the previous cooling period (which may unexpectedly be particularly important in the hepatic artery, where flow rate is lower than other endovascular sites). Embodiments of this approach are described in U.S. Publ. No. 2010/0125268, which is incorporated by reference herein and may be used in conjunction with embodiments described herein. In some embodiments, pulsed energy is used to selectively deliver heat to nerves in the adventitia of the hepatic artery or other target vessels.

In several embodiments, the invention is particularly beneficial because it is unexpectedly useful for concentrating heat at the region of peripheral nerves (and particularly beneficial for treating the peripheral nerves about the hepatic artery). In several embodiments, substantially all of the target tissue treated is healthy tissue.

The treatment time durations can range from 1 second to 1 hour, from 5 seconds to 30 minutes, from 10 seconds to 10 minutes, from 30 seconds to 30 minutes, from 1 minute to 20 minutes, from 1 minute to 3 minutes, from 2 to four minutes, from 5 minutes to 10 minutes, from 10 minutes to 40 minutes, from 30 seconds to 90 seconds, from 5 seconds to 50 seconds, from 60 seconds to 120 seconds, overlapping ranges thereof, less than 1 second, greater than 1 hour, about 120 seconds, or overlapping ranges thereof. The duration may vary depending on various treatment parameters (e.g., amplitude, current density, proximity, continuous or pulsed, type of nerve, size of nerve). In some embodiments, the RF or other electrical energy is controlled such that delivery of the energy heats the target nerves or surrounding tissue in the range of about 50 to about 90 degrees Celsius (e.g., 60 to 75 degrees, 50 to 80 degrees, 70 to 90 degrees, 60 to 90 degrees or overlapping ranges thereof). In some embodiments, the temperature can be less than 50 or greater than 90 degrees Celsius. The electrode tip energy may range from 37 to 100 degrees Celsius. In some embodiments, RF ablation thermal lesion sizes range from about 0 to about 3 cm (e.g., between 1 and 5 mm, between 2 and 4 mm, between 5 and 10 mm, between 15 and 20 mm, between 20 and 30 mm, overlapping ranges thereof, about 2 mm, about 3 mm) or within one to ten (e.g., one to three, two to four, three to five, four to eight, five to ten) media thickness differences from a vessel lumen (for example, research has shown that nerves surrounding the common hepatic artery and other branches of the hepatic artery are generally within this range). In several embodiments, the media thickness of the vessel (e.g., hepatic artery) ranges from about 0.1 cm to about 0.25 cm. In some anatomies, at least a substantial portion of nerve fibers of the hepatic artery branches are localized within 0.5 mm to 1 mm from the lumen wall such that modulation (e.g., denervation) using an endovascular approach is effective with reduced power or energy dose requirements.

Figure 67:
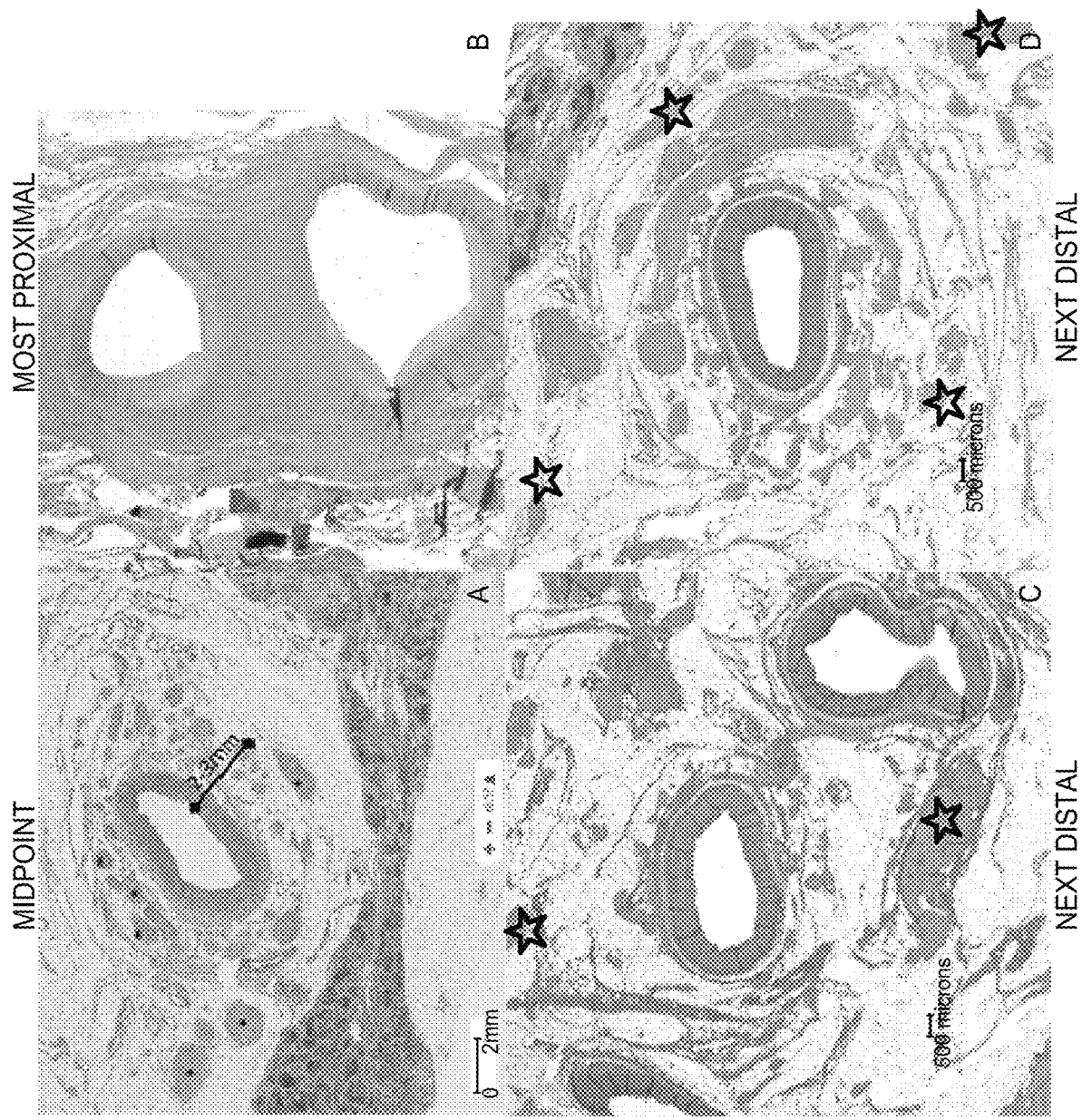
FIG. 67 illustrates images showing locations of nerves surrounding the common hepatic artery.

In some embodiments, an RF ablation catheter is used to perform RF ablation of sympathetic nerve fibers in the hepatic plexus at one or more locations. For example, the RF ablation catheter may perform ablation in a circumferential or radial pattern to ablate sympathetic nerve fibers in the hepatic plexus at one or more locations (e.g., one, two, three, four, five, six, seven, eight, nine, ten, six to eight, four to eight, more than ten locations). Referring now to FIG. 67, cadaver studies have shown that the hepatic nerves are generally focused in the region defined by the midpoint between the origin of the common hepatic artery and the origin of the gastroduodenal artery, as the nerves tend to approach the arterial lumen along non-branching regions of the artery, and diverge from the arterial lumen in regions of branching. The cadaver studies have also shown that the hepatic nerves predominantly reside within an annulus defined by the lumen of the artery and a concentric ring spaced approximately 4 mm from the arterial lumen. In some embodiments, the number of nerves and the proximity to the arterial lumen of the nerves increases towards the common hepatic artery midpoint. In some embodiments, the sympathetic nerve fibers are advantageously modulated (e.g., ablated) at the midpoint between the origin of the common hepatic artery and the origin of the gastroduodenal artery. In some embodiments, the sympathetic nerve fibers are modulated (e.g., ablated) up to a depth of 4-6 mm, 3-5 mm, 3-6 mm, 2-7 mm) from the lumen of the hepatic artery. In other embodiments, the sympathetic nerve fibers in the hepatic plexus are ablated at one or more points by performing RF ablation at a plurality of points that are linearly spaced along a vessel length. For example, RF ablation may be performed at one or more points linearly spaced along a length of the proper hepatic artery to ablate sympathetic nerve fibers in the hepatic plexus. In some embodiments, RF ablation is performed at one or more locations in any pattern to cause ablation of sympathetic nerve fibers in the hepatic plexus as desired and/or required (e.g., a spiral pattern or a series of linear patterns that may or may not intersect). The ablation patterns can comprise continuous patterns or intermittent patterns. In accordance with various embodiments, the RF ablation does not cause any lasting damage to the vascular wall because heat at the wall is dissipated by flowing blood, by cooling provided external to the body, or by increased cooling provided by adjacent organs and tissue structures (e.g., portal vein cooling and/or infusion), thereby creating a gradient with increasing temperature across the intimal and medial layers to the adventitia where the nerves travel. The adventitia is the external layer of the arterial wall, with the media being the middle layer and the intima being the inner layer. The intima comprises a layer of endothelial cells supported by a layer of connective tissue. The media is the thickest of the three vessel layers and comprises smooth muscle and elastic tissue. The adventitia comprises fibrous connective tissue.

h. Modulation and Monitoring of Treatment

In some embodiments, the energy output from the RF energy source may be modulated using constant temperature mode. Constant temperature mode turns the energy source on when a lower temperature threshold is reached and turns the energy source off when an upper temperature threshold is reached (similar to a thermostat). In some embodiments, an ablation catheter system using constant temperature mode requires feedback, which, in one embodiment, is provided by a temperature sensor. In some embodiments, the ablation catheter system comprises a temperature sensor that communicates with energy source (e.g., RF generator). In some of these embodiments, the energy source begins to deliver energy (e.g., turn on) when the temperature sensor registers that the temperature has dropped below a certain lower threshold level, and the energy source terminates energy delivery (e.g., turns off) when the temperature sensor registers that the temperature has exceeded a predetermined upper threshold level.

In some embodiments, the energy output from an energy delivery system may be modulated using a parameter other than temperature, such as tissue impedance. Tissue impedance may increase as tissue temperature increases. Impedance mode may be configured to turn the energy source on when a lower impedance threshold is reached and turn the energy source off when an upper impedance threshold is reached (in the same fashion as the constant temperature mode responds to increases and decreases in temperature). An energy delivery system using constant impedance mode may include some form of feedback mechanism, which, in one embodiment, is provided by an impedance sensor. In some embodiments, impedance is calculated by measuring voltage and current and dividing voltage by the current.

In some embodiments, a catheter-based energy delivery system comprises a first catheter with a first electrode and a second catheter with a second electrode. The first catheter is inserted within a target vessel (e.g., the common hepatic artery) and used to deliver energy to modulate nerves within the target vessel. The second catheter may be inserted within an adjacent vessel and the impedance can be measured between the two electrodes. For example, if the first catheter is inserted within the hepatic arteries, the second catheter can be inserted within the bile duct or the portal vein. In some embodiments, a second electrode is placed on the skin of the subject and the impedance is measured between the second electrode and an electrode of the catheter-based energy delivery system. In some embodiments, the second electrode may be positioned in other locations that are configured to provide a substantially accurate measurement of the impedance of the target tissues.

In some embodiments, the impedance measurement is communicated to the energy source (e.g., pulse generator). In some embodiments, the energy source begins to generate a pulse (i.e., turns on) when the impedance registers that the impedance has dropped below a certain lower threshold level, and the energy source terminates the pulse (i.e., turns off) when the impedance registers that the impedance has exceeded a predetermined upper threshold level.

In some embodiments, the energy output of the energy delivery system is modulated by time. In such embodiments, the energy source of the energy delivery system delivers energy for a predetermined amount of time and then terminates energy delivery for a predetermined amount of time. The cycle may repeat for a desired overall duration of treatment. In some embodiments, the predetermined amount of time for which energy is delivered and the predetermined amount of time for which energy delivery is terminated are empirically optimized lengths of time. In accordance with several embodiments, controlling energy delivery according to impedance and reducing energy delivery when impedance approaches a threshold level (or alternatively, modulating energy in time irrespective of impedance levels) advantageously provides for thermal energy to be focused at locations peripheral to the vessel lumen. For example, when the energy pulse is terminated, the vessel lumen may cool rapidly due to convective heat loss to blood, thereby protecting the endothelial cells from thermal damage. In some embodiments, the heat in the peripheral tissues (e.g., where the targeted nerves are located) dissipates more slowly via thermal conduction. In some embodiments, successive pulses tend to cause preferential heating of the peripheral (e.g., nerve) tissue. In accordance with several embodiments, when the impedance of tissue rises due to vaporization, electrical conductivity drops precipitously, thereby effectively preventing or inhibiting further delivery of energy to target tissues. In some embodiments, by terminating energy pulses before tissue impedance rises to this level (e.g., by impedance monitoring or time modulation), this deleterious effect may be avoided. In accordance with several embodiments, char formation is a consequence of tissue vaporization and carbonization, resulting from rapid increases in impedance, electrical arcing, and thrombus formation. By preventing or inhibiting impedance rises, charring of tissue may be avoided.

In some embodiments, total energy delivery is monitored by calculating the time integral of power output (which may be previously correlated to ablation characteristics) to track the progress of the therapy. In some embodiments, the relationship between temperature, time, and electrical field is monitored to obtain an estimate of the temperature field within the tissue surrounding the ablation electrode using the Arrhenius relationship. In some embodiments, a known thermal input is provided to the ablation electrode, on demand, in order to provide known initial conditions for assessing the surrounding tissue response. In some embodiments, a portion of the ablation region is temporarily cooled, and the resultant temperature is decreased. For example, for an endovascular ablation that has been in progress for a period of time, it may be expected that there is some elevated temperature distribution within the tissue. If a clinician wants to assess the progress of the therapy at a given time (e.g., to), the energy delivery can be interrupted, and cooled saline or gas can be rapidly circulated through the electrode to achieve a predetermined electrode temperature within a short period of time (e.g., about 1 second). In some embodiments, the resulting temperature rise (e.g., over about 5 seconds) measured at the electrode surface is then a representation of the total energy of the surrounding tissue. This process can be repeated through the procedure to track progress.

In some embodiments, a parameter, such as temperature, infrared radiation, or microwave radiation can be monitored to assess the magnitude of energy delivered to tissue, and thus estimate the degree of neuromodulation induced. Both the magnitude of thermal radiation (temperature), infrared radiation, and/or microwave radiation may be indicative of the amount of energy contained within a bodily tissue. In some embodiments, the magnitude is expected to decrease following the completion of the ablation as the tissue cools back towards body temperature, and the rate of this decrease, measured at a specific point (e.g., at the vessel lumen surface) can be used to assess the size of the ablation (e.g., slower decreases may correspond to larger ablation sizes). Any of the embodiments described herein may be used individually or in combination to indicate the actual size of the tissue lesion zone.

Electrode tip temperature control is often used as a control variable and treatment progress indicator for ablation procedures, particularly endovascular and/or cardiac ablation procedures. One potential problem with this approach is that although the goal is to treat tissue at a certain depth into the tissue, the temperature sensing element (thermocouple or thermistor) is generally only able to measure the surface temperature of the cardiac or vascular tissue. Furthermore, due to temperature gradients within the electrode itself, the temperature sensing element tends to measure the bulk temperature of the electrode, rather than precisely measure the surface temperature, which is often strongly influenced by the degree of convective blood flow about the electrode, which is typically about 37° C.

Figure 68:
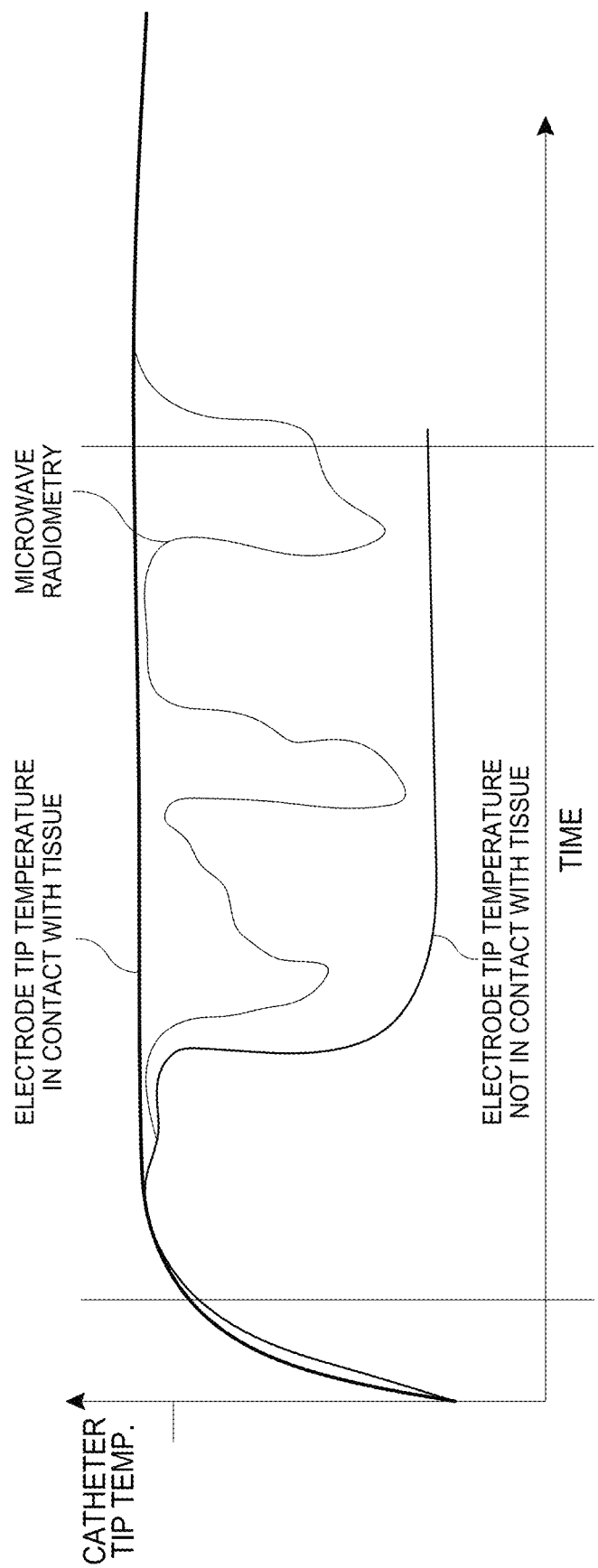
FIG. 68 illustrates a graph of motion of an electrode catheter tip indicated by a microwave radiometry sensor.

In one embodiment, microwave radiometry is used to measure tissue temperature at depth instead of at the electrode surface, such as described in US Publ. No. 2007/0299488 (the entire content of which is hereby expressly incorporated by reference). In addition to providing improved feedback on ablation progress and efficacy, microwave radiometry can also be used to estimate the stability of the treatment electrode within the target, in accordance with several embodiments. FIG. 68 illustrates an example of the effects of using microwave radiometry. FIG. 68 illustrates a base case with conventional electrode tip temperature measurements. Because the electrode tip temperature sensor measures the temperature of a small region of tissue around the electrode, the thermal mass of this tissue is limited. When the electrode is moved, the new tissue in contact with the electrode is heated rapidly, and variations in electrode tip temperature due to motion of the electrode are not significant, making this parameter potentially unreliable as an indicator of electrode and/or catheter motion. In accordance with several embodiments, because microwave radiometry measures the bulk thermal energy of a region of tissue, the temperature measurement corresponds to a region of tissue having a much larger thermal mass. Consequently, in accordance with several embodiments, temperature measurements using microwave radiometry will drop more significantly with motion of the electrode and/or catheter, as illustrated in FIG. 68. This fact can be used to control energy delivery (for example, an alarm can be generated when temperature drops below a certain threshold, indicating excessive catheter motion).

In several embodiments, by accurately measuring tissue temperature at depth using microwave radiometry lesion assessment, treatment efficacy and progress can be estimated more reliably. Excessive electrode and/or catheter motion can also be detected, thereby alerting a physician or other clinician to confirm good, or sufficient, electrode contact angiographically before proceeding with the treatment.

Some strategies for increasing lesion depth during ablation procedures have focused on actively cooling the surface of the electrode (e.g., using infused saline, internally circulated and/or chilled fluid). In some embodiments, electrode cooling allows deeper lesions to be formed without vaporizing the tissue adjacent to the electrode. In some applications, when cooling, it is difficult to have feedback about the peak temperature reached by the tissues, since the typical practice of placing a thermocouple within the electrode will measure a temperature that is biased by the cooling itself, and thus may not be representative of the peak temperature reached by the more distant tissues.

One embodiment for measuring the adventitia peak tissue temperature in an endovascular ablation of the hepatic artery is as follows. A thermocouple, thermistor or other temperature-measurement device may be placed at a location within the hepatic artery and used to measure the wall temperature at a distance of about 5 mm (as a shortest path) from the surface of the electrode, for electrode sizes between 1 mm and 2 mm in diameter. Studies have shown that measuring the wall temperature at such a distance is a fair approximation of the peak temperature reached within the adventitia.

With electrode cooling, the thermocouple within the electrode measures a temperature that is driven by the cooling itself, which may be much lower than the temperature reached by more distal tissues. Thus, for a temperature-controlled ablation, this measurement may not be useful in indicating the temperature reached by the adventitia, where the nerves are located. As a consequence, in one embodiment, the nerves can fail to be ablated if the heat provided is not sufficient to cause ablation within a certain time period, or there can be collateral damage if the heat is excessive. In accordance with several embodiments, a temperature-controlled neuromodulation (e.g., ablation) is desirable, as if one controls the electrical output (e.g., voltage, current, or power), the heat transferred to the tissues depends on a limited number of variables, such as contact force and impedance, thereby reducing the variability of the therapeutic effect. The placement of remote probes placed at discrete locations within the target tissue to address any shortcomings with cooled electrode strategies may be undesirable in several embodiments because they would require transvascular placement, thereby increasing the risk of the procedure.

Using a numerical model of hepatic arterial ablation, the Applicant has demonstrated that measuring the temperature at the arterial lumen at a shortest-path distance of 5 millimeters from the surface of the electrode provides a temperature that is reasonably close to the peak temperature reached at the media-adventitia interface. For the purposes of this analysis, the numerical model is based on the following assumptions, reflecting consolidated physiological knowledge of the hepatic arterial system:

1. artery with a diameter of 4 millimeters
2. thickness of the media is 2 millimeters
3. no external blood cooling (this assumption is appropriate because the electrode cooling dominates the thermal response near the electrode)
4. electrode diameter between 1 and 2 millimeters
5. the electrode is cooled and its surface is maintained around 37° C.

Figure 69:
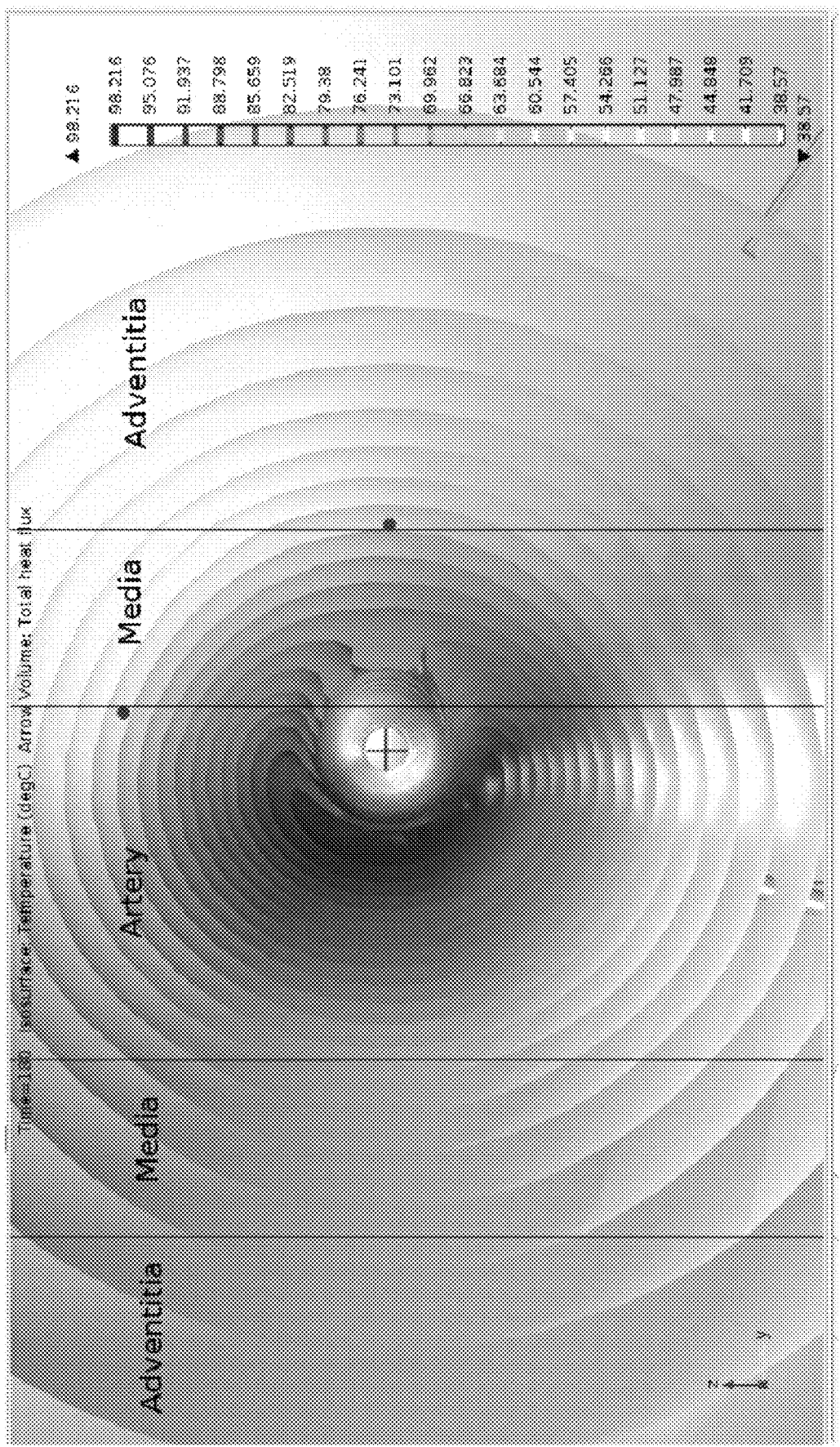
FIGS. 69 and 70 illustrate images obtained from a model of an endovascular ablation within the common hepatic artery.
Figure 70:
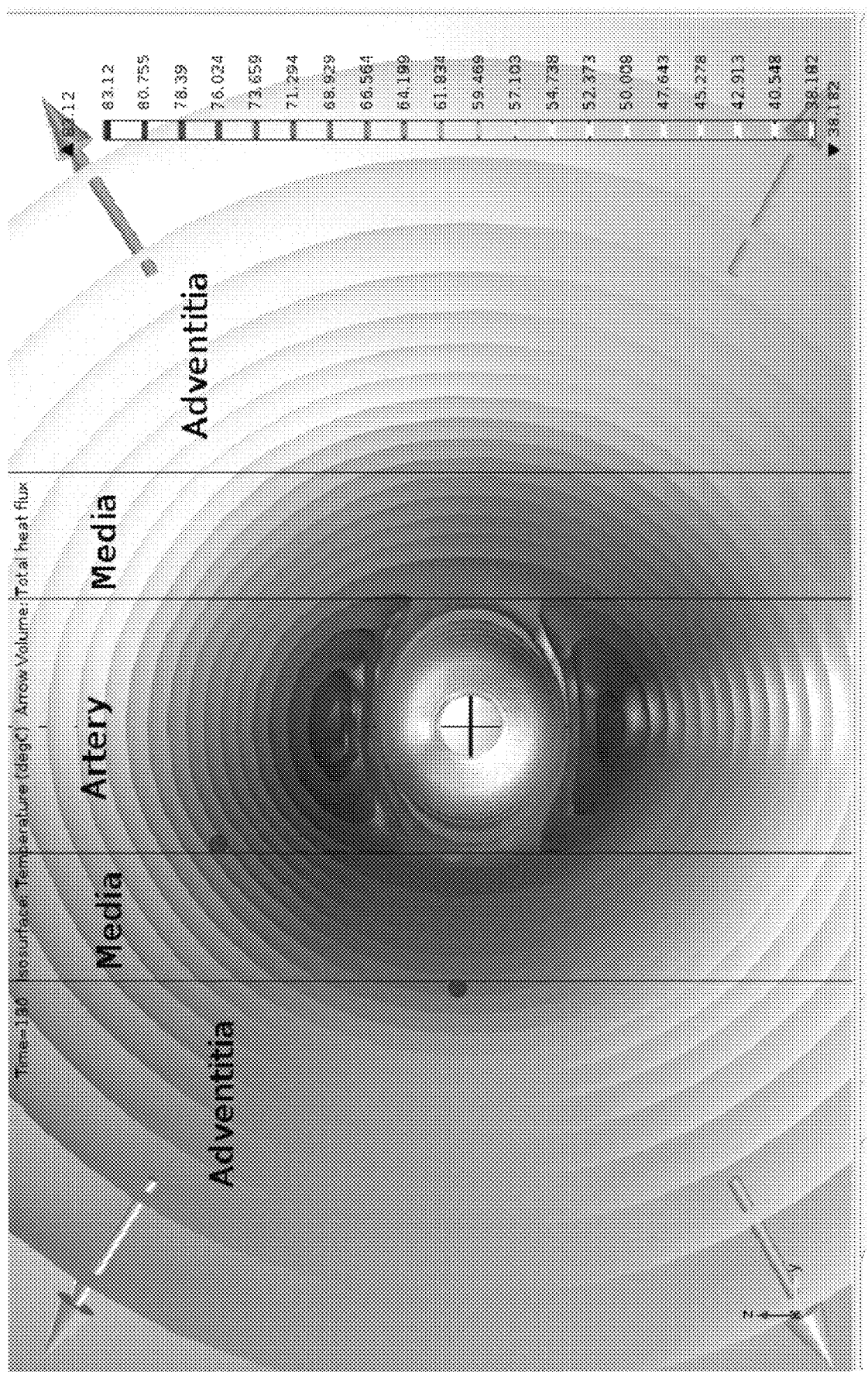

FIGS. 69 and 70 represent isothermal contours after a 3 minute ablation at 25 V. The figures are, respectively, the case of 1 and 2 millimeter diameter electrodes. In FIG. 58, the electrode is in contact with a right side of the artery, while in FIG. 59, the electrode is in contact with the bottom of the artery. The dots within the artery are at a distance of about 5 millimeters from the surface of the electrode. The dots within the adventitia represent the maximum temperature reached within the adventitia itself. In both cases, the pairs of dots belong to the same isothermal surface, and thus are, with good approximation, at the same temperature. In some embodiments, as the electrode gets smaller, the gradient of the temperature increases, and for sizes significantly smaller than 1 millimeter in diameter and for sizes significantly larger than 2 millimeters, the distance of 5 millimeter will likely change.

In several embodiments, the temperature at a distance d (e.g., 5 millimeters) from the electrode is measured using a temperature-sensing device 6005 (e.g., thermocouple) branching out of the catheter 6010, either on the same side of the electrode 6015, or on the opposite side (as shown in FIGS. 71A and 71B, respectively). The distance d between the electrode 6015 and the temperature-measurement device 6005 may be other than 5 millimeters (e.g., 2 mm, 2.5 mm, 3 mm, 3.5 mm, 4 mm, 4.5 mm, 5.5 mm, 6 mm, 6.5 mm, 7 mm, 7.5 mm, 8 mm, 8.5 mm, 9 mm, 9.5 mm, 10 mm or any distance between 2 mm and 10 mm, between 5 mm and 15 mm, between 10 mm and 20 mm or overlapping ranges thereof).

In various embodiments, the rate change of various treatment parameters (e.g., impedance, electrode temperature, tissue temperature, power, current, voltage, time, and/or energy) is monitored substantially in real time and displayed on a user interface. Treatment parameter data may be stored on a data store for later reporting and/or analysis. In some embodiments, an energy delivery system receives inputs transduced from physiologic signals such as blood glucose levels, norepinephrine levels, or other physiological parameters indicative of the status of the progress of treatment.

Other methods of observing the tissue ablation zone and the surrounding anatomy may include prior, concomitant, or subsequent imaging intravascularly by modalities including but not limited to: intravascular ultrasound, echo decorrelation, optical coherence tomography, confocal microscopy, infrared spectroscopy, ultraviolet spectroscopy, Raman spectroscopy, and microwave thermometry. All such imaging modalities may advantageously be adapted to the hepatic artery because of its unique tolerance to low flow. In some embodiments, ultrasound elastography is advantageously used for imaging. Ultrasound elastography may show areas of localized tissue stiffness resulting from the denaturing of collagen proteins during thermal ablation (ablated regions tend to stiffen compared to the native tissue); for example, stiff regions may correspond to ablated regions. Intravascular ultrasound may be used for example, to detect or monitor the presence and depth of ablation lesions. For example, if the lesions are in the range of 2 to 6 mm from the lumen wall, the clinician may be confident that the target nerves were destroyed as a result of thermal coagulation. Extravascular ultrasound imaging may also be used.

Figure 72:
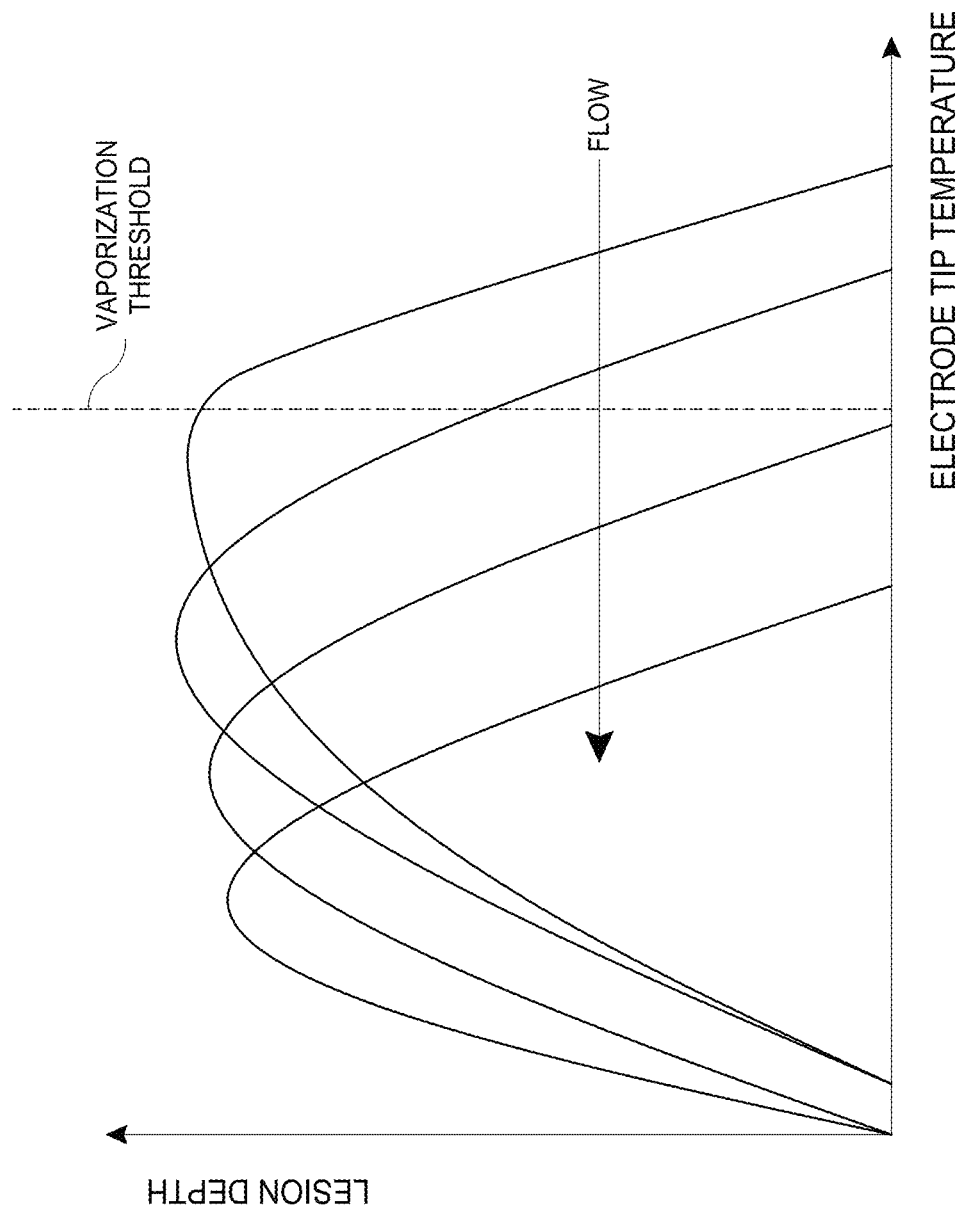
FIG. 72 illustrates a graph of electrode tip temperature and lesion depth as convective blood flow increases.

With respect to constant electrode tip temperature ablations (e.g., controlling RF generator output power to maintain a constant electrode tip temperature), in a physiologic situation, the degree of convective cooling effectively confounds the electrode temperature measurement-whereas for zero or limited convective cooling the temperature and time can be used to "set" the lesion size. In some embodiments, when there is significant convective cooling, the RF generator may end up outputting too much power to maintain a tip temperature, resulting in desiccation and vaporization at some depth (>0 mm from the electrode surface) within the tissue where the maximum temperatures are reached, thereby limiting ablation size. Electrode tip temperature and lesion size are related, as shown in FIG. 72, but there is always a maximum, and particularly, a maximum that shifts towards lower temperatures with increasing convective cooling. In order to assess which curve was applicable for a given physiologic boundary condition (e.g., blood flow velocity), a flow sensor could be added to the catheter to measure the degree of convective cooling. For a given convective cooling rate, the relationship between electrode tip temperature and lesion depth can be established using in vivo and ex vivo techniques to provide a valid look up table for specifying and assessing lesion size.

In one embodiment, electrode tip temperature can be used to prevent or limit thrombus formation, which can start to occur as a result of an edge effect as delivered power increases. As one example, RF power or other energy delivery (such as ultrasound, light, microwave, etc.) can be terminated as a threshold temperature (e.g., 75° C., 80° C., 90° C., etc.) is reached.

One method for assessing blood flow rate includes positioning an electrode within the blood flow stream, preferably in the center of the vessel (e.g., artery or other lumen). A set power (e.g., 2-10 W, 5 W) can be delivered for a set period of time, (e.g., 1-10 seconds, 3 seconds). The corresponding rise in electrode tip temperature measured during this time period may be inversely proportional to the blood flow rate in the target vessel (which is expected to range from 100 to 200 mL/min for the hepatic artery).

Figure 73:
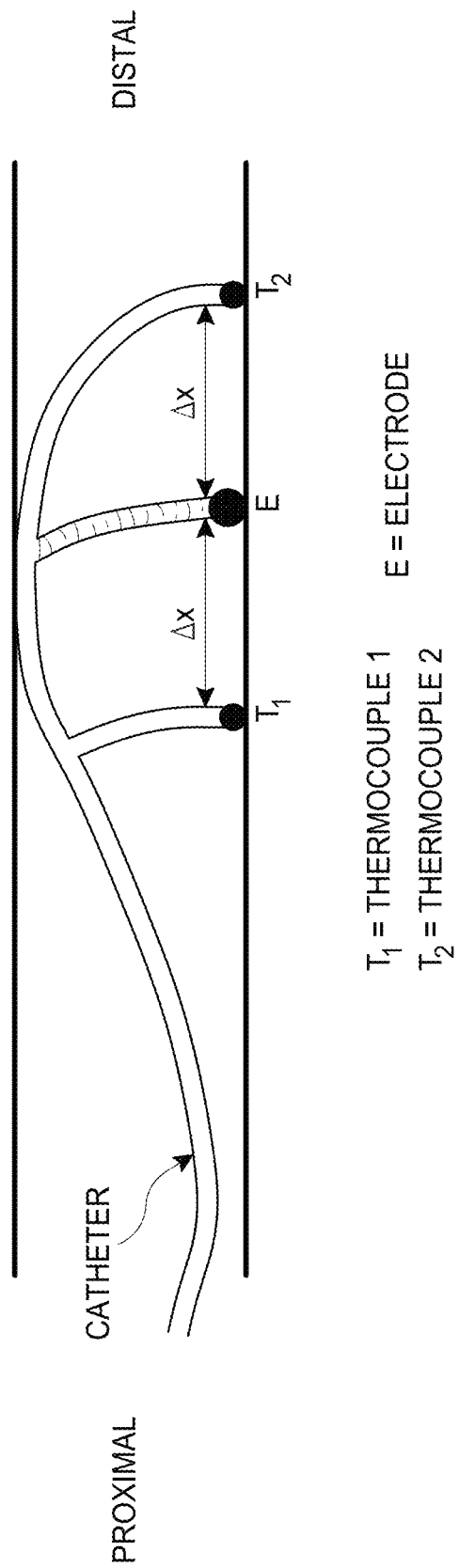
FIG. 73 illustrates an embodiment of a catheter having a thermal mass flow sensor.
Figure 79:
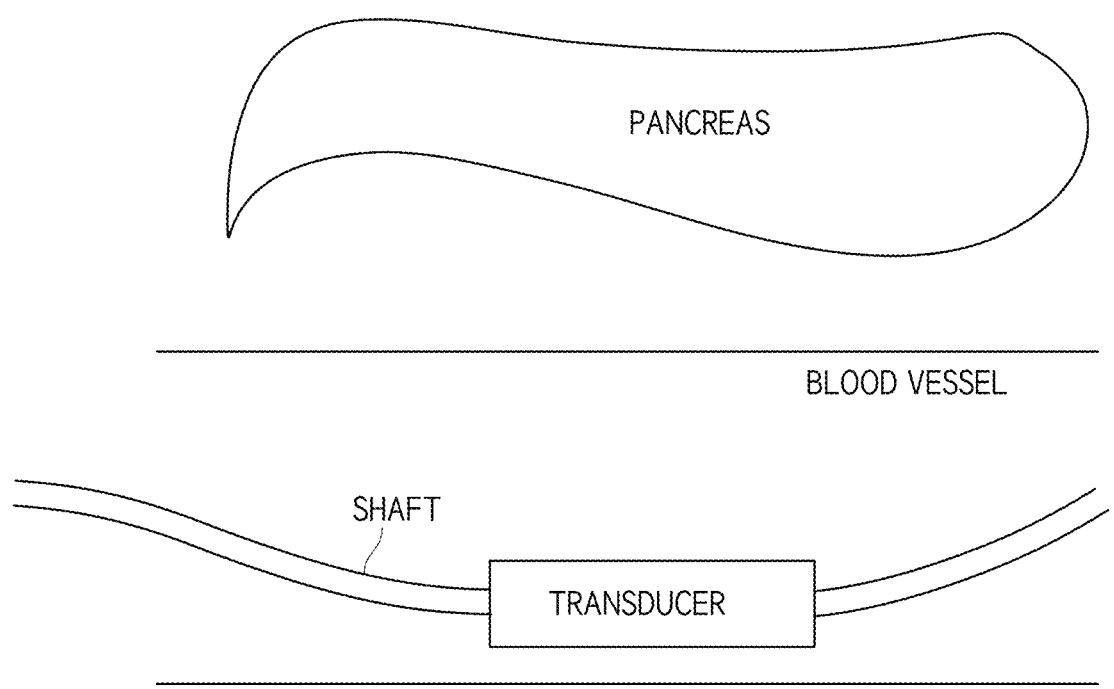
FIG. 79 illustrates a schematic representation of a distal portion of an ultrasound energy delivery device positioned within a blood vessel at a location corresponding to a location in close proximity to an adjacent dense structure.

One embodiment for measuring flow is shown in FIG. 73, depicting a catheter assembly configured to measure blood flow. In accordance with several embodiments described herein, catheter assemblies measure flow without impeding, or with minimal occlusion of, blood flow in the small lumen of the hepatic artery, thereby taking advantage of the potentially beneficial cooling action of the blood. The embodiment shown in FIG. 79 employs the fact that an RF heat source (e.g., an active electrode) is placed in the blood flow, which additionally may include a thermocouple or other temperature-measurement device in the electrode tip. As shown, two more thermocouples or other temperature-measurement devices may be added to the catheter, one upstream and one downstream from the electrode, thereby allowing for the measurement of the heat transferred by the flow. In one embodiment, measurement of the heat transferred by the flow is performed using consolidated technology for thermal mass flow in liquids, such as the LIQUI-FLOW® controller (Bronkhorst High-Tech, Amsterdam, Netherlands). As illustrated in FIG. 79, the two thermocouples may be added to the catheter assembly at discrete locations, for example one at a distance (e.g., 3 millimeters) downstream from the electrode, and one at a distance (e.g., 3 millimeters) upstream from the electrode. Other distances may be used. In some embodiments, the thermocouples may be disposed at the end of bending segments in order to achieve stable and precise positioning of the thermocouples in the vicinity of the electrode.

Figure 74:
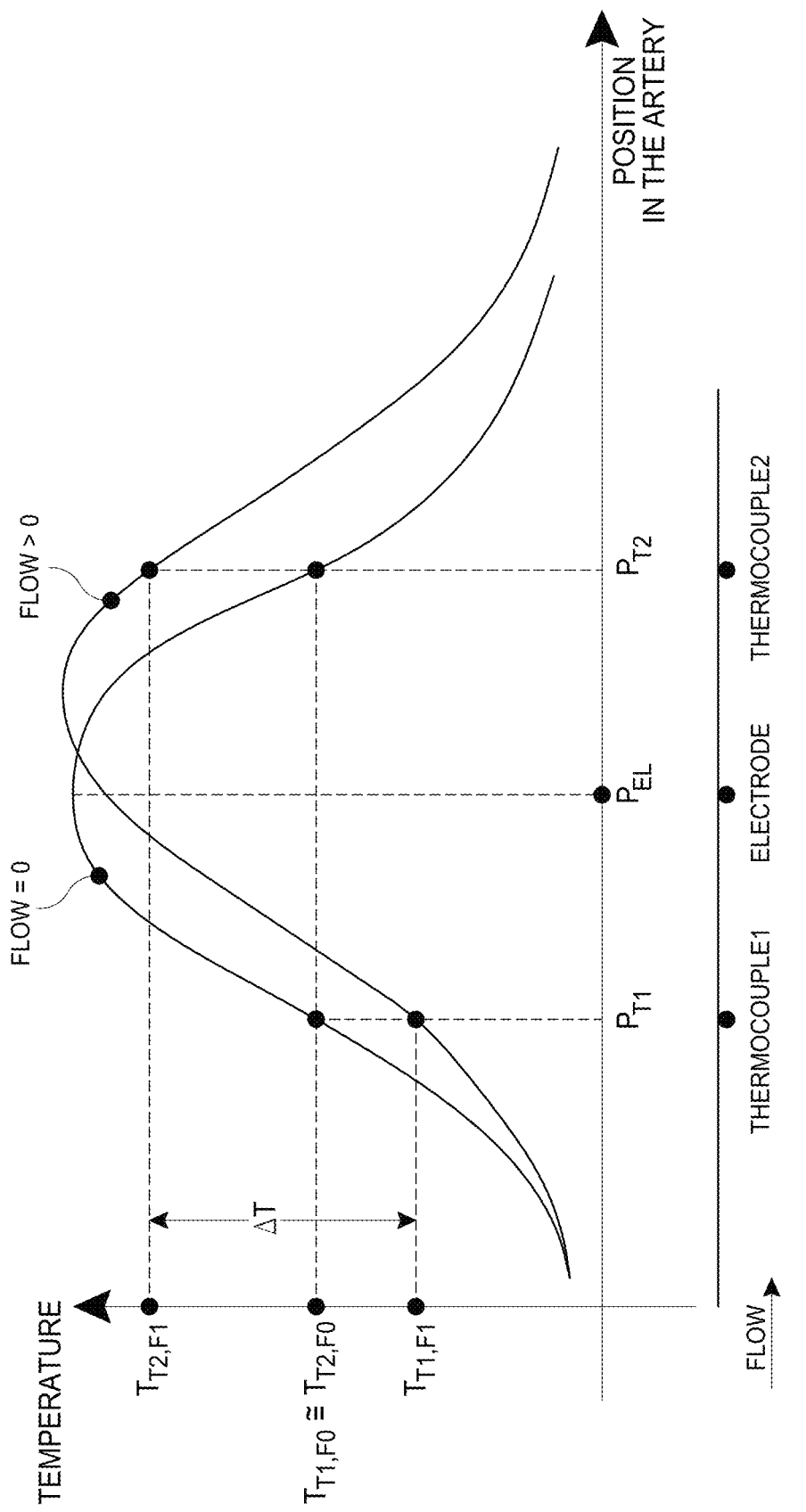
FIG. 74 is a graph illustrating a principle of operation of the thermal mass flow sensor of FIG. 73.

FIG. 74 illustrates the principle of a thermal flow sensor. In some embodiments, the electrode heats the surrounding tissues (e.g., blood and arterial wall) through the application of RF energy. When the arterial flow is zero, the two thermocouples sense the same temperature, as the heat generated in the tissues is conducted symmetrically from the electrode in the proximal and distal directions. When the blood flow is greater than zero, instead, the temperature profile shifts in the direction of the flow (to the right in FIG. 80) due to convective heat transfer, thereby resulting in a difference, $\Delta T$, between the temperatures detected by the two thermocouples as a result of the heat transported by the flowing blood. $\Delta T$ is generally proportional to the magnitude of the flow rate, in some embodiments. By connecting the output of the thermocouples to an A/D converter and microprocessor, the precise flow can be determined from a previously-determined calibration relating $\Delta T$ to flow rate values under known, controlled conditions, which can be approximated as a linear relationship.

Figure 75:
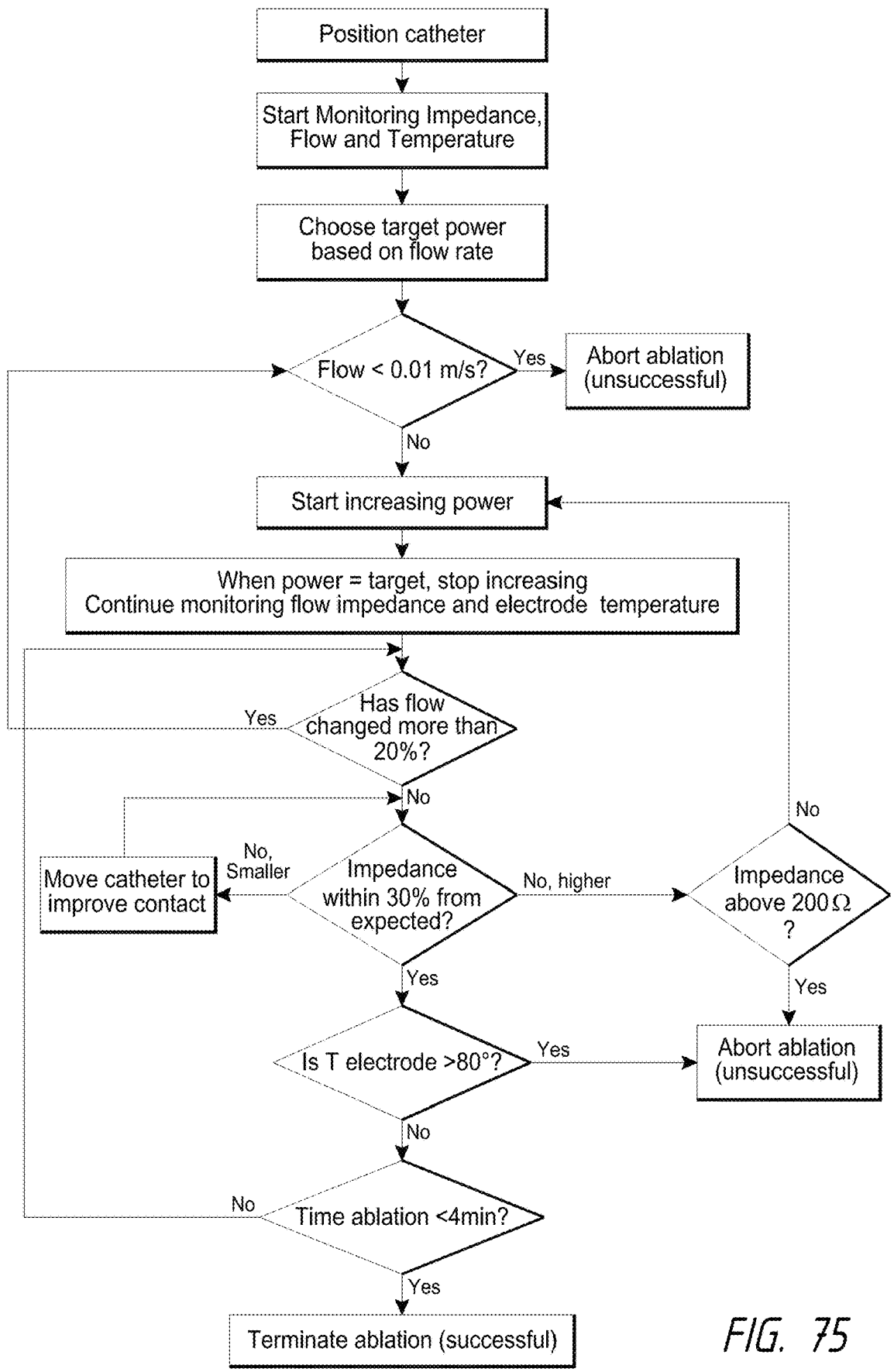
FIG. 75 illustrates a flow chart of an embodiment of an ablation control process.

Referring now to FIG. 75, an embodiment of an ablation control process is provided for achieving successful endovascular ablation of a common hepatic artery. Once the catheter is positioned, flow, impedance and electrode temperature can start being monitored in real time, utilizing any of the various embodiments previously described herein configured to do so. The blood flow rate value determines the target power according to the values previously described herein (see, for example, Table 1). If the value of the flow rate is below the minimum that is needed for a safe and successful ablation (e.g., at least 0.01 m/s), the ablation procedure is immediately terminated.

Figure 76:
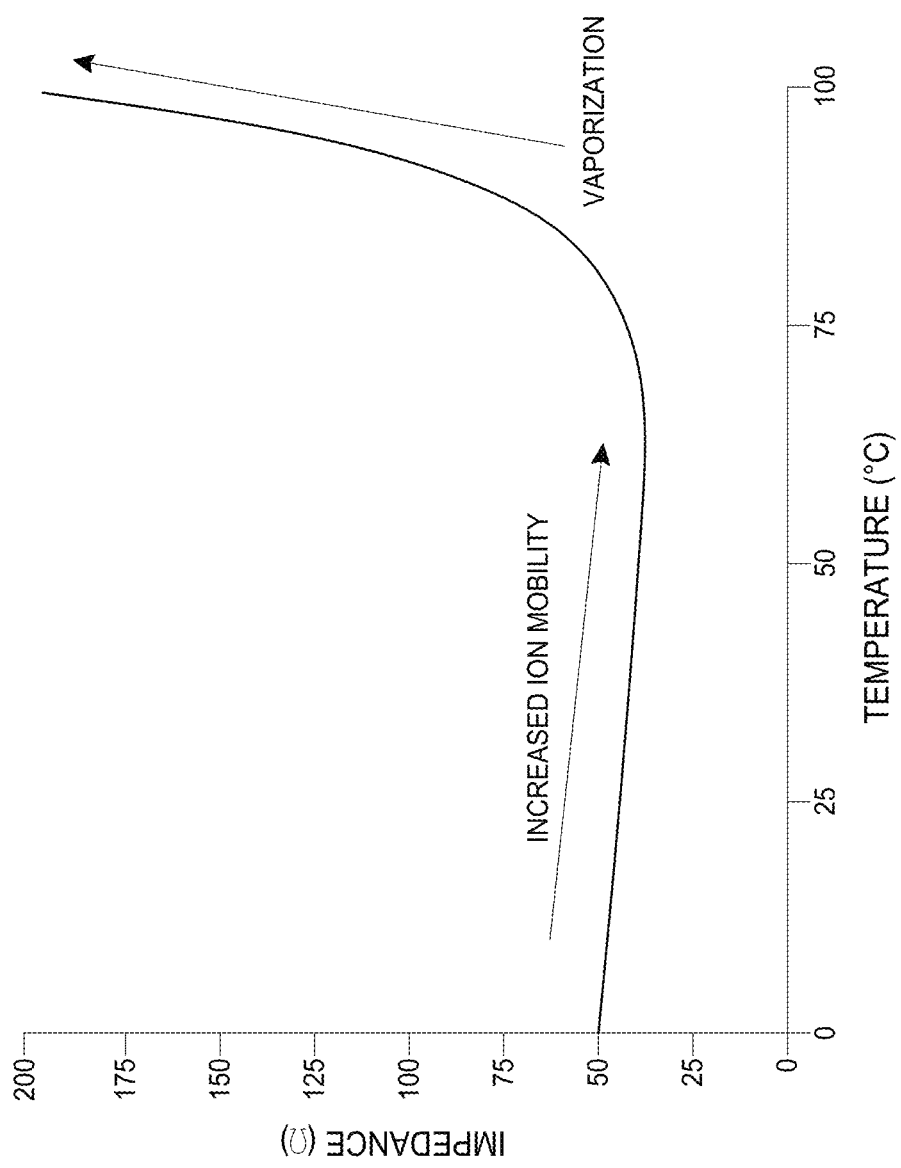
FIG. 76 is a flow chart of an embodiment of impedance-based feedback control.

During application of RF energy, the change in impedance as the tissue temperature increases should be close (e.g., within a 30% tolerance range) to the impedance-temperature curve (see, for example, FIG. 76), where an increase in tissue temperature should correspond to a slight decrease in impedance. If the impedance decreases too much (e.g., >30% from the curve described in FIG. 76), the electrode may not be in contact with the arterial wall and instead may be in substantial direct communication with the blood, which has a significantly lower resistivity. In this situation, the catheter is repositioned to ensure good contact with the arterial wall.

If the impedance remains higher than expected (e.g., per FIG. 76), the tissue may need to be heated further by increasing the RF power level. Alternatively, if the impedance is much higher than expected (e.g., higher than about 200-300Ω), this is likely to indicate formation of thrombus. In such case, the ablations are immediately aborted, as tissue thrombus causes the ablation to become unpredictable and unsafe.

In general, according to the ablation control process in FIG. 75, the power is increased linearly (e.g., at a rate of 0.5 watts per second) until the target power level is reached. After increase of power, the power level is kept steady if the flow rate does not change by more than 20%. If flow rate has changed by more than 20%, the power is adjusted to the new flow rate, as long as the flow rate is above 0.01 m/s or some other threshold.

At any time during the ablation, flow, impedance and electrode temperature are monitored as real time feedback signals, and the power is adjusted (or stopped) according to their values. After 4 minutes, or other suitable time period (e.g., according to the power and time combinations listed in Table 1), RF energy delivery is terminated and the ablation is completed.

In the ablation control process described in FIG. 75, a power-controlled ablation algorithm may be employed instead of a temperature-controlled algorithm because the temperature at the electrode is not always a good indicator of the maximum temperature reached within the tissue. Since the electrode is in contact with the blood, its temperature is not expected to rise significantly beyond 37° C., and may be considerably lower than the temperature within the tissues. Electrode temperature can be used to detect complications during RF ablation treatments of the hepatic artery. For example, if the electrode temperature rises too much (for example, above 80° C.), this may be a sign that something unexpected has happened (for instance, a hole has been formed in the arterial wall and the electrode is inserted directly in the tissue, or alternatively, thrombus formation). In several embodiments, electrode temperature monitoring provides an additional layer of control redundancy to ensure procedure safety, but it may not be used as a primary feedback variable to control RF energy.

FIG. 77A illustrates an embodiment of an energy delivery algorithm based on blood flow measurement. The energy delivery algorithm utilizes the blood flow velocity or rate (or alternatively, generic control variable "X," such as impedance) as a control variable. In some embodiments, the generator conducts a checksum before applying RF energy to assess the initial value of the control variable, for example blood flow rate. Based at least in part on the value of the measured control variable, the proportional-integral-derivative (PID) controller gain values may be adjusted to ensure a stable control feedback loop throughout the duration of the energy application procedure. RF energy delivery may then be delivered for a first period in a manner that adjusts output power to maintain a constant first-derivative of the electrode tip temperature (or other control variable, for example impedance) until a set threshold value (e.g., 75° C.) is reached. RF energy may then be delivered for a second period in a manner that maintains a constant electrode tip temperature (or other control variable). The output power or current output (as shown in the current (i) graph in FIG. 77B) by the generator during time periods 1 and 2 is also shown in FIGS. 77A and 77B for illustrative purposes.

Various embodiments of the RF-based systems and methods described herein may provide one or more of the following advantages: (i) reduces the number of ablations required for effective treatment, (ii) reduces the length of vessel required for effective treatment with an RF ablation device, (iii) enables effective electrode cooling in targeted vessel, (iv) provides a consistent vessel contact area while maintaining ample surface area for electrode cooling; (v) reduces contact pressure of the electrode(s) on the vessel wall; and/or (vi) effective denervation of nerves in a perivascular region while maintaining minimal heating of, or thermal injury to, the inner vessel wall.

2. Ultrasound

Figure 78A:
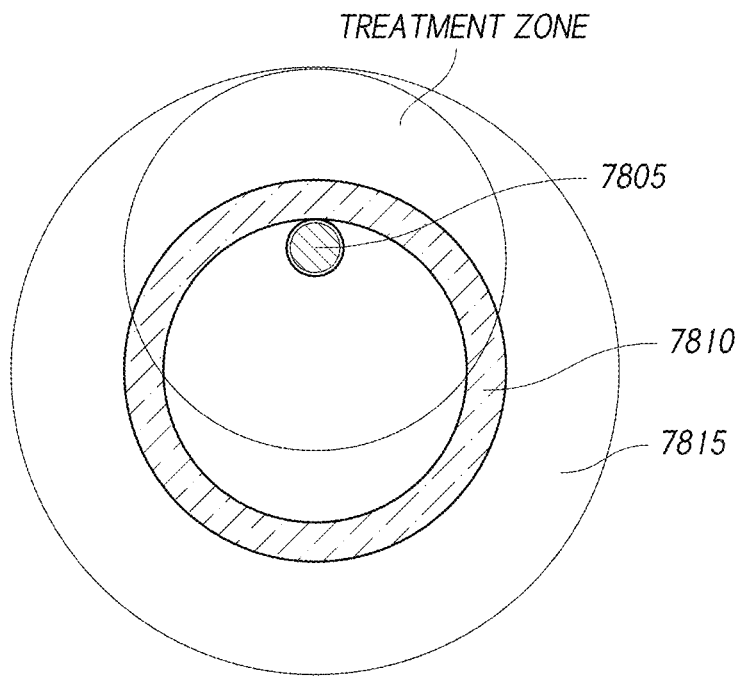
FIGS. 78A and 78B schematically illustrate embodiments of intravascular ablation catheters configured to prevent vessel circumferentiality during ablation therapy.
Figure 78B:
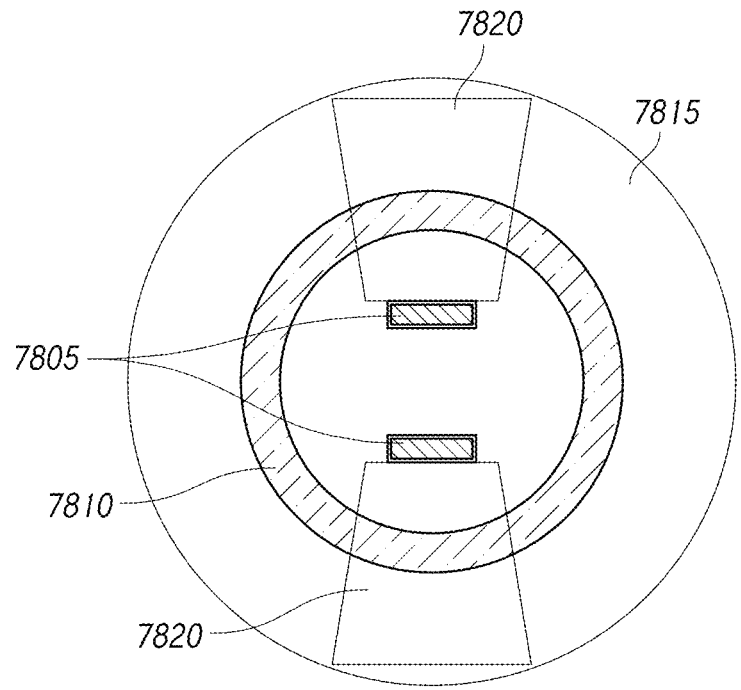

Ultrasound energy delivery devices may also be used to reduce the likelihood of forming a complete circumferential lesion around a target vessel. FIGS. 78A and 78B schematically illustrate embodiments of components of intravascular ablation catheters configured to prevent or inhibit vessel circumferentiality during ablation therapy. FIG. 78A schematically illustrates that an intravascular ablation catheter may comprise a transducer 7805 configured to radially emit ultrasound energy near the distal tip of the ablation catheter. The construction of the ablation catheter may be such that the transducer 7805 is always held off the center of the vessel, similar to the RF ablation catheter approach described in connection with FIG. 59. In some embodiments, the radial emission primarily involves an arc of the vessel wall 7810 and adventitia 7815 (which may be considered an outer layer of the vessel wall 7810) closest to the transducer 7805. Optimization of energy level can occur such that the wall opposite of where the transducer 7805 is located is not involved in the ablation arc. In some embodiments, the intravascular ablation catheter comprises a balloon that positions the transducer 7805 off the center axis of the balloon and vessel. Other embodiments include a concentric balloon that is smaller than the vessel diameter or a catheter comprising a deflectable shaft that holds the transducer off axis. In one embodiment, the catheter comprises a pre-shaped distal shaft that orients the transducer off axis. For example, the shaft could be held straight by a guide wire or mandrel and, once removed, the shaft may deflect off axis. As another example, a removable pre-shaped mandrel could be utilized.

FIG. 78B schematically illustrates an embodiment of an intravascular ablation catheter comprising one or more flat transducers 7805 configured to emit ultrasound energy near the distal tip of the catheter. The transducers 7805 may be placed radially and/or longitudinally along the shaft of the catheter in manner that ensures the ablation pattern formed by all of the transducers does not involve more than 75% of the vessel circumference at any vessel cross-section. FIG. 78B schematically illustrates energy cones 7820 formed by emission of ultrasound energy from the two transducers 7805. In various embodiments, tilted ultrasound transducers may be used to create a narrow oblique circumferential lesion to prevent or inhibit negative remodeling from occurring in any one circumferential plane. The ultrasound energy may be beam-shaped or intensity-modulated to maintain lesion depth.

FIG. 79 illustrates a schematic representation of a distal portion 7900 of an ultrasound energy delivery device (e.g., comprising a transducer 7915 and a shaft 7920) positioned within a blood vessel 7905 (e.g., hepatic artery) at a location corresponding to an identified location along the blood vessel 7905 in which an adjacent dense structure 7910 (a pancreas in this figure) is in close proximity. The pancreas in this figure could be replaced with other dense structures 7910 (e.g., liver, stomach, small intestine, muscle, and/or connective tissue).

The neuromodulation may be performed intravascularly or from a source located external to the subject's skin (e.g., noninvasively). The neuromodulation may comprise ablation or denervation of the nerves (e.g., sympathetic nerves innervating the liver and/or other organ that may influence glucose production). The neuromodulation may be accomplished by delivery of acoustic energy using an ultrasound delivery device (e.g., ultrasound catheter). In some embodiments, neuromodulation may be adjusted based on the identified locations of the adjacent structures 7910 or the distances to such adjacent structures 7910. In accordance with several embodiments, the presence of adjacent structures 7910 may be exploited to identify neuromodulation (e.g., ablation) targets instead of identifying the adjacent structures 7910 to try to avoid the adjacent structures 7910. In some embodiments, a minimum threshold distance is also identified so as to effect modulation of nerves between the hepatic artery and the adjacent dense structure 7910 without ablating the tissue of the adjacent dense structure 7910 itself. For example, a range of acceptable distances may be between 3 mm and 1 cm, between 2 mm and 5 mm, between 3 mm and 7 mm, between 4 mm and 8 mm, between 5 mm and 9 mm, or overlapping ranges thereof.

Several embodiments of ultrasound systems, devices and methods described herein are particularly advantageous because they include one, several or all of the following benefits: (i) fewer treatment locations due to increased efficacy; (ii) ability to effectively treat a short vessel length such as the common hepatic artery; (iii) reduction in blood glucose, cholesterol and/or triglyceride levels, (iv) reduction in lipid and/or norepinephrine levels in the liver, pancreas, and/or duodenum; (v) confirmation of treatment efficacy; (vi) higher likelihood of successful neuromodulation due to modulation of areas of high nerve density; (vii) increased likelihood of modulation having an effect on glucose production due to modulation of areas of high nerve density or concentration; (viii), increased circumferential vessel coverage with reduced axial vessel length coverage; (ix) increased power transmission without increasing transducer size (x) reduced overall power or energy delivery by combining treatment using both radiofrequency and acoustic (ultrasound) energy and/or (xi) denervation of multiple organs or tissue structures from a single location. Several embodiments of the invention are adapted to accomplish one or more of these benefits. For example, some embodiments have one or more of the following features: are constructed to balance steerability with flexibility, have a particular shape to treat target vessels, have a particular pattern, frequency or power of ultrasonic emission to treat nerves while limiting heating of non-target tissue, have a dimension (e.g., length, diameter, cross-section, etc.) to facilitate positioning and movement through the target vasculature (which may be tortuous), have elements to center or stabilize the distal end portion in a vessel, have elements to adjust or control trajectory or focus or dispersion of energy delivery, have at least one ultrasound transducer and at least one electrode so as to deliver both radiofrequency and acoustic energy; have one or more elements to provide confirmation or other assessment of lesion formation or other tissue modulation, have elements or structures to increase operational efficiency while providing increased surface area for cooling, and/or have elements, materials or mechanisms to adjust positioning of the transducers or other energy delivery elements such that the distal end portion of the medical instrument (e.g., catheter) has a reduced-profile configuration during introduction to the target location and an expanded profile configuration in which circumferential coverage or treatment surface area is increased.

FIG. 80 illustrates an embodiment of an energy delivery system 8000 that is configured to modulate targeted tissue so as to treat diabetes or symptoms associated with diabetes (e.g., to reduce glucose levels, to reduce cholesterol levels, to reduce lipid levels, to reduce triglyceride levels). As shown, the energy delivery system 8000 can include a medical instrument 8005 comprising one or more energy delivery members 8010 (for example, ultrasound transducers, radiofrequency electrodes, microwave antennas) along a distal end of the medical instrument 8005. The medical instrument 8005 can be sized, shaped and/or otherwise configured to be passed intraluminally (for example, intravascularly) through a subject being treated. In other embodiments, the medical instrument 8005 is not positioned intravascularly but is positioned extravascularly via laparoscopic or open surgical procedures. In various embodiments, the medical instrument 8005 comprises a catheter, a shaft, a wire, and/or other elongate instrument. The term "distal end" does not necessarily mean the distal terminus or distal end. Distal end could mean the distal terminus or a location spaced from the distal terminus but generally at a distal end portion of the medical instrument 8005.

In some embodiments, the medical instrument 8005 is operatively coupled to one or more devices or components. For example, as depicted in FIG. 80, the medical instrument 8005 can be coupled to a delivery module 8015 (such as an energy delivery module). According to some arrangements, the energy delivery module 8015 includes an energy generation device 8020 that is configured to selectively energize and/or otherwise activate the energy delivery member(s) 8010 (for example, ultrasound transducers) located along the medical instrument 8005. In some embodiments, for instance, the energy generation device 8020 comprises a generator, a radiofrequency generator, a microwave energy source, a laser/light source, another type of energy source or generator, and/or the like, and combinations thereof. In other embodiments, energy generation device 8020 is substituted with or used in addition to a source of fluid, such a cryogenic fluid or other fluid that modulates temperature, or cooling fluid to cool the energy delivery members or surrounding tissue or blood.

With continued reference to the schematic of FIG. 80, the energy delivery module 8015 can include one or more input/output devices or components 8025, such as, for example, a touchscreen device with one or more graphical user interfaces, a screen or other display, a controller (for example, button, knob, switch, dial, etc.), keypad, mouse, joystick, trackpad, microphone or other input device and/or the like. Such devices can permit a physician or other user to enter information into (for example, toggle between operational modes by pressing touchscreen GUI inputs or manipulating physical buttons or switches) and/or receive information from the energy delivery system 8000. In some embodiments, the output device 8025 can include a touchscreen or other display or graphical user interface that displays images or maps, provides temperature information, tissue contact information, other measurement information and/or other data or indicators that can be useful for regulating a particular treatment procedure. The maps may be dynamically updated in real time or may be static maps. The maps may indicate desirable areas of modulation (e.g., ablation) and/or previous modulation (e.g., ablation) sites.

According to some embodiments, the energy delivery module 8015 includes a processor 8030 (for example, a processing or control unit) that is configured to regulate one or more aspects of the energy delivery system 8000. The processor 8030 may include one or more specific-purpose microprocessors that comprise hardware circuitry configured to read computer-executable instructions and to cause portions of the hardware circuitry to perform operations specifically defined by the circuitry. The energy delivery module 8015 can also comprise a memory unit or other storage device 8035 (for example, computer readable medium) that can be used to store operational parameters and/or other data related to the operation of the energy delivery system 8000. The storage device 8035 may include nonvolatile and/or volatile memory such as random access memory ("RAM") for temporary storage of information and a read only memory ("ROM") for permanent storage of information, which may store some or all of the computer-executable instructions prior to being communicated to the processor 8030 for execution, and/or a mass storage device, such as a hard drive, diskette, CD-ROM drive, a DVD-ROM drive, or optical media storage device, that may store the computer-executable instructions for relatively long periods of time, including, for example, when the computer system is turned off.

The modules and sub-modules of the energy delivery system 8000 may be connected using a standard based bus system. In different embodiments, the standard based bus system could be Peripheral Component Interconnect ("PCI"), Microchannel, Small Computer System Interface ("SCSI"), Industrial Standard Architecture ("ISA") and Extended ISA ("EISA") architectures, for example. In addition, the functionality provided for in the components and modules of computing system may be combined into fewer components and modules or further separated into additional components and modules.

The system 8000 may also include one or more multimedia devices, such as speakers, video cards, graphics accelerators, and microphones, for example. A skilled artisan would appreciate that, in light of this disclosure, a system including all hardware components, such as the processor 8030, I/O device(s) 8025, storage device(s) 8035 that are necessary to perform the operations illustrated in this application, is within the scope of the disclosure.

With reference to FIG. 80, the energy delivery system 8000 comprises (or is in configured to be placed in fluid communication with) a cooling system 8040. In some embodiments, as schematically illustrated in FIG. 80, such a cooling system 8040 is at least partially separate from the energy delivery module 8015 and/or other components of the energy delivery system 8000. However, in other embodiments, the cooling system 8040 is incorporated, at least partially, into the energy delivery module 8015. The cooling system 8040 can include one or more pumps or other fluid transfer devices that are configured to selectively move fluid through one or more lumens or other passages of the medical instrument 8005. Such fluid can be used to selectively cool (for example, transfer heat away from) the energy delivery member(s) 8010 and/or to cool surrounding tissue or blood during use.

In one embodiment, the energy delivery system 8000 comprises an ultrasound energy delivery system, the medical instrument 8005 comprises an ultrasound catheter having one or more ultrasound transducers located on a distal segment of the catheter shaft and the energy delivery module 8015 comprises a generator configured to cause the ultrasound catheter to deliver acoustic energy to heat tissue sufficient to modulate (e.g., ablate or denervate) nerves innervating the liver, pancreas, stomach, and/or small intestine.

In some embodiments, the ultrasound catheter is angiographically visible and comprises structures configured to enable mapping locations. For example, if the ultrasound catheter comprises flat transducers, the mapping structures may indicate the plane in which the catheter is rotated. The transducer(s) may advantageously be configured to generate sound waves to modulate (e.g., ablate) tissue and to detect returning sound waves to sense or visualize tissue structures. For example the ultrasound catheter may be used to identify distances from a hepatic or other artery wall to an adjacent dense structure (such as the liver, pancreas, stomach, small intestine). As described above, the ultrasound catheter may be used to detect areas along a hepatic artery in which the adjacent dense structures are less than a threshold distance away from the internal wall of the hepatic artery (e.g., less than 5 mm, less than 6 mm, less than 7 mm, less than 4 mm, less than 3 mm, less than 8 mm, less than 9 mm, less than 10 mm) indicative of a likely high density distribution of nerves.

In various embodiments, the ultrasound energy delivery system is configured to operate in either a sensing (e.g., visualization, imaging or diagnostic) mode or a treatment (e.g., energy delivery) mode. The generator or other energy source may comprise a graphical user interface that enables toggling between the sensing mode and the treatment mode (e.g., by pressing graphical user interface buttons on a touchscreen display of the graphical user interface). In one embodiment, distances of the adjacent dense structures are displayed on the graphical user interface of the generator. In another embodiment, images of the adjacent structures are displayed and the distances to the adjacent structures may be determined from the images. As one example, the output of the sensing mode may be combined with a digital image of the subject's anatomy to provide an operator a visual map of desirable/non-desirable modulation sites along the hepatic artery. In one embodiment, the map comprises a "topographical" map indicative of distances to dense structures either qualitatively (e.g., using colors, highlighting or other visual indicators) or quantitatively (using numerical measurements). In one embodiment, the map comprises highlighted areas of close dense structures longitudinally and/or radially from the hepatic artery.

A single ultrasound catheter may be configured to both sense and deliver energy (e.g., ablative energy) utilizing at least one transducer. The frequencies used to ablate the sympathetic nerves can vary based on expected attenuation, the containment of the beam both laterally and axially, treatment depths, type of nerve, mode of operation (e.g., sensing mode or treatment mode) and/or other parameters. In some embodiments, the frequencies used range from about 20 kHz to about 60 MHz, from about 20 kHz to about 20 MHz, from about 1 MHz to about 15 MHz, from about 20 MHz to about 60 MHz, from about from about 500 kHz to about 10 MHz, from about 1 MHz to about 5 MHz, from about 2 MHz to about 6 MHz, from about 3 MHz to about 8 MHz, less than 20 kHz, greater than 60 MHz or overlapping ranges thereof. The sensing mode may involve use of frequencies ranging from 10-60 MHz (e.g., from 10-20 MHz, from 15-30 MHZ, from 10-40 MHz, from 15-50 MHz, from 20-50 MHz, from 30-60 MHz, or overlapping ranges thereof). The treatment mode may involve use of frequencies ranging from 2-45 MHz (e.g., from 2-10 MHz, from 5-15 MHz, from 5-30 MHz, from 10-40 MHz, from 15-45 MHz, from 30-45 MHz, from 10-45 MHz, or overlapping ranges thereof). However, other frequencies can be used without limiting the scope of the disclosure. In some embodiments, sensing is accomplished using pulse-echo ultrasound signals. In one embodiment, a sensing transducer is advantageously provided with a damping layer on the back surface to provide a narrower pulse width e.g., broad band sensitivity). In one embodiment, narrow transmitted pulses are achieved using active damping (e.g., shaped pulses). In some embodiments, the ultrasound transducer is a ceramic chip, such as lead zirconate titanate, or PZT. In another embodiment, the sensing ultrasound transducer is a polymer transducer, such as a polyvinylidene fluoride ("PVDF") transducer. In various embodiments, the energy delivery system 8000 may adjust an energy delivery algorithm or treatment parameters based on results or feedback acquired while in the sensing mode of operation.

One or more ultrasound transducers of the ultrasound catheter may emit focused or non-focused sound waves. The transducers may be directional or non-directional (e.g., omni-directional). The transducers may comprise flat, rectangular transducers or cylindrical transducers. In various embodiments, one or more transducers are adapted to deliver acoustic energy to modulate tissue and one or more transducers are adapted to provide imaging, visualization or other diagnostic measurements. In some embodiments, transducer(s) may comprise multiple-element transducers or other type of transducer adapted to provide both energy delivery and sensing functions. In embodiments where both imaging and treatment are performed, the imaging element(s) can be co-localized with the treatment element(s), or can be located separately (e.g., in different housings, units, transducers, etc.).

Embodiments of ultrasound catheters or systems may comprise structures for centering the one or more transducers within the hepatic artery or other vessel for maintaining the transducer(s) at a minimum distance from the inner wall of the artery or otherwise not in contact with the wall of the artery. For example, such structures may include one or more balloons or other expandable and retractable members, such as wires, ribbons, coils, spiral members or arms. In several embodiments, the ultrasound catheters or systems comprise structures to cool the transducer(s) or reduce the likelihood of overheating. For example, the transducer(s) may be positioned within balloons having cooling fluid or may comprise structures to transfer, shunt or dissipate heat from the transducer surface. In some embodiments, the catheter comprises flow-directing or diverting structures to increase the velocity of blood over the transducer(s).

In accordance with several embodiments, positioning of the ultrasound transducers is manipulated to control circumferential distribution of power (e.g., to control a shape of an ablation lesion) and, optionally, to avoid damage to adjacent dense structures. The energy delivery system 8000 may comprise a sensing or visualization apparatus to assess position of the transducer(s) in the blood vessel (e.g., hepatic artery) and/or an apparatus adapted to move the transducer within the blood vessel (e.g., to center the transducer or bias the transducer at a distance away from a wall of the blood vessel). The sensing or visualization apparatus and the moving apparatus may be integral components or members of the ultrasound catheter or may comprise one or more distinct, separate devices from the ultrasound catheter to be used in conjunction with the ultrasound catheter.

In one embodiment, the sensing or visualization apparatus may comprise angiographic markers that define margins of the blood vessel. In another embodiment, the apparatus may comprise a dilute contrast-filled balloon that defines the margins of the blood vessel. In some embodiments, one or more of the transducers are radiopaque or the ultrasound catheter comprises separate radiopaque markers to facilitate assessment of positioning.

In some embodiments, the distal end portion of the shaft of the ultrasound catheter may be deflected by pull wire(s), by rotation and/or translation of a curved stylet, by inflation/deflation of eccentric balloons, and/or by insertion and withdrawal of a curved or straight sheath. In accordance with several embodiments, if the general location of the adjacent extravascular structure(s) is known, the transducer(s) can be adjusted accordingly (e.g., anteriorly, posteriorly, superiorly, inferiorly, etc.). In some embodiments, intravascular imaging techniques (e.g., optical coherence tomography, intravascular ultrasound) or extracorporeal noninvasive imaging techniques (e.g., MRI, CT) are used to identify locations of the adjacent extravascular structures. In one embodiment, intravascular imaging is performed using a transducer adapted (e.g., optimized) for imaging (e.g., broad band, higher frequency). In one embodiment, a separate sensing transducer proximate an energy delivery transducer is used to detect backscatter from therapeutic ultrasound waves. The largest echoes may generally be from the internal elastic lamina of the blood vessel. The distance can be accurately measured by pulse echo or correlation algorithms. Averaging of multiple signals may achieve accuracy better than the wavelength of the signal if only a single dominant echo is present.

In accordance with several embodiments, one or more transducers of the ultrasound catheter or other medical instrument is/are specifically configured to deliver ablative energy and to increase (e.g., maximize) ablation lesion size radially while reducing (e.g., minimizing) axial ablation length of the transducer(s) (e.g., for flat transducers). The ultrasound catheter may comprise a pivotable catheter that pivots the longest dimension of a flat transducer from a position largely parallel to the vessel length to a position that is largely parallel to the vessel circumference.

Figure 81A:
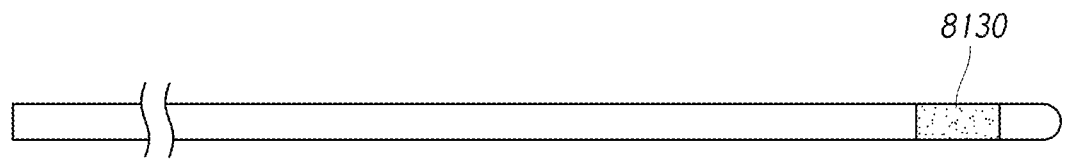
FIGS. 81A-81D illustrate embodiments of a pivoting ultrasound energy delivery device in various pivot conditions.
Figure 81B:
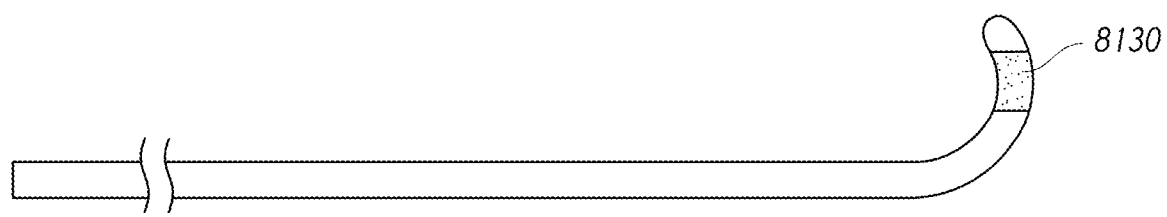
Figure 81C:
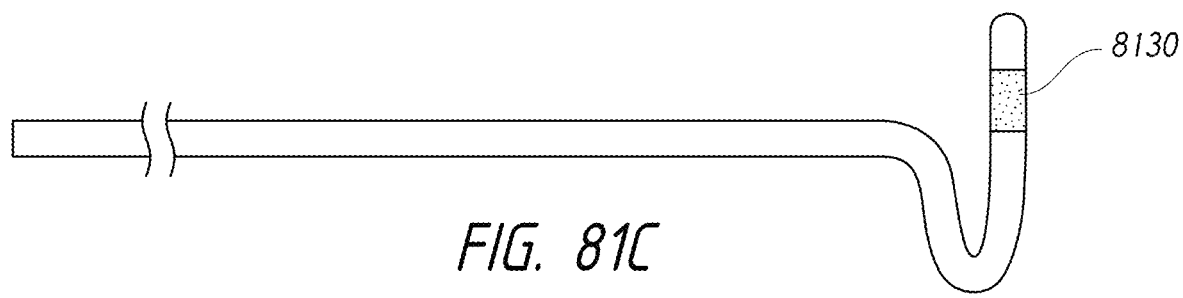
Figure 81D:
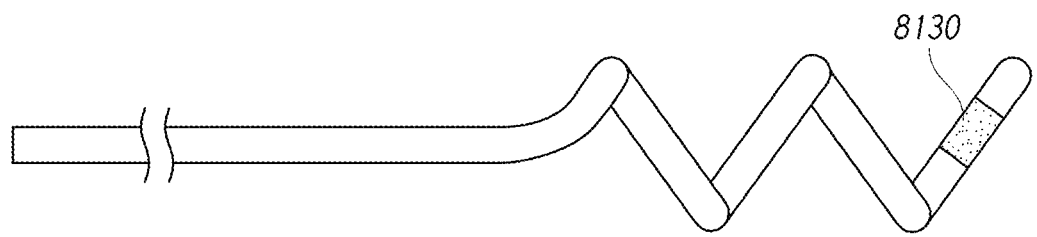

FIGS. 81A-81D illustrate embodiments of pivoting ultrasound energy delivery devices (e.g., comprising one or more energy delivery members 8110 (for example, ultrasound transducers, radiofrequency electrodes, microwave antennas)) in various pivot configurations. FIG. 81A illustrates an embodiment of an ultrasound catheter in a non-pivot configuration prior to energy delivery. The ultrasound catheter is inserted into a guide or sheath catheter with the long dimension of the transducer parallel to the guide, sheath, and/or vessel wall. The ultrasound catheter is then configured to deflect a distal segment of the catheter shaft into a pivoting configuration to orient the longest transducer dimension radially within the vessel. For example, FIG. 81B illustrates the ultrasound catheter in an L-shaped pivot configuration and FIG. 81C illustrates the ultrasound catheter in an alternative T-shaped pivot configuration. In one embodiment, the ultrasound catheter may be configured to deflect the distal segment of the shaft into a spiral shape to orient the longest transducer dimension radially within the vessel, as shown in FIG. 81D.

Several embodiments of the pivoting catheters are particularly advantageous for flat directional transducers because they facilitate insertion of the transducer(s) at a low profile (e.g., lowest possible profile) and the orientation of the directional transducer(s) is increased (e.g., maximized) radially, thereby enabling multiple slices of the circumference to be exposed to energy delivery while reducing (e.g., minimizing) the length of vessel involved.

For ultrasound catheters and systems adapted to deliver power or energy sufficient to ablate tissue, it is particularly advantageous to deliver sufficient power to a small perivascular target volume to create a focal lesion and to deliver power to an oblong region that is longer in the circumferential direction and shorter in the axial direction, in accordance with several embodiments of the invention. Accordingly, embodiments of ultrasound catheters provide relatively large surface area for power or energy delivery but provide a reduced profile for introduction into the blood vessel (e.g., hepatic artery) and increased flexibility to access target vasculature.

Figure 82A:
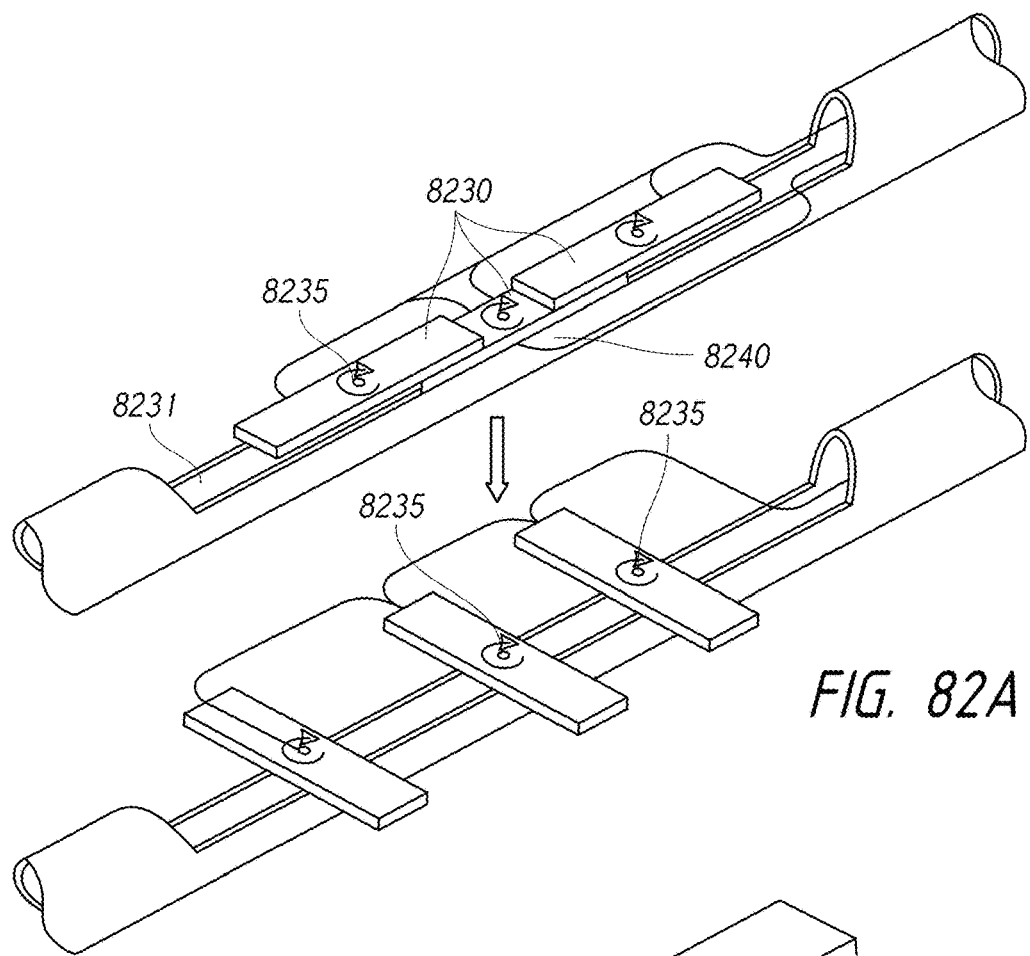
FIG. 82A illustrates an embodiment of a distal portion of an ultrasound energy delivery device having a multiple pivoting transducers.

FIGS. 82A-86 illustrate various embodiments of ultrasound catheters or systems adapted to provide a reduced insertion and delivery profile while also providing increased circumferential vessel coverage. FIG. 82A illustrates an embodiment of a distal portion of an ultrasound energy delivery device having multiple pivoting transducers 8210 adapted to rotate between a generally axial reduced-profile configuration for insertion and a transverse energy delivery configuration for providing an energy delivery profile that is longer in the circumferential direction and shorter in the axial direction. The ultrasound transducers 8210 comprise flat, rectangular transducers.

In the reduced profile configuration, the longer dimension of the transducers 8210 is aligned so as to be in parallel with the longitudinal axis of the shaft of the catheter. As shown, adjacent transducers 8210 may be stacked or offset vertically so as to reduce spacing between the transducers when transitioned to the energy delivery configuration. The transducers 8210 may each pivot about a respective central pivot 8220 as shown in FIG. 82A. In other embodiments, the transducers 8210 may be carried or suspended by mounting structures or carriers that pivot so as not to obstruct or interfere with operation (e.g., beam pattern) or efficiency of the transducers 8210. Also as shown, the transducers 8210 may be positioned in a recessed portion 8215 of the catheter shaft to reduce the overall profile.

In various embodiments, the mechanism to cause the pivoting or rotation of the transducers comprises one or more control or actuation wires 8225 (e.g., pull wires and/or push wires) or elastic self-rotating mechanisms or materials capable of transitioning between the reduced profile configuration and the energy delivery configuration. The wires 8225 may interface directly with the transducers 8210 or with mounting frames or structures holding the transducers 8210. The transducers 8210 may comprise an array of two, three, four, five or more transducers.

In various embodiments, the transducers 8210 have a width of 0.5-2 mm, a length of between 4-6 mm, a spacing of 2-3 mm in the energy delivery configuration and a thickness of half a wavelength using the speed of sound in a piezoelectric crystal. In some embodiments, the active surface of the transducers 8210 is coated with a polymeric matching layer of quarter-wavelength thickness. In some embodiments, the opposite surface of the transducers 8210 is configured to minimize or reduce acoustic coupling and increase efficiency of the transducers. For example, an air pocket may be positioned proximate the opposite surface. When an array of transducers 8210 is used, the transducers 8210 may be offset in a manner such that the sound waves constructively interfere with each other to maximize or increase power transmission.

Figure 82B:
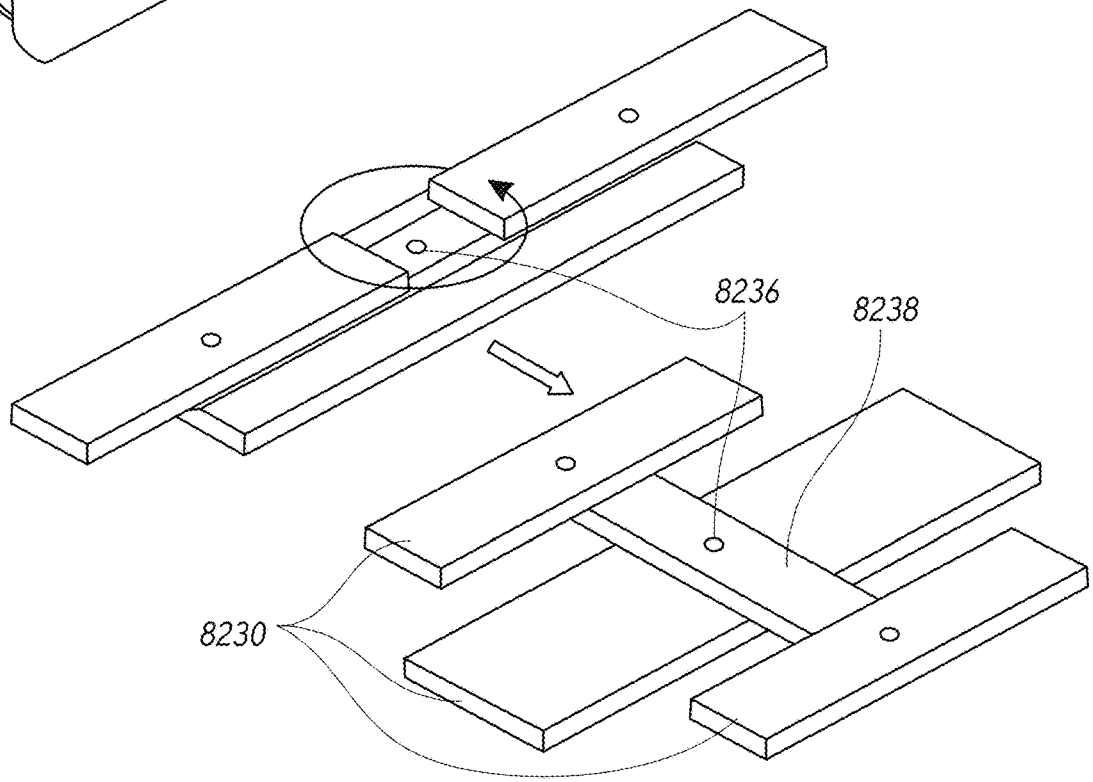
FIG. 82B illustrates an alternative embodiment of an assembly of multiple pivoting transducers of the ultrasound energy delivery device of FIG. 82A.

FIG. 82B illustrates an alternative embodiment of an assembly of multiple pivoting transducers 8210 of the ultrasound energy delivery device of FIG. 82B. As shown, instead of the transducers 8210 each only rotating about their own individual pivot, the transducers 8210 may rotate about a uniform central pivot 8230 through the use of one or more connecting members 8235. The relative spacing and sizing illustrated in the figures is not necessarily to scale or accurate. In some embodiments, the transducers are all the same size and shape and are uniformly spaced in the energy delivery, or deployed, configuration. In other embodiments, the transducers may have different sizes and/or shapes and are not uniformly spaced. The transducers may be mounted on a suspension apparatus that supports the transducers and provides the connections and pivots without interfering with the function of the transducers.

Figure 83A:
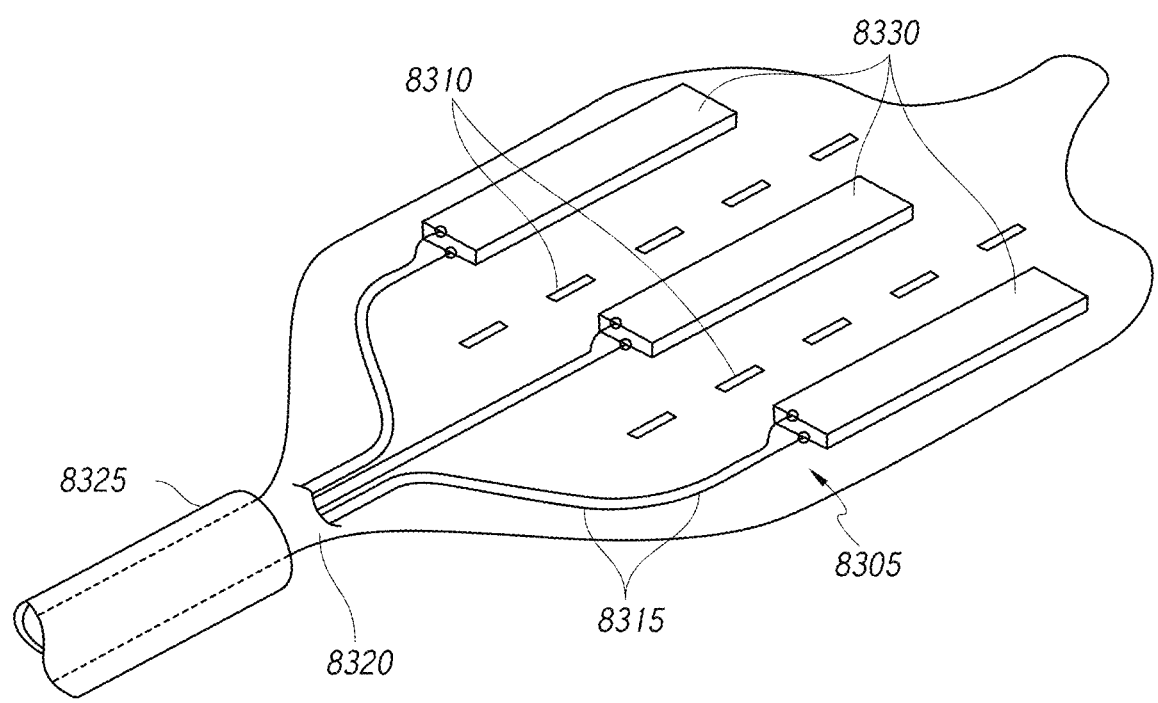

FIG. 83A illustrates an embodiment of a distal end portion of an ultrasound energy delivery device including a foldable flexible circuit substrate 8305 carrying an array of ultrasound transducers 8310. The flexible circuit substrate 8305 comprises perforations, slots or holes 8315 that define and control hinging or folding behavior. In one embodiment, the flexible circuit substrate 8305 is formed of a thin polyimide or other flexible polymeric material. In various embodiments, the thickness of the flexible circuit substrate 8305 ranges from about 0.001 to about 0.003 inches. The transducers 8310 and electrical leads 8325 may be mounted to the flexible circuit substrate 8305. In one embodiment, the substrate 8305 is trimmed to facilitate withdrawal. The flexible circuit 8305 is coupled to the distal end of an elongate delivery member 8320 (e.g., wire, tube, shaft) and may be configured to be introduced through a sheath or tube 8330 in a reduced-profile configuration and then deployed to an energy delivery configuration. The deployment may be facilitated by one or more actuation or control wires or as a natural result of the flexibility of the material of the substrate 8305 and the perforations or slots 8315 in the substrate 8305. As shown in FIG. 83A, electrical leads 8325 may be coupled to the transducers 8310 to deliver electrical energy from a generator or other energy source to activate the transducers 8310 to deliver acoustic energy. Each transducer 8310 may have two separate leads 8325 (one for a top surface and one for a bottom surface) or there may be two leads 8325 total that branch to connect to each of the transducers 8310.

In some embodiments, the flexible circuit 8305 is reinforced with (e.g., affixed to the substrate) metallic, metallic alloy (e.g., Nitinol), ceramic or polymeric material, elements or structures to provide stability and strength and/or to provide further control over deployment and withdrawal and to provide more precision for a desired energy delivery configuration. In one embodiment, the flex circuit 8305 is reinforced with nitinol stays or hinges. In some embodiments, the flexible circuit 8305 is manufactured by plating the substrate with copper and the copper is etched using photolithography to create a desired circuit pattern. In various embodiments, the length of the transducers 8310 is between about 3 mm and about 10 mm (e.g., 3-6 mm, 4-8 mm, 5-10 mm) and the width of the transducers 8310 is less than 2 mm.

FIGS. 83B-1 to 83B-3 illustrate (e.g., via side, top, and open views) another embodiment of a distal end portion of an ultrasound energy delivery device comprising a flexible circuit. In the illustrated embodiment, the flexible circuit substrate 8305 is integral with (or formed from) the elongate delivery member (e.g., shaft or tube made of polyimide or other flexible polymeric material) thereby providing additional stability and strength at the proximal end for manipulation (e.g., insertion and withdrawal). For example, skives or cut-outs 8340 may be formed in the elongate delivery member at spaced-apart locations and a slit 8345 may also be formed in the elongate delivery member between the skives 8340. Similar to FIG. 83A, the ultrasound transducers 8310 may be arranged on the flexible circuit substrate 8305 in any pattern or configuration. The flexible circuit substrate 8305 may comprise one, two, three, four, five or any number of transducers 8310. The transducers 8310 may be coupled to a generator or other energy source by electrical leads or wires 8325. In some embodiments, the leads 8325 travel within a micro-coaxial cable 8335 within the elongate delivery member 8320. In one embodiment, the micro-coaxial cable 8335 is formed of a braided polyimide if the leads or wires 8325 comprise high conductance braid wires made of copper, nickel, nickel plating, gold, silver, tungsten and/or the like. In some embodiments, the leads or wires 8325 comprise two-sided traces with vias.

Figure 84A:
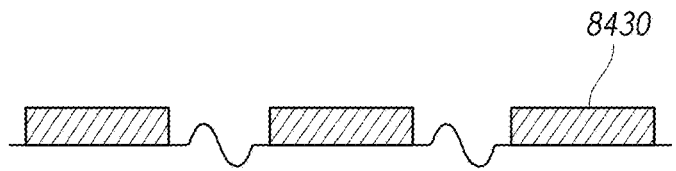
FIGS. 84A-84E illustrate various configurations of the distal portion of the ultrasound energy delivery device of FIG. 83A.
Figure 84B:
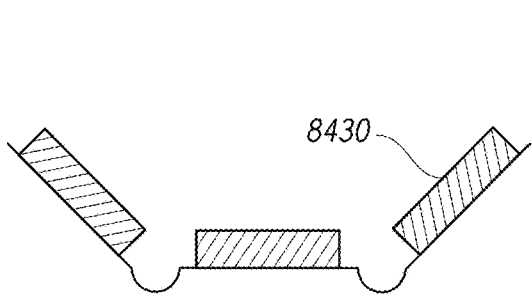
Figure 84C:
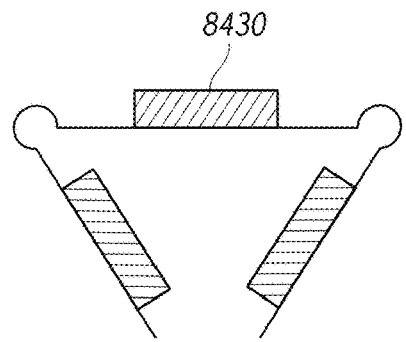
Figure 84D:
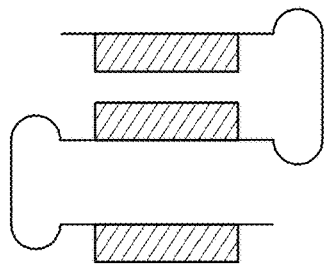
Figure 84E:
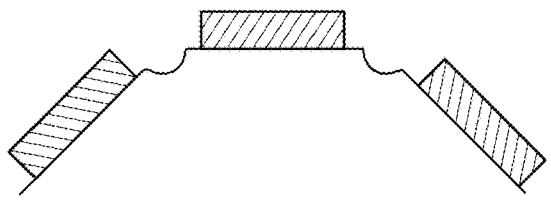

FIGS. 84A-84E illustrate various configurations of a distal portion of the ultrasound energy delivery device of FIG. 83A or FIG. 84B. FIG. 84A illustrates a flat energy delivery configuration. FIG. 84B illustrates an energy delivery configuration in which the transducers 8310 are angled toward a focal point to provide focused energy delivery. FIG. 84C illustrates a folded configuration for introduction of the flexible circuit 8305 through a sheath or sleeve 8330 (e.g., guide or extension catheter). The transducers 8310 may be configured to fold into a triangle, square or other polygonal shape. In some embodiments, the folded configuration of FIG. 84C may be used for larger-width transducers. FIG. 84D illustrates a stacked configuration for introduction of the flexible circuit 8305 through a sheath or sleeve 8330. FIG. 84E illustrates an energy delivery configuration in which the ultrasound transducers 8310 are angled away from each other so as to disperse the power or energy over a wider area. For example, the energy may be delivered in de-focused or unfocused manner in a lateral, circumferential or longitudinal direction.

Figure 85:
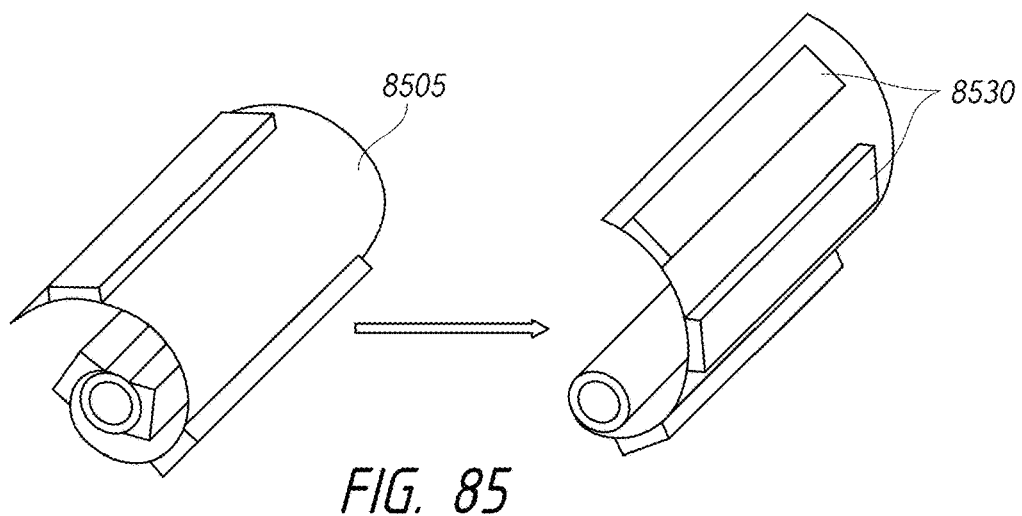
FIG. 85 illustrates an embodiment of a distal portion of an ultrasound energy delivery device configured to deploy by unrolling a flexible circuit.

FIG. 85 illustrates an embodiment of a distal portion of an ultrasound energy delivery device configured to deploy by unrolling a flexible circuit 8505. In some embodiments, the flexible circuit 8505 comprises a plurality of ultrasound transducers 8510 (e.g., array) and the flexible circuit 8505 is configured to transition between a rolled-up configuration for introduction and a deployed, unrolled configuration for energy delivery. As shown, the introductory rolled-up configuration may comprise a spiral or "jelly roll" configuration. The flexible circuit 8505 may be unrolled and rolled by torquing parts of the ultrasound catheter or other medical instrument in opposite directions or as a result of self-expanding, shape memory material (e.g., Nitinol). The flexible circuit 8505 may comprise multiple transducers 8510 spaced relatively close together. In one embodiment, the transducers 8510 are adapted to deliver energy with a more precise focus (e.g., less than half-wavelength in the media). In one embodiment, the transducers 8510 are 0.5 mm wide. The relative spacing illustrated in the figures is not necessarily to scale or accurate.

Figure 86:
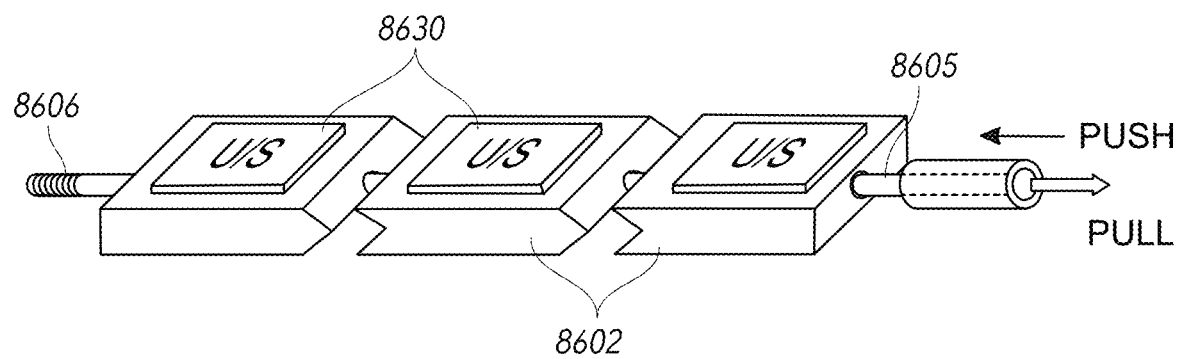
FIG. 86 illustrates another embodiment of a distal portion of an ultrasound energy delivery device comprising multiple interlocking mounting elements.

FIG. 86 illustrates another embodiment of a distal portion of an ultrasound energy delivery device comprising multiple interlocking mounting elements 8602. In this embodiment, multiple transducers 8610 are distributed in an axial direction along a flexible catheter 8605. The transducers 8610 are mounted on mounting elements 8602 that are shaped and formed to interlock with each other. Once at the treatment site, the mounting elements 8602 may be cinched or otherwise caused to come together to form a rigid structure having a predefined shape. The predefined shape may comprise a flat configuration, a concave configuration or a convex configuration. The cinching may be effected by one or more pull and/or push wires extending through the mounting elements. The orientation between mounting elements 8602 may be defined by the shape of interlocking edges of the mounting elements. The distal end of ultrasound energy delivery device may comprise an anchor (not shown) and a soft, steerable tip 8615.

Several embodiments of the ultrasound energy delivery devices comprising flexible circuits are particularly advantageous because they support the electrodes coupled to the transducers and/or provide electrical leads to opposing surfaces of the transducer.

In accordance with several embodiments, acoustic mirrors and/or lenses are used to control distribution of acoustic energy delivered by an ultrasound transducer of the ultrasound catheter in order to control size and shape of the treatment area (e.g., lesion zone). For example, acoustic impedance may be analogous to index of refraction in optics. Sound waves traversing regions of different acoustic impedance may be refracted and/or reflected. Accordingly, a tighter focus can be achieved by large planar or cylindrical transducers.

FIGS. 87A-87F illustrate various embodiments of acoustic mirrors and/or lenses to control distribution of acoustic energy delivered by an ultrasound transducer. Balloons filled with different fluids may be used to focus or de-focus the output of the ultrasound transducer. For example, acoustic mirrors or lenses may be created by a curved surface of a balloon inflated with a media having an acoustic impedance different from the surrounding media (e.g., tissue and/or blood). In accordance with several embodiments, the use of acoustic mirrors and/or lenses advantageously provides more energy to a target treatment area without overheating the transducer or causing cavitation at the transducer surface.

Figure 87A:
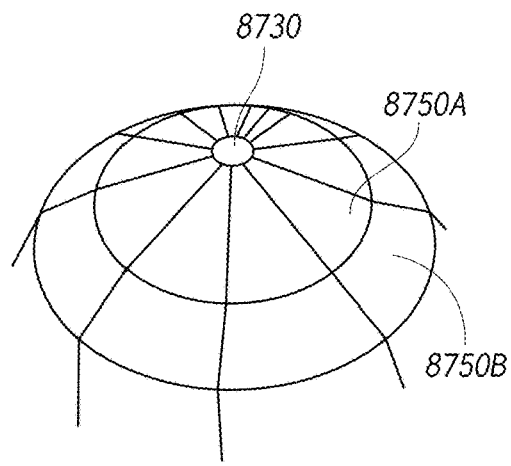
FIGS. 87A-87F illustrate various embodiments of acoustic mirrors and/or lenses to control distribution of acoustic energy delivered by an ultrasound transducer.
Figure 87B:
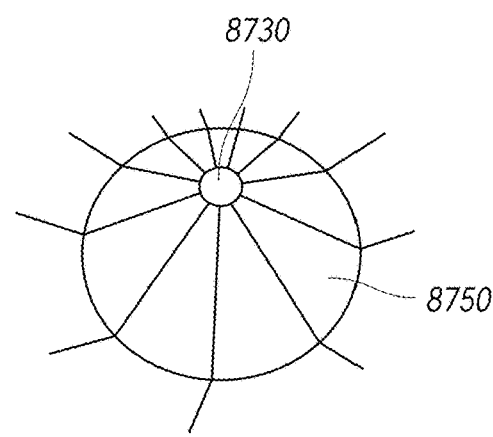

FIG. 87A illustrates a cylindrical transducer 8710 positioned on a single balloon 8705 filled with a liquid having an acoustic impedance different than (e.g., greater than, less than) the surrounding blood and/or tissue, thereby forming an acoustic lens. As can be seen, the balloon 8705 causes the path of the acoustic energy to deviate from the initial trajectory. The acoustic mirror or lens may comprise a single balloon or a double balloon (e.g., an inner balloon and an outer balloon). FIG. 87B illustrates an embodiment comprising a double balloon. The inner balloon 8705A is filled with a first liquid having a first acoustic impedance and the outer balloon 8705B is filled with a second liquid having a second acoustic impedance different than the acoustic impedance of the first liquid. Either the first liquid or the second liquid may have an acoustic impedance that is substantially different than the acoustic impedance of the surrounding tissue and/or blood. For example, fat, blood and soft tissues have an acoustic impedance of 1.3-1.7 MRayls. Fluids (e.g., liquids) in the balloons (in accordance with several embodiments) have an acoustic impedance approximately 10% different from tissue or blood. For example, in some embodiments, the fluids have an acoustic impedance from 0.7 MRayls to 1.8 MRayls. In some embodiments, a first balloon comprises a first fluid having a first acoustic impedance and a second balloon comprises a second fluid having a second acoustic impedance. The cylindrical transducer 8710 is positioned on the inner balloon 8705A.

Figure 87C:
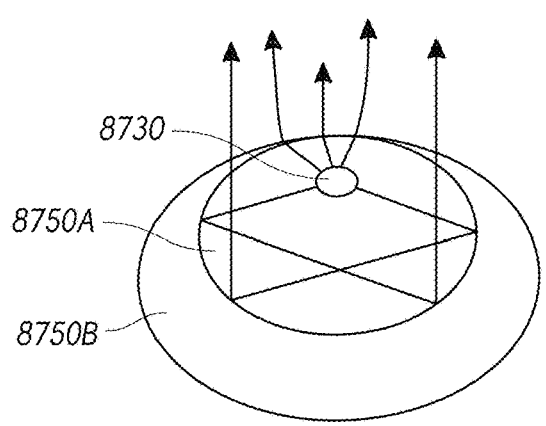
Figure 87D:
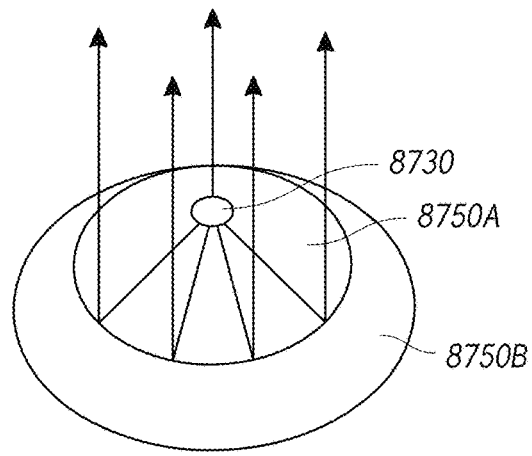

In some embodiments, the outer balloon is filled with air to form an acoustic mirror (as shown in FIGS. 87C and 87D). FIG. 87C illustrates a mirror configuration for generating generally non-columnar trajectories to provide for a wider dispersal and FIG. 87D illustrates a mirror configuration for generating generally columnar trajectories in which the transducer 8710 is positioned at the focus of the air-liquid interface. In the embodiment of FIG. 87D, the outer balloon 8705B may be formed with the inner balloon 8705A to create a crescent-shaped or parabolic-shaped cavity and the transducer 8710 may be positioned at the bottom of the crescent- or parabolic-shaped cavity.

Figure 87E:
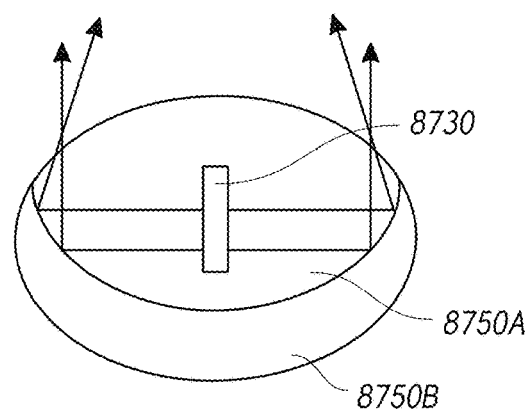
Figure 87F:
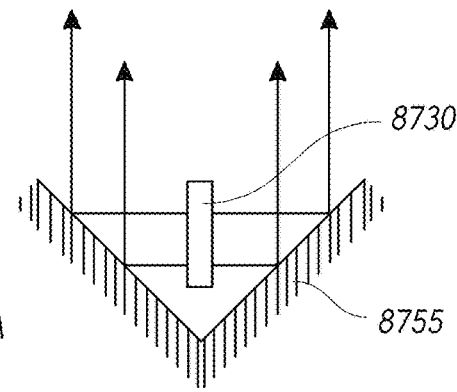

FIG. 87E illustrates an embodiment in which a flat, rectangular ultrasound transducer 8710 is positioned on a double-balloon configuration, in which the inner balloon 8705A is filled with a liquid to form an acoustic lens and the outer balloon 8705B is filled with air to form an acoustic mirror. FIG. 87F shows that the acoustic mirrors may be formed from folding mechanical structures or plates 8715.

In various embodiments, the balloons comprise spherical balloons. The focus of the acoustic lens embodiments may be changed by changing the shape of the balloon(s) through pressurizing or stretching the balloon(s) and/or by changing the media or concentration of the fluid in the balloons. The liquids used may include concentrated saline, concentrated glucose solution, glycerol, propylene glycol, ethylene glycol, heavy water ($D_2O$), fluorocarbons (e.g., Freon), mercury, gallium, perfluorotributylamine, perfluorodecalin, and/or oils. The air may comprise any gas, such as carbon dioxide.

In accordance with several embodiments, it may be particularly advantageous to provide a larger area of treatment (e.g., larger ablation zones) without increasing the size of the transducers. For example, a plurality of transducers may be arranged to acoustically couple with each other such that more power is transmitted from the active surfaces (e.g., increased efficiency) and more surface area is available for cooling.

Figure 88:
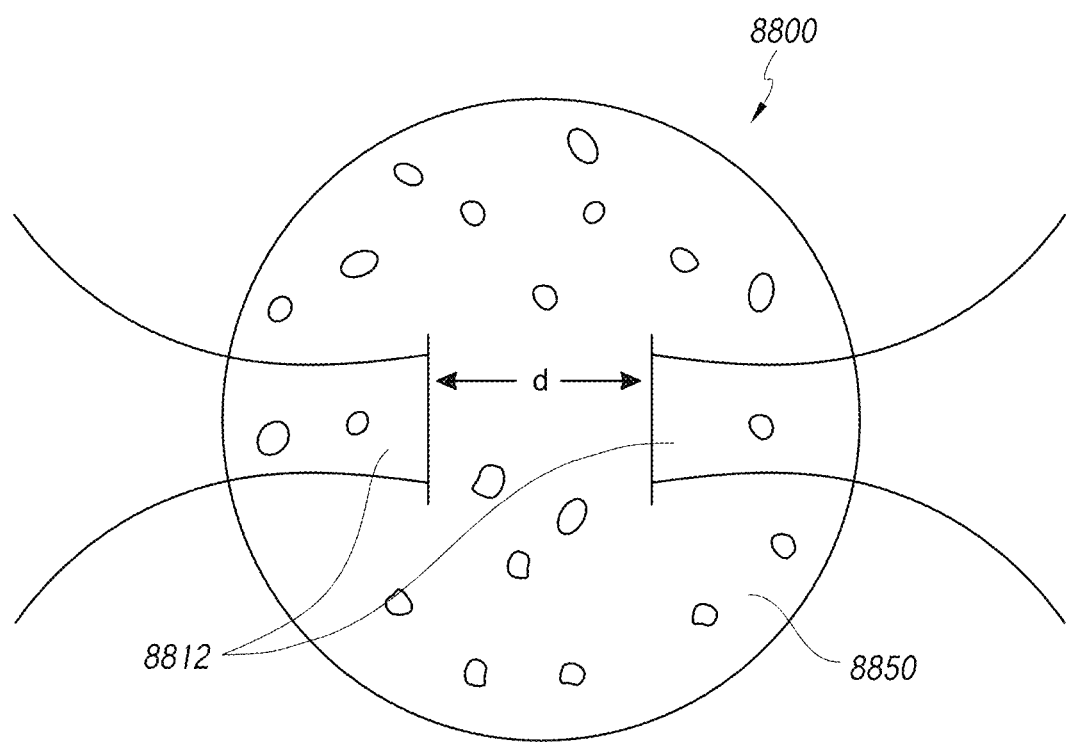
FIG. 88 illustrates a schematic representation of an embodiment of a resonant cavity ultrasound transducer.

FIG. 88 illustrates a schematic representation of an embodiment of a resonant cavity ultrasound transducer 8810 adapted to provide a larger area of treatment (e.g., larger ablation zone). The ultrasound transducer 8810 comprises two parallel flat transducers 8805 spaced apart by a distance d that is a multiple of the wavelength ($d=n\times\lambda$) to achieve resonance and adapted to radiate in opposite directions. The resonant cavity ultrasound transducer 8810 comprises a suspension structure, frame or mechanism (not shown) configured to maintain alignment of the two transducers or plates 8805 in a parallel orientation. The suspension structure or mechanism may be slightly compliant so as to allow for self-adjustment to achieve resonance. All exposed surfaces of the transducers or plates 8805 are surrounded by cooling fluid contained within a balloon 8815. The outside surfaces of the transducers 8805 comprise matching layers and the inside surfaces do not comprise matching layers so as to provide increased cooling to the transducers 8805.

In accordance with several embodiments, embodiments comprising resonant cavity ultrasound transducers advantageously provide one or more of the following advantages or benefits: increased cooling, greater amplitude or power, and ability to move the transducer(s) closer to the wall (e.g., permits a closer focal distance).

Figure 89:
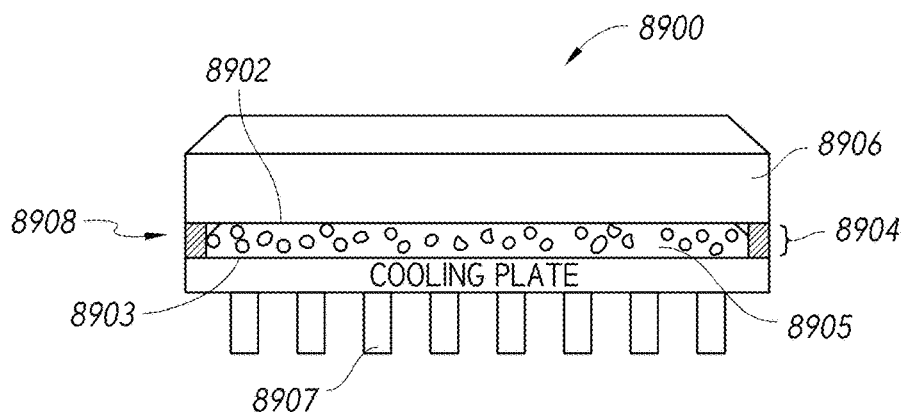
FIG. 89 illustrates an embodiment of an ultrasound transducer comprising a heat pipe to increase heat transfer.

In accordance with several embodiments, it may be advantageous to cool the ultrasound transducer(s) without backside acoustic coupling (e.g., air gaps) that reduces efficiency. FIG. 89 illustrates an embodiment of an ultrasound transducer 8910 comprising a heat pipe configuration to increase heat transfer. In one embodiment, a flat heat pipe may be positioned on the back side of the piezoelectric chip or plate to increase heat transfer without increasing acoustic coupling. The heat pipe configuration comprises a hot surface 8902, a cold surface 8903 and a thin gap 8904 filled with a two-phase fluid 8905 between the hot surface 8902 and the cold surface 8903. The two-phase fluid 8905 comprises liquid and gas. The hot surface 8902 is formed on the back surface of the piezoelectric plate or chip 8906. The fluids may comprise water, alcohol, refrigerants (e.g., Freon, R12), propane, nitrous oxide, etc. The quality (e.g., % liquid) of the two-phase fluid or mixture varies with temperature. In some embodiments, a quality is desired that provides sufficient heat transfer to maintain equilibrium at the operating temperature without damping the transducer. The fluid 8905 migrates or wicks between the hot and cold surfaces. The fluid 8905 may be stirred by microstreaming generated by movement of the piezoelectric plate or chip 8906. In some embodiments, the liquid phase rarely if ever touches the surface of the piezoelectric plate or chip 8906. Accordingly, the effective acoustic impedance is determined by the vapor or gas phase, which is normally very low so that little acoustic energy is transmitted out the back side of the transducer.

Figure 89A:
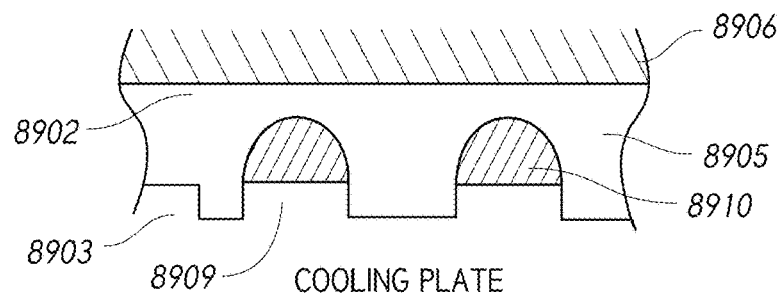
FIG. 89A illustrates a close-up view of a portion of a cooling plate of the ultrasound transducer heat pipe of FIG. 89.
Figure 89B:
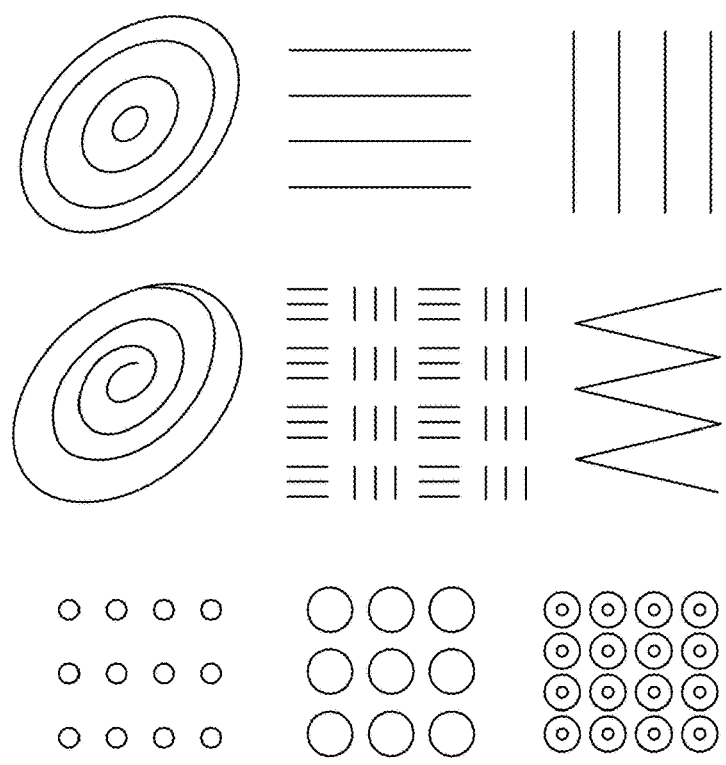
FIG. 89B illustrates various embodiments of texture patterns of the surfaces of the ultrasound transducer heat pipe of FIG. 89.

The interior cold surface 8903 of the cooling plate may be textured or patterned materially to control nucleation, growth and transport of condensate. FIG. 89B illustrates various embodiments of texture patterns of the ultrasound transducer of FIG. 89. The patterns may comprise grooves, slots, holes, cross hatches, bumps, spirals, bumps and holes, and/or the like. In some embodiments, the pattern comprises printed regions of surface coatings having different affinity for the condensate or liquid phase. The piezoelectric back surface (e.g., the hot surface or evaporating surface 8902) has a low affinity for the liquid phase and the cooling plate surface (e.g., cold surface 8903) has a high affinity for the liquid phase. If water is used as the fluid, then the hot surface 8902 is hydrophobic and the cold surface 8903 is hydrophilic. The thin gap 8904 may have a thickness that is several times the wavelength of the piezoelectric plate or chip (the hot plate 8902). The gap 8904 should allow for sufficient growth of distinct regions of condensate nucleation and growth as the piezoelectric chip (e.g., PZT) is heated up. As shown in FIG. 89, the exterior (back) surface of the cooling plate may comprise textured structures 8907 (e.g., grooves, fins) to promote heat transfer. In one embodiment, the cooling plate is larger than the piezoelectric plate or chip 8906 (e.g., hot plate).

The ultrasound transducer 8910 comprising the heat pipe may be fabricated using MEMS technology. In various embodiments, the piezoelectric chip or plate 8906 is hermetically sealed to the backing or cooling plate using a glass weld 8908. The cooling plate or backing may comprise glass, ceramic and/or metal. FIG. 89A illustrates a close-up view of a portion of the cooling plate or backing of the ultrasound transducer 8910 of FIG. 89. As shown, condensate 8915 may be formed on the high-affinity surfaces 8909 of the cold surface 8903. As the condensate collection approaches the hot surface 8902, heat is transferred to the condensate collection or droplets and the droplets evaporate. The cooling plate may transfer heat to a remote location using fluid, heat pipe or thermal conduction. In other embodiments, the high-affinity surfaces may be the lowered regions instead of the raised regions depending on the material used for the various regions. In one embodiment, the surface of the cooling plate is physically flat but is patterned with alternating regions of high-affinity and low-affinity (e.g., hydrophilic and hydrophobic) materials.

Figure 90:
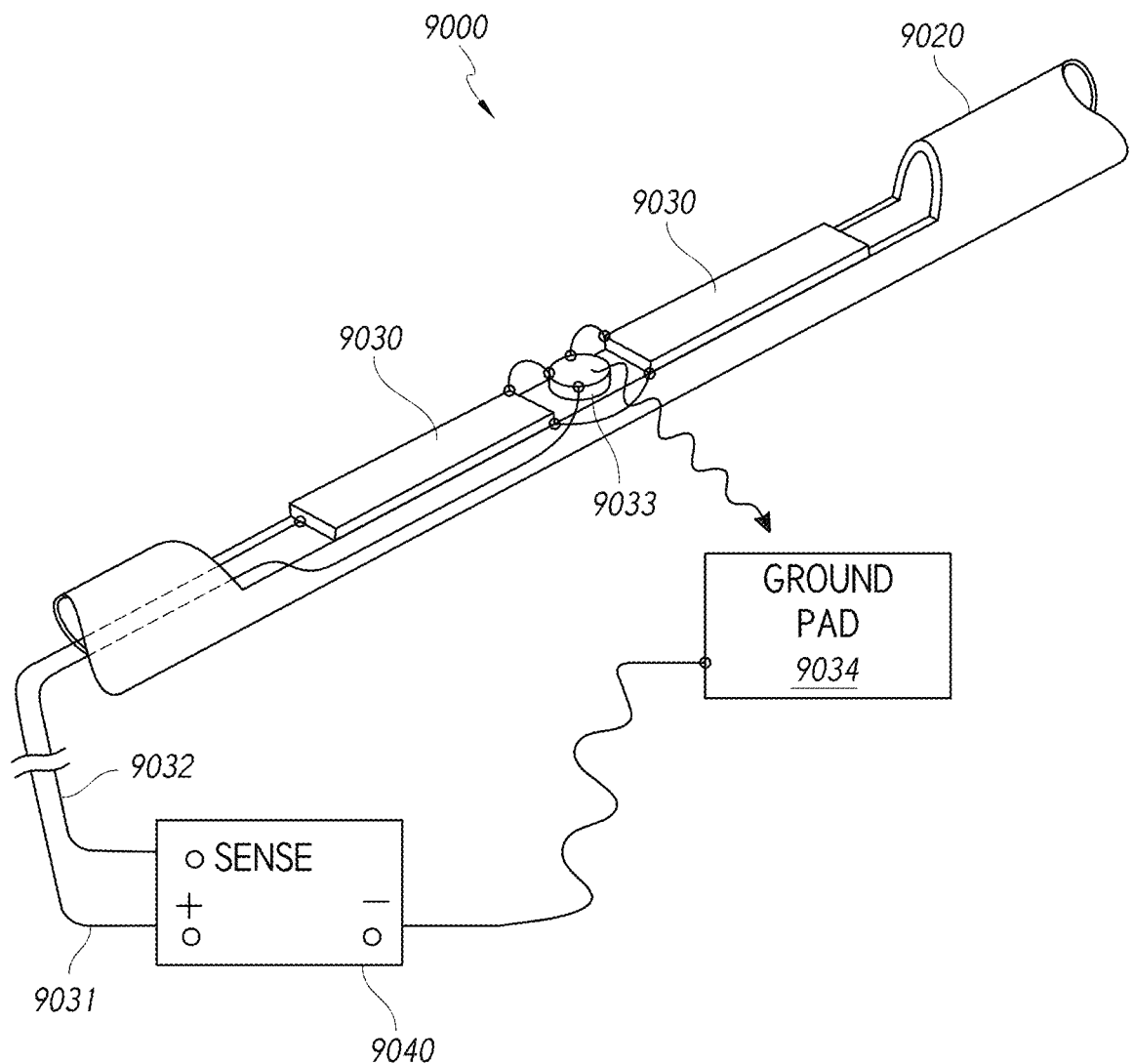
FIG. 90 illustrates an embodiment of an energy delivery system configured to deliver ultrasound and radiofrequency energy to target tissue using a single energy delivery device.

In accordance with several embodiments, energy delivery devices (e.g., catheters) are adapted to deliver both ultrasound and radiofrequency energy to target tissue. For example, the energy devices or systems may be configured to provide unipolar ultrasound and radiofrequency energy delivery. FIG. 90 illustrates an embodiment of an energy delivery system 9000 configured to deliver ultrasound and radiofrequency energy to target tissue using a single energy delivery device. The energy delivery system comprises an energy delivery device 9020 comprising one or more ultrasound transducers 9010 and one or more electrodes 9025, a ground pad 9030 and a generator 9035. The illustrated embodiment of the energy delivery device 9020 comprises two ultrasound transducers 9010 and an electrode 9025 positioned between the ultrasound transducers 9010. The electrode 9025 may be coupled or arranged in series or in parallel with the transducers 9010. In one embodiment, the one or more electrodes 9025 comprise one or more exposed transducer electrodes. In another embodiment, the one or more electrodes 9025 comprise separate, distinct elements from the transducers 9010. The transducers 9010 may comprises focused ultrasound transducers or non-focused ultrasound transducers. The generator 9035 may include the features of the other generators or energy delivery modules described herein.

In one embodiment, a wire 9040 connects the generator 9035 to one electrode layer of the ultrasound transducer(s) 9010 and the electrode 9025 and the circuit is completed by the ground pad 9030, which is also electrically coupled to the generator 9035. Radiofrequency energy is delivered by the electrode 9025 through tissue toward the ground pad 9030. The return path of the ultrasound drive signal also uses tissue conduction to the ground pad 9030. Accordingly, the ultrasound and radiofrequency energy may be delivered in a unipolar fashion through a single wire with the return provided by the ground pad 9030.

In some embodiments, radiofrequency energy is delivered for a period of time before the ultrasound energy is delivered in order to preheat the tissue to a level just below an ablation threshold (e.g., within 1-10 degrees Celsius, within 1-5 degrees Celsius) of the tissue. In one embodiment, the ultrasound energy is then provided to incrementally heat the tissue sufficient to elevate the temperature above the ablation threshold of the tissue, thereby reducing the total amount of power or energy required to ablate the tissue while still providing focused ablation.

In some embodiments, a sensing wire 9045 is provided to measure voltage at the electrode(s) 9025, thereby enabling measurement of both ultrasound and radiofrequency power delivery. The sensing wire 9045 may connect directly from the generator 9035 to the electrode 9025. In some embodiments, the sensing wire 9045 is used to measure tissue impedance. The sensing wire 9045 may be used to adjust the proportion of the electrode to change the proportion of power or energy delivery. For example, the measurements obtained using the sensing wire 9045 may adjust the radiofrequency energy delivery to either deliver more radiofrequency energy or siphon off radiofrequency energy delivery delivered to the target tissue. The proportion of radiofrequency and ultrasound power may be adjusted by varying the frequency with respect to the resonant frequency of the ultrasound transducer(s) 9010. In some embodiments, the ultrasound transducers 9010 deliver treatment energy in the range of 1-10 MHz (e.g., 2-5 MHz, 3-8 MHz, 1-4 MHz, 6-10 MHz, or overlapping ranges thereof) and the electrode 9025 delivers energy in the range of 400 kHz to 1 MHz (e.g., 450 kHz to 650 kHz, 600 kHz to 800 kHz, 700 kHz to 1 MHz, or overlapping ranges thereof).

In several embodiments, changes in impedance of the electrode 9025 are used as an indicator of lesion formation and the impedance measurements may be used to adjust energy delivery. In some embodiments, the impedance measurements or output indicative of lesion formation or completion may be output on a display of the generator 9035. In some embodiments, the electrode 9025 is used only for sensing and not for energy delivery.

In accordance with several embodiments, embodiments of systems configured to deliver both ultrasound and radiofrequency provide one or more of the following advantages or benefits: (i) fewer wires in the shaft, (ii) lesion characterization or lesion formation assessment, (iii) additional heat provided by radiofrequency energy delivery, (iv) simplified catheter construction by reducing transmission line requirements, (v) use of transducers with relatively small surface area (e.g., less than 50 $mm^2$ for cylindrical transducers and less than 15 $mm^2$ for rectangular transducers), (vii) use of tissue conduction to ground pad as return path for ultrasound drive signal, (v) quick formation of small, focal lesions with reduced power delivered by ultrasound transducers and/or (vi) creation of more focal lesions with increased total energy delivered.

In some embodiments, the energy delivery system 8000 delivers ultrasonic energy to modulate (e.g., ablate, stimulate) sympathetic nerve fibers in the hepatic plexus. For example, the energy delivery system 8000 can employ focused ultrasonic energy such as high-intensity focused ultrasonic (HIFU) energy or low-intensity focused ultrasonic (LIFU) energy to ablate sympathetic nerve fibers. As another example, the energy delivery system 8000 delivers non-focused, or unfocused, energy. For example, the ultrasound transducer(s) can deliver ultrasonic energy to one or more target sites to modulate (e.g., ablate) sympathetic nerve fibers in the hepatic plexus or other nerves described herein (e.g., celiac plexus or nerves innervating, surrounding or in proximity to the liver, pancreas, stomach and/or small intestine). The acoustic, or ultrasonic, energy can be controlled by dosing, pulsing, or frequency selection. In some embodiments, HIFU energy can advantageously be focused at a distant point to reduce potential disturbance of the tissue of the blood vessel (e.g., the intima and the media layers) or surrounding tissues. HIFU energy can advantageously reduce the precision required for positioning of the ultrasound catheter. The one or more ultrasound transducers can be refocused during treatment to increase the number of treatment sites or to adjust the depth of treatment. In some embodiments, the use of HIFU energy can result in increased concentrations of heat for a shorter duration and can simultaneously focus energy at multiple focal points, thereby reducing the total time required to administer the neuromodulation procedure.

In some embodiments, the energy delivery system 8000 comprises a focused ultrasound (e.g., HIFU) ablation catheter and an acoustic frequency generator. The ablation catheter can be steerable from outside of the subject using a remote mechanism. The distal end of the ablation catheter can be flexible to allow for deflection or rotational freedom about an axis of the catheter shaft to facilitate positioning within a hepatic or other artery. In some embodiments, the ablation catheter comprises focusing (e.g., parabolic) mirrors or other reflectors, gas-filled or liquid-filled balloons, and/or other structural focusing elements to facilitate delivery of the ultrasonic energy. The one or more transducers can be cylindrical, rectangular, elliptical, or any other shape. The ultrasound catheter can comprise sensors and control circuits to monitor temperature and prevent overheating or to acquire other data corresponding to the one or more ultrasound transducers, the vessel wall and/or the blood flowing across the ultrasound transducer. In some embodiments, the sensors provide feedback to control delivery of the ultrasonic energy. In some embodiments, the ultrasound energy is controlled such that delivery of the ultrasound energy heats the arterial tissue in the range of about 40 to about 90° C. (e.g., 40° C. to 60° C., 60° C. to 75° C., 65° C. to 80° C., 60° C. to 90° C., or overlapping ranges thereof. In some embodiments, the temperature can be less than 40° C. or greater than 90° C.

The average ultrasound intensity for ablation of sympathetic nerve fibers in the hepatic plexus, celiac plexus or other sympathetic nerve fibers can range from about 0.1 $W/cm^2$ to about 10 $kW/cm^2$, from about 0.1 $W/cm^2$ to about 10 $W/cm^2$, from about 0.5 $W/cm^2$ to about 5 $W/cm^2$, from about 1 $W/cm^2$ to about 100 $W/cm^2$, from about 10 $W/cm^2$ to about 10 $kW/cm^2$, from about 500 $W/cm^2$ to about 5 $kW/cm^2$, from about 2 $W/cm^2$ to about 8 $kW/cm^2$, from about 1 $kW/cm^2$ to about 10 $kW/cm^2$, from about 25 $W/cm^2$ to about 200 $W/cm^2$, from about 200 $W/cm^2$ to about 1 $MW/cm^2$, less than 0.1 $W/cm^2$, greater than 10 $kW/cm^2$, or overlapping ranges thereof. Average power levels may range from about 0.1 W to about 1 MW (e.g., from about 0.1 W to about 1 kW, from about 0.1 W to about 10 W, from about 0.5 W to about 5 W, from about 1 W to about 100 W, from about 25 W to about 1 MW, depending on the intensity of the ultrasound energy, pulse duty cycle and/or other parameters). The ultrasound energy can be continuous or pulsed. The average power levels or energy density levels used for pulsed ultrasound energy may be higher than the average power levels used for continuous ultrasound energy.

The treatment time for each target site (e.g., ablation site) can range from about 5 seconds to about 120 seconds, from about 10 seconds to about 60 seconds, from about 20 seconds to about 80 seconds, from about 30 seconds to about 90 seconds, less than 10 seconds, greater than 120 seconds, one minute to fifteen minutes, ten minutes to one hour, or overlapping ranges thereof. In accordance with several embodiments, the parameters used are selected to disable, block, cease or otherwise disrupt conduction of sympathetic nerves (e.g., of the hepatic plexus) for at least several months.

In some embodiments, the ultrasound catheter of the energy delivery system 8000 has a diameter in the range of about 2-8 Fr, about 3-7 Fr, about 4-6 Fr (including about 5 Fr), and overlapping ranges thereof. The catheter (e.g., tube, probe or shaft) may have a varying diameter along its length such that the distal portion of the catheter is small enough to fit into progressively smaller vessels as the catheter is advanced within vasculature. In one embodiment, the catheter has an outside diameter sized to fit within the common hepatic artery (which may be as small as about 1 mm in lumenal diameter) or the proper hepatic artery. In some embodiments, the catheter is at least about 150 cm long, at least about 140 cm long, at least about 130 cm long, at least about 120 cm long, at least about 110 cm long, at least about 100 cm long, at least about 75 cm long, or at least about 90 cm long. In some embodiments the catheter length is sufficient for use with brachial, radial, or femoral artery vascular access techniques. In some embodiments, the flexibility of the catheter is sufficient to navigate tortuous hepatic arterial anatomy having bend radii of about 10 mm, about 9 mm, about 8 mm, about 7 mm, about 6 mm, about 5 mm, about 4 mm, about 3 mm, about 2 mm, about 1 mm, or about 0.5 mm.

In accordance with several embodiments, the ultrasound catheters have actuatable, expandable, steerable, pre-curved, deflectable and/or flexible distal tip components or distal segments. The deflectability or flexibility may advantageously permit accurate positioning of the ultrasound transducers and/or help navigate the ultrasound catheter to the target anatomy. In some embodiments, devices (e.g., catheters) with steerable, curvable or articulatable distal portions provide the ability to cause articulation, bending, or other deployment of the distal end (which may contain one or more transducers). In some embodiments, the ultrasound catheters provide the ability to be delivered over a guidewire. The ultrasound catheters may be configured to enable guidewire exchanges by a single operator. In one embodiment, the ultrasound catheter comprises a lumen that accepts a guidewire along the majority of the portion of the shaft that is inserted within the subject. In another embodiment, the guidewire is only received within a distal-most segment of the shaft of the catheter (e.g., the distal-most 20 cm or less). In one embodiment, the guidewire is received by a structure distal of the distal-most ultrasound transducer. In some embodiments, the ultrasound catheters are inserted within the vasculature through guide sheaths or guide extension catheters. In some embodiments, guidewires are not used.

In accordance with several embodiments, ultrasound energy delivery systems may comprise a guide catheter, a guide extension catheter or support catheter (e.g., a Guidezilla™ catheter or GuideLiner™ catheter), a microcatheter, and/or a guidewire, in addition to an ultrasound catheter. In one embodiment, the guide catheter is a 7 Fr guide catheter that is configured to engage with the inner wall of the celiac artery to provide a stable anchoring and/or reference point. The system may comprise a guidewire (e.g., 0.014" guidewire) that may be configured to be delivered through a lumen of the guide catheter and advanced to a position beyond a target neuromodulation location within a hepatic artery or other vessel or organ. The system may also comprise a microcatheter (e.g., 4 Fr or less) and/or a guide extension catheter (e.g., a 6 Fr guide extension catheter). The guide extension catheter may be configured to fit and be movable within a lumen of the guide catheter to provide support at a lower profile (e.g., outer diameter) than the guide catheter. The microcatheter may be configured to fit and be movable within a lumen of the guide extension catheter and extend beyond a distal end of the guide extension catheter. The microcatheter may facilitate tracking and advancement of the guide extension catheter over the guidewire. In some embodiments, the microcatheter comprises a rapid exchange microcatheter. The guidewire may provide a "rail" to aid catheter tracking and lessen the risk of vessel damage when advancing a neuromodulation device.

In some embodiments, the guide catheter and/or the guide extension catheter comprises an expandable portion that is configured to be advanced to a desired location and then expanded before or during advancement of a neuromodulation device through the guide extension catheter or the guide catheter. The expandable portion may enable transitory, or temporary, expansion of vessel inner diameters. In one embodiment, the expandable portion may be formed of multiple layers that slide over each other. In one embodiment, the expandable portion may be formed of a cylinder with interrupted longitudinal cuts and encapsulated by an elastic layer that keeps the cuts compressed in an unexpanded state. The expandable portion may provide stabilization or anchoring. Stabilization mechanisms (in addition to or instead of the expandable portion) may be provided at various locations along a length of the guide catheter and/or the guide extension catheter (e.g., balloons, ribbons, wires). In some embodiments, portions of the guide catheter or guide extension catheter may be stiffened after introduction of the neuromodulation device to provide stability and maintenance of positioning during neuromodulation procedures. In some embodiments, the system does not comprise a guidewire, as the guide extension catheter may obviate the need for a guidewire.

In some embodiments, ultrasound energy delivery devices or systems may deliver energy from outside the body (e.g., extracorporeally or transcutaneously), extravascularly but within the body, or intravascularly. Extracorporeal neuromodulation may include delivery of ultrasound energy (e.g., high-intensity focused ultrasound energy or low-intensity ultrasound energy) or other forms of radiative energy other than microwave (e.g., X-ray or gamma radiation). In some embodiments the desired, or target, location is defined by external imaging means. The foci or other target locations may be determined by any of the image-guidance techniques described herein. In some embodiments, an internal catheter or other devices (e.g., sensors, beacons or emitters) positioned at or in the proximity of the foci or other target locations may be provided to assist in targeting or defining the target locations. The target catheter may directly sense the transmitted energy. In other embodiments, the target catheter may respond to the transmitted energy by reflecting or retransmitting energy to an external transducer. The external transducer may be the transmitting transducer or a second transducer.

The focus or foci of the ultrasound system may be focused on one or more nerves innervating a liver, pancreas, duodenum or other organ (e.g., nerves of the hepatic plexus, celiac plexus, celiac ganglion). The delivery of energy may be controlled manually or automatically according preconfigured treatment parameters determined by a controller, processor or other computing device (e.g., based on execution of instructions stored in memory).

In addition to external treatment, several embodiments disclosed herein (both internal and external treatment) can be used with imaging (for example, as described elsewhere herein). In some embodiments of the invention, image guidance is provided by external ultrasound imaging. External imaging may provide direct representation of a target device (e.g. catheter) and the surrounding tissues. External imaging may also be used to measure the temperature of tissues. Energy delivery may be adjusted or controlled based on tissue temperature. In some embodiments, the target catheter may be configured to improve visualization. In some embodiments, materials, coatings or surface treatments are provided to increase diffuse reflection of ultrasound waves. In other embodiments, transducers are provided to detect and/or retransmit ultrasound energy to an external transducer. In some embodiments, transducers on the target device (e.g., catheter) transmit or detect ultrasound waves transmitted to or from reference transducers. References may be internal or external. The position of the target device can be reconstructed and compared to reference images or maps. In other embodiments, the catheter may increase the intensity of the externally transmitted energy by resonating and retransmitting energy, or the catheter may transmit energy directly to augment of modify the intensity of external energy delivery. In various embodiments, imaging may be provided via an endoscope or other body-inserted imaging device placed in the stomach, esophagus, colon or intestine. In some embodiments, the target device comprises polymer coatings or surface texture that facilitate scattering. The transducers or transponders may resonate at a different frequency from an excitation wave.

3. Lasers

In several embodiments, lasers may be used to modulate (e.g., ablate) sympathetic nerve activity of the hepatic plexus or other nerves innervating the liver. Although lasers are not generally used for arterial nerve ablation in other arteries, the wall thickness of the hepatic arteries is substantially less than the thickness of other arterial structures, thereby rendering laser energy delivery possible. In some embodiments, one or more lasers are used to ablate nerves located within about 2 mm of the intimal surface, within about 1.5 mm of the intimal surface, within about 1 mm of the intimal surface, or within about 0.5 mm of the intimal surface of a hepatic artery. In some embodiments, chromophore staining of sympathetic fibers is performed to selectively enhance sympathetic nerve absorption of laser energy. In some embodiments, balloons are used to stretch the hepatic artery, thereby thinning the arterial wall and decreasing the depth from the intimal surface to the sympathetic nerve fibers, and thereby improving the delivery of the laser energy.

Other forms of optical or light energy may also be used. The light source may include an LED light source, an electroluminescent light source, an incandescent light source, a fluorescent light source, a gas laser, a chemical laser, a dye laser, a metal-vapor laser, a solid state laser, a semiconductor laser, a vertical cavity surface emitting laser, or other light source. The wavelength of the optical or laser energy may range from about 300 nm to about 2000 nm, from about 500 nm to about 1100 nm, from about 600 nm to about 1000 nm, from about 800 nm to about 1200 nm, from about 1000 nm to about 1600 nm, or overlapping ranges thereof.

4. Externally-Initiated

Figure 91:
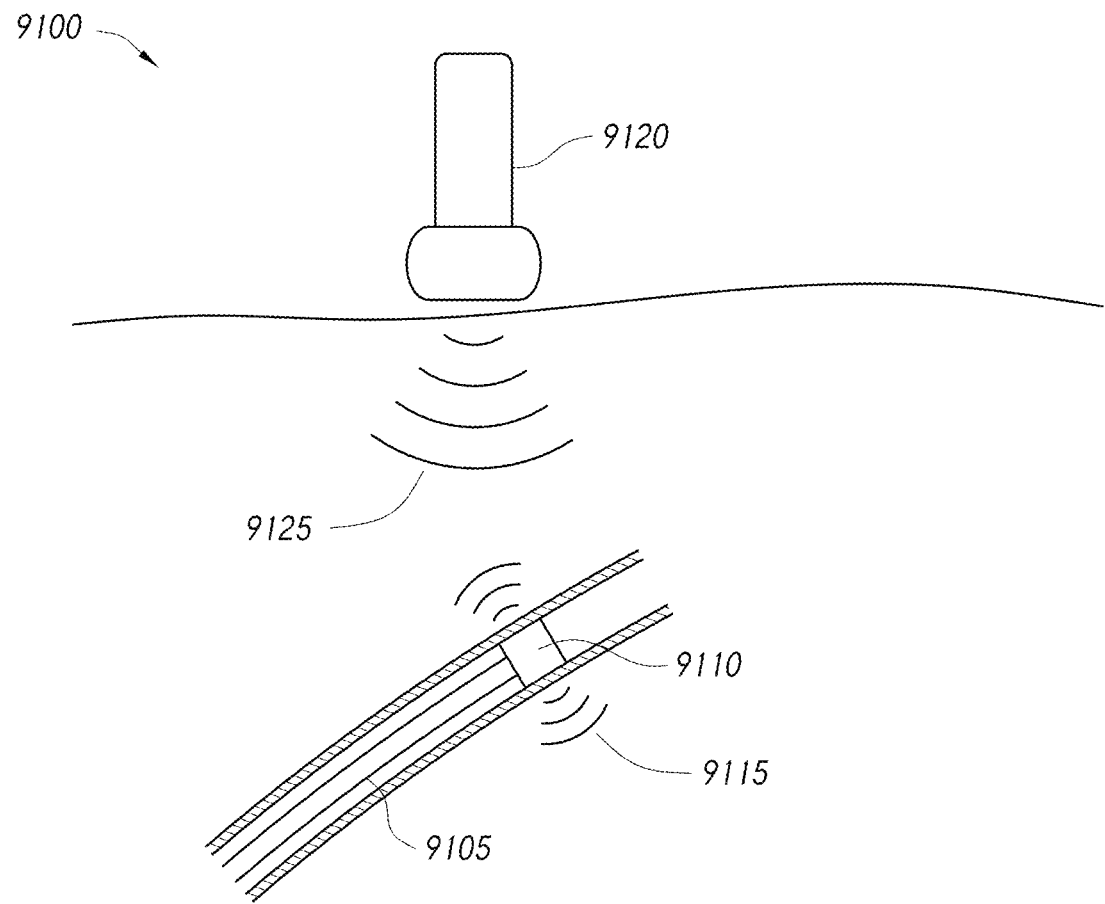
FIG. 91 illustrates an embodiment of a microwave-based ablation catheter system.

In accordance with various embodiments, energy delivery is initiated from a source external to the subject (e.g., extracorporeal activation). FIG. 91 illustrates an embodiment of a microwave-based energy delivery system 9100. The microwave-based energy delivery system 9100 comprises an ablation catheter 9105 and a microwave generating device 9120. In some embodiments, other energy sources may also be delivered externally.

In some embodiments, the ablation catheter 9105 comprises a high conductivity probe 9110 disposed at its distal end. In operation, the ablation catheter 9105 may be inserted into a target vessel and positioned such that the high conductivity probe 9110 is proximate to the site targeted for ablation. The microwave generating device 9120 is located outside a subject's body and positioned such that focused microwaves 9125 are delivered towards the target vessel and the high conductivity probe 9110. In several embodiments, when the delivered focused microwaves 9125 contact the high conductivity probe 9110, they induce eddy currents within the high conductivity probe 9110, thereby heating the high conductivity probe 9110. The thermal energy 9115 generated from the heating of the high conductivity probe can heat the target tissue through conductive heat transfer. In some embodiments, the thermal energy 9115 generated is sufficient to ablate nerves within or disposed on the target tissue (e.g., vessel wall). In various embodiments, the high conductivity probe 9110 has a conductivity greater than 1000 Siemens/meter.

In several embodiments, a neuromodulation device (e.g., catheter) comprises a microwave emitter (e.g., transmission antenna) configured to radiate microwave energy sufficient to modulate (e.g., ablate, denervate) nerves (e.g., perivascular sympathetic nerves) within or surrounding a vessel (e.g., hepatic artery) or nerves that innervate the liver, pancreas, and/or duodenum. In some embodiments, the microwave emitter is electrically coupled to an external microwave energy source via a conductor (e.g., coaxial cable) that extends along the length of a shaft of the neuromodulation device. In one embodiment, the external microwave energy source is coupled to a proximal end of the neuromodulation device. The microwave emitter may be configured to produce an omnidirectional electromagnetic field or a more focused (e.g., unidirectional) electromagnetic field. The neuromodulation device may comprise temperature, pressure, impedance or other sensors to facilitate monitoring and control of the treatment procedures. In various embodiments, the microwave energy has a frequency of between 300 MHz and 300 GHz (e.g., between 900 MHz and 5 GHz, between 500 MHz and 3 GHz, between 1 GHz and 5 GHz, between 10 GHz and 100 GHz, between 100 GHz and 300 GHz, and overlapping ranges thereof). In various embodiments, the average amount of power emitted is between 1 W and 30 W (e.g., between 1 W and 5 W, between 4 W and 10 W, between 6 W and 12 W, between 8 W and 14 W, between 10 W and 20 W, between 15 W and 30 W, or overlapping ranges thereof). The microwave energy may be delivered for between 30 seconds and 15 minutes (e.g., between 30 seconds and 2 minutes, between 1 minute and 5 minutes, between 3 minutes and 8 minutes, between 5 minutes and 10 minutes, between 8 minutes and 15 minutes, or overlapping ranges thereof). In some embodiments, the neuromodulation catheter comprises one, two or more balloons or other like expandable members. The balloon(s) may comprise one or more cooling elements or may be configured to be filled with cooling fluid. In some embodiments, the microwave emitter is positioned within the balloon.

Figure 92:
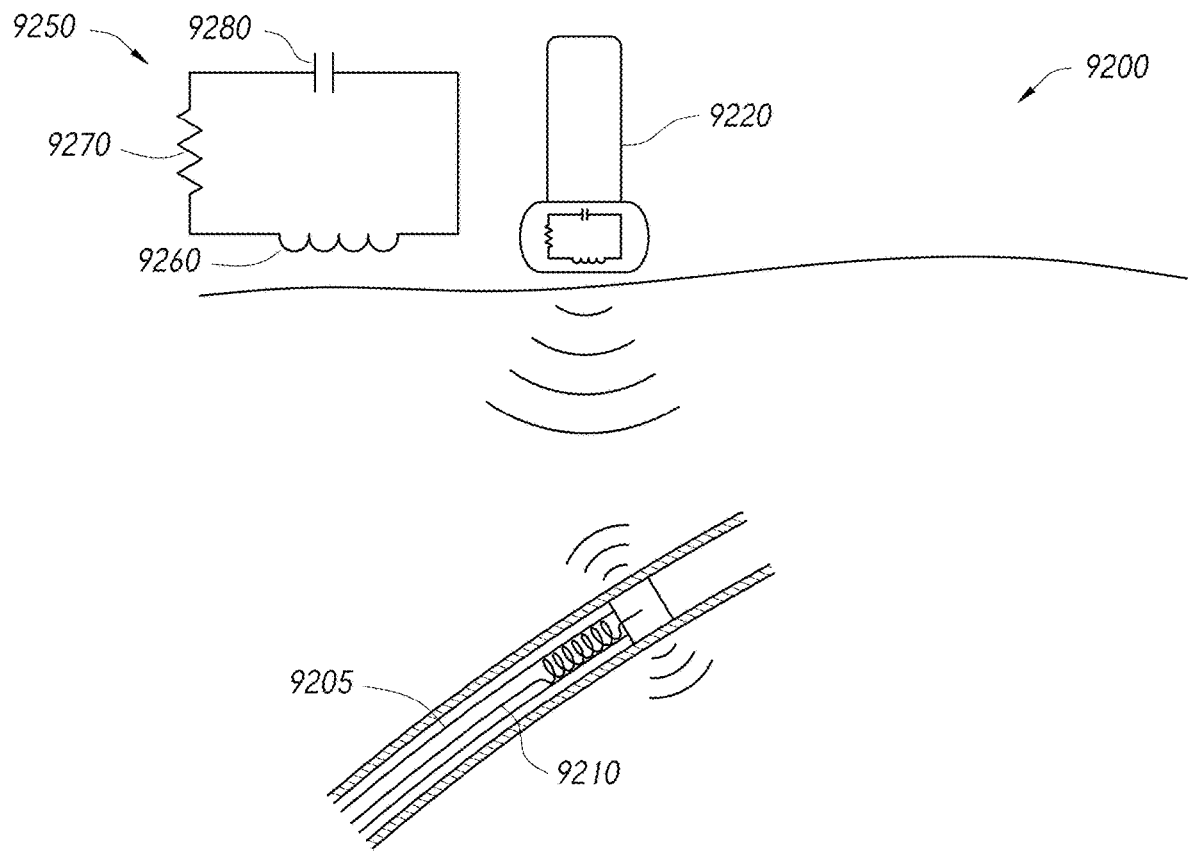
FIG. 92 illustrates an embodiment of an induction-based ablation catheter system.

FIG. 92 illustrates an embodiment of an induction-based energy delivery catheter system 9200. In the illustrated embodiment, the induction-based energy delivery system 9200 comprises a catheter 9205, an induction coil 9210, an external inductor power circuit 9250, an inductor 9260, a resistor 9270, and a capacitor 9280. In one embodiment, the induction coil 9210 is disposed at the distal end of the catheter 9205. In operation, the induction coil 9210 may act as an inductor to receive energy from the external inductive power circuit 9250. In some embodiments, the external inductive power circuit 9250 is positioned such that the inductor 9260 is adjacent the induction coil 9210 within a sufficient induction range. In some embodiments, current is delivered through the external inductive power circuit 9250, thereby causing current to flow in the induction coil 9210 and delivering subsequent ablative energy to surrounding tissues. In one embodiment, an induction coil is used in combination with any of the windowed catheter devices described herein (such as the windowed catheter devices described in connection with FIGS. 55A and 55B). For example, the induction coil may be placed within a lumen of a catheter or sleeve having one or more windows configured to permit the selective delivery of energy to the target tissue.

In some embodiments, one or more synthetic emboli may be inserted within a target vessel and implanted or lodged therein (at least temporarily). The synthetic emboli may advantageously be sized to match the anatomy of the target vessel (e.g., based on angiography of the target location and vessel diameter). The synthetic emboli may be selected based on a measured or estimated dimension of the target vessel. In one embodiment, an energy delivery catheter is coupled to the one or more synthetic emboli inserted within a target vessel to deliver energy. In some embodiments, energy is delivered transcutaneously to the synthetic emboli using inductive coupling as described in connection with FIG. 21, thereby eliminating the need for an energy delivery catheter. The synthetic emboli may comprise an induction coil and a plurality of electrodes embedded within an insulating support structure comprised of high dielectric material. After appropriate energy has been delivered to modulate nerves associated with the target vessel, the one or more emboli may be removed.

In several embodiments of the invention, the energy-based delivery systems comprise cooling systems that are used to, for example, reduce thermal damage to regions surrounding the target area. For example, cooling may lower (or maintain) the temperature of tissue at below a particular threshold temperature (e.g., at or between 40 to 50 degrees Celsius), thereby preventing or reducing cell necrosis. Cooling balloons or other expandable cooling members are used in some embodiments. In one embodiment, ablation electrodes are positioned on a balloon, which is expanded using cooling fluid. In some embodiments, cooling fluid is circulated through a delivery system (e.g., a catheter system). In some embodiments, cooling fluid (such as pre-cooled saline) may be delivered (e.g., ejected) from a catheter device in the treatment region. In further embodiments, cooling fluid is continuously or intermittently circulated internally within the catheter device to cool the endothelial wall in the absence of sufficient blood flow.

Extracorporeal neuromodulation may include delivery of ultrasound energy (e.g., high-intensity focused ultrasound energy or low-intensity ultrasound energy) or other forms of radiative energy other than microwave (e.g., X-ray or gamma radiation). In some embodiments, an ultrasound system is configured to deliver ultrasound at a frequency between about 200 kHz and about 20 MHz (e.g., between 200 kHz and 2 MHz, between 400 kHz and 4 MHz, between 1 MHz and 10 MHz, between 5 MHz and 20 MHz, or overlapping ranges thereof). The parameters of the ultrasound energy may include any of the parameters and ranges of parameters described elsewhere herein. In various embodiments, ultrasound energy may be directed towards the target tissue by means of a single transducer or a plurality of transducers, which may or may not be placed in contact with skin of a patient. The one or more transducers are configured to focus energy at a desired location. In some embodiments the desired, or target, location is defined by external imaging means. The foci or other target locations may be determined by any of the image-guided techniques described herein. In some embodiments, an internal catheter or other devices (e.g., sensors, beacons or emitters) positioned at or in the proximity of the foci or other target locations may be provided to assist in targeting or defining the target locations. The target catheter may directly sense the transmitted energy. In other embodiments, the target catheter may respond to the transmitted energy by reflecting or retransmitting energy to an external transducer. The external transducer may be the transmitting transducer or a second transducer.

The focus or foci of the ultrasound system may be focused on one or more nerves innervating a liver, pancreas, duodenum or other organ (e.g., nerves of the hepatic plexus, celiac plexus, celiac ganglion). The delivery of energy may be controlled manually or automatically according preconfigured treatment parameters determined by a controller, processor or other computing device (e.g., based on execution of instructions stored in memory).

In addition to external treatment, several embodiments disclosed herein (both internal and external treatment) can be used with imaging (for example, as described elsewhere herein). In some embodiments of the invention, image guidance is provided by external ultrasound imaging. External imaging may provide direct representation of a target device (e.g., catheter) and the surrounding tissues. External imaging may also be used to measure the temperature of tissues. Energy delivery may be adjusted or controlled based on tissue temperature. In some embodiments, the target catheter may be configured to improve visualization. In some embodiments, materials, coatings or surface treatments are provided to increase diffuse reflection of ultrasound waves. In other embodiments, transducers are provided to detect and/or retransmit ultrasound energy to an external transducer. In some embodiments, transducers on the target device (e.g., catheter) transmit or detect ultrasound waves transmitted to or from reference transducers. References may be internal or external. The position of the target device can be reconstructed and compared to reference images or maps. In other embodiments, the catheter may increase the intensity of the externally transmitted energy by resonating and retransmitting energy, or the catheter may transmit energy directly to augment of modify the intensity of external energy delivery. In various embodiments, imaging may be provided via an endoscope or other body-inserted imaging device placed in the stomach, esophagus, colon or intestine. In some embodiments, the target device comprises polymer coatings or surface texture that facilitate scattering. The transducers or transponders may resonate at a different frequency from an excitation wave.

In some embodiments, image guidance is provided by external magnetic resonance (MR) imaging or X-ray imaging. External imaging may provide direct representation of the target device (e.g., catheter) and surrounding tissues. External imaging may also measure the temperature of tissues. Energy delivery may be adjusted or controlled based on tissue temperature. In some embodiments, the target device may be configured to improve visualization. In some embodiments, materials, coatings or surface treatments are provided to alter the relaxation of adjacent tissues in a manner that is visible in an MR or X-ray image. In some embodiments, antennas or coils are provided to detect or alter locally emitted energy (e.g., RF energy) that is used to reconstruct the image. In some embodiments, local emissions (such as RF) detected by coils or antennas on the target device (e.g., catheter) are used to calculate the position of the device. In some embodiments, T1 agents accelerate relaxation of polarized hydrogen nuclei, which may appear bright on T1 images, and T2 agents provide magnetic inhomogeneities that may accelerate T2 relaxation (dephasing), which may appear as dark areas on images. Imaging effects may be facilitated by coatings or inherent properties of components (e.g., materials such as metal) of a target device to be visualized (e.g., catheter).

D. Steam/Hot Water Neuromodulation

Figure 93:
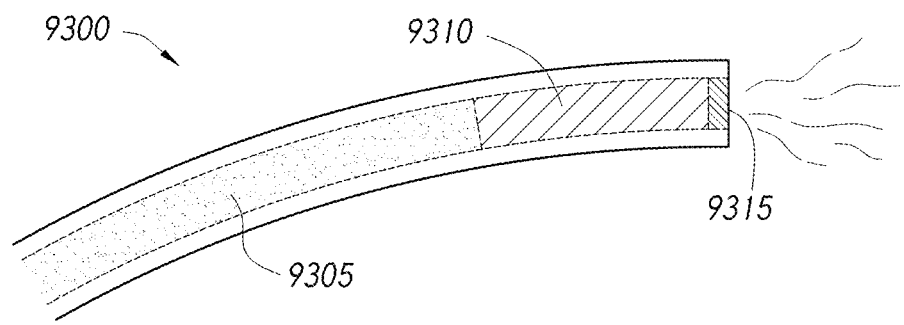
FIG. 93 illustrates an embodiment of a steam ablation catheter.

FIG. 93 illustrates an embodiment of a steam ablation catheter 9300. In the illustrated embodiment, the steam ablation catheter 9300 comprises a water channel 9305, a steam generating head 9310, and a steam outlet 9315. In operation, water may be forced through the water channel 9305 and caused to enter the steam generating head 9310. In one embodiment, the steam generating head 9310 converts the water into steam, which exits the steam ablation catheter 9300 through the steam outlet 9315.

In some embodiments, steam is used to ablate or denervate the target anatomy (e.g., hepatic arteries and nerves associated therewith). In accordance with several embodiments, water is forced through the ablation catheter 9300 and out through the steam generating head 9310 (which converts the water into steam) and the steam is directed to an ablation target. The steam ablation catheter 9300 may comprise one or more window along the length of the catheter body.

Figure 94:
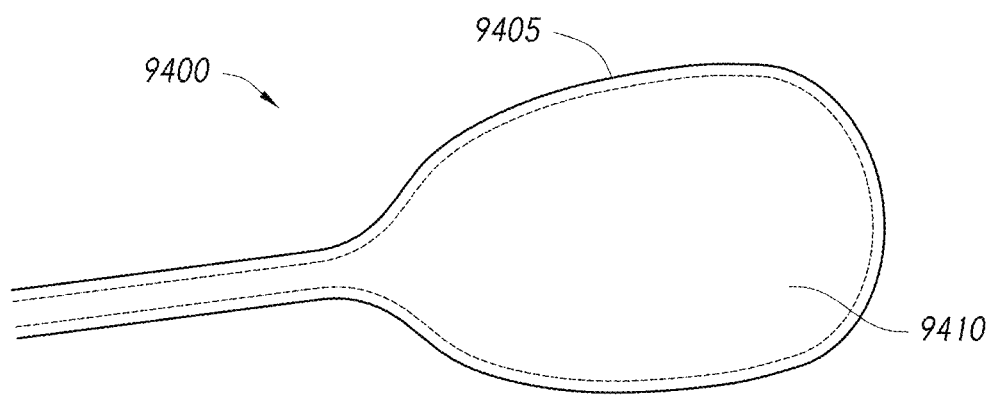
FIG. 94 illustrates an embodiment of a hot water balloon ablation catheter.

FIG. 94 illustrates an embodiment of a hot fluid balloon ablation catheter 9400. In the illustrated embodiment, the hot fluid balloon ablation catheter 9400 comprises an inflatable balloon 9405. In some embodiments, the inflatable balloon 9405 is filled with a temperature variable fluid 9410. In accordance with several embodiments, hot water is the temperature variable fluid 9410 used to fill the inflatable balloon 9405. The heat generated from the hot fluid within the inflatable balloon may be sufficient to ablate or denervate the target anatomy (e.g., hepatic arteries and nerves associated therewith). In some embodiments, the inflatable balloon 9405 is inserted to the ablation site and inflated with scalding or boiling fluid (e.g., water), thereby heating tissue surrounding the inflatable balloon 9405 sufficient to ablate or denervate the tissue. In some embodiments, the hot fluid within the balloon 9405 is within the temperature range of about 120° F. to about 212° F., from about 140° F. to about 212° F., from about 160° F. to about 212° F., from about 180° F. to about 212° F., about 200° F. to about 212° F., or overlapping ranges thereof. In some embodiments, the balloon ablation catheter 9400 comprises a temperature sensor and fluid (e.g., water) at different temperatures may be inserted and withdrawn as treatment dictates. In some embodiments, the inflatable balloon 9405 is made out of polyurethane or any other heat-resistant inflatable material.

E. Chemical Neuromodulation

In some embodiments, drugs are used alone or in combination with another modality to cause neuromodulation of any of the nerves described herein. Drugs include, but are not limited to, muscarinic receptor agonists, anticholinesterase agents, nicotinic receptor agonists, and nicotine receptor antagonists. Drugs that directly affect neurotransmission synthesis, degradation, or reuptake are used in some embodiments.

In some embodiments, drugs (either alone or in combination with energy modalities) can be used for neuromodulation. For example, a delivery device (e.g., catheter) may have one or more internal lumens. In some embodiments, one or more internal lumens are in fluid communication with a proximal opening and with a distal opening of the delivery catheter. In some embodiments, at least one distal opening is located at the distal end of the delivery catheter. In some embodiments, at least one proximal opening is located at the proximal end of the delivery catheter. In some embodiments, the at least one proximal opening is in fluid communication with at least one reservoir.

In some embodiments, at least one reservoir is a drug reservoir that holds drugs or therapeutic agents capable of modulating sympathetic nerve fibers in the hepatic plexus. In some embodiments, a separate drug reservoir is provided for each drug used with the delivery catheter system. In other embodiments, at least one drug reservoir may hold a combination of a plurality of drugs or therapeutic agents. Any drug that is capable of modulating nerve signals may be used in accordance with the embodiments disclosed herein. In some embodiments, neurotoxins (e.g., botulinum toxins) are delivered to the liver, pancreas, or other surrounding organs or nerves associated therewith. In some embodiments, neurotoxins (e.g., botulinum toxins) are not delivered to the liver, pancreas, or other surrounding organs or nerves associated therewith.

In some embodiments, a delivery catheter system includes a delivery device that delivers one or more drugs to one or more target sites. For example, the delivery device may be a pump. Any pump, valve, or other flow regulation member capable of delivering drugs through a catheter may be used. In some embodiments, the pump delivers at least one drug from the at least one drug reservoir through the at least one internal lumen of the catheter delivery system to the one or more target sites.

In some embodiments, the pump selects the drug dosage to be delivered from the reservoir to the target site(s). For example, the pump can selectively vary the total amount of one or more drugs delivered as required for neuromodulation. In some embodiments, a plurality of drugs is delivered substantially simultaneously to the target site. In other embodiments, a plurality of drugs is delivered in series. In other embodiments, a plurality of drugs is delivered substantially simultaneously and at least one other drug is delivered either before or after the plurality of drugs is delivered to the target site(s). Drugs or other agents may be used without delivery catheters in some embodiments. According to several embodiments, drugs may have an inhibitory or stimulatory effect.

In some embodiments, an ablation catheter system uses chemoablation to ablate nerve fibers (e.g., sympathetic nerve fibers in the hepatic plexus). For example, the ablation catheter may have one or more internal lumens. In some embodiments, one or more internal lumens are in fluid communication with a proximal opening and with a distal opening. In some embodiments, at least one distal opening is located in the distal end of an ablation catheter. In some embodiments, at least one proximal opening is located in the proximal end of the ablation catheter. In some embodiments, at least one proximal opening is in fluid communication with at least one reservoir.

In some embodiments, at least one reservoir holds and/or stores one or more chemicals capable of disrupting (e.g., ablating, desensitizing, destroying) nerve fibers (e.g., sympathetic nerve fibers in the hepatic plexus). In some embodiments, a separate reservoir is provided for each chemical used with the ablation catheter system. In other embodiments, at least one reservoir may hold any combination of chemicals. Any chemical that is capable of disrupting nerve signals may be used in accordance with the embodiments disclosed herein. For example, one or more chemicals or desiccants used may include phenol or alcohol, guanethidine, acids, phenol-crotons, zinc sulfate, nanoparticles, radiation sources for brachytherapy, neurostimulants (e.g., methamphetamine), and/or oxygen radicals (e.g., peroxide). However, any chemical that is capable of ablating sympathetic nerve fibers in the hepatic plexus may be used in accordance with the embodiments disclosed herein. In some embodiments, chemoablation is carried out using a fluid delivery needle delivered percutaneously, laparascopically, or via an intravascular approach.

F. Cryomodulation

In some embodiments, the invention comprises cryotherapy or cryomodulation. In one embodiment, the ablation catheter system uses cryoablation techniques (e.g., cryogenic energy delivery) for neuromodulation. In one embodiment, cryoablation is used to ablate sympathetic nerve fibers in the hepatic plexus. For example, the ablation catheter may have one or more internal lumens. In some embodiments, one or more internal lumens are in fluid communication with a proximal opening. In some embodiments, at least one proximal opening is located in the proximal end of the ablation catheter. In some embodiments, at least one proximal opening is in fluid communication with at least one reservoir (e.g., a cryochamber). In some embodiments, the at least one reservoir holds one or more coolants including but not limited to liquid nitrogen, $CO_2$, argon, or nitrous oxide. The ablation catheter can comprise a feed line for delivering coolant to a distal tip of the ablation catheter and a return line for returning spent coolant to the at least one reservoir. The coolant may reach a temperature sufficiently low to freeze and ablate sympathetic nerve fibers in the hepatic plexus. In some embodiments, the coolant can reach a temperature of less than 75 degrees Celsius below zero, less than 80 degrees Celsius below zero, less than 90 degrees Celsius below zero, or less than 100 degrees Celsius below zero.

In some embodiments, the ablation catheter system includes a delivery device that controls delivery of one or more coolants through one or more internal lumens to the target site(s). For example, the delivery device may be a pump. Any pump, valve or other flow regulation member that is capable of delivering coolants through a catheter may be used. In some embodiments, the pump delivers at least one coolant from at least one reservoir, through at least one proximal opening of the catheter body, through at least one internal lumen of the catheter body, and to the distal end of the ablation catheter (e.g., via a feed line or coolant line).

In some embodiments, the target nerves may be irreversibly cooled using an implantable Peltier cooling device. In some embodiments, an implantable cooling device is configured to be refilled with an inert gas that is injected at pressure into a reservoir within the implantable device and then released selectively in the vicinity of the target nerves, cooling them in an adiabatic fashion, thereby slowing or terminating nerve conduction (either temporarily or permanently). In some embodiments, local injections or infusion of ammonium chloride is used to induce a cooling reaction sufficient to alter or inhibit nerve conduction. In some embodiments, delivery of the coolant to the distal end of the ablation catheter, which may comprise one or more ablation electrodes or a metal-wrapped cylindrical tip, causes denervation of sympathetic nerve fibers in the hepatic plexus. For example, when the ablation catheter is positioned in or near the proper hepatic artery or the common hepatic artery, the temperature of the coolant may cause the temperature of the surrounding area to decrease sufficiently to denervate sympathetic nerve fibers in the hepatic plexus. In some embodiments, cryoablation is performed using a cryocatheter. Cryoablation can alternatively be performed using one or more probes alone or in combination with a cryocatheter.

The treatment time for each target ablation site can range from about 5 seconds to about 100 seconds, 5 minutes to about 30 minutes, from about 10 minutes to about 20 minutes from about 5 minutes to about 15 minutes, from about 10 minutes to about 30 minutes, less than 5 seconds, greater than 30 minutes, or overlapping ranges thereof. In accordance with several embodiments, the parameters used are selected to disable, block, cease or otherwise disrupt conduction of, for example, sympathetic nerves of the hepatic plexus. The effects on conduction of the nerves may be permanent or temporary. One, two, three, or more cooling cycles can be used.

In some embodiments, any combination of drug delivery, chemoablation, and/or cryoablation is used for neuromodulation of any of the nerves described herein, and may be used in combination with an energy modality. In several embodiments, cooling systems are provided in conjunction with energy delivery to, for example, protect tissue adjacent the nerve fibers.

III. Catheter Access and Delivery Systems and Methods

A. Access

In accordance with some embodiments, neuromodulation (e.g., the disruption of sympathetic nerve fibers) is performed using a minimally invasive system, such as an ablation catheter system. In some embodiments, an ablation catheter system for ablating nerve fibers is introduced using an intravascular (e.g., intra-arterial) approach. In one embodiment, an ablation catheter system is used to ablate sympathetic nerve fibers in the hepatic plexus and/or nerves innervating the liver. As described above, the hepatic plexus surrounds the common hepatic artery or the proper hepatic artery, where it branches from the common hepatic artery. In some embodiments, a neuromodulation system (e.g., an ablation catheter system) is introduced via an incision in the groin to access the femoral artery. The neuromodulation system may be advanced from the femoral artery to the proper hepatic artery via the iliac artery, the abdominal aorta, the celiac artery, and the common hepatic artery. In other embodiments, any other suitable percutaneous intravascular incision point or approach is used to introduce the ablation catheter system into the arterial system (e.g., a radial approach via a radial artery or a brachial approach via a brachial artery).

In some embodiments, the catheter (e.g., hollow, solid, partially hollow, catheter, probe, shaft or other delivery device with or without a lumen) may be placed into the target region substantially close to the target nerve through percutaneous injection. Using such a percutaneous placement may allow less destructive, less invasive selective destruction or disruption of the target nerve, in accordance with some embodiments.

In some embodiments, the catheter system comprises a visualization or other diagnostic device substantially close to the distal end of the catheter. The visualization device may promote nervous visualization, thereby possibly allowing higher levels of precision in targeted nervous disruption. In some embodiments, the catheter system comprises a light source configured to aid in visualization. In some embodiments, a light source and a visualization device (such as a camera) are used in tandem to promote visibility. A diagnostic device may include a temperature-measurement device (e.g., thermistor, thermocouple, radiometer), contact sensor(s) or one or more ultrasound transducers. In some embodiments, the catheter system comprises a distal opening out of which active elements (such as any camera, light, drug delivery port, and/or cutting device, etc.) are advanced. In some embodiments, the catheter system comprises a side opening out of which the active elements (such as any camera, light, drug delivery port, and/or cutting device, etc.) may be advanced, thereby allowing the user to access the vessel wall in vessels with tortuous curves and thereby allowing nerve treatment (e.g., destruction) with the axis of the catheter aligned parallel to the vessel.

Animal studies have shown that the force of electrode contact against the vessel wall may be a critical parameter for achieving ablative success in embodiments of devices incorporating radiofrequency electrodes to deliver energy. Therefore, ablation catheter devices may advantageously not only be small enough to access the target vasculature, but also to incorporate low-profile features for facilitating sufficient electrode contact force or pressure during the length of the treatments.

In some embodiments, the catheter of the neuromodulation catheter system has a diameter in the range of about 2-8 Fr, about 3-7 Fr, about 4-6 Fr (including about 5 Fr), and overlapping ranges thereof. The catheter (e.g., tube, probe or shaft) may have a varying diameter along its length such that the distal portion of the catheter is small enough to fit into progressively smaller vessels as the catheter is advanced within vasculature. In one embodiment, the catheter has an outside diameter sized to fit within the common hepatic artery (which may be as small as about 1 mm in lumenal diameter) or the proper hepatic artery. In some embodiments, the catheter is at least about 150 cm long, at least about 140 cm long, at least about 130 cm long, at least about 120 cm long, at least about 110 cm long, at least about 100 cm long, at least about 75 cm long, or at least about 90 cm long. In some embodiments, the flexibility of the catheter is sufficient to navigate tortuous hepatic arterial anatomy having bend radii of about 10 mm, about 9 mm, about 8 mm, about 7 mm, about 6 mm, about 5 mm, about 4 mm, about 3 mm, about 2 mm, about 1 mm, or about 0.5 mm.

In accordance with several embodiments, devices of the catheter-based systems described herein have actuatable, expandable, steerable, pre-curved, deflectable and/or flexible distal tip components or distal segments. The deflectability or flexibility may advantageously bias an energy applicator against the arterial wall to ensure effective and/or safe delivery of therapy, permit accurate positioning of the energy applicator, maintain contact of an energy delivery element against a vascular wall, maintain sufficient contact force or pressure with a vascular wall, and/or help navigate the catheter (e.g., neuromodulation catheter) to the target anatomy. In some embodiments, devices (e.g., catheters) with steerable, curvable or articulatable distal portions provide the ability to cause articulation, bending, or other deployment of the distal tip (which may contain an ablation element or energy delivery element) even when a substantial portion of the catheter (e.g., neuromodulation catheter) remains within a guide catheter or guide extension catheter. In some embodiments, the neuromodulation catheters provide the ability to be delivered over a guidewire, as placing guide catheters may be unwieldy and time-consuming to navigate. In some embodiments, the neuromodulation catheters are inserted within the vasculature through guide sheaths or guide extension catheters. In some embodiments, guidewires are not used.

Figure 95:
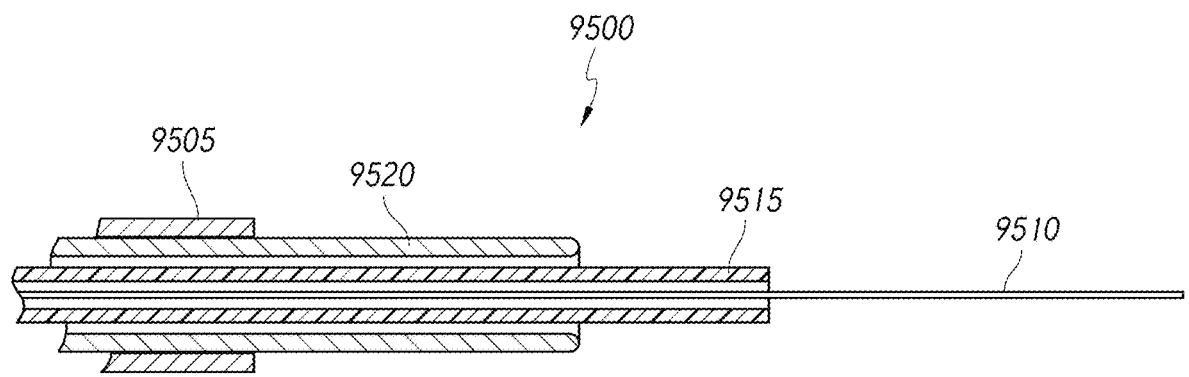
FIG. 95 illustrates an embodiment of a "telescoping" system for facilitating delivery of a low-profile neuromodulation catheter to a hepatic artery branch.

In accordance with several embodiments, catheter-based systems may comprise a guide catheter, a guide extension catheter or support catheter (e.g., a Guidezilla™ catheter or GuideLiner™ catheter), a microcatheter, and/or a guidewire, in addition to a neuromodulation catheter. FIG. 95 illustrates an embodiment of a "telescoping" system 9500 for facilitating delivery of a low-profile neuromodulation catheter to a hepatic artery branch. The "telescoping" system 9500 comprises a guide catheter 9505. In one embodiment, the guide catheter 9505 is a 7 Fr guide catheter that is configured to engage with the inner wall of the celiac artery to provide a stable anchoring and/or reference point. The system 9500 further comprises a guidewire 9510 (e.g., 0.014" guidewire) that may be configured to be delivered through a lumen of the guide catheter 9505 and advanced to a position beyond a target neuromodulation location within a hepatic artery or other vessel or organ. The system 9500 also comprises a microcatheter 9515 (e.g., 4 Fr or less) and a guide extension catheter 9520 (e.g., a 6 Fr guide extension catheter). The guide extension catheter 9520 may be configured to fit and be movable within a lumen of the guide catheter 9505 to provide support at a lower profile (e.g., outer diameter) than the guide catheter 9505. The microcatheter 9515 may be configured to fit and be movable within a lumen of the guide extension catheter 9520 and extend beyond a distal end of the guide extension catheter 9520. The microcatheter 9515 may facilitate tracking and advancement of the guide extension catheter 9520 over the guidewire 9510. In some embodiments, the microcatheter 9515 comprises a rapid exchange microcatheter. The guidewire 9510 may provide a "rail" to aid catheter tracking and lessen the risk of vessel damage when advancing a neuromodulation device.

In some embodiments, the guide catheter 9505 and/or the guide extension catheter 9520 comprises an expandable portion that is configured to be advanced to a desired location and then expanded before or during advancement of a neuromodulation device through the guide extension catheter 9520 or the guide catheter 9505. The expandable portion may enable transitory, or temporary, expansion of vessel inner diameters. In one embodiment, the expandable portion may be formed of multiple layers that slide over each other. In one embodiment, the expandable portion may be formed of a cylinder with interrupted longitudinal cuts and encapsulated by an elastic layer that keeps the cuts compressed in an unexpanded state. The expandable portion may provide stabilization or anchoring. Stabilization mechanisms (in addition to or instead of the expandable portion) may be provided at various locations along a length of the guide catheter 9505 and/or the guide extension catheter 9520 (e.g., balloons, ribbons, wires). In some embodiments, portions of the guide catheter 9505 or guide extension catheter 9520 may be stiffened after introduction of the neuromodulation device to provide stability and maintenance of positioning during neuromodulation procedures. In some embodiments, the "telescoping" system 9500 does not comprise a guidewire, as the guide extension catheter 9520 may obviate the need for a guide wire.

In some embodiments, the system 9500 may include a flexible introducer that provides a tapered transition between the guidewire 9510 and the guide catheter 9505 or guide extension catheter 9520, thereby facilitating access to the tortuous hepatic artery vasculature. The flexible introducer may replace the microcatheter 9515 and/or guide extension catheter 9520. In some embodiments, the flexible introducer comprises elastic or shape-memory materials such as nitinol or low durometer Pebax®. The flexible introducer may have a coil cut pattern or a torque converter or flexure cut pattern (e.g., similar to the cut pattern illustrated in FIGS. 48A-48C) or a metallic coil may be encapsulated within the flexible introducer. Portions of the guide catheter 9505, guide extension catheter 9520 and/or microcatheter 9515 may be deflectable and/or steerable. The mechanisms for deflection and/or steering may comprise any of the deflection or steering mechanisms described herein (e.g., tension wire, hydraulics, magnetism, and/or the like). In some embodiments, portions of the guide catheter 9505, guide extension catheter 9520 and/or microcatheter 9515 are plastically deformable and/or shape set to provide deformability within vasculature, thereby functioning as accessory devices configured to fit unique and patient-specific anatomy.

Figure 96:
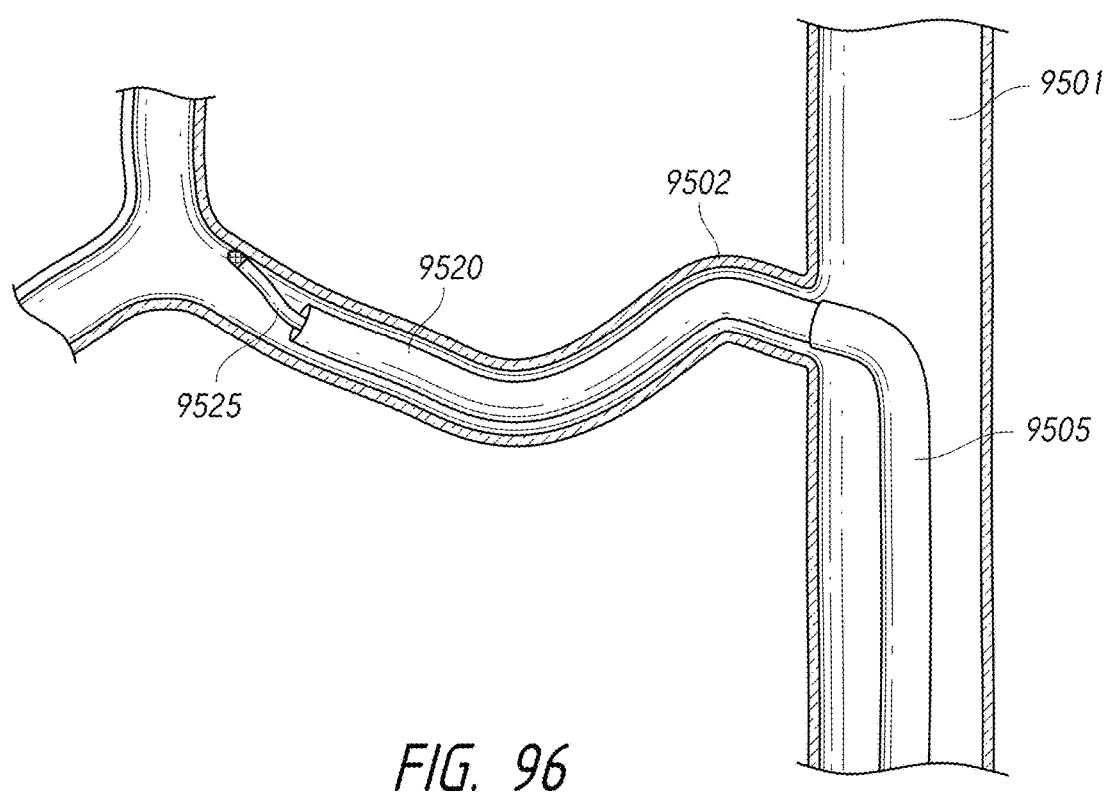
FIG. 96 illustrates an embodiment of use of the system of FIG. 95 to access a target neuromodulation location within a hepatic artery.

FIG. 96 illustrates an embodiment of use of the system of FIG. 95 to access a target neuromodulation location within a hepatic artery. The guide catheter 9505 is advanced to a position within an abdominal aorta 9501 or at an origin of the celiac artery 9502 off the abdominal aorta 9501. In some embodiments, the guidewire 9510 and microcatheter 9515 are then advanced to a position at or adjacent the target neuromodulation location and the guide extension catheter 9520 is advanced over the microcatheter 9515 to the target neuromodulation location. The guide extension catheter 9520 may be advanced over either the guidewire 9510 alone or over the microcatheter 9515 (which in turn is advanced over the guidewire 9510). FIG. 96 illustrates the system 9500 after the guidewire 9510 and/or microcatheter 9515 have been removed. FIG. 96 also illustrates an embodiment of a neuromodulation device 9525 advanced to the target neuromodulation location within the hepatic artery through the guide extension catheter 9520. In some embodiments, a guidewire 9510 or microcatheter 9515 may not be used and the guide extension catheter 9520 may be advanced beyond the target neuromodulation location and the neuromodulation device 9525 advanced to the target neuromodulation location and then the guide extension catheter 9520 is withdrawn to unsheathe the neuromodulation device 9525. In accordance with several embodiments, the guide extension catheter 9520 may facilitate torquing of the neuromodulation device 9525 so as to allow for rotation of the neuromodulation device 9525 to multiple or all quadrants of the hepatic artery or other target vessel. In some embodiments, the guide extension catheter 9520 is removed following the initial "deployment" of the neuromodulation device 9525. Fluid (e.g., cooling fluid, contrast or selective dye) may be infused through the guide catheter 9505 or guide extension catheter 9520 during neuromodulation (e.g., ablation).

In some embodiments, the guide extension catheter 9520, or other access device within which the neuromodulation device 9525 is advanced, is configured to maintain a tight clearance between the inner diameter of the guide extension catheter 9520 or other access device and the outer diameter of the neuromodulation device 9525. For example, the inner diameter may have a low friction surface or coating and/or structures (e.g., raised ribs of a compliant material such as silicone) that reduce the number of contact points and provide an inward radial force against the outer surface of the neuromodulation device that run along the length of the guide extension catheter 9520 or other access device and are coated with a low-friction coating, such as a hydrophilic coating. The enhanced support along the flexible length of the neuromodulation device may allow the neuromodulation device to be more accurately flexed and may support increased torque efficiency.

Movement of the guide catheter 9505 or guide extension catheter 9520 may disturb the position of the neuromodulation device. For example, movement of the guide catheter 9505 or guide extension catheter 9520 may cause an electrode of an RF energy delivery device delivered through a lumen of the guide catheter 9505 or guide extension catheter 9520 to move due to friction between the devices. Accordingly, in some embodiments, anchoring the catheter 9505 or guide extension catheter 9520 may advantageously minimize or reduce movement artifacts.

FIGS. 97A and 97B illustrate embodiments of a catheter-based vascular access system comprising a guide sheath or captive support sleeve 9721 to provide additional support to the shaft of a neuromodulation device 9725 (e.g., electrode treatment catheter). Similar to the systems described above in connection with FIGS. 95 and 96, the system comprises a guide catheter 9705 adapted to be advanced through the abdominal aorta 9701 to a location where the celiac artery 9702 branches off from the abdominal aorta 9501 (e.g., an ostium of the celiac artery). The guide sheath or captive support sleeve 9721 extends out of an open distal end of the guide catheter 9705. In the illustrated embodiment, the captive support sleeve 9721 has a length that corresponds to the length of the celiac artery 9702 from the abdominal aorta 9701 to the junction of the common hepatic artery 9703 and the splenic artery 9704. FIG. 97A illustrates a neuromodulation device 9725 comprising an over-the-wire RF energy delivery catheter having two spaced-apart electrodes positioned along a shaft of the catheter. The two spaced-apart electrodes are positioned such that at least one of the electrodes is in contact with an inner wall of the common hepatic artery 9703 for ablation. The electrodes may both be positioned in contact with the inner wall. The electrodes may comprise monopolar electrodes or a pair of bipolar electrodes.

In accordance with several embodiments, the neuromodulation device 9725 is positioned with the aid of angiographic and fluoroscopic visualization. Contrast media may be provided through the lumen of the guide catheter 9705. Alternatively, contrast media may be delivered through the guide sheath or captive support sleeve 9721, through which the neuromodulation device 9725 extends. If the guide sheath 9721 is positioned near the ostium of the common hepatic artery 9703, visualization may be enhanced as the majority of contrast would flow through the common hepatic artery instead of the splenic artery 9704. The guide sheath or captive support sleeve 9721 may also provide enhanced support to the proximal portion of the neuromodulation device 9725. Alternatively or additionally, the neuromodulation device 9725 can include an additional lumen for contrast delivery, whereby the contrast can exit at an outlet 9727 positioned distally of a major side vessel, such as the splenic artery 9704. FIG. 97B illustrates an embodiment of a neuromodulation device incorporating a contrast lumen. The outlet may be located along a portion of the captive support sleeve 9721 or at a location of the neuromodulation device 9725 distal of the captive support sleeve 9721). Although illustrated and described herein with respect to positioning within a common hepatic artery, the neuromodulation device 9725 could alternatively be positioned in other vessel segments, and catheter delivery could be performed by placement of a guide catheter at the ostium of any appropriate vessel.

Figures 98A, 98B:
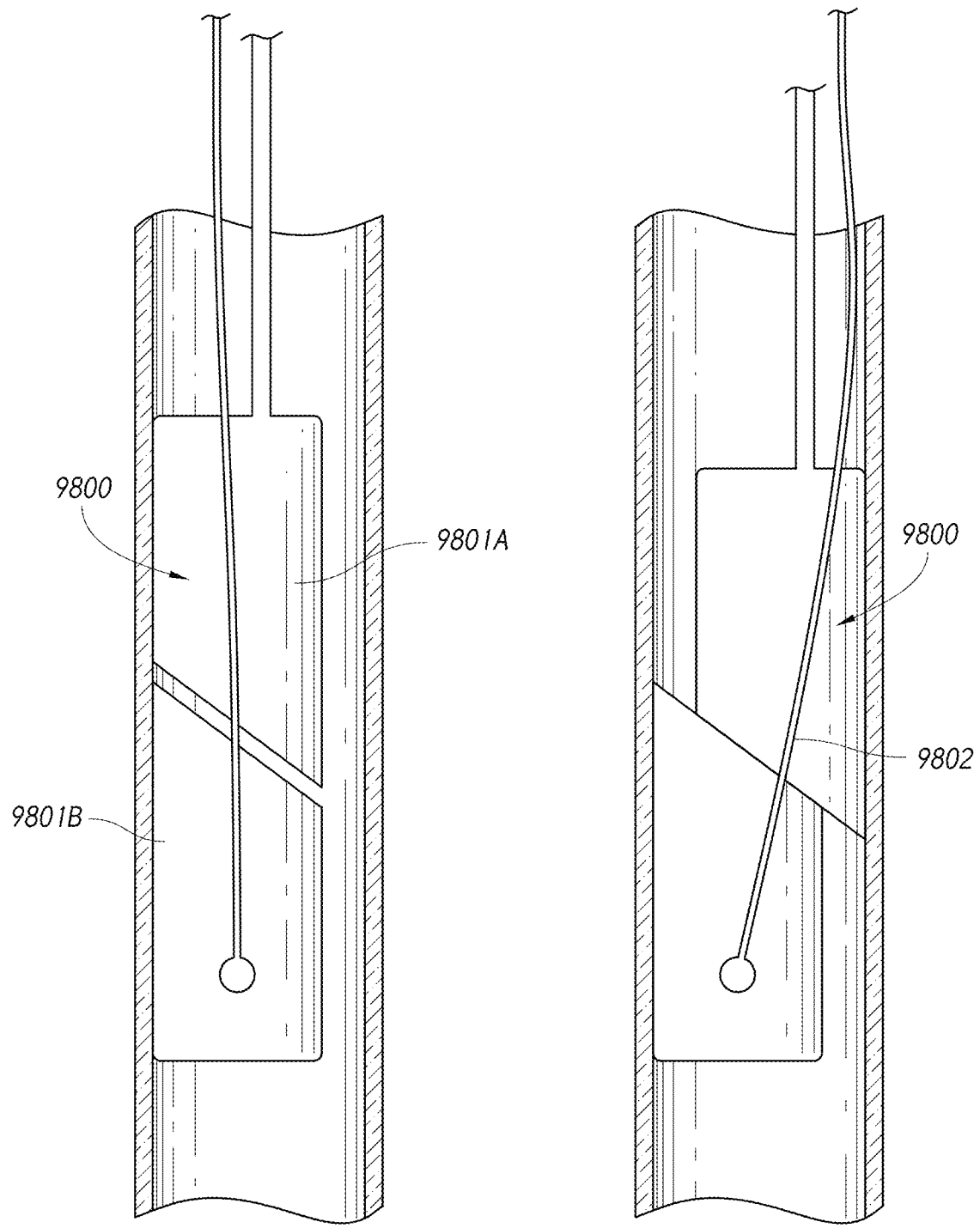
FIGS. 98A and 98B illustrate an embodiment of a wedge-type expanding anchor that can be used to secure a guide catheter or guide extension catheter in place.

FIGS. 98A and 98B illustrate an embodiment of a wedge-type expanding anchor 9800 that can be used to secure a guide catheter 9505 or guide extension catheter 9520 in place. The anchor 9800 may be placed on a distal end of a guide catheter to prevent or reduce the likelihood of movement of the guide catheter or guide extension catheter (e.g., during treatment or during injection of contrast). The anchor 9800 comprises two portions 9801A, 9701B that are cut at a slant and connected by a pull wire 9802 fixed to a joint positioned on portion 9801B. As the two portions 9801 are drawn together (e.g., by pulling the pull wire 9802 and pushing the portion 9801A, the two portions 9801 move sideways and expand into the vessel wall, thereby providing an anchor for the guide catheter, guide extension catheter or guide sheath.

Figure 99A:
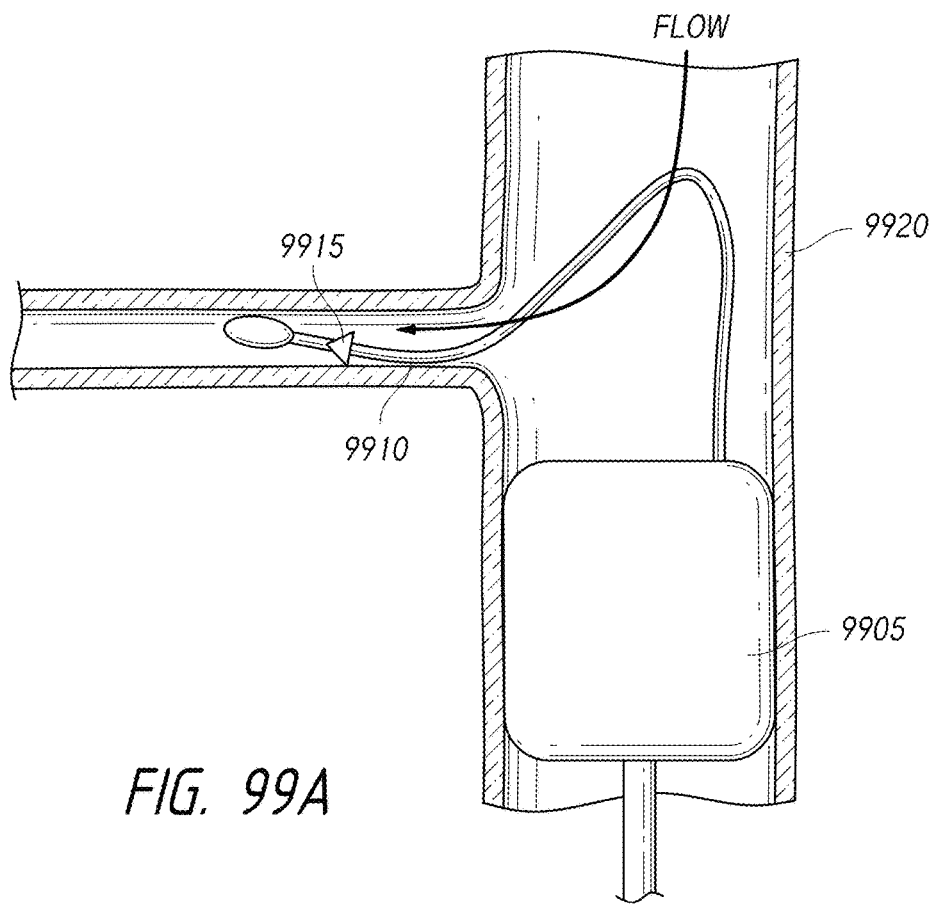
FIGS. 99A and 99B illustrate embodiments of devices (and methods of using such devices) specifically designed to facilitate access to tortuous hepatic vasculature.
Figure 99B:
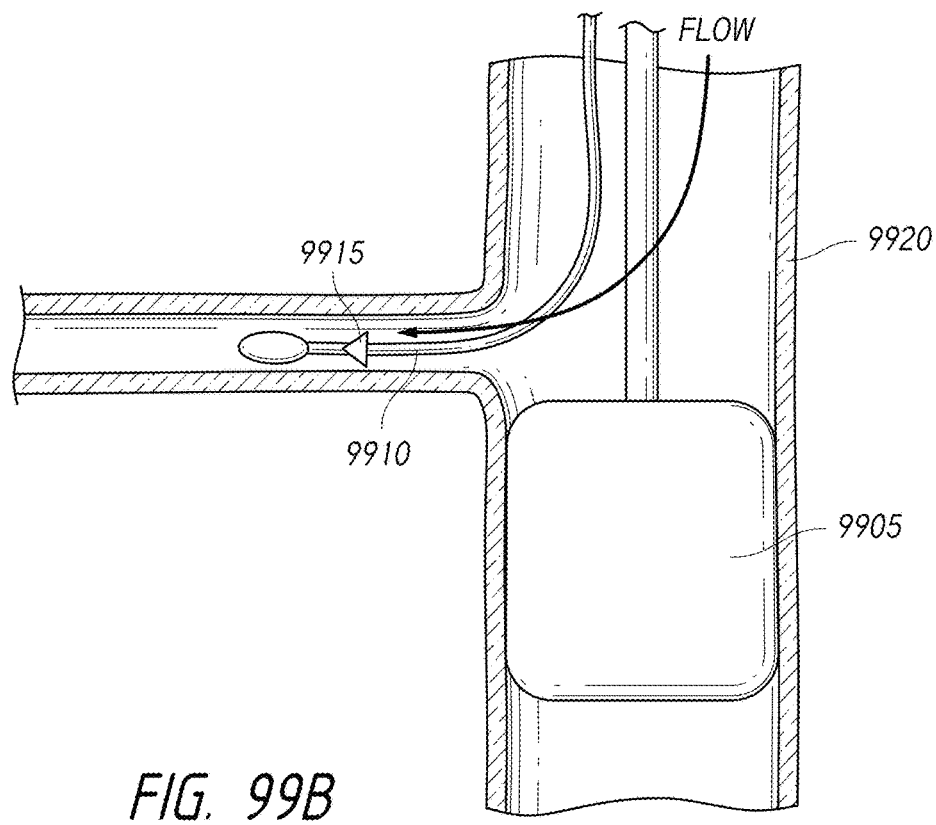

FIGS. 99A and 99B illustrate embodiments of devices (and methods of using such devices) specifically designed to facilitate access to tortuous hepatic vasculature. In certain situations, it may be difficult for a clinician to locate an artery using a guidewire. In accordance with some embodiments, a balloon catheter 9905 may be used to temporarily block distal portions of arteries. An electrode catheter or guidewire 9910 having a very loose, flexible distal portion may be positioned near an origin of a branch vessel where access is desired. The distal portion of the electrode catheter or guidewire may comprise an inflatable or otherwise expandable sail or parachute-like attachment 9915 designed to capture blood flow and drift with the blood flow into a target branch vessel, thereby facilitating access to the target branch vessel. FIG. 99A illustrates advancement of the balloon catheter 9905 and the electrode catheter or guidewire 9910 from a downstream location with respect to a main vessel 9920 and FIG. 99B illustrates advancement of the balloon catheter 9905 and the electrode catheter or guidewire 9910 from an upstream location with respect to the main vessel 9920. In some embodiments, blood flow may facilitate stabilization and maintenance of electrode contact and/or direct the electrode to the wall of the vessel.

In accordance with several embodiments described herein, the electrode catheters advantageously facilitate improved stabilization of the catheter and/or electrode within target vessels, which can lead to more predictable outcomes and more effective procedures. For example, the improved stabilization may prevent or reduce the likelihood of heating, burning or charring of unwanted portions of tissue or of the blood (which may prevent or reduce the likelihood of thrombus formation). Embodiments of catheters described herein may also facilitate access from the origin of the common hepatic artery.

B. Contact Facilitation

In one embodiment, a neuromodulation catheter (e.g., hollow, solid, partially hollow, catheter, probe, shaft or other delivery device with or without a lumen) is provided that comprises one or more customizable bending or deflection regions. In one embodiment, the neuromodulation catheter facilitates adjustment of multiple articulation or bending regions (collectively or independently). In one embodiment, a method of using the neuromodulation catheter comprises performing a computed tomography (CT) scan, digitizing the CT scan to create a three-dimensional (3D) model of a target anatomical region, determining the location(s) of major arterial or other vascular or anatomical bends and bend radii, and adjusting one or more articulation portions of the catheter to correspond to (e.g., match or line up with) the location(s) of the major arterial bends or other vascular or anatomical bends. In some embodiments, the neuromodulation catheter is configured to have a first bend corresponding to a first anatomical bend (e.g., first bend in a first portion of a hepatic artery or branch off of a hepatic artery) and a second bend corresponding to a second anatomical bend (e.g., second bend in a second portion of the hepatic artery or branch off of a hepatic artery). In some embodiments, the neuromodulation catheter is configured to have three or four bends corresponding to third and/or fourth anatomical bends. The bends may be approximately right angle bends or acute bends ranging from 5 degrees to 90 degrees (e.g., 5-10 degrees, 10-20 degrees, 20-40 degrees, 40-60 degrees, 60-90 degrees, and overlapping ranges thereof). One or more of the bends may be pre-formed and/or one or more of the bends may be formed by movement during delivery (e.g., by expansion, inflation, articulation, actuation, unsheathing).

Figure 100:
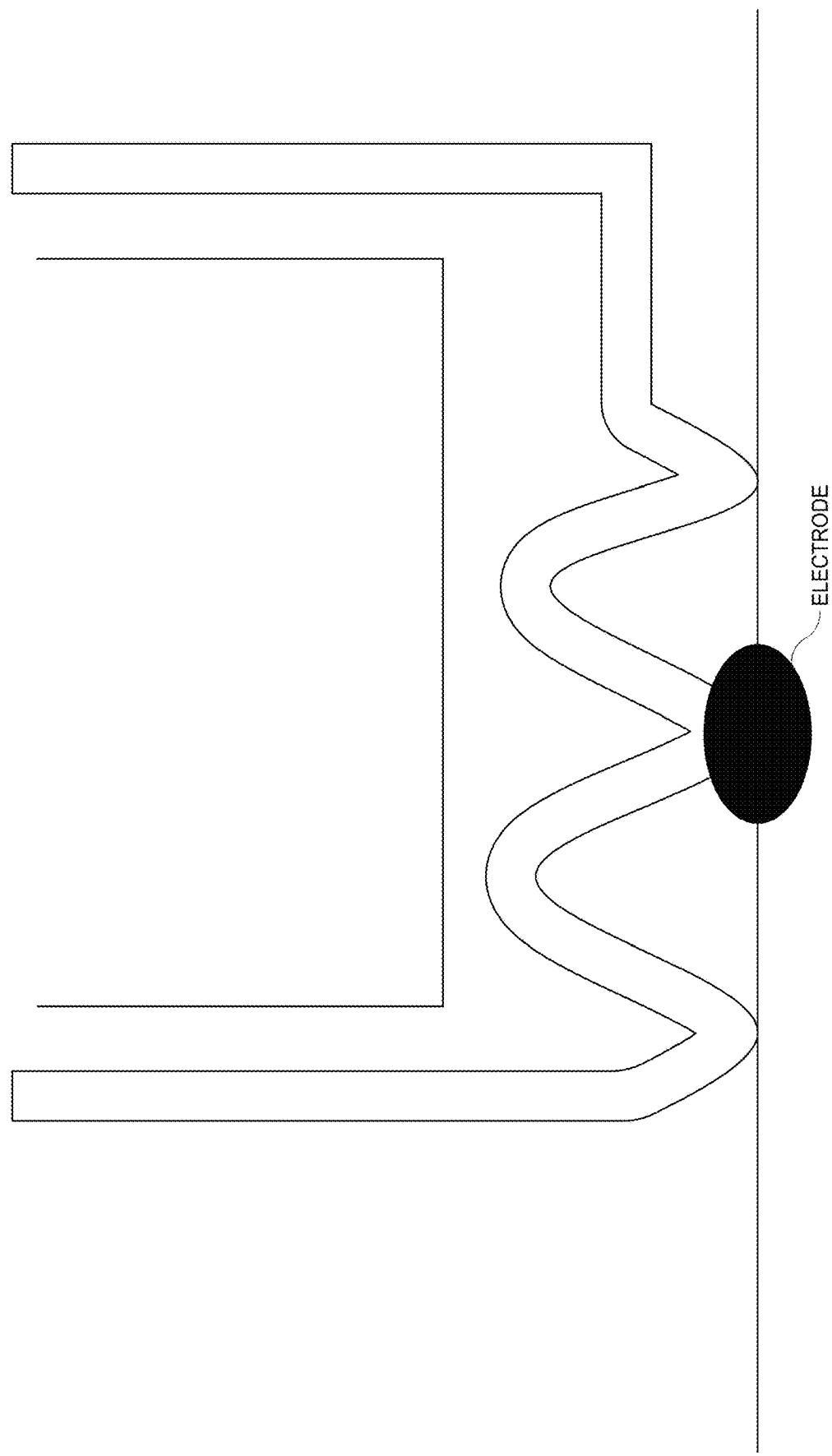

In some embodiments, a first bend is located or formed in the distal 10-40% (e.g., 20%) of the catheter length and a second bend is located or formed in the distal 1-20% (e.g., 5%) of the catheter length. The bends may be partially or wholly pre-formed. In several embodiments, the bends conform to a bend in the vessel wall such that the outer portion of the catheter optionally contacts the interior of the vessel wall. In one embodiment, the catheter bend conforms to the vessel wall but does not touch the vessel wall (e.g., is substantially parallel to the vessel wall but is separated by a distance of 0.1 mm-10 mm, or more). In some embodiments, a first bend is approximately 900 (e.g., 70-110°) in a first plane, about a radius of approximately 0.5 cm (e.g., 0.3 to 0.7 cm), corresponding to the takeoff of the celiac axis from the aorta. In some embodiments, a second bend is approximately 90 (e.g., 70-110°) in a second plane, about a radius of approximately 0.4 cm (e.g., 0.2 to 0.5 cm), the second plane being substantially orthogonal to the first plane, and corresponding to the bifurcation of the common hepatic and splenic arteries. In some embodiments, a third bend is approximately 90° (e.g., 70-110°) in a third plane, about a radius of approximately 0.3 cm (0.2 to 0.4 cm), the third plane being substantially orthogonal to the first and second planes, corresponding to the bend in the common hepatic artery. The bends may be achieved by any of the means described herein, including, but not limited to, hydraulic, pneumatic, pull-wire, resilient deformation, magnetic, and electromagnetic means. In yet another embodiment, a plurality of bends are configured to bias an electrode or other treatment member against the arterial wall, thereby generating an electrode contact force, and further yet provide a defined reaction force to balance the electrode contact force, as illustrated, for example, in FIG. 100. In one embodiment, the catheter comprises one or more spring-like or coil-like members to facilitate electrode contact force.

In various embodiments in which contact is desired and/or required, the contact force exerted on the vessel wall to maintain sufficient contact pressure is between about 1 g to about 500 g, from about 20 g to about 200 g, from about 10 g to about 100 g, from about 50 g to about 150 g, from about 100 g to about 300 g, from about 200 g to about 400 g, from about 300 g to about 500 g, or overlapping ranges thereof. In some embodiments, the same ranges may be used but expressed as g/mm$^2$ pressure numbers. The contact forces/pressures described above may be achieved by any of the neuromodulation (e.g., ablation) devices and systems described herein.

In accordance with several embodiments, the contact force of an RF electrode or other treatment member against the hepatic arterial wall is a key variable determining ablative success. In various embodiments, devices providing tangential electrode contact through bending regions having bend radii of approximately 0.5 cm (e.g., 0.2 cm-0.8 cm) are provided. In other embodiments, devices having means to exert a controllable reaction force to the electrode contact force are provided. In some embodiment, suction is provided to ensure reliable contact between the electrode(s) or other treatment members and the vessel wall (e.g., hepatic arterial wall).

In some embodiments, a portion of an electrode of an RF energy delivery device is comprised of a deformable membrane, with fluid perfused through this region. In one embodiment, the fluid is coolant fluid circulated within the catheter or delivered to the arterial lumen to cool the electrode. An external controller can be configured to maintain a constant flow rate of the coolant, and the resulting driving pressure required to do so may be directly correlated with the contact pressure along the deformable region of the electrode.

Figure 101:
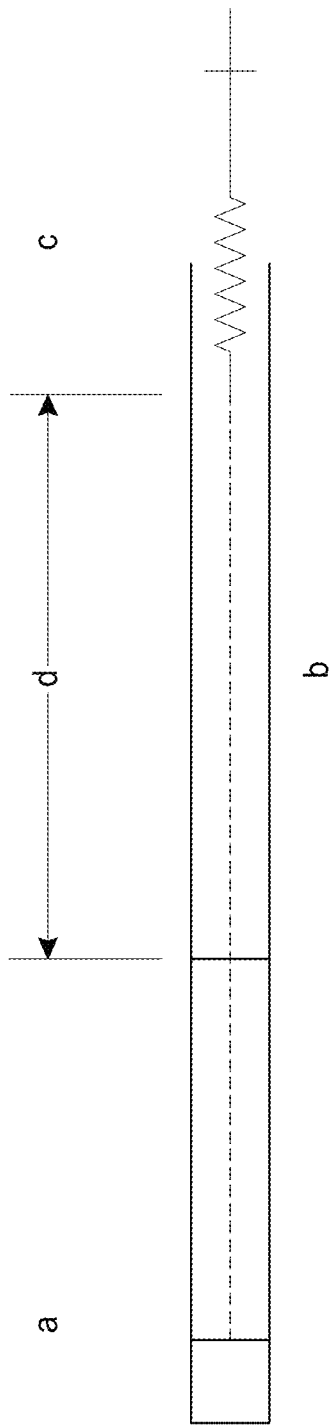

Referring now to FIG. 101, an embodiment of a catheter distal tip design is illustrated having a radiopaque marker disposed within a distal lumen of the catheter and attached to the electrode at one end and an extensible spring anchored at a proximal region of the catheter. The catheter in region A, the flexible region, is configured to be substantially radiopaque, whereas the catheter in region B is configured to be non-radiopaque. Upon contact of the electrode against the arterial wall, which causes deflection of the catheter in region A, the radiopaque marker is urged distally into the radiopaque region A, thereby decreasing the visible length, d, of the radiopaque marker, and thereby providing a visual indicator of the electrode contact force, visible during angiography or other imaging modalities. In some embodiments, the visible length, d, may be indirectly related to the electrode contact force.

Figure 102:
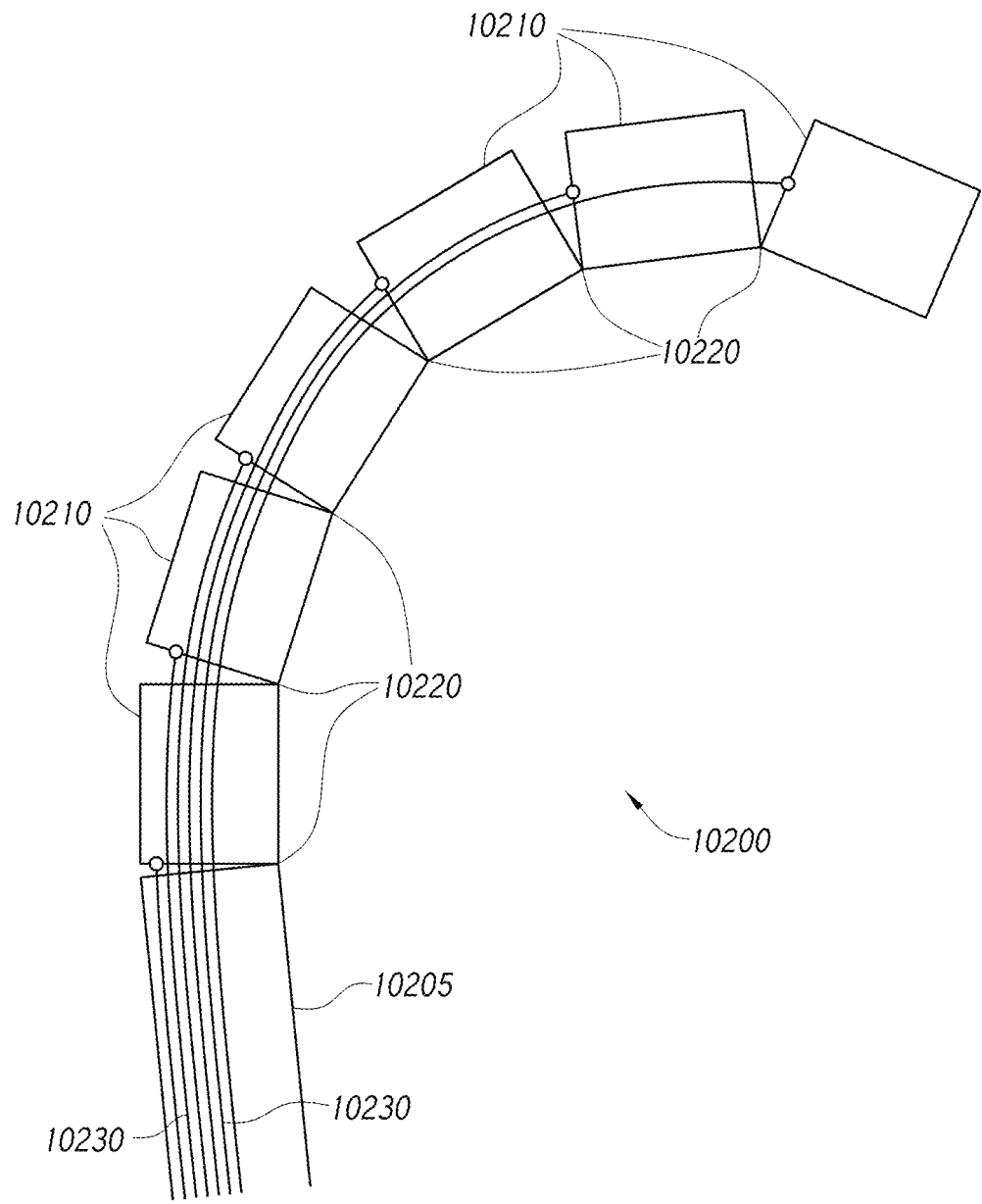

FIG. 102 illustrates an embodiment of a steerable neuromodulation catheter 10200 having an articulatable tip. The neuromodulation catheter 10200 comprises a catheter body 10205, multiple segments 10210, multiple corresponding hinges 10220, and multiple corresponding articulation members (e.g., wires) 10230. In some embodiments, the neuromodulation catheter 10200 includes fewer than six segments, hinges, and/or articulation wires (e.g., two, three, four, or five). In some embodiments, the neuromodulation catheter 10200 includes more than six segments, hinges, and/or articulation wires (e.g., seven, eight, nine, ten, eleven to twenty, or more than twenty). In one embodiment, the segments 10210 and the hinges 10220 are hollow.

Each of the segments 10210 is coupled to adjacent segment(s) by one of the hinges 10220. Each of the articulation wires is attached to at least one of the segments and passes from the segment to which it is attached through the other segments toward the catheter body 10205. In operation, the articulation members (e.g., wires) may be extended or retracted as desired, thereby pivoting the articulatable tip of the catheter 10200. In one embodiment, the steerable neuromodulation catheter comprises an "inchworm" end.

In some embodiments, all of the articulation wires 10230 are extended and retracted in combination. In other embodiments, each of the articulation wires 10230 is individually actuatable. In such embodiments, each individual segment 10210 could be individually actuatable by each corresponding articulation wire 10230. For example, even when the third segment, the fourth segment, the fifth segment, and the sixth segment are constrained within a guide catheter, the first segment and the second segment may be articulated by extending or retracting the first articulation wire and/or the second articulation wire, respectively, with sufficient force. The steerable catheter 10200 may advantageously permit improved contact pressure between the distal tip of the steerable catheter 10200 and the vascular wall of the target vessel, thereby improving treatment efficacy. In various embodiments, a first portion of segments 10210 is actuated to have a first bend shape configured to conform to a first anatomical bend (e.g., a first bend of a hepatic artery branch or portion) and a second portion of segments 10210 is actuated to have a second bend shape configured to conform to a second anatomical bend (e.g., a second bend of a hepatic artery branch or portion). The first portion of segments 10210 and second portion of segments 10210 may be actuated by movement of one or more articulation wires 10230 (if multiple, collectively or independently). In one embodiment, the steerable catheter 10200 substantially locks in a shaped configuration matching the shape of the hepatic artery or other artery or vessel, providing improved stability.

Figure 103:
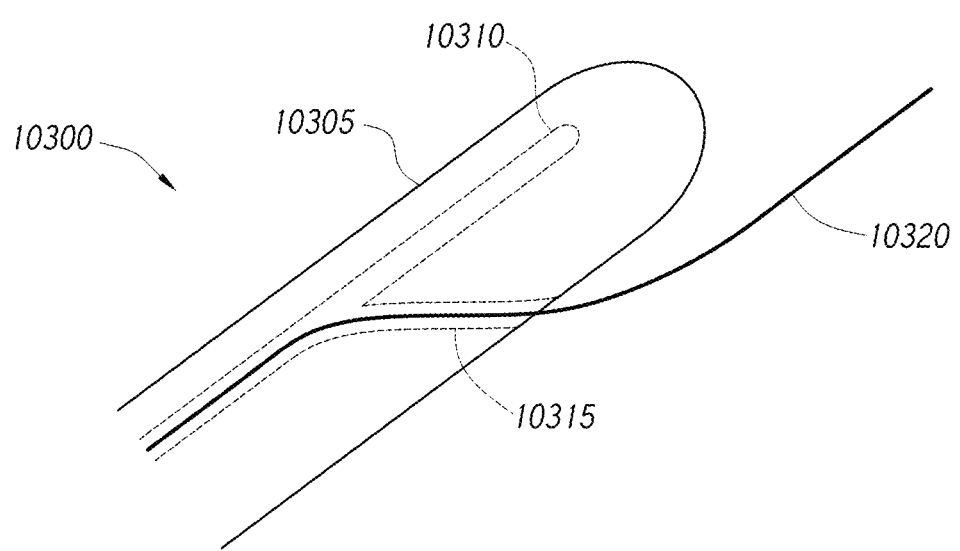

FIG. 103 illustrates an embodiment of a neuromodulation catheter 10300 with a deflectable distal tip. The neuromodulation catheter 10300 comprises a guidewire configured to facilitate steerability. The neuromodulation catheter 10300 includes an ablation catheter tip 10305, a guidewire housing 10310, a guide wire channel 10315, and a guidewire 10320. In operation, the guidewire 10320 may be extended out through guide wire channel 10315 to be used in its guiding capacity to navigate through vasculature. When it is not desirable to use the guidewire 10320 in its guiding capacity, the guide wire 10320 may be retracted into the ablation catheter tip 10305 and then extended into the guide wire housing 10310, where it may be stored until needed or desired. In one embodiment, the steerable neuromodulation catheter comprises an "inchworm" end.

In some embodiments, the guidewire 10320 is plastically deformable with a permanent bend in the distal tip. In such embodiments, the guidewire 10320 may be rotated within the body of the neuromodulation catheter 10300 to plastically deform and be pushed into the guide wire housing 10310, or may be rotated 180 degrees and regain its bent configuration to exit through the guide wire channel 10315. In some embodiments, a thermocouple (e.g., type T thermocouple) temperature sensor may be incorporated into the guidewire 10320. The thermocouple may be used to assess thermal loss delivered to target tissue compared to thermal loss convected away by blood. In some embodiments, the guidewire 10320 is used to deliver ablative energy (such as RF energy) to at least one electrode. In one embodiment, delivery of the ablative energy is facilitated by disposing a conductive gel between the guidewire 10320 and the at least one ablation electrode. In various embodiments, the deflectable distal tip comprises two deflectable, steerable and/or actuatable portions, with a first portion configured to have a first bend shape to conform to a first anatomical bend (e.g., a first bend of a hepatic artery branch) and a second portion configured to have a second bend shape to conform to a second anatomical bend (e.g., a second bend of a hepatic artery branch). In one embodiment, the neuromodulation catheter 10300 comprises one or more pre-bent or pre-curved portions. The pre-bent or pre-curved portions may conform to particular anatomical bend shapes (e.g., within the hepatic arteries or neighboring branches upstream or downstream of the hepatic arteries).

Figure 111:
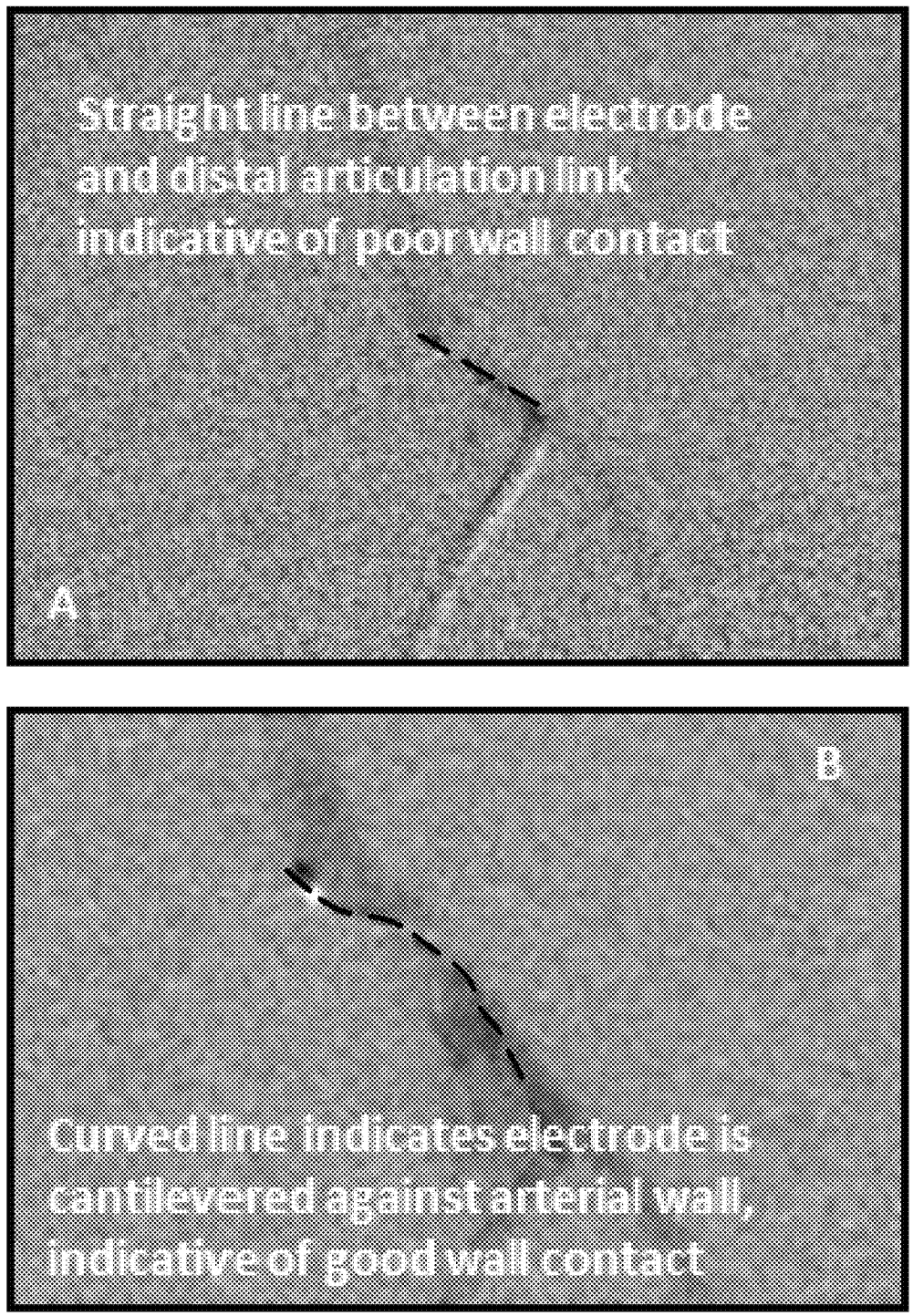
FIG. 111 illustrates an example of poor wall-electrode contact and an example of good wall-electrode contact.

As shown in FIGS. 111, 112A and 113A, the common hepatic artery and celiac trunk can be very tortuous (e.g., can have multiple bends). In some embodiments, accessing this anatomy is performed using a highly flexible catheter or other instrument with sufficiently strong column strength. In some embodiments, the neuromodulation (e.g., ablation) catheters described herein having a single electrode are configured to make contact with multiple points around the circumference of the target vessel, and have excellent torque transfer through the catheter shaft. In some embodiments, the catheters are flexible enough to navigate a tortuous anatomy without kinking or reduce the likelihood of kinking. Kinking can occur because the cross section of the shaft becomes oval as it is bent. For example, after a critical bend radius is reached, the oval may collapse and a kink may be created. In accordance with several embodiments, the catheters described herein prevent, or reduce the likelihood of, "ovalization" while enabling material on the inner and outer arcs to compress and stretch, respectively.

With a single electrode or limited number of electrodes on an ablation device, rotation of the electrodes and multiple ablation doses may be required to create circumferential or increased volume of ablation of the nerves surrounding a vessel (e.g., perivascular space). In the case of denervating the common hepatic artery (CHA), unique vessel tortuosity (multiple acute turns) can make torque transfer more difficult. When a torque is applied at the proximal end of a catheter shaft the torque may first be translated into a distal rotational displacement until the shaft contacts the length of the vessel wall. After the shaft is supported, the torque applied at the proximal end may then cause a rotation of the distal end of the shaft, but may "flip" or otherwise result in uncontrolled rotation of the distal electrode.

Referring now to FIGS. 104A and 104B, an embodiment of a catheter system configured to support the catheter shaft within the vessel lumen, thereby reducing the translation of the shaft into the vessel wall. The illustrated embodiment may advantageously improve torque efficiency by reducing losses along the length of the arterial lumen and allow the proximally applied torque to result in controlled rotation of a distal electrode at a distal end of the catheter shaft. As illustrated in FIG. 104A, a guide catheter 10405 with a lumen that is just larger than the outer diameter of the ablation device 10406 is able to support itself against a section of the vessel wall by means of a support structure 10408. In one embodiment, the support structure 10408 is comprised of multiple wires or ribbons that are pushed out of a plurality of lumens disposed along a length of the guide catheter and exposed to the arterial or other vessel lumen near (e.g., within 1 cm of, within 2 cm of, within 3 cm of) the distal end of the guide catheter. The wires or ribbons, disposed within the lumens and controlled at the proximal end of the guide catheter 10405, expand outward until they contact the vessel wall. In some embodiment, the wires or ribbons exert a force against the vessel wall at multiple points, thereby providing a reaction force to restrict lateral movement of the guide catheter when the ablation device 10406 is rotated within the guide catheter 10405. The inner lumen of the guide catheter 10405 and outer surface of the ablation device 10406 (e.g., electrode/catheter) can be comprised of materials or coatings having low coefficients of friction (e.g., polytetrafluoroethylene or hydrophilic coatings) in order to further reduce the rotational friction between the two devices.

In one embodiment, a plurality of support structures could be used to place the guide catheter 10405 in contact with the vessel wall. Some examples include pressurized support balloons (such as shown in FIG. 104B) that may allow for perfusion, self-expanding stent structures, and basket sections of the guide catheter polymer tube that can be compressed and expanded radially or otherwise deployed.

Figure 105:
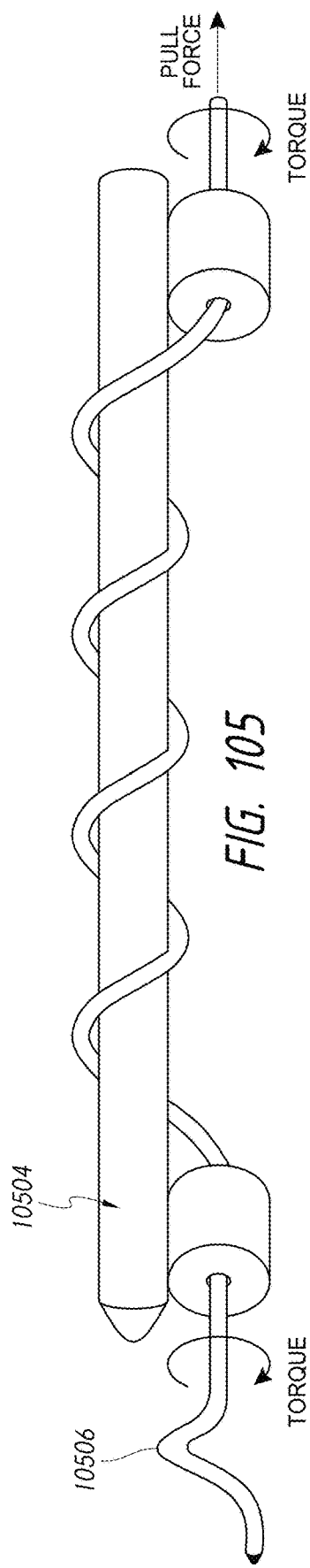

In one embodiment, illustrated in FIG. 105, an inner support member 10504 (e.g., a guidewire) is configured to hold the ablation device. For example, loops 10501 and 10502 can be welded or otherwise fixed or coupled to the inner support member to hold the ablation device. The ablation device may then be passed through the loops and wrapped in a spiral around the inner support member between the loops. When a torque is applied (in one direction) to the ablation device, the ablation device can take up the slack between the inner support member and then transfer the torque to the distal end, "winding" the distal end of the ablation device in one rotational direction. If the torque is applied in the opposite direction, the ablation device wants to "unwind." In one embodiment, this torque improvement mechanism advantageously allows for improved torque efficiency in one direction. In one embodiment, a pull force can be applied to a proximal end of the ablation device, either alone, or in combination with the torque.

Figure 106:
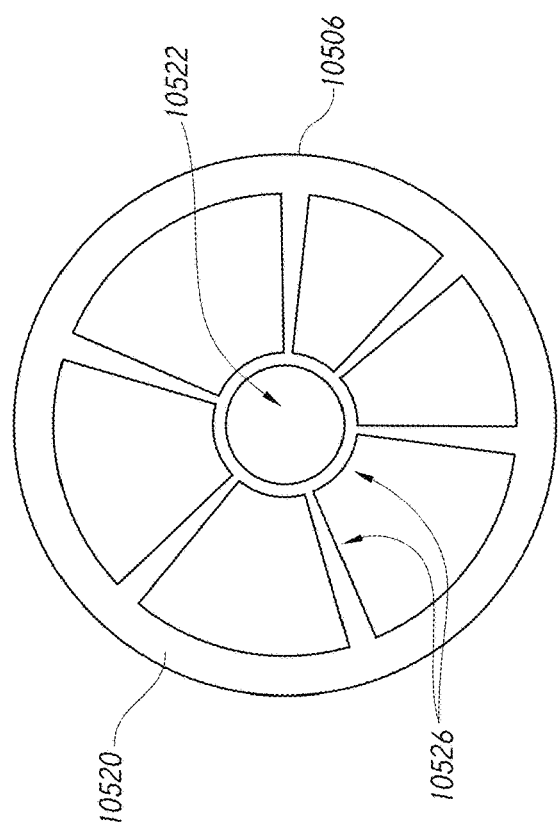

In one embodiment, illustrated in FIG. 106, the guide catheter is comprised of an expandable balloon 10520 having an internal catheter-receiving lumen 10522 and an external, arterial contacting surface 10524, with an external lumen extending between the internal lumen 10522 and the external surface 10524. The internal lumen 10522 and external lumen are connected by a plurality of struts 10526 running along a portion of, or substantially the entire, length of an inflatable guide region of the guide catheter. Upon insertion at the target anatomy (e.g., the celiac axis), the balloon chambers defined by the struts are inflated to maintain the position of the guide catheter and improve navigation and torque response of the ablation catheter inserted within the internal lumen 10522 of the guide catheter.

Figure 107:
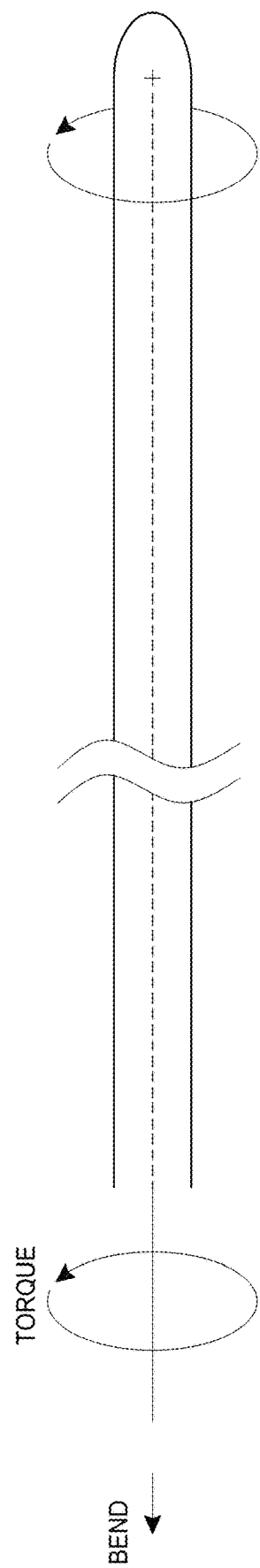

Referring now to FIG. 107, an embodiment of a control mechanism configured to provide precise control of an electrode or other treatment element at the distal end of a catheter by controlling the distal end of the catheter directly is provided. As shown in FIG. 107, the direct control maybe accomplished by applying torque/rotation to a control wire disposed within the catheter shaft and anchored to a distal location of the catheter, such as near the electrode region. In accordance with several embodiments, the challenges associated with torquing a catheter disposed in tortuous anatomy may altogether be avoided or reduced.

Figure 108:
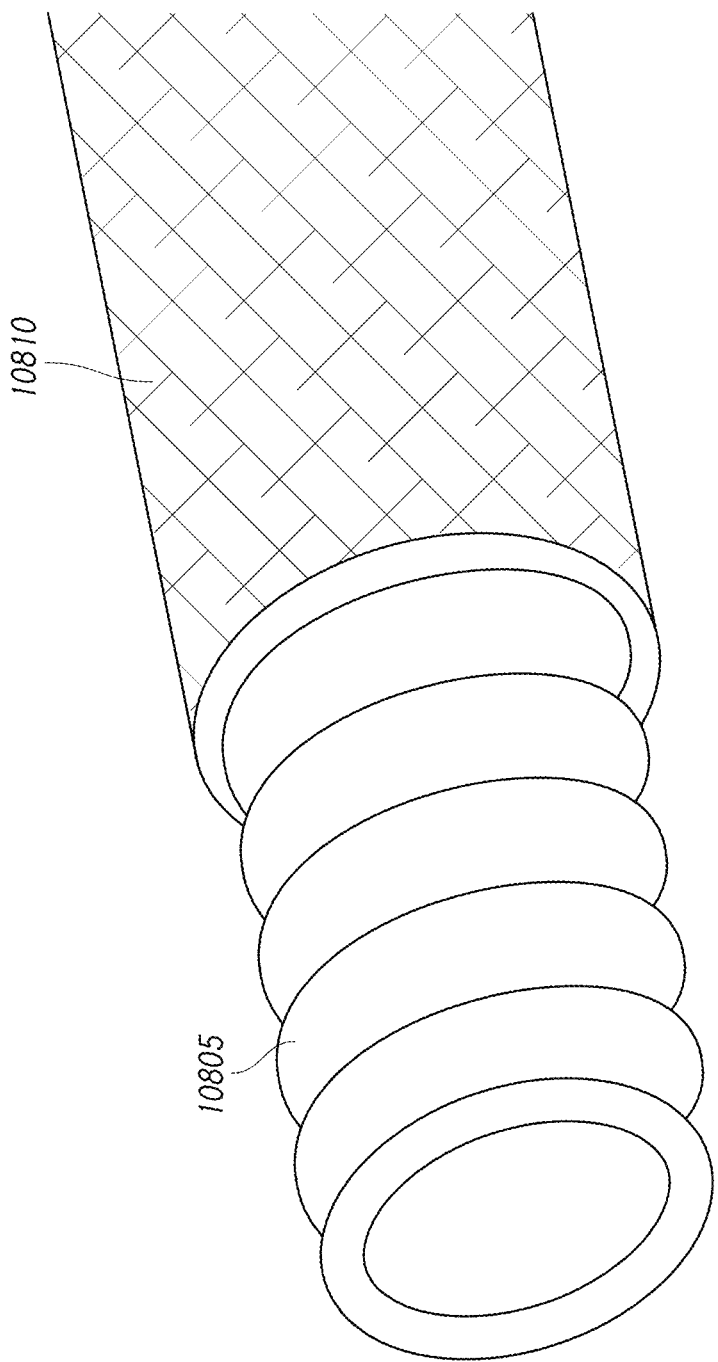

FIG. 108 illustrates one embodiment of a distal portion of a catheter that combines the benefits of a coil 10805 (e.g., kink prevention or inhibition) and a solid rod 10810 (improved torque transfer for a given diameter constraint). The catheter comprises a hose having a coiled and ribbed polymer inner layer (for example, polyimide) and a braided outer layer (for example, Pebax®) that is disposed about the inner layer. The inner layer prevents, or reduces the likelihood of, "ovalization" while the outer layer provides improved column strength and torque transfer properties. In one embodiment, the inner layer comprises a coil (without the ribbed polymer) and the outer layer comprises a round or flat braid.

FIGS. 109A and 109B illustrate an embodiment of a hypotube having a cut pattern that advantageously provides bending flexibility, column strength, and torqueability. Material may be removed around the circumference of a tube so that only a "peninsula" of material connects one ring or portion of material to another, thereby allowing the rings of material to bend towards each other and move into the empty space. Alternating the position of the rings by 90 degrees or about 90 degrees can enable the ring portions to bend in multiple directions. The cut pattern may be formed by laser or mechanical cutting means. In accordance with several embodiments, the hypotube or shaft of the catheter comprises a substantially non-electrically conductive reinforced shaft in order to provide improved dielectric strength and reduced electrical shaft capacitance, thereby improving electrical safety. In some embodiments, the effective shaft capacitance as described in iec60601-2-2-R12 is less than 2 pF/cm of shaft length. In other embodiments, the requirements of IEC60601-2-2-R12 can be met with an over-the-wire catheter having a diameter of less than 5 Fr. The shaft may be formed of a first material selected from a list comprising Polyimide, polyester, polyether block amide, polyurethane, Nylon, polyethylene, Pebax®, grilamid, thermoplastic elastomers and copolymers and a second reinforcing material such as polyether ether ketone (PEEK), liquid crystal polymer (LCP), Vectran, Spectra®, Dyneema, Kevlar® or polyimide material. The reinforcement material may comprise a round or flat braid. In some embodiments the reinforcing material is a coil. In other embodiments, the reinforcing material is a braid. In some embodiments, the hypotube or shaft is lined with polyimide, PTFE or Polyimide/PTFE composite. In some embodiments, the hypotube or shaft comprises a Pebax® outer layer.

Figure 110:
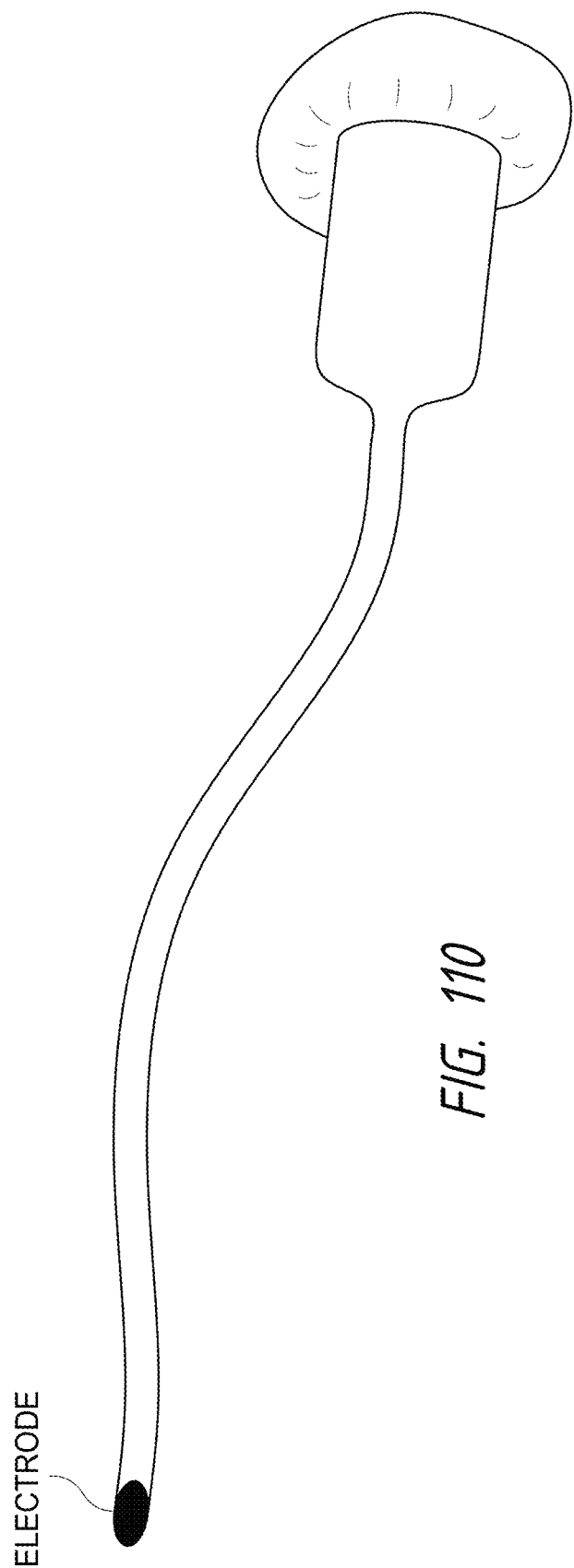

Torqueability can be especially advantageous in branches of the hepatic artery or surrounding arteries, where the small size of the arterial lumen may not permit passage of a multi-tip electrode catheter. In accordance with several embodiments, it is particularly advantageous to have fine control of the rotation of an electrode (e.g., to adjust the position of the electrode in subsequent ablations or other procedural actions to cover the area in the proximity of the efferent nerves). One embodiment of a catheter for improving user control of electrode positioning is schematically shown in FIG. 110. As shown, a small-diameter shaft of the catheter may be connected to a larger-diameter cylindrical shaft, thereby providing a physician or other clinician with a larger control surface for adjustment. In one embodiment, the control surface could comprise the ring gear of a planetary gear system, with the catheter shaft forming the sun gear and the ratio of the rotation of the control surface to the rotation of the catheter being determined by the planetary gears. In one embodiment, the ratio is <1:1 (e.g., 1:10, 1:9, 1:8, 1:7, 1:6, 1:5, 1:4, 1:3, 1:2).

Referring now to FIG. 111, the tortuous anatomy of the hepatic artery and surrounding arteries may provide challenges for access and catheter contact (in embodiments where contact with the arterial wall facilitates modulation of nerves, such as RF catheter ablation with one or more electrodes). For example, FIG. 26 illustrates an electrode catheter within a tortuous artery. As shown in FIG. 111A, a straight line formed between an electrode and a distal articulation link of the catheter may be indicative of poor arterial wall contact, whereas a curved line between the electrode and the distal articulation link (as shown in FIG. 111B) may indicate that the electrode is cantilevered against the arterial wall (which may be indicative of sufficient arterial wall contact).

FIGS. 112A and 112B illustrate an embodiment of a catheter system configured to provide improved wall contact and catheter stabilization within tortuous vasculature (e.g., tortuous vasculature of the common hepatic artery). The catheter system comprises a guide catheter 11205 and an expandable element catheter 11210 (e.g., balloon catheter). In the illustrated embodiment, the expandable element catheter 11210 comprises a balloon catheter having a balloon positioned at a distal end of the balloon catheter. The balloon catheter may be inserted within the common hepatic artery in a deflated state (as shown in FIG. 112A) and then inflated to an expanded state (as shown in FIG. 112B). In some embodiments, expansion of the expandable element 11215 (e.g., inflation of a balloon) straightens out a tortuous vessel (e.g., hepatic artery portion) to facilitate wall contact of one or more electrodes or other treatment members (e.g., transducers, microwave emitters) disposed in or on the expandable element. If multiple electrodes or other treatment members are used, the multiple members may be spaced at various positions along the length and/or circumference of the expandable element, thereby facilitating treatment at multiple locations (simultaneously or separately). The expanded state may also result in improved catheter stabilization, thereby improving efficiency of the treatment procedure and reducing treatment times.

The expandable element may be self-expandable, mechanically expandable, or pneumatically expandable (e.g., inflatable). In one embodiment, the expandable element comprises shape memory material (e.g., a self-expandable stent-like element). In one embodiment, the catheter system comprises a passive segmented catheter (e.g., shape-lock assembly of one or more nested links) that guides the catheter into and through a tortuous vessel in a flexible state and then transitions to a rigid, shape-locked state. In one embodiment, the catheter enters the tortuous vessel in a curved state and then straightens out the vessel to cause the vessel to form a substantially straight cylindrical shape.

Respiration can cause movement of vessels being targeted for nerve modulation. For example, respiration can cause movement by as much as 2-5 cm in the area of the common hepatic artery, which may result in undesirable motion of a neuromodulation catheter or a treatment element (e.g., electrode, transducer or emitter) disposed thereon. The motion caused by respiration may adversely affect continuous and sufficient wall contact of a treatment element (e.g., electrode or transducer) against a vessel wall, and in several embodiments described herein, the adverse effect is reduced or removed.

Figure 113:
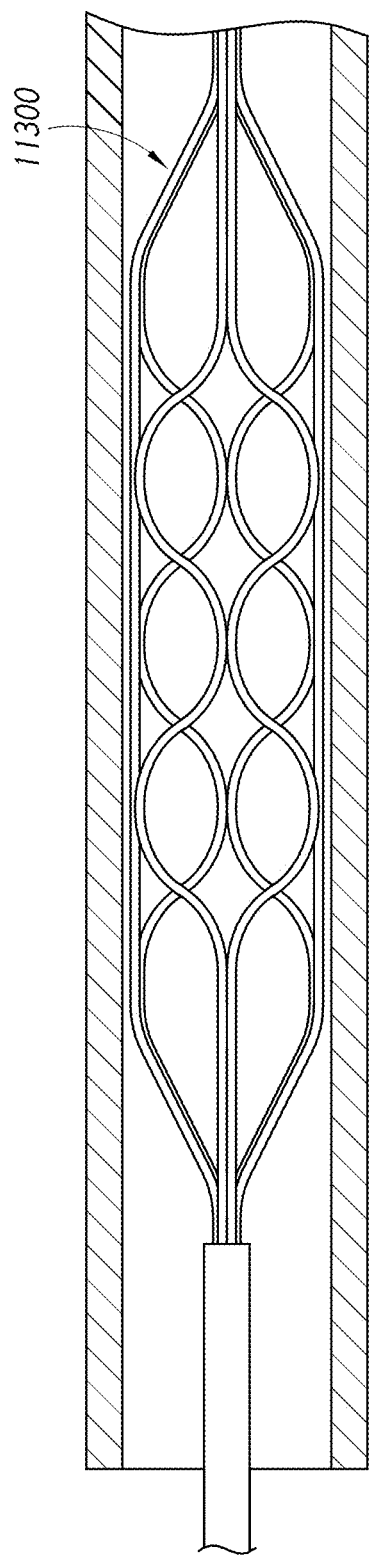

FIG. 113 illustrates an embodiment of a temporary frame or scaffold 11300 configured to provide vessel stabilization and to provide landmarks for positioning treatment elements (e.g., ablation electrodes) of a neuromodulation device or system. The frame 11300 may advantageously stabilize a vessel (e.g., hepatic artery) that has been deformed under forces exerted by a catheter and/or stretched or deflected with respiration. In some embodiments, the frame 11300 provides access to the vascular wall at desired treatment (e.g., ablation) sites. The frame 11300 may stabilize both the general vascular geometry as well as the local wall position. In accordance with several embodiments, the frame 11300 is deployed and retrieved during the procedure.

In the illustrated embodiment, the frame 11300 is a hexagonal wire mesh. The frame 11300 may be fabricated as a slotted tube or a woven wire. The frame 11300 may be constructed of polymer or metal. Metallic materials may include Nitinol, stainless steel, MP35N alloy, elgiloy alloy, and/or the like. The metal may be insulated with a polymer or an oxide layer. Polymeric materials may include polyurethane, parylene, fluorocarbon, polytetrafluoroethylene (PTFE), fluorinated ethylene propylene (FEP), perfluoroalkoxy alkane (PFA), thermoplastic elastomers, nylon, Hytrel®, Pebax®, Arnitel®, and/or the like. Frame elements may be wrapped, folded, or bent to provide desired mechanical properties. Frame elements may be joined or coupled with solder, braze, adhesive, and/or the like. The frame mesh may be a single continuous element or segmented into separate elements. The frame 11300 may be rigid or flexible. The frame 11300 may comprise any polygonal mesh structure. In other embodiments, the frame 11300 may be a braid, coil, weave or other intertwined configuration formed of metal or polymeric wire or filaments.

In some embodiments, the frame 11300 may comprise radiopaque elements or radiopaque material to provide visualization. The frame 11300 may provide radiographic landmarks to aid in positioning ablation electrodes or other treatment elements of an energy delivery device to be inserted through the frame 11300. The radiographic landmarks may include radiopaque markers. In some embodiments, the radiographic landmarks may be based on the structure and visibility of the frame 11300 itself. The entire frame 11300 may be radiopaque or certain portions or elements may be radiopaque.

In several embodiments, the frame 11300 provides for mechanical orientation and positioning of treatment elements (e.g., electrodes). For example, interaction between the frame 11300 and an electrode assembly may provide tactile feedback or direct positioning of the electrode(s) with respect to the frame 11300. When used in conjunction with electrode catheters, the frame 11300 may also provide for electrical position sensing to aid electrode placement. Electrical position sensing may be accomplished by providing a sensing element on the electrode shaft that detects proximity to a corresponding element on the frame 11300 or vice-versa. The sensing element may detect proximity using continuity, resistance, conductivity, magnetoresistance (e.g., GMR), Hall Effect, capacitance, magnetism, light, reflectance, absorbance, refraction, diffraction, sound, acoustic reflection, and/or the like. A separate electrode catheter (not shown) may be advanced within the frame 11300 and manipulated such that the electrode(s) are delivered through openings in the wire mesh of the frame 11300 to contact the vessel wall. The frame 11300 may advantageously stabilize the vessel wall in the region of a target ablation site by placing the vessel wall under slight tension, thereby limiting or reducing the deformation of the vessel wall by the contact forces imposed by the electrode(s). In some cases, these contact forces might otherwise increase the contact area between the electrode and vessel wall and restrict blood flow near the electrode, which may impair cooling and increase vessel injury. In some embodiments, a neuromodulation device may itself comprise a frame instead of the frame being a separate device. The frame 11300 may comprise one or more monopolar electrodes or bipolar electrode pairs for delivering RF energy to the vessel wall.

The hepatic arteries move due to the tidal breathing motions of the hemidiaphragm and the motion of the diaphragm. The vertical motion of the hepatic arteries generally matches that of the right or left hemidiaphragm. In one embodiment, the mean horizontal movement can be up to 1.90 mm. During a porcine study of hepatic arterial ablation, it was observed that the position of a catheter tip post-ablation was consistently up to 1 cm from the initial target location, increasing the variability of the resulting lesion and, correspondingly, the consistency with which hepatic arterial denervation was achieved. In various embodiments, methods and systems aimed at reducing catheter tip and/or electrode motion during the procedure are provided, as breathing suspension may not be feasible for the duration of the procedures (e.g., ablations) required to achieve hepatic denervation or other nerve modulation.

In various embodiments, undesired motion of neuromodulation catheters (e.g., ablation catheters) can be reduced by substantially reducing the friction between the neuromodulation catheter and the guide catheter within which the neuromodulation catheter is inserted. The reduction of friction can be achieved, for example, by means of a hydrophobic (e.g., fluorine-based) lubricant or coating. In some embodiments, the force and/or displacement translation from the proximal end of the catheter (e.g., in contact with an introducer sheath) and the distal end of the catheter (e.g., electrode) can be reduced to address the motion of the catheter. In some embodiments, the friction near the catheter's distal end (e.g., electrode) and the target tissue can be increased to address the motion of the catheter.

FIGS. 114A and 114B illustrate an embodiment of catheter configured to address the effects of respiratory motion on the hepatic arteries. FIG. 114A illustrates the catheter during an inhalation and FIG. 114B illustrates the catheter during an exhalation. The catheter comprises a disconnection or a flexible and/or passive segment. In some embodiments, the flexible and/or passive segment is positioned at an origin of the common hepatic artery (as shown in FIG. 114A and FIG. 114B).

Figure 115:
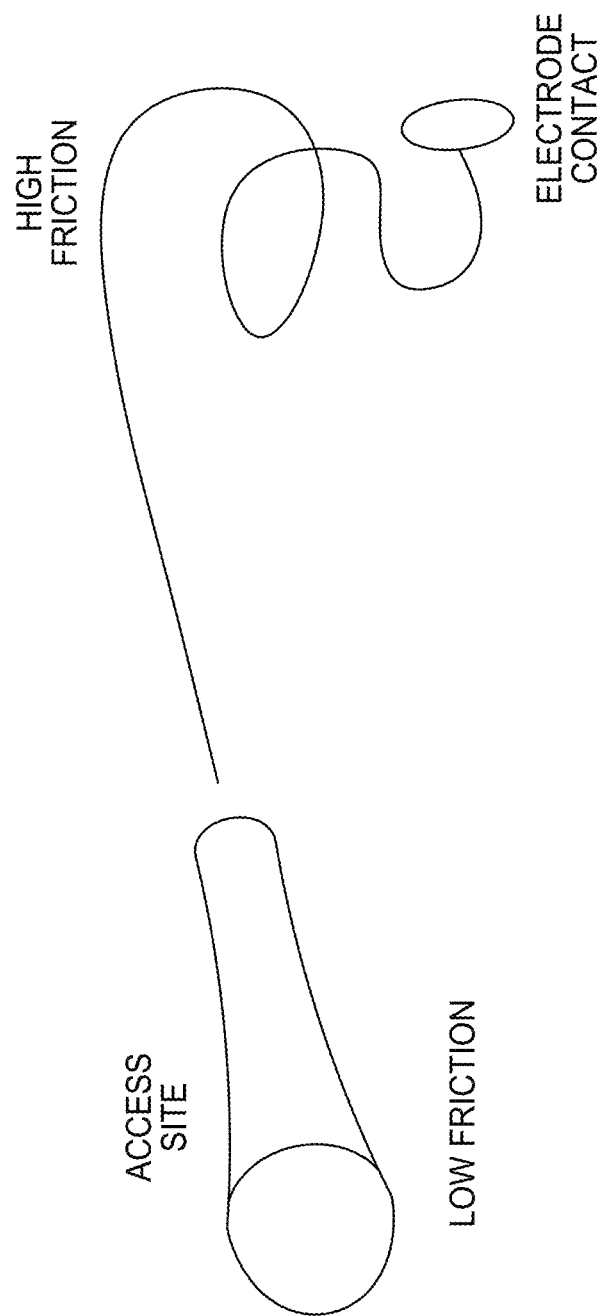

FIG. 115 illustrates an embodiment of a catheter system configured to address motion of the target vessels by reducing the force and/or displacement translation from the proximal end of the catheter and the distal end of the catheter. In methods of using the catheter of FIG. 115, slack can be placed in the catheter system between an access site and a distal end of the catheter (e.g., electrode). In one embodiment, the slack formation is accomplished by fixing the distal end of the catheter and then pushing the flexible catheter forward a few centimeters so additional material lies between the distal end of the catheter and the access site. In one embodiment, any movement of the distal end relative to the access site straightens out the slack in the catheter instead of applying a translational force to the distal end and/or access site.

Figure 116A:
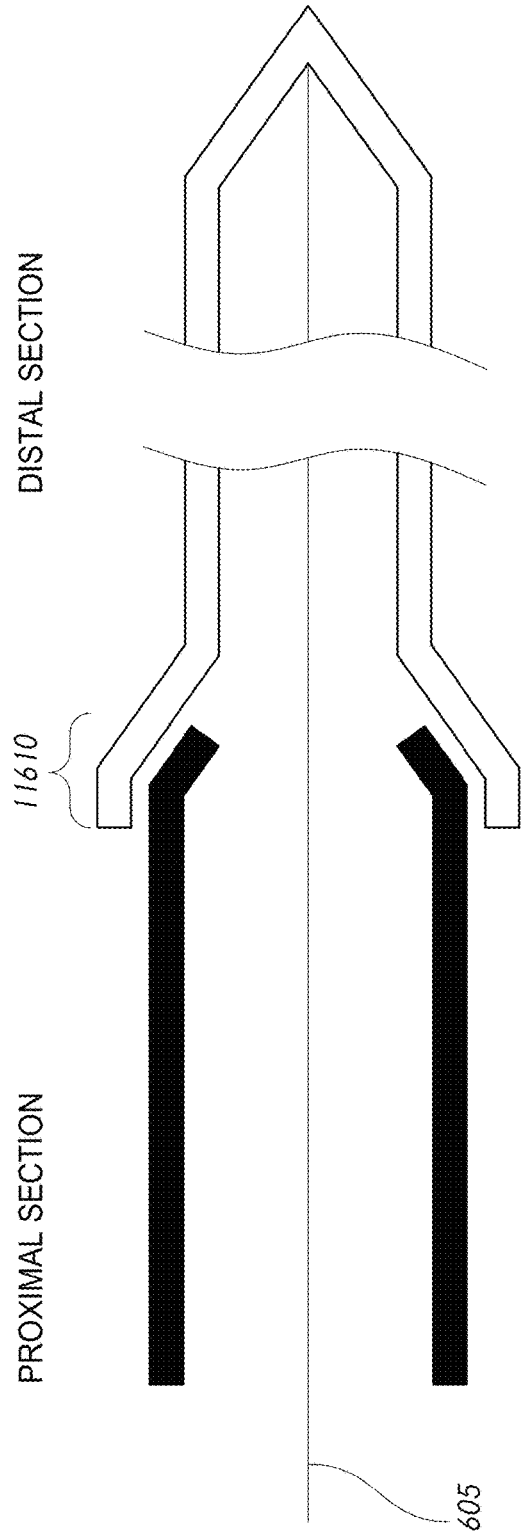
Figure 116B:
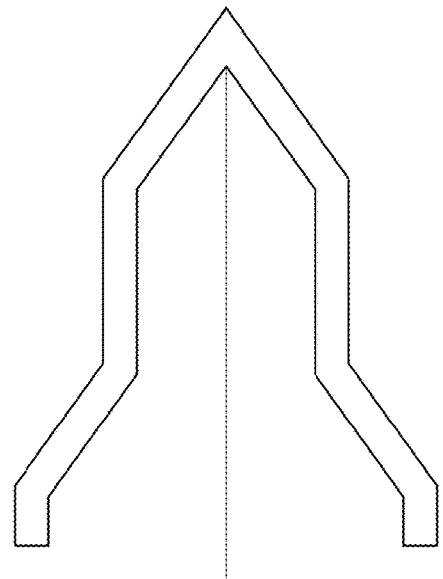

In some embodiments, the catheter could also be designed to selectively create or allow slack between the distal end and proximal end of the catheter. One embodiment of a catheter with a distal segment and a proximal segment is shown in FIGS. 116A and 116B. In one embodiment, a tension wire or tether 11605 runs from the distal segment to the proximal segment. When placed in tension, this wire or tether 11605 can pull the distal segment towards the proximal segment. A mechanical interface 11610 (e.g., a tapered end of the proximal section and a flared end of the distal section), can align the two segments and prevent or inhibit the distal segment from sliding over the proximal segment. During access and navigation of the catheter, the tension wire or tether 11605 can be placed in tension; however, during treatment (e.g., ablation dosage), the tension can be released and the wire or tether 11605 can act as the tether connecting the two segments. The mechanical interface 11610 may be formed by any corresponding mechanical structures (e.g., notch/protrusion, latches) or adhesive structures.

Figure 117:
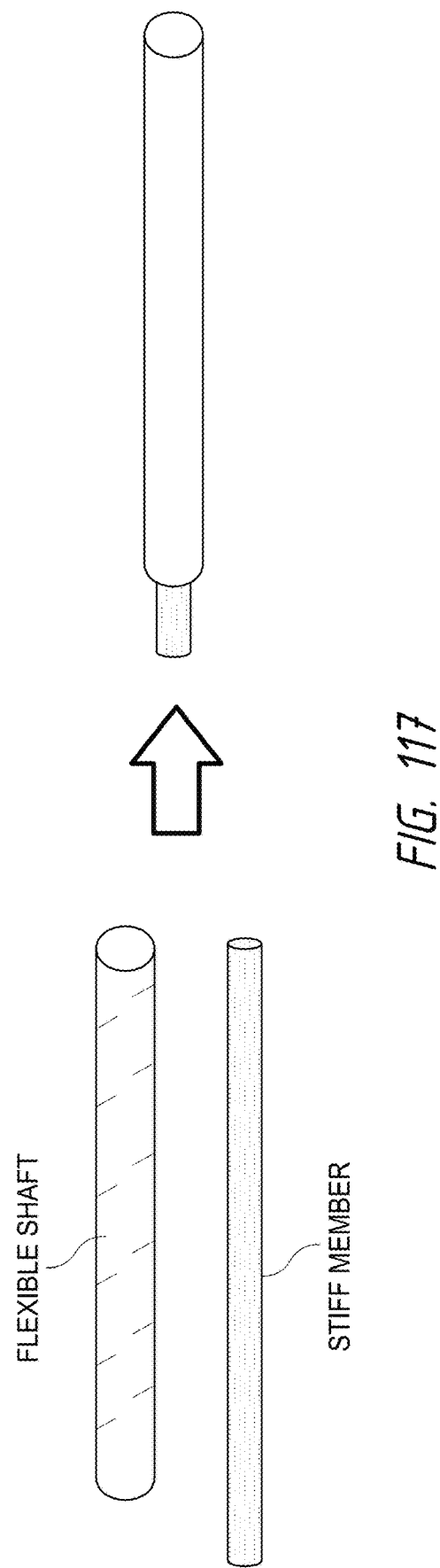

In accordance with some embodiments, flexibility of the catheter allows slack to be added to the system, but also decreases push-efficiency and reduces the catheter's ability to access the hepatic arteries. In some embodiments, a mechanism for switching between a flexible and a stiff configuration is advantageously provided. One embodiment of such a switching mechanism involves moving a stiff member 11705 axially into or out of a nominally flexible catheter shaft 11710, thereby defining a selectably stiff region, as illustrated in FIG. 117. For example, the stiff member could comprise a removable guidewire.

Figure 118:
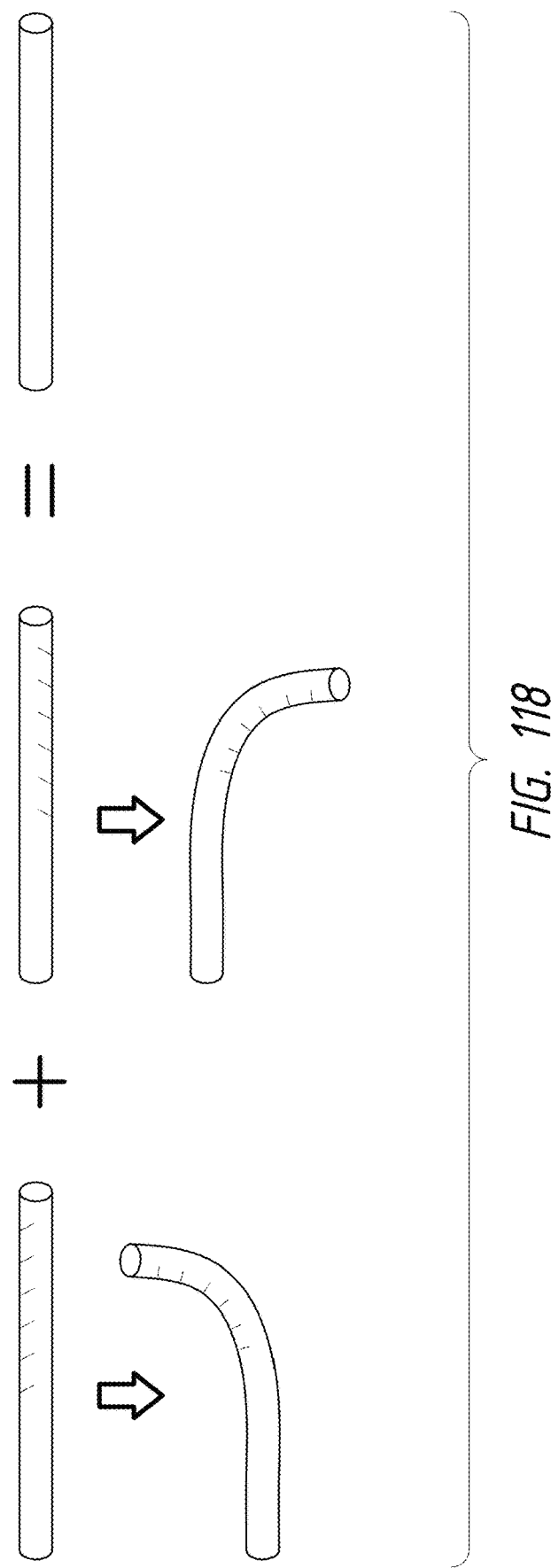

In one embodiment, the switching mechanism involves combining two coaxial members having a flexible region and a singular bending plane, e.g., rotatable members that are flexible in a singular direction, as illustrated in FIG. 118. When the flexible directions of the two rotatable members are aligned, the catheter portion is flexible, and when the rotatable members are rotated relative to each other substantially along their longitudinal axes such that their flexible directions are out of alignment, the catheter portion is stiff or substantially rigid.

Through various studies of the common hepatic artery anatomy, there seems to be greater variation in motion as one proceeds distally down the length of the common hepatic artery, which makes sense physiologically, since more distal points are closer to the diaphragm, which is causing such variation. In some embodiments, catheter stiffness may be varied along its length to compensate for the variation in anticipated motion of the target vessel (e.g., common hepatic artery) due to respiratory motion. One or more portions of the catheter length configured to be positioned in portions of the vessel likely to experience greater movement due to respiration may be constructed to have greater axial compliance, thereby allowing the portion of the catheter to move and stretch with the vessel. In one embodiment, the catheter may have an axial stiffness gradient along the length of the catheter by using alloys that allow for change in stiffness with relative composition of different metals. In one embodiment, the same material (e.g., metal) is used but the thickness of the catheter wall is tapered along its length. In one embodiment, material composition or amount may be changed at discrete locations or "links" along the length of the catheter. In some embodiments, the stiffness of a catheter configured to access and target the common hepatic artery decreases along the length of the catheter from proximal to distal at the portion of the catheter configured to be positioned within the common hepatic artery. In one embodiment, the catheter comprises multiple electrodes positioned at different points along the length of the catheter, and thus at different points of catheter stiffness. The more distal electrodes could track with greater respiratory movement than the more proximal electrodes. Keeping the position of the electrodes stationary may allow for a more consistent spacing between ablations, potentially allowing patients with shorter vessels to achieve more ablations.

In some embodiments, energy delivery may be gated based on respiration using temperature or impedance measurements due to the asymmetric motion of an energy delivery element during a respiratory cycle. The energy delivery element may remain relatively stationary for about two-thirds of the respiratory cycle (expiration) and during this time period the tissue being treated may increase in temperature. When the energy delivery element is in motion during the other third of the respiratory cycle (inspiration), the tissue may cool down. The changes in temperature may be monitored and used to gate the delivery of energy so that energy is only delivered when the energy delivery element is stationary (e.g., during expiration) or power may be increased during the stationary period to maintain a desired average power level (e.g., 10 Watts). Because tissue impedance varies with temperature, impedance measurements could be monitored (either alternatively or in combination with temperature) and used to start and stop the energy delivery. In situations where variation in temperature and/or impedance measurements is not detected, power may be delivered at a constant rate.

In such embodiments in which power output is synchronized with respiration, the ramp of the energy source may be adjusted to achieve an almost instantaneous climb of power. The adjustment may be performed by modifying a ramping algorithm of the energy source. In some embodiments, the energy source may be programmed to ramp up from a power output below 1 W to a peak power output in less than half a second. In accordance with several embodiments, synchronization of power output with respiration takes advantage of the time frame when blood flow in the vessel (e.g., common hepatic artery) is at a maximum, thereby providing enhanced cooling to the energy delivery element and vessel wall, which may reduce charring, notching and vessel spasm.

C. Contact Assessment

In some embodiments, feedback and/or evaluative measures are provided for assessing the quality and/or magnitude of wall contact. For example, fluoroscopic imaging (e.g., angiography) can be used to assess the magnitude of lumen indentation caused by the contact of an electrode against a vessel (e.g., arterial) wall. The indentation size may be directly correlated to the contact force. Additionally, because there is a significant difference between blood and arterial resistivity and permittivity, the electrode impedance can be used as an indicator of contact force, with increased impedance generally correlated with improved contact. Prior to initiating an ablation, a test current can be applied by a generator to measure the impedance of the tissue immediately surrounding the electrode. Complex impedance can be obtained based on electromagnetic property measurements obtained using a single main electrode (monopolar), a split electrode (bipolar), one or more coils (e.g., loops or solenoids), one or more giant magneto resistance devices or other sensors positioned on the neuromodulation device or on separate adjunctive sensors. The complex impedance can be determined based on current, voltage, resistance and/or power measurements available from the generator. The contact sensing methods may use existing frequency content of an energy delivery signal (e.g., ablation signal) provided by the generator. The treatment electrode(s) may be used to perform contact sensing or adjunctive sensors or electrodes may be used. In some embodiments, the frequency used for contact sensing may range from 500 kHz to 10 MHz, which may be within or above the treatment frequency range. In other embodiments, the frequency used for contact sensing may range from 500 kHz to 100 MHz In one embodiment, the sensing frequency is different from the ablation frequency. In some embodiments, loss tangent, magnetic permeability, action potentials and/or components of complex impedance (e.g., resistance and reactance or magnitude and phase angle) are calculated and used to determine contact level. Contact sensing may also be determined based on thermal response using one or more temperature sensors positioned along the neuromodulation device or on stand-alone device(s). For example, an impulse or step response can be measured to facilitate contact assessment. In some embodiments, affirmative contact is not required because contact is guaranteed by a particular design of an intravascular neuromodulation device.

In various embodiments, two electrode elements are provided in close proximity to each other, separated by an adhesive or insulation layer. The at least two electrode elements may be connected in parallel for therapeutic power delivery in a unipolar mode, where the current return path is provided either by a ground pad, indifferent electrode or other return electrode remote from the treatment site. The at least two electrode elements can be excited in a differential or bipolar mode to provide sensing information related to the composition of tissue proximate the electrode elements. In some embodiments, the sensing information (signal) is used to assess the degree of contact between the electrode assembly and the vessel wall. In other embodiments, the sensing signal is used to assess the change in temperature of the tissue proximate the electrode assembly. In still other embodiments, the sensing signal is used to assess the distance between the electrode assembly and a tissue or structure.

In some embodiments, at least two electrode elements are created by splitting a larger electrode into sections of conductive material separated by thermally and/or electrically insulating material. In one embodiment, the larger electrode is substantially cylindrical. In another embodiment, the electrode is substantially spherical. In yet another embodiment, the electrode is comprised of separate cylindrical or spherical elements positioned adjacent to each other. In one embodiment, a first electrode element is positioned between a second and third electrode element. The second and third electrode elements may be connected in parallel. In various embodiments, the electrode elements are distributed coaxially along a shaft of a catheter. In some embodiments, the electrode elements are distributed longitudinally or circumferentially on a shaft of a catheter. In some embodiments, a first electrode element may be substantially contained within a second electrode element.

Figure 119C:
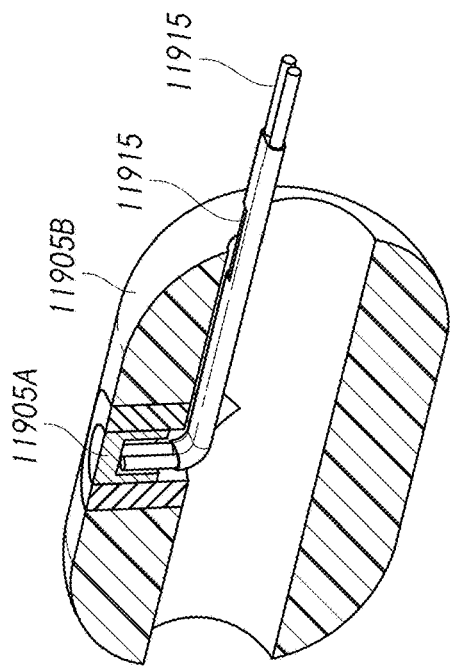
FIGS. 119A-119D illustrate embodiments of split electrode assemblies for tissue contact sensing.
Figure 119D:
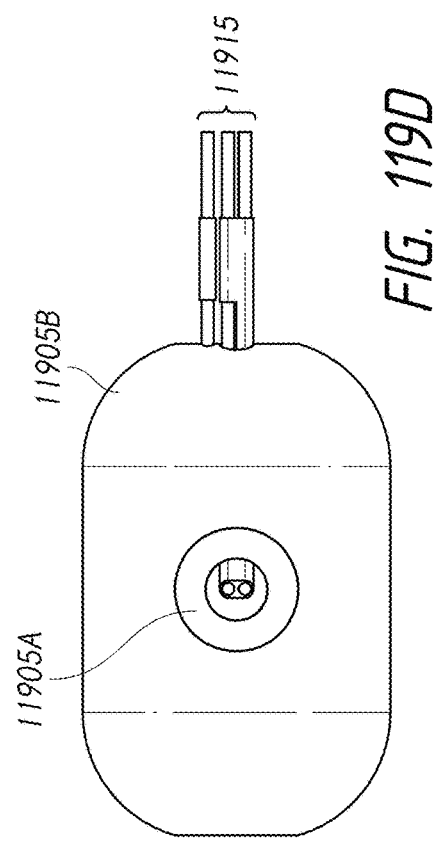
Figure 119A:
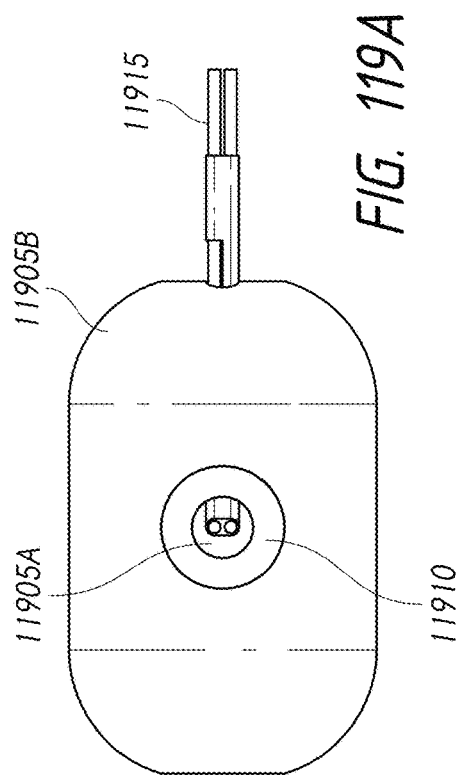
Figure 119B:
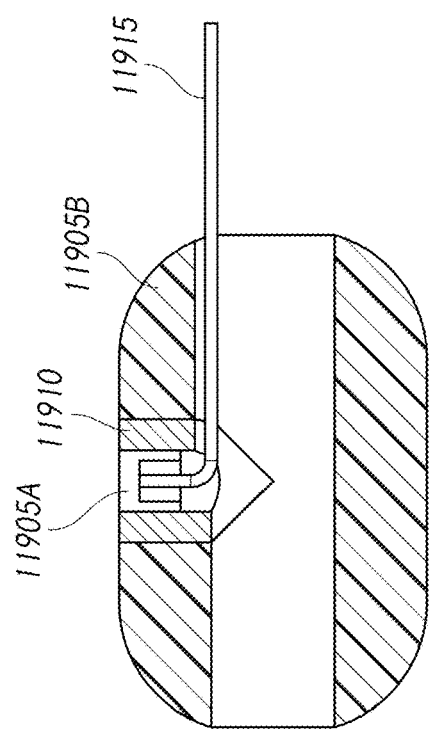

FIGS. 119A-119D illustrate embodiments of an electrode configuration or assembly adapted to provide power delivery for treatment (e.g., ablation or other neuromodulation) and tissue contact sensing comprising two coaxial electrodes. In the illustrated embodiment, a first electrode element 11905A is substantially contained within a second electrode element 11905B in a concentric manner. FIG. 119A is a top view, FIG. 119B is a cross-sectional side view and FIG. 119C is a cross-sectional isometric view of one embodiment of an electrode assembly configured for providing power delivery and tissue contact sensing. FIG. 119D is a top view of a second embodiment of an electrode assembly configured for providing power delivery and tissue contact sensing. In the illustrated embodiment, a first electrode element 11905A forms a circular aperture in a wall of a second electrode element 11905B such that the first electrode element is concentrically positioned within the second electrode element. In some embodiments, at least one of the electrode elements 11905 is configured to be placed near or in contact with the area or region where the electrode assembly contacts the vessel wall. The first electrode element 11905A may be substantially circular or spherical, polygonal, disk shaped or other regular geometric form. The electrode elements 11905 are separated by an electrically and/or thermally insulating material 11910. In some embodiments, the electrically and/or thermally insulating material 11910 may be formed from adhesives, polymers or ceramics selected from a group including, without limitation, delrin, epoxy, nylon, polyurethane, alumina, aluminum oxide, macor, polyethylene, cyano acrylate, acetal, PTFE, PFA, FEP and PEEK. In some embodiments, the shaft provides electrical and/or thermal isolation.

FIGS. 119A-119C illustrate two connecting wires 11915 connecting to the electrode elements 11905. FIG. 119C illustrates that the covering of one of the connecting wires 11915 (e.g., a copper wire) may include a slot 11916 such that a connection may be formed with the first electrode element 11905A and the second electrode element 11905B using a single connecting wire. In some embodiments, ablation current and sensing current can be apportioned among the electrode elements by providing separate connecting wires 11915 for each element, as shown for example in the embodiment illustrated in FIG. 119D. Filtering, modulation and multiplexing methods can be used to distribute power to the various connecting wires 11915. In one embodiment, the connecting wires 11915 in electrical contact with an electrode element form a thermocouple or other temperature measuring apparatus. In another embodiment, the connecting wire(s) 11915 to an electrode element is a single conductor. A non-limiting example of such connecting wire arrangement is to provide a thermocouple lead (e.g., 40 gauge T-type thermocouple lead) to the smaller of the electrode elements 11905A near the vessel wall contact area of the electrode assembly and a single power lead (e.g., 40 Gauge copper wire) to the surrounding electrode element 11905B. In some embodiments, ablative power (e.g., 5 W-20 W, 5 W-15 W, 8 W-12 W, 10 W-20 W) at a frequency between 400 kHz-650 kHz (e.g., 400 kHz, 450 kHz, 500 KHz, 550 kHz, 600 kHz, 650 kHz) may be delivered to the larger or both of the electrode elements in a unipolar mode (e.g., common mode signals delivered to both electrode elements with return signals going to a ground pad or indifferent electrode), while sensing signals (e.g., 1-20 mA (such as 10 mA) of current at 1 MHz to 100 MHz (e.g., 1 MHz to 10 MHz, 5 MHz to 15 MHz, 10 MHz, 15 MHz to 50 MHz, 30 MHz to 60 MHz, 50 MHZ to 100 MHz) may be delivered between the two electrode elements in a bipolar mode. Other power levels, current levels or frequencies may be used as desired and/or required. In accordance with several embodiments, the frequencies for sensing are outside the range of the frequencies used for ablative power. The complex impedance, phase, loss tangent, reactance and resistance of the sensing current can be analyzed at high sensitivity for the adjacent tissue. Sensing current may be provided at multiple frequencies and impedance can be compared or combined into a composite parameter describing the tissue contact. Sensing current may be analyzed in the time domain or the frequency domain. The sensing waveform may be swept, narrow band broad band, pulsed, square wave, chirp, frequency modulated, multitonal, or other suitable waveforms. A sensing system may comprise an external driver and generator to separate the frequencies of the sensing signals between the two electrodes. The sensing system may comprise common mode choke(s), high pass, low pass and/or band pass filters or other filtering circuitry. The sensing system may comprise a processing device adapted to determine whether a sufficient amount of contact exists or to determine a quantitative level of tissue contact based on tissue contact measurements received from the electrode assembly. The processing device may generate an output indicative of contact or the level of tissue contact for display or other output to a user. The tissue contact measurements may comprise bipolar contact impedance measurements or temperature measurements. The contact sensing features and embodiments described in connection with FIGS. 119A-119D may be incorporated into any of the neuromodulation devices (e.g., treatment catheters, ablation catheters or other devices) described herein.

In some embodiments, a temperature sensing device may be provided within a first electrode element in a manner to provide high thermal response and high sensitivity to the surrounding tissue. Temperature sensors may be comprised of thermocouples, resistance temperature detectors (RTDs), thermistors, fluoroptic temperature sensors, Fabry-Perot temperature sensors or other suitable sensors. In one embodiment, power delivered in a unipolar mode through at least one electrode element causes modest, benign, local heating of the tissue proximate the temperature sensor. The rate or magnitude of temperature change as measured by the sensor reflects the degree of contact with tissue or blood. Small contact area and low thermal mass and insulation from non-sensing surfaces increase responsiveness and sensitivity. In one non limiting example, a 40 Gauge type T thermocouple lead is connected to the smaller of the electrode elements 11905A near the vessel wall contact area of the electrode and a single 40 Gauge copper wire is connected to the surrounding electrode element 11905B. Other types or sizes of temperature-measurement devices or wires may be used as desired and/or required. In one embodiment, 1 W of power is delivered in a unipolar or bipolar mode through the electrode elements. The magnitude or rate of temperature rise or decay is taken as an indication of vessel wall contact. Other power levels may be used as desired and/or required.

In some embodiments, fiberoptic sensors may be configured proximate an electrode to measure reflected light from blood or tissue at or near the contact area of the electrode. A non-limiting example of a fiberoptic sensor is as follows: Blood is known to contain a high concentration of hemoglobin. Hemoglobin may exist as oxyhemoglobin or deoxyhemoglobin, oxyhemoglobin being generally more prevalent in the arterial system. Both of these compounds and blood as a whole have well characterized absorption and scattering spectra. The absorption and scattering spectra of arterial vessel walls are also well described, although some variability exists due to various diseases of the vessel wall such as atherosclerosis. As optical characteristics of blood are more consistent, an algorithm compares the measured intensity of reflected light to provide a measure of deviation from the expected values for blood. High deviation is associated with vessel wall contact whereas low deviation is associated with blood contact. Red and green wavelengths may be selected for comparison due to the characteristic red color of blood.

Figure 120A:
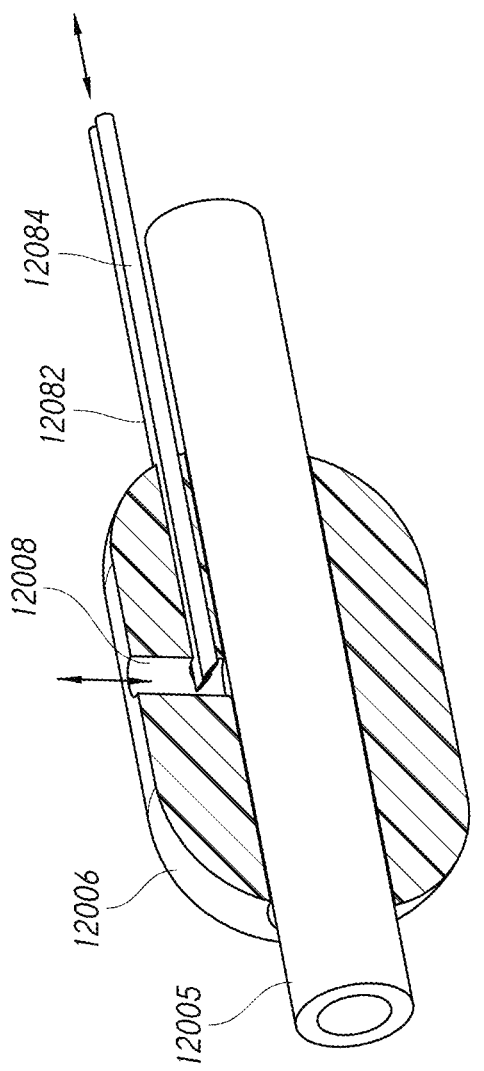
FIGS. 120A and 120B illustrate an embodiment of a fiberoptic sensor for tissue contact sensing.
Figure 120B:
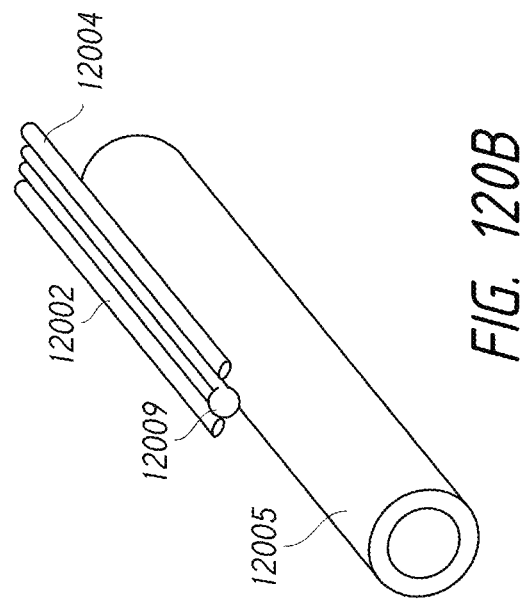

FIGS. 120A and 120B illustrate an embodiment of a neuromodulation device comprising an optical sensor 12000 for tissue contact sensing. The optical sensor 12000 may be incorporated into any of the neuromodulation devices (e.g., treatment catheters, ablation catheters or other devices described herein). The optical sensor 12000 may comprise at least one illumination fiber 12002 and at least one sensing fiber 12004 along or in a catheter or elongated body 12005 of the neuromodulation device that terminate in the electrode 12006. The electrode 12006 may be constructed to have an optical window or side port 12008 near the contact area of the electrode 12006 and vessel wall. The optical fibers 12002, 12004 may be cut at an angle (e.g., 45 degree angle) and the distal tips may be coated with a reflective material (e.g., mirrored coating) to direct both incident and reflected light laterally towards the vessel wall and perpendicular to the fibers 12002, 12004. The optical window 12008, together with the cut ends of the fibers 12002, 12004 may be encapsulated with optical adhesive (e.g., epoxy) having a refractive index similar to the fibers 12002, 12004 in order to improve transmission of incident and reflected light into the tissue. The optical adhesive is not shown in FIG. 120A because it would obscure the view of the optical fibers 12002, 12004. If the optical adhesive has the same index of refraction as the optical fibers 12002, 12004, the light will reflect off of the coating and travel across the boundary between the fibers and the optical adhesive as though it wasn't there. One example is "optical epoxy" or "optical adhesive." In various embodiments, the coating comprises a very thin coating of metal (such as nickel, silver, aluminum and/or the like).

An optical sensing control and/or detection unit external to the body may provide illumination and detection at at least one wavelength. Illumination may be broad band or white light or may be at a single or finite number of wavelengths. Illumination sources may include lasers, light emitting diodes (LEDs), superluminescent diodes, laser diodes, halogen or xenon bulbs or other suitable sources. Detectors may include narrow band or broad band detectors, with or without optical filters. FIG. 120B shows that a thermocouple lead 12009 may run along the catheter (for example in between the optical fibers 12002, 12004). The thermocouple lead may be coupled to the electrode 12006 or may rest within the optical window 12008 of the electrode 12006 (not shown in FIG. 120B).

Other embodiments may employ other types of optical detection including fluorescence, spectroscopy, ultraviolet/visible reflectance spectroscopy, Raman spectroscopy, backscatter analysis or other methods. Separation of the illumination and sensing fibers may advantageously provide measurement of the different degrees of specular and diffuse reflection from the vessel compared to blood.

Figure 121:
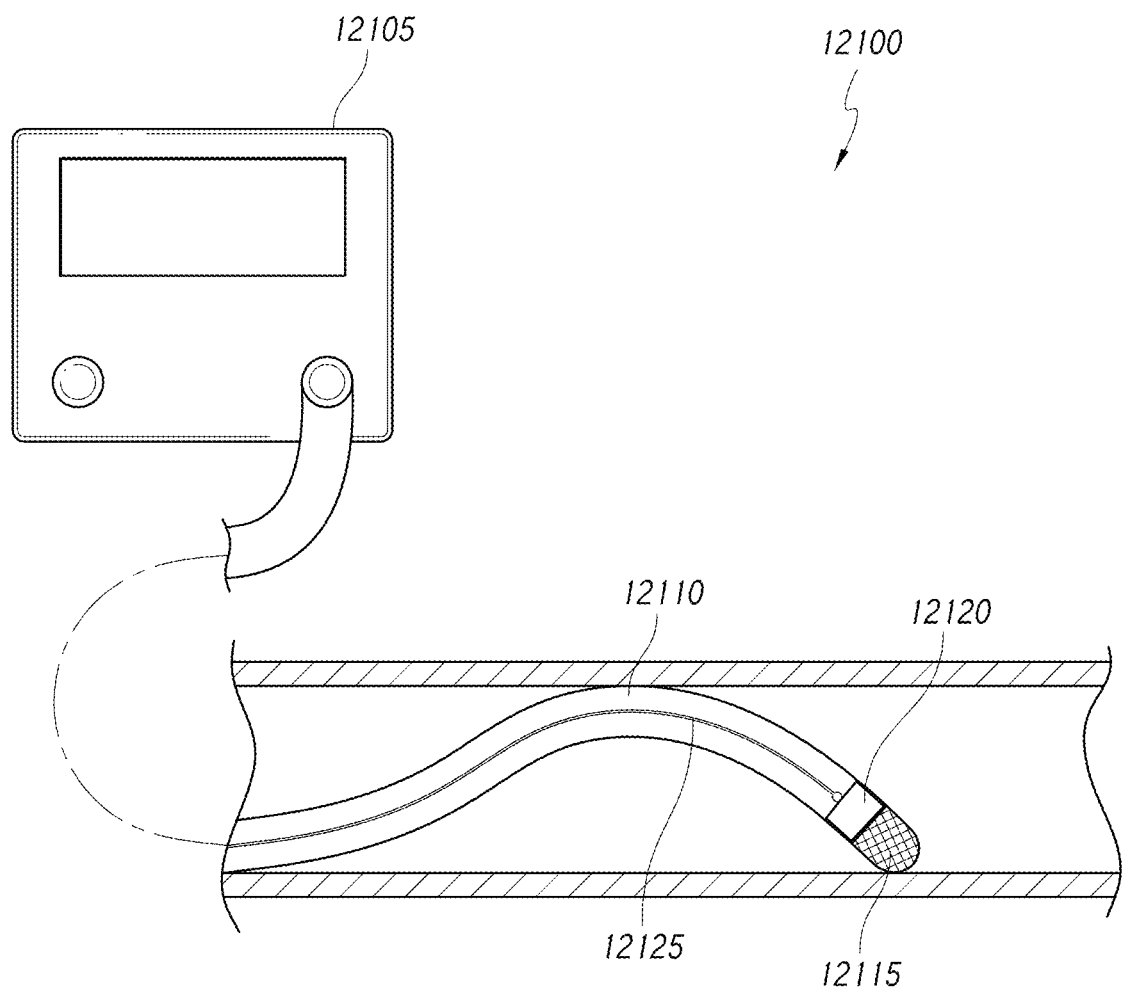
FIG. 121 illustrates an embodiment of a system comprising a controller (e.g., generator) positioned outside of a subject's body that is communicatively coupled (via wired or wireless connection) to an energy delivery device.

In some embodiments, a pressure, force or contact sensor is incorporated directly onto or adjacent the catheter tip, such as the FlexiForce® Force Sensor (Tekscan Inc., South Boston, MA). In some embodiments, the contact force may be displayed on a display of a neuromodulation system (e.g., RF energy delivery) system. In some embodiments, an alert or warning may be provided audibly or visually when the contact force goes above or below a threshold range. Contact of the energy delivery member (e.g., electrode) may be adjusted (manually or automatically) based on feedback (e.g., measurements) received from the sensor. For example, FIG. 121 illustrates an embodiment of a system 12100 comprising a controller 12105 (e.g., generator) positioned outside of a subject's body that is communicatively coupled (via wired or wireless connection) to an energy delivery device 12110. The energy delivery device 12110 includes an energy delivery element 12115 (e.g., electrode) at a distal tip of the energy delivery device 12110 and a force sensor 12120 adjacent the energy delivery element 12115 to sense force exerted by the energy delivery element 12115 on a vessel wall. In the illustrated embodiment, the distal end portion of the energy delivery device 12110 is deflectable via a deflection or actuation wire 12125. A tension force of the wire 12125 may be adjusted based on feedback received from the sensor 12120 in order to maintain a preferred contact force (even during respiration and/or blood flow cycles). The adjustment of the tension force of the wire 12125 may be performed automatically by one or more computing or processing devices of the controller 12105 or manually by an operator. The maintained contact force may advantageously facilitate consistent lesion creation for ablative energy delivery embodiments. The force sensor may also provide real-time feedback of lesion creation due to heat changes resulting from tissue stiffness. The controller 12105 may include a display (e.g., a graphical user interface on a monitor or screen) to display the contact force or temperatures or may cause the contact force or temperature measurements to be displayed on a separate display device. In some embodiments, ultrasound modalities are used to perform contact sensing. For example, ultrasound elastography or ultrasound imaging (e.g., A-mode, B-mode, 3D, Doppler, or interference pattern imaging) may be used to provide an indication of contact state or other contact assessment between a treatment element of a neuromodulation device (e.g., ablation catheter) and target tissue (e.g., vessel wall). Acoustic sensors (such as piezoelectric, capacitive, passive low frequency, mechanical or phased array, beam pattern, IVUS, TEE, TTE, HIFU, fuel gauge, actuators) may be used to provide contact assessment. In some embodiments, optical sensors or sensing methods are used to provide contact assessment. Mechanical devices and methods may also be used to evaluate, for example, elasticity, plasticity, complex impedance (storage modulus/loss modulus), dynamic mechanical analysis (DMA/DMTA), high frequency/low frequency, chirp, or force. Force may be measured by a strain gauge, spring, capacitive sensor, piezo sensor, or displacement transducer.

In various embodiments, contact is required to be above a threshold level prior to initiation of energy delivery. In some embodiments, contact level is continuously monitored during treatment. If the contact level falls below or rises above a threshold level, the controller 12105 may generate an alert to cause a user to terminate the treatment procedure or adjust treatment parameters or the controller 12105 may automatically terminate the treatment procedure or adjust treatment parameters. The controller 12105 may be located within a power or energy source (e.g., a generator) or may be a separate component within a sensing unit or control unit.

IV. Image Guidance, Mapping and Selective Positioning

A. Image Guidance

Image guidance techniques may be used in accordance with several of the embodiments disclosed herein. For example, a visualization element (e.g., a fiber optic scope) may be provided in combination with a catheter-based energy or fluid delivery system to aid in delivery and alignment of a neuromodulation catheter. In other embodiments, fluoroscopic, ultrasound, Doppler or other imaging is used to aid in delivery and alignment of the neuromodulation catheter. In some embodiments, radiopaque markers are located at the distal end of the neuromodulation catheter or at one or more locations along the length of the neuromodulation catheter. For example, for catheters having electrodes, at least one of the electrodes may comprise a radiopaque material. In one embodiment, a proximal radiopaque marker is positioned so as to identify sufficient extension beyond a distal end of the guide catheter. In one embodiment, a distal radiopaque marker indicates registration of axial catheter position with respect to an anatomical landmark (for example, distal bifurcation between the common hepatic artery and the splenic artery or between the hepatic artery proper and the gastroduodenal artery. Computed tomography (CT), fluorescence, radiographic, thermography, Doppler, optical coherence tomography (OCT), intravascular ultrasound (IVUS), and/or magnetic resonance (MR) imaging systems, with or without contrast agents or molecular imaging agents, can also be used to provide image guidance of a neuromodulation catheter system. In some embodiments, the neuromodulation catheter comprises one or more lumens for insertion of imaging, visualization, light delivery, aspiration or other devices.

In accordance with some embodiments, image or visualization techniques and systems are used to provide confirmation of disruption (e.g., ablation, destruction, severance, denervation) of the nerve fibers being targeted. In some embodiments, the neuromodulation catheter comprises one or more sensors (e.g., sensor electrodes) that are used to provide confirmation of disruption (e.g., ablation, destruction, severance, denervation) of communication of the nerve fibers being targeted. Sensors may include but are not limited to: imaging sensors, temperature sensors, impedance sensors, optical sensors, electromagnetic sensors, force sensors, pressure sensors, blood sensors or other sensors configured to measure other treatment or tissue parameters. Treatment or patient parameters may be monitored based on signals received from one or more sensors. The sensors may provide information regarding patient or treatment parameters (such as tissue temperature, treatment element temperature, tissue impedance, blood temperature, blood pressure, contact pressure, blood flow levels, blood sugar levels, triglyceride levels, insulin levels, glucagon levels, norepinephrine levels, lipid levels, gastrointestinal hormone levels, or combinations of two, three or more of any of the foregoing parameters.

B. Mapping

In some embodiments, the sympathetic and parasympathetic nerves are mapped prior to modulation. In some embodiments, a sensor catheter is inserted within the lumen of the vessel near a target modulation area. The sensor catheter may comprise one sensor member or a plurality of sensors distributed along the length of the catheter body. After the sensor catheter is in place, either the sympathetic nerves or the parasympathetic nerves may be stimulated. In some embodiments, the sensor catheter is configured to detect electrical activity. In some embodiments, when the sympathetic nerves are artificially stimulated and parasympathetic nerves are left static, the sensor catheter detects increased electrical activity and the data obtained from the sensor catheter is used to map the sympathetic nervous geometry. In some embodiments, when the parasympathetic nerves are artificially stimulated and sympathetic nerves are left static, the sensor catheter detects increased electrical activity and the data obtained from the sensor catheter is used to map the parasympathetic nervous geometry. In some embodiments, mapping the nervous geometry using nervous stimulation and the sensor catheter advantageously facilitates improved or more informed selection of the target area to modulate, leaving select nerves viable while selectively ablating and disrupting others. As an example of one embodiment, to selectively ablate sympathetic nerves, the sympathetic nerves may be artificially stimulated while a sensor catheter, already inserted, detects and maps areas of increased electrical activity. To disrupt the sympathetic nerves, only the areas registering increased electrical activity may need to be ablated.

In one embodiment, a method of targeting sympathetic nerve fibers involves the use of electrophysiology mapping tools. While applying central or peripheral nervous signals intended to increase sympathetic activity (e.g., by administering noradrenaline or electrical stimulation), a sensing catheter may be used to map the geometry of the target vessel (e.g., hepatic artery) and highlight areas of increased electrical activity. An ablation catheter may then be introduced and activated to ablate the mapped areas of increased electrical activity, as the areas of increased electrical activity are likely to be innervated predominantly by sympathetic nerve fibers. In some embodiments, nerve injury monitoring (NIM) methods and devices are used to provide feedback regarding device proximity to sympathetic nerves located perivascularly. In one embodiment, a NIM electrode is connected laparascopically or thorascopically to sympathetic ganglia.

C. Selective Positioning

In some embodiments, to selectively target the sympathetic nerves, local conductivity may be monitored around the perimeter of the hepatic artery. Locations corresponding to maximum impedance are likely to correspond to the location of the sympathetic nerve fibers, as they are furthest away from the bile duct and portal vein, which course posterior to the hepatic artery and which are highly conductive compared to other tissue surrounding the portal triad. In some methods, to selectively disrupt sympathetic nerves, locations with increased impedance are selectively modulated (e.g., ablated). In some embodiments, one or more return electrodes are placed in the portal vein and/or bile duct to enhance the impedance effects observed in sympathetic nervous tissues. In some embodiments, return electrodes are placed on areas of the skin perfused with large veins and having decreased fat and/or non-vascular tissues (such as the neck or wrist, etc.). The resistance between the portal vein and other veins may be very low because of the increased electrical conductivity of blood relative to other tissues. Therefore, the impedance effects may be enhanced because comparatively small changes in resistance between various positions on the hepatic artery and the portal vein are likely to have a relatively large impact on the overall resistance registered.

In some embodiments, impedance and/or temperature may be measured with a reference transducer placed near the midpoint between adjacent lesions in order to help form continuous lesions with minimal overlap. In some embodiments, impedance is measured with reference to a ground electrode or a local bipolar reference electrode. Impedance changes as the lesion approaches the reference electrode. As one example, if two lesions are placed 5-10 mm apart axially and/or circumferentially along a vessel, a reference transducer may be positioned along a shaft of an ablation catheter at position corresponding to the desired extent of the lesion (e.g., approximately 2.5 mm-5 mm). The reference transducer may be configured to be placed in contact with the vessel wall. In some embodiments, impedance is measured at a different frequency than the ablation frequency. The reference transducer may be filtered to selectively measure the reference signal. In some embodiments, the reference transducer has high input impedance to avoid distorting the ablation field. In other embodiments, the reference transducer is gated so that impedance measurements are interleaved with an ablation signal.

In some embodiments, the sympathetic nerves are targeted locationally. It may be observed in some subjects that sympathetic nerve fibers tend to run along a significant length of the proper hepatic artery while the parasympathetic nerve fibers tend to join towards the distal extent of the proper hepatic artery. In some embodiments, sympathetic nerves are targeted by ablating the proper hepatic artery towards its proximal extent (e.g., generally half-way between the first branch of the celiac artery and the first branch of the common hepatic artery or about one centimeter, about two centimeters, about three centimeters, about four centimeters, or about five centimeters beyond the proper hepatic artery branch). Locational targeting may be advantageous because it can avoid damage to critical structures such as the bile duct and portal vein, which generally approach the hepatic artery as it courses distally towards the liver.

Figure 122:
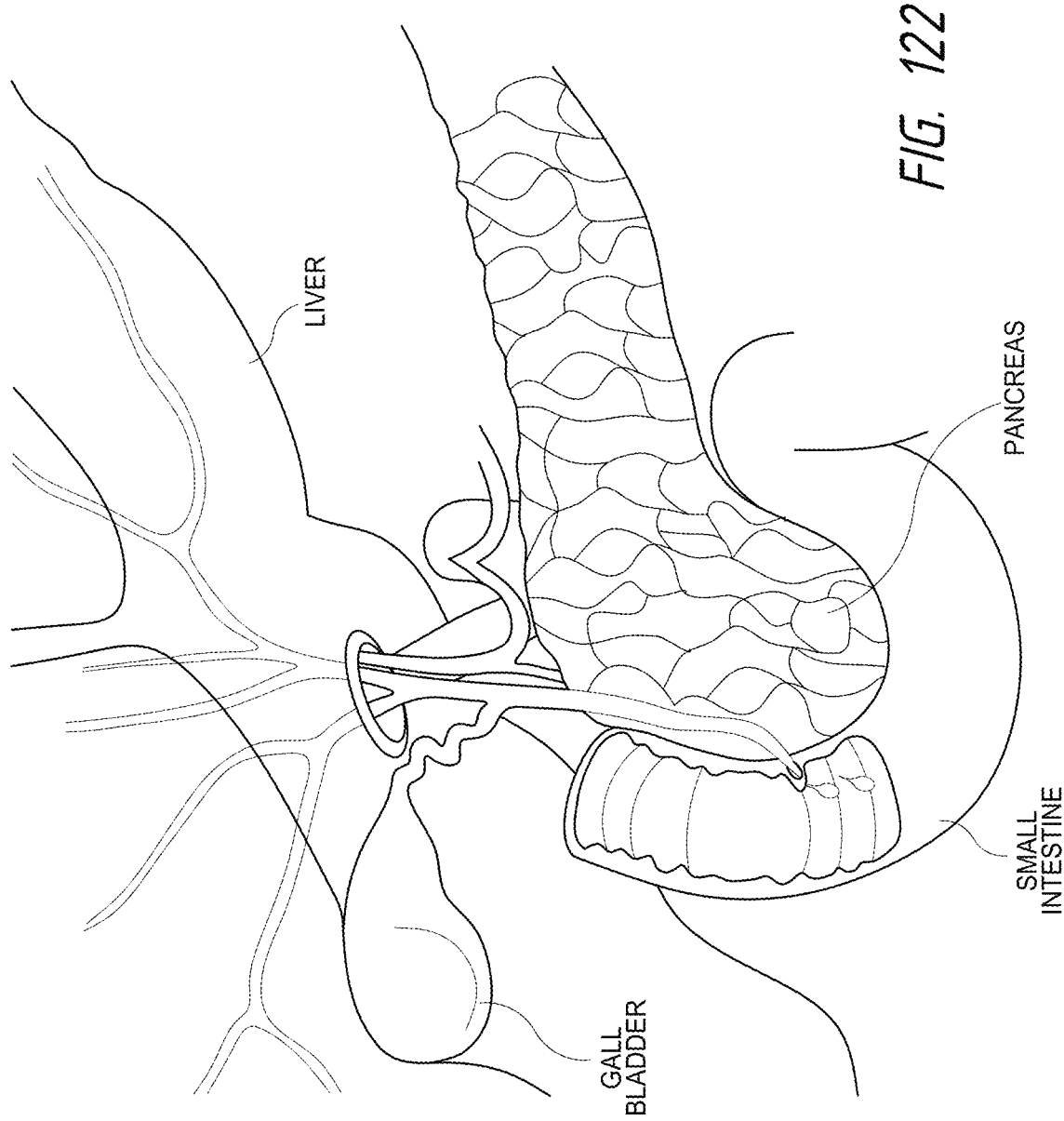
FIG. 122 illustrates a portion of a human anatomy surrounding the liver.

FIG. 122 illustrates a schematic representation of organs adjacent to the liver (e.g., gall bladder, pancreas, stomach). In accordance with several embodiments of the invention, the catheters and procedures described herein may prevent or reduce the likelihood of collateral damage to organs or tissue surrounding the liver (e.g., bile duct, portal vein, pancreas, stomach) during neuromodulation (e.g., RF electrode ablation) of the nerves within or surrounding the hepatic arteries. In various embodiments, the catheters and methods of use described herein can prevent or reduce the likelihood of biliary stenosis, portal vein thrombosis, or pancreatitis. In some embodiments, energy is directed away from the bile duct, portal vein, pancreas, and/or other organs or tissues using bipolar energy delivery devices and methods. In some embodiments, bipolar devices and methods limits the impact of adjacent structures (e.g., bile duct and portal vein) on an ablation region and prevents or inhibits energy from tracking towards the adjacent structures.

In one embodiment, biliary protectant (e.g., a nonconductive, insulating substance) is injected percutaneously into the gall bladder or via endoscopic retrograde cholangiopancreatography (ERCP). In one embodiment, a cooled solution is injected into the biliary tree by the same means. In one embodiment, an insulating "ring" around the artery is injected, similar to hydrodissection but with a non-conductive biocompatible substance (e.g., a polyethylene glycol (PEG) hydrogel).

One method of decreasing likelihood of collateral damage to the gall bladder or other organs in the proximity of the hepatic arteries is to administer a bile acid inhibitor drug to a patient systemically before the neuromodulation procedure or to request that the patient not eat a fatty meal before the procedure in order to minimize or otherwise reduce bile secretion. Other precautionary steps could involve inducing vomiting to drain bile or administering ethanol to the patient prior to the procedure in order to cause "fatty" live protection and/or less conductivity. In one embodiment, protection of the stomach against possible collateral damage may be facilitated by having the patient swallow air or inflating the stomach to provide an air barrier to conduction in the stomach. For protection of the gall bladder, an intra-arterial catheter (e.g., having one or more magnetic portions) can be inserted within a hepatic artery or adjacent artery to "pull" the hepatic artery away from the gall bladder. External magnets may also be used to "pull" the hepatic artery away from the gall bladder.

In some embodiments, neuromodulation location is selected by relation to the vasculature's known branching structure (e.g., directly after a given branch). In some embodiments, neuromodulation location is selected by measurement (e.g., insertion of a certain number of centimeters into the target vessel). Because the relevant nervous and vessel anatomy is highly variable in humans, it may be more effective in some instances to select neuromodulation location based on a position relative to the branching anatomy, rather than based on a distance along the hepatic artery. In some subjects, nerve fiber density is qualitatively increased at branching locations.

D. Angiography

In some embodiments, a method for targeting sympathetic nerve fibers comprises assessing the geometry of arterial structures distal of the celiac axis using angiography. In one embodiment, the method comprises characterizing the geometry into any number of common variations and then selecting neuromodulation (e.g., ablation) locations based on the expected course of the parasympathetic nerve fibers for a given arterial variation. Because arterial length measurements can vary from subject to subject, in some embodiments, this method for targeting sympathetic nerve fibers is performed independent of arterial length measurements. The method may be used for example, when it is desired to denervate or ablate a region adjacent and proximal to the bifurcation of the common hepatic artery into the gastroduodenal and proper hepatic arteries.

E. Physiologic Monitoring

In the absence of nerve identification under direct observation, nerves can be identified based on their physiologic function. In some embodiments, mapping and subsequent modulation is performed using glucose and norepinephrine ("NE") levels. In some embodiments, glucose and NE levels respond with fast time constants. Accordingly, a clinician may stimulate specific areas (e.g., in different directions or circumferential clock positions or longitudinal positions) in a target artery or other vessel, monitor the physiologic response, and then modulate (e.g., ablate) only in the locations that exhibited the undesired physiologic response. Sympathetic nerves tend to run towards the anterior portion of the hepatic artery, while the parasympathetic nerves tend to run towards the posterior portion of the hepatic artery. Therefore, one may choose a location not only anterior, but also (using the aforementioned glucose and NE level measurements) a specific location in the anterior region that demonstrated the strongest physiologic response to stimulation (e.g., increase in glucose levels due to sympathetic stimulation). In some embodiments, stimulation with 0.1 s-on, 4.9 s-off, 14 Hz, 0.3 ms, 4 mA pulsed RF energy is a sympathetic activator and stimulation with 2 s-on, 3 s-off, 40 Hz, 0.3 ms, 4 mA pulsed RF energy is a parasympathetic activator. However, other parameters of RF energy or other energy types may be used.

In some embodiments, using electrical and/or positional selectivity, a clinician could apply a stimulation pulse or signal and monitor a physiologic response. Some physiologic responses that may indicate efficacy of treatment include, but are not limited to, the following: blood glucose levels, blood and/or tissue NE levels, vascular muscle tone, blood insulin levels, blood glucagon levels, blood C peptide levels, blood pressure (systolic, diastolic, average), and heart rate. In some cases, blood glucose and tissue NE levels may be the most accurate and readily measured parameters. The physiologic responses may be monitored or assessed by arterial or venous blood draws, nerve conduction studies, oral or rectal temperature readings, or percutaneous or surgical biopsy. In some embodiments, transjugular liver biopsies are taken after each incremental ablation to measure the resultant reduction in tissue NE levels and treatment may be titrated or adjusted based on the measured levels. For example, in order to measure tissue NE levels in the liver, a biopsy catheter may be inserted by a TIPS approach or other jugular access to capture a sample of liver parenchyma. In some embodiments, the vein wall of the portal vein may safely be violated to obtain the biopsy, as the vein is surrounded by the liver parenchyma, thereby preventing or inhibiting blood loss.

In various embodiments, a signal or response detected by a circuit comprised of sensing electrodes or other diagnostic members on both sides of the ablation or denervation site could be (1) impedance (e.g., a change in dynamic resistance or conductance of the circuit created) and/or (2) action potentials (e.g., the circuit could be probed with a brief voltage impulse and then electrical response monitored, since nerve fibers conduct physiologically using such action potentials). In some embodiments, physiologic responses are monitored, leading to several possibilities depending on the organ and physiology interrogated. Examples of physiologic responses include the following: (1) Liver/glucose: since stimulation of the hepatic sympathetic nerves increases net hepatic glucose production and thus systemic glucose levels, a lesser increase in blood glucose levels may be observed after denervation or ablation; (2) pancreas/insulin-glucagon: since stimulation of the pancreatic sympathetic nerves could increase insulin secretion and decrease glucagon secretion, both of these hormone levels could be measured pre and post denervation; and (3) duodenum-stomach/motility: since stimulation of the gastrointestinal (GI) sympathetics may lead to decreased motility, direct observation of motility or via a number of motility tests could be measured pre and post denervation or ablation. The systems and methods described above may be universally applicable to intravascular denervation regardless of the end organ (e.g., may apply to any organ innervated by nerves around an artery). The measurements (whether electrical or physiologic or other type) may be conducted serially during an ablation procedure, or chronically (e.g., at some period of time after the procedure), to assess success of denervation.

In embodiments involving liver, or hepatic, denervation, confirmation of denervation may be assessed by tissue norepinephrine levels. For example, the tissue norepinephrine levels may be reduced by more than 90%. In some embodiments involving hepatic denervation by ablating the common hepatic artery or other adjacent vessels, there may be a corresponding "dose-response" in the pancreas and duodenum. In other words, in some embodiments, the pancreas and/or duodenum may be sufficiently denervated (e.g., >90%) in addition to the liver being denervated, by ablating the common hepatic artery and/or surrounding vessels as described herein. Accordingly, physiologic assessments (e.g., established clinical tests or measurements) of the pancreas or duodenum that suggest impact of denervation may be used to confirm success of liver denervation. In some embodiments, ablations could be continued until an intended or expected clinical change is detected.

Clinical measurements for measuring pancreatic response affected by denervation may include oral glucose challenges and subsequent insulin response. Denervation of the pancreas in theory should lead to greater insulin secretion, and evidence of this has been observed in dog studies. Thus, multiple oral glucose challenges could be given, and blood insulin levels measured, and if the insulin levels increased, denervation success could be inferred. Clinical measurements for measuring pancreatic response may also include spot insulin measurements without glucose challenge. In some embodiments, glucagon measurements, which is a hormone secreted from the pancreas that may be affected by denervation) may be taken to confirm denervation of the liver.

Clinical measurements for measuring duodenal response may include GI motility testing, since with sympathetic denervation of the duodenum, there may be increased duodenal motility and decreased transit time. Several clinically validated tests exist to measure motility changes, including nuclear medicine tests looking at transit of radioactive food ingested, and C-acetate breath testing. In some embodiments, an endoscopy could be performed and the duodenum visualized directly to look at signs of motility changes.

In some embodiments, system-wide responses (due to possibility that afferent neural connections could be disrupted by ablating the common hepatic artery) may be measured to facilitate confirmation of liver denervation upon ablation of the common hepatic artery. Sympathetic outflow to other organs may be reduced via a reflex path from the liver to the brain to other organs. Parameters that could be affected and measured include, but are not limited to, blood pressure, heart rate and muscle sympathetic nerve activity (MSNA).

F. Sympathetic Tone Measurement

The rate at which sympathetic neurons fire under normal conditions is called the sympathetic tone. Likewise, the rate at which parasympathetic neurons fire under normal conditions is called the parasympathetic tone. Changes in the firing of the neurons, for example due to ablation or stimulation of one or more neurons, can result in changes to the tone. Tone can be measured, detected, or monitored before, during, and/or after treatment to provide information about the procedure. For example, a monitored change in sympathetic tone or physiological responses (e.g., as a way to measure tone) during or after a procedure can provide real-time verification about the efficacy of a sympathetic neuron denervation procedure. For another example, sympathetic tone can be measured before a procedure for patient screening, identifying regional locations for treatment, and the like. The measurement may be global or regional.

In some embodiments, tone can be measured using an intravascular device. For example, noradrenaline (NA) plasma concentration can be measured in an artery and/or a vein. Noradrenaline spillover can be measured throughout the vasculature, including as examples the heart (cardiac NA spillover), forearm (forearm NA spillover), kidney (renal NA spillover), liver (hepatic NA spillover), skeletal muscle vasculature, and the like. For another example, microneurography, for example, measuring MSNA, can be used to measure activity in superficial nerves. Other blood components can also be measured, for example but not limited to norepinephrine (NE). Certain blood components may be measured for the total body and/or proximate to a known or believed origination location. For example, NE may be measured proximate to a specific organ such as the lungs, which are believed to originate about 40% of NE. A measurement may be characterized by the value at a substantially steady-state condition, for example a change less than about 25%, less than about 10%, less than about 5%, etc. over a certain amount of time such as about 30 minutes, about 15 minutes, about 5 minutes, etc. Measurement in body lumens other than blood vessels is also possible. For example, urinary cathecholamines can be indicative of sympathetic tone. Body lumens in which measurement may occur include, for example, arteries, veins, chambers, arterioles, venules, ducts or tracts (e.g., urinary, gastrointestinal), pockets, tubules, and the like.

In an embodiment, a catheter is placed in a body lumen and navigated proximate to an organ. A probe may be deployed into the wall of the lumen, for example at a certain depth and/or angle. The position of the probe may be stabilized, for example by an anchor, barb, balloon, expandable cage or portion thereof, combinations thereof, and the like. The probe may receive electrophysiological signals that can be recorded, for example to generate a metric characteristic of sympathetic tone. Background signals or noise may be removed, for example, by deploying a probe to measure electrophysiological signals away from the organ. The probe may measure one or more of: blood or other fluid analyte level, blood or other fluid flow, blood or other fluid flow differential, blood oxygen saturation, blood perfusion, blood pressure, central sympathetic drive, an electroacoustic event, an electromyographic signal, evoked potential, a local field potential, a mechanomyographic signal, MSNA, nerve traffic, remote stimulation of nervous activity, temperature, tissue tone, vasodilation, vessel wall stiffness, water concentration, combinations thereof, and the like. A plurality of probes may be used to measure multiple signals or other properties, the same signal at different places in the body, and combinations thereof.

In an embodiment, a first catheter is placed in an artery proximate to an organ such as a liver and a second catheter is placed in a vein proximate to the organ. The first catheter comprises a first sensor configured to detect a blood component (e.g., NA, NE, and/or the like). The second catheter comprises a second sensor configured to detect the same blood component (e.g., NA, NE, and/or the like). At least one of the first catheter and the second catheter comprises a flowmeter configured to measure blood flowrate. Blood component spillover (e.g., in ng/min), which may be indicative of sympathetic tone, can be measured by multiplying a flowrate (e.g., in mL/min) by the difference in the concentration (e.g., in ng/mL) of the blood component in the artery and in the vein. In some embodiments, the first catheter and the second catheter may be placed in the same vessel, for example upstream and downstream of the organ.

In some embodiments, tone can be measured using a noninvasive device or a device external to the body. A non-invasive tool may be easier and/or more accurate than existing microneurographs such as for MSNA or an intravascular device. A change in sympathetic tone may be characterized by a change in resting heart rate, as acute modifications in sympathetic tone are paralleled by consensual heart rate changes. Heart rate may be measured using a blood pressure cuff, optical monitor, EKG, smart phone, smart watch, etc.

Spectral analysis of heart rate variability (HRV) can be used to assess changes in sympathetic tone. For example, an EKG can be used to measure spectral power or intensity at various frequencies. An HRV spectrum can be aggregated into three main frequency bands: a high frequency band (about 0.15 Hz to about 0.4 Hz), corresponding to a parasympathetic component, a low frequency band (about 0.04 Hz to about 0.15 Hz), corresponding to both sympathetic and parasympathetic components, and a very low frequency band (about 0.0033 Hz to about 0.04 Hz), which may reflect the influence of several physiological mechanisms including vasomotor tone. The resulting spectral power or intensity can be plotted against frequency. Peaks at certain frequencies can be indicative of sympathetic nerve activity such that changes to peaks can indicate changes in sympathetic nerve activity. In addition or alternatively, changes to the total spectral power, measured as the area under the spectral plot or a portion thereof (e.g., high frequency only, low frequency only, high frequency and low frequency only, etc.), can be indicative of sympathetic nerve activity such that changes to total spectral power can indicate changes in sympathetic nerve activity.

Measurement values of sympathetic tone, for example a static number obtained in a screening phase, may be indicative of a suitable subject for denervation or stimulation. Changes in measurement values of sympathetic tone, for example up or down depending on the measurement type and procedure, may be indicative of success of a procedure that should result in a change to sympathetic tone such as denervation or stimulation. If the expected result was not achieved, the procedure may be repeated or modified for example adjusting position, power, energy type, etc.

G. Fluoroscopy

In some embodiments, ablation is performed using an ablation catheter with radiopaque indicators capable of indicating proper position when viewed using fluoroscopic imaging. Due to the two-dimensional nature of fluoroscopic imaging, device position can only be determined along a single plane, providing a rectangular cross-section view of the target vasculature. In order to overcome the difficulty of determining device position along a vessel circumference without repositioning the fluoroscopic imaging system, rotational positioning indicators that are visible using fluoroscopic imaging may advantageously be incorporated on an endovascular ablation device to indicate the circumferential position of ablation components (e.g., electrodes) relative to the vessel anatomy.

In one embodiment, an ablation catheter having an ablation electrode comprises three radiopaque indicators positioned along the longitudinal axis of the ablation catheter. In one embodiment, the first radiopaque indicator is positioned substantially adjacent to the electrode on the device axis; the second radiopaque indicator is positioned proximal to the electrode on the device axis; and the third radiopaque indicator is positioned off the device axis. In one embodiment, the third radiopaque indicator is positioned between the first and second radiopaque indicators. In embodiments with three radiopaque indicators, the ablation electrode is configured to contact the vessel wall through deflection from the central axis of the catheter. In one embodiment, alignment of the first and second radiopaque indicators means that the ablation electrode is located in a position spaced from, and directly perpendicular to, the imaging plane (e.g., either anteriorly or posteriorly assuming a coronal imaging plane). In one embodiment, the position of the third radiopaque indicator indicates the anterior-posterior orientation. For example, position of the third radiopaque indicator above, on, or below the line formed between the first and second radiopaque indicators may provide the remaining information necessary to allow the user to infer the position of the ablation catheter.

H. Neural Targeting

In accordance with several embodiments, methods of specific neural chemical targeting for labeling and destruction are provided. Nerves within or surrounding the hepatic arteries may be closer to the arterial lumen than for the renal artery. In some instances, the nerves converge towards the arterial lumen at a midpoint of a common hepatic artery segment and diverge thereafter. Nerves innervating the common hepatic artery may be predominantly sympathetic efferent nerves. As shown in FIG. 56, the nerves innervating the common hepatic artery may be embedded mostly in fat tissue In some embodiments, a method of targeting nerves comprises injecting a drug specific to efferent fibers (e.g., a TH inhibitor that spares afferent nerves while destroying efferent). In some embodiments, a chemical solution (e.g., potassium hydroxide) is used to dissolve nerves while leaving fat intact. In one embodiment, fat-specific dissolving drugs are injected to skeletonize nerves, thereby bringing the nerves even closer to the arterial lumen or vascular wall.

In some embodiments, the nerves are targeted mechanically instead of chemically (e.g., by taking advantage of different stiffness properties of nerves versus soft fat. Vibrational energy (e.g., sound, ultrasound) may be used, for example to target nerves. In one embodiment, fluorescent markers are injected in specific lobes of the liver to determine where they innervate around the hepatic artery. In one embodiment, a midpoint specific ablation pattern is used to ablate the common hepatic artery.

I. Lesion Monitoring

In accordance with several embodiments, monitoring lesion growth during ablation can provide a method to produce consistent lesions. In addition, overtreatment can be avoided knowing lesion size and severity during ablation. In some embodiments, echo decorrelation of ultrasound images may be used to map tissue changes during ablation. Echo decorrelation is performed by measuring changes in the local ultrasound signal frame to frame. Degradations in the signal are recorded to produce a cumulative decorrelation map. These resulting images can visualize tissue changes due to injury severity. In some embodiments, an intravascular ultrasound probe is positioned at the site of ablation. In other embodiments, the intravascular ultrasound probe is positioned in a parallel vein or artery or other structure. Echo decorrelation can be performed in real time to monitor the growth of one or more ablation lesions formed in the wall (e.g., intima, media and/or adventitia) of the vessel. In some embodiments, echo decorrelation uses thresholds defined from in vitro empirical tissue ablation data to visualize one or more growing lesions. The monitoring may advantageously be used to stop ablative energy delivery (e.g., from an electrode or ultrasound transducer) when the lesion has reached a sufficient size or if the lesion severity approaches unsafe levels.

As mentioned above, diagnostic probes may be inserted within structures adjacent to the common hepatic artery to be used as a monitoring site to detect formation of ablation lesions or other penetration of ablation. For example, the stomach and duodenum may be accessed via an endoscopic approach using probes placed at the time of the procedure. Diagnostic devices may be inserted into the portal vein through a percutaneous approach directly from outside the abdomen or through venous access crossing the liver tissue from the vena cava. Diagnostic devices may be inserted into the bile duct, which may be accessed, for example, percutaneously from outside the abdomen. Diagnostic devices may be inserted into the inferior vena cava through standard venous approaches. In some embodiments, diagnostic elements are placed external to the patient on the skin of the abdomen. The various diagnostic devices (e.g., probes) may measure temperature using thermocouples, thermistors, microwave detection, volumetric heat mapping, or mechanical changes in tissue (e.g., using ultrasound or optical coherence tomography (OCT) probes). In accordance with several embodiments, the diagnostic devices (e.g., probes) inserted into the adjacent structures may advantageously give the operator confidence that energy was actually delivered to the intended sites (thus suggesting efficacy) and provide assurance that adjacent sensitive structures that were not intended to be ablated (such as the bile duct) were not impacted (thus ensuring safety).

J. Nerve Conduction Monitoring

Various systems and methods are provided herein to provide the ability to detect (acutely and/or chronically) whether nerves have been ablated or denervated and the neural connections to the end-organ (e.g., liver, pancreas, duodenum, etc.) thus disrupted. In accordance with several embodiments, it may be desirable to detect in real-time the actual energy being delivered. Since nerves carry electrical signals, and denervated or ablated nerves can no longer carry these signals, it may be possible to measure conduction along the length of the nerve fibers. In some embodiments, a binary signal (e.g., on/off) or a quantitative signal correlating with degree of nerve disruption could be determined. In some embodiments, expected physiological responses (e.g., glucose changes, insulin or glucagon changes, GI motility, etc.) to stimulation of the target nerves (e.g., nerves surrounding the hepatic arteries) may be monitored directly after a denervation or nerve ablation procedure to determine whether or not the expected physiological responses occur, thereby leading to the possibility of a real-time intra-procedural diagnostic. In some embodiments, real-time feedback during the ablation procedure may facilitate delivery of only enough energy (or formation of only enough lesions) as needed for successful denervation, thereby opening up a wider population to the procedure due to anatomic constraints (e.g., vessel length, tortuosity, etc.) that may limit the number of possible ablations and/or reducing the likelihood of any safety effects (e.g., vascular or adjacent structure injury) due to excessive energy delivery.

In accordance with several embodiments, the catheter used for energy delivery (e.g., ablation) comprises sensing electrodes proximal and/or distal to the site of ablation. The sensing electrodes may be configured to be placed in contact with a vessel wall in order to detect conduction in the targeted nerve fibers (e.g., nerve fibers in the adventitia surrounding a common hepatic artery). Any of the structures and features described herein for facilitating contact of electrodes with vessel walls may be used. For example, a balloon ablation catheter may comprise ablation electrodes in the middle of the balloon and sensing electrodes on the same balloon proximal and distal of the ablation electrodes. In some embodiments, the same electrodes are configured to provide ablation and sensing functions. In some embodiments, a balloon ablation catheter may comprise multiple balloons, with sensing balloons (e.g., balloons with sensing electrodes) on either side of an ablation balloon (or balloon with ablation electrodes).

Similar technologies could be employed on a separate catheter from the ablation catheter, and a diagnostic procedure could be performed with the separate sensing catheter immediately after or within a certain time (e.g., 5 minutes, 10 minutes, 15 minutes, 20 minutes, 30 minutes, 45 minutes, 60 minutes) following the ablation or on some other diagnostic or treatment session in the future. In some embodiments, non-catheter-based diagnostic systems and methods are used. For example, the proximal and distal sensing electrodes may be positioned on cuffs, needles, patches, and/or the like. Access could be percutaneous, placed on the skin outside of the body, placed in adjacent structures (e.g., portal vein, bile duct, inferior vena cava), or placed in organ tissue (e.g., liver tissue) itself. In accordance with several embodiments, the methods advantageously involve monitoring at the physiology that is being targeted (e.g., neural electrical conduction), which provides the most direct measurement conceivable.

V. Alternative Delivery Methods

A. Intravascular

In addition to being delivered intravascularly through an artery, the neuromodulation systems described herein (e.g., ablation catheter systems and other access/delivery systems) can be delivered intravascularly through the venous system. For example, an ablation catheter system may be delivered through the portal vein. In other embodiments, an ablation catheter system is delivered intravascularly through the inferior vena cava. Any other intravascular delivery method or approach may be used to deliver neuromodulation systems, e.g., for modulation of sympathetic nerve fibers in the hepatic plexus.

B. Transluminal, Laparoscopic, Percutaneous or Open Surgical

In some embodiments, the neuromodulation systems (e.g., catheter and other access/delivery systems) are delivered transluminally to modulate nerve fibers. For example, catheter systems may be delivered transluminally through the stomach. In other embodiments, the catheter systems are delivered transluminally through the duodenum, or transluminally through the biliary tree via endoscopic retrograde cholangiopancreatography (ERCP). Any other transluminal or laparoscopic delivery method may be used to deliver the catheter systems according to embodiments described herein.

In some embodiments, the catheter systems are delivered percutaneously to the biliary tree to ablate sympathetic nerve fibers in the hepatic plexus. Any other minimally invasive delivery method may be used to deliver neuromodulation systems for modulation or disruption of sympathetic nerve fibers in the hepatic plexus as desired and/or required.

In some embodiments, an open surgical procedure is used to modulate sympathetic nerve fibers in the hepatic plexus. Any open surgical procedure may be used to access the hepatic plexus. In conjunction with an open surgical procedure, any of the modalities described herein for neuromodulation may be used. For example, RF ablation, ultrasound ablation, HIFU ablation, ablation via drug delivery, chemoablation, cryoablation, ionizing energy delivery (such as X-ray, proton beam, gamma rays, electron beams, and alpha rays) or any combination thereof may be used with an open surgical procedure. In one embodiment, nerve fibers (e.g., in or around the hepatic plexus) are surgically cut in conjunction with an open surgical procedure in order to disrupt sympathetic signaling, e.g., in the hepatic plexus.

C. Non-Invasive

In some embodiments, a non-invasive procedure or approach is used to ablate sympathetic nerve fibers in the hepatic plexus and/or other nerve fibers. In some embodiments, any of the modalities described herein, including, but not limited, to ultrasonic energy, HIFU energy, electrical energy, magnetic energy, light/radiation energy or any other modality that can effect non-invasive ablation of nerve fibers, are used in conjunction with a non-invasive (e.g., transcutaneous) procedure to ablate sympathetic nerve fibers in the hepatic plexus and/or other nerve fibers.

D. Robotic/Automated Treatment

The hepatic or other arteries may lend themselves to robotic or automated treatments based on a predetermined or preselected treatment. The automated treatment may minimize or reduce trauma and risk of deviation from protocol. The preselected treatment may incorporate treatment parameters (e.g., target locations, spacing between treatment locations, duration, frequency, etc.).

In an embodiment, an automated system may be used for automated treatment of a nerve. The automated system may include memory that includes a recipe or protocol. The memory may include a plurality of recipes (e.g., different body parts to be treated, different treatments of such body parts) that may be selected by an input device. The recipe can include information about, for example, how to navigate to the body part and what type of energy (e.g., energy modality, power level, treatment duration, continuous versus intermittent) to apply to effect certain treatment.

The system may include memory that includes information, for example related to the patient, the components of the system, the user, environmental factors, etc. The system may use the information to modify the recipe before, during, and/or after a procedure.

A computing device such as a laptop or tablet may include the memory, input device, a display device, communications devices, and the like to operate as a control center for the procedure. For example, a procedure may start by selecting via an input device of the control center a recipe (e.g., hepatic denervation) and a patient from menus displayed by the control center. The control center may visibly and/or audibly provide instructions for initial setup of the procedure after which the procedure is substantially automated, or the procedure may begin immediately or soon after menu selection.

The system may include a steerable component such as a guidewire or a guide catheter. The steerable component may be inserted into the vasculature distant to the nerve to be treated, for example in a femoral or radial artery. A portion of the steerable component inside the body may include a monitoring device such as IVUS, RFID, etc. to monitor position of the catheter. The control center may receive information from the monitoring device via wired and/or wireless communication. Alternatively or additionally, a portion of the steerable component inside the body may include a radiopaque element (e.g., marker band) and/or other means for monitoring the position of the steerable component external to the body.

Outside of the body, the steerable component may be engaged with an advancement mechanism. For example, one or more motors may advance, retract, and/or rotate the steerable component in response to instructions from the control center. A curvature of at least part of the steerable component may be modified to provide navigability through vasculature. IVUS may be used to monitor the surroundings of the steerable component. The advancement mechanism may advance the steerable component through the vasculature to a body part as indicated in the recipe. For example, the steerable component may be longitudinally distally advanced until the steerable component reaches a branch vessel, for example indicated by a dark, non-walled spot on an IVUS output that can be detected by the control center. Based on the recipe, which may include a map of the vasculature or a turning guide (e.g., straight after first branch, left into second branch, right into third branch, or the like), the steerable component can be advanced into the branch vessel (e.g., by modifying curvature of the steerable component) or continue advancing in the original vessel. If the steerable component is a guidewire, a catheter may be advanced over the guidewire. If the steerable component is a guide catheter, a catheter may be advanced in the guide catheter, or the guide catheter itself may include a treatment tool such as an energy emitter. In a partially automated system, a user may advance a steerable component to a location at or proximate to the body part, and the system can be automated thereafter.

Once the treatment tool is in a position, the recipe may call for an initial diagnosis, for example of a bodily parameter. The bodily parameter may be used as a baseline to evaluate the treatment and/or as a variable to adjust a treatment parameter. The treatment tool can be automatically positioned, for example via longitudinal advancement and/or retraction, rotation, and/or biasing to a side (e.g., via shape-memory wire, balloon, anchor, and/or the like), to modulate a nerve. The recipe may call for denervation or stimulation and may adjust energy application parameters (e.g., frequency, time, cooling, focus, etc.) accordingly. The treatment tool may be moved to a plurality of sites, for example advancing a known or calculated distance in a particular direction. The recipe may call for an ongoing diagnosis, for example of the same or a different bodily parameter, during the treatment. The bodily parameter may be used to adjust a treatment parameter and/or repeat a treatment mid-procedure. The recipe may call for a final or post-procedure diagnosis, for example of the same or a different bodily parameter. The bodily parameter may be used to confirm completion of the procedure. The bodily parameter may be used to adjust a treatment parameter and/or repeat a treatment after the initial completion of the procedure.

A user of the system may be standing by in case non-automated action may be needed. Action may be indicated by the system itself, for example via a warning on a control center.

VI. Stimulation

According to some embodiments, neuromodulation is accomplished by stimulating nerves and/or increasing neurotransmission. Stimulation, in one embodiment, may result in nerve blocking. In other embodiments, stimulation enhances nerve activity (e.g., conduction of signals).

In accordance with some embodiments, therapeutic modulation of nerve fibers is carried out by neurostimulation of autonomic (e.g., sympathetic or parasympathetic) nerve fibers. Neurostimulation can be provided by any of the devices or systems described above (e.g., ablation catheter or delivery catheter systems) and using any of the approaches described above (e.g., intravascular, laparoscopic, percutaneous, non-invasive, open surgical). In some embodiments, neurostimulation is provided using a temporary catheter or probe. In other embodiments, neurostimulation is provided using an implantable device. For example, an electrical neurostimulator can be implanted to stimulate parasympathetic nerve fibers that innervate the liver, which could advantageously result in a reduction in blood glucose levels by counteracting the effects of the sympathetic nerves.

In some embodiments, the implantable neurostimulator includes an implantable pulse generator. In some embodiments, the implantable pulse generator comprises an internal power source. For example, the internal power source may include one or more batteries. In one embodiment, the internal power source is placed in a subcutaneous location separate from the implantable pulse generator (e.g., for easy access for battery replacement). In other embodiments, the implantable pulse generator comprises an external power source. For example, the implantable pulse generator may be powered via an RF link. In other embodiments, the implantable pulse generator is powered via a direct electrical link. Any other internal or external power source may be used to power the implantable pulse generator in accordance with the embodiments disclosed herein.

In some embodiments, the implantable pulse generator is electrically connected to one or more wires or leads. The one or more wires or leads may be electrically connected to one or more electrodes. In some embodiments, one or more electrodes are bipolar. In other embodiments, one or more electrodes are monopolar. In some embodiments, there is at least one bipolar electrode pair and at least one monopolar electrode. In some embodiments, one or more electrodes are nerve cuff electrodes. In other embodiments, one or more electrodes are conductive anchors.

In some embodiments, one or more electrodes are placed on or near parasympathetic nerve fibers that innervate the liver. In some embodiments, the implantable pulse generator delivers an electrical signal to one or more electrodes. In some embodiments, the implantable pulse generator delivers an electrical signal to one or more electrodes that generates a sufficient electric field to stimulate parasympathetic nerve fibers that innervate the liver. For example, the electric field generated may stimulate parasympathetic nerve fibers that innervate the liver by altering the membrane potential of those nerve fibers in order to generate an action potential.

In some embodiments, the implantable pulse generator recruits an increased number of parasympathetic nerve fibers that innervate the liver by varying the electrical signal delivered to the electrodes. For example, the implantable pulse generator may deliver a pulse of varying duration. In some embodiments, the implantable pulse generator varies the amplitude of the pulse. In other embodiments, the implantable pulse generator delivers a plurality of pulses. For example, the implantable pulse generator may deliver a sequence of pulses. In some embodiments, the implantable pulse generator varies the frequency of pulses. In other embodiments, the implantable pulse generator varies any one or more parameters of a pulse including, but not limited to, duration, amplitude, frequency, and total number of pulses.

In some embodiments, an implantable neurostimulator chemically stimulates parasympathetic nerve fibers that innervate the liver. For example, the chemical neurostimulator may be an implantable pump. In some embodiments, the implantable pump delivers chemicals from an implanted reservoir. For example, the implantable pump may deliver chemicals, drugs, or therapeutic agents to stimulate parasympathetic nerve fibers that innervate the liver.

In some embodiments, the implantable neurostimulator uses any combination of electrical stimulation, chemical stimulation, or any other method to stimulate parasympathetic nerve fibers that innervate the liver.

In some embodiments, non-invasive neurostimulation is used to stimulate parasympathetic nerve fibers that innervate the liver. For example, transcutaneous electrical stimulation may be used to stimulate parasympathetic nerve fibers that innervate the liver. In other embodiments, any method of non-invasive neurostimulation is used to stimulate parasympathetic nerve fibers that innervate the liver.

In accordance with the embodiments disclosed herein, parasympathetic nerve fibers other than those that innervate the liver are stimulated to treat diabetes, hypertension and/or other conditions, diseases, disorders, or symptoms related to metabolic conditions. For example, parasympathetic nerve fibers that innervate the pancreas, parasympathetic nerve fibers that innervate the adrenal glands, parasympathetic nerve fibers that innervate the small intestine, parasympathetic nerves that innervate the stomach, parasympathetic nerve fibers that innervate the kidneys (e.g., the renal plexus) or any combination of parasympathetic nerve fibers thereof may be stimulated in accordance with the embodiments herein disclosed. Any autonomic nerve fibers can be therapeutically modulated (e.g., disrupted or stimulated) using the devices, systems, and methods described herein to treat any of the conditions, diseases, disorders, or symptoms described herein (e.g., diabetes or diabetes-related conditions). In some embodiments, visceral fat tissue of the liver or other surrounding organs is stimulated. In some embodiments, intrahepatic stimulation or stimulation to the outer surface of the liver is provided. In some embodiments, stimulation (e.g., electrical stimulation) is not provided to the outer surface of the liver or within the liver (e.g., to the liver parenchyma), is not provided to the vagal or vagus nerves, is not provided to the hepatic portal vein, and/or is not provided to the bile ducts.

Stimulation may be performed endovascularly or extravascularly. In one embodiment, a stimulation lead is positioned intravascularly in the hepatic arterial tree adjacent parasympathetic nerves. The main hepatic branch of the parasympathetic nerves may be stimulated by targeting a location in proximity to the proper hepatic artery or multiple hepatic branches tracking the left and right hepatic artery branches and subdivisions. In one embodiment, the stimulation lead is positioned within a portion of the hepatoesophageal artery and activated to stimulate parasympathetic nerves surrounding the hepatoesophageal artery, as both vagal branches travel along the hepatoesophageal artery.

In one embodiment, the stimulation lead is positioned in the portal vein and activated to stimulate nerve fibers surrounding the portal vein, which may have afferent parasympathetic properties. In one embodiment, the stimulation lead is positioned across the hepatic parenchyma from a central venous approach (e.g., via a TIPS-like procedure) or positioned by arterial access through the hepatic artery and then into the portal vein. In one embodiment, the portal vein is accessed extravascularly through a percutaneous approach. The stimulation lead may be longitudinally placed in the portal vein or wrapped around the portal vein like a cuff. Extravascular stimulation of the portal vein may be performed by placing the stimulation lead directly on the parasympathetic fibers adhered to or within the exterior vessel wall. In various embodiments, the stimulation lead is placed percutaneously under fluoroscopy guidance, using a TIPS-like approach through the wall of the portal vein, by crossing the arterial wall, or by accessing the biliary tree.

In some embodiments, the stimulation lead is stimulated continuously or chronically to influence resting hepatic glucose product and glucose uptake. In various embodiments, stimulation is performed when the subject is in a fasting or a fed state, depending on a subject's glucose excursion profile. In some embodiments, stimulation may be programmed to occur automatically at different times (e.g., periodically or based on feedback). For example, a sensory lead may be positioned in the stomach or other location to detect food ingestion and trigger stimulation upon detection. In some embodiments, the stimulation is controlled or programmed by the subject or remotely by a clinician over a network.

In some embodiments, stimulation with 0.1 s-on, 4.9 s-off, 14 Hz, 0.3 ms, 4 mA pulsed RF energy is used for sympathetic nerve stimulation and stimulation with 2 s-on, 3 s-off, 40 Hz, 0.3 ms, 4 mA pulsed RF energy is used for parasympathetic activation. However, other parameters of RF energy or other energy types may be used.

Parasympathetic stimulation may also cause afferent effects along the vagus nerve, in addition to efferent effects to the liver resulting in changes in hepatic glucose production and uptake. The afferent effects may cause other efferent neurally mediated changes in metabolic state, including, but not limited to one or more of the following: an improvement of beta cell function in the pancreas, increased muscle glucose uptake, changes in gastric or duodenal motility, changes in secretion or important gastric and duodenal hormones (e.g., an increase in ghrelin in the stomach to signal satiety, and/or an increase in glucagon-like peptide-1 (GLP-1) from the duodenum to increase insulin sensitivity).

VII. Examples

Examples provided below are intended to be non-limiting embodiments of the invention.

A. Example 1

Figures 1, 123A:
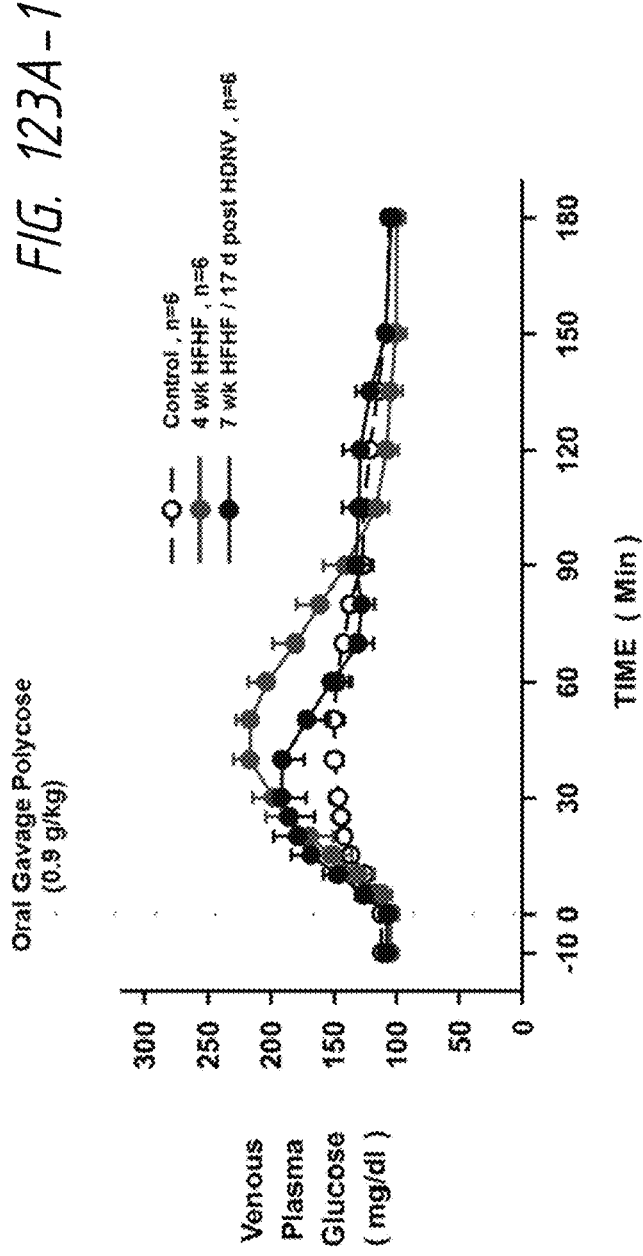
Figures 2, 123A:
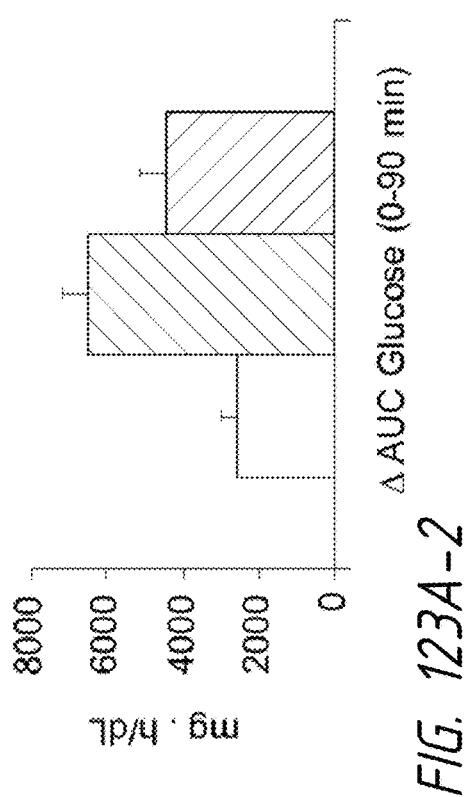
Figure 123B:
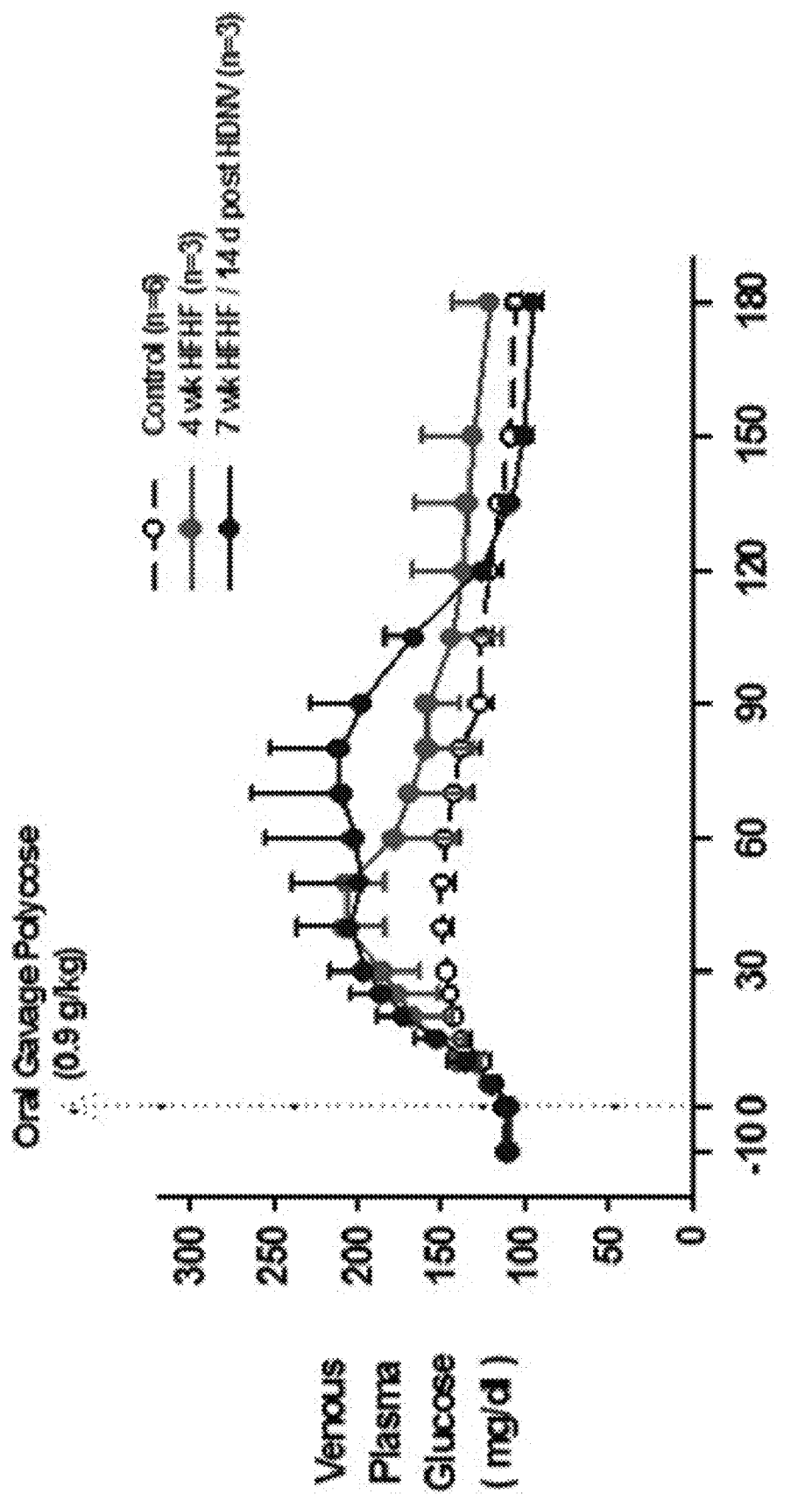

Nine dogs were put on a high fat, high fructose diet for four weeks, thereby rendering the dogs insulin resistant. As controls, a 0.9 g/kg oral gavage polycose dose was administered prior to initiation of the diet and at four weeks after initiation of the diet after an overnight fast and oral glucose tolerance tests were performed at various time intervals to track glucose levels. The common hepatic arteries of six dogs were then surgically denervated, and three dogs underwent a sham operation. Another 0.9 g/kg oral gave polycose dose was administered after an overnight fast about two to three weeks following hepatic denervation. Oral glucose tolerance tests were performed at various time intervals after administration of the polycose. FIG. 123A-1 illustrates a graph of the average venous plasma glucose over time for the six denervated dogs reported by the three oral glucose tolerance tests (OGTTs). The curve with data points represented by open circles represents the average of glucose measurements from the OGTT testing of the six dogs prior to high fat, high fructose diet feeding, and the curve with the data points represented by gray circles represents the average of the glucose measurements from the OGTT testing of the six dogs after the four weeks of high fat, high fructose diet before hepatic denervation. The oral gavage polycose doses were administered at time zero (as shown in FIG. 123A-2). The curve with the data points represented as black circles represents the average of the glucose measurements from the OGTT testing of the same six dogs seventeen days after hepatic denervation. As can be seen in FIG. 123A, the glucose values after hepatic denervation peaked at lower glucose concentrations and dropped much more rapidly than the glucose values prior to hepatic denervation, and the areas under the curve of the OGTTs improved by approximately 50% back to normal, chow fed levels. Interestingly, insulin levels during the OGTT actually increased after denervation, suggesting a beneficial effect on beta cell function. FIG. 123B illustrates a graph of the three sham operated dogs at the same time points, showing an increase over time of glucose area under the curve. The sham operated dogs also had no increase in insulin levels. In accordance with several embodiments, the results of the study provide strong evidence of the efficacy of hepatic denervation for controlling blood glucose levels. In some embodiments, insulin levels may remain constant or not increase or decrease by more than 5%.

B. Example 2

Figure 124:
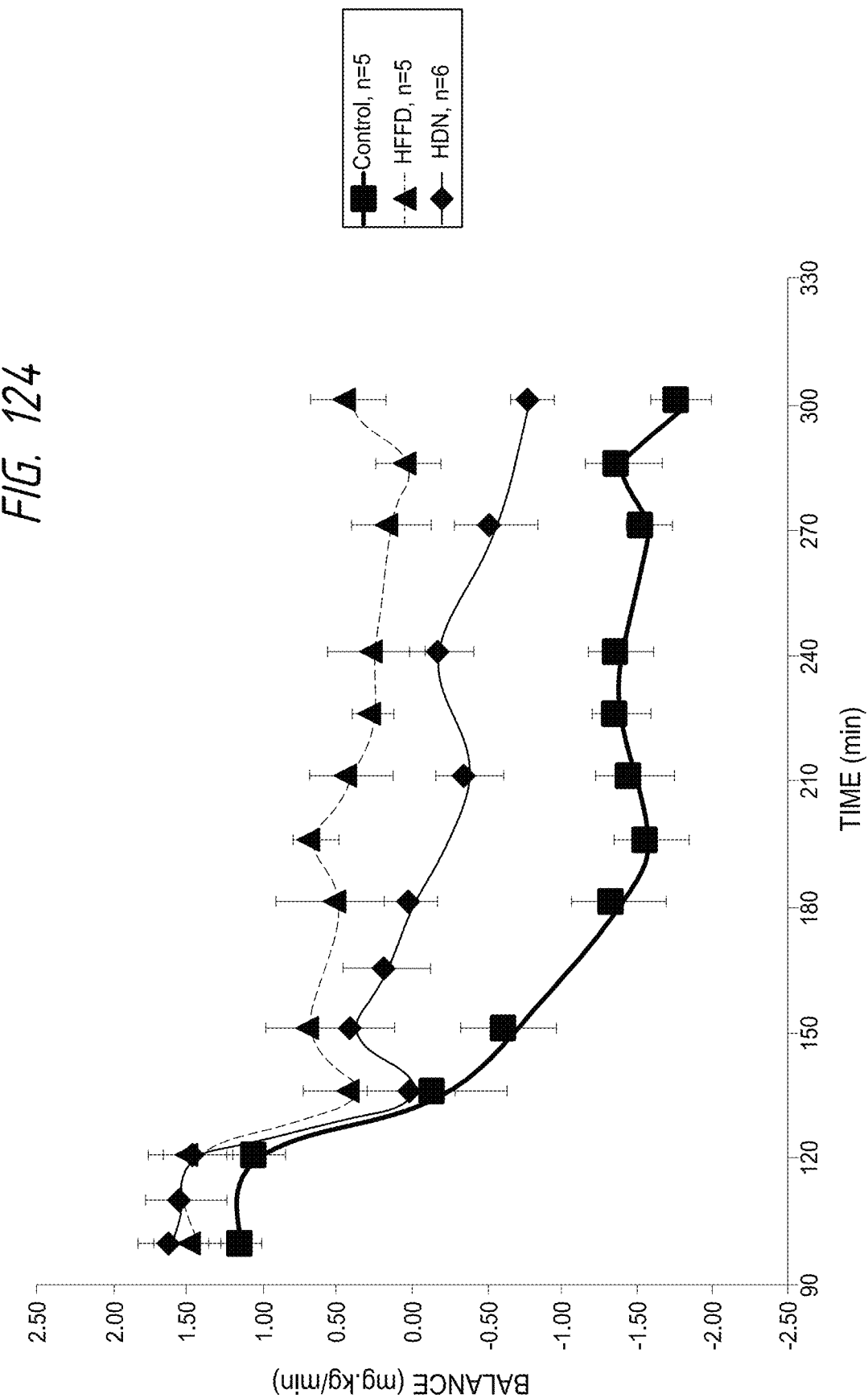

FIG. 124 illustrates the net hepatic glucose balance obtained during a hyperglycemic-hyperinsulinemic clamp study. The data represented with diamond indicators (HDN) represents the average net hepatic glucose levels of the same 6 dogs from Example 1 four weeks after denervation. The data represented with triangle indicators (HF/HF) represents the average net hepatic glucose levels of 5 dogs that were fed a high fat, high fructose diet. The data represented with the square indicators (Control) represents the average net hepatic glucose levels of 5 dogs fed a normal diet. The data shows that toward the end of the curves, hepatic denervation can restore net hepatic glucose balance to about 50% back to baseline, which suggests insulin resistance in the liver in the HF/HF dog model is largely corrected by hepatic denervation, and which indicates that hepatic denervation has an effect on hepatic glucose uptake and/or hepatic glucose production, in accordance with embodiments of the invention.

C. Example 3

A hepatic artery was harvested from a porcine liver as far proximal as the common hepatic artery and as far distal as the bifurcation of the left hepatic artery and the right hepatic artery. The arterial plexus was sandwiched between two sections of liver parenchyma (a "bed" and a "roof"), and placed in a stainless steel tray to serve as a return electrode. A total of 3 arteries were ablated using a RADIONICS RFG-3C RF generator using a NiTi/dilator sheath, having an exposed surface of approximately 1/16" to 3/32" in length. RF energy was applied for 117 seconds in each case, with the generator power setting at 4 (generally delivering 2-3 W into 55-270Ω). For the first 2 sample arteries, a K-type thermocouple was used to monitor extravascular temperatures, which reached 50-63° C. The first ablation was performed in the left hepatic artery, the second ablation was performed in the right hepatic artery, and the third ablation was performed in the proper hepatic artery. For the first ablation in the left hepatic artery having a lumen diameter of 1.15 mm, two ablation zone measurements were obtained (0.57 mm and 0.14 mm). A roughly 3 mm coagulation zone was measured. The electrode exposure distance was 3/32". For the second ablation in the right hepatic artery, an electrode exposure distance of 1/16" was used. The generator impeded out due to high current density and no ablation lesion was observed. For the third ablation of the proper hepatic artery having a lumen diameter of 2 mm and using an electrode exposure distance was 3/32", three ablation zone widths of 0.52 mm, 0.38 mm and 0.43 mm were measured. The measured ablation zone widths support the fact that nerves surrounding the proper hepatic artery (which may be tightly adhered to or within the arterial wall) can be denervated using an intravascular approach. Histological measurements of porcine hepatic artery segments have indicated that hepatic artery nerves are within 1-10 medial thicknesses (approximately 1-3 mm) from the lumen surface, thereby providing support for modulation (e.g., denervation, ablation, blocking conduction of, or disruption) of nerves innervating branches of the hepatic artery endovascularly using low-power RF energy (e.g., less than 10 W and/or less than 1 kJ) or other energy modalities. Nerves innervating the renal artery are generally within the 4-6 mm range from the lumen of the renal artery.

D. Example 4

An acute animal lab was performed on a common hepatic artery and a proper hepatic artery of a porcine model. The common hepatic artery was ablated 7 times and the proper hepatic artery was ablated 3 times. According to one embodiment of the invention, temperature-control algorithms (e.g., adjusting power manually to achieve a desired temperature) were implemented at temperatures ranging from 50° C. to 80° C. and for total ablation times ranging from 2 to 4 minutes. According to one embodiment of the invention, the electrode exposure distance for all of the ablations was 3/32". Across all ablations the ablation parameters generally ranges as follows, according to various embodiments of the invention: resistance ranged from about 0.1 ohms to about 869 ohms (generally about 100 ohms to about 300 ohms), power output ranged from about 0.1 W to about 100 W (generally about 1 Watt to about 10 Watts), generator voltage generally ranged from about 0.1 V to about 50 V, current generally ranged from about 0.01 A to about 0.5 A, and electrode tip temperature generally ranged from about 37° C. to about 99° C. (generally +/−5° C. from the target temperature of each ablation). Energy was titrated on the basis of temperature and time up to approximately 1 kJ or more in many ablations. Notching was observed under fluoroscopy in locations corresponding to completed ablations, which may be a positive indicator of ablative success, as the thermal damage caused arterial spasm.

It was observed that, although separation of ablation regions by 1 cm (in accordance with one embodiment) was attempted, the ablation catheter skipped distally during the ablation procedure, which is believed to have occurred due to the movement of the diaphragm during the ablation procedure, thereby causing movement of the anatomy and hepatic arterial vasculature surrounding the liver (which may be a unique challenge for the liver anatomy).

Unlike previous targets for endovascular ablation (e.g., renal arteries, which course generally straight toward the kidneys), the hepatic arterial vasculature is highly variable and tortuous. It was observed during the study that catheters having a singular articulated shape may not be able to provide adequate and consistent electrode contact force to achieve ablative success. For example, in several ablation attempts using an existing commercially-available RF ablation catheter, with energy delivered according to a manually-implemented constant-temperature algorithm, the power level was relatively high with low variability in voltage output required to maintain the target temperature. This data is generally indicative of poor vessel wall contact, as the electrode is exposed to higher levels of cooling from the blood (thereby requiring higher power output to maintain a particular target temperature). Additionally, tissue resistivity is a function of temperature. Although the tissue within the vessel wall is spatially fixed, there is constant mass flux of "refreshed" blood tissue in contact with the electrode at physiologic temperatures. Consequently, in one embodiment, when the electrode is substantially in contact with "refreshed" blood at physiologic temperatures, the electrode "sees" substantially constant impedance. Due to the correlation between impedance and voltage (e.g., $P=V^2/R$), the substantially constant impedance is reflected in a substantially constant (less variable) voltage input required to maintain a target electrode tip temperature. Therefore, particular embodiments (such as those described, for example, in FIGS. 29 and 30) advantageously enable adequate electrode contact in any degree of hepatic artery tortuosity that may be encountered clinically.

In a follow-up hepatic artery denervation procedure, it was demonstrated that the ability to reduce liver norepinephrine levels by ablating using a monopolar catheter, the results of which are shown in FIG. 125. Compared to historical liver norepinephrine drops observed in dogs following surgical hepatic arterial denervation, the endovascular ablation denervation procedure was estimated to be 72-95% effective at destroying sympathetic communication with the liver.

E. Example 5

A numerical model representing the hepatic artery and surrounding structures was constructed in COMSOL Multiphysics 4.3. using anatomical, thermal, and electrical tissue properties. Thermal and electrical properties are a function of temperature. Electrical conductivity (sigma, or σ) generally varies according to the equation $\sigma=\sigma_0 e^{0.015(T-T_0)}$ where $\sigma_0$ is the electrical conductivity measured at physiologic temperatures ($T_0$) and T is temperature. With reference to FIGS. 126A-126D, model geometry was assessed and included regions representing the hepatic artery lumen, bile duct 12605, and portal vein 12610. The bile 12605 duct and portal vein 12610 were modeled as grounded structures, highlighting the effect of these structures on current flow. By calculating liver blood flow and the relative contributions from the hepatic artery and portal vein 12610, we determined the flow in the hepatic artery was significantly lower than flow rates in other arteries (e.g., renal arteries). In one embodiment, the estimated flow rate was 139.5 mL/min. for the hepatic artery. Using the model described above, independent solutions were first obtained for monopolar and bipolar electrode configuration. A geometric model corresponding to the common hepatic artery was created and a time-dependent solution was calculated in COMSOL using the bioheat equation, $$\rho_b c_{pb} \frac{\partial T}{\partial t} = \nabla(k\nabla T_t) + \rho_b u c_{pb}(T_B - T) + q_m,$$

which, in one embodiment, relates the temperature at any point in the model as a function of the temperature gradient in the tissue, blood perfusion, blood temperature entering the geometric region of interest, and the heat generated ($q_m$) as a function of RF energy deposition.

Figure 126A:
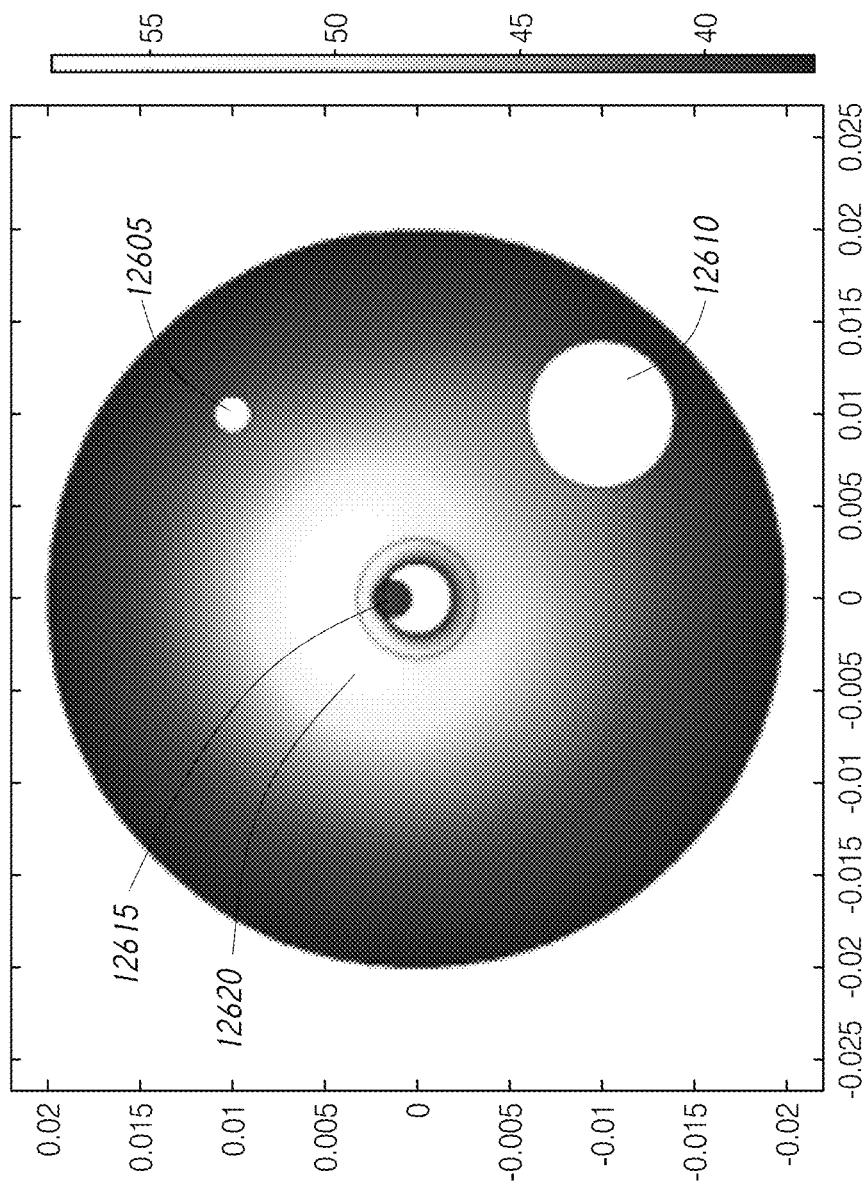
FIGS. 126A-126D illustrate geometric models.
Figure 126B:
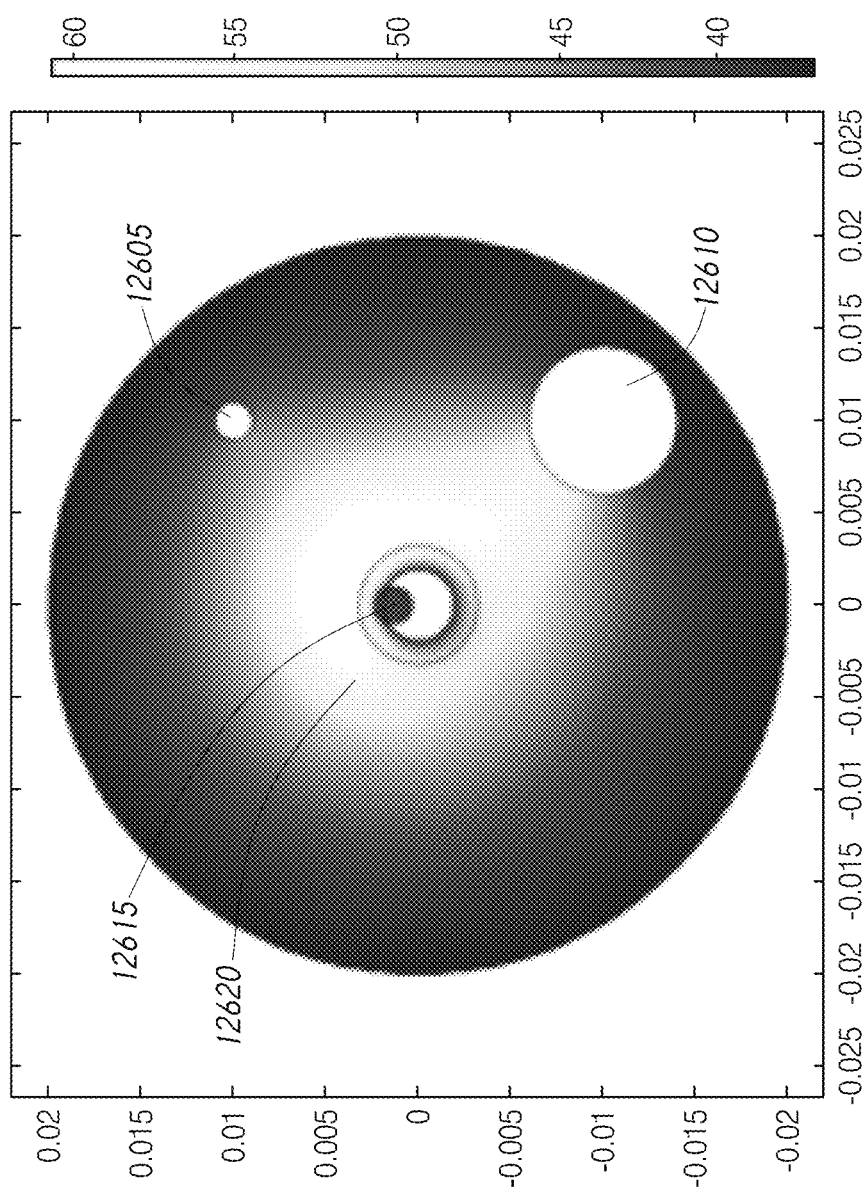
Figure 126C:
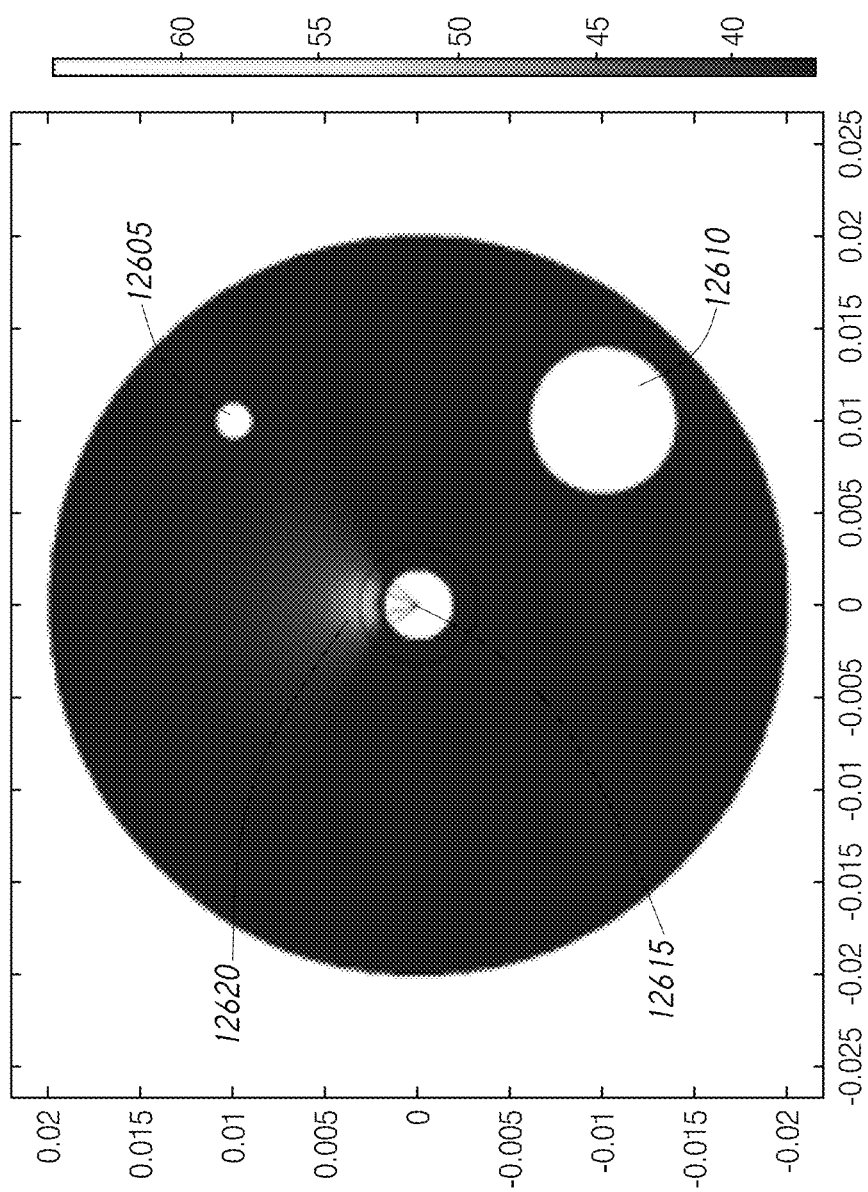
Figure 126D:
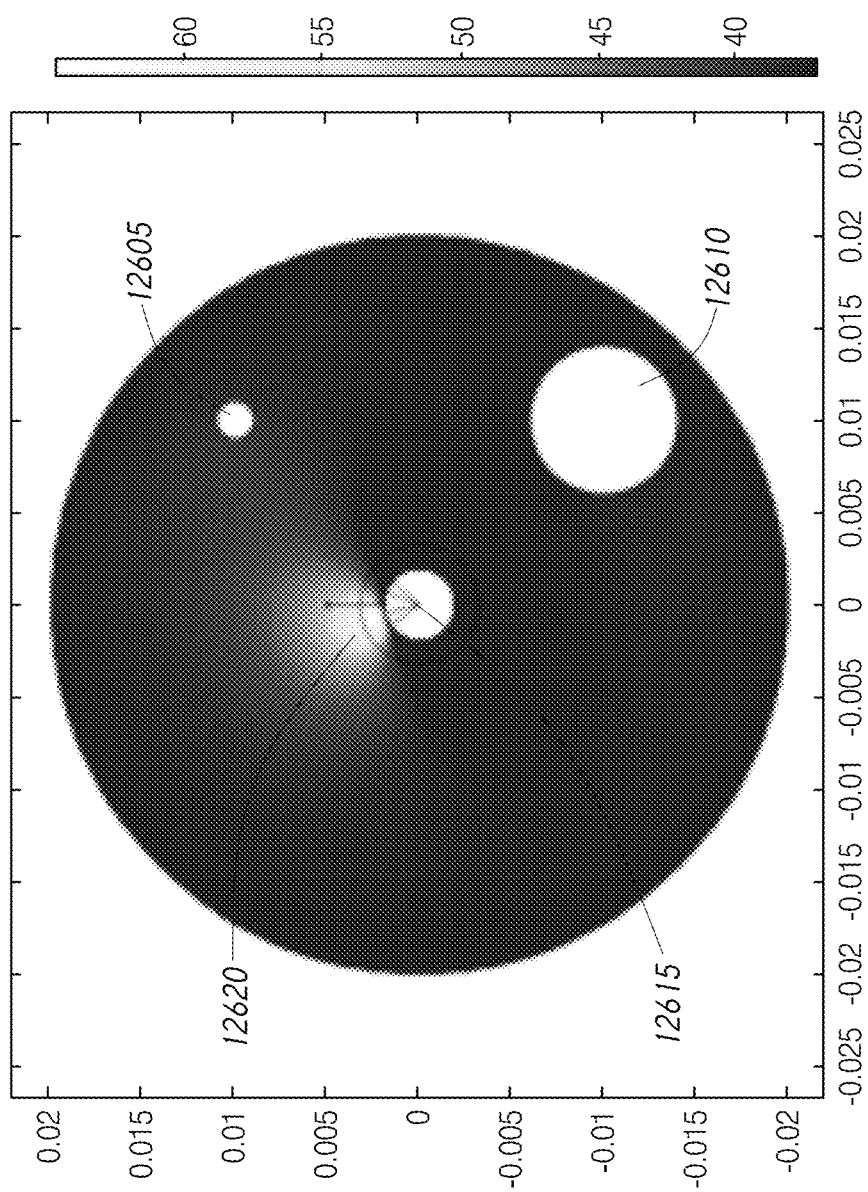

FIGS. 126A and 126B illustrate a geometric model of RF energy deposition in the common hepatic artery using a single electrode, with the conductivity of the bile duct 12605 and the portal vein 12610 grounded (FIG. 126A) and accounted for (FIG. 126B). As shown in FIG. 126B, biliary and portal vein conductivity can influence where ablation energy travels when a single electrode 12615 is used. FIGS. 126C and 126D illustrate a geometric model of RF energy deposition in the common hepatic artery for a bipolar electrode configuration 12615, with the conductivity of the bile duct 12605 and the portal vein 12610 grounded (FIG. 126C) and accounted for (FIG. 126D).

In accordance with an embodiment of the invention, the shape of the electric field and resulting thermal ablation 12620 was significantly affected in the monopolar ablation model due to biliary and portal vein conductivity (as shown in FIGS. 126A and 126B). Minimal effects due to biliary and portal vein conductivity (e.g., shaping effects) were observed in the shape of the electric field and resulting thermal ablation 12620 for the bipolar ablation model (shown in FIGS. 126C and 126D). FIGS. 126A and 126B were obtained when the pair of bipolar electrodes were modeled, according to one embodiment, as disposed at a location that is substantially tangent to the inner lumen of the artery, with each individual electrode having an arc length of 20 degrees and with an inter-electrode spacing of 10 degrees. In one embodiment, the edges of the electrodes have radii sufficient to reduce current concentrations (less than 0.001"). In several embodiments, the bipolar configuration advantageously provides effective ablation (e.g., thermal ablation of the hepatic artery) without significant effect on shaping of the ablation zone, despite the effects of biliary and portal vein conductivity due to proximity of the bile duct and portal vein to the common hepatic artery.

F. Example 6

Independent modeling solutions were obtained for an ablation with convective cooling (e.g., provided by blood flow alone) and for an ablation incorporating active cooling (e.g., 7° C. coolant) using the same bipolar configuration model described above in Example 5. The models showed significantly decreased temperatures at the location corresponding to the lumen (endothelial) interface. Higher power (45% higher power) was delivered to the active cooling model. Even with higher power delivered (e.g., 45% higher power) to the active cooling model, the endothelial region of the common hepatic artery remained cool (e.g., less than hyperthermic temperatures up to 1 mm from the lumen). The effective shaping of the thermal ablation zone was also directed into a more linear shape directed radially in the active cooling model. It was observed, that, in accordance with several embodiments, as cooling power is increased and RF power is increased, the linear shaping effect was magnified, thereby rendering the ablation zone capable of being directed or "programmed" (e.g., toward a more targeted location).

G. Example 7

Using a COMSOL model similar to the one described previously in connection with FIGS. 126A and 126B, the cooling effect of blood flow is observed to play a major role in the success of an ablation procedure, as the cooling effect allows the ablation procedure to achieve greater depth without vaporizing any tissue. The literature reports a considerable variation of the flow rate in the common hepatic artery. Moreover, a sudden constriction of the artery may occur during the procedure, which could considerably change the outcome of the ablation. In the following example, the importance of knowing the blood flow rates in the hepatic artery in real time is quantitatively shown. To do so, results that link the ablation parameters (e.g., maximum temperature reached within the tissue and temperature at 6 millimeters from the lumen) with the flow rates in the common hepatic artery are presented, in accordance with an embodiment of the invention. Measuring the flow rates in real time allows for adjustment of the power during the ablation.

In accordance with several embodiments, one criterion for the definition of a successful ("effective") ablation is one where the maximum temperature reached anywhere in the tissue is less than 98° C. at any time during the application of energy to the tissue. This temperature threshold can advantageously avoid tissue vaporization, which may cause collateral damage, as well as increase the tissue impedance, thereby potentially causing the lesion size to become unpredictable. Moreover, for the ablation to be successful in accordance with several embodiments, a temperature of at least 50° C. at a distance of 6 millimeters from the lumen, and for a period of at least 2 minutes must be achieved. These parameters may provide increased confidence in cellular death at the location of the majority of the nerves around the hepatic artery (e.g., at a distance of about 4 mm from the arterial lumen).

Figure 127:
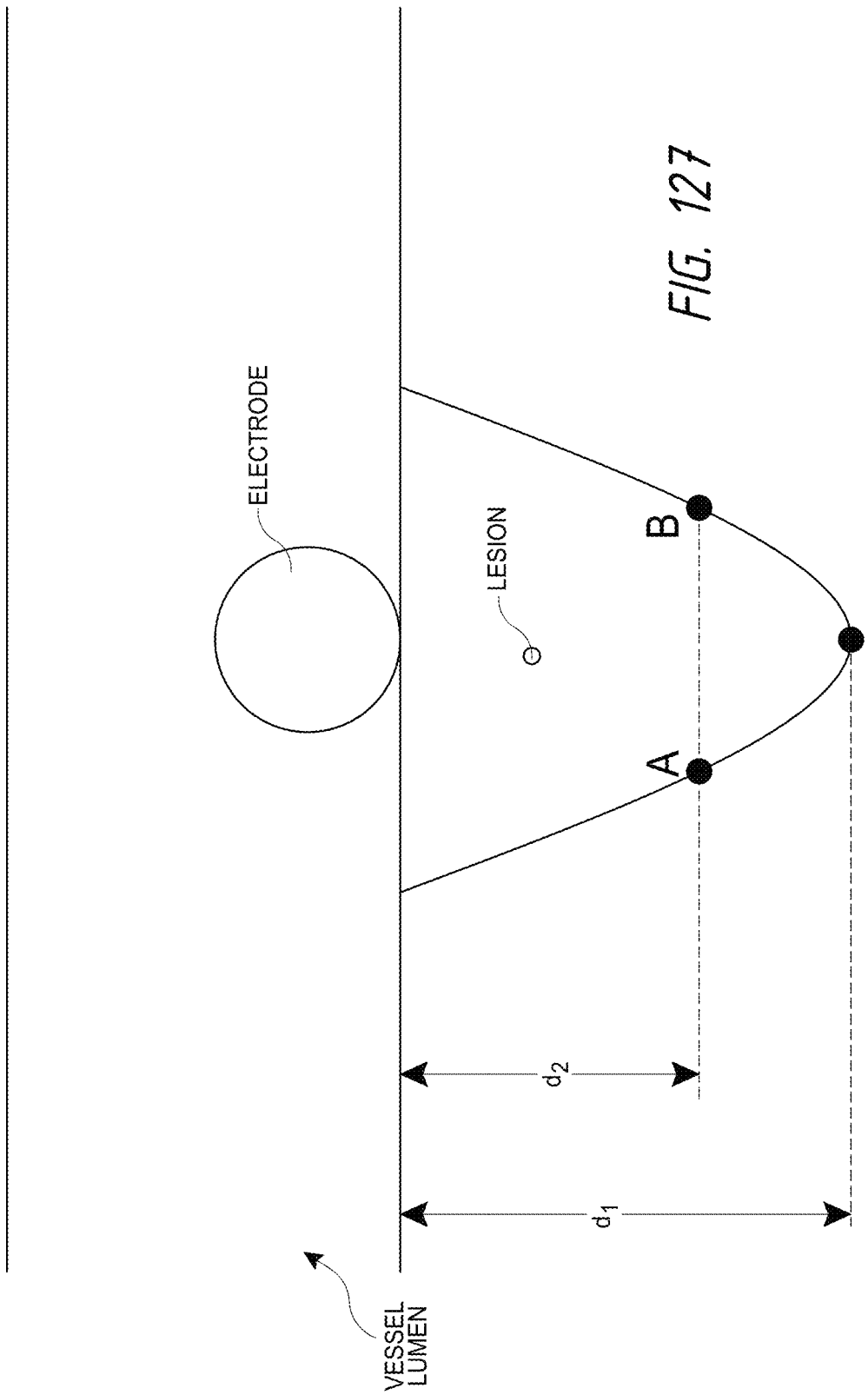
FIG. 127 illustrates a schematic two-dimensional representation of lesion depth, in accordance with an embodiment of the invention.

In accordance with several embodiments, a successful ablation of hepatic nerves is defined as one having a depth of 6 mm, even though the nerves are predominantly located 4 mm from the lumen, because the lesion (in some embodiments) has a conical or frustoconical shape. If we were to take the maximum at exactly 4 mm, the diameter of the lesion at such depth may be very small. By considering the maximum temperature at 6 mm, it can be assured that at 4 mm such temperature is reached for a relatively wide area (as shown in FIG. 127).

Data from simulations allows one to estimate what the power should be, in order to have a desired lesion size of 4 mm in depth, for a given value of flow rate. In accordance with several embodiments, there are two main strategies to achieve a lesion: 1) maximum power-minimum time, and 2) minimum power-maximum time. The first strategy pushes the temperature near the maximum that the tissues can reach without being vaporized, thereby minimizing the total time of ablation. With the second strategy, the temperature at the edge of the lesion is maintained relatively low, but the ablation takes a long time for the cumulative effect of the heat to cause tissue death (according to the Arrhenius equation). Since one of the problems during ablation of the common hepatic artery is movement due to breathing, employing the first strategy (maximum power and minimum time) may be advantageous, as it is reasonable to want to minimize or otherwise reduce the risk of electrode movements. In addition, clinicians generally prefer a shorter procedure time in order to reduce patient risk.

In some embodiments, energy or power delivery may be gated based on respiration using temperature or impedance measurements due to the asymmetric motion of the electrode during a respiratory cycle. The electrode may remain relatively stationary for about two-thirds of the respiratory cycle (expiration) and during this time period the tissue in contact with the electrode increases in temperature. When the electrode is in motion during the other third of the respiratory cycle (inspiration), the tissue may cool down. The changes in temperature may be monitored and used to gate the delivery of RF energy to the electrode so that energy is only delivered when the electrode is stationary (e.g., during expiration) or power is increased during this period to maintain a desired average power level (e.g., 10 Watts). Because tissue impedance varies with temperature, impedance measurements could be monitored (either alternatively or in combination with temperature) and used to start and stop the energy delivery. In situations where variation in temperature and/or impedance measurements is not detected, power may be delivered at a constant rate.

In such embodiments in which power output is synchronized with respiration, the ramp of the RF generator may be adjusted to achieve an almost instantaneous climb of power. The adjustment may be performed by modifying a ramping algorithm of the generator. In some embodiments, the generator may be programmed to ramp up from a power output below 1 W to a peak power output in less than half a second. In accordance with several embodiments, synchronization of power output with respiration takes advantage of the time frame when blood flow in the vessel (e.g., common hepatic artery) is at a maximum, thereby providing enhanced cooling to the electrode and vessel wall, which may reduce charring, notching and vessel spasm.

Figure 128:
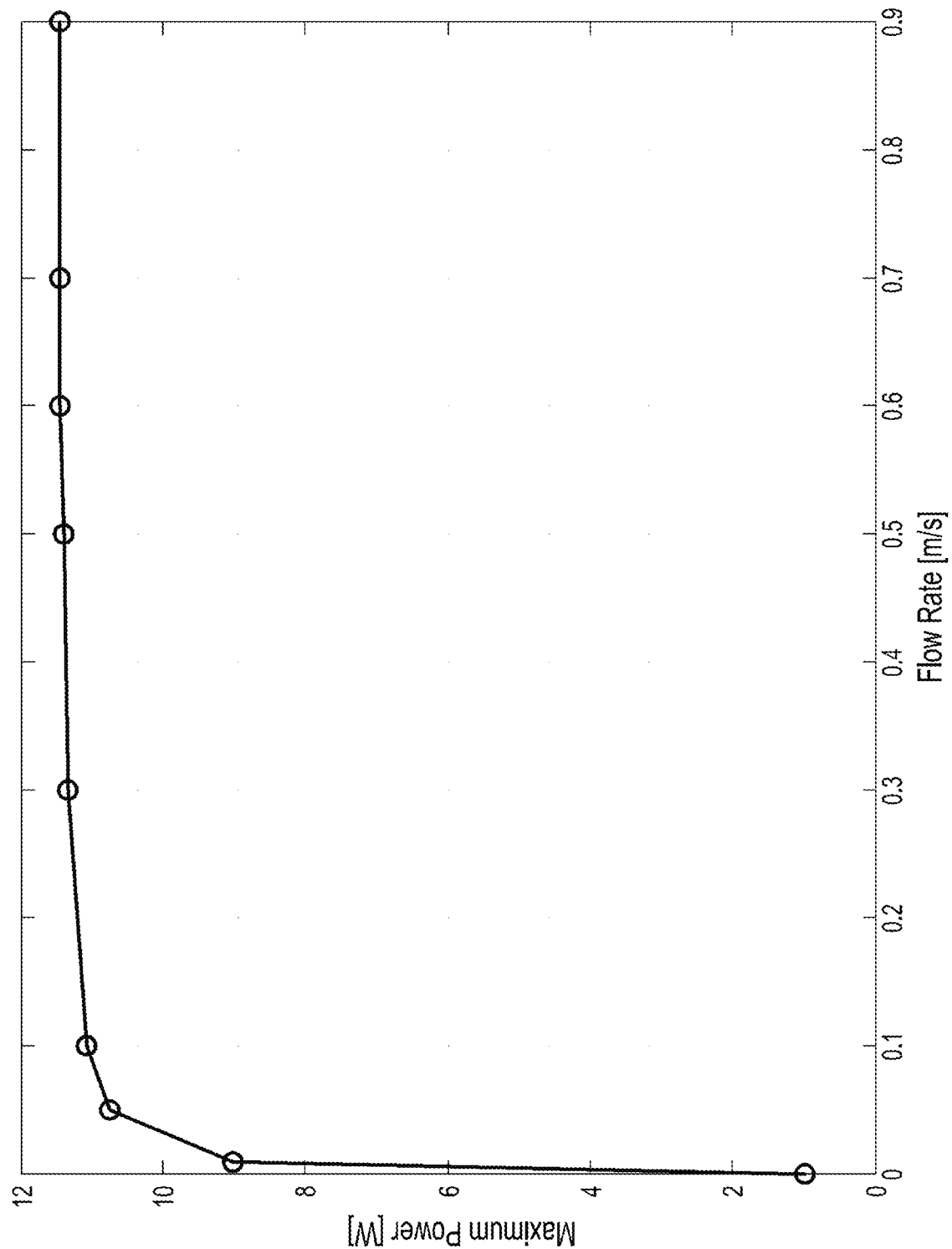
FIG. 128 is a graph illustrating maximum power as a function of arterial flow rate, in accordance with an embodiment of the invention.

FIG. 128 represents the maximum power that can be applied without resulting in vaporization as a function of arterial flow rate. The curve is generated based on the assumption of a 4 to 5 minute ablation, with a 2 millimeter diameter electrode. In several embodiments, to avoid vaporization temperature is maintained below about 97° C. and the lesion temperature is maintained at a minimum temperature of 47° C. for at least two minutes. In certain cases, tissue death may also be caused with a temperature of about 60° C. for a few seconds. In accordance with several embodiments, temperatures significantly higher than 50° C. cannot be reached throughout the lesion without causing tissue vaporization.

As shown in FIG. 128, as the flow rate increases, the maximum power increases rapidly for very low levels of flow rate and plateaus at a flow rate of about 0.6 m/s. The plateau is based at least in part on the fact that cooling capability of the blood reaches a saturation point. Thus, even for higher levels of flow rate, the power cannot be increased. Typical flow rates in the hepatic artery are generally no higher than 0.5 m/s. The flow rate value can easily be lowered unpredictably during an ablation (for example, if the catheter obstructs some of the blood flow).

This means that in reality, hepatic arterial ablation is conducted based on the conditions represented by the left part of the curve in FIG. 128. In this area of the curve, the maximum power varies considerably with small variations of the flow rate. In several embodiments, monitoring the flow is vital to avoid excessive or insufficient power, both of which may cause the ablation to be unsuccessful.

Figure 129:
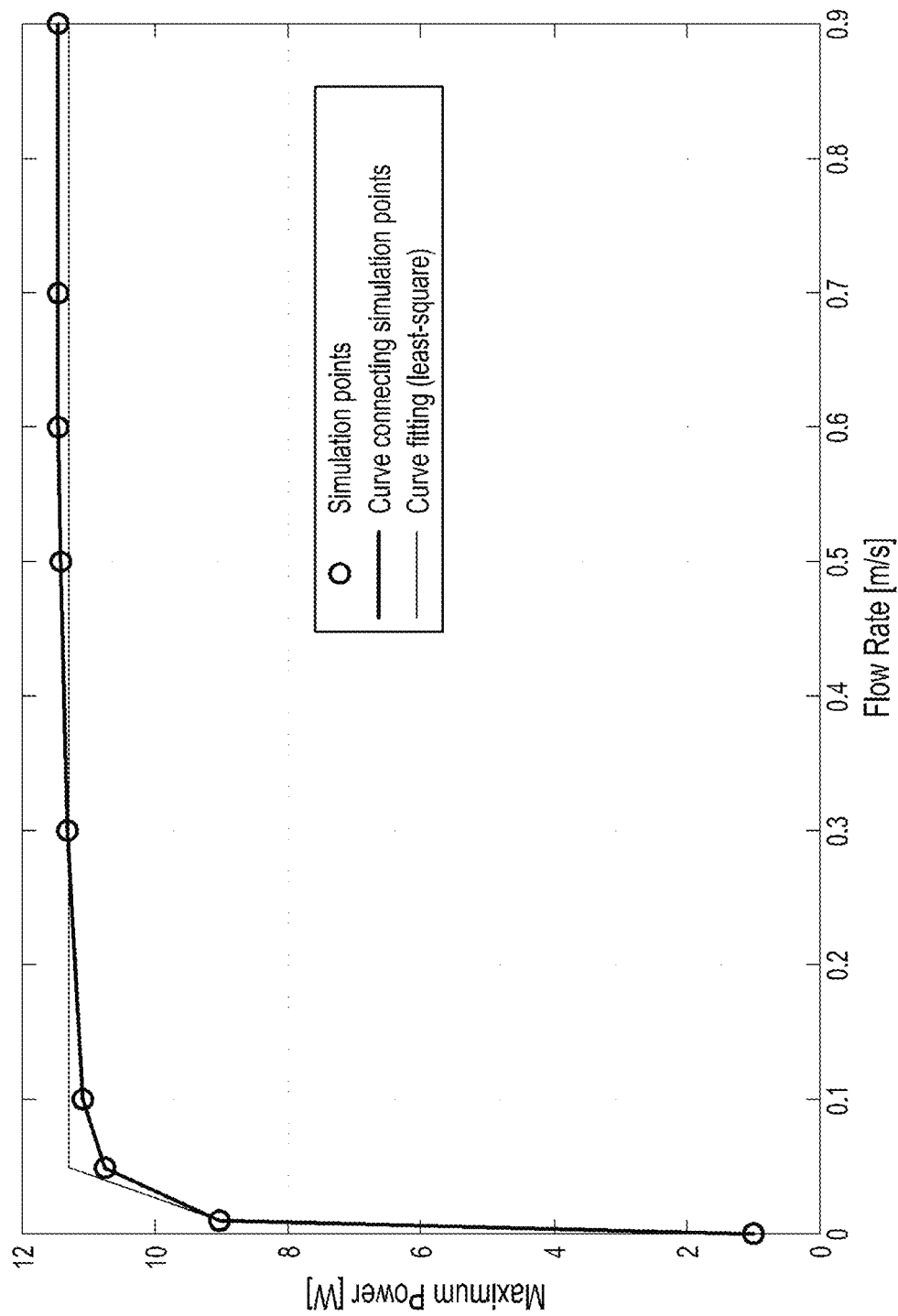
FIG. 129 is a graph of a least-square curve fitting for the relation between maximum power and arterial flow rate, in accordance with an embodiment of the invention.

The curve linking maximum power and flow rate can be approximated (for example, as shown in FIG. 129) with a non-linear least-square curve fitting having the following formula:

$$\text{Power} = K_1 - K_2 e^{(-K_3 * FlowRate)}, \text{ where } K_1 = 11.27, K_2 = 10.28 \text{ and } K_3 = 151.59$$

The table below shows the variation in temperature, for some embodiments, for different durations of RF power applications, both at the peak temperature (typically at about 1 mm from the surface of the electrode) and at about 6 millimeters from the arterial lumen. In some embodiments, the variation of temperature between 120 and 300 seconds is minimal, however, since the temperature at the edge of the lesion is relatively low (slightly less than 50° C.), an ablation lasting at least 240 seconds in order to cause tissue death may be used, in accordance with several embodiments.

TABLE 1

Acceptable power and time combinations for various degrees of hepatic artery blood flow

| Time [s] | Peak Temperature [deg C.] | Temp. at 6 mm from the lumen [deg C.] |
|---|---|---|
| Flow Rate = 0 (free convection; Power = 0.99059) | | |
| 120 | 93.888 | 39.61 |
| 180 | 96.021 | 40.35 |
| 240 | 97.065 | 40.77 |
| 300 | 97.612 | 40.94 |
| Flow Rate = 0.1 m/s; Power = 11.08679 W | | |
| 120 | 96.111 | 47.29 |
| 180 | 96.963 | 48.67 |
| 240 | 97.279 | 49.01 |
| 300 | 97.428 | 49.49 |

TABLE 1-continued

Acceptable power and time combinations for various degrees of hepatic artery blood flow

| Time [s] | Peak Temperature [deg C.] | Temp. at 6 mm from the lumen [deg C.] |
|---|---|---|
| Flow Rate = 0.3 m/s; Power = 11.32912 W | | |
| 120 | 95.831 | 47.14 |
| 180 | 96.718 | 47.98 |
| 240 | 97.09 | 49.28 |
| 300 | 97.291 | 49.66 |
| Flow Rate = 0.5 m/s; Power = 11.40233 W | | |
| 120 | 95.858 | 47.33 |
| 180 | 96.711 | 48.74 |
| 240 | 97.052 | 49.2 |
| 300 | 97.23 | 49.67 |
| Flow Rate = 0.7 m/s; Power = 11.45126 W | | |
| 120 | 95.955 | 47.2 |
| 180 | 96.838 | 48.63 |
| 240 | 97.2 | 49.35 |
| 300 | 97.386 | 49.6 |

From the non-limiting simulations described above, the minimum flow rate that allows a 4 mm deep lesion (e.g., using the criteria of no vaporization and a minimum temperature of about 50° C. at a location 6 mm from the vessel lumen) and avoids vaporization is about 0.01 m/s. Therefore, it may be advantageous to measure flow in the hepatic artery before the procedure to ensure flow is adequate before initiating treatment. Below such a flow rate, other forms of cooling may need to be added, such as internal electrode cooling or irrigation of the artery.

H. Example 8

The hepatic artery has an average estimated diameter of 4 mm in adult humans. In an endovascular ablation, this diameter restricts the size of the electrode(s) that can be used. A study was performed to investigate the optimal size of the electrode to reach a lesion approximately 4 mm deep within the adventitia of the hepatic artery.

Figure 130:
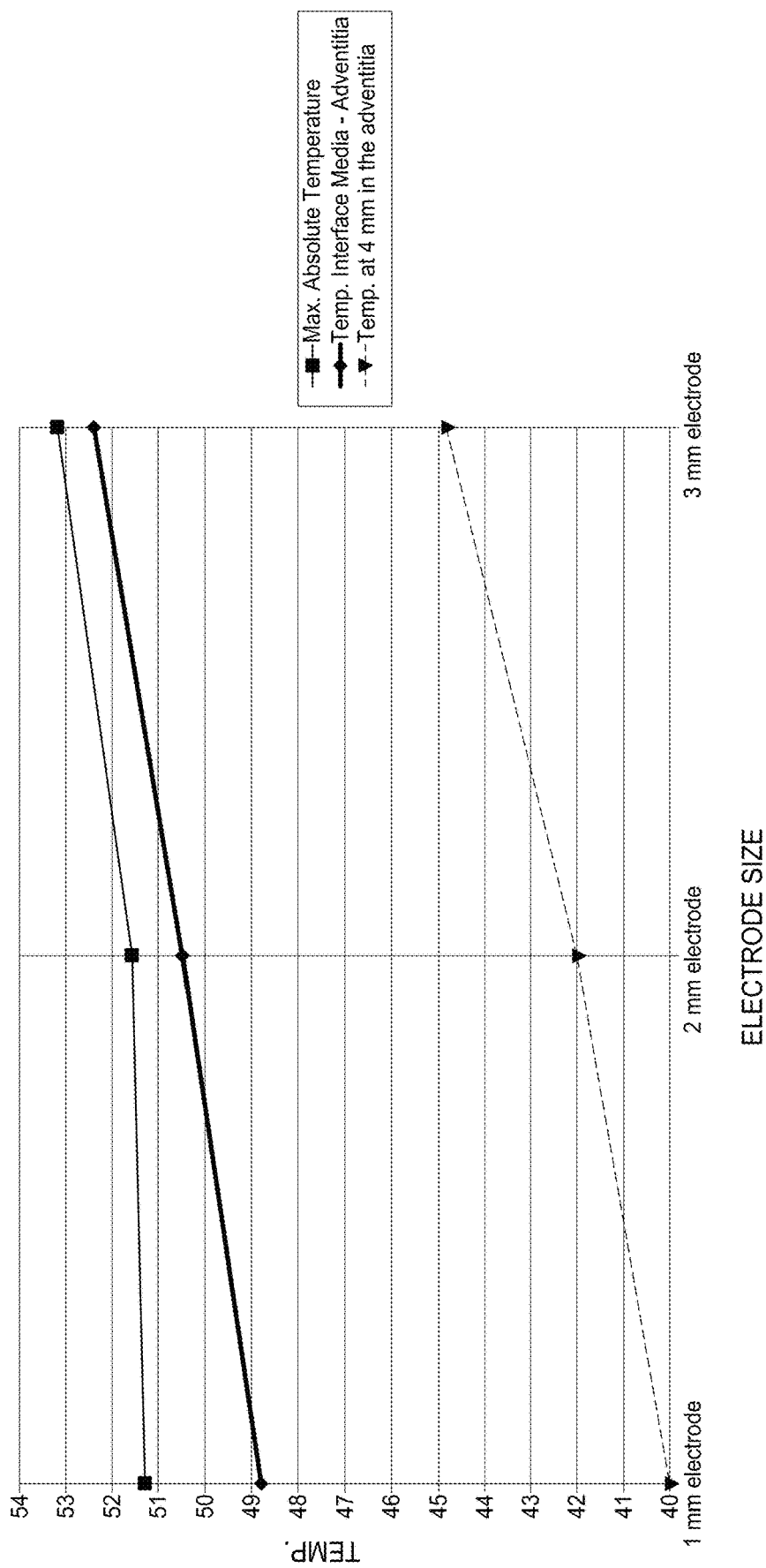
FIG. 130 is a graph illustrating change in lesion temperature as electrode size changes, in accordance with an embodiment of the invention.

In accordance with embodiments of the invention, the models assume an ablation performed in a monopolar setting, with an active spherical electrode of respectively 1, 2, and 3 millimeters diameter. The models also assume that the electrode is externally cooled by a blood flow having a speed of 0.1 m/s, that the media has a thickness of 2 millimeters, and that 25 V are applied with minimal contact force, for 3 minutes, in one embodiment. FIG. 130 shows the trend of the temperature changes with electrode size.

In several embodiments, there are two factors influencing the lesion size, when electrode size changes. The first factor is the electric field lines, which tend to become denser in the region adjacent to the electrode, which may cause a higher temperature near a smaller electrode and a more rapid decrease with distance from the electrode. If this effect was dominating, as the electrode size grows, the temperature would decrease for a given power level.

The second factor is the cooling action of the blood flow. In some embodiments, the electrode diameter is comparable in size with the artery diameter, and thus a bigger electrode blocks or occludes some of the blood flow, thereby causing an increase in temperature as the electrode size increases.

In the case of the common hepatic artery, the second factor may slightly dominate the first factor: there may be a slight increase in temperature as the electrode size increases.

The study was limited to electrodes of 3 millimeters in diameter. The diameter was selected based on the diameter of the hepatic artery to avoid complete occlusion. In various embodiments, the electrode diameter is selected so as to prevent or inhibit complete occlusion by the electrode itself and/or to reduce peak temperature and thereby prevent or inhibit against obtaining the reaching of the vaporization point.

In accordance with several embodiments, systems and methods described herein control neuromodulation (e.g., nerve destruction) over a wide range of anatomical and physiologic conditions (e.g., arterial lumen diameter, blood flow velocity, tissue composition, etc.), which impacts lesion geometry. In accordance with several embodiments, for hepatic artery denervation, it is particularly advantageous to define an energy delivery strategy that is insensitive (e.g., robust) to initial and boundary conditions (e.g., blood flow velocity, arterial lumen diameter, breathing motion). This may be particularly true for hepatic denervation, where anatomy and physiology can vary more significantly than in the renal artery, both patient-to-patient and intraoperatively. For example, the hepatic artery can move up to 5 cm during each ventilated breathing cycle, leading to variations in electrode position and arterial blood flow. It has been observed that only about 60-75% of patients present with normal hepatic arterial anatomy, and pathology studies in human cadavers have indicated that tissue composition (especially the degree of visceral fat in the hepatic arterial region) can vary significantly between subjects.

In several embodiments, means for assessing the progress of an endovascular ablation procedure are provided. Ablations controlled using electrode tip temperature control can vary based on the amount of convective cooling in the treatment region—for high cooling environments, more energy may be delivered to the target tissue, resulting in larger lesions, and for low cooling environments, less energy may be delivered to the target tissue, resulting in smaller lesions. In various embodiments, it may be desirable to employ open-loop energy control as a primary control method, including the appropriate safety-monitoring features and temperature, impedance, or other feedback control schemes as secondary control means. The open-loop control algorithm, by virtue of being developed on the basis of historical in vitro and in vivo studies (e.g., using data mining techniques), can ensure a safe and effective starting point for the treatment that can then be adjusted on the basis of feedback signals.

In one embodiment, a specific power and temperature control algorithm is described that safely, quickly, and reliably achieves hepatic denervation. Based on in vitro and/or in vivo testing, the temperature response of the target tissue to known levels of constant RF power applications is characterized. Energy may then first be delivered at a maximum initial power for a first set time period, followed by a second set time period where power is decremented by a set amount, and so on, until a steady-state tissue temperature is achieved at a given steady-state power. Using the known relationship between impedance and temperature, any marked increases in tissue impedance can be used to decrease applied power or terminate energy delivery in order to prevent or inhibit unpredictable, highly non-linear results. In several embodiments, the power can be applied such that a defined drop in impedance is achieved and maintained throughout the duration of the procedure.

In some embodiments, electrode tip temperature measurements are employed as a power shut-off limit and/or used to provide estimates of blood flow velocity, adjusting target power and impedance levels accordingly.

Figure 131:
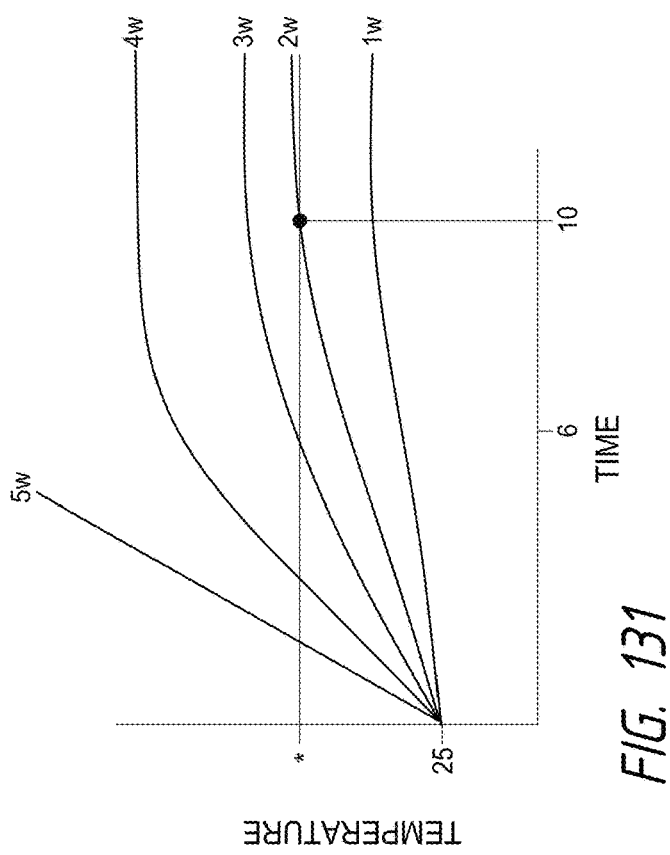
FIG. 131 is a graph illustrating change in temperature over time for different power levels of RF energy, in accordance with an embodiment of the invention.

An idealized tissue response to a range of RF power levels (1 W-5 W) at a given point location is shown in FIG. 131. For some period of time, $t<t_{ss}$, the temperature increases linearly as a function of time, with dT/dt defined by the delivered power. In biological tissues, heat losses due to conduction to surrounding tissues, blood flow, and perfusion causes tissue temperatures to generally approach steady-values over time. Ideally, one would simply increase power in order to achieve higher steady-state temperatures faster. However, because biological tissues have temperature-dependent properties that are highly non-linear at temperatures near vaporization temperatures (e.g., ~100° C.), the temperature progression and resulting lesion size is highly variable and unpredictable (see, for example, FIG. 134).

Figure 135:
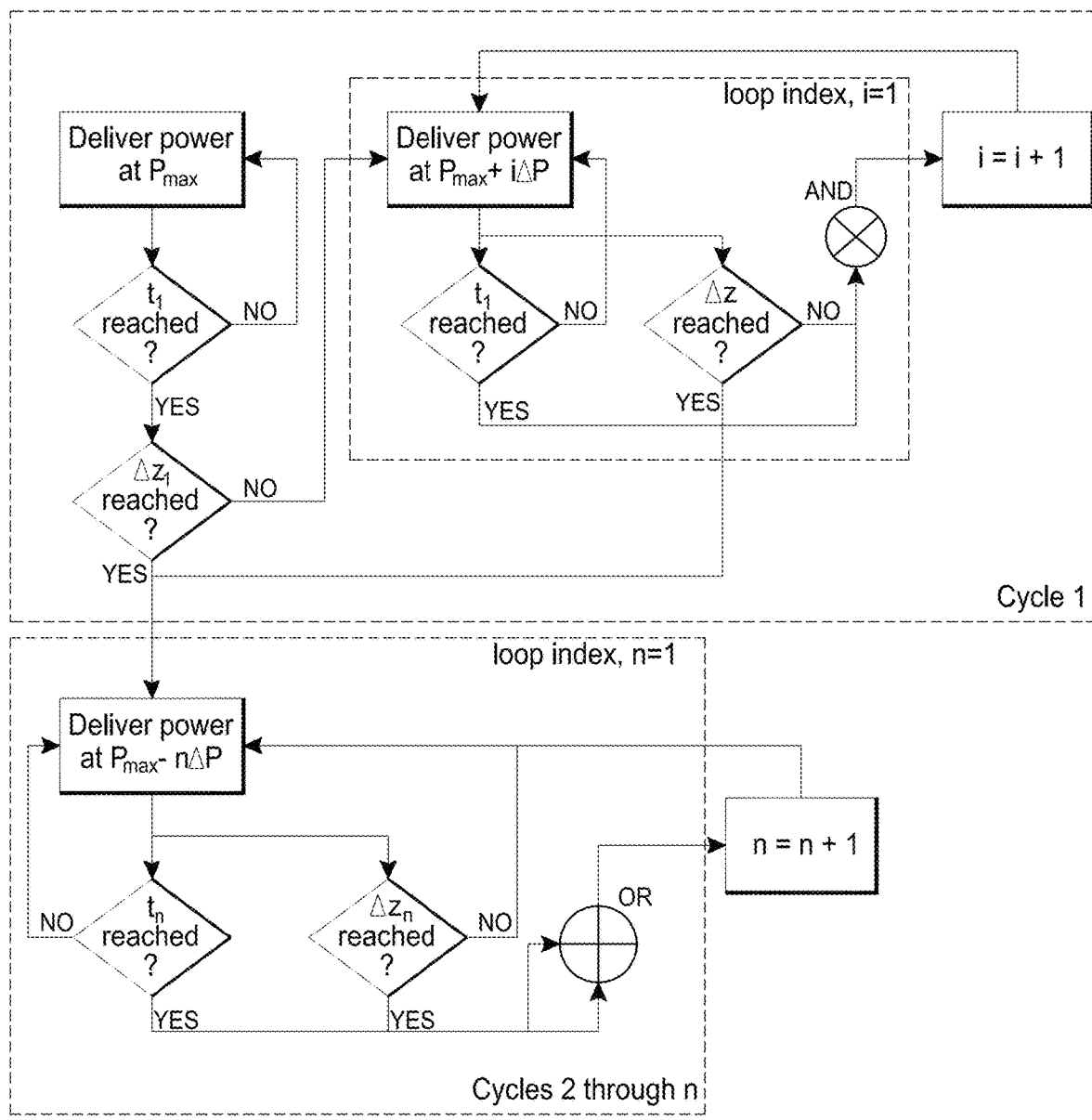
FIG. 135 illustrates an embodiment of a power control process incorporating impedance feedback control.

In accordance with several embodiments, a decremented power delivery algorithm (shown, for example, in FIG. 135) is provided to maximize or otherwise increase steady-state temperatures and increase the speed at which they are reached. In cycle 0 (n=0), a maximum power $P_{max}$ is applied for a time period $t_1$, where $P_{max}$ is the maximum power that can be delivered in a controllable time period without causing tissue vaporization and $t_1$ is the maximum time for which $P_{max}$ can be delivered without causing vaporization. In cycle 1 (n=1), corresponding to $t=t_1$, the applied power is decremented to $P_{max}-\Delta P$ and applied for a period $t_2$, corresponding to the maximum time for which $P_{max}-\Delta P$ can be delivered without causing vaporization. This decrement algorithm may continue for n cycles, where the delivered power in each cycle n is $P_{max}-n\Delta P$, and the power application time t, corresponds to the maximum time for which $P_{max}-n\Delta P$ can be delivered without causing vaporization.

$P_{max}$, $\Delta P$ and $t_1, \ldots, t_n$ can be determined empirically using suitable in vitro and in vivo models and data reported in the literature, with statistical methods employed to choose levels for these parameters that will generally ensure tissue vaporization is avoided (e.g., 99% reliability, 95% confidence lower-bound values for $P_{max}$, $\Delta P$ and $t_1, \ldots, t_n$ to avoid vaporization.)

$\Delta P$ might vary in subsequent cycles and is described here as a single variable for brevity (it may be two, three, four or more variables). In some embodiments, $\Delta P$ decreases (and t, increases) with each subsequent cycle as the steady-state power is approached asymptotically. The algorithm described in FIG. 136 has the effect of delivering the maximum sustainable heating power to tissue without causing vaporization or inducing unpredictable, non-linear tissue responses, in one embodiment.

While, in some embodiments, the open-loop approach provides a good empirical approach based on historically obtained data, it may not account for the anatomic and physiologic variations encountered clinically. Some degree of feedback control may be desired to tailor the core or primary energy deliver algorithm described above to each unique clinical situation. For example, in high cooling environments, less energy may be delivered to the target tissue (since more of the energy is carried away through convection), and alternatively, in low cooling environments, more energy may be delivered to the target tissue. Due to variations in tissue composition, some tissue might reach vaporization or desiccate faster than other tissues, leading to non-linear effects.

Figure 133:
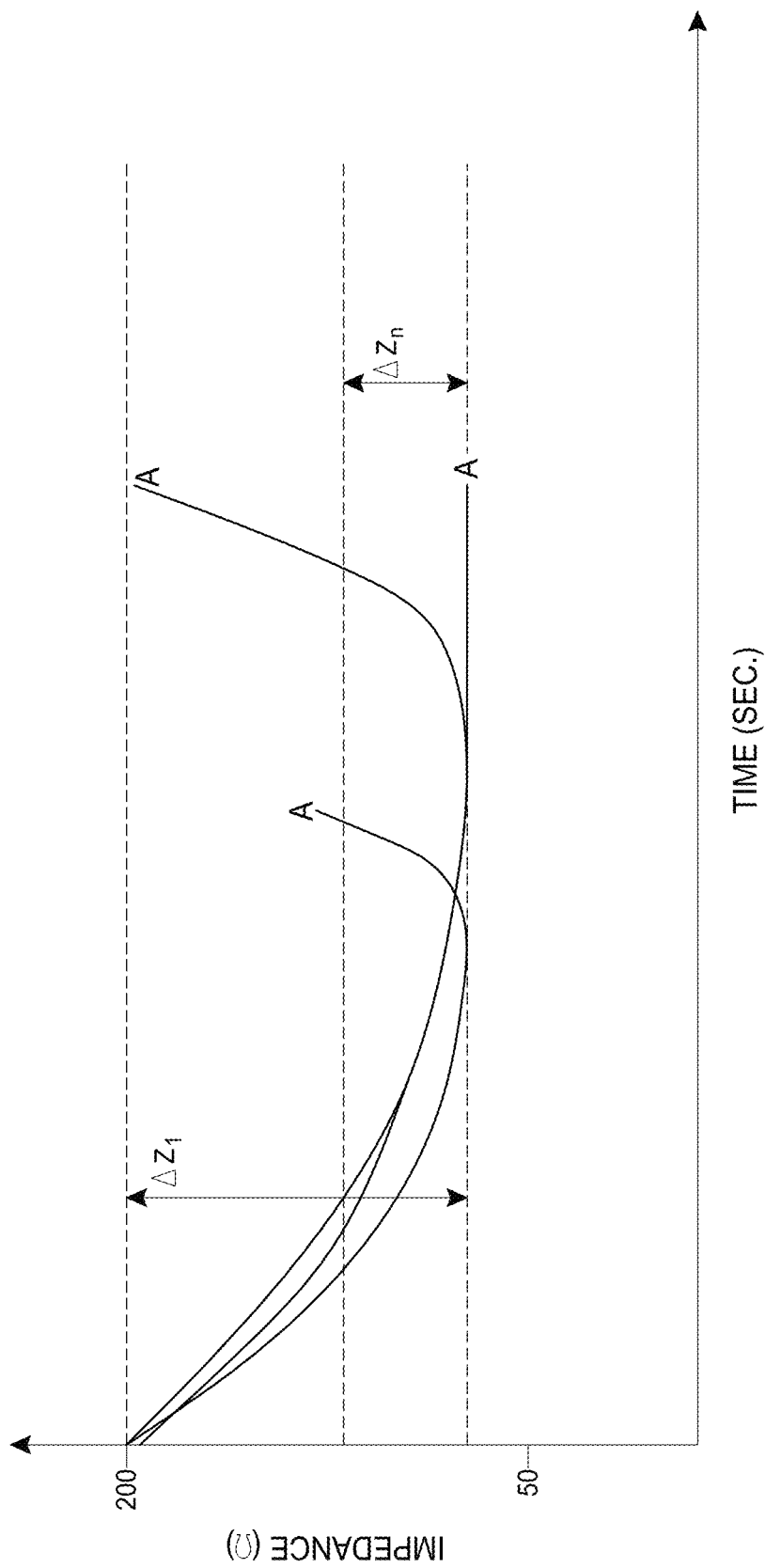

Because impedance is generally related to temperature (as shown, for example, in FIG. 134), impedance can be used as a proxy for the bulk temperature of the tissue surrounding the electrode. A characteristic drop, $\Delta z_1$ in impedance (shown in FIG. 133) during the initial heating period may be indicative of effective heating, whereas impedance increases $\Delta z_n$ after this initial period may be indicative of non-linear effects and vaporization. In some embodiments, non-linear effects and vaporization are avoided.

Figure 132:
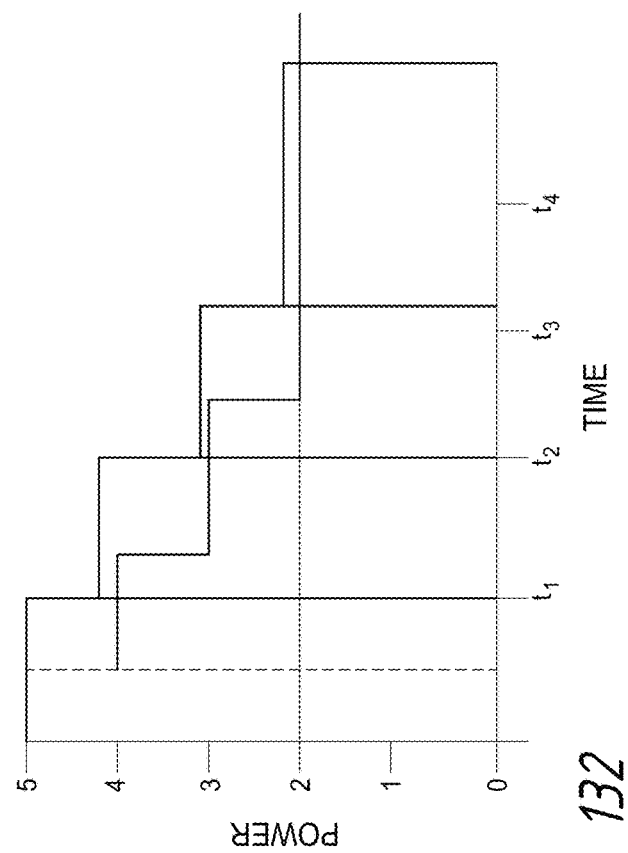
FIGS. 132-134 are graphs illustrating relationships between various treatment parameters, in accordance with embodiments of the invention.
Figure 134:
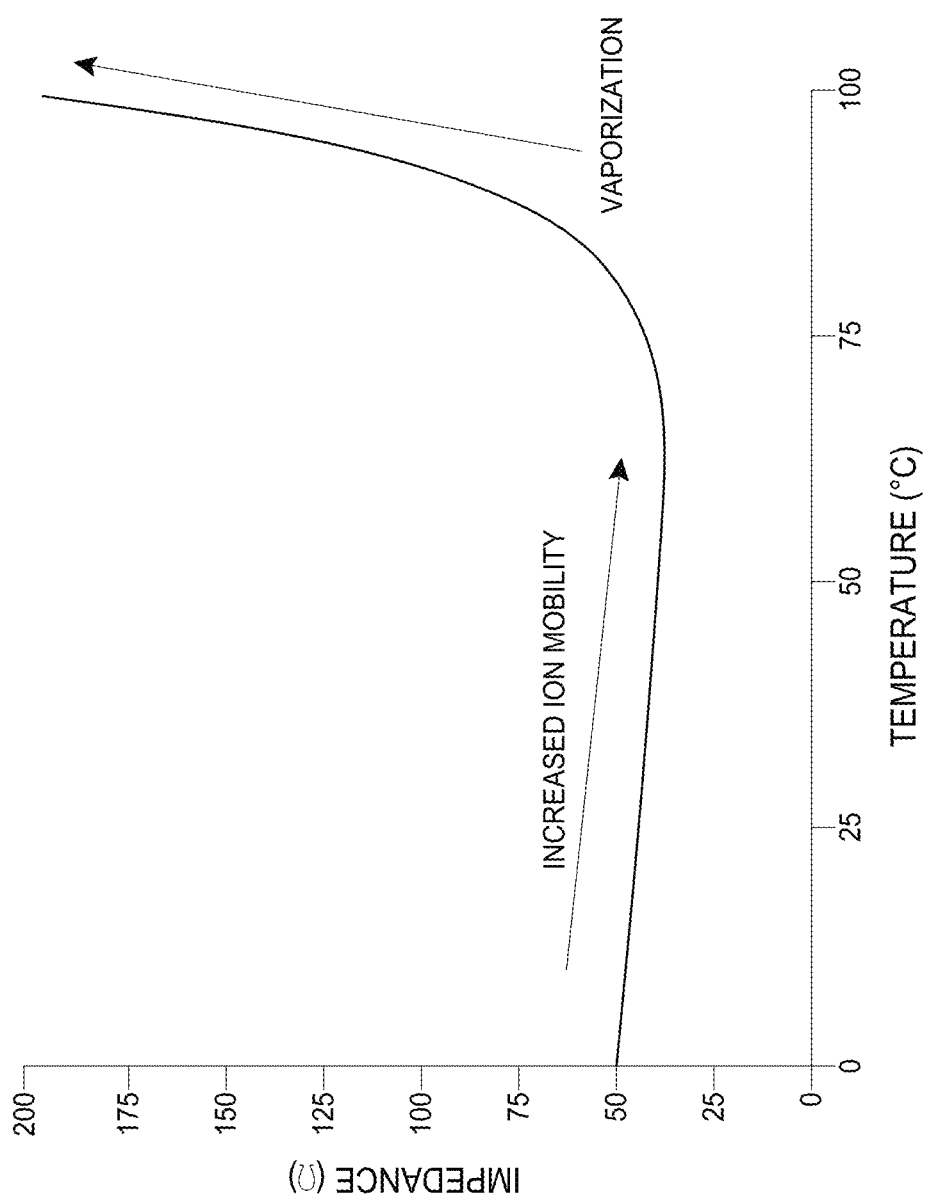

An embodiment of an algorithm for overlaying impedance-based feedback control with the open-loop power control algorithm is illustrated in FIG. 134. In some embodiments, the effect of this algorithm is generally to shift $P_{max}$ (the curve represented in FIG. 132) upwards in order to achieve the desired drop in impedance in the first cycle. In subsequent cycles, power may be decremented after the prescribed time period ($t_n$) defined by the open loop algorithm is reached or until a threshold impedance rise ($\Delta z_n$) is detected, after which power may further be decremented to avoid vaporization. In some embodiments, RF power delivery is interrupted or otherwise terminated upon detection of a threshold impedance rise.

$\Delta z_1$ can be variably defined as a target impedance relative to a reference impedance value (e.g., for a target impedance of 150Ω and initial impedance of 210Ω, $\Delta z_1 = 60Ω$), or alternatively, can be strictly defined relative to the impedance measured at the beginning of energy delivery to tissue (e.g., a fixed value of $\Delta z_1 = 50Ω$ from the impedance measurement at the start of a treatment or procedure). Similarly, $\Delta z_n$ can be defined as an absolute value or can be scaled relative to the target impedance value (e.g., 10% deviation from the target impedance value).

In order to improve the fidelity of the impedance measurement in some embodiments, it may be desirable to implement a filtering or averaging calculation (e.g., a windowed average or other filter) in order to avoid noise in the impedance measurement triggering false positive control signals.

RF generator designs commonly calculate power and impedance by measuring voltage and current (P=VI, and V/I=R). Due to reactance in the system, this measurement can be erroneous, leading to inadequate treatment (e.g., ablation) of the nerves surrounding the hepatic artery or other target artery, vessel or tissue.

Figure 136:
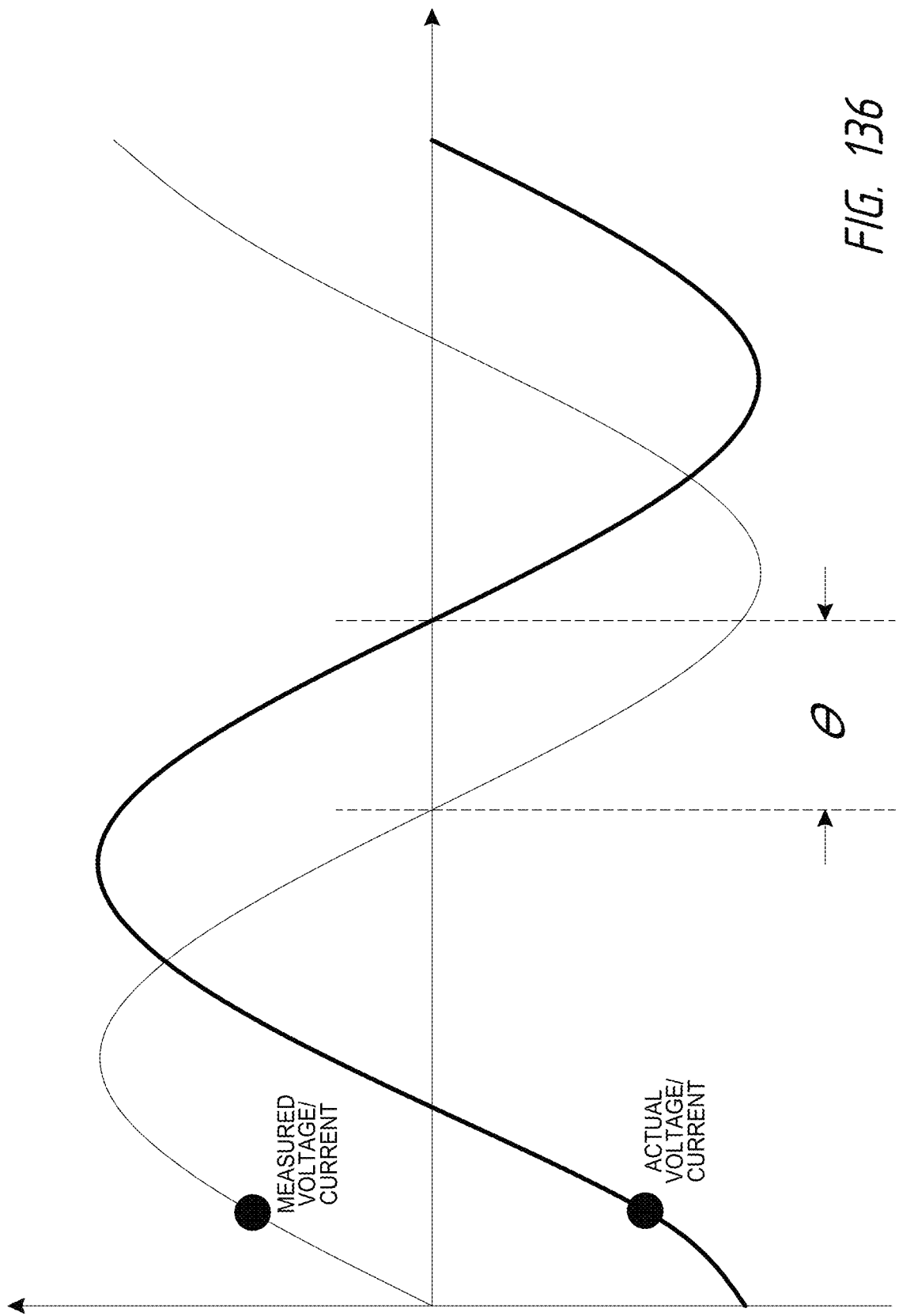
FIG. 136 illustrates how phase shifts can cause inaccurate measurement of current and/or voltage.

Reactance, a result of capacitance and inductance in the RF circuit can lead to a phase shift (as illustrated in FIG. 136), where the voltage and/or current in the target tissue is offset from the voltage and/or current measured by the RF generator. When the measured and actual voltage and current are different, the progress of the therapy is unknown and can lead to unpredictable results, since power and impedance are used as control variables for a wide range of energy control algorithms. Measured power and impedance can often differ by as much as 10% from the actual values.

Inductance is generally a result of the tortuosity of the electrode lead, and for ablation procedures, is generally ignored. In biological tissue, capacitance may be a result of capacitive coupling between the electrode shaft (alternatively, the "electrode leads") and the tissue across the insulating dielectric generally disposed about the non-therapeutic portions of the electrode shaft or electrode leads. Ions in the tissue move in response to changes in the electrode polarity, but the capacitance leads to discrete delays in the flow of ions relative to the driving voltage of the RF generator, manifested as a phase shift. At the tissue level, capacitance may arise due to the variable composition of tissue—for example, lipids, fats, and other non-conducting tissues disposed in the hilus sheath surrounding the hepatic artery can lead to local capacitance causing discrete delays in the flow of ions through the tissue, which may also contribute to the phase shift. In one embodiment, the phase shift may be accounted for by employing a bi-linear transform such as the bi-linear transform described in U.S. Publ. No. 2012/0095461 (e.g., paragraphs [0050] through [0089]), which is incorporated by reference herein. By accurately accounting for phase and magnitude changes at the load, power and impedance can be measured more accurately, leading to more efficacious treatment, e.g., ablation, of the nerves surrounding the hepatic artery.

Referring now again to FIG. 135, not shown is the ability to monitor tip temperature throughout the treatment. The tip temperature measurement can also be used as a feedback signal, for example, to terminate RF power delivery once a threshold temperature is reached. In some embodiments, leveraging the fact that at a given power level, the tip temperature is a function of blood flow velocity, $P_{max}$ can similarly be adjusted up or down to increase (e.g., maximize) effective energy delivery on the basis of the available convective cooling power, which effectively converts the electrode into a hot wire anemometer flow sensor.

The ability to monitor impedance changes for monopolar configurations has not been previously appreciated, and for endovascular ablation, it was generally believed that impedance control algorithms were only useful for bipolar electrode configurations. Because the region of tissue heated in a bipolar configuration is confined to a relatively limited region, the impedance of the system is generally regarded as the impedance of the heated region. However, the impedance of the heated region can be determined for monopolar configurations as well. Although the resistance pathway through biological tissue is generally regarded as a bulk property, it can be resolved into three components for a monopolar configuration, with representative values for each component highlighted in FIG. 137:

1) The resistance of the blood ($R_{blood}$)
2) The "background" or "remote" resistance of the bulk tissue ($R_{remote}$)
3) The resistance of the tissue in the vicinity of the monopolar electrode (the target tissue), $R_{tissue}$.

In some embodiments, by subtracting out the components of impedance contributed by the background tissue and blood, a more sensitive impedance measurement treated tissue region can be obtained, thereby improving the accuracy and applicability of impedance control in a monopolar configuration. By subtracting the power deposited in non-target tissues, a more reliable estimate of the energy delivered to the target tissue can be obtained.

Figure 138:
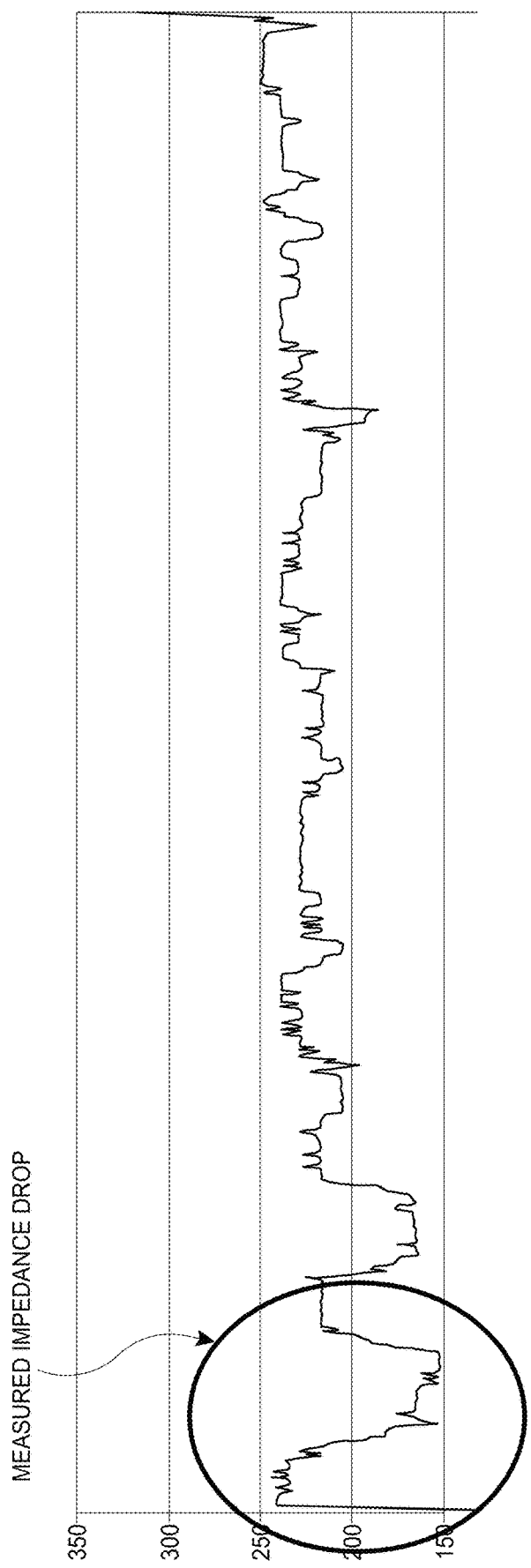
FIG. 138 illustrates an effect on impedance measurements by subtracting a background impedance signal, in accordance with an embodiment of the invention.

As illustrated in FIG. 138, measurable changes in tissue impedance have been demonstrated during hepatic arterial ablation by subtracting out the largely "DC" components of resistance and focusing on the variable component driven by the local tissue response.

In accordance with several embodiments, the treatment control approaches described above unexpectedly provide the effective "decoupling" of the electrode tip temperature measurement from variations in blood flow. Using electrode tip temperature control algorithms, output power may be adjusted to maintain a generally constant electrode tip temperature. Power may then become a de facto measurement of convective cooling due to blood flow, but a lagging indicator as it is the controlled output. By implementing the power control algorithm described above, the electrode tip temperature sensor may be "freed" to perform other functions, such as 1) providing a safety signal to shut-off power in the event excessive temperatures are reached, to avoid thrombus or eschar formation or 2) the steady-state temperature reached for a given power application can be used as a leading indicator of blood flow, which can also be used to generally increase or decrease the overall level of power delivered to the tissue (e.g., increase or decrease $P_{max}$).

While the devices, systems and methods described herein have primarily addressed the treatment of diabetes (e.g., diabetes mellitus), other conditions, diseases, disorders, or syndromes can be treated using the devices, systems and methods described herein, including but not limited to ventricular tachycardia, atrial fibrillation or atrial flutter, inflammatory diseases, endocrine diseases, hepatitis, pancreatitis, gastric ulcers, gastric motility disorders, irritable bowel syndrome, autoimmune disorders (such as Crohn's disease), obesity, Tay-Sachs disease, Wilson's disease, NASH, NAFLD, leukodystrophy, polycystic ovary syndrome, gestational diabetes, diabetes insipidus, thyroid disease, and other metabolic disorders, diseases, or conditions.

In some embodiments, the system comprises one or more of the following: means for tissue modulation (e.g., an ablation or other type of modulation catheter or delivery device), means for energy delivery (e.g., generator or other energy generation module), means for deploying energy delivery members or other treatment elements (e.g., pull wire, preformed shape memory material, retractable sheaths, expansion members), etc.

In some embodiments, the system comprises various features that are present as single features (as opposed to multiple features). For example, in one embodiment, the system includes a single ablation catheter with a single energy delivery member (e.g., radiofrequency electrode). A single thermocouple (or other means for measuring temperature) may also be included. Multiple features or components are provided in alternate embodiments.

The various illustrative logical blocks, modules, and circuits described in connection with the embodiments disclosed herein (e.g., generators) can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

The blocks of the methods and algorithms described in connection with the embodiments disclosed herein can be embodied directly in hardware, in a software module executed by a processor, or in a combination of the two. The modules described herein may comprise structural hardware elements and/or non-structural software elements stored in memory (for example, algorithms or machine-readable instructions executable by processing or computing devices). Memory or computer-readable storage media can include RAM memory, flash memory, ROM memory, EPROM memory, EEPROM memory, registers, a hard disk, a removable disk, a CD-ROM, or any other form of computer-readable storage medium known in the art. Any methods described herein may be embodied in, and partially or fully automated via, software code modules stored in a memory and executed by one or more processors or other computing devices. The methods may be executed on the computing devices in response to execution of software instructions or other executable machine-readable code read from a tangible computer readable medium. A tangible computer readable medium is a data storage device that can store data that is readable by a computer system. Examples of computer readable mediums include read-only memory (for example, EEPROM), random-access memory, other volatile or non-volatile memory devices, CD-ROMs, magnetic tape, flash drives, and optical data storage devices. A storage medium may advantageously be coupled to a processor such that the processor can read information from, and write information to, the storage medium. In the alternative, the storage medium can be integral to the processor.

For example, hardware for performing selected tasks according to embodiments of the invention could be implemented as a chip or a circuit. As software, selected tasks according to embodiments of the invention could be implemented as an algorithm or a plurality of machine-readable instructions being executed by a computer using any suitable operating system. In one embodiment, a network (wired or wireless) connection is provided. A display and/or a user input device (such as a keyboard, mouse, touchscreen, user-actuatable inputs, trackpad) may optionally be provided.

Although certain embodiments and examples have been described herein, aspects of the methods and devices shown and described in the present disclosure may be differently combined and/or modified to form still further embodiments. Additionally, the methods described herein may be practiced using any device suitable for performing the recited steps. Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure (including the figures) herein of any particular feature, aspect, method, property, characteristic, quality, attribute, element, or the like in connection with various embodiments can be used in all other embodiments set forth herein. For example, features described in one figure may be used in conjunction with embodiments illustrated in other figures. Embodiments embodied or carried out in a manner may achieve one advantage or group of advantages as taught herein without necessarily achieving other advantages. The headings used herein are merely provided to enhance readability and are not intended to limit the scope of the embodiments disclosed in a particular section to the features or elements disclosed in that section.

While embodiments are susceptible to various modifications, and alternative forms, specific examples thereof have been shown in the drawings and are herein described in detail. It should be understood, however, that the embodiments are not to be limited to the particular forms or methods disclosed, but to the contrary, the embodiments are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "delivering a neuromodulation catheter within a hepatic artery" include "instructing the delivery of a neuromodulation catheter within a hepatic artery."

Various embodiments of the invention have been presented in a range format. It should be understood that the description in range format is merely for convenience and brevity and should not be construed as an inflexible limitation on the scope of the invention. The ranges disclosed herein encompass any and all overlap, sub-ranges, and combinations thereof, as well as individual numerical values within that range. For example, description of a range such as from about 5 to about 30 minutes should be considered to have specifically disclosed subranges such as from 5 to 10 degrees, from 10 to 20 minutes, from 5 to 25 minutes, from 15 to 30 minutes etc., as well as individual numbers within that range, for example, 5, 10, 15, 20, 25, 12, 15.5 and any whole and partial increments therebetween. Language such as "up to," "at least," "greater than," "less than," "between," and the like includes the number recited. Numbers preceded by a term such as "about" or "approximately" include the recited numbers (for example, "about 3 mm" includes "3 mm"). The terms "approximately", "about", and "substantially" as used herein represent an amount close to the stated amount that still performs a desired function or achieves a desired result.

What is claimed:

1. An actively-cooled neuromodulation device adapted for intravascular neuromodulation, the device comprising:
   an elongated shaft comprising a proximal end portion and a distal end portion;
   an inflatable, expandable member positioned at the distal end portion of the elongated shaft, the inflatable, expandable member being configured to transition from a non-inflated delivery configuration to an inflated deployment configuration,
   wherein the inflatable, expandable member comprises a plurality of electrodes positioned along the inflatable, expandable member so as to provide a treatment pattern designed to provide increased perivascular treatment while reducing vessel wall injury,
   wherein the elongated shaft comprises a lumen, wherein the lumen is adapted to operably couple to a pump configured to continuously infuse coolant into the inflatable, expandable member through an inlet of the inflatable, expandable member and cause the coolant to exit the inflatable, expandable member through an outlet tube while the inflatable, expandable member is in the inflated deployment configuration such that the actively-cooled neuromodulation device provides continuous circulation of the coolant within the inflatable, expandable member to provide cooling to the plurality of electrodes, wherein, when in the inflated deployment configuration, at least one of the plurality of electrodes is adapted to be in contact with a vessel wall; and
   two or more lesion spacing indicators positioned and longitudinally spaced apart along the distal end portion of the elongated shaft to facilitate controlled spacing of lesion zones,
   wherein all lesion spacing indicators of the device are positioned distally to all electrodes of the device, and
   wherein a longitudinal spacing of directly adjacent lesion spacing indicators of the two or more spacing lesion indicators is greater than a longitudinal spacing between two directly adjacent electrodes of the plurality of electrodes.

2. The device of claim 1, wherein a ratio of circumferential perivascular injury to circumferential vessel wall injury caused by the neuromodulation device is greater than or equal to 2:1.

3. The device of claim 1, wherein the two or more spaced apart lesion spacing indicators comprise radiopaque markers.

4. The device of claim 1, wherein each of the electrodes comprises an oblong shape.

5. The device of claim 1, wherein the plurality of electrodes are configured to function as monopolar electrodes.

6. The device of claim 1, wherein at least two electrodes of the plurality of electrodes are positioned 180 degrees offset from each other.

7. The device of claim 1, wherein each of the electrodes has an area of between 3 mm$^2$ and 16 mm$^2$.

8. The device of claim 1, wherein each electrode of the plurality of electrodes is configured to be connected to a radiofrequency generator by a separate connection wire such that each of the electrodes is individually controllable.

9. An actively-cooled neuromodulation device adapted for intravascular neuromodulation, the device comprising:
   an elongated shaft comprising a proximal end portion and a distal end portion;
   an inflatable, expandable member positioned at the distal end portion of the elongated shaft, the inflatable, expandable member being configured to transition from a non-inflated delivery configuration to an inflated deployment configuration so as to cause the inflatable, expandable member to be in contact with a vessel wall,
   wherein the inflatable, expandable member comprises a plurality of electrodes positioned along an outer surface of the inflatable, expandable member so as to provide a treatment pattern that provides increased perivascular treatment while reducing vessel wall injury such that a ratio of circumferential perivascular treatment to circumferential vessel wall injury caused by the neuromodulation device is greater than or equal to 2:1,
   wherein the elongated shaft comprises a lumen,
   wherein the neuromodulation device is adapted to couple to a pump configured to continuously infuse coolant into the inflatable, expandable member through the lumen of the elongated shaft and into an inlet of the inflatable, expandable member and to cause the coolant to exit the inflatable, expandable member through an outlet tube while the inflatable, expandable member is in the inflated deployment configuration, such that the actively-cooled neuromodulation device provides continuous circulation of the coolant within the inflatable, expandable member to provide cooling to the plurality of electrodes,
   wherein each of the electrodes is configured to be connected to a radiofrequency generator by a separate connection wire such that each of the electrodes is individually controllable,
   wherein, when in the inflated deployment configuration, at least one of the plurality of electrodes is adapted to be in contact with the vessel wall; and
   two or more lesion spacing indicators positioned along the distal end portion of the elongated shaft to facilitate controlled spacing between multiple lesion zones,
   wherein all lesion spacing indicators of the device are positioned distally to all electrodes of the device, and
   wherein a longitudinal spacing of directly adjacent lesion spacing indicators of the two or more spacing lesion indicators is greater than a longitudinal spacing between two directly adjacent electrodes of the plurality of electrodes to facilitate a minimum longitudinal spacing between adjacent lesion zones of the multiple lesion zones.

10. The device of claim 9, wherein the plurality of electrodes comprises a plurality of electrode arrays.

11. The device of claim 10, wherein each electrode array comprises a plurality of spaced-apart electrodes.

12. The device of claim 11, wherein the plurality of electrode arrays are arranged to form a spiral pattern along the outer surface of the inflatable, expandable member.

13. The device of claim 9, wherein the inflatable, expandable member comprises four and only four electrodes.

14. The device of claim 9, wherein the inflatable, expandable member comprises a coating covering an entire outer surface of the inflatable, expandable member except for active electrode areas of the electrodes.

15. The device of claim 9 wherein the two or more lesion spacing indicators comprise radiopaque markers.

16. The device of claim 9, wherein each of the electrodes comprises an oblong shape.

17. The device of claim 9, further comprising means for assessing contact based on impedance.

18. The device of claim 9, wherein each electrode of the plurality of electrodes is configured to function as a monopolar electrode.

19. The device of claim 9, wherein at least two electrodes of the plurality of electrodes are positioned 180 degrees offset from each other.

20. The device of claim 9, wherein each of the electrodes has an area of between 4 $mm^2$ and 10 $mm^2$.

21. The device of claim 9, wherein the two directly adjacent electrodes of the plurality of electrodes are circumferentially offset from each other.

\* \* \* \* \*